US012258327B2

(12) United States Patent
Lee et al.

(10) Patent No.: US 12,258,327 B2
(45) Date of Patent: *Mar. 25, 2025

(54) 5-MEMBERED HETEROARYL-CONTAINING AMINOPYRIDINE COMPOUNDS AS EGFR INHIBITORS

(71) Applicants: YUHAN CORPORATION, Seoul (KR); JANSSEN BIOTECH, INC., Horsham, PA (US)

(72) Inventors: Byoungmoon Lee, Hwaseong-si (KR); Hyunjoo Lee, Suwon-si (KR); Gyu Jin Lee, Yongin-si (KR); Su Bin Choi, Hwaseong-si (KR); Misong Kim, Suwon-si (KR); Young Ae Yoon, Seongnam-si (KR); Kwan Hoon Hyun, Incheon (KR); Jae Young Sim, Yongin-si (KR); Marian C. Bryan, Spring House, PA (US); Scott Kuduk, Spring House, PA (US); James Campbell Robertson, Spring House, PA (US); Jaekyoo Lee, North Andover, MA (US); Paresh Devidas Salgaonkar, Lexington, MA (US); Byung-Chul Suh, Lexington, MA (US); Jong Sung Koh, Cambridge, MA (US); So Young Hwang, Lexington, MA (US)

(73) Assignees: YUHAN CORPORATION, Seoul (KR); JANSSEN BIOTECH, INC., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/822,443

(22) Filed: Aug. 26, 2022

(65) Prior Publication Data

US 2023/0085912 A1 Mar. 23, 2023

Related U.S. Application Data

(60) Provisional application No. 63/237,653, filed on Aug. 27, 2021.

(51) Int. Cl.
*C07D 401/14* (2006.01)
*C07D 413/14* (2006.01)
*A61K 31/506* (2006.01)
*A61P 35/00* (2006.01)
*A61P 37/00* (2006.01)
*C07D 405/14* (2006.01)

(52) U.S. Cl.
CPC ......... *C07D 401/14* (2013.01); *C07D 413/14* (2013.01)

(58) Field of Classification Search
CPC .. C07D 401/14; C07D 413/14; C07D 405/14; A61P 35/00; A61P 37/00
See application file for complete search history.

(56) References Cited

U.S. PATENT DOCUMENTS

| | | |
|---|---|---|
| 6,884,804 B2 | 4/2005 | Choon-Moon |
| 7,560,464 B2 | 7/2009 | Wang et al. |
| 7,642,354 B2 | 1/2010 | Wang et al. |
| 8,058,045 B2 | 11/2011 | Collins et al. |
| 8,367,658 B2 | 2/2013 | Collins et al. |
| 9,242,984 B2 | 1/2016 | Machacek et al. |
| 9,868,720 B2 | 1/2018 | Cohen et al. |
| 10,526,309 B2 * | 1/2020 | Wang ..................... A61P 35/00 |
| 10,822,327 B2 | 11/2020 | Liu et al. |
| 2003/0144309 A1 | 7/2003 | Choon-Moon |
| 2004/0236084 A1 | 11/2004 | Biwersi et al. |
| 2005/0239800 A1 | 10/2005 | Wang et al. |
| 2005/0267089 A1 | 12/2005 | Wang et al. |
| 2008/0108600 A1 | 5/2008 | Wang et al. |
| 2010/0311730 A1 | 12/2010 | Collins et al. |
| 2012/0040967 A1 | 2/2012 | Collins et al. |
| 2015/0191461 A1 | 7/2015 | Machacek et al. |
| 2016/0046608 A1 | 2/2016 | Cohen et al. |
| 2019/0375727 A1 | 12/2019 | Liu et al. |
| 2020/0392156 A1 | 12/2020 | Kesicki |
| 2021/0317136 A1 | 10/2021 | Lindstrom et al. |
| 2022/0177459 A1 * | 6/2022 | Du ..................... C07D 417/12 |
| 2022/0298140 A1 | 9/2022 | Chen |
| 2022/0411407 A1 | 12/2022 | Wang et al. |

FOREIGN PATENT DOCUMENTS

| | | | |
|---|---|---|---|
| CN | 104761585 A | 7/2015 | |
| KR | 10-2020-0016567 A | 2/2020 | |
| WO | WO/2005/099711 A1 * | 10/2005 | ........... C07D 401/14 |
| WO | 2019/222538 A1 | 11/2019 | |

OTHER PUBLICATIONS

Chan, Bryan K et al) (Journal of Medicinal Chemistry 2016, 59(19) 9080-9093 (Discovery of a Noncovalent Mutant selective Epidermal Growth factor Receptor Inhibitor (Year: 2016).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022) (Year: 2022).*
Gleeson MP, Hersey A, Montanari D, Overington J. Probing the links between in vitro potency, ADMET and physicochemical parameters. Nat Rev Drug Discov. Mar. 2011;10(3):197-208. doi: 10.1038/nrd3367. PMID: 21358739; PMCID: PMC6317702. (Year: 2011).*

(Continued)

*Primary Examiner* — Bruck Kifle
*Assistant Examiner* — Kevin S Martin
(74) *Attorney, Agent, or Firm* — Vorys, Sater, Seymour and Pease LLP; Mih Suhn Koh

(57) ABSTRACT

Provided are 5-membered heteroaryl-containing aminopyridine compounds and pharmaceutically acceptable compositions thereof which exhibit inhibition activity against certain mutated forms of EGFR.

25 Claims, No Drawings

(56) References Cited

OTHER PUBLICATIONS

Hanan et al., "Discovery of Selective and Noncovalent Diaminopyrimidine-Based Inhibitors of Epidermal Growth Factor Receptor Containing the T790M Resistance Mutation", J. Med. Chem., 2014, vol. 57, pp. 10176-10191.

* cited by examiner

5-MEMBERED HETEROARYL-CONTAINING AMINOPYRIDINE COMPOUNDS AS EGFR INHIBITORS

FIELD OF THE INVENTION

The present invention relates to novel aminopyridine compounds and pharmaceutically acceptable compositions thereof which exhibit inhibition activity against certain mutated forms of EGFR.

BACKGROUND

A distinct subtype of lung cancer is epidermal growth factor receptor (EGFR) mutation positive non-small cell lung cancer (NSCLC). The human EGFR is a membrane-bound receptor tyrosine kinase of the ErbB family. The activation causes downstream effects via several signaling pathways including the RAS/RAF/MEK/ERK/MAPK and PI3K/PTEN/Akt/mTOR (Chen et al., 2020). The EGFR signaling pathway regulate a series of important events including proliferation, migration, differentiation, apoptosis, as well as those that regulate intercellular communication during development (Wee et al., 2017; Huang et al., 2015; Yewale et al., 2013).

Approximately 10% to 50% of NSCLC patients have EGFR activating mutations, such as in-frame deletions in exon 19 deletion (Del19) or a missense mutation in exon 21 (L858R). (Yang et al., 2018; Shigematsu et al., 2005; Shu et al., 2017; Zhang et al., 2010). These patients respond well to first and second-generation EGFR tyrosine kinase inhibitors (TKI), including gefitinib (IRESSA™), erlotinib (TARCEVA™), and afatinib (GIOTRIF™) allowing them as the initial therapy for in patients with advanced NSCLC harboring common EGFR mutations (Kashima et al., 2020; Mok et al., 2009; Zhou et al., 2011; Sequist et al., 2013). But ultimately acquired resistance to therapy with gefitinib or erlotinib arises predominantly by mutation of the gatekeeper residue T790M, which is detected in approximately half of clinically resistant patients, resulting in double mutants, L858R/T790M and Del19/T790M.

Several third-generation EGFR TKIs were being explored to overcome this resistance. Currently, osimertinib is the third-generation EGFR-TKI approved by major regulatory agencies for treatment of T790M-positive patients who have progressed on first- or second generation EGFR-TKIs (Leonetti et al., 2019; Soria et al., 2018).

Osimertinib is a powerful inhibitor that inhibits EGFR mutations and T790M resistant mutations, but it causes ineffective binding and C797S subsequent resistance in NSCLC patients (Arulananda et al., 2017). Unfortunately, it has been reported that acquired resistance mutations occur in lung cancer patients after the treatment with third-generation EGFR-TKIs. The C797S mutation is the frequently arise after the use of third generation EGFR TKIs in 10% to 30% of these patients. (Ramalingam et al., 2018; Thress et al., 2015; Oxnard et al., 2018; Starrett et al., 2020; Mehlman et al., 2019; Rangachari et al., 2019; Zhou et al., 2019). Osimertinib resistance resulting from EGFR triple mutations (Del19/T790M/C797S and L858R/T790M/C797S) has been reported, requiring the next generation EGFR-TKI to overcome the osimertinib resistant EGFR triple mutations (Kashima et al., 2020).

In front-line therapy with third generation TKI, C797S develops in the absence of T790M (Chen et al., 2020). Osimertinib was also approved in 2018 as first-line therapy for locally advanced or metastatic EGFR-mutated NSCLC, regardless of T790M mutation status (Leonetti et al., 2019). When osimertinib was administered as a front-line therapy, the frequency of the C797S mutation was 7%, making it the second most frequent mechanism, behind MET amplification, of drug resistance in this setting (Leonetti et al., 2019; Ramalingam et al., 2018).

When osimertinib was administered as a front-line therapy, the most common resistance mechanisms resulted to be the C797S mutation (7%) and MET amplification (15%). Other mechanisms included HER2 amplification, PIK3CA and RAS mutations (Ramalingam et al., 2018). Also, selectivity to wild-type (WT) EGFR is important for EGFR-TKIs, because WT EGFR inhibition causes adverse effects such as rashes and/or diarrhea, and these WT EGFR-derived toxicities cause dose-limiting effects (Kashima et al., 2020; Fakih et al., 2010; Takeda et al., 2015).

The next generation EGFR compounds would need to inhibit Del19/T790M/C797S, L858R/T790M/C797S, Del19/C797S and L858R/C797S and be highly selective versus WT EGFR to avoid adverse effects. Recently, mutant selective inhibitors, BI-4020 and BLU-945 were reported as potential therapeutic strategies to overcome the EGFR Del19/T790M/C797S mutations (Engelhardt et al., 2019; Schalm et al., 2020).

However, there have been no reports of these compounds inhibiting Del19/C797S and L858R/C797S. Therefore, novel EGFR-TKIs potently effective against EGFR triple/double mutations are urgently needed.

To address this unmet need, we are developing a next generation TKI targeting both C797S triple and double mutants. It is necessary to develop a novel selective (next generation) inhibitor for NSCLC patients with advanced or metastatic diseases carrying Del19/T790M/C797S, L858R/T790M/C797S, Del19/C797S and L858R/C797S mutation following second-line or upfront use of third-generation EGFR TKIs.

REFERENCES

Arulananda S, John T, Dobrovic A. et al. Combination Osimertinib and Gefitinib in C797S and T790M EGFR-Mutated Non-Small Cell Lung Cancer. Journal of Thoracic Oncology Vol. 12 No. 11: 1728-1732, 2017.

Chen J S, Riess J W. Advances in targeting acquired resistance mechanisms to epidermal growth factor receptor tyrosine kinase inhibitors. Justin A. Chen, Jonathan W. Riess. J Thorac Dis 2020; 12(5):2859-2876.

Engelhardt H, et al. Start Selective and Rigidify: The Discovery Path toward a Next Generation of EGFR Tyrosine Kinase Inhibitors. Cite This: J. Med. Chem. 2019, 62, 10272-10293.

Fakih M, Vincent M. Adverse events associated with anti-EGFR therapies for the treatment of metastatic colorectal cancer. Curr. Oncol. 2010; 17: S18-30.

Huang L, Fu L. Mechanisms of resistance to EGFR tyrosine kinase inhibitors. Acta Pharm Sin B 2015; 5:390-401.

Kashima K, et al. CH7233163 Overcomes Osimertinib-Resistant EGFR-Del19/T790M/C797S Mutation. Mol Cancer Ther; 19(11) November 2020.

Leonetti A, et al. Resistance mechanisms to osimertinib in EGFR-mutated non-small cell lung cancer. British Journal of Cancer (2019) 121:725-737.

Mok T S, Wu Y L, Thongprasert S, Yang C H, Chu D T, Saijo N, et al. Gefitinib or carboplatin-paclitaxel in pulmonary adenocarcinoma. N Engl J Med 2009; 361: 947-57.

Mehlman C, Cadranel J, Rousseau-Bussac G, Lacave R, Pujals A, Girard N, et al. Resistance mechanisms to

SUMMARY OF INVENTION

The present invention relates to novel aminopyridine compounds of Formula (I) shown below, or a pharmaceutically acceptable salt thereof:

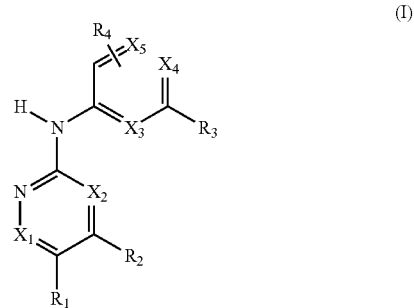

wherein $X_1$ and $X_2$ are, independently each other, —CH═ or —N═, with the proviso that $X_1$ and $X_2$ cannot be —N═ at the same time, $X_3$, $X_4$, and $X_5$ are, independently each other, —CH═ or —N═, with the proviso that $X_3$, $X_4$, and $X_5$ cannot be —CH═ at the same time, $R_1$ is -A-$(R_{1A})_m$, A is 5-membered heteroaryl or 5-membered heteroaryl-containing 7-10 membered heterocyclyl, $R_{1A}$ is independently selected from the group consisting of

H;

OH;

halogen;

cyano;

$C_{1-6}$alkyl optionally substituted by one or more substituents selected from the group consisting of OH, halogen, $C_{1-3}$alkoxy, $C_{3-6}$cycloalkyl, —NH$C_{1-6}$alkyl, —N($C_{1-6}$alkyl)$_2$, and 4-7 membered heterocyclyl optionally or independently substituted by one or more substituents selected from the group consisting of OH, halogen, and $C_{1-6}$alkyl;

$C_{3-6}$cycloalkyl;

$C_{1-3}$alkoxy optionally substituted by one or more substituents selected from the group consisting of OH, halogen, —N($C_{1-6}$alkyl)$_2$, and 3-7 membered heterocyclyl optionally or independently substituted by one or more substituents selected from the group consisting of halogen and $C_{1-6}$alkyl;

—NH$C_{1-6}$alkyl optionally substituted by one or more substituents selected from the group consisting of OH, halogen, —N($C_{1-6}$alkyl)$_2$ and 3-7 membered heterocyclyl optionally substituted by one or more substituents selected from the group consisting of OH, halogen, and $C_{1-6}$alkyl;

—NHC$_{3-6}$cycloalkyl optionally substituted by one or more substituents selected from the group consisting of OH, halogen and C$_{1-6}$alkyl optionally substituted by OH;

—NH 3-7 membered heterocyclyl optionally substituted by one or more substituents selected from the group consisting of OH, halogen, and C$_{1-6}$alkyl;

—N(C$_{1-6}$alkyl)$_2$ optionally substituted by one or more substituents selected from the group consisting of OH and halogen;

—NHC(O)C$_{1-6}$alkyl optionally substituted by one or more substituents selected from the group consisting of OH and halogen;

—NHC(O)C$_{3-6}$cycloalkyl optionally substituted by one or more substituents selected from the group consisting of OH and halogen;

—O-4-7 membered heterocyclyl optionally or independently substituted by one or more substituents selected from the group consisting of C$_{1-6}$alkyl and C$_{1-6}$haloalkyl;

4-7 membered heterocyclyl optionally or independently substituted by one or more substituents selected from the group consisting of OH, halogen, C$_{1-6}$alkyl, C$_{1-3}$alkoxy, C$_{1-6}$hydroxyalkyl, and C$_{1-6}$haloalkyl;

—S(O)$_2$C$_{1-6}$alkyl optionally substituted by one or more halogens;

—S(O)$_2$C$_{3-6}$cycloalkyl optionally substituted by one or more halogens;

—S(O)$_2$N(C$_{1-6}$alkyl)$_2$ optionally substituted by one or more halogens;

—S(O)$_2$-3-7 membered heterocyclyl optionally substituted by one or more substituents selected from the group consisting of OH, halogen, and C$_{1-6}$alkyl;

—C(O)OC$_{1-6}$alkyl;

—C(O)C$_{1-6}$alkyl; and

—C(O)-3-7 membered heterocyclyl optionally substituted by one or more substituents selected from the group consisting of OH, halogen, and C$_{1-6}$alkyl, m is an integer of 0 to 2, R$_2$ is —XC$_{1-6}$alkyl optionally substituted by one or more substituents selected from the group consisting of OH, halogen, and —N(C$_{1-6}$alkyl)$_2$; or —X(CH$_2$)$_n$—B—(R$_{2A}$)$_o$, X is —NH—, —O—, bond or —C≡C—, n is an integer of 0 to 3, is an integer of 0 to 3, B is selected from the group consisting of C$_{3-8}$cycloalkyl, C$_{6-10}$ aryl; 4-11 membered heterocyclyl; and 5-6 membered heteroaryl, R$_{2A}$ is independently selected from the group consisting of

H;

OH;

halogen;

NH$_2$;

C$_{1-6}$alkyl optionally substituted by one or more substituents selected from the group consisting of OH, NH$_2$, halogen, C$_{3-6}$cycloalkyl, C$_{1-3}$alkoxy, —NHC$_{1-6}$alkyl, —NHC$_{1-6}$ hydroxyalkyl, —NHC$_{1-6}$haloalkyl, —NHC$_{3-6}$cycloalkyl, —N(C$_{1-6}$alkyl)$_2$, —N(C$_{1-6}$haloalkyl)$_2$, —N(C$_{1-6}$alkyl)(C$_{1-6}$haloalkyl), —NHC(O)C$_{1-6}$alkyl, —C(O)NHC$_{1-6}$alkyl, —C(O)N(C$_{1-6}$alkyl)$_2$, 3-7 membered heterocyclyl optionally substituted by one or more halogens or and 5-6 membered heteroaryl;

C$_{3-6}$cycloalkyl;

C$_{1-3}$alkoxy optionally substituted by one or more halogens;

—C(O)NHC$_{1-6}$alkyl optionally substituted by one or more substituents selected from the group consisting of OH and halogen;

—C(O)N(C$_{1-6}$alkyl)$_2$ optionally substituted by one or more substituents selected from the group consisting of OH and halogen;

—NHC$_{1-6}$alkyl optionally substituted by one or more substituents selected from the group consisting of OH, halogen, —NHC$_{1-6}$alkyl, —N(C$_{1-6}$alkyl)$_2$, 3-7 membered heterocyclyl optionally substituted by halogen or —N(C$_{1-6}$alkyl)$_2$;

—N(C$_{1-6}$alkyl)$_2$ where C$_{1-6}$alkyl is optionally substituted by one or more halogens;

—NH-4-7 membered heterocyclyl optionally substituted by C$_{1-6}$alkyl;

4-7 membered heterocyclyl; and

=O,

R$_3$ is Y-Q-(R$_{3A}$)$_p$,

Y is —NH— or bond,

Q is selected from the group consisting of —C≡C—; 4-7 membered heterocyclyl; C$_{6-10}$ aryl; and 5-10 membered heteroaryl, p is an integer of 0 to 3, R$_{3A}$ is independently selected from the group consisting of

H;

OH;

halogen;

C$_{1-3}$alkoxy;

C$_{1-6}$alkyl optionally or independently substituted by one or more substituents selected from the group consisting of OH, halogen, C$_{1-3}$alkoxy, C$_{3-6}$cycloalkyl, and S(O)$_2$C$_{1-6}$alkyl;

C$_{2-6}$alkenyl;

C$_{3-6}$cycloalkyl;

4-7 membered heterocyclyl;

—C(O)C$_{1-6}$alkyl;

—C(O)N(C$_{1-6}$alkyl)$_2$;

—S(O)$_2$C$_{1-6}$alkyl optionally substituted by one or more halogens;

—S(O)$_2$C$_{2-6}$alkenyl;

—S(O)$_2$C$_{3-6}$cycloalkyl optionally substituted by one or more halogens;

—S(O)$_2$N(C1$_{-6}$alkyl)$_2$; and

—S(O)$_2$-4-7 membered heterocyclyl optionally substituted by one or more substituents selected from the group consisting of OH, halogen, and C$_{1-6}$alkyl, and R$_4$ is selected from the group consisting of H, halogen and C$_{1-6}$alkyl.

The present invention also relates to methods of treating protein kinase-mediated disease, particularly mutant EGFR-mediated disease in a subject in need thereof comprising administering to said subject a therapeutically effective amount of said compounds of Formula (I) or a pharmaceutically acceptable salt thereof.

The present invention also relates to pharmaceutically acceptable compositions comprising said compounds of Formula (I) or a pharmaceutically acceptable salt thereof, which exhibit inhibition activity against at least one mutant EGFR selectively as compared to wild type EGFR.

DETAILED DESCRIPTION OF THE INVENTION

Hereinafter, the present invention will be described in more detail.

Unless otherwise defined, all technical terms used herein have the same meaning as commonly understood by one of ordinary skill in the art to which this invention belongs. Also, although the invention has been described in conjunction with specific methods and samples, their analogs or equivalents should be within the scope of the present invention. Furthermore, the numerical values set forth herein are considered to include the meaning of "about" unless explicitly stated. All publications and other references mentioned herein are hereby incorporated by reference in their entirety.

The definition of residues used herein is described in detail. Unless otherwise indicated, each residue has the following definition and is used in the sense as commonly understood by one of ordinary skill in the art.

As used herein, the term "halo", "halogen", "halide(s)" includes fluoro, chloro, bromo and iodo.

As used herein, the "alkyl" refers to an aliphatic hydrocarbon radical, and includes both linear and branched hydrocarbon radicals. For example, $C_{1-6}$ alkyl is an aliphatic hydrocarbon having 1 to 6 carbon atoms and includes methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl. Unless otherwise defined, the alkyl refers to $C_{1-6}$ alkyl, preferably $C_{1-4}$ alkyl, more preferably $C_{1-3}$ alkyl.

As used herein, the "alkenyl" refers to an aliphatic hydrocarbon radical comprising at least one carbon-carbon double bond, and includes both linear and branched hydrocarbon radicals. The unlimited example of the "alkenyl" is vinyl, allyl, but-1-enyl or but-2-enyl.

As used herein, the "alkynyl" refers to an aliphatic hydrocarbon radical comprising at least one carbon-carbon triple bond, and includes both linear and branched hydrocarbon radicals. The unlimited example of the "alkynyl" is ethynyl, propargyl, but-1-ynyl or but-2-ynyl.

As used herein, the "haloalkyl" refers to an alkyl group substituted with one or more halogen atom, and the alkyl group is defined as above. The "halo" refers to F, Cl, Br, or I, and the term is compatibly used with the term "halogen". Unless otherwise defined, the haloalkyl refers to fluoromethyl, difluoromethyl, chloromethyl, trifluoromethyl or 2,2,2-trifluoroethyl.

As used herein, the term "alkoxy" refers to O-alkyl or alkyl-O— group, and the alkyl group is defined as shown above. For example, it includes methoxy, ethoxy, n-propoxy, n-butoxy and t-butoxy.

As used herein, the term "hydroxy" or "hydroxyl" alone or in combination with other terms means —OH.

As used herein, the term "hydroxyalkyl" refers to any hydroxyl derivative of alkyl radical. The term "hydroxyalkyl" includes any alkyl radical having one or more hydrogen atoms replaced by a hydroxy group.

As used herein, "amino" refers to —NH$_2$.

As used herein, the term "cycloalkyl" refers to a cyclic alkyl which may be substituted or unsubstituted, and for example, the $C_{3-20}$ cycloalkyl represents a monovalent saturated hydrocarbon ring system having 3 to 20 carbon atoms. Examples of the cycloalkyl include, but are not limited to, cyclopropyl, cyclobutyl, cyclopentyl, cyclohexyl, cycloheptyl, cyclooctyl and the like. Preferably, unless otherwise defined, the cycloalkyl may be $C_{3-8}$ cycloalkyl, or $C_{3-6}$ cycloalkyl.

As used herein, the term "aryl" refers to a monovalent aromatic hydrocarbon having, for example, 6 to 20 carbon atoms ($C_{6-20}$) that is derived by the removal of one hydrogen atom from a single carbon atom of a parent aromatic ring system. The aryl may include a bicyclic radical containing an aromatic ring fused to a saturated or partially unsaturated ring. Exemplary aryl groups may include radicals derived from benzene (phenyl), substituted phenyl, biphenyl, naphthyl, toluyl, naphthalenyl, anthracenyl, indenyl, indanyl, and the like. Unless otherwise defined, the aryl refers to $C_{6-12}$ aryl, preferably $C_{6-10}$ aryl.

As used herein, the "heterocycle" refers to an aromatic, saturated or partially unsaturated mono-, bi- or poly-ring system containing the specified number of ring atoms, and include one or more heteroatoms selected from N, O, and S as a ring member, wherein the heterocyclic ring is connected to the base molecule via a ring atom, which may be C or N.

Bicyclic systems may be connected via a 1,1-fusion (spiro), a 1,2-fusion (fused) or a 1,>2-fusion (bridgehead).

As used herein, the "heteroaryl" refers to a monovalent or divalent substituent derived from a monoheterocyclic or polyheterocyclic aromatic hydrocarbon having 1 to 10 carbon ring members containing one or more, preferably one to three, heteroatoms selected among N, O, and S. Examples of the heteroaryl include, but are not limited to, thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazoly, 1,1,3,4-oxadiazolyl, 1,2,4-thiadiazolyl, 1,3,4-thiadiazolyl, triazolyl, tetrazolyl, triazinyl, indolyl, and the like. Examples of the bicyclic heteroaryl include indolyl, benzothiophenyl, benzofuranyl, benzimidazolyl, benzoxazolyl, benzisoxazolyl, benzthiazolyl, benzthiadiazolyl, quinolinyl, isoquinolinyl, furopyridinyl and similar groups thereof, but are not limited thereto. Unless otherwise defined, the heteroaryl is 4-12 membered heteroaryl 1, preferably 4-10 membered heteroaryl, more preferably 4-7 heteroaryl.

As used herein, the "heterocycloalkyl" refers to monocyclic, bicyclic, tricyclic or higher cyclic alkyl having 3 to 10 carbon ring members containing one or more, for example, one to four, heteroatoms selected among N, O, and S. In addition, the heterocycle according to the present invention may also be a fused or bridged heterocycloalkyl. Examples of non-aromatic rings include azetidinyl, oxetanyl, tetrahydrothienyl, tetrahydrofuranyl, pyrrolinyl, pyrrolidinyl, imidazolinyl, imidazolidinyl, oxazolinyl, oxazolidinyl, oxapiperazinyl, oxapiperidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyranyl, dihydropyranyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, teterahydropyrazolopyridinyl, morpholinyl, indolinyl, thiomorpholinyl, azepanyl, diazepanyl, azaadamantanyl, diazamantanyl, and the like, but are not limited thereto. Attachment of a heterocycloalkyl substituent can occur via a carbon atom or a heteroatom. A heterocycloalkyl group may be optionally substituted with one or more suitable groups via one or more aforementioned groups. Unless otherwise defined, heterocycloalkyl refers to 4-12 membered heterocycloalkyl, preferably 4-10 membered heterocycloalkyl, more preferably 4-7 heterocycloalkyl.

The present invention provides novel compounds, a pharmaceutically acceptable salt, diastereomers, enantiomers, racemates, tautomers, prodrugs, hydrates, and solvates thereof that are useful for inhibiting epidermal growth factor receptor (EGFR) and for treating diseases and disorders that are mediated by the protein kinase, for example, cell proliferative diseases and disorders such as cancer, immune diseases such as arthritis, rheumatoid arthritis or autoimmune diseases, infections, cardiovascular diseases, and neurodegenerative diseases and disorders.

The present invention also provides pharmaceutical compositions comprising at least one of the compounds of Formula (I) together with a pharmaceutically acceptable carrier, diluent or excipient therefor.

The present invention provides compositions and methods for modulating the activity of the epidermal growth factor receptor (EGFR) mutants. In one aspect, the present invention provides compounds which act as inhibitors of EGFR mutants.

In one embodiment, provided herein is a compound of Formula (I) shown below, a pharmaceutically acceptable salt, diastereomers, enantiomers, racemates, tautomers, prodrugs, hydrates, or solvates thereof.

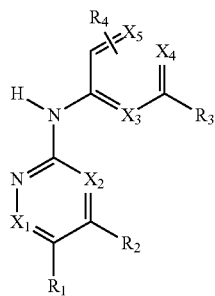

(I)

wherein $X_1$ and $X_2$ are, independently each other, —CH= or —N=, with the proviso that $X_1$ and $X_2$ cannot be —N= at the same time, $X_3$, $X_4$, and $X_5$ are, independently each other, —CH= or —N=, with the proviso that $X_3$, $X_4$, and $X_5$ cannot be —CH= at the same time, $R_1$ is -A-$(R_{1A})_m$, A is 5-membered heteroaryl or 5-membered heteroaryl-containing 7-10 membered heterocyclyl, $R_{1A}$ is independently selected from the group consisting of

H;

OH;

halogen;

cyano;

$C_{1-6}$alkyl optionally substituted by one or more substituents selected from the group consisting of OH, halogen, $C_{1-3}$alkoxy, $C_{3-6}$cycloalkyl, —NHC$_{1-6}$alkyl, —N($C_{1-6}$alkyl)$_2$, and 4-7 membered heterocyclyl optionally or independently substituted by one or more substituents selected from the group consisting of OH, halogen, and $C_{1-6}$alkyl;

$C_{3-6}$cycloalkyl;

$C_{1-3}$alkoxy optionally substituted by one or more substituents selected from the group consisting of OH, halogen, —N($C_{1-6}$alkyl)$_2$, and 3-7 membered heterocyclyl optionally or independently substituted by one or more substituents selected from the group consisting of halogen and $C_{1-6}$alkyl;

—NHC$_{1-6}$alkyl optionally substituted by one or more substituents selected from the group consisting of OH, halogen, —N($C_{1-6}$alkyl)$_2$ and 3-7 membered heterocyclyl optionally substituted by one or more substituents selected from the group consisting of OH, halogen, and $C_{1-6}$alkyl;

—NHC$_{3-6}$cycloalkyl optionally substituted by one or more substituents selected from the group consisting of OH, halogen and $C_{1-6}$alkyl optionally substituted by OH;

—NH 3-7 membered heterocyclyl optionally substituted by one or more substituents selected from the group consisting of OH, halogen, and $C_{1-6}$alkyl;

—N($C_{1-6}$alkyl)$_2$ optionally substituted by one or more substituents selected from the group consisting of OH and halogen;

—NHC(O)C$_{1-6}$alkyl optionally substituted by one or more substituents selected from the group consisting of OH and halogen;

—NHC(O)C$_{3-6}$cycloalkyl optionally substituted by one or more substituents selected from the group consisting of OH and halogen;

—O-4-7 membered heterocyclyl optionally or independently substituted by one or more substituents selected from the group consisting of $C_{1-6}$alkyl and $C_{1-6}$haloalkyl;

4-7 membered heterocyclyl optionally or independently substituted by one or more substituents selected from the group consisting of OH, halogen, $C_{1-6}$alkyl, $C_{1-3}$alkoxy, $C_{1-6}$hydroxyalkyl, and $C_{1-6}$haloalkyl;

—S(O)$_2$C$_{1-6}$alkyl optionally substituted by one or more halogens;

—S(O)$_2$C$_{3-6}$cycloalkyl optionally substituted by one or more halogens;

—S(O)$_2$N($C_{1-6}$alkyl)$_2$ optionally substituted by one or more halogens;

—S(O)$_{2-3}$-7 membered heterocyclyl optionally substituted by one or more substituents selected from the group consisting of OH, halogen, and $C_{1-6}$alkyl;

—C(O)OC$_{1-6}$alkyl;

—C(O)C$_{1-6}$alkyl; and

—C(O)-3-7 membered heterocyclyl optionally substituted by one or more substituents selected from the group consisting of OH, halogen, and $C_{1-6}$alkyl, m is an integer of 0 to 2, $R_2$ is —XC$_{1-6}$alkyl optionally substituted by one or more substituents selected from the group consisting of OH, halogen, and —N($C_{1-6}$alkyl)$_2$; or —X(CH$_2$)$_n$—B—($R_{2A}$)$_o$, X is —NH—, —O—, bond or —C≡C—, n is an integer of 0 to 3, is an integer of 0 to 3, B is selected from the group consisting of $C_{3-8}$cycloalkyl, $C_{6-10}$aryl; 4-11 membered heterocyclyl; and 5-6 membered heteroaryl, $R_{2A}$ is independently selected from the group consisting of

H;

OH;

halogen;

NH$_2$;

$C_{1-6}$alkyl optionally substituted by one or more substituents selected from the group consisting of OH, NH$_2$, halogen, $C_{3-6}$cycloalkyl, $C_{1-3}$alkoxy, —NHC$_{1-6}$alkyl, —NHC$_{1-6}$ hydroxyalkyl, —NHC$_{1-6}$haloalkyl, —NHC$_{3-6}$cycloalkyl, —N($C_{1-6}$alkyl)$_2$, —N($C_{1-6}$haloalkyl)$_2$, —N($C_{1-6}$alkyl)($C_{1-6}$haloalkyl), —NHC(O)C$_{1-6}$alkyl, —C(O)NHC$_{1-6}$alkyl, —C(O)N($C_{1-6}$alkyl)$_2$, 3-7 membered heterocyclyl optionally substituted by one or more halogens or and 5-6 membered heteroaryl;

$C_{3-6}$cycloalkyl;

$C_{1-3}$alkoxy optionally substituted by one or more halogens;

—C(O)NHC$_{1-6}$alkyl optionally substituted by one or more substituents selected from the group consisting of OH and halogen;

—C(O)N(C$_{1-6}$alkyl)$_2$ optionally substituted by one or more substituents selected from the group consisting of OH and halogen;

—NHC$_{1-6}$alkyl optionally substituted by one or more substituents selected from the group consisting of OH, halogen, —NHC$_{1-6}$alkyl, —N(C$_{1-6}$alkyl)$_2$, 3-7 membered heterocyclyl optionally substituted by halogen or —N(C$_{1-6}$alkyl)$_2$;

—N(C$_{1-6}$alkyl)$_2$ where C$_{1-6}$alkyl is optionally substituted by one or more halogens;

—NH-4-7 membered heterocyclyl optionally substituted by C$_{1-6}$alkyl;

4-7 membered heterocyclyl; and

=O,

R$_3$ is Y-Q-(R$_{3A}$)$_p$,

Y is —NH— or bond,

Q is selected from the group consisting of —C≡C—; 4-7 membered heterocyclyl; C$_{6-10}$ aryl; and 5-10 membered heteroaryl, p is an integer of 0 to 3, R$_{3A}$ is independently selected from the group consisting of

H;

OH;

halogen;

C$_{1-3}$alkoxy;

C$_{1-6}$alkyl optionally or independently substituted by one or more substituents selected from the group consisting of OH, halogen, C$_{1-3}$alkoxy, C$_{3-6}$cycloalkyl, and S(O)$_2$C$_{1-6}$alkyl;

C$_{2-6}$alkenyl;

C$_{3-6}$cycloalkyl;

4-7 membered heterocyclyl;

—C(O)C$_{1-6}$alkyl;

—C(O)N(C$_{1-6}$alkyl)$_2$;

—S(O)$_2$C$_{1-6}$alkyl optionally substituted by one or more halogens;

—S(O)$_2$C$_{2-6}$alkenyl;

—S(O)$_2$C$_{3-6}$cycloalkyl optionally substituted by one or more halogens;

—S(O)$_2$N(C1$_{-6}$alkyl)$_2$; and

—S(O)$_2$-4-7 membered heterocyclyl optionally substituted by one or more substituents selected from the group consisting of OH, halogen, and C$_{1-6}$alkyl, and R$_4$ is selected from the group consisting of H, halogen and C$_{1-6}$alkyl.

In certain embodiment, X$_1$ and X$_2$ are —CH=.

In further certain embodiment, X$_1$ is —N= and X$_2$ is —CH=.

In another further certain embodiment, X$_1$ is —CH= and X$_2$ is —N=.

In certain embodiment, X$_3$ and X$_4$ are —N=; and X$_5$ is —CH=.

In further certain embodiment, X$_4$ is —N=; and X$_3$ are X$_5$ are —CH=.

In another further certain embodiment, X$_3$ and X$_5$ are —N=; and X$_4$ is —CH=.

In certain embodiment, A is 5-membered heteroaryl.

In further certain embodiment, A is 5-membered heteroaryl-containing 7-10 membered heterocyclyl.

In another further certain embodiment, A is pyrazolyl, 4,5,6,7-tetrahydropyrazolo[1,5-a]pyridinyl, isoxazolyl, thiazolyl, furanyl, imidazolyl, or 6,7-dihydropyrrolo[1,2-a]imidazolyl.

In certain embodiment, R$_{1A}$ is H; F; Cl; C$_{1-4}$alkyl optionally substituted by one to three substituents selected from the group consisting of OH, F, Cl, C$_{1-3}$alkoxy, C$_{3-6}$cycloalkyl, —NHC$_{1-4}$alkyl, —N(C$_{1-4}$alkyl)$_2$, 4-6 membered heterocyclyl optionally substituted by C$_{1-3}$alkyl; C$_{3-6}$cycloalkyl; C$_{1-2}$alkoxy optionally substituted by one to three F or Cl;

—NHC$_{1-4}$alkyl optionally substituted by one to three substituents selected from the group consisting of OH F and Cl;

—NHC$_{3-6}$cycloalkyl optionally substituted by one to three substituents selected from the group consisting of OH, F and Cl; —N(C$_{1-6}$alkyl)$_2$ optionally substituted by one to three substituents selected from the group consisting of OH, F and Cl; —NHC(O)C$_{1-6}$alkyl optionally substituted by one to three substituents selected from the group consisting of OH, F and Cl; —NHC(O)C$_{3-6}$cycloalkyl optionally substituted by one to three substituents selected from the group consisting of OH, F and Cl; 4-6 membered heterocyclyl optionally or independently substituted by one to three substituents selected from the group consisting of F, Cl, C$_{1-6}$alkyl, C$_{1-6}$hydroxyalkyl, and C$_{1-6}$haloalkyl; —S(O)$_2$C$_{1-6}$alkyl optionally substituted by one or more halogens; or —C(O)OC$_{1-6}$alkyl.

In further certain embodiment, R$_{1A}$ is C$_{1-6}$alkyl optionally substituted by one or more substituents selected from the group consisting of OH, halogen, C$_{3-6}$cycloalkyl, —NHC$_{1-6}$alkyl, —N(C$_{1-6}$alkyl)$_2$, and 4-7 membered heterocyclyl optionally substituted by C$_{1-6}$alkyl.

In another further certain embodiment, R$_{1A}$ is independently selected from the group consisting of

H;

Halogen;

C$_{1-6}$alkyl optionally substituted by one or more substituents selected from the group consisting of OH, halogen, C$_{1-3}$alkoxy, C$_{3-6}$cycloalkyl, and —N(C$_{1-6}$alkyl)$_2$;

C$_{3-6}$cycloalkyl;

C$_{1-3}$alkoxy optionally substituted by one or more halogens;

4-7 membered heterocyclyl optionally or independently substituted by one or more substituents selected from the group consisting of halogen and C$_{1-6}$alkyl;

—S(O)$_2$C$_{1-6}$alkyl; and

—C(O)OC$_{1-6}$alkyl.

In the above embodiments of R$_{1A}$, the 4-7 membered heterocyclyl may be tetrahydropyranyl, morpholinyl, piperazinyl, oxetanyl, or piperidinyl.

In certain embodiment, R$_2$ is —XC$_{1-6}$alkyl optionally substituted by one or more substituents selected from the group consisting of OH and halogen.

In further certain embodiment, R$_2$ is —X(CH$_2$)$_n$—B—(R$_{2A}$)$_o$.

In certain embodiment, B is C$_{3-6}$cycloalkyl; phenyl; 4-10 membered heterocycloalkyl having one to three heteroatoms selected from a group consisting of N, O and S; or 5-6 membered heteroaryl having one to three heteroatoms selected from a group consisting of N, O and S.

In further certain embodiment, B is C$_{3-6}$cycloalkyl.

In another further certain embodiment, B is 4-10 membered heterocycloalkyl or 5-6 membered heteroaryl having one to three heteroatoms selected from a group consisting of N and O.

In another further certain embodiment, B is C$_{3-8}$cycloalkyl, pyrazolyl, azepanyl, azaspiro[4.5]decanonly, azaspiro[3.3]heptanyl, azaspiro[3.5]nonanyl, piperidinonyl, bicyclo[2.2.1]heptanyl, spiro[3.3]hepatanyl, tetrahydropyranyl, imidazolyl, piperidinyl, or oxetanyl.

In certain embodiment, R$_{2A}$ is H; F; Cl; OH; NH$_2$; C$_{1-4}$alkyl optionally substituted by one or more substituents selected from the group consisting of OH, NH$_2$, F, Cl, C$_{3-6}$cycloalkyl, C$_{1-3}$alkoxy, —NHC$_{1-3}$alkyl, —NHC$_{1-3}$hydroxyalkyl, —NHC$_{1-3}$haloalkyl, —NHC$_{3-6}$cycloalkyl, —N(C$_{1-3}$alkyl)$_2$, —N(C$_{1-3}$haloalkyl)$_2$, —N(C$_{1-6}$alkyl)(C$_{1-6}$haloalkyl), —NHC(O)C$_{1-3}$alkyl, —C(O)NHC$_{1-3}$alkyl, —C(O)N(C$_{1-6}$alkyl)$_2$, 3-7 membered heterocyclyl, and 5-6 membered heteroaryl having one to three heteroatoms selected from a group consisting of N, O and S; C$_{3-6}$cycloalkyl; C$_{1-3}$alkoxy optionally substituted by one to three F or Cl; —C(O)NHC$_{1-3}$alkyl optionally substituted by one to three substituents selected from the group consisting of OH, F and Cl; —C(O)N(C$_{1-3}$alkyl)$_2$ optionally substituted by one to three substituents selected from the group consisting of OH, F and Cl; —NHC$_{1-3}$alkyl optionally substituted by one to three substituents selected from the group consisting of OH, F, Cl, —NHC$_{1-3}$alkyl, —N(C$_{1-3}$alkyl)$_2$, 3-6 membered heterocyclyl one to three heteroatoms selected from a group consisting of N, O and S optionally substituted by F, Cl or —N(C$_{1-3}$alkyl)$_2$; —N(C$_{1-3}$alkyl)$_2$ where C$_{1-3}$alkyl is optionally substituted by one to three F or Cl; —NH-4-6 membered heterocyclyl one to three heteroatoms selected from a group consisting of N, O and S optionally substituted by C$_{1-3}$ alkyl; or 4-7 membered heterocyclyl.

In further certain embodiment, R$_{2A}$ is OH; C$_{1-6}$alkyl optionally substituted by one or more substituents selected from the group consisting of OH, NH$_2$, halogen, C$_{3-6}$cycloalkyl, C$_{1-3}$alkoxy, —NHC$_{1-6}$alkyl, —NHC$_{1-6}$hydroxyalkyl, —NHC$_{1-6}$haloalkyl, —NHC$_{3-6}$cycloalkyl, —N(C$_{1-6}$alkyl)$_2$, —N(C$_{1-6}$haloalkyl)$_2$, —N(C$_{1-6}$alkyl)(C$_{1-6}$haloalkyl), —NHC(O)C$_{1-6}$alkyl, —C(O)NHC$_{1-6}$alkyl, —C(O)N(C$_{1-6}$alkyl)$_2$, 3-7 membered heterocyclyl, and 5-6 membered heteroaryl having one to three heteroatoms selected from a group consisting of N, O and S; —C(O)NHC$_{1-3}$alkyl optionally substituted by one to three substituents selected from the group consisting of OH, F and Cl; or —NHC$_{1-3}$alkyl optionally substituted by one to three substituents selected from the group consisting of OH, halogen, —NHC$_{1-3}$alkyl, —N(C$_{1-3}$alkyl)$_2$, 3-7 membered heterocyclyl one to three heteroatoms selected from a group consisting of N, O and S optionally substituted by halogen or —N(C$_{1-3}$alkyl)$_2$.

In another further certain embodiment, R$_{2A}$ is independently selected from the group consisting of H;
OH;
halogen;
NH$_2$;
C$_{1-6}$alkyl optionally substituted by one or more substituents selected from the group consisting of OH, halogen, —NHC$_{1-6}$alkyl, —N(C$_{1-6}$alkyl)$_2$, —N(C$_{1-6}$alkyl)(C$_{1-6}$haloalkyl), —C(O)N(C$_{1-6}$alkyl)$_2$, and azetidinyl;
C$_{3-6}$cycloalkyl;
C$_{1-3}$alkoxy optionally substituted by one or more halogens;
—C(O)NHC$_{1-6}$alkyl;
—C(O)N(C$_{1-6}$alkyl)$_2$ optionally substituted by one or more halogens;
—NHC$_{1-6}$alkyl optionally substituted by one or more substituents selected from the group consisting of OH, halogen, and —N(C$_{1-6}$alkyl)$_2$;
—N(C$_{1-6}$alkyl)$_2$; and
=O.

In certain embodiment, Q is —C≡C—, pyrazolyl, pyrrolyl, piperidinyl, pyridinyl, 2,3-dihydropyrido[2,3-b][1,4]oxazinyl, tetrahydropyridinyl, 3,4-dihydropyrano[2,3-b]pyridinyl, pyrimidinyl, phenyl, or pyrrolidinyl.

In certain embodiment, R$_{3A}$ is independently selected from the group consisting of H;
OH;
halogen;
C$_{1-3}$alkoxy;
C$_{1-6}$alkyl optionally or independently substituted by one or more substituents selected from the group consisting of OH, halogen, C$_{1-3}$alkoxy, C$_{3-6}$cycloalkyl, and S(O)$_2$C$_{1-6}$alkyl;
C$_{2-6}$alkenyl;
C$_{3-6}$cycloalkyl;
4-7 membered heterocyclyl;
—C(O)C$_{1-6}$alkyl;
—C(O)N(C$_{1-6}$alkyl)$_2$;
—S(O)$_2$C$_{1-6}$alkyl;
—S(O)$_2$C$_{2-6}$alkenyl;
—S(O)$_2$C$_{3-6}$cycloalkyl;
—S(O)$_2$N(C1$_{-6}$alkyl)$_2$; and
—S(O)$_2$ 4-7 membered heterocyclyl optionally substituted by one or more halogens.

In the above embodiments of R$_{3A}$, the 4-7 membered heterocyclyl is tetrahydrofuranyl, tetrahydropyranyl, pyrrolidinyl, or azetidinyl.

In certain embodiment, R$_4$H or halogen.

Representative compounds of Formula (I) are listed below:

(1) N-(5-(1-Cyclopropyl-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine;

(2) 2-(1-(Cyclopropylsulfonyl)-1H-pyrazol-4-yl)-N-(5-(1-(difluoromethyl)-1H-pyrazol-4-yl)-4-((1-methyl-1H-pyrazol-4-yl)ethynyl)pyridin-2-yl)pyrimidin-4-amine;

(3) N-(5-(1-(Cyclopropylmethyl)-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine;

(4) 4-(2-((2-(1-(Cyclopropylsulfonyl)-1H-pyrazol-4-yl)pyrimidin-4-yl)amino)-5-(1-methyl-1H-pyrazol-4-yl)pyridin-4-yl)-2-methylbut-3-yn-2-ol;

(5) N-(5-(1-Cyclopropyl-1H-pyrazol-4-yl)-4-((1-cyclopropyl-1H-pyrazol-4-yl)ethynyl)pyridin-2-yl)-2-(1-(cyclopropylsulfonyl)-1H-pyrazol-4-yl)pyrimidin-4-amine;

(6) N-(5-(1-Cyclopropyl-1H-pyrazol-4-yl)-4-((1-isopropyl-1H-pyrazol-4-yl)ethynyl)pyridin-2-yl)-2-(1-(cyclopropylsulfonyl)-1H-pyrazol-4-yl)pyrimidin-4-amine;

(7) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-3-methylbutan-2-ol;

(8) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol;

(9) N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-((2-fluoroethyl)amino)cyclohexyl)pyridine-2,4-diamine;

(10) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(11) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(trifluoromethyl)cyclohexan-1-ol;

(12) (1R,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(13) (1S,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(14) (1R,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(15) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(16) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(methylamino)cyclohexyl)pyridine-2,4-diamine;

(17) (S)-$N^4$-(Azepan-4-yl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(18) ((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(19) (5s,8s)-8-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-azaspiro[4.5]decan-2-one;

(20) (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(21) (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(22) ((1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methanol;

(23) $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(1-(difluoromethyl)-1H-pyrazol-3-yl)pyridine-2,4-diamine;

(24) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-methylcyclohexane-1-carboxamide;

(25) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-(dimethylamino)cyclohexyl)methyl)pyridine-2,4-diamine;

(26) $N^4$-((2-Azaspiro[3.3]heptan-6-yl)methyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(27) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(2-azaspiro[3.5]nonan-7-yl)pyridine-2,4-diamine;

(28) 2-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(29) 2-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(30) (1s,4s)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(31) (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(32) 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(33) 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclopentan-1-ol;

(34) (1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutan-1-ol;

(35) (1s,3s)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutan-1-ol;

(36) (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-1-methylcyclohexan-1-ol;

(37) 5-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylpiperidin-2-one;

(38) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-2-one;

(39) 6-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)bicycle[2.2.1]heptan-2-ol;

(40) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclobutan-1-ol;

(41) $N^4$-(3-(1H-Imidazol-1-yl)propyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(42) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)propan-2-ol;

(43) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(1-methyl-1H-pyrazol-3-yl)pyridine-2,4-diamine;

(44) (5s,8s)-8-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-azaspiro[4.5]decan-2-one;

(45) $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(1-methyl-1H-pyrazol-3-yl)pyridine-2,4-diamine;

(46) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-methylcyclohexane-1-carboxamide;

(47) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclohexan-1-ol;

(48) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-1-methylcyclohexan-1-ol;

(49) 2-((1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexyl)propan-2-ol;

(50) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(2-(trifluoromethyl)thiazol-4-yl)pyridine-2,4-diamine;

(51) (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-methylcyclohexan-1-ol;

(52) (5s,8s)-8-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-azaspiro[4.5]decan-2-one;

(53) $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(2-(trifluoromethyl)thiazol-4-yl)pyridine-2,4-diamine;

(54) 2-(4-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)thiazol-2-yl)propan-2-ol;

(55) 2-(4-(6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)thiazol-2-yl)propan-2-ol;

(56) 2-(4-(6-((2-(1-(Cyclopropylsulfonyl)-1H-pyrazol-4-yl)pyrimidin-4-yl)amino)-4-(((1s,4s)-4-(methylamino)cyclohexyl)amino)pyridin-3-yl)thiazol-2-yl)propan-2-ol;

(57) (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)cyclohexan-1-ol;

(58) (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)-1-methylcyclohexan-1-ol;

(59) (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-methylcyclohexan-1-ol;

(60) ((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)methanol;

(61) 2-((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)propan-2-ol;

(62) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(4,5,6,7-tetrahydropyrazolo[1,5-a]pyridin-2-yl)pyridine-2,4-diamine;

(63) $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(4,5,6,7-tetrahydropyrazolo[1,5-a]pyridin-2-yl)pyridine-2,4-diamine;

(64) (1s,4s)-4-((2-((2-(1-(Cyclopropylsulfonyl)-1H-pyrazol-4-yl)pyrimidin-4-yl)amino)-5-(3-isopropylisoxazol-5-yl)pyridin-4-yl)amino)-1-methylcyclohexan-1-ol;

(65) 2-(1-(Cyclopropylsulfonyl)-1H-pyrazol-4-yl)-N-(5-(1-(difluoromethyl)-1H-pyrazol-3-yl)-4-(((1s,4s)-4-(methylamino)cyclohexyl)oxy)pyridin-2-yl)pyrimidin-4-amine;

(66) 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)cyclohexan-1-ol;

(67) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)cyclopentan-1-ol;

(68) 4-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)oxy)-1-methylcyclohexan-1-ol;

(69) 2-(1-(Cyclopropylsulfonyl)-1H-pyrazol-4-yl)-N-(5-(1-(difluoromethyl)-1H-pyrazol-4-yl)-4-(((1s,4s)-4-(methylamino)cyclohexyl)oxy)pyridin-2-yl)pyrimidin-4-amine;

(70) 2-(1-(Cyclopropylsulfonyl)-1H-pyrazol-4-yl)-N-(4-((4-(difluoromethoxy)cyclohexyl)oxy)-5-(1-(difluoromethyl)-1H-pyrazol-4-yl)pyridin-2-yl)pyrimidin-4-amine;

(71) 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclohexan-1-ol;

(72) 3-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclopentan-1-ol;

(73) 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)-1-methylcyclohexan-1-ol;

(74) N-(4-((4-Amino-4-methylcyclohexyl)oxy)-5-(1-(difluoromethyl)-1H-pyrazol-4-yl)pyridin-2-yl)-2-(1-(cyclopropylsulfonyl)-1H-pyrazol-4-yl)pyrimidin-4-amine;

(75) (1s,4s)-4-((2-((2-(1-(Cyclopropylsulfonyl)-1H-pyrazol-4-yl)pyrimidin-4-yl)amino)-5-(2-methylthiazol-5-yl)pyridin-4-yl)amino)cyclohexan-1-ol;

(76) (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)cyclohexan-1-ol;

(77) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)amino)cyclohexan-1-ol;

(78) (1s,4s)-4-((5-(1-Cyclopropyl-1H-pyrazol-4-yl)-2-((2-(1-(cyclopropylsulfonyl)-1H-pyrazol-4-yl)pyrimidin-4-yl)amino)pyridin-4-yl)amino)cyclohexan-1-ol;

(79) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexan-1-ol;

(80) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(81) (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol;

(82) (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)cyclohexan-1-ol;

(83) (1s,4s)-4-((2-((2-(1-(Cyclopropylsulfonyl)-1H-pyrazol-4-yl)pyrimidin-4-yl)amino)-5-(furan-2-yl)pyridin-4-yl)amino)cyclohexan-1-ol;

(84) (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)-1-methylcyclohexan-1-ol;

(85) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-methylcyclohexan-1-ol;

(86) $N^2$-(2-(1-(Cyclopropylsulfonyl)-1H-pyrazol-4-yl)pyrimidin-4-yl)-5-(1-isopropyl-1H-pyrazol-3-yl)-$N^4$-((1s,4s)-4-(methylamino)cyclohexyl)pyridine-2,4-diamine;

(87) $N^2$-(2-(1-(Cyclopropylsulfonyl)-1H-pyrazol-4-yl)pyrimidin-4-yl)-5-(furan-2-yl)-$N^4$-((1s,4s)-4-(methylamino)cyclohexyl)pyridine-2,4-diamine;

(88) $N^2$-(2-(1-(Cyclopropylsulfonyl)-1H-pyrazol-4-yl)pyrimidin-4-yl)-5-(1-methyl-1H-pyrazol-3-yl)-$N^4$-((1s,4s)-4-(methylamino)cyclohexyl)pyridine-2,4-diamine;

(89) 1-(2-((2-(1-Cyclopropylsulfonylpyrazol-4-yl)pyrimidin-4-yl)amino)-5-(2-methylthiazol-5-yl)-4-pyridyl)piperidin-4-ol;

(90) 3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-2,2-dimethylpropan-1-ol;

(91) (1S,3S)-3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino) cyclohexan-1-ol;

(92) 2-(4-(6-((2-(1-(Cyclopropylsulfonyl)-1H-pyrazol-4-yl)pyrimidin-4-yl)amino)-4-(isopropylamino)pyridin-3-yl)thiazol-2-yl)propan-2-ol;

(93) (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-1-methylcyclohexan-1-ol;

(94) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(trifluoromethyl)cyclohexan-1-ol;

(95) 3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-3-methylbutan-2-ol;

(96) (1S,3R)-3-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol;

(97) 2-((4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexyl)ethan-1-ol;

(98) $N^2$-(2-(1-(Cyclopropylsulfonyl)-1H-pyrazol-4-yl)pyrimidin-4-yl)-$N^4$-(4-((2-(dimethylamino)ethyl)amino)cyclohexyl)-5-(2-(trifluoromethyl)thiazol-4-yl)pyridine-2,4-diamine;

(99) $N^2$-(2-(1-(cyclopropylsulfonyl)-1H-pyrazol-4-yl)pyrimidin-4-yl)-5-(1-(difluoromethyl)-1H-pyrazol-3-yl)-N4-(4-((2-(dimethylamino)ethyl)amino)cyclohexyl)pyridine-2,4-diamine;

(100) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-((dimethylamino)methyl)cyclohexyl)methyl)pyridine-2,4-diamine;

(101) $N^2$-(2-(1-(Cyclopropylsulfonyl)-1H-pyrazol-4-yl)pyrimidin-4-yl)-$N^4$-(((1r,4r)-4-((dimethylamino)methyl)cyclohexyl)methyl)-5-(2-(trifluoromethyl)thiazol-4-yl)pyridine-2,4-diamine;

(102) Ethyl 1-(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)-1H-pyrazole-3-carboxylate;

(103) 6-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)spiro[3.3]heptan-2-ol;

(104) (1s,4s)-4-((5-(1-(Difluoromethyl)-1H-pyrazol-3-yl)-2-((2-(3-methoxyprop-1-yn-1-yl)pyrimidin-4-yl)amino)pyridin-4-yl)amino)-1-methylcyclohexan-1-ol;

(105) 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-2-methylcyclohexan-1-ol;

(106) 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-2,2-dimethylcyclohexan-1-ol;

(107) (S)-1-(2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)-3-methylpiperidin-3-ol;

(108) (1s,4s)-4-((5-(1-(Difluoromethyl)-1H-pyrazol-3-yl)-2-((2-(1-(methylsulfonyl)-1H-pyrrol-3-yl)pyrimidin-4-yl)amino)pyridin-4-yl)amino)-1-methylcyclohexan-1-ol;

(109) 3-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrrole-1-sulfonamide;

(110) 1-Cyclopropyl-4-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(111) (1s,4s)-4-((5-(1-(Difluoromethyl)-1H-pyrazol-3-yl)-2-((2-((3R,4S)-3-fluoro-4-methoxypiperidin-1-yl)pyrimidin-4-yl)amino)pyridin-4-yl)amino)-1-methylcyclohexan-1-ol;

(112) (1s,4s)-4-((5-(1-(Difluoromethyl)-1H-pyrazol-3-yl)-2-((2-(1-(methylsulfonyl)-1H-pyrazol-4-yl)pyrimidin-4-yl)amino)pyridin-4-yl)amino)-1-methylcyclohexan-1-ol;

(113) (1s,4s)-4-((5-(1-(Difluoromethyl)-1H-pyrazol-3-yl)-2-((2-(6-fluoropyridin-3-yl)pyrimidin-4-yl)amino)pyridin-4-yl)amino)-1-methylcyclohexan-1-ol;

(114) (1s,4s)-4-((5-(1-(Difluoromethyl)-1H-pyrazol-3-yl)-2-((2-(1-((tetrahydrofuran-3-yl)sulfonyl)-1H-pyrazol-4-yl)pyrimidin-4-yl)amino)pyridin-4-yl)amino)-1-methylcyclohexan-1-ol;

(115) (1s,4s)-4-((2-((2-(1-(Cyclopentylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(116) (1s,4s)-4-((2-((2-(1-Allyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(117) (1s,4s)-4-((2-((2-(1-(But-3-en-1-ylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(118) (1R,3S)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclopentan-1-ol;

(119) (1R,3S)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclopentan-1-ol;

(120) (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-methylcyclohexan-1-ol;

(121) (1s,4s)-4-((2-((2-(1-(Cyclopropylsulfonyl)-1H-pyrazol-4-yl)pyrimidin-4-yl)amino)-5-(2-(4-methylpiperazin-1-yl)thiazol-4-yl)pyridin-4-yl)amino)-1-methylcyclohexan-1-ol;

(122) (1s,4s)-4-((2-((2-(1-(Cyclopropylsulfonyl)-1H-pyrazol-4-yl)pyrimidin-4-yl)amino)-5-(4-(difluoromethyl)thiazol-2-yl)pyridin-4-yl)amino)-1-methylcyclohexan-1-ol;

(123) $N^2$-(2-(1-(Cyclopropylsulfonyl)-1H-pyrazol-4-yl)pyrimidin-4-yl)-5-(4-(difluoromethyl)thiazol-2-yl)-$N^4$-((1s,4s)-4-((2-fluoroethyl)amino)cyclohexyl)pyridine-2,4-diamine;

(124) $N^2$-(2-(1-(Cyclopropylsulfonyl)-1H-pyrazol-4-yl)pyrimidin-4-yl)-$N^4$-((1s,4s)-4-(dimethylamino)cyclohexyl)-5-(1-methyl-1H-pyrazol-3-yl)pyridine-2,4-diamine;

(125) (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-(hydroxymethyl)cyclohexan-1-ol;

(126) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(2-morpholinothiazol-4-yl)pyridine-2,4-diamine;

(127) 4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-4-methylcyclohexan-1-ol;

(128) 4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-4-methylcyclohexan-1-ol;

(129) $N^2$-(2-(1-(Cyclopropylsulfonyl)-1H-pyrazol-4-yl)pyrimidin-4-yl)-$N^4$-(((1r,4r)-4-((2,2-difluoroethyl)amino)cyclohexyl)methyl)-5-(1-methyl-1H-pyrazol-3-yl)pyridine-2,4-diamine;

(130) $N^2$-(2-(1-(Cyclopropylsulfonyl)-1H-pyrazol-4-yl)pyrimidin-4-yl)-$N^4$-(((1r,4r)-4-((2,2-difluoroethyl)amino)cyclohexyl)methyl)-5-(1-(difluoromethyl)-1H-pyrazol-3-yl)pyridine-2,4-diamine;

(131) $N^2$-(2-(1-(Cyclopropylsulfonyl)-1H-pyrazol-4-yl)pyrimidin-4-yl)-$N^4$-((4-((2-fluoroethyl)amino)cyclohexyl)methyl)-5-(1-methyl-1H-pyrazol-3-yl)pyridine-2,4-diamine;

(132) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((4-((2-fluoroethyl)amino)cyclohexyl)methyl)pyridine-2,4-diamine;

(133) 2-((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(134) 2-((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol;

(135) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(136) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol;

(137) (1s,4s)-4-((5-(1-(Difluoromethyl)-1H-pyrazol-3-yl)-2-((2-(1-(2,2,2-trifluoroethyl)-1H-pyrazol-4-yl)pyrimidin-4-yl)amino)pyridin-4-yl)amino)-1-methylcyclohexan-1-ol;

(138) (1s,4s)-4-((5-(1-(Difluoromethyl)-1H-pyrazol-3-yl)-2-((2-(1-(2-methoxyethyl)-1H-pyrazol-4-yl)pyrimidin-4-yl)amino)pyridin-4-yl)amino)-1-methylcyclohexan-1-ol;

(139) (1s,4s)-4-((5-(1-(Difluoromethyl)-1H-pyrazol-3-yl)-2-((2-(1-methyl-1H-pyrazol-4-yl)pyrimidin-4-yl)amino)pyridin-4-yl)amino)-1-methylcyclohexan-1-ol;

(140) (1s,4s)-4-((2-((2-(1-Cyclopropyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(141) (1s,4s)-4-((2-((2-(1-(Cyclopropylmethyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(142) (1s,4s)-4-((5-(1-(Difluoromethyl)-1H-pyrazol-3-yl)-2-((2-(1-(2-hydroxy-2-methylpropyl)-1H-pyrazol-4-yl)pyrimidin-4-yl)amino)pyridin-4-yl)amino)-1-methylcyclohexan-1-ol;

(143) (1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(144) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-isopropylpyridine-2,4-diamine;

(145) (1s,4s)-4-((5-(1-(Difluoromethyl)-1H-pyrazol-3-yl)-2-((2-(1-(2-fluoroethyl)-1H-pyrazol-4-yl)pyrimidin-4-yl)amino)pyridin-4-yl)amino)-1-methylcyclohexan-1-ol;

(146) 2-((1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(147) 2-((1r,4r)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(148) 2-((1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol;

(149) (1s,4s)-4-((5-(1-(Difluoromethyl)-1H-pyrazol-3-yl)-2-((2-(1-(difluoromethyl)-1H-pyrazol-4-yl)pyrimidin-4-yl)amino)pyridin-4-yl)amino)-1-methylcyclohexan-1-ol;

(150) (1s,4s)-4-((5-(1-(Difluoromethyl)-1H-pyrazol-3-yl)-2-((2-(1-((methylsulfonyl)methyl)-1H-pyrazol-4-yl)pyrimidin-4-yl)amino)pyridin-4-yl)amino)-1-methylcyclohexan-1-ol;

(151) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-fluorocyclohexyl)pyridine-2,4-diamine;

(152) $N^2$-(2-(1-(Cyclopropylsulfonyl)-1H-pyrazol-4-yl)pyrimidin-4-yl)-$N^4$-((4-(difluoromethyl)cyclohexyl)methyl)-5-(1-methyl-1H-pyrazol-3-yl)pyridine-2,4-diamine;

(153) 1-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-4-ol;

(154) (1s,4s)-4-((5-(1-(Difluoromethyl)-1H-pyrazol-3-yl)-2-((2-(2,3-dihydro-1H-pyrido[2,3-b][1,4]oxazin-7-yl)pyrimidin-4-yl)amino)pyridin-4-yl)amino)-1-methylcyclohexan-1-ol;

(155) (1s,4s)-4-((2-((2-((1-(2,2-Difluoroethyl)-1H-pyrazol-5-yl)amino)pyrimidin-4-yl)amino)-5-(1-(difluoromethyl)-1H-pyrazol-3-yl)pyridin-4-yl)amino)-1-methylcyclohexan-1-ol;

(156) (1s,4s)-4-((5-(1-(Difluoromethyl)-1H-pyrazol-3-yl)-2-((2-(1-(methylsulfonyl)-1,2,3,6-tetrahydropyridin-4-yl)pyrimidin-4-yl)amino)pyridin-4-yl)amino)-1-methylcyclohexan-1-ol;

(157) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(difluoromethyl)cyclohexyl)pyridine-2,4-diamine;

(158) (1s,4s)-4-((5-(1-(Difluoromethyl)-1H-pyrazol-3-yl)-2-((2-(1-(methylsulfonyl)piperidin-4-yl)pyrimidin-4-yl)amino)pyridin-4-yl)amino)-1-methylcyclohexan-1-ol;

(159) 1-(4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-3,6-dihydropyridin-1(2H)-yl)ethan-1-one;

(160) 1-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)piperidin-4-ol;

(161) $N^2$-(2-(1-(2,2-Difluoroethyl)-1H-pyrazol-4-yl)pyrimidin-4-yl)-5-(1-(difluoromethyl)-1H-pyrazol-3-yl)-$N^4$-((1s,4s)-4-fluorocyclohexyl)pyridine-2,4-diamine;

(162) 1-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)piperidin-4-ol;

(163) 1-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)piperidin-4-ol;

(164) $N^2$-(2-(1-(Cyclopropylsulfonyl)-1H-pyrazol-4-yl)pyrimidin-4-yl)-5-(4-(difluoromethyl)thiazol-2-yl)-$N^4$-((1s,4s)-4-fluorocyclohexyl)pyridine-2,4-diamine;

(165) (1s,4s)-4-((5-(1-(Difluoromethyl)-1H-pyrazol-3-yl)-2-((2-(6-methoxypyridin-3-yl)pyrimidin-4-yl)amino)pyridin-4-yl)amino)-1-methylcyclohexan-1-ol;

(166) (1s,4s)-4-((5-(1-(Difluoromethyl)-1H-pyrazol-3-yl)-2-((2-(2-fluoro-6-methoxypyridin-3-yl)pyrimidin-4-yl)amino)pyridin-4-yl)amino)-1-methylcyclohexan-1-ol;

(167) (1s,4s)-4-((2-((2-(1-(Cyclopropylsulfonyl)-1H-pyrazol-4-yl)pyrimidin-4-yl)amino)-5-(3-(trifluoromethyl)-1H-pyrazol-1-yl)pyridin-4-yl)amino)-1-methylcyclohexan-1-ol;

(168) (1s,4s)-4-((2-((2-(1-(Cyclopropylsulfonyl)-1H-pyrazol-4-yl)pyrimidin-4-yl)amino)-5-(3-methyl-1H-pyrazol-1-yl)pyridin-4-yl)amino)-1-methylcyclohexan-1-ol;

(169) (1s,4s)-4-((5-(1-(Difluoromethyl)-1H-pyrazol-3-yl)-2-((2-(2-methoxypyridin-4-yl)pyrimidin-4-yl)amino)pyridin-4-yl)amino)-1-methylcyclohexan-1-ol;

(170) (1s,4s)-4-((5-(1-(Difluoromethyl)-1H-pyrazol-3-yl)-2-((2-(2,6-difluoropyridin-3-yl)pyrimidin-4-yl)amino)pyridin-4-yl)amino)-1-methylcyclohexan-1-ol;

(171) (1s,4s)-4-((5-(1-(Difluoromethyl)-1H-pyrazol-3-yl)-2-((2-(2-fluoropyridin-3-yl)pyrimidin-4-yl)amino)pyridin-4-yl)amino)-1-methylcyclohexan-1-ol;

(172) (1s,4s)-4-((2-((2-(1-(Cyclopropylsulfonyl)-1H-pyrazol-4-yl)pyrimidin-4-yl)amino)-5-(3-(difluoromethyl)-1H-pyrazol-1-yl)pyridin-4-yl)amino)-1-methylcyclohexan-1-ol;

(173) (1s,4s)-4-((5-(1-(Difluoromethyl)-1H-pyrazol-3-yl)-2-((2-(1-(3-hydroxy-2,2-dimethylpropyl)-1H-pyrazol-4-yl)pyrimidin-4-yl)amino)pyridin-4-yl)amino)-1-methylcyclohexan-1-ol;

(174) $N^2$-(2-(1-(Cyclopropylsulfonyl)-1H-pyrazol-4-yl)pyrimidin-4-yl)-$N^4$-((1s,4s)-4-fluorocyclohexyl)-5-(1-methyl-1H-pyrazol-3-yl)pyridine-2,4-diamine;

(175) $N^2$-(2-(1-(Cyclopropylsulfonyl)-1H-pyrazol-4-yl)pyrimidin-4-yl)-$N^4$-((1s,4s)-4-fluorocyclohexyl)-5-(1-methyl-5-(trifluoromethyl)-1H-pyrazol-3-yl)pyridine-2,4-diamine;

(176) (1s,4s)-4-((5-(1-(Difluoromethyl)-1H-pyrazol-3-yl)-2-((2-(3,4-dihydro-2H-pyrano[2,3-b]pyridin-6-yl)pyrimidin-4-yl)amino)pyridin-4-yl)amino)-1-methylcyclohexan-1-ol;

(177) (1s,4s)-4-((2-((2-(1-(2,2-Difluoroethyl)-1H-pyrazol-4-yl)pyrimidin-4-yl)amino)-5-(3-(difluoromethyl)-1H-pyrazol-1-yl)pyridin-4-yl)amino)-1-methylcyclohexan-1-ol;

(178) (1s,4s)-4-((5-(1-(Difluoromethyl)-1H-pyrazol-3-yl)-2-((2-(5-fluoro-6-methoxypyridin-3-yl)pyrimidin-4-yl)amino)pyridin-4-yl)amino)-1-methylcyclohexan-1-ol;

(179) $N^2$-(2-(1-(Cyclopropylsulfonyl)-1H-pyrazol-4-yl)pyrimidin-4-yl)-$N^4$-(3,3-difluorocyclopentyl)-5-(1-(difluoromethyl)-1H-pyrazol-3-yl)pyridine-2,4-diamine;

(180) $N^2$-(2-(1-(2,2-Difluoroethyl)-1H-pyrazol-4-yl)pyrimidin-4-yl)-5-(1-(difluoromethyl)-1H-pyrazol-3-yl)-$N^4$-(3-fluorocyclohexyl)pyridine-2,4-diamine;

(181) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(3-fluorocyclohexyl)pyridine-2,4-diamine;

(182) (1s,4s)-4-((2-((2-(1-(Cyclopropylsulfonyl)-1H-pyrazol-4-yl)pyrimidin-4-yl)amino)-5-(3-methyl-4-(trifluoromethyl)-1H-pyrazol-1-yl)pyridin-4-yl)amino)-1-methylcyclohexan-1-ol;

(183) (1s,4s)-4-((2-((2-(1-(Cyclopropylsulfonyl)-1H-pyrazol-4-yl)pyrimidin-4-yl)amino)-5-(3-(methylsulfonyl)-1H-pyrazol-1-yl)pyridin-4-yl)amino)-1-methylcyclohexan-1-ol;

(184) (1s,4s)-4-((2-((2-(1-(Cyclopropylsulfonyl)-1H-pyrazol-4-yl)pyrimidin-4-yl)amino)-5-(4-methyl-1H-pyrazol-1-yl)pyridin-4-yl)amino)-1-methylcyclohexan-1-ol;

(185) $N^2$-(2-(1-(Cyclopropylsulfonyl)-1H-pyrazol-4-yl)pyrimidin-4-yl)-$N^4$-((1s,4s)-4-(2,2-difluoroethyl)cyclohexyl)-5-(1-(difluoromethyl)-1H-pyrazol-3-yl)pyridine-2,4-diamine;

(186) (1s,4s)-4-((2-((2-(1-(Cyclopropylsulfonyl)-1H-pyrazol-4-yl)pyrimidin-4-yl)amino)-5-(4-methyl-3-(trifluoromethyl)-1H-pyrazol-1-yl)pyridin-4-yl)amino)-1-methylcyclohexan-1-ol;

(187) (1s,4s)-4-((2-((2-(1-(Cyclopropylsulfonyl)-1H-pyrazol-4-yl)pyrimidin-4-yl)amino)-5-(3-(difluoromethoxy)-1H-pyrazol-1-yl)pyridin-4-yl)amino)-1-methylcyclohexan-1-ol;

(188) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(hydroxymethyl)cyclohexan-1-ol;

(189) ((1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutyl)methanol;

(190) (4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-fluorocyclohexyl)methanol;

(191) $N^2$-(2-(1-(Cyclopropylsulfonyl)-1H-pyrazol-4-yl)pyrimidin-4-yl)-$N^4$-(3-((2,2-difluoroethyl)amino)cyclohexyl)-5-(1-(difluoromethyl)-1H-pyrazol-3-yl)pyridine-2,4-diamine;

(192) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-((methylamino)methyl)cyclohexyl)methyl)pyridine-2,4-diamine;

(193) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-(methylamino)cyclohexyl)methyl)pyridine-2,4-diamine;

(194) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(3-((2-fluoroethyl)amino)cyclohexyl)pyridine-2,4-diamine;

(195) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((dimethylamino)methyl)cyclohexyl)pyridine-2,4-diamine;

(196) ((2R,5S)-5-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)tetrahydro-2H-pyran-2-yl)methanol;

(197) (3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)oxetan-3-yl)methanol;

(198) ((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(199) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-((dimethylamino)methyl)cyclohexan-1-ol;

(200) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(difluoromethyl)cyclohexan-1-ol;

(201) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N,N-dimethylcyclohexane-1-carboxamide;

(202) ((1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(203) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1s,3s)-3-((dimethylamino)methyl)cyclobutyl)methyl)pyridine-2,4-diamine;

(204) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-(2,2-difluoroethyl)-N-methylcyclohexane-1-carboxamide;

(205) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)-N,N-dimethylacetamide;

(206) $N^2$-(2-(1-(Cyclopropylsulfonyl)-1H-pyrazol-4-yl)pyrimidin-4-yl)-$N^4$-((1s,4s)-4-(((2,2-difluoroethyl)(methyl)amino)methyl)cyclohexyl)-5-(1-(difluoromethyl)-1H-pyrazol-3-yl)pyridine-2,4-diamine;

(207) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-((dimethylamino)methyl)-4-methylcyclohexyl)pyridine-2,4-diamine;

(208) $N^4$-((1s,4s)-4-(Azetidin-1-ylmethyl)cyclohexyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(209) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,3r)-3-((dimethylamino)methyl)cyclobutyl)methyl)pyridine-2,4-diamine;

(210) $N^4$-(sec-Butyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(211) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(2-(dimethylamino)ethyl)cyclohexyl)pyridine-2,4-diamine;

(212) (R)—$N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-fluorobutan-2-yl)pyridine-2,4-diamine;

(213) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(1,1-difluoropropan-2-yl)pyridine-2,4-diamine;

(214) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-fluorocyclohexyl)pyridine-2,4-diamine;

(215) $N^2$-(2-(1-(Cyclopropylsulfonyl)-1H-pyrazol-4-yl)pyrimidin-4-yl)-$N^4$-(4,4-difluorocyclohexyl)-5-(1-(difluoromethyl)-1H-pyrazol-3-yl)pyridine-2,4-diamine;

(216) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-(2-fluoroethyl)cyclohexyl)pyridine-2,4-diamine;

(217) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(1-(2-fluoroethyl)piperidin-4-yl)pyridine-2,4-diamine;

(218) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(1-(2-fluoroethyl)piperidin-3-yl)pyridine-2,4-diamine;

(219) $N^2$-(2-(1-(Cyclopropylsulfonyl)-1H-pyrazol-4-yl)pyrimidin-4-yl)-$N^4$-(1-(2,2-difluoroethyl)piperidin-4-yl)-5-(1-(difluoromethyl)-1H-pyrazol-3-yl)pyridine-2,4-diamine;

(220) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-fluoro-4-methylcyclohexyl)pyridine-2,4-diamine;

(221) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(hydroxymethyl)cyclohexan-1-ol;

(222) (4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-fluorocyclohexyl)methanol;

(223) ((1r,3r)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclobutyl)methanol;

(224) $N^2$-(2-(1-(Cyclopropylsulfonyl)-1H-pyrazol-4-yl)pyrimidin-4-yl)-$N^4$-(3-((2,2-difluoroethyl)amino)cyclohexyl)-5-(1-methyl-1H-pyrazol-3-yl)pyridine-2,4-diamine;

(225) $N^2$-(2-(1-(Cyclopropylsulfonyl)-1H-pyrazol-4-yl)pyrimidin-4-yl)-$N^4$-(3-((2-fluoroethyl)amino)cyclohexyl)-5-(1-methyl-1H-pyrazol-3-yl)pyridine-2,4-diamine;

(226) $N^2$-(2-(1-(Cyclopropylsulfonyl)-1H-pyrazol-4-yl)pyrimidin-4-yl)-$N^4$-((1s,4s)-4-((dimethylamino)methyl)cyclohexyl)-5-(1-methyl-1H-pyrazol-3-yl)pyridine-2,4-diamine;

(227) ((2R,5S)-5-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)tetrahydro-2H-pyran-2-yl)methanol;

(228) (3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)oxetan-3-yl)methanol;

(229) ((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol;

(230) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-((dimethylamino)methyl)cyclohexan-1-ol;

(231) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(difluoromethyl)cyclohexan-1-ol;

(232) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N,N-dimethylcyclohexane-1-carboxamide;

(233) ((1S,3S)-3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol;

(234) $N^2$-(2-(1-(Cyclopropylsulfonyl)-1H-pyrazol-4-yl)pyrimidin-4-yl)-$N^4$-(((1s,3s)-3-((dimethylamino)methyl)cyclobutyl)methyl)-5-(1-methyl-1H-pyrazol-3-yl)pyridine-2,4-diamine;

(235) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-(2,2-difluoroethyl)-N-methylcyclohexane-1-carboxamide;

(236) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)-N,N-dimethylacetamide;

(237) N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-methyl-1H-pyrazol-3-yl)pyridine-2,4-diamine;

(238) N²-(2-(1-(Cyclopropylsulfonyl)-1H-pyrazol-4-yl)pyrimidin-4-yl)-N⁴-(4-((dimethylamino)methyl)-4-methylcyclohexyl)-5-(1-methyl-1H-pyrazol-3-yl)pyridine-2,4-diamine;

(239) N²-(2-(1-(Cyclopropylsulfonyl)-1H-pyrazol-4-yl)pyrimidin-4-yl)-N⁴-(((1r,3r)-3-((dimethylamino)methyl)cyclobutyl)methyl)-5-(1-methyl-1H-pyrazol-3-yl)pyridine-2,4-diamine;

(240) N²-(2-(1-(Cyclopropylsulfonyl)-1H-pyrazol-4-yl)pyrimidin-4-yl)-N⁴-((1s,4s)-4-(2-(dimethylamino)ethyl)cyclohexyl)-5-(1-methyl-1H-pyrazol-3-yl)pyridine-2,4-diamine;

(241) (1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)-1-methylcyclohexan-1-ol;

(242) N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-((1s,4s)-4-((2-fluoroethyl)amino)cyclohexyl)pyridine-2,4-diamine;

(243) 2-((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)propan-2-ol;

(244) ((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)methanol;

(245) N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-(2,2-difluoroethyl)-1H-pyrazol-3-yl)pyridine-2,4-diamine;

(246) N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-(4-((dimethylamino)methyl)-4-methylcyclohexyl)pyridine-2,4-diamine;

(247) N⁴-((1s,4s)-4-(Azetidin-1-ylmethyl)cyclohexyl)-N²-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine;

(248) N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-isopropylpyridine-2,4-diamine;

(249) N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-(((1r,3r)-3-((dimethylamino)methyl)cyclobutyl)methyl)pyridine-2,4-diamine;

(250) N⁴-(sec-Butyl)-N²-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine;

(251) N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-((1s,4s)-4-(2-(dimethylamino)ethyl)cyclohexyl)pyridine-2,4-diamine;

(252) (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(253) ((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol;

(254) 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)propan-2-ol;

(255) N²-(2-(1-(Cyclopropylsulfonyl)-1H-pyrazol-4-yl)pyrimidin-4-yl)-N⁴-((1s,4s)-4-((2-fluoroethyl)amino)cyclohexyl)-5-(1-methyl-5-(trifluoromethyl)-1H-pyrazol-3-yl)pyridine-2,4-diamine;

(256) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(1-methyl-5-(trifluoromethyl)-1H-pyrazol-3-yl)pyridine-2,4-diamine;

(257) (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-N,N-dimethylcyclohexane-1-carboxamide;

(258) 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)-N,N-dimethylacetamide;

(259) N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-methyl-5-(trifluoromethyl)-1H-pyrazol-3-yl)pyridine-2,4-diamine;

(260) ((1S,3S)-3-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol;

(261) (1R,3S)-3-(((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)methyl)cyclopentan-1-ol;

(262) 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(263) 2-((1r,4r)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(264) N⁴-((1s,4s)-4-(Azetidin-1-ylmethyl)cyclohexyl)-N²-(2-(1-(cyclopropylsulfonyl)-1H-pyrazol-4-yl)pyrimidin-4-yl)-5-(1-methyl-5-(trifluoromethyl)-1H-pyrazol-3-yl)pyridine-2,4-diamine;

(265) 2-((1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)propan-2-ol;

(266) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(1-(2,2,2-trifluoroethyl)-1H-pyrazol-3-yl)pyridine-2,4-diamine;

(267) N²-(2-(1-(Cyclopropylsulfonyl)-1H-pyrazol-4-yl)pyrimidin-4-yl)-N⁴-(4-((dimethylamino)methyl)-4-methylcyclohexyl)-5-(1-(2,2,2-trifluoroethyl)-1H-pyrazol-3-yl)pyridine-2,4-diamine;

(268) (1R,3S)-3-(((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)methyl)cyclopentan-1-ol;

(269) 2-((1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol;

(270) 2-((1r,4r)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol;

(271) ((1S,3S)-3-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)methanol;

(272) $N^4$-((1s,4s)-4-(Azetidin-1-ylmethyl)cyclohexyl)-$N^2$-(2-(1-(cyclopropylsulfonyl)-1H-pyrazol-4-yl)pyrimidin-4-yl)-5-(1-(2,2,2-trifluoroethyl)-1H-pyrazol-3-yl)pyridine-2,4-diamine;

(273) (1s,4s)-4-((2-((2-(1-(Cyclopropylsulfonyl)-1H-pyrazol-4-yl)pyrimidin-4-yl)amino)-5-(1-(difluoromethyl)-1H-imidazol-4-yl)pyridin-4-yl)amino)-1-methylcyclohexan-1-ol;

(274) (1s,4s)-4-((2-((2-(1-(Cyclopropylsulfonyl)-1H-pyrazol-4-yl)pyrimidin-4-yl)amino)-5-(6,7-dihydro-5H-pyrrolo[1,2-a]imidazol-2-yl)pyridin-4-yl)amino)-1-methylcyclohexan-1-ol;

(275) (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-(hydroxymethyl)cyclohexan-1-ol;

(276) (4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-fluorocyclohexyl)methanol;

(277) $N^2$-(2-(1-(Cyclopropylsulfonyl)-1H-pyrazol-4-yl)pyrimidin-4-yl)-$N^4$-((1s,4s)-4-((dimethylamino)methyl)cyclohexyl)-5-(4,5,6,7-tetrahydropyrazolo[1,5-a]pyridin-2-yl)pyridine-2,4-diamine;

(278) 2-((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)propan-2-ol;

(279) (3-(((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)methyl)oxetan-3-yl)methanol;

(280) ((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)methanol;

(281) 2-((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)propan-2-ol;

(282) ((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)methanol;

(283) 2-((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)propan-2-ol;

(284) $N^2$-(2-(1-(Cyclopropylsulfonyl)-1H-pyrazol-4-yl)pyrimidin-4-yl)-$N^4$-((1s,4s)-4-((dimethylamino)methyl)cyclohexyl)-5-(1-(oxetan-3-yl)-1H-pyrazol-3-yl)pyridine-2,4-diamine;

(285) (1s,4s)-4-((2-((2-(1-(Cyclopropylsulfonyl)-1H-pyrazol-4-yl)pyrimidin-4-yl)amino)-5-(1-(trifluoromethyl)-1H-pyrazol-3-yl)pyridin-4-yl)amino)-1-methylcyclohexan-1-ol;

(286) $N^2$-(2-(1-(Cyclopropylsulfonyl)-1H-pyrazol-4-yl)pyrimidin-4-yl)-$N^4$-((1s,4s)-4-fluorocyclohexyl)-5-(1-(trifluoromethyl)-1H-pyrazol-3-yl)pyridine-2,4-diamine;

(287) (1s,4s)-4-((2-((2-(1-(Cyclopropylsulfonyl)-1H-pyrazol-4-yl)pyrimidin-4-yl)amino)-5-(1-(1-methylpiperidin-4-yl)-1H-pyrazol-3-yl)pyridin-4-yl)amino)-1-methylcyclohexan-1-ol;

(288) (1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)-1-methylcyclohexan-1-ol;

(289) (1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)-1-methylcyclohexan-1-ol;

(290) (1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)-1-methylcyclohexan-1-ol;

(291) (1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)-1-methylcyclohexan-1-ol;

(292) (1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)-1-methylcyclohexan-1-ol;

(293) (1s,4s)-4-((2-((2-(1-(Cyclopropylsulfonyl)-1H-pyrazol-4-yl)pyrimidin-4-yl)amino)-5-(5-(2-hydroxypropan-2-yl)-1-methyl-1H-pyrazol-3-yl)pyridin-4-yl)amino)-1-methylcyclohexan-1-ol;

(294) (1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)-1-methylcyclohexan-1-ol;

(295) (1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)-1-methylcyclohexan-1-ol;

(296) ((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)methanol;

(297) ((1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)cyclohexyl)methanol;

(298) 2-(3-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-1-methyl-1H-pyrazol-5-yl)propan-2-ol;

(299) 2-((1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)cyclohexyl)propan-2-ol;

(300) 2-((1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)cyclohexyl)propan-2-ol;

(301) $N^2$-(2-(1-(Cyclopropylsulfonyl)-1H-pyrazol-4-yl)pyrimidin-4-yl)-5-(1-(3-(dimethylamino)propyl)-1H-pyrazol-3-yl)-$N^4$-((1s,4s)-4-((2-fluoroethyl)amino)cyclohexyl)pyridine-2,4-diamine;

(302) 2-(3-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)-1-methyl-1H-pyrazol-5-yl)propan-2-ol;

(303) $N^2$-(2-(1-(Cyclopropylsulfonyl)-1H-pyrazol-4-yl)pyrimidin-4-yl)-$N^4$-isopropyl-5-(1-(methoxymethyl)-1H-pyrazol-3-yl)pyridine-2,4-diamine;

(304) N²-(2-(1-(Cyclopropylsulfonyl)-1H-pyrazol-4-yl)pyrimidin-4-yl)-N⁴-isopropyl-5-(1-(3,3,3-trifluoropropyl)-1H-pyrazol-3-yl)pyridine-2,4-diamine;

(305) N²-(2-(1-(Cyclopropylsulfonyl)-1H-pyrazol-4-yl)pyrimidin-4-yl)-N⁴-((1s,4s)-4-fluorocyclohexyl)-5-(1-(2,2,2-trifluoroethyl)-1H-pyrazol-3-yl)pyridine-2,4-diamine;

(306) N²-(2-(1-(Cyclopropylsulfonyl)-1H-pyrazol-4-yl)pyrimidin-4-yl)-N⁴-((1s,4s)-4-fluorocyclohexyl)-5-(1-(3,3,3-trifluoropropyl)-1H-pyrazol-3-yl)pyridine-2,4-diamine;

(307) (1s,4s)-4-((2-((2-(1-(Cyclopropylsulfonyl)-1H-pyrazol-4-yl)pyrimidin-4-yl)amino)-5-(5-(4,4-difluoropiperidin-1-yl)-1-methyl-1H-pyrazol-3-yl)pyridin-4-yl)amino)-1-methylcyclohexan-1-ol;

(308) (1s,4s)-4-((5-(1-(Difluoromethyl)-1H-pyrazol-3-yl)-2-((2-(1-(ethylsulfonyl)-1H-pyrazol-4-yl)pyrimidin-4-yl)amino)pyridin-4-yl)amino)-1-methylcyclohexan-1-ol;

(309) (1s,4s)-4-((5-(1-(Difluoromethyl)-1H-pyrazol-3-yl)-2-((2-(1-(ethylsulfonyl)-1H-pyrazol-3-yl)pyrimidin-4-yl)amino)pyridin-4-yl)amino)-1-methylcyclohexan-1-ol;

(310) (1s,4s)-4-((5-(1-(Difluoromethyl)-1H-pyrazol-3-yl)-2-((2-(1-(methoxymethyl)-1H-pyrazol-4-yl)pyrimidin-4-yl)amino)pyridin-4-yl)amino)-1-methylcyclohexan-1-ol;

(311) 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrazole-1-carboxamide;

(312) (1s,4s)-4-((5-(1-(Difluoromethyl)-1H-pyrazol-3-yl)-2-((2'-methoxy-[2,5'-bipyrimidin]-4-yl)amino)pyridin-4-yl)amino)-1-methylcyclohexan-1-ol;

(313) (1s,4s)-4-((5-(1-(Difluoromethyl)-1H-pyrazol-3-yl)-2-((2-((2-(methylsulfonyl)phenyl)amino)pyrimidin-4-yl)amino)pyridin-4-yl)amino)-1-methylcyclohexan-1-ol;

(314) (1s,4s)-4-((5-(1-(Difluoromethyl)-1H-pyrazol-3-yl)-2-((2-(1-(tetrahydro-2H-pyran-2-yl)-1H-pyrazol-4-yl)pyrimidin-4-yl)amino)pyridin-4-yl)amino)-1-methylcyclohexan-1-ol;

(315) 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N,3-trimethyl-1H-pyrazole-1-sulfonamide;

(316) (1s,4s)-4-((2-((2-(1-(Cyclopropylsulfonyl)-1H-pyrazol-4-yl)-5-fluoropyrimidin-4-yl)amino)-5-(1-(difluoromethyl)-1H-pyrazol-3-yl)pyridin-4-yl)amino)-1-methylcyclohexan-1-ol;

(317) 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrazole-1-sulfonamide;

(318) (1s,4s)-4-((5-(1-(Difluoromethyl)-1H-pyrazol-3-yl)-2-((2-(1-(tetrahydrofuran-2-yl)-1H-pyrazol-4-yl)pyrimidin-4-yl)amino)pyridin-4-yl)amino)-1-methylcyclohexan-1-ol;

(319) (1s,4s)-4-((5-(1-(Difluoromethyl)-1H-pyrazol-3-yl)-2-((2-(5-fluoro-1,3-dimethyl-1H-pyrazol-4-yl)pyrimidin-4-yl)amino)pyridin-4-yl)amino)-1-methylcyclohexan-1-ol;

(320) (1s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)-1-methylcyclohexan-1-ol;

(321) (1s,4s)-4-((2-((2-(1-(2,2-Difluoroethyl)-3,5-dimethyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(322) (1s,4s)-4-((5-(1-(Difluoromethyl)-1H-pyrazol-3-yl)-2-((2-(1-(2,2,3,3-tetrafluoropropyl)-1H-pyrazol-4-yl)pyrimidin-4-yl)amino)pyridin-4-yl)amino)-1-methylcyclohexan-1-ol;

(323) (1s,4s)-4-((5-(1-(Difluoromethyl)-1H-pyrazol-3-yl)-2-((2-(1-(pyrrolidin-1-ylsulfonyl)-1H-pyrazol-4-yl)pyrimidin-4-yl)amino)pyridin-4-yl)amino)-1-methylcyclohexan-1-ol;

(324) (1s,4s)-4-((5-(1-(Difluoromethyl)-1H-pyrazol-3-yl)-2-((2-(1-((3-fluoroazetidin-1-yl)sulfonyl)-1H-pyrazol-4-yl)pyrimidin-4-yl)amino)pyridin-4-yl)amino)-1-methylcyclohexan-1-ol;

(325) N²-(2-(1-(Cyclopropylsulfonyl)-1H-pyrazol-4-yl)-5-fluoropyrimidin-4-yl)-5-(1-(difluoromethyl)-1H-pyrazol-3-yl)-N⁴-((1s,4s)-4-(2-(dimethylamino)ethyl)cyclohexyl)pyridine-2,4-diamine;

(326) 2-((1s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)cyclohexyl)ethan-1-ol;

(327) N⁴-((1s,4s)-4-(Azetidin-1-ylmethyl)cyclohexyl)-N²-(2-(1-(cyclopropylsulfonyl)-1H-pyrazol-4-yl)-5-fluoropyrimidin-4-yl)-5-(1-(difluoromethyl)-1H-pyrazol-3-yl)pyridine-2,4-diamine;

(328) (1s,4s)-4-((2-((2-(1-(Cyclopropylsulfonyl)-1H-pyrazol-4-yl)-5-fluoropyrimidin-4-yl)amino)-5-(1-methyl-5-(trifluoromethyl)-1H-pyrazol-3-yl)pyridin-4-yl)amino)-1-methylcyclohexan-1-ol;

(329) (1s,4s)-1-Methyl-4-((5-(1-methyl-5-(trifluoromethyl)-1H-pyrazol-3-yl)-2-((2-(1-(2,2,2-trifluoroethyl)-1H-pyrazol-4-yl)pyrimidin-4-yl)amino)pyridin-4-yl)amino)cyclohexan-1-ol;

(330) 4-(4-((4-(((1s,4s)-4-Hydroxy-4-methylcyclohexyl)amino)-5-(1-methyl-5-(trifluoromethyl)-1H-pyrazol-3-yl)pyridin-2-yl)amino)pyrimidin-2-yl)-N,N-dimethyl-1H-pyrazole-1-sulfonamide;

(331) (1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(332) (1s,4s)-1-Methyl-4-((2-((2-(3-methyl-1-(2,2,2-trifluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexan-1-ol;

(333) 2-((1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(334) 2-((1s,4s)-4-((2-((2-(3-Methyl-1-(2,2,2-trifluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(335) (1s,4s)-4-((5-(1-(2,2-Difluoroethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)-1-methylcyclohexan-1-ol;

(336) 2-((1s,4s)-4-((2-((2-(1-(Cyclopropylsulfonyl)-1H-pyrazol-4-yl)-5-fluoropyrimidin-4-yl)amino)-5-(1-(2,2-difluoroethyl)-1H-pyrazol-3-yl)pyridin-4-yl)amino)cyclohexyl)ethan-1-ol;

(337) 2-((1s,4s)-4-((5-(1-(2,2-Difluoroethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)cyclohexyl)ethan-1-ol;

(338) 2-((1s,4s)-4-((2-((2-(1-(2,2-Difluoroethyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol;

(339) $N^2$-(2-(1-(2,2-Difluoroethyl)-1H-pyrazol-4-yl)pyrimidin-4-yl)-$N^4$-((1s,4s)-4-fluorocyclohexyl)-5-(1-(2,2,2-trifluoroethyl)-1H-pyrazol-3-yl)pyridine-2,4-diamine;

(340) (1s,4s)-4-((2-((2-(1-(2,2-Difluoroethyl)-1H-pyrazol-4-yl)pyrimidin-4-yl)amino)-5-(1-(trifluoromethyl)-1H-pyrazol-3-yl)pyridin-4-yl)amino)-1-methylcyclohexan-1-ol;

(341) (1s,4s)-1-Methyl-4-((2-((2-(3-methyl-1-(2,2,2-trifluoroethyl)-1H-pyrazol-4-yl)pyrimidin-4-yl)amino)-5-(1-(trifluoromethyl)-1H-pyrazol-3-yl)pyridin-4-yl)amino)cyclohexan-1-ol;

(342) (1s,4s)-4-((2-((2-(1-(2,2-Difluoroethyl)-1H-pyrazol-4-yl)pyrimidin-4-yl)amino)-5-(1-(1-methylpiperidin-4-yl)-1H-pyrazol-3-yl)pyridin-4-yl)amino)-1-methylcyclohexan-1-ol;

(343) (1s,4s)-4-((5-(1-(2,2-Difluoroethyl)-1H-pyrazol-3-yl)-2-((2-(1-(2,2-difluoroethyl)-1H-pyrazol-4-yl)pyrimidin-4-yl)amino)pyridin-4-yl)amino)-1-methylcyclohexan-1-ol;

(344) (1s,4s)-4-((5-(1-(2,2-Difluoroethyl)-1H-pyrazol-3-yl)-2-((2-(1-(2,2,2-trifluoroethyl)-1H-pyrazol-4-yl)pyrimidin-4-yl)amino)pyridin-4-yl)amino)-1-methylcyclohexan-1-ol;

(345) (1s,4s)-4-((2-((2-(1-(Cyclopropylsulfonyl)-1H-pyrazol-4-yl)-5-fluoropyrimidin-4-yl)amino)-5-(1-(2,2-difluoroethyl)-1H-pyrazol-3-yl)pyridin-4-yl)amino)-1-methylcyclohexan-1-ol;

(346) (1s,4s)-4-((2-((2-(3,3-Difluoro-4-(hydroxymethyl)pyrrolidin-1-yl)pyrimidin-4-yl)amino)-5-(1-(difluoromethyl)-1H-pyrazol-3-yl)pyridin-4-yl)amino)-1-methylcyclohexan-1-ol;

(347) (1s,4s)-4-((5-(1-(Difluoromethyl)-1H-pyrazol-3-yl)-2-((2-(4-(hydroxymethyl)-3,3-dimethylpyrrolidin-1-yl)pyrimidin-4-yl)amino)pyridin-4-yl)amino)-1-methylcyclohexan-1-ol;

(348) 1-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-3,3-difluoropiperidin-4-ol;

(349) 1-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-4,4-difluoropyrrolidin-3-ol;

(350) 1-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-4,4-difluoropiperidin-3-ol;

(351) (S)-1-(4-((5-(1-(Difluoromethyl)-1H-pyrazol-3-yl)-4-(((1s,4R)-4-hydroxy-4-methylcyclohexyl)amino)pyridin-2-yl)amino)pyrimidin-2-yl)piperidin-3-ol;

(352) (R)-1-(4-((5-(1-(Difluoromethyl)-1H-pyrazol-3-yl)-4-(((1s,4S)-4-hydroxy-4-methylcyclohexyl)amino)pyridin-2-yl)amino)pyrimidin-2-yl)piperidin-3-ol;

(353) 3,3-Difluoro-1-(4-((4-(((1s,4s)-4-hydroxy-4-methylcyclohexyl)amino)-5-(1-methyl-5-(trifluoromethyl)-1H-pyrazol-3-yl)pyridin-2-yl)amino)pyrimidin-2-yl)piperidin-4-ol;

(354) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(355) (1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyridin-4-yl)amino)-1-methylcyclohexan-1-ol;

(356) (1s,4s)-4-((2-((2-(1-(Cyclopropylsulfonyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol;

(357) (1s,4s)-4-((2-((2-(1-(Cyclopropylsulfonyl)-1H-pyrazol-4-yl)pyridin-4-yl)amino)-5-(1-(2,2-difluoroethyl)-1H-pyrazol-3-yl)pyrimidin-4-yl)amino)-1-methylcyclohexan-1-ol;

(358) (1s,4s)-4-((2-((2-(1-(Cyclopropylsulfonyl)-1H-pyrazol-4-yl)pyridin-4-yl)amino)-5-(1-(methoxymethyl)-1H-pyrazol-3-yl)pyrimidin-4-yl)amino)-1-methylcyclohexan-1-ol;

(359) (1s,4s)-4-((2-((2-(1-(Cyclopropylsulfonyl)-1H-pyrazol-4-yl)pyridin-4-yl)amino)-5-(1-(3,3,3-trifluoropropyl)-1H-pyrazol-3-yl)pyrimidin-4-yl)amino)-1-methylcyclohexan-1-ol;

(360) (1s,4s)-4-((2-((2-(1-(Cyclopropylsulfonyl)-1H-pyrazol-4-yl)pyridin-4-yl)amino)-5-(1-(2,2,2-trifluoroethyl)-1H-pyrazol-3-yl)pyrimidin-4-yl)amino)-1-methylcyclohexan-1-ol;

(361) (1s,4s)-4-((2-((2-(1-(2,2-Difluoroethyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol;

(362) (1s,4s)-4-((2-((2-(1-(2,2-Difluoroethyl)-1H-pyrazol-4-yl)pyridin-4-yl)amino)-5-(1-(difluoromethyl)-1H-pyrazol-3-yl)pyrimidin-4-yl)amino)-1-methylcyclohexan-1-ol;

(363) $N^2$-(2-(1-(Cyclopropylsulfonyl)-1H-pyrazol-4-yl)pyridin-4-yl)-5-(1-(difluoromethyl)-1H-pyrazol-3-yl)-$N^4$-isopropylpyrimidine-2,4-diamine;

(364) ((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)methanol;

(365) 2-((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)propan-2-ol;

(366) $N^2$-(2-(1-(Cyclopropylsulfonyl)-1H-pyrazol-4-yl)pyridin-4-yl)-$N^4$-((1s,4s)-4-fluorocyclohexyl)-5-(1-(2,2,2-trifluoroethyl)-1H-pyrazol-3-yl)pyrimidine-2,4-diamine;

(367) $N^2$-(2-(1-(Cyclopropylsulfonyl)-1H-pyrazol-4-yl)pyridin-4-yl)-$N^4$-((1s,4s)-4-fluorocyclohexyl)-5-(1-(3,3,3-trifluoropropyl)-1H-pyrazol-3-yl)pyrimidine-2,4-diamine;

(368) (1s,4s)-4-((5-(1-(Difluoromethyl)-1H-pyrazol-3-yl)-2-((2-(3-methyl-1-(2,2,2-trifluoroethyl)-1H-pyrazol-4-yl)pyridin-4-yl)amino)pyrimidin-4-yl)amino)-1-methylcyclohexan-1-ol;

(369) (1s,4s)-1-Methyl-4-((2-((2-(3-methyl-1-(2,2,2-trifluoroethyl)-1H-pyrazol-4-yl)pyridin-4-yl)amino)-5-(1-methyl-5-(trifluoromethyl)-1H-pyrazol-3-yl)pyrimidin-4-yl)amino)cyclohexan-1-ol;

(370) (1s,4s)-1-Methyl-4-((2-((2-(3-methyl-1-(2,2,2-trifluoroethyl)-1H-pyrazol-4-yl)pyridin-4-yl)amino)-5-(1-(2,2,2-trifluoroethyl)-1H-pyrazol-3-yl)pyrimidin-4-yl)amino)cyclohexan-1-ol;

(371) $N^2$-(2-(1-(Cyclopropylsulfonyl)-1H-pyrazol-4-yl)pyridin-4-yl)-$N^4$-((1s,4s)-4-fluorocyclohexyl)-5-(1-methyl-5-(trifluoromethyl)-1H-pyrazol-3-yl)pyrimidine-2,4-diamine;

(372) (1s,4s)-4-((6-((2-(1-(Cyclopropylsulfonyl)-1H-pyrazol-4-yl)pyrimidin-4-yl)amino)-3-(1-(difluoromethyl)-1H-pyrazol-3-yl)pyridazin-4-yl)amino)-1-methylcyclohexan-1-ol;

(373) (1s,4s)-4-((6-((2-(1-(Cyclopropylsulfonyl)-1H-pyrazol-4-yl)pyrimidin-4-yl)amino)-3-(1-methyl-5-(trifluoromethyl)-1H-pyrazol-3-yl)pyridazin-4-yl)amino)-1-methylcyclohexan-1-ol;

(374) (1s,4s)-4-((6-((2-(1-(Cyclopropylsulfonyl)-1H-pyrazol-4-yl)pyrimidin-4-yl)amino)-3-(1-(2,2,2-trifluoroethyl)-1H-pyrazol-3-yl)pyridazin-4-yl)amino)-1-methylcyclohexan-1-ol;

(375) (1s,4s)-4-((3-(1-(Difluoromethyl)-1H-pyrazol-3-yl)-6-((2-(3-methyl-1-(2,2,2-trifluoroethyl)-1H-pyrazol-4-yl)pyrimidin-4-yl)amino)pyridazin-4-yl)amino)-1-methylcyclohexan-1-ol;

(376) (1s,4s)-4-((2-((2-(1-(Cyclopropylsulfonyl)-1H-pyrazol-4-yl)pyrimidin-4-yl)amino)-5-(1H-pyrazol-1-yl)pyridin-4-yl)amino)-1-methylcyclohexan-1-ol;

(377) ((1s,3s)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclobutyl)methanol;

(378) ((1s,3s)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclobutyl)methanol;

(379) (1s,4s)-4-((2-((2-(1-(Butylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(380) 1-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-4-methylpiperidin-4-ol;

(381) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-(fluoromethyl)piperidin-1-yl)pyridine-2,4-diamine;

(382) (1s,4s)-4-((2-((2-(1-(Cyclopropylsulfonyl)-1H-pyrazol-4-yl)pyrimidin-4-yl)amino)-5-(5-fluoro-1-methyl-1H-pyrazol-3-yl)pyridin-4-yl)amino)-1-methylcyclohexan-1-ol;

(383) (1s,4s)-4-((2-((2-(1-(Cyclopropylsulfonyl)-1H-pyrazol-4-yl)pyrimidin-4-yl)amino)-5-(2-(difluoromethyl)-1-methyl-1H-imidazol-4-yl)pyridin-4-yl)amino)-1-methylcyclohexan-1-ol;

(384) $N^2$-(2-(1-(Cyclopropylsulfonyl)-1H-pyrazol-4-yl)pyrimidin-4-yl)-$N^4$-((1r,4r)-4-(fluoromethyl)cyclohexyl)-5-(1-methyl-5-(trifluoromethyl)-1H-pyrazol-3-yl)pyridine-2,4-diamine;

(385) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1r,4r)-4-fluorocyclohexyl)pyridine-2,4-diamine;

(386) $N^2$-(2-(1-(Cyclopropylsulfonyl)-1H-pyrazol-4-yl)pyrimidin-4-yl)-$N^4$-((1r,4r)-4-fluorocyclohexyl)-5-(1-methyl-5-(trifluoromethyl)-1H-pyrazol-3-yl)pyridine-2,4-diamine;

(387) (1s,4s)-4-((2-((2-(1-(Cyclopropylsulfonyl)-1H-pyrazol-4-yl)pyrimidin-4-yl)amino)-5-(4-fluoro-1-methyl-1H-pyrazol-3-yl)pyridin-4-yl)amino)-1-methylcyclohexan-1-ol; and (388) (1s,4s)-4-((2-((6-(1-(Cyclopropylsulfonyl)-1H-pyrazol-4-yl)pyrazin-2-yl)amino)-5-(1-(difluoromethyl)-1H-pyrazol-3-yl)pyridin-4-yl)amino)-1-methylcyclohexan-1-ol.

Further representative compounds of Formula (I) are listed below:

(1) N-(5-(1-Cyclopropyl-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine;

(3) N-(5-(1-(Cyclopropylmethyl)-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine;

(8) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol;

(9) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((2-fluoroethyl)amino)cyclohexyl)pyridine-2,4-diamine;

(10) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(12) (1R,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(13) (1S,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(14) (1R,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(15) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(18) ((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(19) (5s,8s)-8-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-azaspiro[4.5]decan-2-one;

(20) (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(21) (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(22) ((1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methanol;

(23) $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(1-(difluoromethyl)-1H-pyrazol-3-yl)pyridine-2,4-diamine;

(24) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-methylcyclohexane-1-carboxamide;

(30) (1s,4s)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(31) (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(32) 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(33) 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclopentan-1-ol;

(34) (1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutan-1-ol;

(36) (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-1-methylcyclohexan-1-ol;

(42) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)propan-2-ol;

(43) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(1-methyl-1H-pyrazol-3-yl)pyridine-2,4-diamine;

(44) (5s,8s)-8-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-azaspiro[4.5]decan-2-one;

(45) $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(1-methyl-1H-pyrazol-3-yl)pyridine-2,4-diamine;

(46) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-methylcyclohexane-1-carboxamide;

(47) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclohexan-1-ol;

(48) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-1-methylcyclohexan-1-ol;

(51) (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-methylcyclohexan-1-ol;

(52) (5s,8s)-8-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-azaspiro[4.5]decan-2-one;

(54) 2-(4-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)thiazol-2-yl)propan-2-ol;

(55) 2-(4-(6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)thiazol-2-yl)propan-2-ol;

(57) (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)cyclohexan-1-ol;

(58) (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)-1-methylcyclohexan-1-ol;

(59) (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-methylcyclohexan-1-ol;

(60) ((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)methanol;

(61) 2-((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)propan-2-ol;

(62) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(4,5,6,7-tetrahydropyrazolo[1,5-a]pyridin-2-yl)pyridine-2,4-diamine;

(63) $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(4,5,6,7-tetrahydropyrazolo[1,5-a]pyridin-2-yl)pyridine-2,4-diamine;

(64) (1s,4s)-4-((2-((2-(1-(Cyclopropylsulfonyl)-1H-pyrazol-4-yl)pyrimidin-4-yl)amino)-5-(3-isopropylisoxazol-5-yl)pyridin-4-yl)amino)-1-methylcyclohexan-1-ol;

(71) 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclohexan-1-ol;

(73) 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)-1-methylcyclohexan-1-ol;

(75) (1s,4s)-4-((2-((2-(1-(Cyclopropylsulfonyl)-1H-pyrazol-4-yl)pyrimidin-4-yl)amino)-5-(2-methylthiazol-5-yl)pyridin-4-yl)amino)cyclohexan-1-ol;

(76) (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)cyclohexan-1-ol;

(79) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexan-1-ol;

(80) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(81) (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol;

(82) (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)cyclohexan-1-ol;

(83) (1s,4s)-4-((2-((2-(1-(Cyclopropylsulfonyl)-1H-pyrazol-4-yl)pyrimidin-4-yl)amino)-5-(furan-2-yl)pyridin-4-yl)amino)cyclohexan-1-ol;

(84) (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)-1-methylcyclohexan-1-ol;

(85) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-methylcyclohexan-1-ol;

(88) $N^2$-(2-(1-(Cyclopropylsulfonyl)-1H-pyrazol-4-yl)pyrimidin-4-yl)-5-(1-methyl-1H-pyrazol-3-yl)-$N^4$-((1s,4s)-4-(methylamino)cyclohexyl)pyridine-2,4-diamine;

(89) 1-(2-((2-(1-Cyclopropylsulfonylpyrazol-4-yl)pyrimidin-4-yl)amino)-5-(2-methylthiazol-5-yl)-4-pyridyl)piperidin-4-ol;

(91) (1S,3S)-3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino) cyclohexan-1-ol;

(92) 2-(4-(6-((2-(1-(Cyclopropylsulfonyl)-1H-pyrazol-4-yl)pyrimidin-4-yl)amino)-4-(isopropylamino)pyridin-3-yl)thiazol-2-yl)propan-2-ol;

(93) (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-1-methylcyclohexan-1-ol;

(99) N²-(2-(1-(cyclopropylsulfonyl)-1H-pyrazol-4-yl)pyrimidin-4-yl)-5-(1-(difluoromethyl)-1H-pyrazol-3-yl)-N⁴-(4-((2-(dimethylamino)ethyl)amino)cyclohexyl)pyridine-2,4-diamine;

(100) N²-(2-(1-(Cyclopropylsulfonyl)-1H-pyrazol-4-yl)pyrimidin-4-yl)-5-(1-(difluoromethyl)-1H-pyrazol-3-yl)-N⁴-(((1r,4r)-4-((dimethylamino)methyl)cyclohexyl)methyl)pyridine-2,4-diamine;

(101) N²-(2-(1-(Cyclopropylsulfonyl)-1H-pyrazol-4-yl)pyrimidin-4-yl)-N⁴-(((1r,4r)-4-((dimethylamino)methyl)cyclohexyl)methyl)-5-(2-(trifluoromethyl)thiazol-4-yl)pyridine-2,4-diamine;

(106) 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-2,2-dimethylcyclohexan-1-ol;

(110) 1-Cyclopropyl-4-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(114) (1s,4s)-4-((5-(1-(Difluoromethyl)-1H-pyrazol-3-yl)-2-((2-(1-((tetrahydrofuran-3-yl)sulfonyl)-1H-pyrazol-4-yl)pyrimidin-4-yl)amino)pyridin-4-yl)amino)-1-methylcyclohexan-1-ol;

(115) (1s,4s)-4-((2-((2-(1-(Cyclopentylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(117) (1s,4s)-4-((2-((2-(1-(But-3-en-1-ylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(118) (1R,3S)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclopentan-1-ol;

(119) (1R,3S)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclopentan-1-ol;

(120) (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-methylcyclohexan-1-ol;

(122) (1s,4s)-4-((2-((2-(1-(Cyclopropylsulfonyl)-1H-pyrazol-4-yl)pyrimidin-4-yl)amino)-5-(4-(difluoromethyl)thiazol-2-yl)pyridin-4-yl)amino)-1-methylcyclohexan-1-ol;

(133) 2-((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(134) 2-((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol;

(136) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol;

(137) (1s,4s)-4-((5-(1-(Difluoromethyl)-1H-pyrazol-3-yl)-2-((2-(1-(2,2,2-trifluoroethyl)-1H-pyrazol-4-yl)pyrimidin-4-yl)amino)pyridin-4-yl)amino)-1-methylcyclohexan-1-ol;

(143) (1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(144) N²-(2-(1-(Cyclopropylsulfonyl)-1H-pyrazol-4-yl)pyrimidin-4-yl)-5-(1-(difluoromethyl)-1H-pyrazol-3-yl)-N⁴-isopropylpyridine-2,4-diamine;

(146) 2-((1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(148) 2-((1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol;

(151) N²-(2-(1-(Cyclopropylsulfonyl)-1H-pyrazol-4-yl)pyrimidin-4-yl)-5-(1-(difluoromethyl)-1H-pyrazol-3-yl)-N⁴-((1s,4s)-4-fluorocyclohexyl)pyridine-2,4-diamine;

(153) 1-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-4-ol;

(157) N²-(2-(1-(Cyclopropylsulfonyl)-1H-pyrazol-4-yl)pyrimidin-4-yl)-5-(1-(difluoromethyl)-1H-pyrazol-3-yl)-N⁴-((1s,4s)-4-(difluoromethyl)cyclohexyl)pyridine-2,4-diamine;

(160) 1-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)piperidin-4-ol;

(168) (1s,4s)-4-((2-((2-(1-(Cyclopropylsulfonyl)-1H-pyrazol-4-yl)pyrimidin-4-yl)amino)-5-(3-methyl-1H-pyrazol-1-yl)pyridin-4-yl)amino)-1-methylcyclohexan-1-ol;

(171) (1s,4s)-4-((5-(1-(Difluoromethyl)-1H-pyrazol-3-yl)-2-((2-(2-fluoropyridin-3-yl)pyrimidin-4-yl)amino)pyridin-4-yl)amino)-1-methylcyclohexan-1-ol;

(172) (1s,4s)-4-((2-((2-(1-(Cyclopropylsulfonyl)-1H-pyrazol-4-yl)pyrimidin-4-yl)amino)-5-(3-(difluoromethyl)-1H-pyrazol-1-yl)pyridin-4-yl)amino)-1-methylcyclohexan-1-ol;

(174) N²-(2-(1-(Cyclopropylsulfonyl)-1H-pyrazol-4-yl)pyrimidin-4-yl)-N⁴-((1s,4s)-4-fluorocyclohexyl)-5-(1-methyl-1H-pyrazol-3-yl)pyridine-2,4-diamine;

(181) N²-(2-(1-(Cyclopropylsulfonyl)-1H-pyrazol-4-yl)pyrimidin-4-yl)-5-(1-(difluoromethyl)-1H-pyrazol-3-yl)-N⁴-(3-fluorocyclohexyl)pyridine-2,4-diamine;

(188) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(hydroxymethyl)cyclohexan-1-ol;

(189) ((1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutyl)methanol;

(195) N²-(2-(1-(Cyclopropylsulfonyl)-1H-pyrazol-4-yl)pyrimidin-4-yl)-5-(1-(difluoromethyl)-1H-pyrazol-3-yl)-N⁴-((1s,4s)-4-((dimethylamino)methyl)cyclohexyl)pyridine-2,4-diamine;

(198) ((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(201) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N,N-dimethylcyclohexane-1-carboxamide;

(202) ((1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(204) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-(2,2-difluoroethyl)-N-methylcyclohexane-1-carboxamide;

(205) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)-N,N-dimethylacetamide;

(208) $N^4$-((1s,4s)-4-(Azetidin-1-ylmethyl)cyclohexyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(211) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(2-(dimethylamino)ethyl)cyclohexyl)pyridine-2,4-diamine;

(212) (R)—$N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-fluorobutan-2-yl)pyridine-2,4-diamine;

(221) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(hydroxymethyl)cyclohexan-1-ol;

(222) (4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-fluorocyclohexyl)methanol;

(223) ((1r,3r)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclobutyl)methanol;

(226) $N^2$-(2-(1-(Cyclopropylsulfonyl)-1H-pyrazol-4-yl)pyrimidin-4-yl)-$N^4$-((1s,4s)-4-((dimethylamino)methyl)cyclohexyl)-5-(1-methyl-1H-pyrazol-3-yl)pyridine-2,4-diamine;

(228) (3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)oxetan-3-yl)methanol;

(229) ((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol;

(231) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(difluoromethyl)cyclohexan-1-ol;

(232) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N,N-dimethylcyclohexane-1-carboxamide;

(233) ((1S,3S)-3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol;

(235) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-(2,2-difluoroethyl)-N-methylcyclohexane-1-carboxamide;

(236) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)-N,N-dimethylacetamide;

(237) $N^2$-(2-(1-(Cyclopropylsulfonyl)-1H-pyrazol-4-yl)pyrimidin-4-yl)-$N^4$-((1s,4s)-4-(((2,2-difluoroethyl)(methyl)amino)methyl)cyclohexyl)-5-(1-methyl-1H-pyrazol-3-yl)pyridine-2,4-diamine;

(240) $N^2$-(2-(1-(Cyclopropylsulfonyl)-1H-pyrazol-4-yl)pyrimidin-4-yl)-$N^4$-((1s,4s)-4-(2-(dimethylamino)ethyl)cyclohexyl)-5-(1-methyl-1H-pyrazol-3-yl)pyridine-2,4-diamine;

(241) (1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)-1-methylcyclohexan-1-ol;

(242) $N^2$-(2-(1-(Cyclopropylsulfonyl)-1H-pyrazol-4-yl)pyrimidin-4-yl)-5-(1-(2,2-difluoroethyl)-1H-pyrazol-3-yl)-$N^4$-((1s,4s)-4-((2-fluoroethyl)amino)cyclohexyl)pyridine-2,4-diamine;

(243) 2-((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)propan-2-ol;

(244) ((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)methanol;

(247) $N^4$-((1s,4s)-4-(Azetidin-1-ylmethyl)cyclohexyl)-$N^2$-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine;

(248) $N^2$-(2-(1-(Cyclopropylsulfonyl)-1H-pyrazol-4-yl)pyrimidin-4-yl)-5-(1-(2,2-difluoroethyl)-1H-pyrazol-3-yl)-$N^4$-isopropylpyridine-2,4-diamine;

(251) $N^2$-(2-(1-(Cyclopropylsulfonyl)-1H-pyrazol-4-yl)pyrimidin-4-yl)-5-(1-(2,2-difluoroethyl)-1H-pyrazol-3-yl)-$N^4$-((1s,4s)-4-(2-(dimethylamino)ethyl)cyclohexyl)pyridine-2,4-diamine;

(252) (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(253) ((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol;

(254) 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)propan-2-ol;

(256) $N^2$-(2-(1-(Cyclopropylsulfonyl)-1H-pyrazol-4-yl)pyrimidin-4-yl)-$N^4$-((1s,4s)-4-((dimethylamino)methyl)cyclohexyl)-5-(1-methyl-5-(trifluoromethyl)-1H-pyrazol-3-yl)pyridine-2,4-diamine;

(257) (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-N,N-dimethylcyclohexane-1-carboxamide;

(258) 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)-N,N-dimethylacetamide;

(260) ((1S,3S)-3-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol;

(261) (1R,3S)-3-(((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)methyl)cyclopentan-1-ol;

(262) 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(264) $N^4$-((1s,4s)-4-(Azetidin-1-ylmethyl)cyclohexyl)-$N^2$-(2-(1-(cyclopropylsulfonyl)-1H-pyrazol-4-yl)pyrimidin-4-yl)-5-(1-methyl-5-(trifluoromethyl)-1H-pyrazol-3-yl)pyridine-2,4-diamine;

(265) 2-((1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)propan-2-ol;

(266) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(1-(2,2,2-trifluoroethyl)-1H-pyrazol-3-yl)pyridine-2,4-diamine;

(269) 2-((1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol;

(272) N⁴-((1s,4s)-4-(Azetidin-1-ylmethyl)cyclohexyl)-N²-(2-(1-(cyclopropylsulfonyl)-1H-pyrazol-4-yl)pyrimidin-4-yl)-5-(1-(2,2,2-trifluoroethyl)-1H-pyrazol-3-yl)pyridine-2,4-diamine;

(273) (1s,4s)-4-((2-((2-(1-(Cyclopropylsulfonyl)-1H-pyrazol-4-yl)pyrimidin-4-yl)amino)-5-(1-(difluoromethyl)-1H-imidazol-4-yl)pyridin-4-yl)amino)-1-methylcyclohexan-1-ol;

(274) (1s,4s)-4-((2-((2-(1-(Cyclopropylsulfonyl)-1H-pyrazol-4-yl)pyrimidin-4-yl)amino)-5-(6,7-dihydro-5H-pyrrolo[1,2-a]imidazol-2-yl)pyridin-4-yl)amino)-1-methylcyclohexan-1-ol;

(275) (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-(hydroxymethyl)cyclohexan-1-ol;

(276) (4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-fluorocyclohexyl)methanol;

(277) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(4,5,6,7-tetrahydropyrazolo[1,5-a]pyridin-2-yl)pyridine-2,4-diamine;

(278) 2-((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)propan-2-ol;

(280) ((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)methanol;

(281) 2-((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)propan-2-ol;

(282) ((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)methanol;

(283) 2-((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)propan-2-ol;

(284) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(1-(oxetan-3-yl)-1H-pyrazol-3-yl)pyridine-2,4-diamine;

(285) (1s,4s)-4-((2-((2-(1-(Cyclopropylsulfonyl)-1H-pyrazol-4-yl)pyrimidin-4-yl)amino)-5-(1-(trifluoromethyl)-1H-pyrazol-3-yl)pyridin-4-yl)amino)-1-methylcyclohexan-1-ol;

(287) (1s,4s)-4-((2-((2-(1-(Cyclopropylsulfonyl)-1H-pyrazol-4-yl)pyrimidin-4-yl)amino)-5-(1-(1-methylpiperidin-4-yl)-1H-pyrazol-3-yl)pyridin-4-yl)amino)-1-methylcyclohexan-1-ol;

(288) (1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)-1-methylcyclohexan-1-ol;

(289) (1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)-1-methylcyclohexan-1-ol;

(290) (1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)-1-methylcyclohexan-1-ol;

(291) (1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)-1-methylcyclohexan-1-ol;

(292) (1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)-1-methylcyclohexan-1-ol;

(293) (1s,4s)-4-((2-((2-(1-(Cyclopropylsulfonyl)-1H-pyrazol-4-yl)pyrimidin-4-yl)amino)-5-(5-(2-hydroxypropan-2-yl)-1-methyl-1H-pyrazol-3-yl)pyridin-4-yl)amino)-1-methylcyclohexan-1-ol;

(294) (1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)-1-methylcyclohexan-1-ol;

(295) (1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)-1-methylcyclohexan-1-ol;

(296) ((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)methanol;

(297) ((1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)cyclohexyl)methanol;

(298) 2-(3-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-1-methyl-1H-pyrazol-5-yl)propan-2-ol;

(299) 2-((1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)cyclohexyl)propan-2-ol;

(302) 2-(3-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)-1-methyl-1H-pyrazol-5-yl)propan-2-ol;

(305) N²-(2-(1-(Cyclopropylsulfonyl)-1H-pyrazol-4-yl)pyrimidin-4-yl)-N⁴-((1s,4s)-4-fluorocyclohexyl)-5-(1-(2,2,2-trifluoroethyl)-1H-pyrazol-3-yl)pyridine-2,4-diamine;

(307) (1s,4s)-4-((2-((2-(1-(Cyclopropylsulfonyl)-1H-pyrazol-4-yl)pyrimidin-4-yl)amino)-5-(5-(4,4-difluoropiperidin-1-yl)-1-methyl-1H-pyrazol-3-yl)pyridin-4-yl)amino)-1-methylcyclohexan-1-ol;

(308) (1s,4s)-4-((5-(1-(Difluoromethyl)-1H-pyrazol-3-yl)-2-((2-(1-(ethylsulfonyl)-1H-pyrazol-4-yl)pyrimidin-4-yl)amino)pyridin-4-yl)amino)-1-methylcyclohexan-1-ol;

(315) 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N,3-trimethyl-1H-pyrazole-1-sulfonamide;

(317) 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrazole-1-sulfonamide;

(320) (1s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)-1-methylcyclohexan-1-ol;

(324) (1s,4s)-4-((5-(1-(Difluoromethyl)-1H-pyrazol-3-yl)-2-((2-(1-((3-fluoroazetidin-1-yl)sulfonyl)-1H-pyrazol-4-yl)pyrimidin-4-yl)amino)pyridin-4-yl)amino)-1-methylcyclohexan-1-ol;

(326) 2-((1s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)cyclohexyl)ethan-1-ol;

(330) 4-(4-((4-(((1s,4s)-4-Hydroxy-4-methylcyclohexyl)amino)-5-(1-methyl-5-(trifluoromethyl)-1H-pyrazol-3-yl)pyridin-2-yl)amino)pyrimidin-2-yl)-N,N-dimethyl-1H-pyrazole-1-sulfonamide;

(331) (1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(333) 2-((1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(334) 2-((1s,4s)-4-((2-((2-(3-Methyl-1-(2,2,2-trifluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(337) 2-((1s,4s)-4-((5-(1-(2,2-Difluoroethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)cyclohexyl)ethan-1-ol;

(338) 2-((1s,4s)-4-((2-((2-(1-(2,2-Difluoroethyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol;

(343) (1s,4s)-4-((5-(1-(2,2-Difluoroethyl)-1H-pyrazol-3-yl)-2-((2-(1-(2,2-difluoroethyl)-1H-pyrazol-4-yl)pyrimidin-4-yl)amino)pyridin-4-yl)amino)-1-methylcyclohexan-1-ol;

(348) 1-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-3,3-difluoropiperidin-4-ol;

(355) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(356) (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyrimidin-4-yl)amino)-1-methylcyclohexan-1-ol;

(357) (1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyrimidin-4-yl)amino)-1-methylcyclohexan-1-ol;

(358) (1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyrimidin-4-yl)amino)-1-methylcyclohexan-1-ol;

(360) (1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyrimidin-4-yl)amino)-1-methylcyclohexan-1-ol;

(361) (1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyrimidin-4-yl)amino)-1-methylcyclohexan-1-ol;

(362) (1s,4s)-4-((2-((2-(1-(2,2-Difluoroethyl)-1H-pyrazol-4-yl)pyridin-4-yl)amino)-5-(1-(difluoromethyl)-1H-pyrazol-3-yl)pyrimidin-4-yl)amino)-1-methylcyclohexan-1-ol;

(364) ((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)methanol;

(365) 2-((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)propan-2-ol;

(372) (1s,4s)-4-((6-((2-(1-(Cyclopropylsulfonyl)-1H-pyrazol-4-yl)pyrimidin-4-yl)amino)-3-(1-(difluoromethyl)-1H-pyrazol-3-yl)pyridazin-4-yl)amino)-1-methylcyclohexan-1-ol;

(374) (1s,4s)-4-((6-((2-(1-(Cyclopropylsulfonyl)-1H-pyrazol-4-yl)pyrimidin-4-yl)amino)-3-(1-(2,2,2-trifluoroethyl)-1H-pyrazol-3-yl)pyridazin-4-yl)amino)-1-methylcyclohexan-1-ol;

(379) (1s,4s)-4-((2-((2-(1-(Butylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(382) (1s,4s)-4-((2-((2-(1-(Cyclopropylsulfonyl)-1H-pyrazol-4-yl)pyrimidin-4-yl)amino)-5-(5-fluoro-1-methyl-1H-pyrazol-3-yl)pyridin-4-yl)amino)-1-methylcyclohexan-1-ol;

(383) (1s,4s)-4-((2-((2-(1-(Cyclopropylsulfonyl)-1H-pyrazol-4-yl)pyrimidin-4-yl)amino)-5-(2-(difluoromethyl)-1-methyl-1H-imidazol-4-yl)pyridin-4-yl)amino)-1-methylcyclohexan-1-ol; and (387) (1s,4s)-4-((2-((2-(1-(Cyclopropylsulfonyl)-1H-pyrazol-4-yl)pyrimidin-4-yl)amino)-5-(4-fluoro-1-methyl-1H-pyrazol-3-yl)pyridin-4-yl)amino)-1-methylcyclohexan-1-ol.

Further preferable representative compounds of Formula (I) are listed below:

(8) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol;

(9) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((2-fluoroethyl)amino)cyclohexyl)pyridine-2,4-diamine;

(10) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(14) (1R,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(18) ((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(21) (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(22) ((1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methanol;

(31) (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(36) (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-1-methylcyclohexan-1-ol;

(42) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)propan-2-ol;

(47) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclohexan-1-ol;

(48) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-1-methylcyclohexan-1-ol;

(51) (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-methylcyclohexan-1-ol;

(59) (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-methylcyclohexan-1-ol;

(60) ((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)methanol;

(61) 2-((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)propan-2-ol;

(62) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(4,5,6,7-tetrahydropyrazolo[1,5-a]pyridin-2-yl)pyridine-2,4-diamine;

(76) (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)cyclohexan-1-ol;

(80) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(100) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-((dimethylamino)methyl)cyclohexyl)methyl)pyridine-2,4-diamine;

(144) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-isopropylpyridine-2,4-diamine;

(151) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-fluorocyclohexyl)pyridine-2,4-diamine;

(181) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(3-fluorocyclohexyl)pyridine-2,4-diamine;

(195) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((dimethylamino)methyl)cyclohexyl)pyridine-2,4-diamine;

(241) (1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)-1-methylcyclohexan-1-ol;

(243) 2-((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)propan-2-ol;

(252) (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(253) ((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol;

(274) (1s,4s)-4-((2-((2-(1-(Cyclopropylsulfonyl)-1H-pyrazol-4-yl)pyrimidin-4-yl)amino)-5-(6,7-dihydro-5H-pyrrolo[1,2-a]imidazol-2-yl)pyridin-4-yl)amino)-1-methylcyclohexan-1-ol;

(305) $N^2$-(2-(1-(Cyclopropylsulfonyl)-1H-pyrazol-4-yl)pyrimidin-4-yl)-$N^4$-((1s,4s)-4-fluorocyclohexyl)-5-(1-(2,2,2-trifluoroethyl)-1H-pyrazol-3-yl)pyridine-2,4-diamine;

(316) (1s,4s)-4-((2-((2-(1-(Cyclopropylsulfonyl)-1H-pyrazol-4-yl)-5-fluoropyrimidin-4-yl)amino)-5-(1-(difluoromethyl)-1H-pyrazol-3-yl)pyridin-4-yl)amino)-1-methylcyclohexan-1-ol;

(331) (1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(356) (1s,4s)-4-((2-((2-(1-(Cyclopropylsulfonyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol;

(360) (1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyrimidin-4-yl)amino)-1-methylcyclohexan-1-ol;

and (361) (1s,4s)-4-((2-((2-(1-(2,2-Difluoroethyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol.

Further more preferable representative compounds of Formula (I) are listed below:

(8) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol;

(9) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((2-fluoroethyl)amino)cyclohexyl)pyridine-2,4-diamine;

(10) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(18) ((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(42) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)propan-2-ol;

(47) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclohexan-1-ol;

(51) (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-methylcyclohexan-1-ol;

(59) (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-methylcyclohexan-1-ol;

(62) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(4,5,6,7-tetrahydropyrazolo[1,5-a]pyridin-2-yl)pyridine-2,4-diamine;

(76) (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)cyclohexan-1-ol;

(80) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(100) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-((dimethylamino)methyl)cyclohexyl)methyl)pyridine-2,4-diamine;

(144) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-isopropylpyridine-2,4-diamine;

(151) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-fluorocyclohexyl)pyridine-2,4-diamine;

(243) 2-((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)propan-2-ol;

(252) (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(253) ((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol;

(331) (1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(356) (1s,4s)-4-((2-((2-(1-(Cyclopropylsulfonyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol;

(360) (1s,4s)-4-((2-((2-(1-(Cyclopropylsulfonyl)-1H-pyrazol-4-yl)pyridin-4-yl)amino)-5-(1-(2,2,2-trifluoroethyl)-1H-pyrazol-3-yl)pyrimidin-4-yl)amino)-1-methylcyclohexan-1-ol; and (361) (1s,4s)-4-((2-((2-(1-(2,2-Difluoroethyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol.

Single stereochemical isomers, enantiomers, diastereomers, and pharmaceutically acceptable salts of the above exemplified compounds are also within the scope of the present invention. Pharmaceutically acceptable salts may be, for example, derived from suitable inorganic and organic acids and bases.

Acid addition salts can be prepared by reacting the purified compound in its free-based form, if possible, with a suitable organic or inorganic acid and isolating the salt thus formed. Examples of pharmaceutically acceptable acid addition salts include, without limitations, salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid.

Base addition salts can be prepared by reacting the purified compound in its acid form with a suitable organic or inorganic base and isolating the salt thus formed. Such salts include, without limitations, alkali metal (e.g., sodium, lithium, and potassium), alkaline earth metal (e.g., magnesium and calcium), ammonium and $N^+(C_{1-4}alkyl)_4$ salts.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, and valerate salts.

The compounds of the present invention may be synthesized by methods known in the art or by methods illustrated in Examples 1-388 below.

Pharmaceutical Compositions, Methods and Use

In one embodiment, the present invention relates to a method for treating protein kinase-mediated disease in a subject in need thereof, comprising administering to said subject a therapeutically effective amount of a compound of Formula (I) or a pharmaceutically acceptable salt, diastereomers, enantiomers, racemates, tautomers, prodrugs, hydrates, or solvates thereof In specific embodiment, the protein kinase-mediated disease is a cancer or immune disease.

As used herein, the term "cancer" refers to an abnormal growth of cells which tend to proliferate in an uncontrolled way and, in some cases, to metastasize. The types of cancer include, but is not limited to, solid tumors, such as those of the bladder cancer, colorectal cancer, brain cancer, breast cancer, ovarian cancer, endometrium cancer, uterine cancer, heart cancer, kidney cancer, lung cancer, liver cancer, stomach cancer, lymphoma, pancreatic cancer, head and neck cancer, or other endocrine organ (thyroid cancer), prostate cancer, skin (melanoma) or hematological tumors (such as the leukemias). In another embodiment, the cancer is non-small cell lung cancer (NSCLC).

In one embodiment, the method disclosed herein relates to treatment of cancer, wherein the cancer results from at least one mutation of EGFR.

In one embodiment, the method of treatment of cancer is particularly useful for patient who is resistant to a kinase inhibitor other that a compound of the invention, or a pharmaceutically acceptable salt, solvate, ester, or prodrug thereof. In another embodiment, the kinase inhibitor is a mutated EGFR inhibitor.

The invention also relates to a method for inhibiting at least one mutant of EGFR selectively as compared to wild type EGFR, in biological sample or in a patient, comprising contacting the biological sample with or administering to the patient a compound to the patient a therapeutically effective amount of a compound of the invention, or a pharmaceutically acceptable salt thereof.

In one embodiment, the at least one mutant is at least one single mutant selected from Table 1 shown below.

In one embodiment, the at least one mutant is at least one double mutant selected from Table 1 shown below.

In one embodiment, the at least one mutant is at least one triple mutant selected from Table 1 shown below.

TABLE 1

| Number (#) | Mutation type |
| --- | --- |
| 1 | EGFR Del19 (Del E746-A750) |
| 2 | EGFR L858R |
| 3 | EGFR Del19/T790M |
| 4 | EGFR Del19/C797S |
| 5 | EGFR Del19/C797X (X = G, N) |
| 6 | EGFR Del19/L792X (X = F, H, P, R, V, Y) |
| 7 | EGFR Del19/L718X (X = Q, V) |
| 8 | EGFR L858R/T790M |
| 9 | EGFR L858R/C797S |
| 10 | EGFR L858R/C797X (X = G, N) |
| 11 | EGFR L858R/L792X (X = F, H, P, R, V, Y) |
| 12 | EGFR L858R/L718X (X = Q, V) |
| 13 | EGFR Del19/T790M/C797S |
| 14 | EGFR Del19/T790M/C797X (X = G, N) |
| 15 | EGFR Del19/T790M/L792X (X = F, H, P, R, V, Y) |
| 16 | EGFR Del19/T790M/L718X (X = Q, V) |
| 17 | EGFR L858R/T790M/C797S |
| 18 | EGFR L858R/T790M/C797X (X = G, N) |
| 19 | EGFR L858R/T790M/L792X (X = F, H, P, R, V, Y) |
| 20 | EGFR L858R/T790M/L718X (X = Q, V) |

The invention further relates to therapeutic methods and uses comprising administering the compounds of the invention, or a pharmaceutically acceptable salt, diastereomers, enantiomers, racemates, tautomers, prodrugs, hydrates, or solvates thereof alone or in combination with other therapeutic or palliative agents.

A further embodiment of the invention relates to a compound of the invention for use as a medicament, and in particular for use in the treatment of diseases where the inhibition of mutated EGFR protein (e.g., those described in Table 1) activity may induce benefit, such as cancer. A still further embodiment of the present invention relates to the use of the compounds of the invention, or a pharmaceutically acceptable salt, diastereomers, enantiomers, racemates, tautomers, prodrugs, hydrates, or solvates thereof, for the manufacture of a drug having an EGFR inhibitory activity for the treatment of EGFR mediated diseases and/or conditions, in particular the diseases and/or conditions listed above.

The term "therapeutically effective amount" refers to that amount of a compound being administered which will relieve to some extent one or more of the symptoms of the disorder being treated. Regarding the treatment of cancer, a therapeutically effective amount refers to that amount which has the effect of reducing the size of the tumor, inhibiting (i.e., slowing or stopping) tumor metastases, inhibiting (i.e. slowing or stopping) tumor growth or tumor invasiveness, and/or relieving to some extent one or more signs or symptoms related to the cancer.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

The term "treating", as used herein, unless otherwise indicated, means reversing, alleviating, inhibiting the progress of, or preventing the disorder or condition to which such term applies, or one or more symptoms of such disorder or condition. The term "treatment" also refers to the act of treating as "treating" is defined immediately above. The term "treating" also includes adjuvant treatment of a mammal.

As used herein, the term "subject" or "patient" encompasses mammals and nonmammals. Examples of mammals include, but are not limited to, humans, chimpanzees, apes monkeys, cattle, horses, sheep, goats, swine; rabbits, dogs, cats, rats, mice, guineapigs, and the like. Examples of non-mammals include, but are not limited to, birds, fish and the like.

As used herein, the term "biological sample" encompasses cells, tissues, and body fluids obtained (isolated) from mammals, such as humans (e.g., patients having cancers) or nonmammals exemplified hereinabove, and cultures thereof.

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Also provided herein, in other aspects, is a pharmaceutical composition comprising a compound of t Formula (I), a pharmaceutically acceptable salt, diastereomers, enantiomers, racemates, tautomers, prodrugs, hydrates, or solvates thereof as an active ingredient, and pharmaceutically acceptable excipients. In one embodiment, the pharmaceutical composition is for treating a protein kinase-mediated disease. In another embodiment, the pharmaceutical composition is for selectively inhibiting at least one mutant of EGFR as compared to wild type EGFR.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid.

Examples of carriers, excipients and diluents that can be included in the composition, may include lactose, dextrose, sucrose, sorbitol, mannitol, xylitol, erythritol, maltitol, starch, arabic gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil, but are not limited thereto. When formulated into a preparation, a diluting agent or an excipient, such as commonly-used fillers, stabilizing agents, binding agents, disintegrating agents, and surfactants can be used. Solid preparations for oral administration include tablets, pills, powders, granules, capsules, and the like, and these solid preparations may be prepared by mixing the compound of the present invention with at least one excipient, for example, starch, microcrystalline cellulose, sucrose, lactose, low-substituted hydroxypropyl cellulose, hypromellose or the like. In addition to the simple excipient, a lubricant such as magnesium stearate and talc are also used. Liquid preparations for oral administration include a suspension, a liquid for internal use, an emulsion, a syrup, etc. In addition to a commonly used simple diluent such as water and liquid paraffin, various excipients such as a humectant, a sweetener, an aromatic, a preservative, etc. may also be contained. Formulations for parenteral administration include a sterilized aqueous solution, a non-aqueous solution, a suspension, an emulsion, a lyophilized formulation and a suppository. The non-aqueous solution or suspension may contain propylene glycol, polyethylene glycol, a vegetable oil such as olive oil, an injectable ester such as ethyl oleate, etc. As a base of the suppository, witepsol, macrogol, tween 61, cocoa butter, laurin butter, glycerogelatin, etc. may be used. In order to formulate the formulation for parenteral administration, the compound of Formula I or a pharmaceutically acceptable salt thereof may be mixed in water together with sterilized and/or contain adjuvants such as preservatives, stabilizers, auxiliary agents such as wettable powder or emulsifying accelerators, salt for controlling osmotic pressure and/or buffers and the like, and other therapeutically useful substances, to prepare a solution or suspension, which is then manufactured in the form of an ampoule or vial unit administration.

General Reaction Scheme and Summary of the Synthesis Route

The present invention includes, within its scope, a process for preparing a compound of formula (I) or a pharmaceutically acceptable salt, diastereomers, enantiomers, racemates, tautomers, prodrugs, hydrates, or solvates thereof, in accordance with the following Scheme 1:

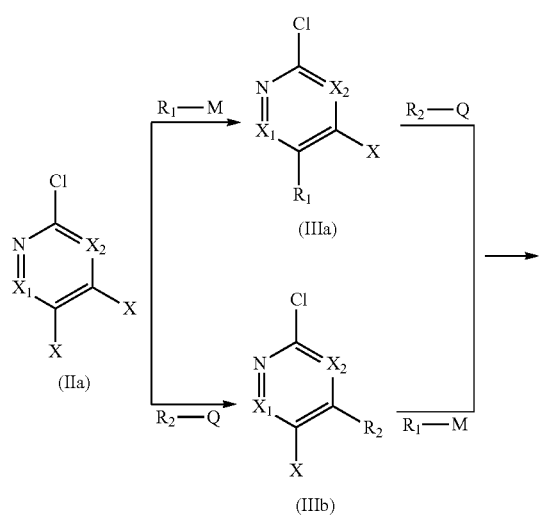

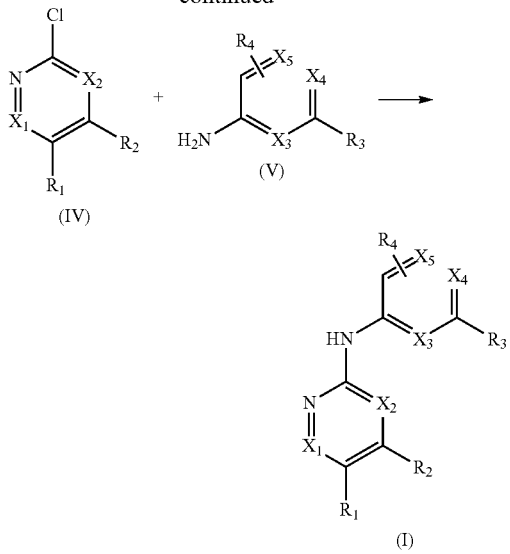

wherein, $R_1$, $R_2$, $R_3$, $R_4$, $X_1$, $X_2$, $X_3$, $X_4$, and $X_5$ are the same as defined in the above; X is halogen; M is $B(OH)_2$ or BPin; and Q is hydrogen, $B(OH)_2$ or BPin.

Specifically, the compound of formula (I) or its pharmaceutically acceptable salt may be prepared using a process which comprises: reacting a compound of formula (IIa) with $R_1$-M to obtain a compound of formula (IIIa), reacting the compound of formula (IIIa) with $R_2$-Q to obtain a compound of formula (IV) and reacting the compound of formula (IV) with a compound of formula (V) to obtain the compound of formula (I).

In the processes of Scheme 1, the compounds of formula (IIa), $R_1$-M, $R_2$-Q and (V) are commercially available. The reaction of the compound of formula (IIa) and $R_1$-M may be performed in the presence of a base, such as sodium carbonate, potassium carbonate, etc. and a ligand-coupled palladium catalyst such as $Pd(dppf)Cl_2$, $Pd(PPh_3)_4$, etc. Further, the reaction may be carried out in an anhydrous organic solvent, e.g., DME, THF, 1,4-dioxane, etc. under heating, e.g. at a temperature of 40-120° C.

The reaction of the compound of formula (IIIa) and $R_2$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that Q is $B(OH)_2$ or BPin, the reaction may be carried out in the presence of a base such as sodium carbonate, potassium carbonate, etc. and a ligand-coupled palladium catalyst such as $Pd(dppf)Cl_2$, $Pd(PPh_3)_4$, etc. Further, in case that Q is $B(OH)_2$ or BPin, the reaction may be carried out in an anhydrous organic solvent, e.g., DME, THF, 1,4-dioxane, etc. under heating, e.g. at a temperature of 40-120° C.

The compound of formula (IV) is coupled with a compound of formula (V) to obtain a compound of formula (I) by Buchwald-Hartwig reaction. The reaction of the compound of formula (IV) and (V) may be performed in the presence of a base such as sodium carbonate potassium carbonate, cesium carbonate, etc. Further, the reaction may be performed in the presence of a palladium catalyst such as $Pd(OAc)_2$, $Pd_2(dba)_3$, $Pd(PPh_3)_4$, $Pd(dppf)Cl_2$, BrettPhos Pd G1 methyl t-butyl ether adduct, etc. and a ligand such as BINAP, SPhos, XPhos, Xantphos, BrettPhos, etc. Further, the reaction may be carried out in an anhydrous organic solvent, e.g., 1,4-dioxane or toluene, etc. under heating, e.g. at a temperature of 80-120° C.

Alternately, the compound of formula (IV) may be prepared by reacting a compound of formula (IIa) with $R_2$-Q to obtain a compound of formula (IIb) and reacting the compound of formula (IIIb) with $R_1$-M.

The reaction of the compound of formula (IIa) and $R_2$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that Q is $B(OH)_2$ or BPin, the reaction may be carried out in the presence of a base such as sodium carbonate, potassium carbonate, etc. and a ligand-coupled palladium catalyst such as Pd(dppf)$Cl_2$, Pd(PPh$_3$)$_4$, etc. Further, in case that Q is $B(OH)_2$ or BPin, the reaction may be carried out in an anhydrous organic solvent, e.g., DME, THF, 1,4-dioxane, etc. under heating, e.g. at a temperature of 40-120° C.

The reaction of the compound of formula (IIIb) and $R_1$-M may be performed in the presence of a base, such as sodium carbonate, potassium carbonate, etc. and a ligand-coupled palladium catalyst such as Pd(dppf)$Cl_2$, Pd(PPh$_3$)$_4$, etc. Further, the reaction may be carried out in an anhydrous organic solvent, e.g., DME, THF, 1,4-dioxane, etc. under heating, e.g. at a temperature of 40-120° C.

In accordance with another aspect of the present invention, the compound of formula (I) or its pharmaceutically acceptable salt may be prepared in accordance with the following Scheme 2:

Scheme 2.

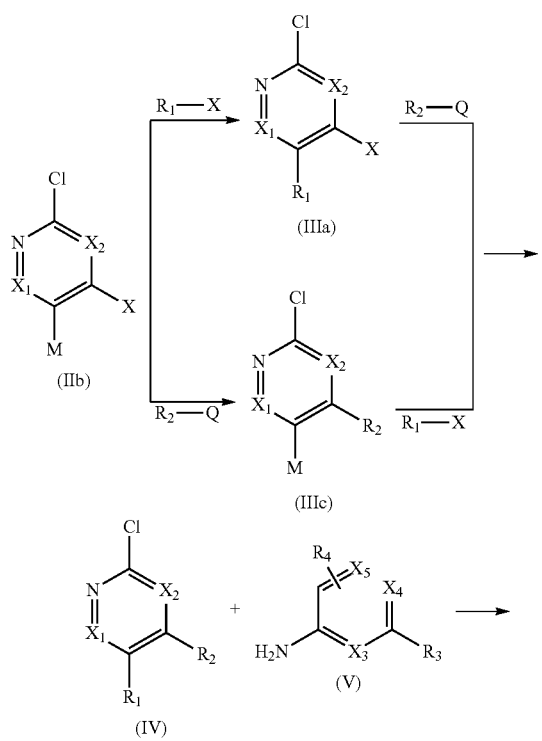

-continued

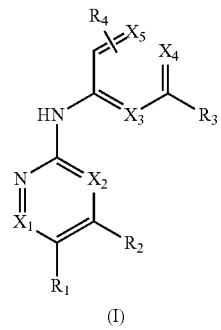

(I)

wherein, $R_1$, $R_2$, $R_3$, $R_4$, $X_1$, $X_2$, $X_3$, $X_4$ and $X_5$ are the same as defined in the above; X is halogen; M is $B(OH)_2$ or BPin; and Q is hydrogen, $B(OH)_2$ or BPin.

Specifically, the compound of formula (I) or its pharmaceutically acceptable salt may be prepared using a process which comprises: reacting a compound of formula (IIb) with $R_1$—X to obtain a compound of formula (IIIa), reacting the compound of formula (IIIa) with $R_2$-Q to obtain a compound of formula (IV) and reacting the compound of formula (IV) with a compound of formula (V) to obtain the compound of formula (I).

In the processes of Scheme 2, the compounds of formula (IIb), $R_1$—X, $R_2$-Q and (V) are commercially available. The reaction of the compound of formula (IIb) and $R_1$—X may be performed in the presence of a base, such as sodium carbonate, potassium carbonate, etc. and a ligand-coupled palladium catalyst such as Pd(dppf)$Cl_2$, Pd(PPh$_3$)$_4$, etc. Further, the reaction may be carried out in an anhydrous organic solvent, e.g., DME, THF, 1,4-dioxane, etc. under heating, e.g. at a temperature of 40-120° C.

The reaction of the compound of formula (IIIa) and $R_2$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that Q is $B(OH)_2$ or BPin, the reaction may be carried out in the presence of a base such as sodium carbonate, potassium carbonate, etc. and a ligand-coupled palladium catalyst such as Pd(dppf)$Cl_2$, Pd(PPh$_3$)$_4$, etc. Further, in case that Q is $B(OH)_2$ or BPin, the reaction may be carried out in an anhydrous organic solvent, e.g., DME, THF, 1,4-dioxane, etc. under heating, e.g. at a temperature of 40-120° C.

The compound of formula (IV) is coupled with a compound of formula (V) to obtain a compound of formula (I) by Buchwald-Hartwig reaction. The reaction of the compound of formula (IV) and (V) may be performed in the presence of a base such as sodium carbonate potassium carbonate, cesium carbonate, etc. Further, the reaction may be performed in the presence of a palladium catalyst such as Pd(OAc)$_2$, Pd$_2$(dba)$_3$, Pd(PPh$_3$)$_4$, Pd(dppf)$Cl_2$, BrettPhos Pd G1 methyl t-butyl ether adduct, etc. and a ligand such as BINAP, SPhos, XPhos, Xantphos, BrettPhos, etc. Further, the reaction may be carried out in an anhydrous organic solvent, e.g., 1,4-dioxane or toluene, etc. under heating, e.g. at a temperature of 80-120° C.

Alternately, the compound of formula (IV) may be prepared by reacting a compound of formula (IIb) with $R_2$-Q to obtain a compound of formula (IIIc) and reacting the compound of formula (IIIc) with $R_1$—X.

The reaction of the compound of formula (IIb) and R$_2$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that Q is B(OH)$_2$ or BPin, the reaction may be carried out in the presence of a base such as sodium carbonate, potassium carbonate, etc. and a ligand-coupled palladium catalyst such as Pd(dppf)Cl$_2$, Pd(PPh$_3$)$_4$, etc. Further, in case that Q is B(OH)$_2$ or BPin, the reaction may be carried out in an anhydrous organic solvent, e.g., DME, THF, 1,4-dioxane, etc. under heating, e.g. at a temperature of 40-120° C.

The reaction of the compound of formula (IIIc) and R$_1$—X may be performed in the presence of a base, such as sodium carbonate, potassium carbonate, etc. and a ligand-coupled palladium catalyst such as Pd(dppf)Cl$_2$, Pd(PPh$_3$)$_4$, etc. Further, the reaction may be carried out in an anhydrous organic solvent, e.g., DME, THF, 1,4-dioxane, etc. under heating, e.g. at a temperature of 40-120° C.

In accordance with another aspect of the present invention, the compound of formula (V) may be obtained by reacting a compound of formula (VI) with a compound of formula R$_3$-Q in accordance with the following Scheme 3:

Scheme 3.

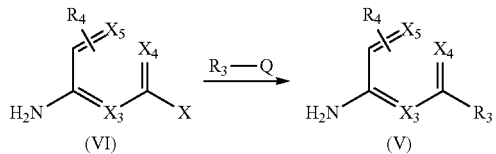

(VI)             (V)

wherein, R$_3$, R$_4$, X$_3$, X$_4$ and X$_5$ are the same as defined in the above; X is halogen; and Q is hydrogen, B(OH)$_2$ or BPin.

The reaction of the compound of formula (VI) and R$_3$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. at room temperature or under heating, e.g., at a temperature of 40-140° C. In case that Q is B(OH)$_2$ or BPin, the reaction may be carried out in the presence of a base such as sodium carbonate, potassium carbonate, etc. and a ligand-coupled palladium catalyst such as PdCl$_2$(PPh$_3$)$_2$, Pd(dppf)Cl$_2$, Pd(PPh$_3$)$_4$, etc. Further, in case that Q is B(OH)$_2$ or BPin, the reaction may be carried out in an anhydrous organic solvent, e.g., THF, 1,4-dioxane, acetonitrile, etc. under heating, e.g. at a temperature of 40-120° C.

EXAMPLES

The present invention is further exemplified by the following examples that illustrate the preparation of compounds of Formula (I) according to the invention. The examples are for illustrative purpose only and are not intended, nor should they be construed as limiting the invention in any manner. Those skilled in the art will appreciate that variations and modifications can be made without changing the scope of the invention.

The analyses of the compounds prepared in the following examples were carried out as follows: Nuclear magnetic resonance (NMR) spectrum analysis was carried out using Bruker 400 MHz spectrometer and Agilent 600 MHz spectrometer and chemical shifts thereof were analyzed in ppm. Further, the indicated molecular weights were measured by using liquid chromatography/mass selective detector (MSD) of Agilent 1260 Infinity series equipped with an electrostatic spray interface (by using Single Quadrupole, it indicates a value of m/z in ESI+ (ESI-MS (cation), which is represented by the (M+H)$^+$ peak). Column chromatography was carried out on silica gel (Merck, 70-230 mesH) (W. C. Still, J. Org. Chem., 43, 2923, 1978). Further, the starting materials in each Example are known compounds, which were synthesized according to literatures or obtained from the market such as Sigma-Aldrich. Further, the abbreviations used in the following examples are as follows:

TABLE 2

| List of abbreviations | |
|---|---|
| DCM | Methylene chloride |
| DIPEA | N,N-Diisopropylethylamine |
| DMA | N,N-Dimethylacetamide |
| DMF | N,N-Dimethylformamide |
| DMSO | Dimethyl sulfoxide |
| EA | Ethyl acetate |
| HATU | Hexafluorophosphate azabenzotriazole tetramethyl uronium |
| K$_2$CO$_3$ | Potassium carbonate |
| MeCN | Acetonitrile |
| MeOH | Methanol |
| MgSO$_4$ | Magnesium sulfate |
| n-Hex | n-Hexane |
| sat. NaHCO$_3$ soln. | saturated sodium bicarbonate solution |
| TFA | Trifluoroacetic acid |
| XPhos | [2-Dicyclohexylphosphino-2',4',6'-triisopropylbiphenyl] |

Reference Example 1. 5-Bromo-2-chloro-4-(2-(1-methylpyrazol-4-yl)ethynyl)pyridine The reaction mixture of 5-bromo-2-chloro-4-iodopyridine (1.00 g, 3.141 mmol), 4-ethynyl-1-methyl-1H-pyrazole (350 mg, 3.298 mmol), tetrakis(triphenylphosphine)palladium(0) (182 mg, 0.157 mmol), copper(I) Iodide (60 mg, 0.314 mmol) and TEA (0.88 mL, 6.283 mmol) in DMF (5 mL) was stirred at 90° C. for 3 hours. The reaction mixture was cooled to room temperature, quenched with water, and then extracted with DCM. The organic layer was dried over MgSO$_4$, filtered, and concentrated.

The crude product was purified by column chromatography (EA/n-Hex=0-50%) to yield 5-bromo-2-chloro-4-(2-(1-methylpyrazol-4-yl)ethynyl)pyridine (582 mg) as a pale yellow solid. $^1$H-NMR (CDCl$_3$, 400 MHz) δ 8.52 (s, 1H), 7.72 (s, 1H), 7.67 (s, 1H), 7.40 (s, 1H), 3.95 (s, 3H)

Reference Example 2. 2-Chloro-5-(1-(difluoromethyl)-1H-pyrazol-3-yl)-4-fluoropyridine The reaction mixture of 2-chloro-4-fluoro-5-iodopyridine (1.00 g, 3.885 mmol), 1-(difluoromethyl)-3-(4,4,5,5-tetramethyl-1,3,2-dioxaborolan-2-yl)pyrazole (1.23 g, 5.050 mmol), [1,1'-bis(diphenylphosphino)ferrocene]dichloropalladium(II) dichloromethane complex (317 mg, 0.388 mmol) and 2 M K$_2$CO$_3$ soln. (5.83 mL) in 1,4-dioxane (20 mL) was stirred at 90° C. for 3 hours. The reaction mixture was cooled, diluted in DCM, washed by water, dried over MgSO$_4$, and then concentrated. The crude product was purified by column chromatography (EA/n-Hex=0-20%) to yield 2-chloro-5-(1-(difluoromethyl)-1H-pyrazol-3-yl)-4-fluoropyridine (815 mg) as a white solid. $^1$H-NMR (CDCl$_3$,

Reference Example 3. 2-Chloro-4-fluoro-5-(1-methyl-1H-pyrazol-3-yl)pyridine

The title compound as a white solid (761 mg) was prepared in the same fashion as Reference Example 2, except that 1-methyl-3-(4,4,5,5-tetramethyl-1,3,2-dioxaborolan-2-yl)-1H-pyrazole (1.05 g, 5.05 mmol) was used instead of 1-(difluoromethyl)-3-(4,4,5,5-tetramethyl-1,3,2-dioxaborolan-2-yl)pyrazole. $^1$H-NMR (CDCl$_3$, 400 MHz) δ 8.98 (d, 1H), 7.44 (d, 1H), 7.14 (d, 1H), 6.65 (dd, 1H), 3.98 (s, 3H); MS (ESI) m/z=212.0 (M+H)$^+$

Reference Example 4. 4-(6-Chloro-4-fluoro-3-pyridyl)-2-(trifluoromethyl)thiazole The title compound as a white solid (809 mg) was prepared in the same fashion as Reference Example 2 except that 4-(4,4,5,5-tetramethyl-1,3,2-dioxaborolan-2-yl)-2-(trifluoromethyl)thiazole (1.41 g, 5.050 mmol) was used instead of 1-(difluoromethyl)-3-(4,4,5,5-tetramethyl-1,3,2-dioxaborolan-2-yl)pyrazole. $^1$H-NMR (CDCl$_3$, 400 MHz) δ 9.24 (d, 1H), 8.01 (s, 1H), 7.24 (d, 1H)

Reference Example 5. 2-(4-(6-Chloro-4-fluoro-3-pyridyl)thiazol-2-yl)propan-2-ol The title compound as a white solid (896 mg) was prepared in the same fashion as Reference Example 2 except that 2-(4-(4,4,5,5-tetramethyl-1,3,2-dioxaborolan-2-yl)thiazol-2-yl)propan-2-ol (1.36 g, 5.050 mmol) was used instead of 1-(difluoromethyl)-3-(4,4,5,5-tetramethyl-1,3,2-dioxaborolan-2-yl)pyrazole. $^1$H-NMR (CDCl$_3$, 400 MHz) δ 9.21 (d, 1H), 7.71 (s, 1H), 7.19 (d, 1H), 2.87 (s, 1H), 1.75 (s, 6H)

Reference Example 6. 2-Chloro-4-fluoro-5-(1-(tetrahydro-2H-pyran-4-yl)-1H-pyrazol-3-yl)pyridine The title compound as a white solid (1.67 g) was prepared in the same fashion as Reference Example 2 except that 1-tetrahydropyran-4-yl-3-(4,4,5,5-tetramethyl-1,3,2-dioxaborolan-2-yl)pyrazole (2.81 g, 10.100 mmol) was used instead of 1-(difluoromethyl)-3-(4,4,5,5-tetramethyl-1,3,2-dioxaborolan-2-yl)pyrazole. MS (ESI) m/z=282.0 (M+H)$^+$

Reference Example 7. 2-(6-Chloro-4-fluoropyridin-3-yl)-4,5,6,7-tetrahydropyrazolo[1,5-a]pyridine The title compound as a white solid (796 mg) was prepared in the same fashion as Reference Example 2 except that 2-(4,4,5,5-tetramethyl-1,3,2-dioxaborolan-2-yl)-4,5,6,7-tetrahydropyrazolo[1,5-a]pyridine (1.00 g, 4.055 mmol) was used instead of 1-(difluoromethyl)-3-(4,4,5,5-tetramethyl-1,3,2-dioxaborolan-2-yl)pyrazole. $^1$H-NMR (CDCl$_3$, 400 MHz) δ 8.96 (d, 1H), 7.14 (d, 1H), 6.40 (d, 1H), 4.22 (t, 2H), 2.86 (t, 2H), 2.13-2.07 (m, 2H), 1.94-1.88 (m, 2H); MS (ESI) m/z=251.9 (M+H)$^+$

Reference Example 8. 2-Chloro-5-(1-(difluoromethyl)-1H-pyrazol-4-yl)-4-fluoropyridine The title compound as a white solid (773 mg) was prepared in the same fashion as Reference Example 2, except that 1-(difluoromethyl)pyrazole-4-boronic acid pinacol ester (1.23 g, 5.050 mmol) was used instead of 1-(difluoromethyl)-3-(4,4,5,5-tetramethyl-1,3,2-dioxaborolan-2-yl)pyrazole. $^1$H-NMR (CDCl$_3$, 400 MHz) δ 8.63 (d, 1H), 8.23 (s, 1H), 8.04 (s, 1H), 7.27 (t, 1H), 7.22 (d, 1H); MS (ESI) m/z=247.9 (M+H)$^+$

Reference Example 9. (1s,4s)-4-((2-Chloro-5-iodopyridin-4-yl)amino)cyclohexan-1-ol The reaction mixture of 2-chloro-4-fluoro-5-iodopyridine (500 mg, 1.942 mmol), cis-4-aminocyclohexanol hydrochloride (442 mg, 2.913 mmol) and DIPEA (1.01 mL, 5.827 mmol) in DMA (10 mL) was stirred at 70° C. for overnight. The reaction mixture was cooled to room temperature, diluted in DCM, washed by water, dried over MgSO$_4$, and then concentrated.

The crude product was purified by column chromatography (EA/n-Hex=0-50%) to yield (1s,4s)-4-((2-chloro-5-iodopyridin-4-yl)amino)cyclohexan-1-ol (562.5 mg) as a pale yellow liquid. MS (ESI) m/z=353.0 (M+H)$^+$

Reference Example 10. (1s,4s)-4-((2-Chloro-5-iodopyridin-4-yl)amino)-1-methylcyclohexan-1-ol The title compound as a white solid (1.33 g) was prepared in the same fashion as Reference Example 9, except that (1s,4s)-4-amino-1-methylcyclohexan-1-ol (1.13 g, 8.740 mmol) was used instead of cis-4-aminocyclohexanol hydrochloride. MS (ESI) m/z=367.0 (M+H)$^+$

Reference Example 11. (1s,4s)-N$^1$-(2-Chloro-5-iodopyridin-4-yl)-N$^4$-methylcyclohexane-1,4-diamine The title compound as a pale yellow liquid (1.89 g) was prepared in the same fashion as Reference Example 9, except that (1s,4s)-N$^1$-methylcyclohexane-1,4-diamine (1.12 g, 8.740 mmol) was used instead of cis-4-aminocyclohexanol hydrochloride. MS (ESI) m/z=366.0 (M+H)$^+$

Reference Example 12. 4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-one Step 1. 4-((2-Chloro-5-(2-(trifluoromethyl)thiazol-4-yl)-4-pyridyl)amino)cyclohexanone The title compound as an off-white solid (485 mg) was prepared in the same fashion as Reference Example 9, except that 4-aminocyclohexanone hydrochloride (529 mg, 3.538 mmol) and 4-(6-chloro-4-fluoro-3-pyridyl)-2-(trifluoromethyl)thiazole (500 mg, 1.769 mmol) prepared in Reference Example 4 were used instead of cis-4-aminocyclohexanol hydrochloride and 2-chloro-4-fluoro-5-iodopyridine. MS (ESI) m/z=376.0 (M+H)$^+$ Step 2. 4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-one The suspension of 2-(1-(cyclopropylsulfonyl)-1H-pyrazol-4-yl)pyrimidin-4-amine (240 mg, 0.905 mmol), tris(dibenzylideneacetone)dipalladium(0) (83 mg, 0.090 mmol), Xphos (86 mg, 0.181 mmol), cesium carbonate (884 mg, 2.714 mmol) and 4-((2-chloro-5-(2-(trifluoromethyl)

thiazol-4-yl)-4-pyridyl)amino)cyclohexanone (374 mg, 0.995 mmol) prepared in Step 1 in 1,4-dioxane (5 mL) was stirred at room temperature for 30 min, and then heated to 90° C. for overnight. The mixture was cooled at room temperature, filtered through Celite, and then concentrated. The crude product was crystallised by DCM/MeOH and triturated with EA/isopropyl ether to yield 4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-one (67 mg) as an off white solid. MS (ESI) m/z=605.0 (M+H)$^+$

Reference Example 13. 2-Chloro-N-(((1r,4r)-4-((dimethylamino)methyl)cyclohexyl)methyl)-5-iodopyridin-4-amine

Step 1. tert-Butyl (((1r,4r)-4-(((2-chloro-5-iodopyridin-4-yl)amino)methyl)cyclohexyl)methyl)carbamate The reaction mixture of 2,4-dichloro-5-iodopyridine (1.50 g, 5.477 mmol), tert-butyl (((1r,4r)-4-(aminomethyl)cyclohexyl)methyl)carbamate (1.46 g, 6.02 mmol) and cesium carbonate (3.57 g, 10.95 mmol) in DMF (15 mL) was stirred at 100° C. for 5 hours. The reaction mixture was cooled, diluted in DCM, washed by water, dried over MgSO$_4$, and then concentrated. The crude product was crystallised by DCM and triturated with isopropyl ether to yield tert-butyl (((1r,4r)-4-(((2-chloro-5-(cyclopropanecarbonyl)pyridin-4-yl)amino)methyl)cyclohexyl)methyl)carbamate (1.73 g) as a pale yellow solid. MS (ESI) m/z=480.1 (M+H)$^+$

Step 2. N-(((1r,4r)-4-(Aminomethyl)cyclohexyl)methyl)-2-chloro-5-iodopyridin-4-amine The reaction mixture of tert-butyl (((1r,4r)-4-(((2-chloro-5-iodopyridin-4-yl)amino)methyl)cyclohexyl)methyl)carbamate (1.75 g, 3.60 mmol) prepared in Step 1 and TFA (2.75 mL, 35.95 mmol) in DCM (13.75 mL) was stirred at room temperature overnight, and then concentrated. The residue was diluted in DCM, added 1 N NaOH soln. (>pH 8), washed by water, dried over MgSO$_4$, and then concentrated. The crude product was purified by column chromatography (MeOH/DCM=0-20%) to yield N-(((1r,4r)-4-(aminomethyl)cyclohexyl)methyl)-2-chloro-5-iodopyridin-4-amine (1.28 g) as a white solid. $^1$H-NMR (CDCl$_3$, 400 MHz) δ 8.23 (s, 1H), 6.36 (s, 1H), 4.94-74.72 (m, 1H), 3.03 (t, 2H), 2.53 (d, 2H), 1.85 (dd, 4H), 1.62-1.54 (m, 1H), 1.31-1.25 (m, 3H), 1.07-0.89 (m, 4H); MS (ESI) m/z=380.1 (M+H)$^+$

Step 3. 2-Chloro-N-(((1r,4r)-4-((dimethylamino)methyl)cyclohexyl)methyl)-5-iodopyridin-4-amine The reaction mixture of N-(((1r,4r)-4-(aminomethyl)cyclohexyl)methyl)-2-chloro-5-iodopyridin-4-amine (1.28 g, 3.358 mmol) prepared in Step 2, formaldehyde (7.5 mL, 100.75 mmol) and sodium triacetoxyborohydride (2.14 g, 10.07 mmol) in MeOH (10 mL) was stirred at 70° C. overnight. The reaction mixture was cooled, concentrated, diluted in DCM, washed by water, dried over MgSO$_4$, and then concentrated. The crude product was purified by column chromatography (MeOH/DCM=0-20%) to yield 2-chloro-N-(((1r,4r)-4-((dimethylamino)methyl)cyclohexyl)methyl)-5-iodopyridin-4-amine (825 mg) as a colorless oil. MS (ESI) m/z=408.1 (M+H)$^+$

Reference Example 14. Di-tert-butyl (2-bromopyrimidin-4-yl)iminodicarbonate

To a stirred solution of 2-bromopyrimidin-4-amine (3 g, 17.24 mmol) in THF (60 mL) was added di-tert-butyl dicarbonate (11.88 mL, 51.72 mmol), TEA (9.61 mL, 68.97 mmol) and 4-dimethylaminopyridine (211 mg, 1.72 mmol) at 0° C. The mixture was stirred at room temperature overnight. The reaction was quenched with water and extracted in DCM. The organic layer was dried over MgSO$_4$ and concentrated. The crude product was purified by column chromatography (EA/n-Hex=0-10%) to yield di-tert-butyl (2-bromopyrimidin-4-yl)iminodicarbonate (5.66 g) as a white solid. $^1$H-NMR (CDCl$_3$, 400 MHz) δ 8.40 (d, 1H), 7.75 (d, 1H), 1.57 (s, 18H)

Reference Example 15. (1s,4s)-4-((2-Chloro-5-(1-(difluoromethyl)-1H-pyrazol-3-yl)pyridin-4-yl)amino)-1-methylcyclohexan-1-ol To a solution of 2-chloro-5-(1-(difluoromethyl)-1H-pyrazol-3-yl)-4-fluoropyridine (4.48 g, 18.09 mmol) prepared in Reference Example 2 in DMA (40 mL) was added (1s,4s)-4-amino-1-methylcyclohexan-1-ol (3.51 g, 27.13 mmol) and DIPEA (9.45 mL, 54.26 mmol) was stirred at 100° C. for 2 hours. The reaction mixture was cooled to room temperature, quenched with water and extracted with EA. The organic layer was dried over MgSO$_4$, filtered, and concentrated. The crude product was purified by column chromatography (EA/n-Hex=10-65%) to yield (1s,4s)-4-((2-chloro-5-(1-(difluoromethyl)-1H-pyrazol-3-yl)pyridin-4-yl)amino)-1-methylcyclohexan-1-ol (6.04 g) as a white solid. $^1$H-NMR (CDCl$_3$, 400 MHz) δ 8.35 (s, 1H), 7.95 (d, 1H), 7.87 (d, 1H), 7.21 (t, 1H), 6.83 (d, 1H), 6.58 (s, 1H), 3.42-3.35 (m, 1H), 1.97-1.95 (m, 2H), 1.79-1.69 (m, 4H), 1.61-1.56 (m, 2H), 1.32 (s, 3H); MS (ESI) m/z=357.1 (M+H)$^+$

Reference Example 16. (1s,4s)-4-((2-Chloro-5-(1-methyl-5-(trifluoromethyl)-1H-pyrazol-3-yl)pyridin-4-yl)amino)-1-methylcyclohexan-1-ol

Step 1. 2-Chloro-4-fluoro-5-(1-methyl-5-(trifluoromethyl)-1H-pyrazol-3-yl)pyridine To a solution of 2-chloro-4-fluoro-5-iodopyridine (1.5 g, 5.83 mmol) in 1,4-dioxane (18 mL) were added 1-methyl-3-(tetramethyl-1,3,2-dioxaborolan-2-yl)-5-(trifluoromethyl)-1H-pyrazole (1.93 g, 6.99 mmol), [1,1'-bis(diphenylphosphino)ferrocene]dichloropalladium(II) dichloromethane complex (476 mg, 0.580 mmol) and 3M K$_2$CO$_3$ soln. (5.83 mL, 17.48 mmol). The reaction mixture was stirred at 90° C. for 2 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-30%) to give 2-chloro-4-fluoro-5-(1-methyl-5-(trifluoromethyl)-1H-pyrazol-3-yl)pyridine (1.26 g) as a white solid. $^1$H-NMR (DMSO-d$_6$, 400 MHz) δ 8.89 (d, 1H), 7.77 (d, 1H), 7.31 (s, 1H), 4.06 (s, 3H); MS (ESI) m/z 280.0= (M+H)$^+$

Step 2. (1s,4s)-4-((2-Chloro-5-(1-methyl-5-(trifluoromethyl)-1H-pyrazol-3-yl)pyridin-4-yl)amino)-1-methylcyclohexan-1-ol To a solution of 2-chloro-4-fluoro-5-(1-methyl-5-(trifluoromethyl)-1H-pyrazol-3-yl)pyridine (100 mg, 0.358 mmol)

prepared in Step 1 in DMA (3 mL) was added (1s,4s)-4-amino-1-methylcyclohexan-1-ol (69.31 g, 0.536 mmol) and DIPEA (0.19 mL, 1.073 mmol) and the reaction mixture was stirred at 90° C. for 4 hours. The reaction mixture was cooled to room temperature, quenched with water and extracted with EA. The organic layer was dried over MgSO$_4$, filtered, and concentrated. The crude product was purified by column chromatography (EA/n-Hex=10-65%) to yield (1s,4s)-4-((2-Chloro-5-(1-methyl-5-(trifluoromethyl)-1H-pyrazol-3-yl)pyridin-4-yl)amino)-1-methylcyclohexan-1-ol (92.6 mg) as a white solid. $^1$H-NMR (CDCl$_3$, 400 MHz) δ 8.28 (s, 1H), 7.96 (d, 1H), 6.95 (s, 1H), 6.56 (s, 1H), 4.03 (s, 3H), 3.37 (brs, 1H), 1.97-1.94 (m, 2H), 1.80-1.56 (m, 6H), 1.32 (s, 3H); MS (ESI) m/z=389.1 (M+H)$^+$ Reference Example 17. (1s,4s)-4-((2-Chloro-5-(1-(2,2-difluoroethyl)-1H-pyrazol-3-yl)pyridin-4-yl)amino)-1-methylcyclohexan-1-ol Step 1. 2-Chloro-5-(1-(2,2-difluoroethyl)-1H-pyrazol-3-yl)-4-fluoropyridine The reaction mixture of 2-chloro-4-fluoro-5-iodopyridine (3.00 g, 11.65 mmol), 1-(2,2-difluoroethyl)-3-(4,4,5,5-tetramethyl-1,3,2-dioxaborolan-2-yl)pyrazole (3.61 g, 13.98 mmol), [1,1'-bis(diphenylphosphino)ferrocene]dichloropalladium(II) dichloromethane complex (952 mg, 1.17 mmol) and 3M K$_2$CO$_3$ soln. (11.65 mL, 34.96 mmol) in 1,4-dioxane (36 mL) was stirred at 90° C. for 4 hours. The reaction mixture was cooled, diluted in DCM, washed by water, dried over MgSO$_4$, and then concentrated. The crude product was purified by column chromatography (EA/n-Hex=0-20%) to yield 2-chloro-5-(1-(2,2-difluoroethyl)-1H-pyrazol-3-yl)-4-fluoropyridine (2.15 g) as a white solid. $^1$H-NMR (CDCl$_3$, 400 MHz) δ 8.98 (d, 1H), 7.56 (d, 1H), 7.17 (d, 1H), 6.74 (t, 1H), 6.16 (tt, 1H), 4.54 (td, 2H); MS (ESI) m/z=262.0 (M+H)$^+$ Step 2. (1s,4s)-4-((2-Chloro-5-(1-(2,2-difluoroethyl)-1H-pyrazol-3-yl)pyridin-4-yl)amino)-1-methylcyclohexan-1-ol The reaction mixture of 2-chloro-5-(1-(2,2-difluoroethyl)-1H-pyrazol-3-yl)-4-fluoropyridine (100 mg, 0.38 mmol), (1s,4s)-4-amino-1-methylcyclohexan-1-ol (74 mg, 0.57 mmol), DIPEA (0.2 mL, 1.15 mmol) in DMA (1.5 mL) was stirred at 90° C. for 6 hours. The reaction mixture was cooled to room temperature, diluted in DCM, washed by water, dried over MgSO$_4$, and then concentrated. The crude product was purified by column chromatography (EA/n-Hex=0-60%) to yield (1s,4s)-4-((2-chloro-5-(1-(2,2-difluoroethyl)-1H-pyrazol-3-yl)pyridin-4-yl)amino)-1-methylcyclohexan-1-ol (123 mg) as pale yellow solid. $^1$H-NMR (CDCl$_3$, 400 MHz) δ 8.28 (s, 1H), 8.09 (d, 1H), 7.50 (d, 1H), 6.63 (d, 1H), 6.52 (s, 1H), 6.07 (tt, 1H), 4.48 (td, 2H), 3.37-3.31 (m 1H), 2.19 (brs, 1H), 1.92-1.85 (m, 2H), 1.77-1.67 (m, 4H), 1.58-1.50 (m, 2H), 1.28 (s, 3H); MS (ESI) m/z=371.1 (M+H)$^+$ Reference Example 18. (1s,4s)-4-((2-Chloro-5-(1-(2,2,2-trifluoroethyl)-1H-pyrazol-3-yl)pyridin-4-yl)amino)-1-methylcyclohexan-1-ol The title compound as a white solid (143 mg) was prepared in the same fashion as Reference Example 2, except that (1s,4s)-4-((2-chloro-5-iodopyridin-4-yl)amino)-1-methylcyclohexan-1-ol (150 mg, 0.41 mmol) prepared in Reference Example 10 and 3-(4,4,5,5-tetramethyl-1,3,2-dioxaborolan-2-yl)-1-(2,2,2-trifluoroethyl)pyrazole (147 mg, 0.53 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=389.1 (M+H)$^+$.

Reference Example 19. (1s,4s)-4-((2-Chloro-5-(1-(difluoromethyl)-1H-imidazol-4-yl)pyridin-4-yl)amino)-1-methylcyclohexan-1-ol Step 1. 2-Chloro-5-(1-(difluoromethyl)-1H-imidazol-4-yl)-4-fluoropyridine To a solution of 4-bromo-1-(difluoromethyl)imidazole (153 mg, 0.78 mmol) in 1,4-dioxane (4.0 mL) were added 2-chloro-4-fluoro-5-(4,4,5,5-tetramethyl-1,3,2-dioxaborolan-2-yl)pyridine (200 mg, 0.78 mmol), [1,1'-bis(diphenylphosphino)ferrocene]dichloropalladium(II) dichloromethane complex (32 mg, 0.04 mmol) and 3M K$_2$CO$_3$ soln. (0.78 mL, 2.33 mmol). The reaction mixture was stirred at 90° C. for 2 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-30%) to give 2-chloro-5-(1-(difluoromethyl)-1H-imidazol-4-yl)-4-fluoropyridine (20.1 mg) as a pale brown solid. MS (ESI) m/z=248.0 (M+H)$^+$.

Step 2. (1s,4s)-4-((2-Chloro-5-(1-(difluoromethyl)-1H-imidazol-4-yl)pyridin-4-yl)amino)-1-methylcyclohexan-1-ol The title compound as a colorless oil (27 mg) was prepared in the same fashion as Reference Example 15, except 2-chloro-5-(1-(difluoromethyl)-1H-imidazol-4-yl)-4-fluoropyridine (20 mg, 0.08 mmol) prepared in Step 1 was used instead of 2-chloro-5-(1-(difluoromethyl)-1H-pyrazol-3-yl)-4-fluoropyridine. MS (ESI) m/z=357.0 (M+H)$^+$.

Reference Example 20. (1s,4s)-4-((2-Chloro-5-(6,7-dihydro-5H-pyrrolo[1,2-a]imidazol-2-yl)pyridin-4-yl)amino)-1-methylcyclohexan-1-ol Step 1. 2-(6-Chloro-4-fluoropyridin-3-yl)-6,7-dihydro-5H-pyrrolo[1,2-a]imidazole The title compound as a pale brown solid (21.3 mg) was prepared in the same fashion as Step 1 in Reference Example 19, except that 2-bromo-6,7-dihydro-5H-pyrrolo[1,2-a]imidazole (145 mg, 0.778 mmol) was used instead of 4-bromo-1-(difluoromethyl)imidazole. MS (ESI) m/z=238.0 (M+H)$^+$.

Step 2. (1s,4s)-4-((2-Chloro-5-(6,7-dihydro-5H-pyrrolo[1,2-a]imidazol-2-yl)pyridin-4-yl)amino)-1-methylcyclohexan-1-ol The title compound as a pale yellow solid (22 mg) was prepared in the same fashion as Reference Example 15, except 2-(6-chloro-4-fluoropyridin-3-yl)-6,7-dihydro-5H-pyrrolo[1,2-a]imidazole (20 mg, 0.084 mmol) prepared in Step 1 was used instead of 2-chloro-5-(1-(difluoromethyl)-1H-pyrazol-3-yl)-4-fluoropyridine. MS (ESI) m/z=347.1 (M+H)$^+$.

Reference Example 21. 2-Chloro-4-fluoro-5-(1-(2,2,2-trifluoroethyl)-1H-pyrazol-3-yl)pyridine To a solution of 2-chloro-4-fluoro-5-iodopyridine (1.5 g, 5.83 mmol) in 1,4-dioxane (18 mL) were added (1-(2,2,2-trifluoroethyl)-1H-pyrazol-3-yl)boronic acid (1.36 g, 6.99 mmol), [1,1'-bis(diphenylphosphino)ferrocene]dichloropalladium(II) dichloromethane complex (476 mg, 0.58 mmol) and 3M $K_2CO_3$ soln. (5.83 mL, 17.48 mmol). The reaction mixture was stirred at 90° C. for 2 hours. The reaction mixture was cooled to room temperature, quenched with water, and then extracted with DCM. The organic layer was dried over $MgSO_4$, filtered, and concentrated. The crude residue was purified by silica gel column chromatography (EA/n-Hex=0-30%) to give 2-chloro-4-fluoro-5-[1-(2,2,2-trifluoroethyl)pyrazol-3-yl]pyridine (1.36 g) as a white solid. $^1$H-NMR (DMSO-$d_6$, 400 MHz) δ 8.89 (d, 1H), 7.77 (d, 1H), 7.31 (s, 1H), 4.06 (s, 3H); MS (ESI) m/z=280.0 $(M+H)^+$

Reference Example 22. 3-(3-(6-Chloro-4-fluoropyridin-3-yl)-1H-pyrazol-1-yl)-N,N-dimethylpropan-1-amine The title compound as a white solid (300.9 mg) was prepared in the same fashion as Reference Example 2, except that N,N-dimethyl-3-(3-(4,4,5,5-tetramethyl-1,3,2-dioxaborolan-2-yl)-1H-pyrazol-1-yl)propan-1-amine (423 mg, 1.52 mmol) was used instead of 1-(difluoromethyl)-3-(4,4,5,5-tetramethyl-1,3,2-dioxaborolan-2-yl)pyrazole. MS (ESI) m/z=283.0 $(M+H)^+$.

Reference Example 23. 2-Chloro-5-(1,5-dimethyl-1H-pyrazol-3-yl)-4-fluoropyridine The title compound as a white solid (603.2 mg) was prepared in the same fashion as Reference Example 2, except that 1,5-dimethyl-3-(4,4,5,5-tetramethyl-1,3,2-dioxaborolan-2-yl)-1H-pyrazole (797 mg, 3.59 mmol) was used instead of 1-(difluoromethyl)-3-(4,4,5,5-tetramethyl-1,3,2-dioxaborolan-2-yl)pyrazole. $^1$H-NMR (CDCl$_3$, 400 MHz) δ 8.94 (d, 1H), 7.13 (d, 1H), 6.43 (d, 1H), 3.85 (s, 3H), 2.33 (s, 3H)

Reference Example 24. 2-Chloro-4-fluoro-5-(1-(oxetan-3-yl)-1H-pyrazol-3-yl)pyridine The title compound as a white solid (456 mg) was prepared in the same fashion as Reference Example 2, except that (1-(oxetan-3-yl)-1H-pyrazol-3-yl)boronic acid (603 mg, 3.59 mmol) was used instead of 1-(difluoromethyl)-3-(4,4,5,5-tetramethyl-1,3,2-dioxaborolan-2-yl)pyrazole. $^1$H-NMR (CDCl$_3$, 400 MHz) δ 9.05 (d, 1H), 7.67 (d, 1H), 7.17 (d, 1H), 6.75 (d, 1H), 5.57-5.50 (m, 1H), 5.15-5.08 (m, 4H)

Reference Example 25. 2-Chloro-4-fluoro-5-(1-(trifluoromethyl)-1H-pyrazol-3-yl)pyridine The title compound as a pale yellow solid (106.2 mg) was prepared in the same fashion as Step 1 of Reference Example 19, except that 3-bromo-1-(trifluoromethyl)-1H-pyrazole (240 mg, 1.12 mmol) was used instead of 4-bromo-1-(difluoromethyl)imidazole. $^1$H-NMR (CDC$_3$, 400 MHz) δ 9.06 (d, 1H), 7.94 (s, 1H), 7.22 (d, 1H), 6.88 (s, 1H)

Reference Example 26. 2-Chloro-4-fluoro-5-(1-(1-methylpiperidin-4-yl)-1H-pyrazol-3-yl)pyridine The title compound as a pale yellow solid (567 mg) was prepared in the same fashion as Step 1 of Reference Example 19, except that 4-(3-bromo-1H-pyrazol-1-yl)-1-methylpiperidine (810 mg, 3.32 mmol) was used instead of 4-bromo-1-(difluoromethyl)imidazole. MS (ESI) m/z=295.1 $(M+H)^+$

Reference Example 27. 2-Chloro-N-((1s,4s)-4-((dimethylamino)methyl)cyclohexyl)-5-iodopyridin-4-amine The title compound as pale yellow liquid (661.2 mg) was prepared in the same fashion as Reference Example 9, except that (1s,4s)-4-((dimethylamino)methyl)cyclohexan-1-amine dihydrochloride (668 mg, 2.91 mmol) was used instead of cis-4-aminocyclohexanol hydrochloride. MS (ESI) m/z=394.0 $(M+H)^+$

Reference Example 28. ((1s,4s)-4-((2-Chloro-5-iodopyridin-4-yl)amino)cyclohexyl)methanol The title compound as pale yellow liquid (606.3 mg) was prepared in the same fashion as Reference Example 9, except that ((1s,4s)-4-aminocyclohexyl)methanol (129 mg, 2.91 mmol) was used instead of cis-4-aminocyclohexanol hydrochloride. MS (ESI) m/z=367.0 $(M+H)^+$

Reference Example 29. (1s,4s)-$N^1$-(2-Chloro-5-iodopyridin-4-yl)-$N^4$-(2-fluoroethyl)cyclohexane-1,4-diamine The title compound as pale yellow liquid (635 mg) was prepared in the same fashion as Reference Example 9, except that (1s,4s)-$N^1$-(2-fluoroethyl)cyclohexane-1,4-diamine (160 mg, 2.91 mmol) was used instead of cis-4-aminocyclohexanol hydrochloride. MS (ESI) m/z=398.0 $(M+H)^+$

Reference Example 30. 2-Chloro-N-((1s,4s)-4-fluorocyclohexyl)-5-iodopyridin-4-amine The title compound as a white solid (435 mg) was prepared in the same fashion as Reference Example 9, except that cis-4-fluorocyclohexan-1-amine hydrochloride (388 mg, 2.53 mmol) was used instead of cis-4-aminocyclohexanol hydrochloride. MS (ESI) m/z=355.0 $(M+H)^+$

Reference Example 31. (1s,4s)-4-((2-Chloro-5-(4,4,5,5-tetramethyl-1,3,2-dioxaborolan-2-yl)pyridin-4-yl)amino)-1-methylcyclohexan-1-ol To a solution of 2-chloro-4-fluoro-5-(4,4,5,5-tetramethyl-1,3,2-dioxaborolan-2-yl)pyridine (1.00 g, 3.88 mmol) in DMA (10 mL) were added (1s,4s)-4-amino-1-methylcyclohexan-1-ol (753 mg, 5.83 mmol) and DIPEA (1.73 mL, 9.71 mmol). The reaction mixture was heated to 90° C. for 4 hours. The reaction mixture was cooled to room temperature, quenched with water, and then extracted with DCM. The organic layer was dried over $MgSO_4$, filtered, and concentrated. The crude residue was purified by silica gel column chromatography (EA/n-Hex=0-50%) to give (1s,4s)-4-((2-chloro-5-(4,4,5,5-tetramethyl-1,3,2-dioxaborolan- 2-yl)pyridin-4-yl)amino)-1-methylcyclohexan-1-ol (1.31 g) as a pale yellow solid. MS (ESI) m/z=285.1 (M+H)$^+$

Reference Example 32. (1s,4s)-4-((5-Bromo-2-chloropyrimidin-4-yl)amino)-1-methylcyclohexan-1-ol The title compound as a white solid (322 mg) was prepared in the same fashion as Reference Example 9, except that 5-bromo-2,4-dichloropyrimidine (300 mg, 1.32 mmol) and (1s,4s)-4-amino-1-methylcyclohexan-1-ol (388 mg, 2.53 mmol) were used instead of 2-chloro-4-fluoro-5-iodopyridine and cis-4-aminocyclohexanol hydrochloride. $^1$H-NMR (MeOD, 400 MHz) δ 8.11 (s, 1H), 4.05-3.97 (m, 1H), 1.82-1.69 (m, 6H), 1.59-1.51 (m, 2H), 1.23 (s, 3H)

Reference Example 33. 2-Chloro-N-((1s,4s)-4-fluorocyclohexyl)-5-iodopyrimidin-4-amine The title compound as a white solid (95 mg) was prepared in the same fashion as Reference Example 9, except that 2-chloro-4-fluoro-5-iodopyrimidine (90 mg, 0.33 mmol) and cis-4-fluorocyclohexan-1-amine hydrochloride (65 mg, 0.43 mmol) was used instead of 2-chloro-4-fluoro-5-iodopyridine and cis-4-aminocyclohexanol hydrochloride. $^1$H-NMR (MeOD, 400 MHz) δ 8.27 (s, 1H), 4.80 (d, 1H), 4.12-4.07 (m, 1H), 2.07-2.03 (m, 2H), 1.83-1.62 (m, 6H)

Reference Example 34. (1s,4s)-4-((3-Bromo-6-chloropyridazin-4-yl)amino)-1-methylcyclohexan-1-ol The title compound as a white solid (506 mg) was prepared in the same fashion as Reference Example 9, except that 3-bromo-4,6-dichloro-pyridazine (400 mg, 1.76 mmol) and (1s,4s)-4-amino-1-methylcyclohexan-1-ol (340 mg, 2.63 mmol) was used instead of 2-chloro-4-fluoro-5-iodopyridine and cis-4-aminocyclohexanol hydrochloride. $^1$H-NMR (MeOD, 400 MHz) δ 6.45 (s, 1H), 5.05 (d, 1H), 3.31-3.22 (m, 1H), 1.92-1.89 (m, 2H), 1.80-1.69 (m, 4H), 1.58-1.50 (m, 2H), 1.31 (s, 1H)

Reference Example 35. 2-(1-(Cyclopropylsulfonyl)-1H-pyrazol-4-yl)-5-fluoropyrimidin-4-amine To a solution of 4-amino-2-chloro-5-fluoropyrimidine (1.50 g, 10.17 mmol) in 1,4-dioxane (50.85 mL) were added 1-(cyclopropanesulfonyl)-4-(tetramethyl-1,3,2-dioxaborolan-2-yl)-1H-pyrazole (3.64 g, 12.2 mmol), [1,1'-bis(diphenylphosphino)ferrocene]dichloropalladium(II) dichloromethane complex (830 mg, 1.02 mmol) and 3M K$_2$CO$_3$ soln. (10.17 mL, 30.5 mmol). The reaction mixture was stirred at 90° C. for 3 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-80%) to give 2-(1-(cyclopropylsulfonyl)-1H-pyrazol-4-yl)-5-fluoropyrimidin-4-amine (1.49 g) as yellowish solid. $^1$H-NMR (DMSO-d$_6$, 400 MHz) δ 8.47 (s, 1H), 8.29 (s, 1H), 8.19 (d, 1H), 7.38 (s, 2H), 3.26-3.19 (m, 1H), 1.33-1.20 (m, 4H); MS (ESI) m/z=284.0 (M+H)$^+$

Reference Example 36. 2-(1-(2,2-Difluoroethyl)-1H-pyrazol-4-yl)pyrimidin-4-amine To a solution of 2-bromo-4-pyrimidinamine (500 mg, 2.87 mmol) in 1,4-dioxane (9 mL) were added 1-(2,2-difluoroethyl)-4-(4,4,5,5-tetramethyl-1,3,2-dioxaborolan-2-yl)pyrazole (964 mg, 3.74 mmol), [[1,1'-bis(diphenylphosphino)ferrocene]dichloropalladium(II) dichloromethane complex (235 mg, 0.29 mmol) and 3M K$_2$CO$_3$ soln. (2.87 mL, 8.62 mmol). The reaction mixture was stirred at 90° C. for 3 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-70%) to give 2-(1-(2,2-difluoroethyl)-1H-pyrazol-4-yl)pyrimidin-4-amine (325 mg) as yellowish solid. $^1$H-NMR (CDCl$_3$, 400 MHz) δ 8.23 (d, 1H), 8.18 (s, 1H), 8.12 (s, 1H), 6.27 (d, 1H), 6.13 (tt, 1H), 4.87 (s, 2H), 4.50 (td, 2H); MS (ESI) m/z=226.0 (M+H)$^+$

Reference Example 37. 2-(1-(2,2,2-Trifluoroethyl)-1H-pyrazol-4-yl)pyrimidin-4-amine The title compound as a white solid (303 mg) was prepared in the same fashion as Reference Example 36, except that 4-(4,4,5,5-tetramethyl-1,3,2-dioxaborolan-2-yl)-1-(2,2,2-trifluoroethyl)-1H-pyrazole (619 mg, 2.24 mmol) was used instead of 1-(2,2-difluoroethyl)-4-(4,4,5,5-tetramethyl-1,3,2-dioxaborolan-2-yl)pyrazole. $^1$H-NMR (MeOD, 400 MHz) δ 8.30 (s, 1H), 8.13 (s, 1H), 8.04 (d, 1H), 6.36 (d, 1H), 5.01 (q, 2H); MS (ESI) m/z=244.0 (M+H)$^+$.

Reference Example 38. 2-(3-Methyl-1-(2,2,2-trifluoroethyl)-1H-pyrazol-4-yl)pyrimidin-4-amine The title compound as a white solid (325 mg) was prepared in the same fashion as Reference Example 36, except 3-methyl-4-(4,4,5,5-tetramethyl-1,3,2-dioxaborolan-2-yl)-1-(2,2,2-trifluoroethyl)pyrazole (650 mg, 2.24 mmol) was used instead of 1-(2,2-difluoroethyl)-4-(4,4,5,5-tetramethyl-1,3,2-dioxaborolan-2-yl)pyrazole. MS (ESI) m/z=284.0 (M+H)$^+$.

Reference Example 39. 4-(4-Aminopyrimidin-2-yl)-N,N-dimethyl-1H-pyrazole-1-sulfonamide The title compound as a white solid (344 mg) was prepared in the same fashion as Reference Example 36, except that 4-amino-2-chloropyrimidine (250 mg, 1.93 mmol) and N,N-dimethyl-4-(4,4,5,5-tetramethyl-1,3,2-dioxaborolan-2-yl)pyrazole-1-sulfonamide (697 mg, 2.32 mmol) were used instead of 2-bromo-4-pyrimidinamine and 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.59 (s, 1H), 8.33 (s, 1H), 8.25 (sd, 1H), 6.31 (d, 1H), 4.95 (s, 2H), 2.98 (s, 6H)

Reference Example 40. 2-(1-(Ethylsulfonyl)-1H-pyrazol-4-yl)pyrimidin-4-amine The title compound as pale yellow solid (469.1 mg) was prepared in the same fashion as Reference Example 36, except that 4-amino-2-chloropyrimidine (500 mg, 3.86 mmol) and 1-ethylsulfonyl-4-(4,4,5,5-tetramethyl-1,3,2-dioxaborolan-2-yl)pyrazole (1.33 g, 4.63 mmol) were used instead of 2-bromo-4-pyrimidinamine and 1-(2,2-difluoroethyl)-4-(4,4,5,5-tetramethyl-1,3,2-dioxaborolan-2-yl)pyrazole. MS (ESI) m/z=254.0 (M+H)$^+$.

Reference Example 41. 2-(1-(Ethylsulfonyl)-1H-pyrazol-3-yl)pyrimidin-4-amine The title compound as pale yellow solid (103.2 mg) was prepared in the same fashion as Reference Example 36, except that 4-amino-2-chloropyrimidine (500 mg, 3.86 mmol) and 1-ethylsulfonyl-3-(4,4,5,5-tetramethyl-1,3,2-dioxaborolan-2-yl)pyrazole (1.33 g, 4.63 mmol) were used instead of 2-bromo-4-pyrimidinamine and 1-(2,2-difluoroethyl)-4-(4,4,5,5-tetramethyl-1,3,2-dioxaborolan-2-yl)pyrazole. MS (ESI) m/z=254.0 (M+H)+.

Reference Example 42. 2-(1-(Methoxymethyl)-1H-pyrazol-4-yl)pyrimidin-4-amine The title compound as pale yellow solid (231 mg) was prepared in the same fashion as Reference Example 36, except that 4-amino-2-chloropyrimidine (500 mg, 3.86 mmol) and 1-(methoxymethyl)-4-(4,4,5,5-tetramethyl-1,3,2-dioxaborolan-2-yl)pyrazole (1.10 g, 4.63 mmol) were used instead of 2-bromo-4-pyrimidinamine and 1-(2,2-difluoroethyl)-4-(4,4,5,5-tetramethyl-1,3,2-dioxaborolan-2-yl)pyrazole. MS (ESI) m/z=206.1 (M+H)+.

Reference Example 43. 4-(4-Aminopyrimidin-2-yl)-N,N-dimethyl-1H-pyrazole-1-carboxamide The title compound as off-white solid (298 mg) was prepared in the same fashion as Reference Example 36, except that 4-amino-2-chloropyrimidine (500 mg, 3.86 mmol) and N,N-dimethyl-4-(4,4,5,5-tetramethyl-1,3,2-dioxaborolan-2-yl)-1H-pyrazole-1-carboxamide (1.23 g, 4.63 mmol) were used instead of 2-bromo-4-pyrimidinamine and 1-(2,2-difluoroethyl)-4-(4,4,5,5-tetramethyl-1,3,2-dioxaborolan-2-yl)pyrazole. MS (ESI) m/z=233.1 (M+H)+

Reference Example 44. 2'-Methoxy-[2,5'-bipyrimidin]-4-amine

The title compound as a white solid (203.2 mg) was prepared in the same fashion as Reference Example 36, except that 4-amino-2-chloropyrimidine (300 mg, 2.32 mmol) and 2-methoxy-5-(4,4,5,5-tetramethyl-1,3,2-dioxaborolan-2-yl)pyrimidine (656 mg, 2.78 mmol) were used instead of 2-bromo-4-pyrimidinamine and 1-(2,2-difluoroethyl)-4-(4,4,5,5-tetramethyl-1,3,2-dioxaborolan-2-yl)pyrazole. MS (ESI) m/z=204.2 (M+H)+

Reference Example 45. 2-(1-(Tetrahydro-2H-pyran-2-yl)-1H-pyrazol-4-yl)pyrimidin-4-amine The title compound as a white solid (456 mg) was prepared in the same fashion as Reference Example 36, except that 4-amino-2-chloropyrimidine (400 mg, 3.09 mmol) and 1-(tetrahydro-2H-pyran-2-yl)-4-(4,4,5,5-tetramethyl-1,3,2-dioxaborolan-2-yl)-1H-pyrazole (1.03 g, 3.71 mmol) were used instead of 2-bromo-4-pyrimidinamine and 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.28 (s, 1H), 8.22 (d, 1H), 8.17 (s, 1H), 6.24 (d, 1H), 5.42 (dd, 1H), 4.87 (s, 2H), 4.08-4.05 (m, 1H), 3.72 (td, 1H), 2.20-2.03 (m, 3H), 1.76-1.61 (m, 3H); MS (ESI) m/z=246.1 (M+H)+

Reference Example 46. 4-(4-Aminopyrimidin-2-yl)-N,N,3-trimethyl-1H-pyrazole-1-sulfonamide The title compound as a white solid (325 mg) was prepared in the same fashion as Reference Example 36, except that 4-amino-2-chloropyrimidine (300 mg, 2.32 mmol) and (1-(N,N-dimethylsulfamoyl)-3-methyl-1H-pyrazol-4-yl)boronic acid (648 mg, 2.78 mmol) were used instead of 2-bromo-4-pyrimidinamine and 1-(2,2-difluoroethyl)-4-(4,4,5,5-tetramethyl-1,3,2-dioxaborolan-2-yl)pyrazole. MS (ESI) m/z=283.2 (M+H)+

Reference Example 47. 2-(1-(Tetrahydrofuran-2-yl)-1H-pyrazol-4-yl)pyrimidin-4-amine The title compound as a white solid (231.3 g) was prepared in the same fashion as Reference Example 36, except that 4-amino-2-chloropyrimidine (250 mg, 1.93 mmol) and 1-(tetrahydrofuran-2-yl)-4-(4,4,5,5-tetramethyl-1,3,2-dioxaborolan-2-yl)-1H-pyrazole (765 g, 2.89 mmol) were used instead of 2-bromo-4-pyrimidinamine and 1-(2,2-difluoroethyl)-4-(4,4,5,5-tetramethyl-1,3,2-dioxaborolan-2-yl)pyrazole. $^1$H-NMR (MeOD, 400 MHz) δ 8.29 (s, 1H), 8.08 (s, 1H), 8.03 (d, 1H), 6.34 (d, 1H), 6.05 (dd, 1H), 4.19-4.14 (m, 1H), 4.00 (q, 1H), 2.52-2.35 (m, 2H), 2.24-2.02 (m, 2H); MS (ESI) m/z=232.1 (M+H)+.

Reference Example 48. 2-(5-Fluoro-1,3-dimethyl-1H-pyrazol-4-yl)pyrimidin-4-amine The title compound as yellow solid (92 mg) was prepared in the same fashion as Reference Example 36, except that 5-fluoro-1,3-dimethyl-4-(4,4,5,5-tetramethyl-1,3,2-dioxaborolan-2-yl)-1H-pyrazole (414 mg, 1.72 mmol) was used instead of 1-(2,2-difluoroethyl)-4-(4,4,5,5-tetramethyl-1,3,2-dioxaborolan-2-yl)pyrazole. $^1$H-NMR (MeOD, 400 MHz) δ 8.07 (d, 1H), 6.33 (d, 1H), 3.71 (s, 3H), 2.46 (s, 3H)

Reference Example 49. 2-(1-(2,2-Difluoroethyl)-3,5-dimethyl-1H-pyrazol-4-yl)pyrimidin-4-amine The title compound as a white solid (122.7 mg) was prepared in the same fashion as Reference Example 36, except that 1-(2,2-difluoroethyl)-3,5-dimethyl-4-(4,4,5,5-tetramethyl-1,3,2-dioxaborolan-2-yl)-1H-pyrazole (641 mg, 2.24 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.29 (d, 1H), 6.26 (d, 1H), 6.12 (tt, 1H), 4.78 (s, 2H), 4.39 (td, 2H), 2.62 (s, 3H), 2.52 (s, 3H)

Reference Example 50. 2-(1-(2,2,3,3-Tetrafluoropropyl)-1H-pyrazol-4-yl)pyrimidin-4-amine The title compound as a white solid (293.1 mg) was prepared in the same fashion as Reference Example 36, except that 1-(2,2,3,3-tetrafluoropropyl)-4-(4,4,5,5-tetramethyl-1,3,2-dioxaborolan-2-yl)-1H-pyrazole (691 mg, 2.24 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.24 (d, 1H), 8.20 (s, 1H), 8.16 (s, 1H), 6.28 (d, 1H), 5.88 (tt, 1H), 4.85 (s, 2H), 4.70 (t, 2H)

Reference Example 51. 2-(1-(Pyrrolidin-1-ylsulfonyl)-1H-pyrazol-4-yl)pyrimidin-4-amine To a solution of 4-(4,4,5,5-tetramethyl-1,3,2-dioxaborolan-2-yl)pyrazole (250 mg, 1.29 mmol) in DMF (5 mL) was added sodium hydride, 60% in mineral oil (62 mg, 1.55 mmol) with ice bath cooling. Ice bath was removed and it was stirred at rt for 15 min. To the reaction mixture was added pyrrolidine-1-sulfonyl chloride (328 mg, 1.93 mmol) at room temperature. After being stirred at room temperature for 5 hours, volatiles were removed in vacuo. To this were added sat. NH$_4$Cl soln. and DCM. The mixture was extracted with DCM, dried over Na$_2$SO$_4$, and concentrated. The crude residue diluted in 1,4-dioxane (5 mL) were added 2-bromo-4-pyrimidinamine (224 mg, 1.29 mmol), [1,1'-bis(diphenylphosphino)ferrocene]dichloropalladium(II) dichloromethane complex (105 mg, 0.1300 mmol) and 3M K$_2$CO$_3$ soln. (1.29 mL, 3.87 mmol). The reaction mixture was stirred at 90° C. for 3 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-80%) to give 2-(1-(pyrrolidin-1-ylsulfonyl)-1H-pyrazol-4-yl)pyrimidin-4-amine (96.5 mg) as a pale yellow oil. $^1$H-NMR (CDCl$_3$, 400 MHz) δ 8.62 (s, 1H), 8.31 (s, 1H), 8.25 (d, 1H), 6.31 (d, 1H), 4.91 (s, 2H), 3.52-3.49 (m, 4H), 1.88-1.84 (m, 4H); MS (ESI) m/z=295.1 (M+H)$^+$.

Reference Example 52. 2-(1-((3-Fluoroazetidin-1-yl)sulfonyl)-1H-pyrazol-4-yl)pyrimidin-4-amine The title compound as pale yellow oil (122 mg) was prepared in the same fashion as Reference Example 51, except that 3-fluoroazetidine-1-sulfonyl chloride (335 mg, 1.93 mmol) was used instead of pyrrolidine-1-sulfonyl chloride. $^1$H-NMR (CDCl$_3$, 400 MHz) δ 8.63 (s, 1H), 8.41 (s, 1H), 8.25 (d, 1H), 6.33 (d, 1H), 5.25-5.07 (m, 1H), 5.02 (s, 2H), 4.43-4.22 (m, 4H); MS (ESI) m/z=299.0 (M+H)$^+$ Reference Example 53. (1-(4-Aminopyrimidin-2-yl)-4,4-difluoropyrrolidin-3-yl)methanol To a solution of 4-amino-2-chloropyrimidine (100 mg, 0.77 mmol) in DMA (2 mL) were added DIPEA (0.34 mL, 1.93 mmol) and (4,4-difluoropyrrolidin-3-yl)methanol (159 mg, 1.16 mmol). The reaction mixture was stirred at 90° C. overnight. The reaction mixture was cooled to room temperature, quenched with water, and then extracted with DCM. The organic layer was dried over MgSO$_4$, filtered, and concentrated. The crude residue was purified by silica gel column chromatography (EA/MeOH=0-20%) to give (1-(4-aminopyrimidin-2-yl)-4,4-difluoropyrrolidin-3-yl)methanol (36.8 mg) as a yellowish solid. $^1$H-NMR (MeOD, 400 MHz) δ 7.75 (d, 1H), 5.90 (d, 1H), 3.93-3.83 (m, 4H), 3.72-3.67 (m, 1H), 3.55-3.50 (m, 1H), 2.82-2.75 (m, 1H)

Reference Example 54. (1-(4-Aminopyrimidin-2-yl)-4,4-dimethylpyrrolidin-3-yl)methanol The title compound as pale yellow oil (88.7 mg) was prepared in the same fashion as Reference Example 53, except that (4,4-dimethylpyrrolidin-3-yl)methanol (150 mg, 1.16 mmol) was used instead of (4,4-difluoropyrrolidin-3-yl)methanol. $^1$H-NMR (CDCl$_3$, 400 MHz) δ 7.92 (d, 1H), 5.74 (d, 1H), 4.95 (s, 2H), 3.87-3.80 (m, 2H), 3.66-3.61 (m, 1H), 3.47 (d, 1H), 3.39 (t, 1H), 3.27 (d, 1H), 2.19-2.12 (m, 1H), 1.18 (s, 3H), 0.99 (s, 3H)

Reference Example 55. 1-(4-Aminopyrimidin-2-yl)-4,4-difluoropyrrolidin-3-ol

The title compound as pale yellow oil (52 mg) was prepared in the same fashion as Reference Example 53, except that 4,4-difluoropyrrolidin-3-ol hydrochloride (240 mg, 1.51 mmol) was used instead of (4,4-difluoropyrrolidin-3-yl)methanol. $^1$H-NMR (CDCl$_3$, 400 MHz) δ 7.92 (d, 1H), 5.81 (d, 1H), 4.70 (s, 2H), 4.34 (brs, 1H), 3.95-3.85 (m, 3H), 3.72-3.69 (m, 1H); MS (ESI) m/z=217.0 (M+H)$^+$ Reference Example 56. 1-(4-Aminopyrimidin-2-yl)-3,3-difluoropiperidin-4-ol The title compound as pale yellow oil (87.3 mg) was prepared in the same fashion as Reference Example 53, except that 3,3-difluoropiperidin-4-ol hydrochloride (201 mg 1.16 mmol) was used instead of (4,4-difluoropyrrolidin-3-yl)methanol. $^1$H-NMR (CDCl$_3$, 400 MHz) δ 7.74 (d, 1H), 5.85 (d, 1H), 4.23-4.13 (m, 1H), 3.96-3.82 (m, 3H), 3.67-3.62 (m, 1H), 1.96-1.90 (m, 1H), 1.79-1.72 (m, 1H); MS (ESI) m/z=231.0 (M+H)$^+$ Reference Example 57. 1-(4-Aminopyrimidin-2-yl)-4,4-difluoropiperidin-3-ol The title compound as pale yellow oil (123 mg) was prepared in the same fashion as Reference Example 53, except that 4,4-difluoropiperidin-3-ol hydrochloride (301 mg, 1.74 mmol) was used instead of (4,4-difluoropyrrolidin-3-yl)methanol. $^1$H-NMR (MeOD, 400 MHz) δ 7.75 (d, 1H), 5.85 (d, 1H), 4.13-4.00 (m, 1H), 3.99-3.96 (m, 1H), 3.77-3.70 (m, 1H), 3.68-3.58 (m, 2H), 2.23-2.10 (m, 1H), 1.94-1.81 (m, 1H); MS (ESI) m/z=231.1 (M+H)$^+$ Reference Example 58. (S)-1-(4-Aminopyrimidin-2-yl)piperidin-3-ol The title compound as pale yellow oil (99.5 mg) was prepared in the same fashion as Reference Example 53, except that (S)-piperidin-3-ol hydrochloride (239 mg, 1.74 mmol) was used instead of (4,4-difluoropyrrolidin-3-yl)methanol. $^1$H-NMR (DMSO-d$_6$, 400 MHz) δ 7.70 (d, 1H), 6.30 (s, 2H), 5.67 (d, 1H), 4.80 (d, 1H), 4.49-4.45 (m, 1H), 4.33-4.30 (m, 1H), 2.78-2.71 (m, 1H), 2.59 (dd, 1H), 1.89-1.86 (m, 1H), 1.64-1.62 (m, 1H), 1.32-1.22 (m, 2H)

Reference Example 59. (R)-1-(4-Aminopyrimidin-2-yl)piperidin-3-ol

The title compound as pale yellow oil (103.4 mg) was prepared in the same fashion as Reference Example 53, except that (R)-piperidin-3-ol hydrochloride (239 mg, 1.74 mmol) was used instead of (4,4-difluoropyrrolidin-3-yl)methanol. $^1$H-NMR (DMSO-d$_6$, 400 MHz) δ 7.70 (d, 1H), 6.30 (s, 2H), 5.67 (d, 1H), 4.80 (d, 1H), 4.49-4.45 (m, 1H), 4.33-4.30 (m, 1H), 2.78-2.71 (m, 1H), 2.59 (dd, 1H), 1.89-1.85 (m, 1H), 1.66-1.60 (m, 1H), 1.32-1.23 (m, 2H)

Reference Example 60. 2-(1-(Cyclopropylsulfonyl)-1H-pyrazol-4-yl)pyridin-4-amine The title compound as a white solid (528 mg) was prepared in the same fashion as Reference Example 35, except that 2-iodopyridin-4-amine (500 mg, 2.27 mmol) was used instead of 4-amino-2-chloro-5-fluoropyrimidine. $^1$H-NMR (CDCl$_3$, 400 MHz) δ 8.43 (s, 1H), 8.23 (s, 1H), 8.22 (d, 1H), 6.77 (d, 1H), 6.47 (dd, 1H), 4.29 (s, 2H), 2.83-2.76 (m, 1H), 1.52-1.48 (m, 2H), 1.28-1.19 (m, 2H)

Reference Example 61. 2-(1-(2,2-Difluoroethyl)-1H-pyrazol-4-yl)pyridin-4-amine

The title compound as a white solid (388 mg) was prepared in the same fashion as Reference Example 36, except that 2-iodopyridin-4-amine (500 mg, 2.27 mmol) was used instead of 2-bromo-4-pyrimidinamine. $^1$H-NMR (CDCl$_3$, 400 MHz) δ 8.20 (d, 1H), 7.99 (s, 1H), 7.96 (s, 1H), 6.73 (s, 1H), 6.41 (d, 1H), 6.12 (tt, 1H), 4.49 (td, 2H), 4.19 (s, 2H)

Reference Example 62. 2-(3-Methyl-1-(2,2,2-trifluoroethyl)-1H-pyrazol-4-yl)pyridin-4-amine The title compound as a white solid (80 mg) was prepared in the same fashion as Reference Example 35, except that 2-iodopyridin-4-amine (125 mg, 2.27 mmol) and 3-methyl-4-(4,4,5,5-tetramethyl-1,3,2-dioxaborolan-2-yl)-1-(2,2,2-trifluoroethyl)pyrazole (198 mg, 0.682 mmol) were used instead of 4-amino-2-chloro-5-fluoropyrimidine and 1-(cyclopropanesulfonyl)-4-(tetramethyl-1,3,2-dioxaborolan-2-yl)-1H-pyrazole. $^1$H-NMR (CDCl$_3$, 400 MHz) δ 8.24 (d, 1H), 7.91 (s, 1H), 6.70 (d, 1H), 6.43 (dd, 1H), 4.65 (q, 2H), 4.19 (s, 2H)

Example 1. N-(5-(1-Cyclopropyl-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine

Step 1. 2-Chloro-5-(1-cyclopropyl-1H-pyrazol-4-yl)-4-((1-methyl-1H-pyrazol-4-yl)ethynyl)pyridine The reaction mixture of 5-bromo-2-chloro-4-(2-(1-methylpyrazol-4-yl)ethynyl)pyridine (150 mg, 0.506 mmol) prepared in Reference Example 1, 1-cyclopropyl-4-(4,4,5,5-tetramethyl-1,3,2-dioxaborolan-2-yl)pyrazole (130 mg, 0.556 mmol), bis(triphenylphosphine)palladium(II) dichloride (18 mg, 0.025 mmol) and 2 M Na$_2$CO$_3$ soln. (0.76 mL) in 1,4-dioxane (5 mL) was stirred at 90° C. for 3 hours. The reaction mixture was cooled, diluted in DCM, washed by water, dried over MgSO$_4$, and then concentrated. The crude product was purified by column chromatography (EA/n-Hex=0-20%) to yield 2-chloro-5-(1-cyclopropyl-1H-pyrazol-4-yl)-4-((1-methyl-1H-pyrazol-4-yl)ethynyl)pyridine (32.9 mg) as a white solid. $^1$H-NMR (CDCl$_3$, 400 MHz) δ 9.02 (d, 1H), 7.93 (d, 1H), 7.29 (t, 1H), 7.20 (d, 1H), 6.88 (t, 1H); MS (ESI) m/z=324.1 (M+H)$^+$

Step 2. N-(5-(1-Cyclopropyl-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine The suspension of 2-(1-(cyclopropylsulfonyl)-1H-pyrazol-4-yl)pyrimidin-4-amine (20 mg, 0.08 mmol), tris(dibenzylideneacetone)dipalladium(0) (3.5 mg, 0.004 mmol), Xphos (3.6 mg, 0.01 mmol), cesium carbonate (61.4 mg, 0.19 mmol) and 2-chloro-5-(1-cyclopropyl-1H-pyrazol-4-yl)-4-((1-methyl-1H-pyrazol-4-yl)ethynyl)pyridine (24 mg, 0.075 mmol) prepared in Step 1 in 1,4-dioxane (1 mL) was stirred at 110° C. overnight. The mixture was diluted in DCM, filtered through Celite, and then concentrated. The crude product was crystallised by EA/n-Hex and triturated with EA/isopropyl ether to yield N-(5-(1-Cyclopropyl-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine (4 mg) as an off-white solid. MS (ESI) m/z=553.2 (M+H)$^+$

Example 2. 2-(1-(Cyclopropylsulfonyl)-1H-pyrazol-4-yl)-N-(5-(1-(difluoromethyl)-1H-pyrazol-4-yl)-4-((1-methyl-1H-pyrazol-4-yl)ethynyl)pyridin-2-yl)pyrimidin-4-amine

Step 1. 2-Chloro-5-(1-(difluoromethyl)-1H-pyrazol-4-yl)-4-((1-methyl-1H-pyrazol-4-yl)ethynyl)pyridine The title compound as a white solid (54 mg) was prepared in the same fashion as Step 1 in Example 1 except that 1-(difluoromethyl)-4-(4,4,5,5-tetramethyl-1,3,2-dioxaborolan-2-yl)pyrazole (90.5 mg, 0.371 mmol) was used instead of 1-cyclopropyl-4-(4,4,5,5-tetramethyl-1,3,2-dioxaborolan-2-yl)pyrazole. MS (ESI) m/z=334.0 (M+H)$^+$

Step 2. 2-(1-(Cyclopropylsulfonyl)-1H-pyrazol-4-yl)-N-(5-(1-(difluoromethyl)-1H-pyrazol-4-yl)-4-((1-methyl-1H-pyrazol-4-yl)ethynyl)pyridin-2-yl)pyrimidin-4-amine The title compound as an off white solid (8 mg) was prepared in the same fashion as Step 2 in Example 1, except that 2-chloro-5-(1-(difluoromethyl)-1H-pyrazol-4-yl)-4-((1-methyl-1H-pyrazol-4-yl)ethynyl)pyridine (50 mg, 0.151 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=563.2 (M+H)$^+$

Example 3. N-(5-(1-(Cyclopropylmethyl)-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine

Step 1. 2-Chloro-5-(1-(cyclopropylmethyl)-1H-pyrazol-4-yl)-4-((1-methyl-1H-pyrazol-4-yl)ethynyl)pyridine The title compound as a white solid (53 mg) was prepared in the same fashion as Step 1 in Example 1 except that 1-(cyclopropylmethyl)-4-(4,4,5,5-tetramethyl-1,3,2-dioxaborolan-2-yl)pyrazole (92 mg, 0.371 mmol) was used instead of 1-cyclopropyl-4-(4,4,5,5-tetramethyl-1,3,2-dioxaborolan-2-yl)pyrazole. MS (ESI) m/z=338.1 (M+H)$^+$

Step 2. N-(5-(1-(Cyclopropylmethyl)-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine The title compound as an off white solid (12 mg) was prepared in the same fashion as Step 2 in Example 1, except that 2-chloro-5-(1-(cyclopropylmethyl)-1H-pyrazol-4-yl)-4-((1-methyl-1H-pyrazol-4-yl)ethynyl)pyridine (51 mg, 0.151 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=567.2 (M+H)$^+$

Example 4. 4-(2-((2-(1-(Cyclopropylsulfonyl)-1H-pyrazol-4-yl)pyrimidin-4-yl)amino)-5-(1-methyl-1H-pyrazol-4-yl)pyridin-4-yl)-2-methylbut-3-yn-2-ol

Step 1. 4-(5-Bromo-2-chloro-4-pyridyl)-2-methylbut-3-yn-2-ol

The title compound as a white solid (389 mg) was prepared in the same fashion as Reference Example 1 except that 3-methyl-1-butyn-3-ol (145 mg, 1.728 mmol) was used instead of 4-ethynyl-1-methyl-1H-pyrazole. MS (ESI) m/z=274.0 (M+H)+

Step 2. 4-(2-Chloro-5-(1-methyl-1H-pyrazol-4-yl) pyridin-4-yl)-2-methylbut-3-yn-2-ol The title compound as a white solid (41 mg) was prepared in the same fashion as Step 1 in Example 1 except that 1-methyl-4-(4,4,5,5-tetramethyl-1,3,2-dioxaborolan-2-yl)-1H-pyrazole (80 mg, 0.382 mmol) and 4-(5-bromo-2-chloro-4-pyridyl)-2-methylbut-3-yn-2-ol (100 mg, 0.364 mmol) prepared in Step 1 were used instead of 1-cyclopropyl-4-(4,4,5,5-tetramethyl-1,3,2-dioxaborolan-2-yl)pyrazole and 5-bromo-2-chloro-4-(2-(1-methylpyrazol-4-yl)ethynyl)pyridine. MS (ESI) m/z=576.2 (M+H)+

Step 3. 4-(2-((2-(1-(Cyclopropylsulfonyl)-1H-pyrazol-4-yl)pyrimidin-4-yl)amino)-5-(1-methyl-1H-pyrazol-4-yl)pyridin-4-yl)-2-methylbut-3-yn-2-ol The title compound as an off white solid (2 mg) was prepared in the same fashion as Step 2 in Example 1, except that 4-(2-chloro-5-(1-methyl-1H-pyrazol-4-yl)pyridin-4-yl)-2-methylbut-3-yn-2-ol (31 mg, 0.113 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.71 (s, 1H), 8.49-8.46 (m, 3H), 8.16 (s, 1H), 7.94 (s, 2H), 7.54 (s, 1H), 7.16 (d, 1H), 4.01 (s, 3H), 3.55 (s, 1H), 2.86-2.82 (m, 1H), 1.61 (s, 6H), 1.56-1.53 (m, 2H), 1.26-1.23 (m, 2H)

Example 5. N-(5-(1-Cyclopropyl-1H-pyrazol-4-yl)-4-((1-cyclopropyl-1H-pyrazol-4-yl)ethynyl)pyridin-2-yl)-2-(1-(cyclopropylsulfonyl)-1H-pyrazol-4-yl) pyrimidin-4-amine Step 1. 5-Bromo-2-chloro-4-((1-cyclopropyl-1H-pyrazol-4-yl)ethynyl)pyridine The title compound as a white solid (664 mg) was prepared in the same fashion as Reference Example 1 except that 1-cyclopropyl-4-ethynyl-pyrazole (436 mg, 3.298 mmol) was used instead of 4-ethynyl-1-methyl-1H-pyrazole. $^1$H-NMR (CDCl$_3$, 400 MHz) δ 8.52 (s, 1H), 7.75 (s, 1H), 7.68 (s, 1H), 7.38 (s, 1H), 3.67-3.63 (m, 1H), 1.19-1.09 (m, 4H)

Step 2. 2-Chloro-5-(1-cyclopropyl-1H-pyrazol-4-yl)-4-((1-cyclopropyl-1H-pyrazol-4-yl)ethynyl)pyridine The title compound as a white solid (253 mg) was prepared in the same fashion as Step 1 in Example 1 except that 5-bromo-2-chloro-4-((1-cyclopropyl-1H-pyrazol-4-yl)ethynyl)pyridine (276 mg, 0.854 mmol) prepared in Step 1 were used instead of 5-bromo-2-chloro-4-(2-(1-methylpyrazol-4-yl)ethynyl)pyridine. MS (ESI) m/z=350.1 (M+H)+

Step 3. N-(5-(1-Cyclopropyl-1H-pyrazol-4-yl)-4-((1-cyclopropyl-1H-pyrazol-4-yl)ethynyl)pyridin-2-yl)-2-(1-(cyclopropylsulfonyl)-1H-pyrazol-4-yl)pyrimidin-4-amine The title compound as an off-white solid (20 mg) was prepared in the same fashion as Step 2 in Example 1, except that 2-chloro-5-(1-cyclopropyl-1H-pyrazol-4-yl)-4-((1-cyclopropyl-1H-pyrazol-4-yl)ethynyl)pyridine (66 mg, 0.188 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.72 (s, 1H), 8.51 (s, 1H), 8.44 (d, 2H), 8.16 (s, 1H), 8.00 (d, 2H), 7.86 (s, 1H), 7.72 (s, 1H), 7.58 (s, 1H), 7.09 (d, 1H), 3.74-3.63 (m, 2H), 2.89-2.82 (m, 1H), 1.58-1.51 (m, 2H), 1.27-1.17 (m, 6H), 1.14-1.06 (m, 4H)

Example 6. N-(5-(1-Cyclopropyl-1H-pyrazol-4-yl)-4-((1-isopropyl-1H-pyrazol-4-yl)ethynyl)pyridin-2-yl)-2-(1-(cyclopropylsulfonyl)-1H-pyrazol-4-yl)pyrimidin-4-amine Step 1. 5-Bromo-2-chloro-4-((1-isopropyl-1H-pyrazol-4-yl)ethynyl)pyridine The title compound as a white solid (602 mg) was prepared in the same fashion as Reference Example 1 except that 4-ethynyl-1-isopropyl-pyrazole (443 mg, 3.298 mmol) was used instead of 4-ethynyl-1-methyl-1H-pyrazole. $^1$H-NMR (CDCl$_3$, 400 MHz) δ 8.51 (s, 1H), 7.73 (d, 2H), 7.39 (s, 1H), 4.57-4.48 (m, 1H), 1.55 (d, 6H)

Step 2. 2-Chloro-5-(1-cyclopropyl-1H-pyrazol-4-yl)-4-((1-isopropyl-1H-pyrazol-4-yl)ethynyl)pyridine The title compound as a white solid (260 mg) was prepared in the same fashion as Step 1 in Example 1 except that 5-bromo-2-chloro-4-((1-isopropyl-1H-pyrazol-4-yl)ethynyl)pyridine (227 mg, 0.854 mmol) prepared in Step 1 were used instead of 5-bromo-2-chloro-4-(2-(1-methylpyrazol-4-yl)ethynyl)pyridine. MS (ESI) m/z=352.0 (M+H)+

Step 3. N-(5-(1-Cyclopropyl-1H-pyrazol-4-yl)-4-((1-isopropyl-1H-pyrazol-4-yl)ethynyl)pyridin-2-yl)-2-(1-(cyclopropylsulfonyl)-1H-pyrazol-4-yl)pyrimidin-4-amine The title compound as an off white solid (17 mg) was prepared in the same fashion as Step 2 in Example 1, except that 2-chloro-5-(1-cyclopropyl-1H-pyrazol-4-yl)-4-((1-isopropyl-1H-pyrazol-4-yl)ethynyl)pyridine (66 mg, 0.188 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.73 (s, 1H), 8.51 (s, 1H), 8.45 (d, 2H), 8.16 (s, 1H), 8.04 (s, 1H), 7.99 (s, 1H), 7.86 (s, 1H), 7.75 (s, 1H), 7.59 (s, 1H), 7.08 (d, 1H), 4.61-4.52 (m, 1H), 3.73-3.66 (m, 1H), 2.89-2.82 (m, 1H), 1.58 (d, 6H), 1.55-1.50 (m, 2H), 1.25-1.18 (m, 4H), 1.17-1.07 (m, 2H)

Example 7. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-3-methylbutan-2-ol Step 1. 3-((2-Chloro-5-(1-(difluoromethyl)-1H-pyrazol-3-yl)pyridin-4-yl)amino)-3-methylbutan-2-ol The reaction mixture of 2-chloro-5-(1-(difluoromethyl)-1H-pyrazol-3-yl)-4-fluoropyridine (300 mg, 1.212 mmol) prepared in Reference Example 2, 3-amino-3-methylbutan-2-ol (187.5 mg, 1.817 mmol) and DIPEA (0.63 mL, 3.63 mmol) in DMA (10 mL) was stirred at 90° C. overnight. The reaction mixture was cooled, diluted in EA, washed by water, dried over MgSO$_4$, and then concentrated. The crude product was purified by column chromatography (EA/n-Hex=0-50%) to yield 3-((2-chloro-5-(1-(difluoromethyl)pyrazol-3-yl)-4-pyridyl)amino)-3-methylbutan-2-ol (257 mg) as a white solid. MS (ESI) m/z=331.0 (M+H)$^+$ Step 2. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-3-methylbutan-2-ol The title compound as an off white solid (21 mg) was prepared in the same fashion as Step 2 in Example 1, except that 3-((2-chloro-5-(1-(difluoromethyl)-1H-pyrazol-3-yl)pyridin-4-yl)amino)-3-methylbutan-2-ol (137 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.70 (s, 1H), 8.47 (s, 1H), 8.38 (d, 1H), 8.34 (s, 1H), 8.25 (s, 1H), 7.84 (d, 1H), 7.25 (d, 2H), 7.20 (t, 1H), 6.78 (d, 1H), 4.14 (q, 1H), 2.87-2.80 (m, 1H), 1.53 (s, 3H), 1.53-1.50 (m, 2H), 1.50 (s, 3H), 1.29 (d, 3H), 1.23-1.19 (m, 2H)

Example 8. 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol Step 1. 2-((1s,4s)-4-((2-Chloro-5-(1-(difluoromethyl)-1H-pyrazol-3-yl)pyridin-4-yl)amino)cyclohexyl)propan-2-ol The title compound as a white solid (364 mg) was prepared in the same fashion as Step 1 in Example 7, except that 2-((1s,4s)-4-aminocyclohexyl)propan-2-ol (286 mg, 1.817 mmol) was used instead of 3-amino-3-methylbutan-2-ol. MS (ESI) m/z=385.1 (M+H)$^+$ Step 2. 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol The title compound as an off white solid (41 mg) was prepared in the same fashion as Step 2 in Example 1, except that 2-((1s,4s)-4-((2-chloro-5-(1-(difluoromethyl)-1H-pyrazol-3-yl)pyridin-4-yl)amino)cyclohexyl)propan-2-ol (160 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.40-8.37 (m, 3H), 7.86 (d, 1H), 7.37 (s, 1H), 7.28 (t, 1H), 7.06 (d, 1H), 6.84 (d, 1H), 4.04 (q, 1H), 2.88-2.81 (m, 1H), 2.11 (d, 2H), 1.81-1.70 (m, 6H), 1.55-1.53 (m, 2H), 1.45 (s, 1H), 1.23 (s, 8H); MS (ESI) m/z=614.1 (M+H)$^+$ Example 9. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-((2-fluoroethyl)amino)cyclohexyl)pyridine-2,4-diamine Step 1. (1s,4s)-N$^1$-(2-Chloro-5-(1-(difluoromethyl)-1H-pyrazol-3-yl)pyridin-4-yl)-N$^4$-(2-fluoroethyl)cyclohexane-1,4-diamine The title compound as a white solid (364 mg) was prepared in the same fashion as Step 1 in Example 7, except that (1s,4s)-N$^1$-(2-fluoroethyl)cyclohexane-1,4-diamine (291 mg, 1.817 mmol) was used instead of 3-amino-3-methylbutan-2-ol. $^1$H-NMR (CDCl$_3$, 400 MHz) δ 8.35 (s, 1H), 8.21 (d, 1H), 7.87 (d, 1H), 7.27 (t, 1H), 6.83 (d, 2H), 6.58 (s, 1H), 4.61 (t, 1H), 4.49 (t, 1H), 3.74-3.67 (m, 1H), 2.97 (t, 1H), 2.90 (t, 1H), 2.74-2.63 (m, 1H), 1.98-1.86 (m, 2H), 1.86-1.65 (m, 4H), 1.57-1.44 (m, 2H); MS (ESI) m/z=388.1 (M+H)$^+$.

Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-((2-fluoroethyl)amino)cyclohexyl)pyridine-2,4-diamine The title compound as an off white solid (37 mg) was prepared in the same fashion as Step 2 in Example 1, except that (1s,4s)-N$^1$-(2-chloro-5-(1-(difluoromethyl)-1H-pyrazol-3-yl)pyridin-4-yl)-N-(2-fluoroethyl)cyclohexane-1,4-diamine (161 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.38 (d, 2H), 8.27 (d, 1H), 7.87 (d, 1H), 7.35 (t, 1H), 7.33 (s, 1H), 7.07 (d, 1H), 6.82 (d, 1H), 4.62 (t, 1H), 4.51 (t, 1H), 3.92 (s, 1H), 2.99 (t, 1H), 2.92 (t, 1H), 2.86-2.82 (m, 1H), 2.70-2.65 (m, 1H), 2.05-2.01 (m, 2H), 1.86-1.79 (m, 4H), 1.54-1.47 (m, 4H), 1.25-1.20 (m, 2H); MS (ESI) m/z=617.1 (M+H)$^+$ Example 10. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol The title compound as an off white solid (25 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (148 mg, 0.415 mmol) prepared in Reference Example 15 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.48 (s, 1H), 8.40 (d, 1H), 8.37 (s, 1H), 7.98 (d, 1H), 7.86 (d, 1H), 7.81 (s, 1H), 7.26 (s, 1H), 7.23 (t, 1H), 7.08 (s, 1H), 6.82 (s, 1H), 3.57-3.52 (m, 1H), 2.86-2.80 (m, 1H), 2.04-1.99 (m, 2H), 1.83-1.55 (m, 4H), 1.55-1.51 (m, 2H), 1.32 (s, 3H), 1.31-1.24 (m 2H), 1.24-1.18 (m, 2H); MS (ESI) m/z=586.1 (M+H)$^+$ Example 11. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(trifluoromethyl)cyclohexan-1-ol Step 1. (1s,4s)-4-((2-Chloro-5-(1-(difluoromethyl)-1H-pyrazol-3-yl)pyridin-4-yl)amino)-1-(trifluoromethyl)cyclohexan-1-ol The title compound as a white solid (312 mg) was prepared in the same fashion as Step 1 in Example 7, except that (1s,4s)-4-amino-1-(trifluoromethyl)cyclohexan-1-ol (333 mg, 1.817 mmol) was used instead of 3-amino-3-methylbutan-2-ol. MS (ESI) m/z=411.0 (M+H)$^+$ Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(trifluoromethyl)cyclohexan-1-ol The title compound as an off white solid (34 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-(trifluoromethyl)cyclohexan-1-ol (170 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.45 (s, 1H), 8.41 (d, 1H), 8.35 (s, 1H), 7.98 (d, 1H), 7.87 (d, 1H), 7.31 (d, 1H), 7.22 (t, 1H), 7.03 (s, 1H), 6.81 (d, 1H), 3.54-3.50 (m, 1H), 2.84-2.78 (m, 1H), 2.20-2.05 (m, 2H), 1.96-1.93 (m, 2H), 1.87-1.75 (m, 4H), 1.54-1.50 (m, 2H), 1.23-1.18 (m, 2H)

Example 12. (1R,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol Step 1. (1R,3R)-3-((2-Chloro-5-(1-(difluoromethyl)-1H-pyrazol-3-yl)pyridin-4-yl)amino)cyclopentan-1-ol The title compound as a white solid (278 mg) was prepared in the same fashion as Step 1 in Example 7, except that (1R,3R)-3-aminocyclopentan-1-ol (208 mg, 1.515 mmol)) was used instead of 3-amino-3-methylbutan-2-ol. MS (ESI) m/z=329.1 (M+H)$^+$ Step 2. (1R,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol The title compound as an off white solid (17 mg) was prepared in the same fashion as Step 2 in Example 1, except that (1R,3R)-3-((2-chloro-5-(1-(difluoromethyl)-1H-pyrazol-3-yl)pyridin-4-yl)amino)cyclopentan-1-ol (136 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.69 (s, 1H), 8.50 (s, 1H), 8.41 (d, 1H), 8.36 (s, 1H), 7.95 (d, 1H), 7.86 (d, 1H), 7.22 (s, 1H), 7.20 (t, 1H), 7.16 (d, 1H), 6.82 (d, 1H), 4.55-4.51 (m, 1H), 4.35-4.27 (m, 1H), 2.89-2.83 (m, 1H), 2.50-2.41 (m, 1H), 2.32-2.27 (m, 1H), 2.18-2.09 (m, 1H), 2.05-2.03 (m, 1H), 1.92-1.62 (m, 2H), 1.56-1.52 (m, 2H), 1.25-1.19 (m, 2H)

Example 13. (1S,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol Step 1. (1S,3R)-3-((2-Chloro-5-(1-(difluoromethyl)-1H-pyrazol-3-yl)pyridin-4-yl)amino)cyclopentan-1-ol The title compound as a white solid (278 mg) was prepared in the same fashion as Step 1 in Example 7, except that (1S,3R)-3-aminocyclopentan-1-ol (208 mg, 1.515 mmol) was used instead of 3-amino-3-methylbutan-2-ol. MS (ESI) m/z=329.1 (M+H)$^+$ Step 2. (1S,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol The title compound as an off white solid (14 mg) was prepared in the same fashion as Step 2 in Example 1, except that (1S,3R)-3-((2-chloro-5-(1-(difluoromethyl)-1H-pyrazol-3-yl)pyridin-4-yl)amino)cyclopentan-1-ol (136 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.39 (d, 1H), 8.34 (s, 2H), 7.85 (d, 1H), 7.27 (s, 1H), 7.23 (t, 1H), 7.11 (d, 1H), 6.80 (d, 1H), 4.53-4.50 (m, 1H), 4.16-4.10 (m, 1H), 2.86-2.80 (m, 1H), 2.39-2.33 (m, 1H), 2.23-2.15 (m, 1H), 2.04-1.87 (m, 4H), 1.55-1.50 (m, 2H), 1.25-1.19 (m, 2H)

Example 14. (1R,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol Step 1. (1R,3S)-3-((2-Chloro-5-(1-(difluoromethyl)-1H-pyrazol-3-yl)pyridin-4-yl)amino)cyclopentan-1-ol The title compound as a white solid (278 mg) was prepared in the same fashion as Step 1 in Example 7, except that (1R,3S)-3-aminocyclopentan-1-ol (208 mg, 1.515 mmol) was used instead of 3-amino-3-methylbutan-2-ol. MS (ESI) m/z=329.1 (M+H)$^+$ Step 2. (1R,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol The title compound as an off white solid (37 mg) was prepared in the same fashion as Step 2 in Example 1, except that (1R,3S)-3-((2-chloro-5-(1-(difluoromethyl)-1H-pyrazol-3-yl)pyridin-4-yl)amino)cyclopentan-1-ol (136 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.40 (d, 1H), 8.35 (s, 1H), 8.31 (d, 1H), 7.85 (d, 1H), 7.23 (t, 1H), 7.15 (d, 1H), 6.81 (d, 1H), 4.53-4.50 (m, 1H), 4.16-4.11 (m, 1H), 2.86-2.80 (m, 1H), 2.40-2.33 (m, 1H), 2.23-2.15 (m, 1H), 2.10-1.94 (m, 3H), 1.87-1.84 (m, 2H), 1.55-1.51 (m, 2H), 1.25-1.19 (m, 2H)

Example 15. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol Step 1. 3-((2-Chloro-5-(1-(difluoromethyl)-1H-pyrazol-3-yl)pyridin-4-yl)amino)cyclopentan-1-ol The title compound as a white solid (278 mg) was prepared in the same fashion as Step 1 in Example 7, except that 3-aminocyclopentan-1-ol (208 mg, 1.515 mmol) was used instead of 3-amino-3-methylbutan-2-ol. MS (ESI) m/z=329.1 (M+H)$^+$ Step 2. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol The title compound as an off white solid (42 mg) was prepared in the same fashion as Step 2 in Example 1, except that 3-((2-chloro-5-(1-(difluoromethyl)-1H-pyrazol-3-yl)

pyridin-4-yl)amino)cyclopentan-1-ol (136 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.40 (d, 1H), 8.35 (s, 1H), 8.30 (d, 1H), 7.85 (d, 1H), 7.23 (t, 1H), 7.14 (d, 1H), 6.81 (d, 1H), 4.54-4.50 (m, 1H), 4.17-4.10 (m, 1H), 2.86-2.80 (m, 1H), 2.40-2.33 (m, 1H), 2.21-2.15 (m, 1H), 2.10-1.94 (m, 3H), 1.87-1.84 (m, 2H), 1.55-1.51 (m, 2H), 1.25-1.19 (m, 2H)

Example 16. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(methylamino)cyclohexyl)pyridine-2,4-diamine Step 1. (1s,4s)-$N^1$-(2-Chloro-5-(1-(difluoromethyl)-1H-pyrazol-3-yl)pyridin-4-yl)-$N^4$-methylcyclohexane-1,4-diamine The title compound as a white solid (303 mg) was prepared in the same fashion as Step 1 in Example 7, except that (1s,4s)-$N^1$-methylcyclohexane-1,4-diamine (194 mg, 1.515 mmol) was used instead of 3-amino-3-methylbutan-2-ol. $^1$H-NMR (CDCl$_3$, 400 MHz) δ 8.35 (s, 1H), 8.20 (d, 1H), 7.87 (d, 1H), 7.34 (t, 1H), 6.83 (d, 1H), 6.58 (s, 1H), 3.75 (brs, 1H), 2.59-2.53 (m, 1H), 2.45 (s, 3H), 1.92-1.70 (m, 6H), 1.55-1.48 (m, 2H)

Step 2. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(methylamino)cyclohexyl)pyridine-2,4-diamine The title compound as an off white solid (24 mg) was prepared in the same fashion as Step 2 in Example 1, except that (1s,4s)-$N^1$-(2-chloro-5-(1-(difluoromethyl)-1H-pyrazol-3-yl)pyridin-4-yl)-$N^4$-methylcyclohexane-1,4-diamine (134 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.41 (d, 1H), 8.36 (s, 1H), 8.21 (d, 1H), 7.87 (d, 1H), 7.61 (s, 1H), 7.28 (t, 1H), 7.21 (s, 1H), 7.17 (d, 1H), 6.83 (d, 1H), 3.88 (brs, 1H), 2.87-2.81 (m, 1H), 2.58-2.52 (m, 1H), 2.46 (s, 3H), 2.03-1.97 (m, 2H), 1.88-1.78 (m, 4H), 1.56-1.47 (m, 4H), 1.25-1.20 (m, 2H); MS (ESI) m/z=585.2 (M+H)$^+$ Example 17. (S)-$N^4$-(Azepan-4-yl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine Step 1. tert-Butyl (S)-4-((2-chloro-5-(1-(difluoromethyl)-1H-pyrazol-3-yl)pyridin-4-yl)amino)azepane-1-carboxylate The title compound as a white solid (364 mg) was prepared in the same fashion as Step 1 in Example 7, except that tert-butyl (S)-4-aminoazepane-1-carboxylate (595 mg, 2.777 mmol) was used instead of 3-amino-3-methylbutan-2-ol. MS (ESI) m/z=442.1 (M+H)$^+$ Step 2. (S)-$N^4$-(Azepan-4-yl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine The suspension of 2-(1-(cyclopropylsulfonyl)-1H-pyrazol-4-yl)pyrimidin-4-amine (100 mg, 0.380 mmol), tris(dibenzylideneacetone)dipalladium(0) (34.5 mg, 0.04 mmol), Xphos (36 mg, 0.08 mmol), cesium carbonate (307 mg, 0.94 mmol) and tert-butyl (S)-4-((2-chloro-5-(1-(difluoromethyl)-1H-pyrazol-3-yl)pyridin-4-yl)amino)azepane-1-carboxylate (167 mg, 0.377 mmol) prepared in Step 1 in 1,4-dioxane (3 mL) was stirred at 110° C. overnight. The mixture was diluted in DCM, filtered through Celite, and then concentrated. The crude product and TFA (0.5 mL) in DCM (5 mL) was stirred at room temperature for 3 hours, and then concentrated. The residue was diluted in DCM, added 1 N NaOH soln. (>pH 8), washed by water, dried over MgSO$_4$, and then concentrated. The crude product was purified by column chromatography (MeOH/DCM=0-20%) to yield (S)-$N^4$-(azepan-4-yl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine (48 mg) as a pale yellow solid. $^1$H-NMR (CDCl$_3$, 400 MHz) δ 8.67 (s, 1H), 8.47 (s, 1H), 8.42 (d, 1H), 8.39 (s, 1H), 8.09 (d, 1H), 7.86 (d, 1H), 7.74 (s, 1H), 7.35 (d, 1H), 7.21 (t, 1H), 6.95 (s, 1H), 6.83 (d, 1H), 3.98-3.92 (m 1H), 3.00-2.95 (m, 4H), 2.87-2.81 (m, 1H), 2.22-2.15 (m, 1H), 2.10-2.03 (m, 1H), 1.99-1.68 (m, 4H), 1.56-1.52 (m, 2H), 1.24-1.19 (m, 2H); MS (ESI) m/z=671.2 (M+H)$^+$ Example 18. ((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol Step 1. ((1s,4s)-4-((2-Chloro-5-(1-(difluoromethyl)-1H-pyrazol-3-yl)pyridin-4-yl)amino)cyclohexyl)methanol The title compound as a white solid (327 mg) was prepared in the same fashion as Step 1 in Example 7, except that ((1s,4s)-4-aminocyclohexyl)methanol (196 mg, 1.515 mmol) was used instead of 3-amino-3-methylbutan-2-ol. $^1$H-NMR (CDCl$_3$, 400 MHz) δ 8.38 (d, 1H), 8.31 (s, 1H), 7.84 (s, 1H), 7.28 (t, 1H), 6.79 (d, 1H), 6.56 (s, 1H), 3.85-3.78 (m, 1H), 3.53-3.46 (m, 2H), 2.74-2.69 (m, 1H), 1.92-1.83 (m, 2H), 1.71-1.54 (m, 4H), 1.44-1.33 (m, 2H); MS (ESI) m/z=357.2 (M+H)$^+$ Step 2. ((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol The title compound as an off white solid (82 mg) was prepared in the same fashion as Step 2 in Example 1, except that ((1s,4s)-4-((2-chloro-5-(1-(difluoromethyl)-1H-pyrazol-3-yl)pyridin-4-yl)amino)cyclohexyl)methanol (242 mg, 0.679 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H NMR (CDCl$_3$, 400 MHz) δ 8.66 (s, 1H), 8.47 (s, 1H), 8.41-8.37 (m, 3H), 7.87 (d, 1H), 7.70 (s, 1H), 7.32 (s, 1H), 7.27 (t, 1H), 7.10 (d, 1H), 6.84 (d, 1H), 4.07-4.01 (m, 1H), 3.56 (d, 2H), 2.86-2.81 (m, 1H), 2.08-2.01 (m, 2H), 1.86-1.77 (m, 2H), 1.75-1.59 (m, 5H), 1.56-1.52 (m, 2H), 1.05-1.40 (m, 2H), 1.27-1.20 (m, 2H); MS (ESI) m/z=586.1 (M+H)$^+$ Example 19. (5s,8s)-8-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-azaspiro[4.5]decan-2-one Step 1. (5s,8s)-8-((2-Chloro-5-(1-(difluoromethyl)-1H-pyrazol-3-yl)pyridin-4-yl)amino)-1-azaspiro[4.5]decan-2-one The title compound as a white solid (223 mg) was prepared in the same fashion as Step 1 in Example 7, except that (5s,8s)-8-amino-1-azaspiro[4.5]decan-2-one hydrochloride (372 mg, 1.817 mmol) was used instead of 3-amino-3-methylbutan-2-ol. MS (ESI) m/z=396.1 (M+H)$^+$ Step 2. (5s,8s)-8-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-azaspiro[4.5]decan-2-one The title compound as an off white solid (97 mg) was prepared in the same fashion as Step 2 in Example 1, except that (5s,8s)-8-((2-chloro-5-(1-(difluoromethyl)-1H-pyrazol-3-yl)pyridin-4-yl)amino)-1-azaspiro[4.5]decan-2-one (224 mg, 0.565 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.04 (s, 1H), 8.65 (s, 1H), 8.51 (s, 1H), 8.47 (s, 1H), 8.42 (d, 1H), 8.35 (d, 1H), 8.14 (s, 1H), 8.06 (d, 1H), 7.83 (t, 1H), 7.48 (s 1H), 7.39 (s, 1H), 7.16 (d, 1H), 3.29-3.23 (m, 2H), 2.19 (t, 2H), 1.95-1.91 (m, 2H), 1.83 (t, 2H), 1.73-1.65 (m, 4H), 1.57-1.52 (m, 2H), 1.37-1.32 (m, 2H), 1.28-1.22 (m, 2H); MS (ESI) m/z=625.2 (M+H)$^+$ Example 20. (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol Step 1. (1S,3S)-3-((2-chloro-5-(1-(difluoromethyl)-1H-pyrazol-3-yl)pyridin-4-yl)amino)cyclopentan-1-ol The title compound as a white solid (180 mg) was prepared in the same fashion as Step 1 in Example 7, except that (1S,3S)-3-aminocyclopentan-1-ol hydrochloride (125 mg, 0.909 mmol) was used instead of 3-amino-3-methylbutan-2-ol. MS (ESI) m/z=328.8 (M+H)$^+$ Step 2. (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol The title compound as an off white solid (135 mg) was prepared in the same fashion as Step 2 in Example 1, except that (1S,3S)-3-((2-chloro-5-(1-(difluoromethyl)-1H-pyrazol-3-yl)pyridin-4-yl)amino)cyclopentan-1-ol (178 mg, 0.543 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H NMR (DMSO-d$_6$, 400 MHz) δ 8.65 (s, 1H), 8.51 (s, 1H), 8.44 (s, 1H), 8.43 (d, 1H), 8.32 (s, 1H), 8.04 (d, 1H), 7.88 (s, 1H), 7.69 (brs, 1H), 7.14 (d, 2H), 4.67 (d, 1H), 4.33-4.24 (m, 1H), 4.15-4.07 (m, 1H), 3.32-3.24 (m, 1H), 2.37-2.26 (m, 1H), 2.10-2.01 (m, 1H), 1.97-1.89 (m, 1H), 1.79-1.70 (m, 1H), 1.62-1.48 (m, 2H), 1.38-1.32 (m, 2H), 1.28-1.22 (m, 2H); MS (ESI) m/z=558.0 (M+H)$^+$ Example 21. (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol Step 1. (1S,3S)-3-((2-Chloro-5-(1-(difluoromethyl)-1H-pyrazol-3-yl)pyridin-4-yl)amino)cyclohexan-1-ol The title compound as a white solid (188 mg) was prepared in the same fashion as Step 1 in Example 7, except that (1S,3S)-3-aminocyclohexan-1-ol hydrochloride (138 mg, 0.909 mmol) was used instead of 3-amino-3-methylbutan-2-ol. MS (ESI) m/z=343.0 (M+H)$^+$ Step 2. (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol The title compound as an off white solid (150.5 mg) was prepared in the same fashion as Step 2 in Example 1, except that (1S,3S)-3-((2-chloro-5-(1-(difluoromethyl)-1H-pyrazol-3-yl)pyridin-4-yl)amino)cyclohexan-1-ol (186 mg, 0.543 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.49 (s, 1H), 8.40 (d, 1H), 8.38 (s, 1H), 8.00 (d, 1H), 7.86 (d, 1H), 7.76 (brs, 1H), 7.23 (d, 1H), 7.19 (t, 1H), 7.14 (brs, 1H), 6.82 (d, 1H), 4.14-4.04 (m, 2H), 2.89-2.81 (m, 1H), 2.03-1.56 (m, 8H), 1.56-0.50 (m, 2H), 1.28-1.22 (m, 2H); MS (ESI) m/z=572.0 (M+H)$^+$ Example 22. ((1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methanol Step 1. ((1r,4r)-4-(((2-Chloro-5-(1-(difluoromethyl)-1H-pyrazol-3-yl)pyridin-4-yl)amino)methyl)cyclohexyl)methanol The title compound as a white solid (336 mg) was prepared in the same fashion as Step 1 in Example 7, except that trans-4-(aminomethyl)cyclohexanemethanol hydrochloride (212 mg, 1.181 mmol) and was used instead of 3-amino-3-methylbutan-2-ol. MS (ESI) m/z=371.1 (M+H)$^+$ Step 2. ((1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methanol The title compound as an off white solid (226 mg) was prepared in the same fashion as Step 2 in Example 1, except that ((1r,4r)-4-(((2-chloro-5-(1-(difluoromethyl)-1H-pyrazol-3-yl)pyridin-4-yl)amino)methyl)cyclohexyl)methanol (335.5 mg, 0.905 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 10.07 (s, 1H), 8.66 (s, 1H), 8.51 (s, 1H), 8.45 (s, 1H), 8.42 (d, 1H), 8.31 (s, 1H), 8.15 (t, 1H), 7.84 (t, 1H), 7.49 (s, 1H), 7.35 (s, 1H), 7.14 (d, 1H), 4.38 (t, 1H), 3.29-3.24 (m, 1H), 3.24-3.15 (m, 4H), 1.88-1.85 (m, 2H), 1.80-1.77 (m, 2H), 1.66 (s, 1H), 1.37-1.30 (m, 3H), 1.28-1.22 (m, 2H), 1.19-1.09 (m, 2H), 0.97-0.88 (m, 2H); MS (ESI) m/z=600.2 (M+H)$^+$ Example 23. $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(1-(difluoromethyl)-1H-pyrazol-3-yl)pyridine-2,4-diamine Step 1. (1s,4s)-$N^1$-(2-Chloro-5-(1-(difluoromethyl)-1H-pyrazol-3-yl)pyridin-4-yl)-$N^4$-(2,2-difluoroethyl)cyclohexane-1,4-diamine The title compound as a white solid (467 mg) was prepared in the same fashion as Step 1 in Example 7, except that (1s,4s)-$N^1$-(2,2-difluoroethyl)cyclohexane-1,4-diamine (324 mg, 1.817 mmol) was used instead of 3-amino-3-methylbutan-2-ol. $^1$H-NMR (CDCl$_3$, 400 MHz) δ 8.35 (s, 1H), 8.23 (d, 1H), 7.87 (d, 1H), 7.24 (t, 1H), 6.83 (d, 1H), 6.58 (s, 1H), 5.83 (tt, 1H), 3.74-3.67 (m, 1H), 3.00 (td, 2H), 2.73-2.66 (m, 1H), 1.92-1.68 (m, 6H), 1.53-1.44 (m, 2H), 1.63-1.53 (m, 2H)

Step 2. $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(1-(difluoromethyl)-1H-pyrazol-3-yl)pyridine-2,4-diamine The title compound as an off white solid (126 mg) was prepared in the same fashion as Step 2 in Example 1, except that (1s,4s)-$N^1$-(2-chloro-5-(1-(difluoromethyl)-1H-pyrazol-3-yl)pyridin-4-yl)-$N^4$-(2,2-difluoroethyl)cyclohexane-1,4-diamine (202 mg, 0.498 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.40 (s, 1H), 8.39 (d, 1H), 8.27 (d, 1H), 8.09 (s, 1H), 7.87 (d, 1H), 7.31 (s, 1H), 7.25 (t, 1H), 7.08 (s, 1H), 6.83 (d, 1H), 5.85 (tt, 1H), 3.94-3.89 (m, 1H), 3.02 (td, 2H), 2.87-2.80 (m, 1H), 2.72-2.66 (m, 1H), 2.05-1.99 (m, 2H), 1.87-1.78 (m, 4H), 1.55-1.43 (m, 4H), 1.23-1.19 (m, 2H); MS (ESI) m/z=635.2 (M+H)$^+$ Example 24. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-methylcyclohexane-1-carboxamide Step 1. (1s,4s)-4-((2-Chloro-5-(1-(difluoromethyl)-1H-pyrazol-3-yl)pyridin-4-yl)amino)-N-methylcyclohexane-1-carboxamide The title compound as a white solid (399.2 mg) was prepared in the same fashion as Step 1 in Example 7, except that (1s,4s)-4-amino-N-methylcyclohexane-1-carboxamide dihydrochloride (416.5 mg, 1.817 mmol) was used instead of 3-amino-3-methylbutan-2-ol. $^1$H-NMR (CDCl$_3$, 400 MHz) δ 8.58 (d, 1H), 8.36 (s, 1H), 7.89 (d, 1H), 7.69 (t, 1H), 6.83 (d, 1H), 6.59 (s, 1H), 5.67 (brs, 1H), 3.90-3.86 (m, 1H), 2.82 (d, 3H), 2.24-2.17 (m, 1H), 1.94-1.84 (m, 4H), 1.78-1.66 (m, 4H)

Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-methylcyclohexane-1-carboxamide The title compound as an off white solid (52 mg) was prepared in the same fashion as Step 2 in Example 1, except that (1s,4s)-4-((2-chloro-5-(1-(difluoromethyl)-1H-pyrazol-3-yl)pyridin-4-yl)amino)-N-methylcyclohexane-1-carboxamide (191 mg, 0.498 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.64 (s, 1H), 8.58 (d, 1H), 8.46 (s, 1H), 8.39 (d, 1H), 8.38 (d, 1H), 8.26 (s, 1H), 7.89 (d, 1H), 7.66 (t, 1H), 7.41 (s, 1H), 7.02 (brs 1H), 6.83 (d, 1H), 5.60 (d, 1H), 4.02 (brs, 1H), 2.86-2.80 (m, 4H), 2.28-2.20 (m, 1H), 2.03-1.97 (m, 2H), 1.95-1.88 (m, 2H), 1.81-1.75 (m, 4H), 1.55-1.50 (m, 2H), 1.26-1.20 (m, 2H); MS (ESI) m/z=613.2 (M+H)$^+$ Example 25. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-(dimethylamino)cyclohexyl)methyl)pyridine-2,4-diamine Step 1. 2-Chloro-5-(1-(difluoromethyl)-1H-pyrazol-3-yl)-N-(((1r,4r)-4-(dimethylamino)cyclohexyl)methyl)pyridin-4-amine The title compound as a white solid (300 mg) was prepared in the same fashion as Step 1 in Example 7, except that (1r,4r)-4-(aminomethyl)-N,N-dimethylcyclohexan-1-amine (237 mg, 1.515 mmol) was used instead of 3-amino-3-methylbutan-2-ol. $^1$H-NMR (CDCl$_3$, 400 MHz) δ 8.35 (s, 1H), 8.01 (s, 1H), 7.86 (s, 1H), 7.18 (t, 1H), 6.83 (s, 1H), 6.56 (s, 1H), 3.48 (s, 1H), 3.11 (t, 2H), 2.29 (s, 6H), 2.22-2.15 (m, 1H), 1.98-1.93 (m, 4H), 1.69-1.58 (m, 1H), 1.32-1.22 (m, 2H), 1.17-1.07 (m, 2H); MS (ESI) m/z=384.1 (M+H)$^+$ Step 2. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-(dimethylamino)cyclohexyl)methyl)pyridine-2,4-diamine The title compound as an off white solid (41 mg) was prepared in the same fashion as Step 2 in Example 1, except that 2-chloro-5-(1-(difluoromethyl)-1H-pyrazol-3-yl)-N-(((1r,4r)-4-(dimethylamino)cyclohexyl)methyl)pyridin-4-amine (145 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.42 (d, 1H), 8.38 (s, 1H), 7.98 (brs, 1H), 7.87 (d, 1H), 7.62 (brs, 1H), 7.32 (d, 1H), 7.19 (t, 1H), 7.00 (brs, 1H), 6.84 (d, 1H), 3.23 (t, 2H), 2.87-2.80 (m, 1H), 2.30 (s, 6H), 2.27-2.18 (m, 1H), 1.99 (d, 4H), 1.84 (brs, 1H), 1.72 (brs, 1H), 1.56-1.51 (m, 2H), 1.34-1.15 (m, 4H)

Example 26. $N^4$-((2-Azaspiro[3.3]heptan-6-yl)methyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine Step 1. tert-Butyl 6-(((2-chloro-5-(1-(difluoromethyl)-1H-pyrazol-3-yl)pyridin-4-yl)amino)methyl)-2-azaspiro[3.3]heptane-2-carboxylate The title compound as a white solid (300 mg) was prepared in the same fashion as Step 1 in Example 7, except that tert-butyl 6-(aminomethyl)-2-azaspiro[3.3]heptane-2-carboxylate hydrochloride (398 mg, 1.515 mmol) was used instead of 3-amino-3-methylbutan-2-ol. $^1$H-NMR (CDCl$_3$, 400 MHz) δ 8.36 (s, 1H), 8.01 (s, 1H), 7.87 (d, 1H), 7.17 (t, 1H), 6.84 (d, 1H), 6.55 (s, 1H), 3.98 (s, 2H), 3.85 (s, 2H), 3.24 (t, 2H), 2.63-2.52 (m, 1H), 2.40-2.34 (m, 2H), 2.03-1.98 (m, 2H), 1.44 (s, 9H); MS (ESI) m/z=454.1 (M+H)+

Step 2. tert-Butyl 6-(((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-2-azaspiro[3.3]heptane-2-carboxylate The title compound as an off white solid (56 mg) was prepared in the same fashion as Step 2 in Example 1, except that tert-butyl 6-(((2-chloro-5-(1-(difluoromethyl)-1H-pyrazol-3-yl)pyridin-4-yl)amino)methyl)-2-azaspiro[3.3]heptane-2-carboxylate (205 mg, 0.452 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=683.2 (M+H)+

Step 3. N4-((2-Azaspiro[3.3]heptan-6-yl)methyl)-N2-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine The suspension of tert-butyl 6-(((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-2-azaspiro[3.3]heptane-2-carboxylate (56 mg, 0.082 mmol) prepared in Step 2 and TFA (0.5 mL) in DCM (5 mL) was stirred at room temperature for 3 hours, and then concentrated. The residue was diluted in DCM, added 1 N NaOH soln. (>pH8), washed by water, dried over MgSO4, and then concentrated. The crude product was purified by column chromatography (MeOH/DCM=0-30%) to yield N4-((2-azaspiro(3.3)heptan-6-yl)methyl)-N2-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine (11 mg) as a pale yellow solid. MS (ESI) m/z=583.2 (M+H)+

Example 27. N2-(2-(1-(Cyclopropylsulfonyl)-1H-pyrazol-4-yl)pyrimidin-4-yl)-5-(1-(difluoromethyl)-1H-pyrazol-3-yl)-N4-(2-azaspiro[3.5]nonan-7-yl)pyridine-2,4-diamine Step 1. tert-Butyl 7-((2-chloro-5-(1-(difluoromethyl)-1H-pyrazol-3-yl)pyridin-4-yl)amino)-2-azaspiro[3.5]nonane-2-carboxylate The title compound as a white solid (361 mg) was prepared in the same fashion as Step 1 in Example 7, except that tert-butyl 7-amino-2-azaspiro[3.5]nonane-2-carboxylate hydrochloride (419 mg, 1.515 mmol) was used instead of 3-amino-3-methylbutan-2-ol. 1H-NMR (CDCl3, 400 MHz) δ 8.36 (s, 1H), 7.96 (d, 1H), 7.87 (d, 1H), 7.19 (t, 1H), 6.83 (d, 1H), 6.57 (s, 1H), 3.66 (d, 4H), 3.44 (s, 1H), 2.00-1.94 (m, 4H), 1.70-1.62 (m, 2H), 1.46 (s, 9H), 1.46-1.43 (m, 2H); MS (ESI) m/z=468.2 (M+H)+

Step 2. tert-Butyl 7-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)-2-azaspiro[3.5]nonane-2-carboxylate The title compound as an off white solid (74 mg) was prepared in the same fashion as Step 2 in Example 1, except that tert-butyl 7-((2-chloro-5-(1-(difluoromethyl)-1H-pyrazol-3-yl)pyridin-4-yl)amino)-2-azaspiro[3.5]nonane-2-carboxylate (212 mg, 0.452 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=697.2 (M+H)+

Step 3. N2-(2-(1-(Cyclopropylsulfonyl)-1H-pyrazol-4-yl)pyrimidin-4-yl)-5-(1-(difluoromethyl)-1H-pyrazol-3-yl)-N4-(2-azaspiro[3.5]nonan-7-yl)pyridine-2,4-diamine The title compound as a pale yellow solid (30 mg) was prepared in the same fashion as Step 3 in Example 26, except that tert-butyl 7-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)-2-azaspiro[3.5]nonane-2-carboxylate (74 mg, 0.106 mmol) prepared in Step 2 was used instead of tert-butyl 6-(((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-2-azaspiro[3.3]heptane-2-carboxylate. 1H-NMR (MeOD, 400 MHz) δ 8.71 (s, 1H), 8.45 (s, 1H), 8.39 (s, 1H), 8.34 (d, 1H), 8.26 (s, 1H), 8.10 (d, 1H), 7.55 (t, 1H), 7.38 (s, 1H), 7.30 (dt, 1H), 6.95 (d, 1H), 3.70 (brs, 1H), 3.52 (d, 4H), 3.08-3.02 (m, 1H), 2.06-1.95 (m, 4H), 1.82-1.70 (m, 2H), 1.65-1.54 (m, 2H), 1.47-1.43 (m, 2H), 1.30-1.25 (m, 2H)

Example 28. 2-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol Step 1. 2-((2-Chloro-5-(1-(difluoromethyl)-1H-pyrazol-3-yl)pyridin-4-yl)amino)cyclohexan-1-ol The title compound as a pale yellow solid (410 mg) was prepared in the same fashion as Step 1 in Example 7, except that 2-aminocyclohexanol (209 mg, 1.820 mmol) was used instead of 3-amino-3-methylbutan-2-ol. 1H-NMR (DMSO-d6, 400 MHz) δ 8.49-8.44 (s, 2H), 8.37-8.35 (m, 1H), 8.28-8.26 (m, 1H), 8.03-7.66 (m, 1H), 7.20-7.17 (m, 1H), 6.85-6.79 (m, 1H), 4.89-4.85 (m, 1H), 3.81-3.80 (m, 1H), 3.71-3.69 (m, 1H), 1.98-1.65 (m, 1H), 1.62-1.52 (m, 5H), 1.39-1.22 (m, 3H); MS (ESI) m/z=343.1 (M+H)+

Step 2. 2-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol The title compound as a white solid (21 mg) was prepared in the same fashion as Step 2 in Example 1, except that 2-((2-chloro-5-(1-(difluoromethyl)-1H-pyrazol-3-yl)pyridin-4-yl)amino)cyclohexan-1-ol (310 mg, 0.900 mmol) prepared in Step 1 was used instead of 2-chloro-5-(1-cyclopropyl-1H-pyrazol-4-yl)-4-((1-methyl-1H-pyrazol-4-yl)ethynyl)pyridine. 1H-NMR (DMSO-d6, 400 MHz) δ 11.87 (s, 1H), 9.45 (d, 1H), 8.96 (s, 1H), 8.78 (s, 1H), 8.67 (s, 1H), 8.65 (d, 1H), 8.50 (s, 1H), 7.19 (d, 1H), 7.10 (t, 1H), 7.04 (d, 1H), 6.96 (s, 1H), 3.92 (s, 1H), 3.78-3.77 (m, 2H), 3.28-3.25 (m, 2H), 1.73-1.58 (m, 6H), 1.38-1.30 (m, 3H), 1.21-1.23 (m, 2H); MS (ESI) m/z=572.2 (M+H)+

Example 29. 2-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol Step 1. 2-((2-Chloro-5-(1-(difluoromethyl)-1H-pyrazol-3-yl)pyridin-4-yl)amino)cyclopentan-1-ol The title compound as a pale yellow solid (420 mg) was prepared in the same fashion as Step 1 in Example 7, except that 2-aminocyclopentanol (184 mg, 1.820 mmol) and was used instead of 3-amino-3-methylbutan-2-ol. $^1$H-NMR (DMSO-d$_6$, 400 MHz) δ 8.52 (s, 1H), 8.37 (d, 1H), 8.20 (d, 1H), 7.89 (t, 1H), 7.20 (d, 1H), 6.90 (s, 1H), 5.07 (d, 1H), 3.91 (brs, 1H), 3.69-3.67 (m, 1H), 2.23-2.17 (m, 1H), 1.84-1.69 (m, 3H), 1.58-1.48 (m, 2H); MS (ESI) m/z=329.0 (M+H)$^+$ Step 2. 2-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol The title compound as a white solid (4 mg) was prepared in the same fashion as Step 2 in Example 1, except that 2-((2-chloro-5-(1-(difluoromethyl)-1H-pyrazol-3-yl)pyridin-4-yl)amino)cyclopentan-1-ol (111.5 mg, 0.3400 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 8.84 (s, 1H), 8.50 (d, 1H), 8.42 (d, 1H), 8.15 (s, 1H), 8.14 (s, 1H), 7.59 (t, 1H), 7.32 (d, 1H), 7.07 (s, 1H), 7.00 (d, 1H), 4.17-4.14 (m, 1H), 3.88-3.87 (m, 1H), 3.08-3.04 (m, 1H), 2.40-2.36 (m, 1H), 2.06-1.85 (m, 3H), 1.76-1.67 (m, 2H), 1.47-1.44 (m, 2H), 1.28-1.25 (m, 2H); MS (ESI) m/z=558.1 (M+H)$^+$ Example 30. (1s,4s)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol Step 1. (1s,4s)-4-(((2-Chloro-5-(1-(difluoromethyl)-1H-pyrazol-3-yl)pyridin-4-yl)amino)methyl)cyclohexan-1-ol The title compound as a pale yellow solid (420 mg) was prepared in the same fashion as Step 1 in Example 7, except that cis-4-(aminomethyl)cyclohexanol hydrochloride (184 mg, 1.820 mmol) was used instead of 3-amino-3-methylbutan-2-ol. $^1$H-NMR (CDCl$_3$, 400 MHz) δ 8.51 (s, 1H), 8.37 (d, 1H), 8.29 (t, 1H) 7.85 (t, 1H), 7.20 (d, 1H), 6.74 (s, 1H), 4.38 (d, 1H), 3.78 (s, 1H), 3.15-3.13 (m, 2H), 1.64-1.60 (m, 3H), 1.49-1.43 (m, 6H); MS (ESI) m/z=357.1 (M+H)$^+$ Step 2. (1s,4s)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol The title compound as a white solid (140 mg) was prepared in the same fashion as Step 2 in Example 1, except that (1s,4s)-4-(((2-chloro-5-(1-(difluoromethyl)-1H-pyrazol-3-yl)pyridin-4-yl)amino)methyl)cyclohexan-1-ol (355 mg, 1.000 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.49 (s, 1H), 8.42 (d, 1H), 8.39 (s, 1H), 8.11 (t, 1H), 7.87 (d, 1H), 7.61 (s, 1H), 7.32 (t, 1H), 7.22 (d, 1H), 7.12 (s, 1H), 6.84 (d, 1H), 4.07 (s, 1H), 3.32-3.29 (m, 2H), 2.86-2.82 (m, 1H), 1.86-1.77 (m, 3H), 1.74-1.68 (m, 2H), 1.66-1.58 (m, 6H), 1.56-1.52 (m, 2H), 1.23-1.21 (m, 2H); MS (ESI) m/z=586.0 (M+H)$^+$ Example 31. (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol Step 1. (1r,4r)-4-(((2-Chloro-5-(1-(difluoromethyl)-1H-pyrazol-3-yl)pyridin-4-yl)amino)methyl)cyclohexan-1-ol The title compound as a pale yellow solid (380 mg) was prepared in the same fashion as Step 1 in Example 7, except that trans-4-(aminomethyl)cyclohexanol hydrochloride (251 mg, 1.510 mmol) was used instead of 3-amino-3-methylbutan-2-ol. $^1$H-NMR (DMSO-d$_6$, 400 MHz) δ 8.51 (s, 1H), 8.35 (d, 1H), 8.27 (t, 1H), 7.86 (t, 1H), 7.19 (d, 1H), 6.72 (s, 1H), 4.56 (d, 1H), 3.13 (t, 2H), 1.84 (d, 2H), 1.76 (d, 2H), 1.53 (m, 1H), 1.19-1.04 (m, 4H); MS (ESI) m/z=357.1 (M+H)$^+$ Step 2. (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol The title compound as a white solid (140 mg) was prepared in the same fashion as Step 2 in Example 1, except that (1r,4r)-4-(((2-chloro-5-(1-(difluoromethyl)-1H-pyrazol-3-yl)pyridin-4-yl)amino)methyl)cyclohexan-1-ol (355 mg, 1.000 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.41 (d, 1H), 8.37 (s, 1H), 7.99 (t, 1H), 7.86 (d, 1H), 7.72 (brs, 1H), 7.27 (s, 1H), 7.18 (t, 1H), 7.06 (s, 1H), 6.83 (d, 1H), 3.62-3.50 (m, 1H), 3.25-3.22 (m, 2H), 2.85-2.81 (m, 1H), 2.08 (d, 2H), 2.01 (d, 2H), 1.93-1.72 (m, 2H), 1.55-1.51 (m, 2H), 1.35-1.28 (m, 3H), 1.24-1.20 (m, 4H); MS (ESI) m/z=586.0 (M+H)$^+$ Example 32. 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol Step 1. 3-(((2-Chloro-5-(1-(difluoromethyl)-1H-pyrazol-3-yl)pyridin-4-yl)amino)methyl)cyclohexan-1-ol The title compound as a pale yellow solid (369 mg) was prepared in the same fashion as Step 1 in Example 7, except that 3-(aminomethyl)cyclohexanol (196 mg, 1.510 mmol) was used instead of 3-amino-3-methylbutan-2-ol. $^1$H-NMR (CDCl$_3$, 400 MHz) δ 8.35 (s, 1H), 8.06 (s, 1H), 7.87 (s, 1H), 7.20 (t, 1H), 6.83 (d, 1H), 6.57 (s, 1H), 3.68-3.63 (m, 1H), 3.19-3.02 (m, 2H), 2.18-2.05 (m, 2H), 1.88-1.75 (m, 4H), 1.37-1.20 (m, 2H), 1.12-0.97 (m, 2H); MS (ESI) m/z=357.1 (M+H)$^+$ Step 2. 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol The title compound as a white solid (140 mg) was prepared in the same fashion as Step 2 in Example 1, except that 3-(((2-chloro-5-(1-(difluoromethyl)-1H-pyrazol-3-yl)pyridin-4-yl)amino)methyl)cyclohexan-1-ol (355 mg, 1.000 mmol) prepared in Step 1 was used instead of 2-chloro-5-

(1-cyclopropyl-1H-pyrazol-4-yl)-4-((1-methyl-1H-pyrazol-4-yl)ethynyl)pyridine. ¹H-NMR (CDCl₃, 400 MHz) δ 8.68 (s, 1H), 8.47 (s, 1H), 8.43 (d, 1H), 8.38 (s, 1H), 8.04 (t, 1H), 7.87 (d, 1H), 7.47 (s, 1H), 7.20 (t, 1H), 7.08 (s, 1H), 6.84 (d, 1H), 3.70-3.64 (m, 1H), 3.30 (t, 1H), 2.87-2.83 (s, 1H), 2.16 (d, 1H), 2.04 (d, 1H), 1.89-1.86 (m, 3H), 1.54-1.52 (m, 2H), 1.38-1.05 (m, 7H); MS (ESI) m/z=586.0 (M+H)⁺

Example 33. 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino) methyl)cyclopentan-1-ol Step 1. 3-(((2-Chloro-5-(1-(difluoromethyl)-1H-pyrazol-3-yl)pyridin-4-yl)amino)methyl)cyclopentan-1-ol The title compound as a pale yellow solid (334 mg) was prepared in the same fashion as Step 1 in Example 7, except that 3-(aminomethyl)cyclopentanol (174 mg, 1.51 mmol) and was used instead of 3-amino-3-methylbutan-2-ol. ¹H-NMR (CDCl₃, 400 MHz) δ 8.34 (s, 1H), 8.33-8.03 (m, 1H), 7.87 (s, 1H), 7.42-7.04 (m, 1H), 6.83-6.81 (m, 1H), 6.58-6.57 (m, 1H), 4.46-4.41 (m, 1H), 3.30-3.17 (m, 2H), 2.65-2.32 (m, 1H), 2.13-2.05 (m, 1H), 1.91-1.45 (m, 6H); MS (ESI) m/z=343.1 (M+H)⁺

Step 2. 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl) cyclopentan-1-ol The title compound as a white solid (102 mg) was prepared in the same fashion as Step 2 in Example 1, except that 3-(((2-chloro-5-(1-(difluoromethyl)-1H-pyrazol-3-yl)pyridin-4-yl)amino)methyl)cyclopentan-1-ol (326 mg, 0.9500 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.67 (s, 1H), 8.49-8.47 (m, 1H), 8.41-8.32 (m, 2H), 8.00-7.95 (m, 1H), 7.87-7.83 (m, 1H), 7.44-7.05 (m, 1H), 7.21-7.20 (m, 1H), 7.14-7.11 (m, 1H), 6.83-6.82 (m, 1H), 4.48-4.41 (m, 1H), 3.44-3.27 (m, 2H), 2.87-2.80 (m, 1H), 2.72-2.42 (m, 1H), 2.68-1.96 (m, 3H), 1.95-1.60 (m, 6H), 1.23-1.21 (m, 2H); MS (ESI) m/z=572.0 (M+H)⁺

Example 34. (1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl) amino)methyl)cyclobutan-1-ol Step 1. (1r,3r)-3-(((2-Chloro-5-(1-(difluoromethyl)-1H-pyrazol-3-yl)pyridin-4-yl)amino)methyl)cyclobutan-1-ol The title compound as a pale yellow solid (340 mg) was prepared in the same fashion as Step 1 in Example 7, except that trans-3-(aminomethyl)cyclobutanol hydrochloride (208 mg, 1.51 mmol) was used instead of 3-amino-3-methylbutan-2-ol. ¹H-NMR (CDCl₃, 400 MHz) δ 8.35 (s, 1H), 7.94 (s, 1H), 7.87 (d, 1H), 7.17 (t, 1H), 6.83 (d, 1H), 6.58 (s, 1H), 4.53 (t, 1H), 3.31-3.28 (m, 2H), 2.68-2.62 (m, 1H), 2.28-2.20 (m, 5H); MS (ESI) m/z=329.1 (M+H)⁺

Step 2. (1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino) methyl)cyclobutan-1-ol The title compound as a white solid (8 mg) was prepared in the same fashion as Step 2 in Example 1, except that (1r,3r)-3-(((2-chloro-5-(1-(difluoromethyl)-1H-pyrazol-3-yl)pyridin-4-yl)amino)methyl)cyclobutan-1-ol (327 mg, 1.000 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.67 (s, 1H), 8.47 (s, 1H), 8.43 (d, 1H), 8.39 (s, 1H), 7.92 (t, 1H), 7.87 (d, 1H), 7.48 (s, 1H), 7.18 (t, 1H), 7.23 (d, 1H), 7.13 (s, 1H), 6.84 (d, 1H), 4.57-4.53 (m, 1H), 3.43-3.40 (m, 2H), 2.86-2.84 (m, 1H), 2.82-2.74 (m, 1H), 2.36-2.30 (m, 2H), 2.24-2.19 (m, 2H), 1.58 (s, 1H), 1.56-1.52 (m, 3H), 1.25-1.22 (m, 2H); MS (ESI) m/z=558.0 (M+H)⁺

Example 35. (1s,3s)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl) amino)methyl)cyclobutan-1-ol Step 1. (1s,3s)-3-(((2-Chloro-5-(1-(difluoromethyl)-1H-pyrazol-3-yl)pyridin-4-yl)amino)methyl)cyclobutan-1-ol The title compound as a pale yellow solid (338 mg) was prepared in the same fashion as Step 1 in Example 7, except that cis-3-(aminomethyl)cyclobutanol hydrochloride (20 mg, 1.510 mmol) was used instead of 3-amino-3-methylbutan-2-ol. ¹H-NMR (CDCl₃, 400 MHz) δ 8.36 (s, 1H), 8.09 (s, 1H), 7.88 (d, 1H), 7.33 (t, 1H), 6.84 (d, 1H), 6.55 (s, 1H), 4.30-4.26 (m, 1H), 3.29-3.27 (m, 2H), 2.57-2.50 (m, 2H), 2.29-2.17 (m, 2H), 1.87-1.80 (m, 2H); MS (ESI) m/z=328.9 (M+H)⁺

Step 2. (1s,3s)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino) methyl)cyclobutan-1-ol The title compound as a white solid (3 mg) was prepared in the same fashion as Step 2 in Example 1, except that (1s,3s)-3-(((2-chloro-5-(1-(difluoromethyl)-1H-pyrazol-3-yl)pyridin-4-yl)amino)methyl)cyclobutan-1-ol (327 mg, 1.000 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.68 (s, 1H), 8.48 (s, 1H), 8.42 (d, 1H), 8.39 (s, 1H), 8.07 (s, 1H), 7.88 (d, 1H), 7.53 (s, 1H), 7.36 (t, 1H), 7.23 (s, 1H), 7.12 (d, 1H), 6.85 (d, 1H), 4.30-4.26 (m, 1H), 3.42-3.40 (m, 2H), 2.86-2.82 (m, 1H), 2.59-2.54 (m, 2H), 2.34-2.31 (m, 1H), 1.95-1.88 (m, 2H), 1.57-1.52 (m, 2H), 1.26-1.21 (m, 3H); MS (ESI) m/z=558.2 (M+H)⁺

Example 36. (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl) amino)methyl)-1-methylcyclohexan-1-ol Step 1. (1r,4r)-4-(((2-Chloro-5-(1-(difluoromethyl)-1H-pyrazol-3-yl)pyridin-4-yl)amino)methyl)-1-methylcyclohexan-1-ol The title compound as a pale yellow solid (300 mg) was prepared in the same fashion as Step 1 in Example 7, except that trans-4-(aminomethyl)-1-methylcyclohexan-1-ol hydrochloride (200 mg, 1.11 mmol) w used instead of 3-amino-3-methylbutan-2-ol. $^1$H-NMR (CDCl$_3$, 400 MHz) δ 8.37 (s, 1H), 8.00 (s, 1H), 7.88 (d, 1H), 7.17 (t, 1H), 6.85 (d, 1H), 6.58 (s, 1H), 3.19-3.16 (m, 2H), 1.89-1.85 (m, 2H), 1.79-1.72 (m, 3H), 1.56-1.49 (m, 2H), 1.36 (s, 1H), 1.30-1.25 (m, 5H); MS (ESI) m/z=371.1 (M+H)$^+$

Step 2. (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-1-methylcyclohexan-1-ol The title compound as a white solid (12 mg) was prepared in the same fashion as Step 2 in Example 1, except that (1r,4r)-4-(((2-chloro-5-(1-(difluoromethyl)-1H-pyrazol-3-yl)pyridin-4-yl)amino)methyl)-1-methylcyclohexan-1-ol (277 mg, 0.746 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.47 (s, 1H), 8.42 (d, 1H), 8.39 (s, 1H), 8.07 (s, 1H), 7.96 (t, 1H), 7.87 (d, 1H), 7.58 (s, 1H), 7.30 (d, 1H), 7.18 (t, 1H), 7.03 (s, 1H), 6.84 (d, 1H), 3.50-3.26 (m, 2H), 2.84-2.81 (m, 1H), 1.91-1.90 (m, 2H), 1.88-1.81 (m, 3H), 1.79-1.50 (m, 2H), 1.37-1.30 (m, 3H), 1.28 (s, 3H), 1.24-1.21 (m, 2H); MS (ESI) m/z=600.2 (M+H)$^+$

Example 37. 5-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylpiperidin-2-one

Step 1. 5-((2-Chloro-5-(1-(difluoromethyl)-1H-pyrazol-3-yl)pyridin-4-yl)amino)-1-methylpiperidin-2-one The title compound as a pale yellow solid (71 mg) was prepared in the same fashion as Step 1 in Example 7, except that 5-amino-1-methylpiperidin-2-one (47 mg, 0.363 mmol) was used instead of 3-amino-3-methylbutan-2-ol. $^1$H-NMR (CDCl$_3$, 400 MHz) δ 8.37-8.36 (m, 2H), 7.86 (d, 1H), 7.18 (t, 1H), 6.80 (d, 1H), 6.61 (s, 1H), 4.02-3.98-(m, 1H), 3.70-3.66 (m, 1H), 3.32-3.28 (m, 1H), 2.97 (s, 3H), 2.51 (s, 2H), 2.15-2.06 (m, 2H)

Step 2. 5-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylpiperidin-2-one The title compound as a white solid (12 mg) was prepared in the same fashion as Step 2 in Example 1, except that 5-((2-chloro-5-(1-(difluoromethyl)-1H-pyrazol-3-yl)pyridin-4-yl)amino)-1-methylpiperidin-2-one (71 mg, 0.200 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.64 (d, 1H), 8.46-8.40 (m, 3H), 7.87 (d, 1H), 7.60 (brs, 1H), 7.40-7.05 (m, 3H), 6.32 (s, 1H), 4.19 (brs, 1H), 3.86-3.83 (m, 1H), 3.43-3.40 (m, 1H), 3.02 (d, 3H), 2.87-2.83 (m, 1H), 2.56-2.54 (m, 2H), 2.26-2.21 (m, 2H), 1.48-1.46 (m, 2H), 1.28-1.25 (m, 2H); MS (ESI) m/z=585.0 (M+H)$^+$

Example 38. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-2-one

Step 1. 3-((2-Chloro-5-(1-(difluoromethyl)-1H-pyrazol-3-yl)pyridin-4-yl)amino)piperidin-2-one The title compound as a pale yellow solid (43 mg) was prepared in the same fashion as Step 1 in Example 7, except that 3-aminopiperidin-2-one (41.5 mg, 0.363 mmol) was used instead of 3-amino-3-methylbutan-2-ol. $^1$H-NMR (CDCl$_3$, 400 MHz) δ 8.67 (d, 1H), 8.39 (s, 21H), 7.25 (t, 1H), 6.82 (d, 1H), 6.60 (s, 1H), 6.60 (brs, 1H), 4.46-4.07 (m, 1H), 3.46-3.43 (m, 2H), 2.57-2.50 (m, 1H), 2.08-2.01 (m, 2H), 1.80-1.07 (m, 1H)

Step 2. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-2-one The title compound as a white solid (9 mg) was prepared in the same fashion as Step 2 in Example 1, except that 3-((2-chloro-5-(1-(difluoromethyl)-1H-pyrazol-3-yl)pyridin-4-yl)amino)piperidin-2-one (51.5 mg, 0.151 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (MeOD, 400 MHz) δ 8.72 (s, 1H), 8.51 (s, 1H), 8.46-8.39 (m, 3H), 8.32 (d, 1H), 7.81 (t, 1H), 7.74 (s, 1H), 7.60 (brs, 1H), 7.31 (brs, 1H), 7.13 (d, 1H), 4.13-4.10 (m, 1H), 3.25-3.22 (m, 2H), 2.41-2.36 (m, 1H), 1.87-1.84 (m, 2H), 1.71-1.64 (m, 1H), 1.35-1.33 (m, 2H), 1.30-1.29 (m, 2H); MS (ESI) m/z=571.1 (M+H)$^+$

Example 39. 6-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)bicycle[2.2.1]heptan-2-ol

Step 1. 6-((2-Chloro-5-(1-(difluoromethyl)-1H-pyrazol-3-yl)pyridin-4-yl)amino)bicyclo[2.2.1]heptan-2-ol The title compound as a pale yellow solid (60 mg) was prepared in the same fashion as Step 1 in Example 7, except that 6-aminobicyclo[2.2.1]heptan-2-ol (67 mg, 0.525 mmol) was used instead of 3-amino-3-methylbutan-2-ol. $^1$H-NMR (CDCl$_3$, 400 MHz) δ 8.30 (s, 1H), 7.92 (d, 1H), 7.84 (d, 1H), 7.17 (t, 1H), 6.78 (d, 1H), 6.50 (s, 1H), 3.91 (d, 1H), 3.79-3.61 (m, 1H), 3.24-3.21 (m, 1H), 2.37-2.33 (m, 1H), 2.22-2.19 (m, 1H), 1.81-1.77 (m, 1H), 1.71-1.67 (m, 1H), 1.39-1.34 (m, 2H), 0.85-0.81 (m, 1H)

Step 2. 6-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)bicyclo[2.2.1]heptan-2-ol The title compound as a white solid (31 mg) was prepared in the same fashion as Step 2 in Example 1, except that 6-((2-chloro-5-(1-(difluoromethyl)-1H-pyrazol-3-yl)pyridin-4-yl)amino)bicyclo[2.2.1]heptan-2-ol (60 mg, 0.171 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.62 (s, 1H), 8.35 (s, 1H), 8.26 (s, 1H), 8.20 (d, 1H), 7.99 (d, 1H), 7.81 (d, 1H), 7.24 (brs, 1H), 7.17 (t, 1H), 6.98 (brs, 1H), 6.72 (d, 1H), 4.21 (d, 1H), 3.94-3.92 (m, 1H), 2.83-2.79 (m, 1H), 2.70-2.68 (m, 1H), 2.40-2.39 (m, 1H), 2.30-2.26 (m, 1H), 1.86-1.78 (m, 2H), 1.52-1.49 (m, 4H), 1.22-1.19 (m, 2H), 0.92-0.88 (m, 1H); MS (ESI) m/z=584.0 (M+H)$^+$ Example 40. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclobutan-1-ol Step 1. 3-((2-Chloro-5-(1-(difluoromethyl)-1H-pyrazol-3-yl)pyridin-4-yl)amino)cyclobutan-1-ol The title compound as a pale yellow solid (71 mg) was prepared in the same fashion as Step 1 in Example 7, except that 3-aminocyclobutan-1-ol (46 mg, 0.525 mmol) was used instead of 3-amino-3-methylbutan-2-ol. $^1$H-NMR (CDCl$_3$, 400 MHz) δ 8.34 (d, 1H), 8.06 (brs, 1H), 7.87 (s, 1H), 7.22 (t, 1H), 6.81 (s, 1H), 6.42 (d, 1H), 4.30-4.21 (m, 1H), 3.66-3.51 (m, 1H), 2.64 (brs, 1H), 2.55-2.35 (m, 2H), 1.99-1.94 (m, 2H); MS (ESI) m/z=314.9 (M+H)$^+$ Step 2. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclobutan-1-ol The title compound as a white solid (14 mg) was prepared in the same fashion as Step 2 in Example 1, except that 3-((2-chloro-5-(1-(difluoromethyl)-1H-pyrazol-3-yl)pyridin-4-yl)amino)cyclobutan-1-ol (53 mg, 0.171 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.46-8.38 (m, 2H), 8.01 (d, 1H), 7.87 (d, 1H), 7.86 (s, 1H), 7.27-7.19 (m, 2H), 7.09 (s, 1H), 6.82 (d, 1H), 4.33-4.29 (m, 1H), 3.76-3.66 (m, 1H), 3.04-3.01 (m, 1H), 2.87-2.81 (m, 1H), 2.55-2.35 (m, 2H), 1.99-1.94 (m, 2H), 1.57-1.52 (m, 2H), 1.28-1.21 (m, 2H); MS (ESI) m/z=544.0 (M+H)$^+$ Example 41. N$^4$-(3-(1H-Imidazol-1-yl)propyl)-N$^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine Step 1. N-(3-(1H-Imidazol-1-yl)propyl)-2-chloro-5-(1-(difluoromethyl)-1H-pyrazol-3-yl)pyridin-4-amine The title compound as a pale yellow solid (89 mg) was prepared in the same fashion as Step 1 in Example 7, except that 3-(1H-imidazol-1-yl)propan-1-amine (66 mg, 0.525 mmol) was used instead of 3-amino-3-methylbutan-2-ol. $^1$H-NMR (CDCl$_3$, 400 MHz) δ 8.33 (s, 1H), 7.96 (t, 1H), 7.86 (d, 1H), 7.48 (s, 1H), 7.25 (t, 1H), 7.06 (s, 1H), 6.92 (s, 1H), 6.79 (d, 1H), 6.48 (s, 1H), 4.08 (t, 2H), 3.23-3.19 (m, 2H), 2.19-2.12 (m, 2H)

Step 2. N$^4$-(3-(1H-Imidazol-1-yl)propyl)-N$^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine The title compound as a white solid (36 mg) was prepared in the same fashion as Step 2 in Example 1, except that N-(3-(1H-imidazol-1-yl)propyl)-2-chloro-5-(1-(difluoromethyl)-1H-pyrazol-3-yl)pyridin-4-amine (60 mg, 0.171 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46-8.39 (m, 3H), 7.99 (s, 1H), 7.89 (d, 1H), 7.54 (s, 1H), 7.26-7.24 (m, 2H), 7.11-7.08 (m, 2H), 6.98 (s, 1H), 6.85 (d, 1H), 4.89 (brs, 1H), 4.18 (t, 2H), 3.43-3.38 (m, 2H), 2.86-2.82 (m, 1H), 2.33-2.28 (m, 2H), 1.56-1.52 (m, 2H), 1.29-1.23 (m, 2H); MS (ESI) m/z=582.0 (M+H)$^+$ Example 42. 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)propan-2-ol Step 1. 2-((1s,4s)-4-((2-Chloro-5-(1-methyl-1H-pyrazol-3-yl)pyridin-4-yl)amino)cyclohexyl)propan-2-ol The title compound as a white solid (302.5 mg) was prepared in the same fashion as Step 1 in Example 7, except that 2-((1s,4s)-4-aminocyclohexyl)propan-2-ol (223 mg, 1.418 mmol) and 2-chloro-4-fluoro-5-(1-methyl-1H-pyrazol-3-yl)pyridine (200 mg, 0.945 mmol) prepared in Reference Example 3 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.64 (s, 1H), 8.30 (s, 1H), 7.38 (s, 1H), 6.58 (d, 1H), 6.52 (s, 1H), 3.91 (s, 3H), 3.81 (d, 1H), 2.04-1.93 (m, 2H), 1.81-1.69 (m, 2H), 1.69-1.53 (m, 3H), 1.45-1.32 (m, 3H), 1.20 (s, 6H); MS (ESI) m/z=349.1 (M+H)$^+$ Step 2. 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)propan-2-ol The title compound as an off white solid (30 mg) was prepared in the same fashion as Step 2 in Example 1, except that 2-((1s,4s)-4-((2-chloro-5-(1-methyl-1H-pyrazol-3-yl)pyridin-4-yl)amino)cyclohexyl)propan-2-ol (131.5 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.63 (d, 1H), 8.46 (s, 1H), 8.36 (s, 1H), 8.35 (d, 1H), 8.14 (s, 1H), 7.40 (d, 1H), 7.30 (brs, 1H), 7.06 (d, 1H), 6.61 (d, 1H), 4.01 (s, 1H), 3.95 (s, 3H), 2.87-2.80 (m, 1H), 2.16-2.08 (m, 2H), 1.83-1.71 (m, 4H), 1.55-1.43 (m, 6H), 1.27-1.18 (m, 8H); MS (ESI) m/z=578.1 (M+H)$^+$ Example 43. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-(1-methyl-1H-pyrazol-3-yl)pyridine-2,4-diamine Step 1. (1s,4s)-N$^1$-(2-Chloro-5-(1-methyl-1H-pyrazol-3-yl)pyridin-4-yl)-N$^4$-(2-fluoroethyl)cyclohexane-1,4-diamine The title compound as a white solid (253 mg) was prepared in the same fashion as Step 1 in Example 7, except that (1s,4s)-N$^1$-(2-fluoroethyl)cyclohexane-1,4-diamine (227 mg, 1.418 mmol) and 2-chloro-4-fluoro-5-(1-methyl-1H-pyrazol-3-yl)pyridine (200 mg, 0.945 mmol) prepared in Reference Example 3 were used instead of 3-amino-3- methylbutan-2-ol and 2-chloro-5-(1-(difluoromethyl)-1H-pyrazol-3-yl)-4-fluoropyridine. MS (ESI) m/z=352.1 (M+H)$^+$

Step 2. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-(1-methyl-1H-pyrazol-3-yl)pyridine-2,4-diamine The title compound as an off white solid (45 mg) was prepared in the same fashion as Step 2 in Example 1, except that (1s,4s)-N$^1$-(2-chloro-5-(1-methyl-1H-pyrazol-3-yl)pyridin-4-yl)-N$^4$-(2-fluoroethyl)cyclohexane-1,4-diamine (133 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.57 (d, 1H), 8.46 (s, 1H), 8.38 (d, 1H), 8.33 (s, 1H), 7.40 (d, 1H), 7.21 (brs, 1H), 7.13 (d, 1H), 6.59 (d, 1H), 4.62 (t, 1H), 4.51 (t, 1H), 3.96 (s, 3H), 3.00 (t, 1H), 2.93 (t, 1H), 2.87-2.80 (m, 1H), 2.71-2.64 (m, 1H), 2.08-2.03 (m, 2H), 1.87-1.79 (m, 4H), 1.56-1.52 (m, 4H), 1.25-1.19 (m, 2H); MS (ESI) m/z=581.1 (M+H)$^+$

Example 44. (5s,8s)-8-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-azaspiro[4.5]decan-2-one

Step 1. (5s,8s)-8-((2-Chloro-5-(1-methyl-1H-pyrazol-3-yl)pyridin-4-yl)amino)-1-azaspiro[4.5]decan-2-one The title compound as a white solid (202 mg) was prepared in the same fashion as Step 1 in Example 7, except that (5s,8s)-8-amino-1-azaspiro[4.5]decan-2-one hydrochloride (363 mg, 1.772 mmol) and 2-chloro-4-fluoro-5-(1-methyl-1H-pyrazol-3-yl)pyridine (250 mg, 1.181 mmol) prepared in Reference Example 3 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.41 (d, 1H), 8.33 (s, 1H), 7.41 (d, 1H), 6.61 (d, 1H), 6.53 (s, 1H), 6.52 (s, 1H), 3.96 (s, 3H), 3.56-3.47 (m, 1H), 2.84 (t, 2H), 1.98-1.88 (m, 3H), 1.87-1.84 (m, 3H), 1.71-1.64 (m, 2H), 1.63-1.53 (m, 2H); MS (ESI) m/z=360.1 (M+H)$^+$

Step 2. (5s,8s)-8-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-azaspiro[4.5]decan-2-one The title compound as an off white solid (35 mg) was prepared in the same fashion as Step 2 in Example 1, except that (5s,8s)-8-((2-chloro-5-(1-methyl-1H-pyrazol-3-yl)pyridin-4-yl)amino)-1-azaspiro[4.5]decan-2-one (179 mg, 0.498 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.95 (s, 1H), 8.64 (s, 1H), 8.46-8.38 (m, 3H), 8.16 (s, 1H), 7.79 (d, 1H), 7.45 (s, 1H), 7.35 (s, 1H), 6.78 (d, 1H), 3.93 (s, 3H), 3.61-3.56 (m, 1H), 3.30-3.24 (m, 1H), 2.19 (t, 2H), 1.95-1.90 (m, 2H), 1.84 (t, 2H), 1.77-1.68 (m, 4H), 1.58-1.52 (m, 2H), 1.37-1.32 (m, 2H), 1.30-1.21 (m, 2H); MS (ESI) m/z=589.2 (M+H)$^+$

Example 45. N$^2$-(2-(1-(Cyclopropylsulfonyl)-1H-pyrazol-4-yl)pyrimidin-4-yl)-N$^4$-((1s,4s)-4-((2,2-difluoroethyl)amino)cyclohexyl)-5-(1-methyl-1H-pyrazol-3-yl)pyridine-2,4-diamine

Step 1. (1s,4s)-N$^1$-(2-Chloro-5-(1-methyl-1H-pyrazol-3-yl)pyridin-4-yl)-N$^4$-(2,2-difluoroethyl)cyclohexane-1,4-diamine The title compound as a white solid (355 mg) was prepared in the same fashion as Step 1 in Example 7, except that (1s,4s)-N$^1$-(2,2-difluoroethyl)cyclohexane-1,4-diamine (316 mg, 1.772 mmol) and 2-chloro-4-fluoro-5-(1-methyl-1H-pyrazol-3-yl)pyridine (250 mg, 1.181 mmol) prepared in Reference Example 3 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.53 (d, 1H), 8.32 (s, 1H), 7.41 (s, 1H), 6.61 (s, 1H), 6.54 (s, 1H), 5.85 (dt, 1H), 3.95 (s, 3H), 3.69 (s, 1H), 3.01 (dt, 2H), 2.72-2.67 (m, 1H), 1.94-1.88 (m, 2H), 1.83-1.78 (m, 2H), 1.76-1.69 (m, 2H), 1.57-1.48 (m, 2H); MS (ESI) m/z=370.1 (M+H)$^+$

Step 2. N$^2$-(2-(1-(Cyclopropylsulfonyl)-1H-pyrazol-4-yl)pyrimidin-4-yl)-N$^4$-((1s,4s)-4-((2,2-difluoroethyl)amino)cyclohexyl)-5-(1-methyl-1H-pyrazol-3-yl)pyridine-2,4-diamine The title compound as an off white solid (107 mg) was prepared in the same fashion as Step 2 in Example 1, except that (1s,4s)-N$^1$-(2-chloro-5-(1-methyl-1H-pyrazol-3-yl)pyridin-4-yl)-N$^4$-(2,2-difluoroethyl)cyclohexane-1,4-diamine (167 mg, 0.452 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.55 (d, 1H), 8.46 (s, 1H), 8.38 (d, 1H), 8.36 (s, 1H), 7.96 (s, 1H), 7.41 (d, 1H), 7.22 (s, 1H), 7.11 (d 1H), 6.60 (d, 1H), 5.85 (tt, 1H), 3.96 (s, 3H), 3.94-3.89 (m, 1H), 3.02 (td, 2H), 2.86-2.80 (m, 1H), 2.72-2.65 (m, 1H), 2.06-2.01 (m, 2H), 1.87-1.77 (m, 4H), 1.57-1.47 (m, 4H), 1.25-1.19 (m, 2H); MS (ESI) m/z=599.1 (M+H)$^+$

Example 46. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-methylcyclohexane-1-carboxamide

Step 1. (1s,4s)-4-((2-Chloro-5-(1-methyl-1H-pyrazol-3-yl)pyridin-4-yl)amino)-N-methylcyclohexane-1-carboxamide The title compound as a white solid (341 mg) was prepared in the same fashion as Step 1 in Example 7, except that (1s,4s)-4-amino-N-methylcyclohexane-1-carboxamide dihydrochloride (406 mg, 1.772 mmol) and 2-chloro-4-fluoro-5-(1-methyl-1H-pyrazol-3-yl)pyridine (250 mg, 1.181 mmol) prepared in Reference Example 3 were used instead of 3-amino-3-methylbutan-2-ol and 2-chloro-5-(1-(difluoromethyl)-1H-pyrazol-3-yl)-4-fluoropyridine.
$^1$H-NMR (CDCl$_3$, 400 MHz) δ 8.82 (s, 1H), 8.27 (s, 1H), 7.37 (s, 1H), 6.55 (s, 1H), 6.49 (s, 1H), 6.09 (s, 1H), 3.98 (s, 3H), 3.76 (s, 1H), 2.75 (s, 3H), 2.19 (s, 1H), 1.91-1.89 (m, 4H), 1.63-1.57 (m, 4H); MS (ESI) m/z=348.1 (M+H)$^+$

Step 2. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-methylcyclohexane-1-carboxamide The title compound as an off white solid (133.5 mg) was prepared in the same fashion as Step 2 in Example 1, except (1s,4s)-4-((2-chloro-5-(1-methyl-1H-pyrazol-3-yl)pyridin-4-yl)amino)-N-methylcyclohexane-1-carboxamide (157 mg, 0.452 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.82 (d, 1H), 8.65 (s, 1H), 8.46 (s, 1H), 8.37 (d, 1H), 8.36 (d, 1H), 7.94 (brs, 1H), 7.41 (d, 1H), 7.27 (s, 1H), 7.05 (d, 1H), 6.60 (d, 1H), 5.59 (d, 1H), 4.03 (s, 3H), 3.98 (s, 1H), 2.86-2.80 (m, 1H), 2.82 (d, 3H), 2.27-2.21 (m, 1H), 2.09-2.04 (m, 2H), 1.99-1.90 (m, 2H), 1.82-1.75 (m, 4H), 1.55-1.51 (m, 2H), 1.25-1.19 (m, 2H)

Example 47. (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclohexan-1-ol

Step 1. (1r,4r)-4-(((2-Chloro-5-(1-methyl-1H-pyrazol-3-yl)pyridin-4-yl)amino)methyl)cyclohexan-1-ol The title compound as a white solid (233 mg) was prepared in the same fashion as Step 1 in Example 7, except that trans-4-(aminomethyl)cyclohexanol hydrochloride (211 mg, 1.28 mmol) and 2-chloro-4-fluoro-5-(1-methyl-1H-pyrazol-3-yl)pyridine (200 mg, 0.945 mmol) prepared in Reference Example 3 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.32 (s, 2H), 7.41 (d, 1H), 6.61 (d, 1H), 6.52 (s, 1H) 3.94 (s, 3H), 3.66-3.60 (m, 1H), 3.50 (d, 1H), 3.11 (t, 2H), 2.08-2.05 (m, 2H), 1.96-1.92 (m, 2H), 1.71-1.63 (m, 2H), 1.39-1.22 (m, 4H); MS (ESI) m/z=343.1 (M+H)$^+$

Step 2. (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclohexan-1-ol The title compound as a pale yellow solid (25 mg) was prepared in the same fashion as Step 2 in Example 1, except that (1r,4r)-4-(((2-chloro-5-(1-methyl-1H-pyrazol-3-yl)pyridin-4-yl)amino)methyl)cyclohexan-1-ol (250 mg, 0.750 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.40 (d, 1H), 8.35 (s, 1H), 8.29 (s, 1H), 7.53 (s, 1H), 7.46 (s, 1H), 7.41 (d, 1H), 6.93 (s, 1H), 6.61 (d, 1H), 3.95 (s, 3H), 3.65-3.63 (m, 1H), 3.24-3.21 (m, 2H), 2.85-2.81 (m, 1H), 2.09-2.06 (m, 2H), 2.00-1.97 (m, 2H), 1.76-1.75 (m, 2H), 1.60-1.51 (m, 3H), 1.42-1.22 (m, 5H); MS (ESI) m/z=550.2 (M+H)$^+$

Example 48. (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-1-methylcyclohexan-1-ol

Step 1. (1r,4r)-4-(((2-Chloro-5-(1-methyl-1H-pyrazol-3-yl)pyridin-4-yl)amino)methyl)-1-methylcyclohexan-1-ol The title compound as a white solid (245 mg) was prepared in the same fashion as Step 1 in Example 7, except that trans-4-(aminomethyl)-1-methylcyclohexan-1-ol hydrochloride (200 mg, 1.11 mmol) and 2-chloro-4-fluoro-5-(1-methyl-1H-pyrazol-3-yl)pyridine (200 mg, 0.945 mmol) prepared in Reference Example 3 were used instead of isopropylamine and 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.32 (s, 1H), 8.31 (s, 1H), 7.41 (d, 1H), 6.61 (d, 1H), 6.53 (s, 1H), 3.94 (s, 3H), 3.17-3.14 (m, 2H), 1.91-1.86 (m, 2H), 1.78-1.72 (m, 2H), 1.63 (s, 1H), 1.56-1.39 (m, 2H), 1.32 (s, 1H), 1.31-1.23 (m, 5H); MS (ESI) m/z=335.1 (M+H)$^+$

Step 2. (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-1-methylcyclohexan-1-ol The title compound as a pale yellow solid (88 mg) was prepared in the same fashion as Step 2 in Example 1, except that (1r,4r)-4-(((2-chloro-5-(1-methyl-1H-pyrazol-3-yl)pyridin-4-yl)amino)methyl)-1-methylcyclohexan-1-ol (250 mg, 0.746 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.41 (d, 1H), 8.35 (s, 1H), 8.28-8.25 (m, 1H), 7.50 (s, 1H), 7.41 (d, 1H), 6.96 (s, 1H), 6.61 (d, 1H), 3.95 (s, 3H), 3.27-3.25 (m, 2H), 2.86-2.80 (m, 1H), 1.94-1.89 (m, 2H), 1.86-1.77 (m, 2H), 1.61-1.50 (m, 4H), 1.40-1.39 (m, 2H), 1.37 (s, 3H), 1.30-1.20 (m, 2H); MS (ESI) m/z=564.2 (M+H)$^+$

Example 49. 2-((1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexyl)propan-2-ol

Step 1. 2-((1s,4s)-4-((2-Chloro-5-(2-(trifluoromethyl)thiazol-4-yl)pyridin-4-yl)amino)cyclohexyl)propan-2-ol The title compound as a white solid (407 mg) was prepared in the same fashion as Step 1 in Example 7, except that 2-((1s,4s)-4-aminocyclohexyl)propan-2-ol (250 mg, 1.592 mmol) and 4-(6-chloro-4-fluoro-3-pyridyl)-2-(trifluoromethyl)thiazole (300 mg, 1.061 mmol) prepared in Reference Example 4 were used instead of 3-amino-3-methylbutan-2-ol and 2-chloro-5-(1-(difluoromethyl)-1H-pyrazol-3-yl)-4-fluoropyridine. MS (ESI) m/z=420.0 (M+H)$^+$

Step 2. 2-((1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexyl)propan-2-ol The title compound as an off white solid (37 mg) was prepared in the same fashion as Step 2 in Example 1, except that 2-((1s,4s)-4-((2-chloro-5-(2-(trifluoromethyl)thiazol-4-yl)pyridin-4-yl)amino)cyclohexyl)propan-2-ol (174 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.41 (d, 1H), 8.37 (s, 1H), 8.11 (d, 1H), 7.72 (s, 1H), 7.60 (s, 1H), 7.29 (s, 1H), 7.10 (d, 1H), 3.96 (q, 1H), 2.88-2.82 (m, 1H), 2.13 (d, 2H), 1.80-1.74 (m, 4H), 1.57-1.53 (m, 2H), 1.44-1.34 (m, 2H), 1.29-1.23 (m, 3H), 1.20 (s, 6H)

Example 50. N²-(2-(1-(Cyclopropylsulfonyl)-1H-pyrazol-4-yl)pyrimidin-4-yl)-N⁴-((1s,4s)-4-((2-fluoroethyl)amino)cyclohexyl)-5-(2-(trifluoromethyl)thiazol-4-yl)pyridine-2,4-diamine

Step 1. (1s,4s)-N¹-(2-Chloro-5-(2-(trifluoromethyl)thiazol-4-yl)pyridin-4-yl)-N⁴-(2-fluoroethyl)cyclohexane-1,4-diamine The title compound as a white solid (342 mg) was prepared in the same fashion as Step 1 in Example 7, except that (1s,4s)-N¹-(2-fluoroethyl)cyclohexane-1,4-diamine (255 mg, 1.592 mmol) and 4-(6-chloro-4-fluoro-3-pyridyl)-2-(trifluoromethyl)thiazole (300 mg, 1.061 mmol) prepared in Reference Example 4 were used instead of 3-amino-3-methylbutan-2-ol and 2-chloro-5-(1-(difluoromethyl)-1H-pyrazol-3-yl)-4-fluoropyridine. MS (ESI) m/z=423.0 (M+H)⁺

Step 2. N²-(2-(1-(Cyclopropylsulfonyl)-1H-pyrazol-4-yl)pyrimidin-4-yl)-N-((1s,4s)-4-((2-fluoroethyl)amino)cyclohexyl)-5-(2-(trifluoromethyl)thiazol-4-yl)pyridine-2,4-diamine The title compound as an off white solid (37 mg) was prepared in the same fashion as Step 2 in Example 1, except that (1s,4s)-N¹-(2-chloro-5-(2-(trifluoromethyl)thiazol-4-yl)pyridin-4-yl)-N⁴-(2-fluoroethyl)cyclohexane-1,4-diamine (175 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.65 (s, 1H), 8.46 (s, 1H), 8.38 (d, 2H), 8.27 (d, 1H), 7.87 (d, 1H), 7.35 (t, 1H), 7.33 (s, 1H), 7.07 (d, 1H), 6.82 (d, 1H), 4.62 (t, 1H), 4.51 (t, 1H), 3.92 (s, 1H), 2.99 (t, 1H), 2.92 (t, 1H), 2.86-2.82 (m, 1H), 2.70-2.65 (m, 1H), 2.05-2.01 (m, 2H), 1.86-1.79 (m, 4H), 1.54-1.47 (m, 4H), 1.25-1.20 (m, 2H)

Example 51. (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-methylcyclohexan-1-ol

Step 1. (1s,4s)-4-((2-Chloro-5-(2-(trifluoromethyl)thiazol-4-yl)pyridin-4-yl)amino)-1-methylcyclohexan-1-ol The title compound as a white solid (496 mg) was prepared in the same fashion as Step 1 in Example 7, except that (1s,4s)-4-amino-1-methylcyclohexan-1-ol (586 mg, 3.538 mmol) and 4-(6-chloro-4-fluoro-3-pyridyl)-2-(trifluoromethyl)thiazole (500 mg, 3.538 mmol) prepared in Reference Example 4 were used instead of 3-amino-3-methylbutan-2-ol and 2-chloro-5-(1-(difluoromethyl)-1H-pyrazol-3-yl)-4-fluoropyridine. MS (ESI) m/z=392.1 (M+H)⁺

Step 2. (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-methylcyclohexan-1-ol The title compound as an off white solid (12 mg) was prepared in the same fashion as Step 2 in Example 1, except that (1s,4s)-4-((2-chloro-5-(2-(trifluoromethyl)thiazol-4-yl)pyridin-4-yl)amino)-1-methylcyclohexan-1-ol (81 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.66 (s, 1H), 8.48 (s, 1H), 8.44 (d, 1H), 8.34 (s, 1H), 7.76 (d, 1H), 7.69 (s, 1H), 7.53 (d, 1H), 7.31 (d, 1H), 7.03 (s, 1H), 3.52 (brs, 1H), 2.87-2.80 (m, 1H), 2.02-1.98 (m, 2H), 1.77-1.73 (m, 4H), 1.62-1.58 (m, 2H), 1.56-1.52 (m, 2H), 1.32 (s, 3H), 1.25-1.20 (m, 2H); MS (ESI) m/z=621.0 (M+H)⁺

Example 52. (5s,8s)-8-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-azaspiro[4.5]decan-2-one

Step 1. (5s,8s)-8-((2-Chloro-5-(2-(trifluoromethyl)thiazol-4-yl)pyridin-4-yl)amino)-1-azaspiro[4.5]decan-2-one The title compound as a white solid (235 mg) was prepared in the same fashion as Step 1 in Example 7, except that (5s,8s)-8-amino-1-azaspiro[4.5]decan-2-one hydrochloride (362 mg, 1.769 mmol) and 4-(6-chloro-4-fluoro-3-pyridyl)-2-(trifluoromethyl)thiazole (300 mg, 1.061 mmol) prepared in Reference Example 4 were used instead of 3-amino-3-methylbutan-2-ol and 2-chloro-5-(1-(difluoromethyl)-1H-pyrazol-3-yl)-4-fluoropyridine. MS (ESI) m/z=431.1 (M+H)⁺

Step 2. (5s,8s)-8-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-azaspiro[4.5]decan-2-one The title compound as an off white solid (74 mg) was prepared in the same fashion as Step 2 in Example 1, except that (5s,8s)-8-((2-chloro-5-(2-(trifluoromethyl)thiazol-4-yl)pyridin-4-yl)amino)-1-azaspiro[4.5]decan-2-one (162 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (DMSO-d₆, 400 MHz) δ 10.08 (s, 1H), 8.65 (s, 1H), 8.52 (s, 1H), 8.49 (s, 1H), 8.47 (s, 1H), 8.43 (d, 1H), 8.14 (s, 1H), 7.54 (s, 2H), 7.36 (s 1H), 3.54 (brs, 1H), 3.29-3.23 (m, 1H), 2.18 (t, 2H), 1.95-1.90 (m, 2H), 1.80 (t, 2H), 1.71-1.62 (m, 4H), 1.54-1.48 (m, 2H), 1.36-1.33 (m, 2H), 1.27-1.24 (m, 2H); MS (ESI) m/z=660.2 (M+H)⁺

Example 53. N²-(2-(1-(Cyclopropylsulfonyl)-1H-pyrazol-4-yl)pyrimidin-4-yl)-N⁴-((1s,4s)-4-((2,2-difluoroethyl)amino)cyclohexyl)-5-(2-(trifluoromethyl)thiazol-4-yl)pyridine-2,4-diamine

Step 1. (1s,4s)-N¹-(2-Chloro-5-(2-(trifluoromethyl)thiazol-4-yl)pyridin-4-yl)-N⁴-(2,2-difluoroethyl)cyclohexane-1,4-diamine The title compound as a white solid (360.5 mg) was prepared in the same fashion as Step 1 in Example 7, except that (1s,4s)-N¹-(2,2-difluoroethyl)cyclohexane-1,4-diamine (236.5 mg, 1.327 mmol) and 4-(6-chloro-4-fluoro-3-pyridyl)-2-(trifluoromethyl)thiazole (250 mg, 0.884 mmol) prepared in Reference Example 4 were used instead of 3-amino-3-methylbutan-2-ol and 2-chloro-5-(1-(difluoromethyl)-1H-pyrazol-3-yl)-4-fluoropyridine. ¹H-NMR (CDCl₃, 400 MHz) δ 8.35 (s, 1H), 8.02 (d, 1H), 7.79 (s, 1H), 6.59 (s, 1H), 5.82 (tt, 1H), 3.72-3.68 (m, 1H), 2.99 (td, 2H), 2.68-2.64 (m, 1H), 1.93-1.88 (m, 2H), 1.85-1.81 (m, 2H), 1.75-1.68 (m, 2H), 1.47-1.38 (m, 2H); MS (ESI) m/z=441.0 (M+H)$^+$ Step 2. N$^2$-(2-(1-(Cyclopropylsulfonyl)-1H-pyrazol-4-yl)pyrimidin-4-yl)-N$^4$-((1s,4s)-4-((2,2-difluoroethyl)amino)cyclohexyl)-5-(2-(trifluoromethyl)thiazol-4-yl)pyridine-2,4-diamine The title compound as an off white solid (140 mg) was prepared in the same fashion as Step 2 in Example 1, except that (1s,4s)-N$^1$-(2-chloro-5-(2-(trifluoromethyl)thiazol-4-yl)pyridin-4-yl)-N$^4$-(2,2-difluoroethyl)cyclohexane-1,4-diamine (347 mg, 0.788 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.41 (d, 1H), 8.36 (s, 1H), 8.04 (d, 1H), 7.89 (s, 1H), 7.70 (s, 1H), 7.30 (s, 1H), 7.10 (d, 1H), 5.84 (tt, 1H), 3.90-3.88 (m, 1H), 3.01 (td, 2H), 2.87-2.81 (m, 1H), 2.68-2.62 (m, 1H), 2.04-2.01 (m, 2H), 1.88-1.77 (m, 4H), 1.56-1.52 (m, 2H), 1.47-1.38 (m, 2H), 1.26-1.20 (m, 2H); MS (ESI) m/z=670.1 (M+H)$^+$ Example 54. 2-(4-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)thiazol-2-yl)propan-2-ol Step 1. 2-(4-(6-Chloro-4-(((1s,4s)-4-(2-hydroxypropan-2-yl)cyclohexyl)amino)pyridin-3-yl)thiazol-2-yl)propan-2-ol The title compound as a white solid (332 mg) was prepared in the same fashion as Step 1 in Example 7, except that 2-((1s,4s)-4-aminocyclohexyl)propan-2-ol (259.5 mg, 1.650 mmol) and 2-(4-(6-chloro-4-fluoro-3-pyridyl)thiazol-2-yl)propan-2-ol (300 mg, 1.100 mmol) prepared in Reference Example 5 were used instead of 3-amino-3-methylbutan-2-ol and 2-chloro-5-(1-(difluoromethyl)-1H-pyrazol-3-yl)-4-fluoropyridine. MS (ESI) m/z=410.1 (M+H)$^+$ Step 2. 2-(4-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)thiazol-2-yl)propan-2-ol The title compound as an off white solid (36 mg) was prepared in the same fashion as Step 2 in Example 1, except that 2-(4-(6-chloro-4-(((1s,4s)-4-(2-hydroxypropan-2-yl)cyclohexyl)amino)pyridin-3-yl)thiazol-2-yl)propan-2-ol (170 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.45 (s, 1H), 8.36 (d, 1H), 8.24 (s, 1H), 8.03 (d, 1H), 7.33 (s, 2H), 7.04 (d, 1H), 3.94 (s, 1H), 2.87-2.81 (m, 1H), 2.15-2.11 (m, 2H), 1.78-1.74 (m, 2H), 1.74 (s, 6H), 1.55-1.51 (m, 2H), 1.47-1.37 (m, 4H), 1.23-1.99 (m, 2H), 1.18 (s, 6H)

Example 55. 2-(4-(6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)thiazol-2-yl)propan-2-ol Step 1. 2-(4-(6-Chloro-4-(((1s,4s)-4-((2-fluoroethyl)amino)cyclohexyl)amino)pyridin-3-yl)thiazol-2-yl)propan-2-ol The title compound as a white solid (259 mg) was prepared in the same fashion as Step 1 in Example 7, except that (1s,4s)-N$^1$-(2-fluoroethyl)cyclohexane-1,4-diamine (259.5 mg, 1.65 mmol) and 2-(4-(6-chloro-4-fluoro-3-pyridyl)thiazol-2-yl)propan-2-ol (300 mg, 1.100 mmol) prepared in Reference Example 5 were used instead of 3-amino-3-methylbutan-2-ol and 2-chloro-5-(1-(difluoromethyl)-1H-pyrazol-3-yl)-4-fluoropyridine. MS (ESI) m/z=413.1 (M+H)$^+$ Step 2. 2-(4-(6-((2-(1-(Cyclopropylsulfonyl)-1H-pyrazol-4-yl)pyrimidin-4-yl)amino)-4-(((1s,4s)-4-((2-fluoroethyl)amino)cyclohexyl)amino)pyridin-3-yl)thiazol-2-yl)propan-2-ol The title compound as an off white solid (33 mg) was prepared in the same fashion as Step 2 in Example 1, except that 2-(4-(6-chloro-4-(((1s,4s)-4-((2-fluoroethyl)amino)cyclohexyl)amino)pyridin-3-yl)thiazol-2-yl)propan-2-ol (171 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.39 (d, 1H), 8.23 (s, 1H), 7.95 (d, 1H), 7.35 (s, 1H), 7.33 (s, 1H), 7.09 (d, 1H), 4.67 (t, 1H), 4.55 (t, 1H), 4.00 (s, 1H), 2.99 (t, 1H), 2.92 (t, 1H), 2.87-2.81 (m, 1H), 2.74-2.69 (m, 1H), 2.00-1.97 (m, 2H), 1.84-1.76 (m, 4H), 1.76 (s, 6H), 1.76-1.70 (m, 2H), 1.56-1.51 (m, 2H), 1.25-1.19 (m, 2H)

Example 56. 2-(4-(6-((2-(1-(Cyclopropylsulfonyl)-1H-pyrazol-4-yl)pyrimidin-4-yl)amino)-4-(((1s,4s)-4-(methylamino)cyclohexyl)amino)pyridin-3-yl)thiazol-2-yl)propan-2-ol Step 1. 2-(4-(6-Chloro-4-(((1s,4s)-4-(methylamino)cyclohexyl)amino)pyridin-3-yl)thiazol-2-yl)propan-2-ol The title compound as a white solid (272 mg) was prepared in the same fashion as Step 1 in Example 7, except that (1s,4s)-N$^1$-methylcyclohexane-1,4-diamine (141 mg, 1.100 mmol) and 2-(4-(6-chloro-4-fluoro-3-pyridyl)thiazol-2-yl)propan-2-ol (200 mg, 0.733 mmol) prepared in Reference Example 5 were used instead of 3-amino-3-methylbutan-2-ol and 2-chloro-5-(1-(difluoromethyl)-1H-pyrazol-3-yl)-4-fluoropyridine. MS (ESI) m/z=381.1 (M+H)$^+$ Step 2. 2-(4-(6-((2-(1-(Cyclopropylsulfonyl)-1H-pyrazol-4-yl)pyrimidin-4-yl)amino)-4-(((1s,4s)-4-(methylamino)cyclohexyl)amino)pyridin-3-yl)thiazol-2-yl)propan-2-ol The title compound as an off white solid (54 mg) was prepared in the same fashion as Step 2 in Example 1, except that 2-(4-(6-chloro-4-(((1s,4s)-4-(methylamino)cyclohexyl)amino)pyridin-3-yl)thiazol-2-yl)propan-2-ol (144 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=611.1 (M+H)$^+$ Example 57. (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)cyclohexan-1-ol Step 1. (1s,4s)-4-((2-Chloro-5-(1-(tetrahydro-2H-pyran-4-yl)-1H-pyrazol-3-yl)pyridin-4-yl)amino)cyclohexan-1-ol The title compound as a white solid (235 mg) was prepared in the same fashion as Step 1 in Example 7, except that cis-4-aminocyclohexanol hydrochloride (215 mg, 1.420 mmol) and 2-chloro-4-fluoro-5-(1-(tetrahydro-2H-pyran-4-yl)-1H-pyrazol-3-yl)pyridine (200 mg, 0.710 mmol) prepared in Reference Example 6 were used instead of 3-amino-3-methylbutan-2-ol and 2-chloro-5-(1-(difluoromethyl)-1H-pyrazol-3-yl)-4-fluoropyridine. MS (ESI) m/z=377.1 (M+H)$^+$ Step 2. (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)cyclohexan-1-ol The title compound as an off white solid (31 mg) was prepared in the same fashion as Step 2 in Example 1, except that (1s,4s)-4-((2-chloro-5-(1-(tetrahydro-2H-pyran-4-yl)-1H-pyrazol-3-yl)pyridin-4-yl)amino)cyclohexan-1-ol (234 mg, 0.622 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.56 (d, 1H), 8.46 (s, 1H), 8.37 (d, 1H), 8.34 (s, 1H), 7.50 (d, 1H), 7.22 (brs, 1H), 7.15 (d, 1H), 6.61 (d, 1H), 4.41-4.34 (m, 1H), 4.17-4.14 (m, 2H), 3.92-3.86 (m, 1H), 3.79 (s, 3H), 3.58 (dt, 2H), 2.86-2.80 (m, 1H), 2.25-2.14 (m, 4H), 2.05-1.93 (m, 2H), 1.92-1.84 (m, 4H), 1.80-1.72 (m, 2H), 1.55-1.51 (m, 2H), 1.24-1.19 (m, 2H)

Example 58. (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)-1-methylcyclohexan-1-ol Step 1. (1s,4s)-4-((2-Chloro-5-(1-(tetrahydro-2H-pyran-4-yl)-1H-pyrazol-3-yl)pyridin-4-yl)amino)-1-methylcyclohexan-1-ol The title compound as a white solid (247 mg) was prepared in the same fashion as Step 1 in Example 7, except that (1s,4s)-4-amino-1-methylcyclohexan-1-ol (183 mg, 1.420 mmol) and 2-chloro-4-fluoro-5-(1-(tetrahydro-2H-pyran-4-yl)-1H-pyrazol-3-yl)pyridine (200 mg, 0.710 mmol) prepared in Reference Example 6 were used instead of 3-amino-3-methylbutan-2-ol and 2-chloro-5-(1-(difluoromethyl)-1H-pyrazol-3-yl)-4-fluoropyridine. MS (ESI) m/z=391.1 (M+H)$^+$ Step 2. (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)-1-methylcyclohexan-1-ol The title compound as an off white solid (36 mg) was prepared in the same fashion as Step 2 in Example 1, except that (1s,4s)-4-((2-chloro-5-(1-(tetrahydro-2H-pyran-4-yl)-1H-pyrazol-3-yl)pyridin-4-yl)amino)-1-methylcyclohexan-1-ol (234 mg, 0.622 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.47 (s, 1H), 8.37-8.34 (m, 3H), 7.48 (d, 1H), 7.24 (d, 1H), 7.06 (s, 1H), 6.60 (d, 1H), 4.40-4.32 (m 1H), 4.14 (td, 2H), 3.62-3.54 (m, 3H), 2.85-2.79 (m, 1H), 2.17-2.11 (m, 4H), 2.05-2.01 (m, 2H), 1.81-1.73 (m, 4H), 1.63-1.60 (m, 2H), 1.54-1.50 (m, 2H), 1.31 (s, 3H), 1.23-1.18 (m, 2H)

Example 59. (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-methylcyclohexan-1-ol Step 1. (1s,4s)-4-((2-Chloro-5-(4,5,6,7-tetrahydropyrazolo[1,5-a]pyridin-2-yl)pyridin-4-yl)amino)-1-methylcyclohexan-1-ol The title compound as a white solid (69 mg) was prepared in the same fashion as Step 1 in Example 7, except that (1s,4s)-4-amino-1-methylcyclohexan-1-ol (38.5 mg, 0.298 mmol) and 2-(6-chloro-4-fluoropyridin-3-yl)-4,5,6,7-tetrahydropyrazolo[1,5-a]pyridine (50 mg, 0.199 mmol) prepared in Reference Example 7 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.34 (d, 1H), 8.28 (s, 1H), 6.52 (s, 1H), 6.32 (s, 1H), 4.15 (t, 2H), 3.36 (s, 1H), 2.85 (t, 2H), 2.08-2.06 (m, 2H), 1.92-1.88 (m, 4H), 1.78-1.69 (m, 4H), 1.60-1.54 (m, 2H), 1.31 (s, 3H); MS (ESI) m/z=361.0 (M+H)$^+$ Step 2. (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-methylcyclohexan-1-ol The title compound as an off white solid (29 mg) was prepared in the same fashion as Step 2 in Example 1, except that (1s,4s)-4-((2-chloro-5-(4,5,6,7-tetrahydropyrazolo[1,5-a]pyridin-2-yl)pyridin-4-yl)amino)-1-methylcyclohexan-1-ol (60 mg, 0.166 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H NMR (CDCl$_3$, 400 MHz) δ 8.65 (s, 1H), 8.47 (s, 1H), 8.38 (d, 2H), 8.31 (s, 1H), 7.74 (s, 1H), 7.31 (s, 1H), 6.94 (s, 1H), 6.31 (s, 1H), 4.16-4.12 (m, 2H), 3.53 (s, 1H), 2.85-2.80 (m, 3H), 2.08-2.05 (m, 2H), 2.02-1.99 (m, 2H), 1.95-1.90 (m, 2H), 1.83-1.75 (m, 4H), 1.63-1.52 (m, 4H), 1.31 (s, 3H), 1.29-1.20 (m, 2H) 6; MS (ESI) m/z=590.2 (M+H)$^+$ Example 60. ((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)methanol Step 1. ((1s,4s)-4-((2-Chloro-5-(4,5,6,7-tetrahydropyrazolo[1,5-a]pyridin-2-yl)pyridin-4-yl)amino)cyclohexyl)methanol The title compound as a white solid (66 mg) was prepared in the same fashion as Step 1 in Example 7, except that ((1s,4s)-4-aminocyclohexyl)methanol (38.5 mg, 0.298 mmol) and 2-(6-chloro-4-fluoropyridin-3-yl)-4,5,6,7-tetrahydropyrazolo[1,5-a]pyridine (50 mg, 0.199 mmol) prepared in Reference Example 7 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.78 (d, 1H), 8.30 (s, 1H), 6.53 (s, 1H), 6.35 (s, 1H), 4.15 (t, 2H), 3.84-3.82 (m, 1H), 3.54 (d, 2H), 2.85 (t, 2H), 2.11-2.05 (m, 2H), 1.95-1.87 (m, 4H), 1.73-1.62 (m, 4H), 1.44-1.38 (m, 2H); MS (ESI) m/z=361.0 (M+H)$^+$ Step 2. ((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)methanol The title compound as an off white solid (14 mg) was prepared in the same fashion as Step 2 in Example 1, except that ((1s,4s)-4-((2-chloro-5-(4,5,6,7-tetrahydropyrazolo[1,5-a]pyridin-2-yl)pyridin-4-yl)amino)cyclohexyl)methanol (60 mg, 0.166 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H NMR (CDCl$_3$, 400 MHz) δ 8.78 (d, 1H), 8.66 (s, 1H), 8.46 (s, 1H), 8.37 (d, 1H), 8.32 (s, 1H), 7.73 (brs, 1H), 7.22 (brs, 1H), 7.11 (brs, 1H), 6.35 (s, 1H), 4.16 (t, 2H), 4.03-3.97 (m, 1H), 3.55 (d, 2H), 2.88-2.80 (m, 3H), 2.13-1.99 (m, 4H), 1.94-1.87 (m, 2H), 1.83-1.63 (m, 5H), 1.50-1.38 (m, 4H), 1.31-1.18 (m, 2H); MS (ESI) m/z=590.2 (M+H)$^+$ Example 61. 2-((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)propan-2-ol Step 1. 2-((1s,4s)-4-((2-Chloro-5-(4,5,6,7-tetrahydropyrazolo[1,5-a]pyridin-2-yl)pyridin-4-yl)amino)cyclohexyl)propan-2-ol The title compound as a white solid (68 mg) was prepared in the same fashion as Step 1 in Example 7, except that 2-((1s,4s)-4-aminocyclohexyl)propan-2-ol (47 mg, 0.298 mmol) and 2-(6-chloro-4-fluoropyridin-3-yl)-4,5,6,7-tetrahydropyrazolo[1,5-a]pyridine (50 mg, 0.199 mmol) prepared in Reference Example 7 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.74 (d, 2H), 8.28 (s, 1H), 6.51 (s, 1H), 6.34 (s, 1H), 4.11 (t, 3H), 3.86-3.78 (m, 2H), 2.83 (t, 3H), 2.06-1.95 (m, 1H), 1.93-1.82 (m, 2H), 1.80-1.70 (m, 2H), 1.66-1.55 (m, 2H), 1.47-1.36 (m, 2H), 1.21 (s, 1H); MS (ESI) m/z=389.1 (M+H)$^+$ Step 2. 2-((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)propan-2-ol The title compound as an off white solid (30.5 mg) was prepared in the same fashion as Step 2 in Example 1, except that 2-((1s,4s)-4-((2-chloro-5-(4,5,6,7-tetrahydropyrazolo[1,5-a]pyridin-2-yl)pyridin-4-yl)amino)cyclohexyl)propan-2-ol (64.5 mg, 0.166 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H NMR (CDCl$_3$, 400 MHz) δ 8.73 (d, 1H), 8.66 (s, 1H), 8.47 (s, 1H), 8.37 (d, 1H), 8.33 (s, 1H), 7.75 (brs, 1H), 7.24 (brs, 1H), 7.09 (brs, 1H), 6.35 (s, 1H), 4.15 (t, 2H), 4.02-3.97 (m, 1H), 2.88-2.81 (m, 3H), 2.13-2.03 (m, 4H), 1.93-1.87 (m, 2H), 1.81-1.72 (m, 4H), 1.56-1.42 (m, 5H), 1.24 (s, 6H), 1.22-1.17 (m, 2H); MS (ESI) m/z=618.3 (M+H)$^+$ Example 62. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-(4,5,6,7-tetrahydropyrazolo[1,5-a]pyridin-2-yl)pyridine-2,4-diamine Step 1. (1s,4s)-N$^1$-(2-Chloro-5-(4,5,6,7-tetrahydropyrazolo[1,5-a]pyridin-2-yl)pyridin-4-yl)-N$^4$-(2-fluoroethyl)cyclohexane-1,4-diamine The title compound as a white solid (61 mg) was prepared in the same fashion as Step 1 in Example 7, except that (1s,4s)-N$^1$-(2-fluoroethyl)cyclohexane-1,4-diamine (48 mg, 0.298 mmol) and 2-(6-chloro-4-fluoropyridin-3-yl)-4,5,6,7-tetrahydropyrazolo[1,5-a]pyridine (50 mg, 0.199 mmol) prepared in Reference Example 7 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.64 (d, 1H), 8.28 (s, 1H), 6.52 (s, 1H), 6.33 (s, 1H), 4.62 (t, 1H), 4.50 (t, 1H), 4.16 (t, 2H), 3.70-3.66 (m, 1H), 2.98 (t, 1H), 2.91 (t, 1H), 2.85 (t, 2H), 2.66-2.64 (m, 1H), 2.10-2.05 (m, 2H), 1.95-1.87 (m, 4H), 1.82-1.78 (m, 2H), 1.75-1.68 (m, 2H), 1.57-1.51 (m, 2H); MS (ESI) m/z=392.0 (M+H)$^+$ Step 2. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-(4,5,6,7-tetrahydropyrazolo[1,5-a]pyridin-2-yl)pyridine-2,4-diamine The title compound as an off white solid (40 mg) was prepared in the same fashion as Step 2 in Example 1, except that (1s,4s)-N$^1$-(2-chloro-5-(4,5,6,7-tetrahydropyrazolo[1,5-a]pyridin-2-yl)pyridin-4-yl)-N$^4$-(2-fluoroethyl)cyclohexane-1,4-diamine (59 mg, 0.151 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (d, 1H), 8.65 (s, 1H), 8.46 (s, 1H), 8.37 (d, 1H), 8.31 (s, 1H), 7.83 (brs, 1H), 7.16 (d, 2H), 6.32 (s, 1H), 4.62 (t, 1H), 4.50 (t, 1H), 4.17 (t, 2H), 3.88 (brs, 1H), 3.00 (t, 1H), 2.93 (t, 1H), 2.89-2.80 (m, 3H), 2.70-2.62 (m, 1H), 2.13-2.03 (m, 4H), 1.94-1.77 (m, 6H), 1.58-1.47 (m, 4H), 1.25-1.19 (m, 2H); MS (ESI) m/z=621.3 (M+H)$^+$ Example 63. N$^2$-(2-(1-(Cyclopropylsulfonyl)-1H-pyrazol-4-yl)pyrimidin-4-yl)-N$^4$-((1s,4s)-4-((2,2-difluoroethyl)amino)cyclohexyl)-5-(4,5,6,7-tetrahydropyrazolo[1,5-a]pyridin-2-yl)pyridine-2,4-diamine Step 1. (1s,4s)-N$^1$-(2-Chloro-5-(4,5,6,7-tetrahydropyrazolo[1,5-a]pyridin-2-yl)pyridin-4-yl)-N-(2,2-difluoroethyl)cyclohexane-1,4-diamine The title compound as a white solid (100 mg) was prepared in the same fashion as Step 1 in Example 7, except that (1s,4s)-N$^1$-(2,2-difluoroethyl)cyclohexane-1,4-diamine (74 mg, 0.417 mmol) and 2-(6-chloro-4-fluoropyridin-3-yl)-4,5,6,7-tetrahydropyrazolo[1,5-a]pyridine (70 mg, 0.278 mmol) prepared in Reference Example 7 were used instead of 3-amino-3-methylbutan-2-ol and 2-chloro-5-(1-(difluoromethyl)-1H-pyrazol-3-yl)-4-fluoropyridine. $^1$H-NMR (CDCl$_3$, 400 MHz) δ 8.64 (d, 1H), 8.30 (s, 1H), 6.52 (s, 1H), 6.34 (s, 1H), 5.84 (tt, 1H), 4.16 (t, 2H), 3.71-3.67 (m, 1H), 3.01 (td, 2H), 2.85 (t, 2H), 2.70-2.65 (m, 1H), 2.12-2.05 (m, 2H), 1.94-1.89 (m, 4H), 1.82-1.78 (m, 2H), 1.75-1.67 (m, 2H), 1.57-1.48 (m, 2H); MS (ESI) m/z=410.1 (M+H)$^+$ Step 2. N$^2$-(2-(1-(Cyclopropylsulfonyl)-1H-pyrazol-4-yl)pyrimidin-4-yl)-N$^4$-((1s,4s)-4-((2,2-difluoroethyl)amino)cyclohexyl)-5-(4,5,6,7-tetrahydropyrazolo[1,5-a]pyridin-2-yl)pyridine-2,4-diamine The title compound as an off white solid (29 mg) was prepared in the same fashion as Step 2 in Example 1, except that (1s,4s)-N$^1$-(2-chloro-5-(4,5,6,7-tetrahydropyrazolo[1,5-a]pyridin-2-yl)pyridin-4-yl)-N$^4$-(2,2-difluoroethyl)cyclohexane-1,4-diamine (98.5 mg, 0.228 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (d, 1H), 8.65 (s, 1H), 8.46 (s, 1H), 8.36 (s, 1H), 8.31 (s, 1H), 8.01 (brs, 1H), 7.23 (s, 1H), 7.09 (s, 1H), 6.33 (s, 1H), 5.85 (tt, 1H), 4.17 (t, 2H), 3.88 (s, 1H), 3.02 (td, 2H), 2.88-2.80 (m, 3H), 2.70-2.64 (m, 1H), 2.10-2.02 (m, 4H), 1.94-1.89 (m, 2H), 1.84-1.76 (m, 4H), 1.57-1.47 (m, 4H), 1.24-1.89 (m, 2H); MS (ESI) m/z=639.3 (M+H)$^+$ Example 64. (1s,4s)-4-((2-((2-(1-(Cyclopropylsulfonyl)-1H-pyrazol-4-yl)pyrimidin-4-yl)amino)-5-(3-isopropylisoxazol-5-yl)pyridin-4-yl)amino)-1-methylcyclohexan-1-ol Step 1. 5-(6-Chloro-4-fluoro-3-pyridyl)-3-isopropylisoxazole The title compound as a white solid (506 mg) was prepared in the same fashion as Reference Example 2 except that 3-isopropyl-5-(4,4,5,5-tetramethyl-1,3,2-dioxaborolan-2-yl)isoxazole (958 mg, 4.040 mmol) was used instead of 1-(difluoromethyl)-3-(4,4,5,5-tetramethyl-1,3,2-dioxaborolan-2-yl)pyrazole. $^1$H-NMR (CDCl$_3$, 400 MHz) δ 8.95 (s, 1H) 7.25 (s, 1H), 6.62 (s, 1H), 3.18-3.11 (m, 1H), 1.35 (d, 6H)

Step 2. (1s,4s)-4-((2-Chloro-5-(3-isopropylisoxazol-5-yl)pyridin-4-yl)amino)-1-methylcyclohexan-1-ol The title compound as a white solid (245 mg) was prepared in the same fashion as Step 1 in Example 7, except that (1s,4s)-4-amino-1-methylcyclohexan-1-ol (161 mg, 1.247 mmol) and 5-(6-chloro-4-fluoro-3-pyridyl)-3-isopropylisoxazole (200 mg, 0.831 mmol) prepared in Step 1 were used instead of 3-amino-3-methylbutan-2-ol and 2-chloro-5-(1-(difluoromethyl)-1H-pyrazol-3-yl)-4-fluoropyridine. MS (ESI) m/z=350.1 (M+H)$^+$ Step 3. (1s,4s)-4-((2-((2-(1-(Cyclopropylsulfonyl)-1H-pyrazol-4-yl)pyrimidin-4-yl)amino)-5-(3-isopropylisoxazol-5-yl)pyridin-4-yl)amino)-1-methylcyclohexan-1-ol The title compound as an off white solid (33 mg) was prepared in the same fashion as Step 2 in Example 1, except that (1s,4s)-4-((2-chloro-5-(3-isopropylisoxazol-5-yl)pyridin-4-yl)amino)-1-methylcyclohexan-1-ol (145 mg, 0.415 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.43 (d, 1H), 8.26 (s, 1H), 8.00 (s, 1H), 7.25 (d, 1H), 7.09 (s, 1H), 6.29 (d, 1H), 6.04 (d, 1H), 3.50-3.48 (m 1H), 3.15-3.09 (m, 1H), 2.85-2.79 (m, 1H), 2.00-1.97 (m, 2H), 1.78-1.72 (m, 4H), 1.61-1.55 (m, 2H), 1.55-1.51 (m, 2H), 1.36 (d, 6H), 1.30 (s, 3H), 1.24-1.19 (m, 2H); MS (ESI) m/z=579.1 (M+H)$^+$ Example 65. 2-(1-(Cyclopropylsulfonyl)-1H-pyrazol-4-yl)-N-(5-(1-(difluoromethyl)-1H-pyrazol-3-yl)-4-(((1s,4s)-4-(methylamino)cyclohexyl)oxy)pyridin-2-yl)pyrimidin-4-amine Step 1. (1s,4s)-4-((2-Chloro-5-(1-(difluoromethyl)-1H-pyrazol-3-yl)pyridin-4-yl)oxy)-N-methylcyclohexan-1-amine Sodium hydride, 60% in mineral oil (51 mg, 1.277 mmol) was added to the solution of (1s,4s)-4-(methylamino)cyclohexan-1-ol (150 mg, 1.161 mmol) in DMF (10 mL) at 0° C. and the reaction mixture was stirred for 30 minutes. After 2-chloro-5-(1-(difluoromethyl)-1H-pyrazol-3-yl)-4-fluoropyridine (287.5 mg, 1.161 mmol) prepared in Reference Example 2 being added, the reaction mixture was stirred at 70° C. overnight. The reaction mixture was cooled, diluted in DCM, washed by water, dried over MgSO$_4$, and then concentrated. The crude product was purified by column chromatography (EA/n-Hex=0-50%) to yield (1s,4s)-4-((2-chloro-5-(1-(difluoromethyl)-1H-pyrazol-3-yl)pyridin-4-yl)oxy)-N-methylcyclohexan-1-amine (120 mg) as a white solid. $^1$H-NMR (CDCl$_3$, 400 MHz) δ 8.79 (s, 1H), 7.86 (d, 1H), 7.27 (t, 1H), 6.95 (d, 1H), 6.89 (s, 1H), 4.70-4.63 (m, 1H), 2.56-2.50 (m, 1H), 2.45 (s, 3H), 2.18-2.05 (m, 2H), 1.86-1.69 (m, 4H), 1.59-1.44 (m, 2H)

Step 2. 2-(1-(Cyclopropylsulfonyl)-1H-pyrazol-4-yl)-N-(5-(1-(difluoromethyl)-1H-pyrazol-3-yl)-4-(((1s,4s)-4-(methylamino)cyclohexyl)oxy)pyridin-2-yl)pyrimidin-4-amine The title compound as an off white solid (41 mg) was prepared in the same fashion as Step 2 in Example 1, except that (1s,4s)-4-((2-chloro-5-(1-(difluoromethyl)-1H-pyrazol-3-yl)pyridin-4-yl)oxy)-N-methylcyclohexan-1-amine (134.5 mg, 0.337 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.75 (s, 1H), 8.64 (s, 1H), 8.46 (s, 1H), 8.43 (d, 1H), 7.95 (s, 1H), 7.86 (d, 1H), 7.84 (s, 1H), 7.28 (t, 1H), 6.98 (d, 2H), 4.87 (brs, 1H), 2.86-2.81 (m, 1H), 2.58-2.53 (m, 1H), 2.47 (s, 3H), 2.25-2.22 (m, 2H), 1.88-1.75 (m, 4H), 1.57-1.51 (m, 4H), 1.27-1.22 (m, 2H); MS (ESI) m/z=586.1 (M+H)

Example 66. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)cyclohexan-1-ol Step 1. 4-((2-Chloro-5-(1-(difluoromethyl)-1H-pyrazol-3-yl)pyridin-4-yl)oxy)cyclohexan-1-ol The title compound as a white solid (60 mg) was prepared in the same fashion as Step 1 in Example 65, except that cyclohexane-1,4-diol (94 mg, 0.808 mmol) was used instead of (1s,4s)-4-(methylamino)cyclohexan-1-ol. $^1$H-NMR (CDCl$_3$, 400 MHz) δ 8.81-8.79 (m, 1H), 7.87-7.85 (m, 1H), 7.27 (t, 1H), 6.95-6.89 (m, 2H), 4.60-4.50 (m, 1H), 3.89-3.86 (m, 1H), 2.20-2.01 (m, 3H), 1.84-1.53 (m, 5H); MS (ESI) m/z=343.8 (M+H)$^+$ Step 2. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)cyclohexan-1-ol The title compound as a white solid (12 mg) was prepared in the same fashion as Step 2 in Example 1, except that 4-((2-chloro-5-(1-(difluoromethyl)-1H-pyrazol-3-yl)pyridin-4-yl)oxy)cyclohexan-1-ol (39 mg, 0.113 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.77 (d, 1H), 8.64 (d, 1H), 8.48-8.43 (m, 2H), 7.96 (brs, 1H), 7.88-7.82 (m, 2H), 7.28 (t, 1H), 7.11-6.92 (m, 2H), 4.82-4.60 (m, 1H), 3.89-3.86 (m, 1H), 2.89-2.83 (m, 1H), 2.35-

2.19 (m, 2H), 2.08-2.02 (m, 1H), 1.89-1.83 (m, 2H), 1.78-1.52 (m, 5H), 1.27-1.23 (m, 2H); MS (ESI) m/z=573.2 (M+H)+

Example 67. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)cyclopentan-1-ol Step 1. 3-((2-Chloro-5-(1-(difluoromethyl)-1H-pyrazol-3-yl)pyridin-4-yl)oxy)cyclopentan-1-ol The title compound as a white solid (80 mg) was prepared in the same fashion as Step 1 in Example 65, except that cyclopentane-1,3-diol (83 mg, 0.808 mmol) was used instead of (1s,4s)-4-(methylamino)cyclohexan-1-ol. $^1$H-NMR (CDCl$_3$, 400 MHz) δ 8.81 (s, 1H), 8.84 (d, 1H), 7.27 (t, 1H), 6.88-6.85 (m, 2H), 5.09-5.06 (m, 1H), 4.60-4.56 (m, 1H), 2.40-2.33 (m, 1H), 2.22-2.04 (m, 3H), 1.99-1.92 (m, 1H), 1.81-1.75 (m, 1H); MS (ESI) m/z=329.9 (M+H)+

Step 2. 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)cyclopentan-1-ol The title compound as a white solid (19 mg) was prepared in the same fashion as Step 2 in Example 1, except that 3-((2-chloro-5-(1-(difluoromethyl)-1H-pyrazol-3-yl)pyridin-4-yl)oxy)cyclopentan-1-ol (37 mg, 0.113 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.79 (s, 1H), 8.68 (s, 1H), 8.48 (s, 1H), 8.43 (d, 1H), 8.15 (s, 1H), 7.85 (d, 1H), 7.72 (s, 1H), 7.28 (t, 1H), 7.03 (d, 1H), 6.88 (d, 1H), 5.31-5.22 (m, 1H), 4.58-4.56 (m, 1H), 2.88-2.84 (m, 1H), 2.43-2.40 (m, 1H), 2.27 (t, 2H), 2.12-2.01 (m, 2H), 1.84-1.80 (m, 1H), 1.56-1.53 (m, 2H), 1.27-1.22 (m, 1H); MS (ESI) m/z=559.2 (M+H)+

Example 68. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)-1-methylcyclohexan-1-ol Step 1. 4-((2-chloro-5-(1-(difluoromethyl)-1H-pyrazol-3-yl)pyridin-4-yl)oxy)-1-methylcyclohexan-1-ol The title compound as a white solid (112 mg) was prepared in the same fashion as Step 1 in Example 65, except that 1-methylcyclohexane-1,4-diol (200 mg, 0.808 mmol) was used instead of (1s,4s)-4-(methylamino)cyclohexan-1-ol. $^1$H-NMR (CDCl$_3$, 400 MHz) δ 8.82 (s, 1H), 7.84 (d, 1H), 7.27 (t, 1H), 6.95 (d, 1H), 6.84 (d, 1H), 4.46-4.39 (m, 1H), 2.02-1.96 (m, 4H), 1.83-1.79 (m, 2H), 1.61-1.53 (m, 2H), 1.31 (s, 3H); MS (ESI) m/z=358.1 (M+H)+

Step 2. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)-1-methylcyclohexan-1-ol The title compound as a white solid (18 mg) was prepared in the same fashion as Step 2 in Example 1, except that 4-((2-chloro-5-(1-(difluoromethyl)-1H-pyrazol-3-yl)pyridin-4-yl)oxy)-1-methylcyclohexan-1-ol (40.5 mg, 0.114 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.80 (s, 1H), 8.65 (s, 1H), 8.47-8.437 (m, 2H), 7.85 (d, 1H), 7.69 (s, 1H), 7.28 (t, 1H), 7.08 (d, 1H), 6.98 (d, 1H), 4.63-4.60 (m, 1H), 2.85-2.81 (m, 1H), 2.06-2.01 (m, 4H), 1.83-1.52 (m, 6H), 1.32 (s, 3H), 1.27-1.20 (m, 2H); MS (ESI) m/z=587.1 (M+H)+

Example 69. 2-(1-(Cyclopropylsulfonyl)-1H-pyrazol-4-yl)-N-(5-(1-(difluoromethyl)-1H-pyrazol-4-yl)-4-(((1s,4s)-4-(methylamino)cyclohexyl)oxy)pyridin-2-yl)pyrimidin-4-amine Step 1. (1s,4s)-4-((2-Chloro-5-(1-(difluoromethyl)-1H-pyrazol-4-yl)pyridin-4-yl)oxy)-N-methylcyclohexan-1-amine The title compound as a white solid (173 mg) was prepared in the same fashion as Step 1 in Example 65, except that 2-chloro-5-(1-(difluoromethyl)-1H-pyrazol-4-yl)-4-fluoropyridine (287 mg, 1.616 mmol) prepared in Reference Example 8 was used instead of 2-chloro-5-(1-(difluoromethyl)-1H-pyrazol-3-yl)-4-fluoropyridine. $^1$H-NMR (CDCl$_3$, 400 MHz) δ 8.41 (s, 1H), 8.24 (s, 1H), 8.03 (s, 1H), 7.25 (t, 1H), 6.88 (s, 1H), 4.66 (brs, 1H), 2.58-2.54 (m, 1H), 2.44 (s, 3H), 2.14-2.11 (m, 2H), 1.83-1.74 (m, 4H), 1.55-1.50 (m, 2H)

Step 2. 2-(1-(Cyclopropylsulfonyl)-1H-pyrazol-4-yl)-N-(5-(1-(difluoromethyl)-1H-pyrazol-4-yl)-4-(((1s,4s)-4-(methylamino)cyclohexyl)oxy)pyridin-2-yl)pyrimidin-4-amine The title compound as an off white solid (52 mg) was prepared in the same fashion as Step 2 in Example 1, except that (1s,4s)-4-((2-chloro-5-(1-(difluoromethyl)-1H-pyrazol-4-yl)pyridin-4-yl)oxy)-N-methylcyclohexan-1-amine (134 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.64 (s, 1H), 8.45 (s, 1H), 8.43 (d, 1H), 8.37 (s, 1H), 8.24 (s, 1H), 8.05 (s, 1H), 7.82 (s, 1H), 7.75 (s, 1H), 7.26 (t, 1H), 7.04 (d, 1H), 4.84 (brs, 1H), 2.87-2.81 (m, 1H), 2.59-2.54 (m, 1H), 2.45 (s, 3H), 2.25-2.22 (m, 2H), 1.89-1.74 (m, 4H), 1.57-1.48 (m, 4H), 1.27-1.22 (m, 2H); MS (ESI) m/z=586.2 (M+H)+

Example 70. 2-(1-(Cyclopropylsulfonyl)-1H-pyrazol-4-yl)-N-(4-((4-(difluoromethoxy)cyclohexyl)oxy)-5-(1-(difluoromethyl)-1H-pyrazol-4-yl)pyridin-2-yl)pyrimidin-4-amine Step 1. 2-Chloro-4-((4-(difluoromethoxy)cyclohexyl)oxy)-5-(1-(difluoromethyl)-1H-pyrazol-4-yl)pyridine The title compound as a white solid (210 mg) was prepared in the same fashion as Step 1 in Example 65, except that 4-(difluoromethoxy)cyclohexanol (161 mg, 0.9700 mmol) and 2-chloro-5-(1-(difluoromethyl)-1H-pyrazol-4-yl)-4-fluoropyridine (240 mg, 0.9700 mmol) prepared in Reference Example 8 were used instead of (1s,4s)-4-(methylamino)cyclohexan-1-ol and 2-chloro-5-(1-(difluoromethyl)-1H-pyrazol-3-yl)-4-fluoropyridine. $^1$H-NMR (CDCl$_3$, 400 MHz) δ 8.45 (s, 1H), 8.43 (s, 1H), 8.18 (s, 1H), 7.24 (t, 1H), 6.90 (s, 1H), 6.27 (t, 1H), 4.63-4.60 (m, 1H), 4.37-4.33 (m, 1H), 2.23-2.02 (m, 2H), 2.19-1.98 (m, 2H), 1.85-1.73 (m, 4H); MS (ESI) m/z=394.0 (M+H)$^+$

Step 2. 2-(1-(Cyclopropylsulfonyl)-1H-pyrazol-4-yl)-N-(4-((4-(difluoromethoxy)cyclohexyl)oxy)-5-(1-(difluoromethyl)-1H-pyrazol-4-yl)pyridin-2-yl)pyrimidin-4-amine The title compound as a pale yellow solid (25 mg) was prepared in the same fashion as Step 2 in Example 1, except that 2-chloro-4-((4-(difluoromethoxy)cyclohexyl)oxy)-5-(1-(difluoromethyl)-1H-pyrazol-4-yl)pyridine (134 mg, 0.3400 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.45 (s, 1H), 8.39 (s, 1H), 8.17 (s, 1H), 8.02 (s, 1H), 7.66 (s, 1H), 7.58 (s, 1H), 7.25 (t, 1H), 7.18 (d, 1H), 6.27 (t, 1H), 4.78-4.76 (m, 1H), 4.38-4.10 (m, 1H), 2.86-2.85 (m, 1H), 2.26-2.23 (m, 2H), 2.07-1.80 (m, 6H), 1.78 (s, 1H), 1.77-1.75 (m, 2H), 1.29-1.22 (m, 1H); MS (ESI) m/z=623.2 (M+H)$^+$

Example 71. 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclohexan-1-ol

Step 1. 4-((2-Chloro-5-(1-(difluoromethyl)-1H-pyrazol-4-yl)pyridin-4-yl)oxy)cyclohexan-1-ol The title compound as a white solid (40 mg) was prepared in the same fashion as Step 1 in Example 65, except that cyclohexane-1,4-diol (94 mg, 0.808 mmol) and 2-chloro-5-(1-(difluoromethyl)-1H-pyrazol-4-yl)-4-fluoropyridine (200 mg, 0.808 mmol) prepared in Reference Example 8 were used instead of (1s,4s)-4-(methylamino)cyclohexan-1-ol and 2-chloro-5-(1-(difluoromethyl)-1H-pyrazol-3-yl)-4-fluoropyridine. $^1$H-NMR (CDCl$_3$, 400 MHz) δ 8.43 (s, 1H), 8.23 (d, 1H), 8.03 (d, 1H), 7.24 (t, 1H), 6.89 (d, 1H), 4.62-4.48 (m, 1H), 3.99-3.80 (m, 1H), 2.25-2.02 (m, 3H), 1.86-1.54 (m, 5H); MS (ESI) m/z=343.9 (M+H)$^+$

Step 2. 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclohexan-1-ol The title compound as a white solid (5.5 mg) was prepared in the same fashion as Step 2 in Example 1, except that 4-((2-chloro-5-(1-(difluoromethyl)-1H-pyrazol-4-yl)pyridin-4-yl)oxy)cyclohexan-1-ol (39 mg, 0.113 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (d, 1H), 8.47-8.44 (m, 1H), 8.39 (d, 1H), 8.23 (d, 1H), 8.05 (d, 1H), 7.70-7.60 (m, 2H), 7.26 (t, 1H), 7.16-7.05 (m, 1H), 4.80-4.65 (m, 1H), 3.87 (brs, 1H), 2.90-2.82 (m, 1H), 2.35-2.15 (m, 2H), 2.10-2.01 (m, 1H), 1.92-1.52 (m, 7H), 1.27-1.23 (m, 2H); MS (ESI) m/z=573.2 (M+H)$^+$

Example 72. 3-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclopentan-1-ol

Step 1. 3-((2-Chloro-5-(1-(difluoromethyl)-1H-pyrazol-4-yl)pyridin-4-yl)oxy)cyclopentan-1-ol The title compound as a white solid (52 mg) was prepared in the same fashion as Step 1 in Example 65, except that cyclopentane-1,3-diol (83 mg, 0.808 mmol) and 2-chloro-5-(1-(difluoromethyl)-1H-pyrazol-4-yl)-4-fluoropyridine (200 mg, 0.808 mmol) prepared in Reference Example 8 were used instead of (1s,4s)-4-(methylamino)cyclohexan-1-ol and 2-chloro-5-(1-(difluoromethyl)-1H-pyrazol-3-yl)-4-fluoropyridine. $^1$H-NMR (CDCl$_3$, 400 MHz) δ 8.42 (s, 1H), 8.16 (s, 1H), 8.01 (s, 1H), 7.24 (t, 1H), 6.88 (s, 1H), 5.12-5.07 (m, 1H), 4.59 (brs, 1H), 2.43-2.07 (m, 4H), 1.99-1.94 (m, 1H), 1.83-1.79 (m, 1H); MS (ESI) m/z=329.8 (M+H)$^+$

Step 2. 3-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclopentan-1-ol The title compound as a white solid (12 mg) was prepared in the same fashion as Step 2 in Example 1, except that 3-((2-chloro-5-(1-(difluoromethyl)-1H-pyrazol-4-yl)pyridin-4-yl)oxy)cyclopentan-1-ol (37 mg, 0.113 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.48 (s, 1H), 8.45 (d, 1H), 8.39 (s, 1H), 8.16 (s, 1H), 8.03 (s, 1H), 7.66 (d, 1H), 7.25 (t, 1H), 7.09 (t, 1H), 5.25-5.22 (m, 1H), 4.59-4.57 (m, 1H), 2.88-2.83 (m, 1H), 2.43-2.03 (m, 4H), 1.87-1.83 (m, 2H), 1.57-1.53 (m, 2H), 1.24-1.22 (m, 2H); MS (ESI) m/z=559.1 (M+H)$^+$

Example 73. 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)-1-methylcyclohexan-1-ol

Step 1. 4-((2-Chloro-5-(1-(difluoromethyl)-1H-pyrazol-4-yl)pyridin-4-yl)oxy)-1-methylcyclohexan-1-ol The title compound as a white solid (108 mg) was prepared in the same fashion as Step 1 in Example 65, except that 1-methylcyclohexane-1,4-diol (105 mg, 0.808 mmol) and 2-chloro-5-(1-(difluoromethyl)-1H-pyrazol-4-yl)-4-fluoropyridine (200 mg, 0.808 mmol) prepared in Reference Example 8 were used instead of (1s,4s)-4-(methylamino)cyclohexan-1-ol and 2-chloro-5-(1-(difluoromethyl)-1H-pyrazol-3-yl)-4-fluoropyridine. $^1$H-NMR (CDCl$_3$, 400 MHz) δ 8.42 (s, 1H), 8.23 (s, 1H), 8.03 (s, 1H), 7.25 (t, 1H), 6.88 (s, 1H), 4.45-4.38 (m, 1H), 2.03-1.97 (m, 4H), 1.83-1.79 (m, 2H), 1.65-1.54-(m, 2H), 1.31 (s, 3H); MS (ESI) m/z=358.1 (M+H)$^+$

Step 2. 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)-1-methylcyclohexan-1-ol The title compound as a white solid (17 mg) was prepared in the same fashion as Step 2 in Example 1, except that 4-((2-chloro-5-(1-(difluoromethyl)-1H-pyrazol-4-yl)pyridin-4-yl)oxy)-1-methylcyclohexan-1-ol (40 mg, 0.114 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46-8.43 (m, 2H), 8.37 (s, 1H), 8.34 (t, 1H), 8.24 (s, 1H), 8.05 (s, 1H), 7.70 (s, 1H), 7.26 (t, 1H), 7.13-7.10 (m, 1H), 4.62-4.58 (m, 1H), 2.86-2.82 (m, 1H), 2.09-2.02 (m, 4H), 1.81-1.76 (m, 2H), 1.65-1.56 (m, 2H), 1.55-1.53 (m, 2H), 1.32 (s, 3H), 1.26-1.22 (m, 2H); MS (ESI) m/z=587.0 (M+H)$^+$ Example 74. N-(4-((4-Amino-4-methylcyclohexyl)oxy)-5-(1-(difluoromethyl)-1H-pyrazol-4-yl)pyridin-2-yl)-2-(1-(cyclopropylsulfonyl)-1H-pyrazol-4-yl)pyrimidin-4-amine Step 1. 4-((2-Chloro-5-(1-(difluoromethyl)-1H-pyrazol-4-yl)pyridin-4-yl)oxy)-1-methylcyclohexan-1-amine The title compound as a white solid (110 mg) was prepared in the same fashion as Step 1 in Example 65, except that 4-amino-4-methyl-cyclohexanol (104 mg, 0.808 mmol) and 2-chloro-5-(1-(difluoromethyl)-1H-pyrazol-4-yl)-4-fluoropyridine (200 mg, 0.808 mmol) prepared in Reference Example 8 were used instead of (1s,4s)-4-(methylamino)cyclohexan-1-ol and 2-chloro-5-(1-(difluoromethyl)-1H-pyrazol-3-yl)-4-fluoropyridine. $^1$H-NMR (CDCl$_3$, 400 MHz) 8.40 (s, 1H), 8.21 (s, 1H), 8.00 (s, 1H), 7.24 (t, 1H), 6.87 (d, 1H), 4.63-4.59 (m, 1H), 2.09-2.02 (m, 2H), 1.85-1.77 (m, 2H), 1.69-1.62 (m, 2H), 1.47-1.41 (m, 2H), 1.18 (s, 3H); MS (ESI) m/z=357.1 (M+H)$^+$ Step 2. N-(4-((4-Amino-4-methylcyclohexyl)oxy)-5-(1-(difluoromethyl)-1H-pyrazol-4-yl)pyridin-2-yl)-2-(1-(cyclopropylsulfonyl)-1H-pyrazol-4-yl)pyrimidin-4-amine The title compound as a white solid (19 mg) was prepared in the same fashion as Step 2 in Example 1, except that 4-((2-chloro-5-(1-(difluoromethyl)-1H-pyrazol-4-yl)pyridin-4-yl)oxy)-1-methylcyclohexan-1-amine (40 mg, 0.113 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.61 (s, 2H), 8.43 (s, 1H), 8.39-8.35 (m, 2H), 8.20 (s, 1H), 8.02 (s, 1H), 7.74 (brs, 1H), 7.25 (t, 1H), 7.12 (d, 1H), 4.77 (brs, 1H), 2.88-2.82 (m, 1H), 2.75 (brs, 2H), 2.15-2.09 (m, 2H), 1.93-1.88 (m, 2H), 1.73-1.66 (m, 2H), 1.54-1.43-(m, 4H), 1.25-1.20 (m, 2H), 1.20 (s, 3H); MS (ESI) m/z=586.1 (M+H)$^+$ Example 75. (1s,4s)-4-((2-((2-(1-(Cyclopropylsulfonyl)-1H-pyrazol-4-yl)pyrimidin-4-yl)amino)-5-(2-methylthiazol-5-yl)pyridin-4-yl)amino)cyclohexan-1-ol Step 1. (1s,4s)-4-((2-Chloro-5-(2-methylthiazol-5-yl)pyridin-4-yl)amino)cyclohexan-1-ol The title compound as a white solid (142 mg) was prepared in the same fashion as Reference Example 2, except that (1s,4s)-4-((2-chloro-5-iodopyridin-4-yl)amino)cyclohexan-1-ol (300 mg, 0.851 mmol) prepared in Reference Example 9 and 2-methyl-5-(4,4,5,5-tetramethyl-1,3,2-dioxaborolan-2-yl)thiazole (230 mg, 1.021 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=324.1 (M+H)$^+$ Step 2. (1s,4s)-4-((2-((2-(1-(Cyclopropylsulfonyl)-1H-pyrazol-4-yl)pyrimidin-4-yl)amino)-5-(2-methylthiazol-5-yl)pyridin-4-yl)amino)cyclohexan-1-ol The title compound as an off white solid (20 mg) was prepared in the same fashion as Step 2 in Example 1, except that (1s,4s)-4-((2-chloro-5-(2-methylthiazol-5-yl)pyridin-4-yl)amino)cyclohexan-1-ol (101 mg, 0.311 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.45 (s, 1H), 8.43 (d, 1H), 7.94 (s, 1H), 7.62 (s, 1H), 7.43 (s, 1H), 7.24 (s, 1H), 7.07 (s, 1H), 4.74 (d, 1H), 3.92 (brs, 1H), 3.62-3.60 (m, 1H), 2.85-2.81 (m, 1H), 2.79 (s, 3H), 1.87-1.74 (m, 4H), 1.66-1.59 (m, 4H), 1.55-1.52 (m, 2H), 1.24-1.20 (m, 2H); MS (ESI) m/z=553.2 (M+H)$^+$ Example 76. (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)cyclohexan-1-ol Step 1. (1s,4s)-4-((2-Chloro-5-(2-(2-hydroxypropan-2-yl)thiazol-4-yl)pyridin-4-yl)amino)cyclohexan-1-ol The title compound as a white solid (825 mg) was prepared in the same fashion as Reference Example 2, except that (1s,4s)-4-((2-chloro-5-iodopyridin-4-yl)amino)cyclohexan-1-ol (1 g, 2.836 mmol) prepared in Reference Example 9 and 2-(4-(4,4,5,5-tetramethyl-1,3,2-dioxaborolan-2-yl)thiazol-2-yl)propan-2-ol (1.15 g, 4.250 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=368.1 (M+H)$^+$ Step 2. (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)cyclohexan-1-ol The title compound as an off white solid (12 mg) was prepared in the same fashion as Step 2 in Example 1, except that (1s,4s)-4-((2-chloro-5-(2-(2-hydroxypropan-2-yl)thiazol-4-yl)pyridin-4-yl)amino)cyclohexan-1-ol (76 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.45 (s, 1H), 8.38 (d, 1H), 8.26 (s, 1H), 7.95 (d, 1H), 7.36 (s, 1H), 7.18 (s, 1H), 7.14 (d, 1H), 3.90-3.84 (m, 1H), 3.73-3.62 (m, 1H), 2.86-2.80 (m, 1H), 1.93-1.81 (m, 6H), 1.73-1.68 (m, 2H), 1.55-1.50 (m, 2H), 1.24-1.19 (m, 2H); MS (ESI) m/z=597.2 (M+H)$^+$ Example 77. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)amino)cyclohexan-1-ol Step 1. (1s,4s)-4-((2-Chloro-5-(1-(difluoromethyl)-1H-pyrazol-4-yl)pyridin-4-yl)amino)cyclohexan-1-ol The title compound as a white solid (293 mg) was prepared in the same fashion as Reference Example 2, except that (1s,4s)-4-((2-chloro-5-iodopyridin-4-yl)amino)cyclohexan-1-ol (300 mg, 0.851 mmol) prepared in Reference Example 9 and 1-(difluoromethyl)-4-(4,4,5,5-tetramethyl-1,3,2-dioxaborolan-2-yl)pyrazole (291 mg, 1.191 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=343.1 (M+H)$^+$

Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)amino)cyclohexan-1-ol The title compound as an off white solid (6 mg) was prepared in the same fashion as Step 2 in Example 1, except that (1s,4s)-4-((2-chloro-5-(1-(difluoromethyl)-1H-pyrazol-4-yl)pyridin-4-yl)amino)cyclohexan-1-ol (71 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.45 (s, 1H), 8.42 (d, 1H), 7.94 (s, 1H), 7.88 (s, 1H), 7.90 (s, 1H), 7.61 (d, 1H), 7.27 (t, 1H), 7.24 (d, 1H), 7.08 (s, 1H), 4.48 (d, 1H), 3.95 (brs, 1H), 3.58 (brs, 1H), 2.86-2.80 (m, 1H), 1.89-1.84 (m, 4H), 1.65-1.55 (m, 2H), 1.55-1.51 (m, 2H), 1.25-1.19 (m, 2H); MS (ESI) m/z=572.2 (M+H)$^+$

Example 78. (1s,4s)-4-((5-(1-Cyclopropyl-1H-pyrazol-4-yl)-2-((2-(1-(cyclopropylsulfonyl)-1H-pyrazol-4-yl)pyrimidin-4-yl)amino)pyridin-4-yl)amino)cyclohexan-1-ol

Step 1. (1s,4s)-4-((2-Chloro-5-(1-cyclopropyl-1H-pyrazol-4-yl)pyridin-4-yl)amino)cyclohexan-1-ol The title compound as a white solid (269 mg) was prepared in the same fashion as Reference Example 2, except that (1s,4s)-4-((2-chloro-5-iodopyridin-4-yl)amino)cyclohexan-1-ol (300 mg, 0.851 mmol) prepared in Reference Example 9 and 1-cyclopropyl-4-(4,4,5,5-tetramethyl-1,3,2-dioxaborolan-2-yl)-1H-pyrazole (279 mg, 1.191 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=333.1 (M+H)$^+$

Step 2. (1s,4s)-4-((5-(1-Cyclopropyl-1H-pyrazol-4-yl)-2-((2-(1-(cyclopropylsulfonyl)-1H-pyrazol-4-yl)pyrimidin-4-yl)amino)pyridin-4-yl)amino)cyclohexan-1-ol The title compound as an off white solid (11 mg) was prepared in the same fashion as Step 2 in Example 1, except that (1s,4s)-4-((2-chloro-5-(1-cyclopropyl-1H-pyrazol-4-yl)pyridin-4-yl)amino)cyclohexan-1-ol (69 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.64 (s, 1H), 8.45 (s, 1H), 8.38 (d, 1H), 7.84 (s, 1H), 7.59 (s, 1H), 7.57 (s, 1H), 7.21 (d, 1H), 7.05 (s, 1H), 4.67 (d, 1H), 3.94-3.91 (m, 1H), 3.71-3.65 (m, 1H), 2.85-2.79 (m, 1H), 1.87-1.60 (m, 8H), 1.54-1.50 (m, 2H), 1.22-1.20 (m, 4H), 1.12-1.07 (m, 2H); MS (ESI) m/z=562.2 (M+H)$^+$

Example 79. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexan-1-ol

Step 1. (1s,4s)-4-((2-Chloro-5-(1-methyl-1H-pyrazol-3-yl)pyridin-4-yl)amino)cyclohexan-1-ol The title compound as a white solid (118 mg) was prepared in the same fashion as Reference Example 2, except that (1s,4s)-4-((2-chloro-5-iodopyridin-4-yl)amino)cyclohexan-1-ol (300 mg, 0.851 mmol) prepared in Reference Example 9 and 1-methyl-3-(4,4,5,5-tetramethyl-1,3,2-dioxaborolan-2-yl)-1H-pyrazole (230 mg, 1.106 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=307.0 (M+H)$^+$

Step 2. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexan-1-ol The title compound as an off white solid (18 mg) was prepared in the same fashion as Step 2 in Example 1, except that (1s,4s)-4-((2-chloro-5-(1-methyl-1H-pyrazol-3-yl)pyridin-4-yl)amino)cyclohexan-1-ol (29 mg, 0.094 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.93 (s, 1H), 8.62 (s, 1H), 8.47 (d, 1H), 8.44 (s, 1H), 8.40 (s, 1H), 8.39 (s, 1H), 7.78 (d, 1H), 7.48 (s, 1H), 7.32 (s, 1H), 6.79 (d, 1H), 4.56 (d, 1H), 3.91 (s, 3H), 3.67-3.63 (m, 1H), 3.63-3.58 (m, 1H), 3.29-3.23 (m, 1H), 1.82-1.74 (m, 4H), 1.71-1.66 (m, 2H), 1.55-1.53 (m, 2H), 1.36-1.32 (m, 2H), 1.29-1.23 (m, 2H); MS (ESI) m/z=536.2 (M+H)$^+$

Example 80. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol

Step 1. (1s,4s)-4-((2-Chloro-5-(1-(difluoromethyl)-1H-pyrazol-3-yl)pyridin-4-yl)amino)cyclohexan-1-ol The title compound as a white solid (162 mg) was prepared in the same fashion as Reference Example 2, except that (1s,4s)-4-((2-chloro-5-iodopyridin-4-yl)amino)cyclohexan-1-ol (300 mg, 0.851 mmol) prepared in Reference Example 9 was used instead of 2-chloro-4-fluoro-5-iodopyridine. $^1$H-NMR (CDCl$_3$, 400 MHz) δ 8.37 (s, 1H), 8.15 (d, 1H), 7.88 (d, 1H), 7.21 (t, 1H), 6.84 (d, 1H), 6.59 (s, 1H), 3.93 (brs, 1H), 3.59 (brs, 1H), 1.90-1.72 (m, 8H); MS (ESI) m/z=343.1 (M+H)$^+$

Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol The title compound as an off white solid (12 mg) was prepared in the same fashion as Step 2 in Example 1, except that (1s,4s)-4-((2-chloro-5-(1-(difluoromethyl)-1H-pyrazol-3-yl)pyridin-4-yl)amino)cyclohexan-1-ol (32 mg, 0.094 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) 8.66 (s, 1H), 8.46 (s, 1H), 8.42 (d, 1H), 8.39 (s, 1H), 8.19 (d, 1H), 7.87 (d, 1H), 7.58-7.53 (m, 1H), 7.23 (t, 1H), 7.21-7.16 (m, 2H), 6.84 (d, 1H), 3.93-3.86 (m, 1H), 3.79 (s, 1H), 2.87-2.80 (m, 1H), 2.02-1.94 (m, 2H), 1.92-1.83 (m, 4H), 1.75-1.66 (m, 2H), 1.64-1.58 (m, 1H), 1.56-1.52 (m, 2H), 1.25-1.20 (m, 2H); MS (ESI) m/z=572.2 (M+H)$^+$

Example 81. (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol

Step 1. (1s,4s)-4-((2-Chloro-5-(2-(trifluoromethyl)thiazol-4-yl)pyridin-4-yl)amino)cyclohexan-1-ol The title compound as a white solid (183 mg) was prepared in the same fashion as Reference Example 2, except that (1s,4s)-4-((2-chloro-5-iodopyridin-4-yl)amino)cyclohexan-1-ol (300 mg, 0.851 mmol) prepared in Reference Example 9 and 4-(4,4,5,5-tetramethyl-1,3,2-dioxaborolan-2-yl)-2-(trifluoromethyl)thiazole (309 mg, 1.106 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=378.1 (M+H)$^+$ Step 2. (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol The title compound as an off white solid (7 mg) was prepared in the same fashion as Step 2 in Example 1, except that (1s,4s)-4-((2-chloro-5-(2-(trifluoromethyl)thiazol-4-yl)pyridin-4-yl)amino)cyclohexan-1-ol (36 mg, 0.094 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.42 (d, 1H), 8.36 (s, 1H), 7.99 (d, 1H), 7.71 (s, 1H), 7.60 (s, 1H), 7.19 (s, 2H), 3.84-3.77 (m, 2H), 2.87-2.81 (m, 1H), 1.99-1.95 (m, 2H), 1.89-1.83 (m, 4H), 1.70-1.63 (m, 2H), 1.56-1.52 (m, 2H), 1.25-1.20 (m, 2H); MS (ESI) m/z=607.1 (M+H)$^+$ Example 82. (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)cyclohexan-1-ol Step 1. (1s,4s)-4-((2-Chloro-5-(1-isopropyl-1H-pyrazol-3-yl)pyridin-4-yl)amino)cyclohexan-1-ol The title compound as a white solid (200 mg) was prepared in the same fashion as Reference Example 2, except that (1s,4s)-4-((2-chloro-5-iodopyridin-4-yl)amino)cyclohexan-1-ol (300 mg, 0.851 mmol) prepared in Reference Example 9 and 1-isopropyl-3-(4,4,5,5-tetramethyl-1,3,2-dioxaborolan-2-yl)pyrazole (201 mg, 0.851 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=335.2 (M+H)$^+$ Step 2. (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)cyclohexan-1-ol The title compound as an off white solid (11 mg) was prepared in the same fashion as Step 2 in Example 1, except that (1s,4s)-4-((2-chloro-5-(1-isopropyl-1H-pyrazol-3-yl)pyridin-4-yl)amino)cyclohexan-1-ol (169 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.60 (d, 1H), 8.46 (s, 1H), 8.38 (d, 1H), 8.35 (s, 1H), 8.33 (d, 1H), 7.47 (d, 1H), 7.20 (s, 1H), 7.14 (s, 1H), 6.59 (d, 1H), 4.57-4.50 (m, 1H), 3.91-3.87 (m, 3H), 3.77 (brs, 1H), 2.86-2.80 (m, 1H), 2.00-1.96 (m, 2H), 1.92-1.83 (m, 4H), 1.80-1.72 (m, 2H), 1.57 (d, 6H), 1.56-1.51 (m, 2H), 1.24-1.19 (m, 2H)

Example 83. (1s,4s)-4-((2-((2-(1-(Cyclopropylsulfonyl)-1H-pyrazol-4-yl)pyrimidin-4-yl)amino)-5-(furan-2-yl)pyridin-4-yl)amino)cyclohexan-1-ol Step 1. (1s,4s)-4-((2-Chloro-5-(furan-2-yl)pyridin-4-yl)amino)cyclohexan-1-ol The title compound as a white solid (132 mg) was prepared in the same fashion as Reference Example 2, except that (1s,4s)-4-((2-chloro-5-iodopyridin-4-yl)amino)cyclohexan-1-ol (300 mg, 0.851 mmol) prepared in Reference Example 9 and 2-(2-furyl)-4,4,5,5-tetramethyl-1,3,2-dioxaborolane (206 mg, 1.064 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=293.0 (M+H)$^+$ Step 2. (1s,4s)-4-((2-((2-(1-(Cyclopropylsulfonyl)-1H-pyrazol-4-yl)pyrimidin-4-yl)amino)-5-(furan-2-yl)pyridin-4-yl)amino)cyclohexan-1-ol The title compound as an off white solid (18 mg) was prepared in the same fashion as Step 2 in Example 1, except that (1s,4s)-4-((2-chloro-5-(furan-2-yl)pyridin-4-yl)amino)cyclohexan-1-ol (110 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.41 (d, 1H), 8.18 (s, 1H), 7.56 (s, 1H), 7.22 (d, 1H), 7.09 (s, 1H), 6.55 (s, 2H), 5.82 (d, 1H), 4.00-3.94 (m, 1H), 3.67-3.66 (m, 1H), 2.86-2.81 (m, 1H), 1.92-1.64 (m, 8H), 1.56-1.51 (m, 2H), 1.25-1.20 (m, 2H); MS (ESI) m/z=522.1 (M+H)$^+$ Example 84. (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)-1-methylcyclohexan-1-ol Step 1. (1s,4s)-4-((2-Chloro-5-(1-isopropyl-1H-pyrazol-3-yl)pyridin-4-yl)amino)-1-methylcyclohexan-1-ol The title compound as a pale yellow solid (177 mg) was prepared in the same fashion as Reference Example 2, except that (1s,4s)-4-((2-chloro-5-iodopyridin-4-yl)amino)-1-methylcyclohexan-1-ol (250 mg, 0.682 mmol) prepared in Reference Example 10 and 1-isopropyl-3-(4,4,5,5-tetramethyl-1,3,2-dioxaborolan-2-yl)pyrazole (193 mg, 0.818 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=349.2 (M+H)$^+$ Step 2. (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)-1-methylcyclohexan-1-ol The title compound as an off white solid (35 mg) was prepared in the same fashion as Step 2 in Example 1, except that (1s,4s)-4-((2-chloro-5-(1-isopropyl-1H-pyrazol-3-yl)pyridin-4-yl)amino)-1-methylcyclohexan-1-ol (132 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.48 (s, 1H), 8.44 (d, 1H), 8.37 (d, 1H), 8.35 (s, 1H), 7.46 (d, 1H), 7.27 (s, 1H), 7.00 (s, 1H), 6.57 (d, 1H), 4.54-4.48 (m, 1H), 3.52 (brs, 1H), 2.85-2.79 (m, 1H), 2.05-2.02 (m, 2H), 1.82-1.76 (m, 4H), 1.64-1.60 (m, 2H), 1.56 (d, 6H), 1.54-1.50 (m, 2H), 1.31 (s, 3H), 1.23-1.18 (m, 2H); MS (ESI) m/z=578.1 (M+H)$^+$

Example 85. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-methylcyclohexan-1-ol

Step 1. (1s,4s)-4-((2-Chloro-5-(1-methyl-1H-pyrazol-3-yl)pyridin-4-yl)amino)-1-methylcyclohexan-1-ol The title compound as a pale yellow solid (187 mg) was prepared in the same fashion as Reference Example 2, except that (1s,4s)-4-((2-chloro-5-iodopyridin-4-yl)amino)-1-methylcyclohexan-1-ol (250 mg, 0.682 mmol) prepared in Reference Example 10 and 1-methyl-3-(4,4,5,5-tetramethyl-1,3,2-dioxaborolan-2-yl)-1H-pyrazole (184 mg, 0.886 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=321.1 (M+H)$^+$

Step 2. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-methylcyclohexan-1-ol The title compound as an off white solid (17 mg) was prepared in the same fashion as Step 2 in Example 1, except that (1s,4s)-4-((2-chloro-5-(1-methyl-1H-pyrazol-3-yl)pyridin-4-yl)amino)-1-methylcyclohexan-1-ol (133 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.48 (s, 1H), 8.39 (d, 1H), 8.33 (s, 1H), 8.30 (d, 1H), 7.40 (d, 1H), 7.31 (d, 2H), 6.97 (s, 1H), 6.58 (d, 1H), 3.95 (s, 3H), 3.53 (brs, 1H), 2.86-2.79 (m, 1H), 2.05-2.00 (m, 2H), 1.81-1.76 (m, 4H), 1.65-1.59 (m, 2H), 1.55-1.51 (m, 2H), 1.33 (s, 3H), 1.24-1.19 (m, 2H)

Example 86. N$^2$-(2-(1-(Cyclopropylsulfonyl)-1H-pyrazol-4-yl)pyrimidin-4-yl)-5-(1-isopropyl-1H-pyrazol-3-yl)-N$^4$-((1s,4s)-4-(methylamino)cyclohexyl)pyridine-2,4-diamine

Step 1. (1s,4s)-N$^1$-(2-Chloro-5-(1-isopropyl-1H-pyrazol-3-yl)pyridin-4-yl)-N$^4$-methylcyclohexane-1,4-diamine The title compound as a pale yellow solid (180 mg) was prepared in the same fashion as Reference Example 2, except that (1s,4s)-N$^1$-(2-chloro-5-iodopyridin-4-yl)-N$^4$-methylcyclohexane-1,4-diamine (250 mg, 0.684 mmol) prepared in Reference Example 11 and 1-isopropyl-3-(4,4,5,5-tetramethyl-1,3,2-dioxaborolan-2-yl)pyrazole (194 mg, 0.820 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=348.2 (M+H)$^+$

Step 2. N$^2$-(2-(1-(Cyclopropylsulfonyl)-1H-pyrazol-4-yl)pyrimidin-4-yl)-5-(1-isopropyl-1H-pyrazol-3-yl)-N$^4$-((1s,4s)-4-(methylamino)cyclohexyl)pyridine-2,4-diamine The title compound as an off white solid (34 mg) was prepared in the same fashion as Step 2 in Example 1, except that (1s,4s)-N$^1$-(2-chloro-5-(1-isopropyl-1H-pyrazol-3-yl)pyridin-4-yl)-N$^4$-methylcyclohexane-1,4-diamine (131 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.53 (d, 1H), 8.47 (s, 1H), 8.38 (d, 1H), 8.33 (s, 1H), 7.46 (d, 1H), 7.16 (brs, 2H), 6.58 (d, 1H), 4.57-4.50 (m, 1H), 3.85 (brs, 1H), 2.87-2.81 (m, 1H), 2.56-2.51 (m, 1H), 2.45 (s, 3H), 2.05-2.03 (m, 2H), 1.87-1.80 (m, 4H), 1.65-1.58 (m, 2H), 1.55 (d, 6H), 1.53-1.51 (m, 2H), 1.24-1.19 (m, 2H); MS (ESI) m/z=578.1 (M+H)$^+$

Example 87. N$^2$-(2-(1-(Cyclopropylsulfonyl)-1H-pyrazol-4-yl)pyrimidin-4-yl)-5-(furan-2-yl)-N$^4$-((1s,4s)-4-(methylamino)cyclohexyl)pyridine-2,4-diamine

Step 1. (1s,4s)-N$^1$-(2-Chloro-5-(furan-2-yl)pyridin-4-yl)-N$^4$-methylcyclohexane-1,4-diamine The title compound as a pale yellow solid (171 mg) was prepared in the same fashion as Reference Example 2, except that (1s,4s)-N$^1$-(2-chloro-5-iodopyridin-4-yl)-N$^4$-methylcyclohexane-1,4-diamine (250 mg, 0.684 mmol) prepared in Reference Example 11 and 2-(2-furyl)-4,4,5,5-tetramethyl-1,3,2-dioxaborolane (159 mg, 0.820 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=306.1 (M+H)$^+$

Step 2. N$^2$-(2-(1-(Cyclopropylsulfonyl)-1H-pyrazol-4-yl)pyrimidin-4-yl)-5-(furan-2-yl)-N$^4$-((1s,4s)-4-(methylamino)cyclohexyl)pyridine-2,4-diamine The title compound as an off white solid (42 mg) was prepared in the same fashion as Step 2 in Example 1, except that (1s,4s)-N$^1$-(2-chloro-5-(furan-2-yl)pyridin-4-yl)-N$^4$-methylcyclohexane-1,4-diamine (115 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.39 (d, 1H), 8.17 (s, 1H), 8.16 (s, 1H), 7.55 (s, 1H), 7.19 (s, 2H), 7.14 (d, 1H), 5.87 (d, 1H), 3.77 (brs, 1H), 3.57 (brs, 1H), 2.86-2.80 (m, 1H), 2.59-2.54 (m, 2H), 2.44 (s, 3H), 1.92-1.91 (m, 2H), 1.86-1.72 (m, 4H), 1.55-1.51 (m, 2H), 1.24-1.19 (m, 2H); MS (ESI) m/z=535.1 (M+H)$^+$

Example 88. N$^2$-(2-(1-(Cyclopropylsulfonyl)-1H-pyrazol-4-yl)pyrimidin-4-yl)-5-(1-methyl-1H-pyrazol-3-yl)-N$^4$-((1s,4s)-4-(methylamino)cyclohexyl)pyridine-2,4-diamine

Step 1. (1s,4s)-N$^1$-(2-Chloro-5-(1-methyl-1H-pyrazol-3-yl)pyridin-4-yl)-N$^4$-methylcyclohexane-1,4-diamine The title compound as a pale yellow solid (157 mg) was prepared in the same fashion as Reference Example 2, except that (1s,4s)-N$^1$-(2-chloro-5-iodopyridin-4-yl)-N$^4$-methylcyclohexane-1,4-diamine (250 mg, 0.684 mmol) prepared in Reference Example 11 and 1-methyl-3-(4,4,5,5-tetramethyl-1,3,2-dioxaborolan-2-yl)-1H-pyrazole (185 mg, 0.889 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=320.2 (M+H)$^+$ Step 2. N²-(2-(1-(Cyclopropylsulfonyl)-1H-pyrazol-4-yl)pyrimidin-4-yl)-5-(1-methyl-1H-pyrazol-3-yl)-N⁴-((1s,4s)-4-(methylamino)cyclohexyl)pyridine-2,4-diamine The title compound as an off white solid (10 mg) was prepared in the same fashion as Step 2 in Example 1, except that (1s,4s)-N¹-(2-chloro-5-(1-methyl-1H-pyrazol-3-yl)pyridin-4-yl)-N⁴-methylcyclohexane-1,4-diamine (121 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.66 (s, 1H), 8.53 (d, 1H), 8.47 (s, 1H), 8.39 (d, 1H), 8.32 (s, 1H), 7.40 (d, 1H), 7.17 (s, 2H), 6.59 (d, 1H), 3.96 (s, 3H), 3.87 (brs, 1H), 2.87-2.81 (m, 1H), 2.57-2.52 (m, 1H), 2.48 (s, 3H), 2.05-2.03 (m, 2H), 1.86-1.80 (m, 4H), 1.56-1.52 (m, 4H), 1.25-1.20 (m, 2H)

Example 89. 1-(2-((2-(1-Cyclopropylsulfonylpyrazol-4-yl)pyrimidin-4-yl)amino)-5-(2-methylthiazol-5-yl)-4-pyridyl)piperidin-4-ol Step 1. 1-(2-Chloro-5-iodo-4-pyridyl)piperidin-4-ol The title compound as a white solid (782 mg) was prepared in the same fashion Reference Example 9 except that 4-hydroxypiperidine (554 mg, 5.48 mmol) was used instead of cis-4-aminocyclohexanol hydrochloride. MS (ESI) m/z=339.0 (M+H)⁺

Step 2. 1-(2-Chloro-5-(2-methylthiazol-5-yl)-4-pyridyl)piperidin-4-ol

The title compound as a pale yellow solid (110 mg) was prepared in the same fashion as Reference Example 2, except that 1-(2-chloro-5-iodo-4-pyridyl)piperidin-4-ol (300 mg, 0.886 mmol) prepared in Step 1 and 2-methyl-5-(4,4,5,5-tetramethyl-1,3,2-dioxaborolan-2-yl)thiazole (239.37 mg, 1.063 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=310.1 (M+H)⁺

Step 3. 1-(2-((2-(1-Cyclopropylsulfonylpyrazol-4-yl)pyrimidin-4-yl)amino)-5-(2-methylthiazol-5-yl)-4-pyridyl)piperidin-4-ol The title compound as an off white solid (35 mg) was prepared in the same fashion as Step 2 in Example 1, except that 1-(2-chloro-5-(2-methylthiazol-5-yl)-4-pyridyl)piperidin-4-ol (58 mg, 0.188 mmol) prepared in Step 2 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.70 (s, 1H), 8.47 (s, 1H), 8.44 (d, 1H), 8.18 (s, 1H), 7.81 (s, 1H), 7.79 (s, 1H), 7.55 (s, 1H), 7.03 (d, 1H), 3.99-3.93 (m, 1H), 3.36-3.31 (m, 2H), 2.94-2.88 (m, 2H), 2.87-2.81 (m, 1H), 2.76 (s, 3H), 2.04-1.99 (m, 2H), 1.80-1.73 (m, 2H), 1.59-1.54 (m, 2H), 1.26-1.23 (m, 2H)

Example 90. 3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-2,2-dimethylpropan-1-ol Step 1. 3-((2-Chloro-5-iodo-4-pyridyl)amino)-2,2-dimethylpropan-1-ol The title compound as a white solid (573 mg) was prepared in the same fashion Reference Example 9 except 3-amino-2,2-dimethyl-1-propanol (301 mg, 2.910 mmol) was used instead of cis-4-aminocyclohexanol hydrochloride. MS (ESI) m/z=341.0 (M+H)⁺

Step 2. 3-((2-Chloro-5-(2-(2-hydroxypropan-2-yl)thiazol-4-yl)pyridin-4-yl)amino)-2,2-dimethylpropan-1-ol The title compound as a pale yellow solid (78 mg) was prepared in the same fashion as Reference Example 2, except that 3-((2-chloro-5-iodo-4-pyridyl)amino)-2,2-dimethyl-propan-1-ol (300 mg, 0.877 mmol) prepared in Step 1 and 2-(4-(4,4,5,5-tetramethyl-1,3,2-dioxaborolan-2-yl)thiazol-2-yl)propan-2-ol (283 mg, 1.05 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=356.1 (M+H)⁺

Step 3. 3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-2,2-dimethylpropan-1-ol The title compound as an off white solid (20 mg) was prepared in the same fashion as Step 2 in Example 1, except that 3-((2-chloro-5-(2-(2-hydroxypropan-2-yl)thiazol-4-yl)pyridin-4-yl)amino)-2,2-dimethylpropan-1-ol (100 mg, 0.311 mmol) prepared in Step 2 was used instead of 2-chloro-5-(1-cyclopropyl-1H-pyrazol-4-yl)-4-((1-methyl-1H-pyrazol-4-yl)ethynyl)pyridine. ¹H-NMR (MeOD, 400 MHz) δ 8.74 (s, 1H), 8.48 (s, 1H), 8.34 (d, 1H), 8.30 (s, 1H), 7.65 (s, 1H), 7.40 (d, 1H), 7.18 (s, 1H), 4.59 (s, 1H), 3.45 (s, 2H), 3.23 (s, 2H), 3.06-3.00 (m, 1H), 1.70 (s, 6H), 1.47-1.42 (m, 2H), 1.33-1.23 (m, 2H), 1.07 (s, 6H); MS (ESI) m/z=585.2 (M+H)⁺

Example 91. (1S,3S)-3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino) cyclohexan-1-ol Step 1. (1S,3S)-3-((2-Chloro-5-iodo-4-pyridyl)amino)cyclohexanol The title compound as a white solid (986 mg) was prepared in the same fashion as Reference Example 9 except (1S,3S)-3-aminocyclohexanol hydrochloride (883 mg, 5.827 mmol) was used instead of cis-4-aminocyclohexanol hydrochloride. MS (ESI) m/z=353.0 (M+H)⁺

Step 2. (1S,3S)-3-((2-Chloro-5-(2-(2-hydroxypropan-2-yl)thiazol-4-yl)pyridin-4-yl)amino)cyclohexan-1-ol The title compound as a pale yellow solid (306 mg) was prepared in the same fashion as Reference Example 2, except that (1S,3S)-3-((2-chloro-5-iodo-4-pyridyl)amino)cyclohexanol (350 mg, 0.993 mmol) prepared in Step 1 and 2-(4-(4,4,5,5-tetramethyl-1,3,2-dioxaborolan-2-yl)thiazol-2-yl)propan-2-ol (321 mg, 1.191 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=368.2 (M+H)⁺

Step 3. (1S,3S)-3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino) cyclohexan-1-ol The title compound as an off white solid (8 mg) was prepared in the same fashion as Step 2 in Example 1, except that (1S,3S)-3-((2-chloro-5-(2-(2-hydroxypropan-2-yl)thiazol-4-yl)pyridin-4-yl)amino)cyclohexan-1-ol (83 mg, 0.226 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.49 (s, 1H), 8.40 (d, 1H), 8.26 (s, 1H), 7.89 (d, 1H), 7.36 (s, 1H), 7.26 (s, 1H), 7.08 (s, 1H), 4.15-4.12 (m, 1H), 4.04-3.97 (m, 1H), 2.89-2.82 (m, 1H), 2.09-1.99 (m, 3H), 1.75 (s, 6H), 1.75-1.64 (m, 5H), 1.56-1.52 (m, 2H), 1.24-1.19 (m, 2H)

Example 92. 2-(4-(6-((2-(1-(Cyclopropylsulfonyl)-1H-pyrazol-4-yl)pyrimidin-4-yl)amino)-4-(isopropylamino)pyridin-3-yl)thiazol-2-yl)propan-2-ol Step 1. 2-Chloro-5-iodo-N-isopropylpyridin-4-amine The title compound as a white solid (765 mg) was prepared in the same fashion as Reference Example 9 except isopropylamine (344.42 mg, 5.827 mmol) was used instead of 4 cis-4-aminocyclohexanol hydrochloride. MS (ESI) m/z=297.0 (M+H)$^+$ Step 2. 2-(4-(6-Chloro-4-(isopropylamino)-3-pyridyl)thiazol-2-yl)propan-2-ol The title compound as a pale yellow solid (217 mg) was prepared in the same fashion as Reference Example 2, except that 2-chloro-5-iodo-N-isopropylpyridin-4-amine (300 mg, 1.012 mmol) prepared in Step 1 and 2-(4-(4,4,5,5-tetramethyl-1,3,2-dioxaborolan-2-yl)thiazol-2-yl)propan-2-ol (327 mg, 1.214 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=312.1 (M+H)$^+$ Step 3. 2-(4-(6-((2-(1-(Cyclopropylsulfonyl)-1H-pyrazol-4-yl)pyrimidin-4-yl)amino)-4-(isopropylamino)pyridin-3-yl)thiazol-2-yl)propan-2-ol The title compound as an off white solid (10 mg) was prepared in the same fashion as Step 2 in Example 1, except that 2-(4-(6-chloro-4-(isopropylamino)-3-pyridyl)thiazol-2-yl)propan-2-ol (71 mg, 0.226 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.40 (d, 1H), 8.28 (s, 1H), 7.92 (d, 1H), 7.36 (s, 1H), 7.20 (s, 1H), 7.15 (d, 1H), 3.88-3.81 (m, 1H), 2.87-2.81 (m, 1H), 1.76 (s, 6H), 1.56-1.52 (m, 2H), 1.38 (d, 6H), 1.25-1.20 (m, 2H)

Example 93. (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-1-methylcyclohexan-1-ol Step 1. (1s,4s)-4-((2-Chloro-5-(2-(2-hydroxypropan-2-yl)thiazol-4-yl)pyridin-4-yl)amino)-1-methylcyclohexan-1-ol The title compound as a pale yellow solid (258 mg) was prepared in the same fashion as Reference Example 2, except that (1s,4s)-4-((2-chloro-5-iodopyridin-4-yl)amino)-1-methylcyclohexan-1-ol (300 mg, 0.818 mmol) prepared in Reference Example 10 and 2-(4-(4,4,5,5-tetramethyl-1,3,2-dioxaborolan-2-yl)thiazol-2-yl)propan-2-ol (264 mg, 0.982 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=382.2 (M+H)$^+$ Step 2. (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-1-methylcyclohexan-1-ol The title compound as an off white solid (28 mg) was prepared in the same fashion as Step 2 in Example 1, except that (1s,4s)-4-((2-chloro-5-(2-(2-hydroxypropan-2-yl)thiazol-4-yl)pyridin-4-yl)amino)-1-methylcyclohexan-1-ol (72 mg, 0.188 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.41 (d, 1H), 8.28 (s, 1H), 7.93 (d, 1H), 7.36 (s, 1H), 7.27 (s, 1H), 7.00 (s, 1H), 3.50 (brs, 1H), 2.86-2.80 (m, 1H), 2.01-1.98 (m, 2H), 1.76 (s, 6H), 1.72-1.58 (m, 6H), 1.56-1.51 (m, 2H), 1.31 (s, 3H), 1.24-1.22 (m, 2H); MS (ESI) m/z=611.2 (M+H)$^+$ Example 94. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(trifluoromethyl)cyclohexan-1-ol Step 1. (1s,4s)-4-((2-Chloro-5-iodopyridin-4-yl)amino)-1-(trifluoromethyl)cyclohexan-1-ol The title compound as a white solid (912 mg) was prepared in the same fashion as Reference Example 9 except (1s,4s)-4-amino-1-(trifluoromethyl)cyclohexan-1-ol hydrochloride (1.28 g, 5.827 mmol) was used instead of cis-4-aminocyclohexanol hydrochloride. MS (ESI) m/z=421.0 (M+H)$^+$ Step 2. (1s,4s)-4-((2-Chloro-5-(1-methyl-1H-pyrazol-3-yl)pyridin-4-yl)amino)-1-(trifluoromethyl)cyclohexan-1-ol The title compound as a pale yellow solid (116 mg) was prepared in the same fashion as Reference Example 2, except that (1s,4s)-4-((2-chloro-5-iodopyridin-4-yl)amino)-1-(trifluoromethyl)cyclohexan-1-ol (200 mg, 0.476 mmol) prepared in Step 1 and 1-methyl-3-(4,4,5,5-tetramethyl-1,3,2-dioxaborolan-2-yl)-1H-pyrazole (129 mg, 0.618 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=375.1 (M+H)$^+$ Step 3. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(trifluoromethyl)cyclohexan-1-ol The title compound as an off white solid (3 mg) was prepared in the same fashion as Step 2 in Example 1, except that (1s,4s)-4-((2-chloro-5-(1-methyl-1H-pyrazol-3-yl)pyridin-4-yl)amino)-1-(trifluoromethyl)cyclohexan-1-ol (35.32 mg, 0.094 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.41 (d, 1H), 8.36 (s, 1H), 8.24 (d, 1H), 7.43-7.40 (m, 2H), 6.79 (s, 1H), 6.59 (d, 1H), 3.95 (s, 3H), 3.50 (brs, 1H), 2.85-2.78 (m, 1H), 2.21-2.18 (m, 2H), 1.97-1.94 (m, 2H), 1.89-1.75 (m, 4H), 1.55-1.51 (m, 2H), 1.23-1.18 (m, 2H)

Example 95. 3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-3-methylbutan-2-ol Step 1. 3-((2-Chloro-5-iodopyridin-4-yl)amino)-3-methylbutan-2-ol The title compound as a white solid (842 mg) was prepared in the same fashion as Step 1 in Reference Example 9 except that 3-amino-3-methylbutan-2-ol (601 mg, 5.827 mmol) was used instead of cis-4-aminocyclohexanol hydrochloride. MS (ESI) m/z=341.0 (M+H)$^+$ Step 2. 3-((2-Chloro-5-(1-methylpyrazol-3-yl)-4-pyridyl)amino)-3-methylbutan-2-ol The title compound as a pale yellow solid (102 mg) was prepared in the same fashion as Reference Example 2, except that 3-((2-chloro-5-iodopyridin-4-yl)amino)-3-methylbutan-2-ol (150 mg, 0.44 mmol) prepared in Step 1 and 1-methyl-3-(4,4,5,5-tetramethyl-1,3,2-dioxaborolan-2-yl)-1H-pyrazole (119.13 mg, 0.573 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=295.1 (M+H)$^+$ Step 3. 3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-3-methylbutan-2-ol The title compound as an off white solid (8 mg) was prepared in the same fashion as Step 2 in Example 1, except that 3-((2-chloro-5-(1-methylpyrazol-3-yl)-4-pyridyl)amino)-3-methyl-butan-2-ol (28 mg, 0.094 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.47 (s, 1H), 8.37 (d, 1H), 8.36 (s, 1H), 8.32 (s, 1H), 7.39 (d, 1H), 7.31 (d, 1H), 7.13 (s, 1H), 6.55 (d, 1H), 4.19 (q, 1H), 3.93 (s, 3H), 2.86-2.80 (m, 1H), 1.55 (s, 3H), 1.53-1.50 (m, 2H), 1.48 (s, 3H), 1.29 (d, 3H), 1.23-1.17 (m, 2H); MS (ESI) m/z=524.2 (M+H)$^+$ Example 96. (1S,3R)-3-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol Step 1. (1S,3R)-3-((2-Chloro-5-iodo-4-pyridyl)amino)cyclohexanol The title compound as a white solid (1.73 g) was prepared in the same fashion as Step 1 in Reference Example 9 except that (1S,3R)-3-aminocyclohexanol hydrochloride (1.33 g, 8.74 mmol) was used instead of cis-4-aminocyclohexanol hydrochloride. MS (ESI) m/z=353.0 (M+H)$^+$ Step 2. (1S,3R)-3-((2-Chloro-5-(2-(trifluoromethyl)thiazol-4-yl)pyridin-4-yl)amino)cyclohexan-1-ol The title compound as a pale yellow solid (161 mg) was prepared in the same fashion as Reference Example 2, except that (1S,3R)-3-((2-chloro-5-iodo-4-pyridyl)amino)cyclohexanol (200 mg, 0.567 mmol) prepared in Step 1 and 4-(tetramethyl-1,3,2-dioxaborolan-2-yl)-2-(trifluoromethyl)-1,3-thiazole (206 mg, 0.737 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=378.0 (M+H)$^+$ Step 3. (1S,3R)-3-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol The title compound as an off white solid (2 mg) was prepared in the same fashion as Step 2 in Example 1, except that (1S,3R)-3-((2-chloro-5-(2-(trifluoromethyl)thiazol-4-yl)pyridin-4-yl)amino)cyclohexan-1-ol (157 mg, 0.415 mmol) prepared in Step 2 was used instead of 2-chloro-5-(1-cyclopropyl-1H-pyrazol-4-yl)-4-((1-methyl-1H-pyrazol-4-yl)ethynyl)pyridine. MS (ESI) m/z=607.0 (M+H)$^+$ Example 97. 2-((4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexyl)amino)ethan-1-ol The suspension of ethanolamine (14.97 uL, 0.248 mmol), DIPEA (86.42 uL, 0.500 mmol) and 4-((2-((2-(1-(cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-one (30 mg, 0.050 mmol) prepared in Reference Example 12 in MeOH (10 mL) was stirred for 30 minutes, added sodium triacetoxyborohydride (105.16 mg, 0.500 mmol)) at 0° C. ice bath, and then the reaction mixture was stirred at. 50° C. overnight. The reaction mixture was cooled, added to NaHCO$_3$ soln. and extracted with DCM, washed by water, dried over MgSO$_4$, and then concentrated. The crude product was purified by column chromatography (MeOH/DCM=0-100%) to yield N-2-((4-((2-((2-(1-(cyclopropylsulfonyl)-1H-pyrazol-4-yl)pyrimidin-4-yl)amino)-5-(2-(trifluoromethyl)thiazol-4-yl)pyridin-4-yl)amino)cyclohexyl)amino)ethan-1-ol (17 mg) as an off-white solid. $^1$H-NMR (CDC$_3$, 400 MHz) δ 8.66 (d, 1H), 8.51-8.45 (m, 3H), 8.42 (d, 1H), 8.33 (d, 1H), 7.77 (d, 1H), 7.70 (s, 1H), 7.10 (s, 1H), 3.68-3.6 (m, 2H), 2.94-2.78 (m, 3H), 2.66-2.55 (m, 1H), 2.29-2.2 (m, 1H), 2.12-1.98 (m, 2H), 1.93-1.85 (m, 4H), 1.58-1.5 (m, 2H), 1.45-1.19 (m, 4H); MS (ESI) m/z=650.0 (M+H)$^+$ Example 98. N$^2$-(2-(1-(Cyclopropylsulfonyl)-1H-pyrazol-4-yl)pyrimidin-4-yl)-N$^4$-(4-((2-(dimethylamino)ethyl)amino)cyclohexyl)-5-(2-(trifluoromethyl)thiazol-4-yl)pyridine-2,4-diamine The title compound as an off white solid (19 mg) was prepared in the same fashion as Example 97, except N$^1$,N$^1$-dimethylethane-1,2-diamine (22 mg, 0.248 mmol) was used instead of ethanolamine. $^1$H-NMR (CDCl$_3$, 400 MHz) δ 8.66 (d, 1H), 8.51-8.45 (m, 3H), 8.42 (d, 1H), 8.33 (d, 1H), 7.77 (d, 1H), 7.70 (s, 1H), 7.10 (s, 1H), 3.68-3.60 (m, 2H), 2.94-2.78 (m, 3H), 2.66-2.55 (m, 1H), 2.29-2.20 (m, 1H), 2.12-1.98 (m, 2H), 1.93-1.85 (m, 4H), 1.58-1.50 (m, 2H), 1.45-1.19 (m, 4H); MS (ESI) m/z=677.0 (M+H)$^+$ Example 99. $N^2$-(2-(1-(cyclopropylsulfonyl)-1H-pyrazol-4-yl)pyrimidin-4-yl)-5-(1-(difluoromethyl)-1H-pyrazol-3-yl)-N4-(4-((2-(dimethylamino)ethyl)amino)cyclohexyl)pyridine-2,4-diamine Step 1. 4-((2-Chloro-5-(1-(difluoromethyl)-1H-pyrazol-3-yl)pyridin-4-yl)amino)cyclohexan-1-one The title compound as an off-white solid (581 mg) was prepared in the same fashion as Reference Example 9, except that 4-aminocyclohexanone hydrochloride (453 mg, 3.029 mmol) and 2-chloro-5-(1-(difluoromethyl)-1H-pyrazol-3-yl)-4-fluoropyridine (500 mg, 2.019 mmol) prepared in Reference Example 2 were used instead of cis-4-aminocyclohexanol hydrochloride and 2-chloro-4-fluoro-5-iodopyridine. MS (ESI) m/z=341.0 (M+H)$^+$ Step 2. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-one The title compound as an off-white solid (52 mg) was prepared in the same fashion as Step 2 in Reference Example 12, except that 4-((2-chloro-5-(1-(difluoromethyl)-1H-pyrazol-3-yl)pyridin-4-yl)amino)cyclohexan-1-one (339 mg, 0.995 mmol) prepared in Step 1 were used instead of 4-((2-chloro-5-(2-(trifluoromethyl)thiazol-4-yl)-4-pyridyl)amino)cyclohexanone. MS (ESI) m/z=570.0 (M+H)$^+$ Step 3. $N^2$-(2-(1-(cyclopropylsulfonyl)-1H-pyrazol-4-yl)pyrimidin-4-yl)-5-(1-(difluoromethyl)-1H-pyrazol-3-yl)-N4-(4-((2-(dimethylamino)ethyl)amino)cyclohexyl)pyridine-2,4-diamine The title compound as an off white solid (13 mg) was prepared in the same fashion as Example 97, except that 4-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-one (40 mg, 0.07 mmol) prepared in Step 2 and $N^1,N^1$-dimethylethane-1,2-diamine (31 mg, 0.351 mmol) were used instead of 4-((2-((2-(1-cyclopropylsulfonylpyrazol-4-yl)pyrimidin-4-yl)amino)-5-(2-(trifluoromethyl)thiazol-4-yl)-4-pyridyl)amino)cyclohexanone and ethanolamine. MS (ESI) m/z=643.1 (M+H)$^+$ Example 100. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-((dimethylamino)methyl)cyclohexyl)methyl)pyridine-2,4-diamine Step 1. 2-Chloro-5-(1-(difluoromethyl)-1H-pyrazol-3-yl)-N-(((1r,4r)-4-((dimethylamino)methyl)cyclohexyl)methyl)pyridin-4-amine The title compound as a pale yellow solid (422 mg) was prepared in the same fashion as Reference Example 2, except that 2-chloro-N-(((1r,4r)-4-((dimethylamino)methyl)cyclohexyl)methyl)-5-iodopyridin-4-amine (500 mg, 1.226 mmol) prepared in Reference Example 13 was used instead of 2-chloro-4-fluoro-5-iodopyridine. MS (ESI) m/z=398.1 (M+H)$^+$ Step 2. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-((dimethylamino)methyl)cyclohexyl)methyl)pyridine-2,4-diamine The title compound as a pale yellow solid (33 mg) was prepared in the same fashion as Step 2 in Example 1, except that 2-chloro-5-(1-(difluoromethyl)-1H-pyrazol-3-yl)-N-(((1r,4r)-4-((dimethylamino)methyl)cyclohexyl)methyl)pyridin-4-amine (75 mg, 0.188 mmol) prepared in Step 1 was used instead of 2-chloro-5-(1-cyclopropyl-1H-pyrazol-4-yl)-4-((1-methyl-1H-pyrazol-4-yl)ethynyl)pyridine.
$^1$H-NMR (CDCl$_3$, 400 MHz) δ 8.67 (s, 1H), 8.46 (s, 1H), 8.41 (d, 1H), 8.37 (s, 1H), 8.02 (t, 1H), 7.86 (d, 1H), 7.29 (d, 1H), 7.17 (t, 1H), 7.05 (s, 1H), 6.82 (d, 2H), 3.22 (t, 2H), 2.86-2.80 (m, 1H), 2.23 (s, 6H), 2.13 (d, 2H), 1.93 (t, 4H), 1.77-1.69 (m, 1H), 1.55-1.51 (m, 2H), 1.51-1.46 (m, 1H), 1.28-1.13 (m, 4H), 1.02-0.93 (m, 2H); MS (ESI) m/z=627.2 (M+H)$^+$ Example 101. $N^2$-(2-(1-(Cyclopropylsulfonyl)-1H-pyrazol-4-yl)pyrimidin-4-yl)-$N^4$-(((1r,4r)-4-((dimethylamino)methyl)cyclohexyl)methyl)-5-(2-(trifluoromethyl)thiazol-4-yl)pyridine-2,4-diamine Step 1. 2-Chloro-N-(((1r,4r)-4-((dimethylamino)methyl)cyclohexyl)methyl)-5-(2-(trifluoromethyl)thiazol-4-yl)pyridin-4-amine The title compound as a pale yellow solid (171 mg) was prepared in the same fashion as Reference Example 2, except that 2-chloro-N-(((1r,4r)-4-((dimethylamino)methyl)cyclohexyl)methyl)-5-iodopyridin-4-amine (200 mg, 0.491 mmol) prepared in Reference Example 13 and 4-(tetramethyl-1,3,2-dioxaborolan-2-yl)-2-(trifluoromethyl)-1,3-thiazole (178 mg, 0.638 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=433.1 (M+H)$^+$ Step 2. $N^2$-(2-(1-(Cyclopropylsulfonyl)-1H-pyrazol-4-yl)pyrimidin-4-yl)-$N^4$-(((1r,4r)-4-((dimethylamino)methyl)cyclohexyl)methyl)-5-(2-(trifluoromethyl)thiazol-4-yl)pyridine-2,4-diamine The title compound as a pale yellow solid (49 mg) was prepared in the same fashion as Step 2 in Example 1, except that 2-chloro-N-(((1r,4r)-4-((dimethylamino)methyl)cyclohexyl)methyl)-5-(2-(trifluoromethyl)thiazol-4-yl)pyridin-4-amine (147 mg, 0.339 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.43 (d, 1H), 8.36 (s, 1H), 7.87 (s, 1H), 7.70 (s, 1H), 7.62 (s, 1H), 7.31 (d, 1H), 7.01 (s, 1H), 3.18 (t, 2H), 2.86-2.80 (m, 1H), 2.22 (s, 6H), 2.11 (d, 2H), 1.95-1.91 (m, 4H), 1.73 (brs, 1H), 1.55-1.46 (m, 3H), 1.26-1.17 (m, 4H), 1.03-0.94 (m, 2H); MS (ESI) m/z=662.2 (M+H)$^+$ Example 102. Ethyl 1-(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)-1H-pyrazole-3-carboxylate Step 1. Ethyl 1-(6-chloro-4-(((1s,4s)-4-hydroxy-4-methylcyclohexyl)amino)pyridin-3-yl)-1H-pyrazole-3-carboxylate To a solution of (1s,4s)-4-((2-chloro-5-iodopyridin-4-yl)amino)-1-methylcyclohexan-1-ol (50 mg, 0.14 mmol) prepared in Reference Example 10 in 1,4-dioxane (2.7 mL) were added ethyl pyrazole-3-carboxylate (19 mg, 0.140 mmol), copper(I) iodide (5 mg, 0.030 mmol), K$_2$CO$_3$ (38 mg, 0.270 mmol) and trans-(1R,2R)—N,N'-dimethyl-1,2- cyclohexanediamine (12 mg, 0.080 mmol). The reaction mixture was stirred at 110° C. for 14 hours. The reaction mixture was diluted with DCM and the filtrate was concentrated in vacuo. The crude residue was purified by silica gel column chromatography (MeOH/DCM=0-10%) to give ethyl 1-(6-chloro-4-(((1s,4s)-4-hydroxy-4-methylcyclohexyl)amino)pyridin-3-yl)-1H-pyrazole-3-carboxylate (18 mg) as white solid. $^1$H-NMR (CDCl$_3$, 400 MHz) δ 8.05 (s, 1H), 7.78 (dd, 1H), 6.99 (dd, 1H), 6.88 (brs, 1H), 6.62 (s, 1H), 4.43-4.36 (m, 2H), 3.40-3.34 (m, 1H), 1.87-1.52 (m, 8H), 1.39 (dd, 3H), 1.30 (s, 3H); MS (ESI) m/z=379.1 (M+H)$^+$ Step 2. Ethyl 1-(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)-1H-pyrazole-3-carboxylate The title compound (5 mg) was prepared in the same fashion as Step 2 in Example 1, except that ethyl 1-(6-chloro-4-(((1s,4s)-4-hydroxy-4-methylcyclohexyl)amino)pyridin-3-yl)-1H-pyrazole-3-carboxylate (18 mg, 0.048 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.64 (s, 1H), 8.47-8.44 (m, 2H), 7.96 (s, 1H), 7.80-7.77 (m, 2H), 7.10 (brs, 1H), 7.06-7.03 (m, 2H), 4.47-4.42 (m, 2H), 3.66 (brs, 1H), 2.86-2.82 (m, 1H), 1.99-1.94 (m, 2H), 1.79-1.74 (m, 4H), 1.67-1.61 (m, 2H), 1.55-1.52 (m, 2H), 1.42 (dd, 3H), 1.31 (s, 3H), 1.26-1.22 (m, 2H); MS (ESI) m/z=608.2 (M+H)$^+$ Example 103. 6-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)spiro[3.3]heptan-2-ol Step 1. 6-((2-Chloro-5-iodopyridin-4-yl)amino)spiro[3.3]heptan-2-ol The title compound as a colorless oil (780 mg) was prepared in the same fashion as Reference Example 9, except that 6-aminospiro[3.3]heptan-2-ol hydrochloride (572 mg, 3.50 mmol) was used instead of cis-4-aminocyclohexanol hydrochloride. $^1$H-NMR (CDCl$_3$, 400 MHz) δ 8.28 (s, 1H), 6.28 (s, 1H), 4.86-4.85 (m, 1H), 4.27 (t, 1H), 3.87-3.86 (m, 1H), 2.56-2.55 (m, 3H), 2.40-2.38 (m, 1H), 2.06-1.98 (m, 3H), 1.72 (brs, 1H); MS (ESI) m/z=365.0 (M+H)$^+$ Step 2. 6-((2-Chloro-5-(1-(difluoromethyl)-1H-pyrazol-3-yl)pyridin-4-yl)amino)spiro[3.3]heptan-2-ol The title compound as a beige solid (133 mg) was prepared in the same fashion as Reference Example 2, except that 6-((2-chloro-5-iodopyridin-4-yl)amino)spiro[3.3]heptan-2-ol (200 mg, 0.55 mmol) prepared in Step 1 was used instead of 2-chloro-4-fluoro-5-iodopyridine. $^1$H-NMR (CDCl$_3$, 400 MHz) δ 8.31 (s, 1H), 7.98 (d, 1H), 7.86 (d, 1H), 7.27 (dd, 1H), 6.79 (d, 1H), 6.40 (s, 1H), 4.27-4.23 (m, 1H), 3.89-3.88 (m, 1H), 2.83 (brs, 1H), 2.56-2.51 (m, 3H), 2.37-2.35 (m, 1H), 2.03-1.98 (m, 3H); MS (ESI) m/z=355.0 (M+H)$^+$ Step 3. 6-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)spiro[3.3]heptan-2-ol The title compound as an off-white solid (6 mg) was prepared in the same fashion as Step 2 in Reference Example 12, except that 6-((2-chloro-5-(1-(difluoromethyl)-1H-pyrazol-3-yl)pyridin-4-yl)amino)spiro[3.3]heptan-2-ol (65 mg, 0.18 mmol) prepared in Step 2 was used instead of 4-((2-chloro-5-(2-(trifluoromethyl)thiazol-4-yl)-4-pyridyl)amino)cyclohexanone. $^1$H-NMR (CDCl$_3$, 400 MHz) δ 8.68 (s, 1H), 8.47 (s, 1H), 8.44 (d, 1H), 8.36 (s, 1H), 7.98 (d, 1H), 7.88-7.87 (m, 1H), 7.70 (brs, 1H), 7.38-7.34 (m, 1H), 7.23 (dd, 1H), 6.83-6.81 (m, 2H), 4.25-4.22 (m, 1H), 4.02 (q, 1H), 3.67-3.64 (m, 1H), 2.84 (t, 1H), 2.64-2.56 (m, 3H), 2.41-2.40 (m, 1H), 2.04-2.01 (m, 3H), 1.54-1.50 (m, 2H), 1.24-1.22 (m, 2H); MS (ESI) m/z=584.2 (M+H)$^+$ Example 104. (1s,4s)-4-((5-(1-(Difluoromethyl)-1H-pyrazol-3-yl)-2-((2-(3-methoxyprop-1-yn-1-yl)pyrimidin-4-yl)amino)pyridin-4-yl)amino)-1-methylcyclohexan-1-ol Step 1. tert-Butyl (tert-butoxycarbonyl)(2-(3-methoxyprop-1-yn-1-yl)pyrimidin-4-yl)carbamate The reaction mixture of PdCl$_2$(PPh$_3$)$_2$ (60 mg, 0.08 mmol), copper(I) (60 mg, 0.32 mmol), TEA (0.45 mL, 3.21 mmol), di-tert-butyl (2-bromopyrimidin-4-yl)iminodicarbonate (600 mg, 1.6 mmol) prepared in Reference Example 14 and methyl propargyl ether (0.14 mL, 1.6 mmol) in DMF (6 mL) was stirred at 60° C. overnight. The reaction mixture was cooled, diluted in EA, washed by water, dried over MgSO$_4$ and then concentrated. The crude product was purified by column chromatography (EA/n-Hex=0-30%) to yield tert-butyl (tert-butoxycarbonyl)(2-(3-methoxyprop-1-yn-1-yl)pyrimidin-4-yl)carbamate (295 mg) as a yellow oil. $^1$H-NMR (CDCl$_3$, 400 MHz) δ 8.54 (d, 1H), 7.58 (d, 1H), 4.29 (s, 2H), 3.40 (s, 3H), 1.50 (s, 18H); MS (ESI) m/z=365.0 (M+H)$^+$ Step 2. 2-(3-Methoxyprop-1-yn-1-yl)pyrimidin-4-amine TFA (1.24 mL, 16.23 mmol) was added to the solution of tert-butyl (tert-butoxycarbonyl)(2-(3-methoxyprop-1-yn-1-yl)pyrimidin-4-yl)carbamate (295 mg, 0.81 mmol) in DCM (4 mL) at 0° C. The reaction mixture was stirred overnight while being slowly warmed to room temperature. Upon completion, the reaction mixture was concentrated in-vacuo and the residue was dissolved in DCM, basified with sat. NaHCO$_3$ solution, and extracted with DCM. The organic layer was collected, dried over MgSO$_4$ and concentrated. The crude product was purified by column chromatography (MeOH/DCM=0-10%) to give 2-(3-methoxyprop-1-yn-1-yl)pyrimidin-4-amine (110 mg) as an off-white solid. $^1$H-NMR (CDCl$_3$, 400 MHz) δ 8.19 (d, 1H), 6.37 (d, 1H), 5.30 (brs, 2NH), 4.33 (s, 2H), 3.46 (s, 3H); MS (ESI) m/z=163.9 (M+H)$^+$ Step 3. (1s,4s)-4-((5-(1-(Difluoromethyl)-1H-pyrazol-3-yl)-2-((2-(3-methoxyprop-1-yn-1-yl)pyrimidin-4-yl)amino)pyridin-4-yl)amino)-1-methylcyclohexan-1-ol The title compound as an off-white solid (4 mg) was prepared in the same fashion as Step 2 in Reference Example 12, except that (1s,4s)-4-((2-chloro-5-(1-(difluoromethyl)-1H-pyrazol-3-yl)pyridin-4-yl)amino)-1-methylcyclohexan-1-ol (100 mg, 0.28 mmol) prepared in Reference Example 15 and 2-(3-methoxyprop-1-yn-1-yl)pyrimidin-4-amine (37 mg, 0.22 mmol) prepared in Step 2 were used instead of 4-((2-chloro-5-(2-(trifluoromethyl)thiazol-4-yl)-4-pyridyl)

amino)cyclohexanone and 2-(1-(cyclopropylsulfonyl)-1H-pyrazol-4-yl)pyrimidin-4-amine. $^1$H-NMR (MeOD, 400 MHz) δ 8.37 (s, 1H), 8.26 (d, 1H), 8.10-8.09 (m, 2H), 7.56 (dd, 1H), 7.37-7.35 (m, 2H), 4.37 (s, 2H), 3.53-3.52 (m, 1H), 3.47 (s, 3H), 2.04-2.02 (m, 2H), 1.80-1.77 (m, 4H), 1.67-1.64 (m, 2H), 1.28 (s, 3H); MS (ESI) m/z=484.2 (M+H)$^+$ Example 105. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-2-methylcyclohexan-1-ol Step 1. 4-((2-Chloro-5-(1-(difluoromethyl)-1H-pyrazol-3-yl)pyridin-4-yl)amino)-2-methylcyclohexan-1-ol The reaction mixture of 2-chloro-5-(1-(difluoromethyl)-1H-pyrazol-3-yl)-4-fluoropyridine (100 mg, 0.40 mmol) prepared in Reference Example 2, 4-amino-2-methylcyclohexan-1-ol (51 mg, 0.40 mmol) and DIPEA (0.14 mL, 0.81 mmol) in DMF (6 mL) was stirred at 80° C. overnight. The reaction mixture was cooled, diluted in EA, washed by water, dried over MgSO$_4$ and then concentrated. The crude product was purified by column chromatography (EA/n-Hex=0-70%) to yield 4-((2-chloro-5-(1-(difluoromethyl)-1H-pyrazol-3-yl)pyridin-4-yl)amino)-2-methylcyclohexan-1-ol (102 mg) as a white soild. $^1$H-NMR (CDCl$_3$, 400 MHz) δ 8.34 (s, 1H), 7.87-7.82 (m, 2H), 7.35-7.19 (m, 1H), 6.82-6.82 (d, 1H), 6.58 (s, 1H), 3.44-3.42 (d, 1H), 3.26-3.25 (d, 1H), 2.22-2.07 (m, 3H), 1.70 (s, 2H), 1.57-1.48 (m, 4H), 1.37 (s, 3H)

Step 2. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-2-methylcyclohexan-1-ol The title compound as an off white solid (4.1 mg) was prepared in the same fashion as Step 2 in Example 1, except that 4-((2-chloro-5-(1-(difluoromethyl)-1H-pyrazol-3-yl)pyridin-4-yl)amino)-2-methylcyclohexan-1-ol (102 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65-8.62 (d, 1H), 8.48-8.44 (t, 1H), 8.22-8.18 (t, 2H), 7.89-7.88 (d, 1H), 7.53 (s, 1H), 7.36-7.20 (m, 1H), 6.79-6.79 (d, 1H), 3.65 (s, 1H), 3.19 (s, 2H), 2.92-2.82 (m, 4H), 2.28-2.07 (m, 4H), 1.56-1.52 (m, 2H), 1.44-1.40 (d, 2H), 1.37-1.32 (t, 3H), 1.25-1.10 (m, 4H); MS (ESI) m/z=586.1 (M+H)$^+$ Example 106. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-2,2-dimethylcyclohexan-1-ol Step 1. 4-((2-Chloro-5-(1-(difluoromethyl)-1H-pyrazol-3-yl)pyridin-4-yl)amino)-2,2-dimethylcyclohexan-1-ol The title compound as a white solid (81 mg) was prepared in the same fashion as Step 1 in Example 105, except that 4-amino-2,2-dimethylcyclohexan-1-ol hydrochloride (71 mg, 0.40 mmol) was used instead of 4-amino-2-methylcyclohexan-1-ol. $^1$H-NMR (CDCl$_3$, 400 MHz) δ 8.34 (s, 1H), 7.87-7.83 (m, 2H), 7.21 (d, 1H), 6.82 (d, 1H), 6.56 (d, 1H), 3.58-3.52 (m, 1H), 1.94-1.82 (m, 3H), 1.70-1.60 (m, 4H), 1.27-1.21 (m, 1H), 1.06 (d, 6H)

Step 2. 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-2,2-dimethylcyclohexan-1-ol The title compound as an off white solid (4.9 mg) was prepared in the same fashion as Step 2 in Example 1, except that 4-((2-chloro-5-(1-(difluoromethyl)-1H-pyrazol-3-yl)pyridin-4-yl)amino)-2,2-dimethylcyclohexan-1-ol (81 mg, 0.22 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=600.2 (M+H)$^+$ Example 107. (S)-1-(2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)-3-methylpiperidin-3-ol Step 1. (S)-1-(2-Chloro-5-(1-(difluoromethyl)-1H-pyrazol-3-yl)pyridin-4-yl)-3-methylpiperidin-3-ol The title compound as a white solid (174 mg) was prepared in the same fashion as Step 1 in Example 105, except that (3S)-3-methylpiperidine-3-ol hydrochloride (90 mg, 0.59 mmol) was used instead of 4-amino-2-methylcyclohexan-1-ol. $^1$H-NMR (CDCl$_3$, 400 MHz) δ 8.22 (s, 1H), 7.87 (d, 2H), 7.27-7.22 (d, 1H), 6.84 (s, 1H), 6.69 (d, 1H), 3.43 (s, 1H), 3.07-2.99 (m, 2H), 2.66-2.54 (m, 2H), 1.81-1.78 (d, 1H), 1.64 (d, 1H), 1.46-1.41 (m, 2H), 1.38-1.33 (q, 1H), 1.31 (s, 3H)

Step 2. (S)-1-(2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)-3-methylpiperidin-3-ol The title compound as an off white solid (16.6 mg) was prepared in the same fashion as Step 2 in Example 1, except that (S)-1-(2-chloro-5-(1-(difluoromethyl)-1H-pyrazol-3-yl)pyridin-4-yl)-3-methylpiperidin-3-ol (174 mg, 0.51 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=572.2 (M+H)$^+$ Example 108. (1s,4s)-4-((5-(1-(Difluoromethyl)-1H-pyrazol-3-yl)-2-((2-(1-(methylsulfonyl)-1H-pyrrol-3-yl)pyrimidin-4-yl)amino)pyridin-4-yl)amino)-1-methylcyclohexan-1-ol Step 1. 2-(1-(Methylsulfonyl)-1H-pyrrol-3-yl)pyrimidin-4-amine The reaction mixture of PdCl$_2$(PPh$_3$)$_2$ (70 mg, 0.09 mmol), 2-bromo-4-pyrimidinamine (300 mg, 1.72 mmol), 1-(methylsulfonyl)pyrrole-3-boronic acid pinacol ester (444 mg, 1.64 mmol) and 3M K$_2$CO$_3$ soln. (1.72 mL, 5.17 mmol) in 1,4-dioxane (5 mL) was stirred at 90° C. for 4 hours. The reaction mixture was cooled, diluted in EA, washed by water, dried over MgSO$_4$ and then concentrated. The crude product was purified by column chromatography (MeOH/DCM=0-20%) to yield 2-(1-(methylsulfonyl)-1H-pyrrol-3-yl)pyrimidin-4-amine (220 mg) as a yellow solid. $^1$H-NMR (CDCl$_3$, 400 MHz) δ 8.24 (d, 1H), 7.88 (t, 1H), 7.15 (t, 1H), 7.00-6.99 (q, 1H), 6.28 (d, 1H), 4.99 (brs, 2H), 4.12-4.09 (m, 1H), 3.19 (s, 3H), 2.04 (s, 2H), 1.27-1.23 (m, 2H)

Step 2. (1s,4s)-4-((5-(1-(Difluoromethyl)-1H-pyrazol-3-yl)-2-((2-(1-(methylsulfonyl)-1H-pyrrol-3-yl)pyrimidin-4-yl)amino)pyridin-4-yl)amino)-1-methylcyclohexan-1-ol The title compound as an off-white solid (4 mg) was prepared in the same fashion as Step 2 in Reference Example 12, except that (1s,4s)-4-((2-chloro-5-(1-(difluoromethyl)-1H-pyrazol-3-yl)pyridin-4-yl)amino)-1-methylcyclohexan-1-ol (62.6 mg, 0.18 mmol) prepared in Reference Example 15 and 2-(1-(methylsulfonyl)-1H-pyrrol-3-yl)pyrimidin-4-amine (95 mg, 0.40 mmol) prepared in Step 1 were used instead of 4-((2-chloro-5-(2-(trifluoromethyl)thiazol-4-yl)-4-pyridyl)amino)cyclohexanone and 2-(1-(cyclopropylsulfonyl)-1H-pyrazol-4-yl)pyrimidin-4-amine. $^1$H-NMR (CDCl$_3$, 400 MHz) δ 8.58 (s, 1H), 8.46 (s, 1H), 8.44 (s, 1H), 8.13 (s, 1H), 7.93-7.90 (m, 2H), 7.23-7.19 (m, 2H), 7.10 (d, 1H), 7.03 (d, 1H), 6.79 (d, 1H), 3.70 (s, 1H), 3.23 (s, 3H), 2.06-2.02 (m, 2H), 1.83 (d, 2H), 1.73 (d, 2H), 1.61-1.54 (m, 2H), 1.31 (s, 3H); MS (ESI) m/z=559.2 (M+H)$^+$

Example 109. 3-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrrole-1-sulfonamide

Step 1. 3-(4-Aminopyrimidin-2-yl)-N,N-dimethyl-1H-pyrrole-1-sulfonamide

The title compound as a yellow solid (270 mg) was prepared in the same fashion as Step 1 in Example 108, except that 1-(N,N-dimethylsulfamoyl)pyrrole-3-boronic acid pinacol ester (491 mg, 1.64 mmol) was used instead of 1-(methylsulfonyl)pyrrole-3-boronic acid pinacol ester. $^1$H-NMR (CDCl$_3$, 400 MHz) δ 8.23-8.19 (m, 1H), 7.83-7.81 (m, 1H), 7.10-7.06 (m, 1H), 6.96-6.93 (m, 1H), 6.26-6.23 (m, 1H), 5.13 (d, 1H), 4.99 (s, 1H), 2.84-2.80 (m, 6H)

Step 2. 3-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrrole-1-sulfonamide The title compound as an off-white solid (22.8 mg) was prepared in the same fashion as Step 2 in Reference Example 12, except that (1s,4s)-4-((2-chloro-5-(1-(difluoromethyl)-1H-pyrazol-3-yl)pyridin-4-yl)amino)-1-methylcyclohexan-1-ol (62.6 mg, 0.18 mmol) prepared in Reference Example 15 and 3-(4-aminopyrimidin-2-yl)-N,N-dimethyl-1H-pyrrole-1-sulfonamide (66 mg, 0.25 mmol) prepared in Step 1 were used instead of 4-((2-chloro-5-(2-(trifluoromethyl)thiazol-4-yl)-4-pyridyl)amino)cyclohexanone and 2-(1-(cyclopropylsulfonyl)-1H-pyrazol-4-yl)pyrimidin-4-amine. $^1$H-NMR (MeOD, 400 MHz) δ 8.42 (d, 1H), 8.31 (s, 1H), 8.09 (d, 1H), 7.87 (t, 2H), 7.37 (s, 1H), 7.29-7.22 (m, 1H), 7.16-7.12 (m, 2H), 7.07-7.04 (q, 1H), 6.81 (d, 1H), 3.59 (s, 1H), 2.83 (s, 5H), 2.22 (d, 1H), 2.05-2.01 (m, 3H), 1.82-1.73 (q, 6H), 1.63-1.56 (q, 4H), 1.31 (s, 5H), 1.27 (d, 2H); MS (ESI) m/z=588.2 (M+H)$^+$

Example 110. 1-Cyclopropyl-4-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol

Step 1. 4-((2-Chloro-5-(1-(difluoromethyl)-1H-pyrazol-3-yl)pyridin-4-yl)amino)-1-cyclopropylcyclohexan-1-ol The title compound as a white solid (352 mg) was prepared in the same fashion as Step 1 in Example 105, except that 4-amino-1-cyclopropylcyclohexanol (313 mg, 2.02 mmol) was used instead of 4-amino-2-methylcyclohexan-1-ol. $^1$H-NMR (CDCl$_3$, 400 MHz) δ 8.36 (s, 1H), 8.25 (d, 1H), 7.87 (d, 1H), 7.32 (d, 1H), 6.84 (d, 1H), 6.59 (s, 1H), 3.77 (d, 1H), 2.04 (t, 4H), 1.76-1.64 (m, 4H), 1.57-1.53 (q, 2H), 1.25 (t, 3H), 0.99-0.87 (d, 1H), 0.39 (d, 4H)

Step 2. 1-Cyclopropyl-4-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol The title compound as an off white solid (5.5 mg) was prepared in the same fashion as Step 2 in Example 1, except that 4-((2-chloro-5-(1-(difluoromethyl)-1H-pyrazol-3-yl)pyridin-4-yl)amino)-1-cyclopropylcyclohexan-1-ol (110 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.71 (s, 1H), 8.67 (d, 1H), 8.44 (t, 2H), 8.22-8.21 (d, 1H), 7.90 (d, 1H), 7.79 (s, 1H), 7.19 (s, 1H), 7.09 (d, 1H), 6.81 (d, 1H), 4.03 (t, 1H), 2.87 (t, 1H), 2.21 (t, 2H), 1.91-1.86 (q, 2H), 1.75-1.68 (m, 2H), 1.61-1.53 (m, 5H), 1.26-1.22 (q, 2H), 0.47 (d, 4H); MS (ESI) m/z=612.2 (M+H)$^+$

Example 111. (1s,4s)-4-((5-(1-(Difluoromethyl)-1H-pyrazol-3-yl)-2-((2-((3R,4S)-3-fluoro-4-methoxypiperidin-1-yl)pyrimidin-4-yl)amino)pyridin-4-yl)amino)-1-methylcyclohexan-1-ol

Step 1. 2-((3R,4S)-3-Fluoro-4-methoxypiperidin-1-yl)pyrimidin-4-amine

To a stirred solution of 2-chloropyrimidine-4-amine (255 mg, 1.5 mmol) in isopropyl alcohol (3 mL) were added (3R,4S)-3-fluoro-4-methoxy-piperidine hydrochloride (255 mg, 1.5 mmol), TEA (0.42 mL, 3 mmol). The mixture was stirred at 130° C. for 1.5 hours. The reaction was quenched with water and extracted in DCM. The organic layer was dried over MgSO$_4$ and concentrated. The crude product was purified by column chromatography (MeOH/DCM=0-10%) to give 2-((3R,4S)-3-Fluoro-4-methoxypiperidin-1-yl)pyrimidin-4-amine (110 mg) as an off-white solid. $^1$H-NMR (CDCl$_3$, 400 MHz) δ 7.89 (d, 1H), 5.74 (d, 1H), 4.81 (brs, 2NH), 4.70-4.47 (m, 1H), 4.23-4.18 (m, 1H), 3.61-3.51 (m, 2H), 3.45 (s, 3H), 3.36 (m, 2H), 1.93-1.88 (m, 1H), 1.79-1.74 (m, 1H); MS (ESI) m/z=227.0 (M+H)$^+$

Step 2. (1s,4s)-4-((5-(1-(Difluoromethyl)-1H-pyrazol-3-yl)-2-((2-((3R,4S)-3-fluoro-4-methoxypiperidin-1-yl)pyrimidin-4-yl)amino)pyridin-4-yl)amino)-1-methylcyclohexan-1-ol The title compound as an off white solid (37 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (94.6 mg, 0.265 mmol) prepared in Reference Example 15 and 2-((3R,4S)-3-fluoro-4-methoxypiperidin-1-yl)pyrimidin-4-amine (50 mg, 0.221 mmol) prepared in Step 1 and were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.31 (s, 1H), 8.05 (d, 2H), 7.94 (d, 1H), 7.83 (s, 1H), 7.21 (t, 1H), 7.14 (s, 1H), 6.78 (s, 1H), 6.39 (d, 1H), 4.82-4.70 (m, 1H), 4.39-4.34 (m, 1H), 4.09-4.06 (m, 1H), 3.92-3.83 (m, 1H), 3.64-3.48 (m, 3H), 3.49 (s, 3H), 1.98-1.92 (m, 3H), 1.78-1.69 (m, 5H), 1.61-1.54 (m, 2H), 1.30 (s, 3H); MS (ESI) m/z=547.2 (M+H)$^+$ Example 112. (1s,4s)-4-((5-(1-(Difluoromethyl)-1H-pyrazol-3-yl)-2-((2-(1-(methylsulfonyl)-1H-pyrazol-4-yl)pyrimidin-4-yl)amino)pyridin-4-yl)amino)-1-methylcyclohexan-1-ol Step 1. 2-(1-(Methylsulfonyl)-1H-pyrazol-4-yl)pyrimidin-4-amine The title compound as an off white solid (210 mg) was prepared in the same fashion as Step 1 in Example 1, except that 2-chloropyrimidine-4-amine (150 mg, 1.16 mmol) and (1-(methylsulfonyl)-4-pyrazolyl)boronic acid (330 mg, 1.74 mmol) were used instead of 5-bromo-2-chloro-4-(2-(1-methylpyrazol-4-yl)ethynyl)pyridine and 1-cyclopropyl-4-(4,4,5,5-tetramethyl-1,3,2-dioxaborolan-2-yl)pyrazole. $^1$H-NMR (CDCl$_3$, 400 MHz) δ 8.66 (s, 1H), 8.41 (s, 1H), 8.25 (d, 1H), 6.33 (d, 1H), 4.95 (brs, 2NH), 3.35 (s, 3H); MS (ESI) m/z=239.8 (M+H)$^+$ Step 2. (1s,4s)-4-((5-(1-(Difluoromethyl)-1H-pyrazol-3-yl)-2-((2-(1-(methylsulfonyl)-1H-pyrazol-4-yl)pyrimidin-4-yl)amino)pyridin-4-yl)amino)-1-methylcyclohexan-1-ol The title compound as an off white solid (11 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (89.4 mg, 0.251 mmol) prepared in Reference Example 15 and 2-(1-(methylsulfonyl)-1H-pyrazol-4-yl)pyrimidin-4-amine (40 mg, 0.167 mmol) prepared in Step 1 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.71 (brs, 1H), 8.35 (d, 1H), 8.30 (s, 1H), 8.18 (s, 1H), 8.10 (s, 1H), 8.03 (m, 1H), 7.86 (s, 1H), 7.35 (s, 1H), 7.22 (t, 1H), 7.07 (s, 1H), 6.80 (s, 1H), 3.96 (s, 3H), 3.58 (m, 1H), 2.05-1.99 (m, 2H), 1.79-1.70 (m, 4H), 1.64-1.57 (m, 2H), 1.32 (s, 3H)

Example 113. (1s,4s)-4-((5-(1-(Difluoromethyl)-1H-pyrazol-3-yl)-2-((2-(6-fluoropyridin-3-yl)pyrimidin-4-yl)amino)pyridin-4-yl)amino)-1-methylcyclohexan-1-ol Step 1. 2-(6-Fluoropyridin-3-yl)pyrimidin-4-amine The title compound as an off white solid (168 mg) was prepared in the same fashion as Step 1 in Example 1, except that 4-amino-2-chloropyrimidine (160 mg, 1.235 mmol) and 6-fluoropyridine-3-boronic acid (261 mg, 1.853 mmol) were used instead of 5-bromo-2-chloro-4-(2-(1-methylpyrazol-4-yl)ethynyl)pyridine and 1-cyclopropyl-4-(4,4,5,5-tetramethyl-1,3,2-dioxaborolan-2-yl)pyrazole. $^1$H-NMR (CDCl$_3$, 400 MHz) δ 9.19 (s, 1H), 8.73 (t, 1H), 8.33 (d, 1H), 6.99 (d, 1H), 6.39 (d, 1H), 5.02 (brs, 2NH); MS (ESI) m/z=190.8 (M+H)$^+$ Step 2. (1s,4s)-4-((5-(1-(Difluoromethyl)-1H-pyrazol-3-yl)-2-((2-(6-fluoropyridin-3-yl)pyrimidin-4-yl)amino)pyridin-4-yl)amino)-1-methylcyclohexan-1-ol The title compound as an off white solid (11 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (94.6 mg, 0.265 mmol) prepared in Reference Example 15 and 2-(6-fluoropyridin-3-yl)pyrimidin-4-amine (30 mg, 0.158 mmol) prepared in Step 1 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 9.24 (s, 1H), 8.79 (t, 1H), 8.47 (d, 1H), 8.38 (s, 1H), 8.02 (brs, 1H), 7.94 (d, 1H), 7.87 (s, 1H), 7.35 (s, 1H), 7.23 (t, 1H), 7.18 (s, 1H), 7.03 (d, 1H), 6.82 (s, 1H), 3.57 (m, 1H), 2.05-2.00 (m, 2H), 1.75-1.65 (m, 4H), 1.63-1.57 (m, 2H), 1.33 (s, 3H); MS (ESI) m/z=511.1 (M+H)$^+$ Example 114. (1s,4s)-4-((5-(1-(Difluoromethyl)-1H-pyrazol-3-yl)-2-((2-(1-((tetrahydrofuran-3-yl)sulfonyl)-1H-pyrazol-4-yl)pyrimidin-4-yl)amino)pyridin-4-yl)amino)-1-methylcyclohexan-1-ol Step 1. 1-((Tetrahydrofuran-3-yl)sulfonyl)-4-(4,4,5,5-tetramethyl-1,3,2-dioxaborolan-2-yl)-1H-pyrazole To a stirred solution of 4-(4,4,5,5-tetramethyl-1,3,2-dioxaborolan-2-yl)-1H-pyrazole (900 mg, 4.64 mmol) in DMF (8.6 mL) were added sodium hydride, 60% in mineral oil (463 mg, 11.6 mmol) and tetrahydrofuran-3-sulfonyl chloride (950 mg, 5.57 mmol). The mixture was stirred at rt for 5 hours. The reaction was quenched with water and extracted in DCM. The organic layer was dried over MgSO$_4$ and concentrated. The crude product was purified by column chromatography (MeOH/DCM=0-10%) to give 1-((tetrahydrofuran-3-yl)sulfonyl)-4-(4,4,5,5-tetramethyl-1,3,2-dioxaborolan-2-yl)-1H-pyrazole (328 mg) as an off-white solid. $^1$H-NMR (CDCl$_3$, 400 MHz) δ 8.32 (s, 1H), 8.11 (s, 1H), 4.25-4.16 (m, 2H), 4.00-3.77 (m, 3H), 2.49-2.41 (m, 1H), 2.28-2.19 (m, 1H), 1.32 (s, 12H)

Step 2. 2-(1-((Tetrahydrofuran-3-yl)sulfonyl)-1H-pyrazol-4-yl)pyrimidin-4-amine

The title compound as an off white solid (210 mg) was prepared in the same fashion as Step 1 in Example 1, except that 2-bromopyrimidine-4-amine (227 mg, 1.31 mmol) and 1-((tetrahydrofuran-3-yl)sulfonyl)-4-(4,4,5,5-tetramethyl-1,3,2-dioxaborolan-2-yl)-1H-pyrazole (330 mg, 1.00 mmol) prepared in Step 1 were used instead of 5-bromo-2-chloro-4-(2-(1-methylpyrazol-4-yl)ethynyl)pyridine and 1-cyclopropyl-4-(4,4,5,5-tetramethyl-1,3,2-dioxaborolan-2-yl)pyrazole. $^1$H-NMR (CDCl$_3$, 400 MHz) δ 8.66 (s, 1H), 8.41 (s, 1H), 8.22 (d, 1H), 6.33 (d, 1H), 5.12 (brs, 2NH), 4.29-4.22 (m, 2H), 4.02-3.78 (m, 3H), 2.53-2.45 (m, 1H), 2.31-2.23 (m, 1H); MS (ESI) m/z=295.9 (M+H)$^+$ Step 3. (1s,4s)-4-((5-(1-(Difluoromethyl)-1H-pyra-
zol-3-yl)-2-((2-(1-((tetrahydrofuran-3-yl)sulfonyl)-
1H-pyrazol-4-yl)pyrimidin-4-yl)amino)pyridin-4-yl)
amino)-1-methylcyclohexan-1-ol The title compound as an off white solid (17.6 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (95 mg, 0.265 mmol) prepared in Reference Example 15 and 2-(1-((tetrahydrofuran-3-yl)sulfonyl)-1H-pyrazol-4-yl)pyrimidin-4-amine (70 mg, 0.237 mmol) prepared in Step 2 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.70 (s, 1H), 8.49 (s, 1H), 8.41 (d, 1H), 8.37 (s, 1H), 8.02 (brd, 1H), 7.87 (s, 1H), 7.32 (brs, 1H), 7.22 (t, 1H), 7.05 (brs, 1H), 6.82 (d, 1H), 4.31-4.25 (m, 2H), 4.05-4.00 (m, 1H), 3.94-3.90 (m, 1H), 3.86-3.82 (m, 1H), 3.53 (m, 1H), 2.04-1.99 (m, 2H), 1.83-1.75 (m, 4H), 1.64-1.57 (m, 2H), 1.32 (s, 3H); MS (ESI) m/z=616.2 (M+H)$^+$ Example 115. (1s,4s)-4-((2-((2-(1-(Cyclopen-
tylsulfonyl)-1H-pyrazol-4-yl)pyrimidin-4-yl)amino)-
5-(1-(difluoromethyl)-1H-pyrazol-3-yl)pyridin-4-yl)
amino)-1-methylcyclohexan-1-ol Step 1. 1-(Cyclopentylsulfonyl)-4-(4,4,5,5-tetram-
ethyl-1,3,2-dioxaborolan-2-yl)-1H-pyrazole The title compound as an off white solid (490 mg) was prepared in the same fashion as Step 1 in Example 114, except that cyclopentanesulfonylchloride (938 mg, 5.57 mmol) was used instead of tetrahydrofuran-3-sulfonyl chloride. $^1$H-NMR (CDCl$_3$, 400 MHz) δ 8.29 (s, 1H), 7.98 (s, 1H), 3.99-3.91 (m, 1H), 2.09-2.03 (m, 2H), 1.95-1.88 (m, 2H), 1.76-1.72 (m, 2H), 1.63-1.58 (m, 2H), 1.31 (s, 12H)

Step 2. 2-(1-(Cyclopentylsulfonyl)-1H-pyrazol-4-yl)
pyrimidin-4-amine

The title compound as an off white solid (46 mg) was prepared in the same fashion as Step 1 in Example 1, except that 2-bromopyrimidine-4-amine (92 mg, 0.526 mmol) and 1-(cyclopentylsulfonyl)-4-(4,4,5,5-tetramethyl-1,3,2-dioxaborolan-2-yl)-1H-pyrazole (143 mg, 0.438 mmol) prepared in Step 1 were used instead of 5-bromo-2-chloro-4-(2-(1-methylpyrazol-4-yl)ethynyl)pyridine and 1-cyclopropyl-4-(4,4,5,5-tetramethyl-1,3,2-dioxaborolan-2-yl)pyrazole. MS (ESI) m/z=294.0 (M+H)$^+$ Step 3. (1s,4s)-4-((2-((2-(1-(Cyclopentylsulfonyl)-
1H-pyrazol-4-yl)pyrimidin-4-yl)amino)-5-(1-(difluo-
romethyl)-1H-pyrazol-3-yl)pyridin-4-yl)amino)-1-
methylcyclohexan-1-ol The title compound as an off white solid (32.5 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (112 mg, 0.314 mmol) prepared in Reference Example 15 and 2-(1-(cyclopentylsulfonyl)-1H-pyrazol-4-yl)pyrimidin-4-amine (46 mg, 0.157 mmol) prepared in Step 2 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine.

$^1$H-NMR (CDCl$_3$, 400 MHz) δ 8.69 (s, 1H), 8.47 (s, 1H), 8.39 (d, 1H), 8.38 (s, 1H), 8.29 (s, 1H), 7.98 (d, 1H), 7.86 (d, 1H), 7.24 (t, 1H), 7.22 (t, 1H), 7.10 (brs, 1H), 6.81 (d, 1H), 4.04-3.98 (m, 1H), 3.55-3.49 (m, 1H), 2.15-2.08 (m, 2H), 2.03-1.94 (m, 4H), 1.82-1.73 (m, 6H), 1.66-1.55 (m, 4H), 1.31 (s, 3H); MS (ESI) m/z=614.2 (M+H)$^+$ Example 116. (1s,4s)-4-((2-((2-(1-Allyl-1H-pyrazol-
4-yl)pyrimidin-4-yl)amino)-5-(1-(difluoromethyl)-
1H-pyrazol-3-yl)pyridin-4-yl)amino)-1-methylcyclo-
hexan-1-ol Step 1.
2-(1-Allyl-1H-pyrazol-4-yl)pyrimidin-4-amine The title compound as an off white solid (110 mg) was prepared in the same fashion as Step 1 in Example 1, except that 2-bromopyrimidine-4-amine (100 mg, 0.575 mmol) and 1-allyl-4-(4,4,5,5-tetramethyl-1,3,2-dioxaborolan-2-yl) pyrazole (135 mg, 0.575 mmol) were used instead of 5-bromo-2-chloro-4-(2-(1-methylpyrazol-4-yl)ethynyl)pyridine and 1-cyclopropyl-4-(4,4,5,5-tetramethyl-1,3,2-dioxaborolan-2-yl)pyrazole. $^1$H-NMR (MeOD, 400 MHz) δ 8.16 (s, 1H), 8.07 (s, 1H), 8.02 (d, 1H), 6.33 (d, 1H), 6.08-6.00 (m, 1H), 5.27-5.17 (m, 2H), 4.78 (d, 1H); MS (ESI) m/z=202.0 (M+H)$^+$ Step 2. (1s,4s)-4-((2-((2-(1-Allyl-1H-pyrazol-4-yl)
pyrimidin-4-yl)amino)-5-(1-(difluoromethyl)-1H-
pyrazol-3-yl)pyridin-4-yl)amino)-1-methylcyclo-
hexan-1-ol The title compound as an off white solid (44.3 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (135.5 mg, 0.38 mmol) prepared in Reference Example 15 and 2-(1-allyl-1H-pyrazol-4-yl)pyrimidin-4-amine (38.2 mg, 0.19 mmol) prepared in Step 1 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.38 (s, 1H), 8.36 (d, 1H), 8.34 (s, 1H), 8.10 (s, 1H), 7.89 (d, 1H), 7.84 (d, 1H), 7.21 (t, 1H), 7.10 (brs, 1H), 6.80 (d, 1H), 6.07-5.99 (m, 1H), 5.30-5.23 (m, 2H), 4.78 (d, 1H), 3.51 (m, 1H), 2.00-1.94 (m, 2H), 1.79-1.71 (m, 4H), 1.60-1.52 (m, 2H), 1.28 (s, 3H); MS (ESI) m/z=522.2 (M+H)$^+$ Example 117. (1s,4s)-4-((2-((2-(1-(But-3-en-1-
ylsulfonyl)-1H-pyrazol-4-yl)pyrimidin-4-yl)amino)-
5-(1-(difluoromethyl)-1H-pyrazol-3-yl)pyridin-4-yl)
amino)-1-methylcyclohexan-1-ol Step 1. 1-(But-3-en-1-ylsulfonyl)-4-(4,4,5,5-tetram-
ethyl-1,3,2-dioxaborolan-2-yl)-1H-pyrazole The title compound as an off white solid (349 mg) was prepared in the same fashion as Step 1 in Example 114, except that but-3-ene-1-sulfonyl chloride (598 mg, 3.87 mmol) was used instead of tetrahydrofuran-3-sulfonyl chloride. $^1$H-NMR (CDCl$_3$, 400 MHz) δ 8.34 (s, 1H), 7.99 (s, 1H), 5.75-5.65 (m, 1H), 5.10-5.00 (m, 2H), 3.69-3.64 (m, 2H), 2.40-2.35 (m, 2H), 1.33 (s, 12H)

Step 2. 2-(1-(But-3-en-1-ylsulfonyl)-1H-pyrazol-4-
yl)pyrimidin-4-amine

The title compound as an off white solid (220 mg) was prepared in the same fashion as Step 1 in Example 1, except that 2-bromopyrimidine-4-amine (160 mg, 0.92 mmol) and 1-(but-3-en-1-ylsulfonyl)-4-(4,4,5,5-tetramethyl-1,3,2-dioxaborolan-2-yl)-1H-pyrazole (373 mg, 1.20 mmol) prepared in Step 1 were used instead of 5-bromo-2-chloro-4-(2-(1-methylpyrazol-4-yl)ethynyl)pyridine and 1-cyclopropyl-4-(4,4,5,5-tetramethyl-1,3,2-dioxaborolan-2-yl)pyrazole. $^{1}$H-NMR (CDCl$_3$, 400 MHz) δ 8.64 (s, 1H), 8.41 (s, 1H), 8.24 (d, 1H), 6.32 (d, 1H), 5.75-5.63 (m, 1H), 5.13-5.06 (m, 2H), 4.99 (brs, 2H), 3.62-3.56 (m, 2H), 2.51-2.42 (m, 2H); MS (ESI) m/z=279.9 (M+H)$^+$ Step 3. (1s,4s)-4-((2-((2-(1-(But-3-en-1-ylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol The title compound as an off white solid (23.4 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (100 mg, 0.279 mmol) prepared in Reference Example 15 and 2-(1-(but-3-en-1-ylsulfonyl)-1H-pyrazol-4-yl)pyrimidin-4-amine (52 mg, 0.186 mmol) prepared in Step 2 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^{1}$H-NMR (CDCl$_3$, 400 MHz) δ 8.69 (s, 1H), 8.49 (s, 1H), 8.39 (d, 1H), 8.38 (s, 1H), 8.37 (s, 1H), 8.03 (brs, 1H), 7.98 (d, 1H), 7.86 (d, 1H), 7.27 (s, 1H), 7.23 (t, 1H), 7.06 (brs, 1H), 6.82 (d, 1H), 5.74-5.67 (m, 1H), 5.74-5.07 (m, 2H), 3.63-3.58 (m, 2H), 3.54 (m, 2H), 2.50-2.44 (m, 2H), 2.03-1.99 (m, 2H), 1.83-1.74 (m, 4H), 1.63-1.56 (m, 2H), 1.32 (s, 3H); MS (ESI) m/z=600.2 (M+H)$^+$ Example 118. (1R,3S)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclopentan-1-ol Step 1. (1R,3S)-3-(((2-Chloro-5-(1-methyl-1H-pyrazol-3-yl)pyridin-4-yl)amino)methyl)cyclopentan-1-ol The title compound as a white solid (136 mg) was prepared in the same fashion as Reference Example 15, except that (1R,3S)-3-(aminomethyl)cyclopentan-1-ol (54 mg, 0.473 mmol) and 2-chloro-4-fluoro-5-(1-methyl-1H-pyrazol-3-yl)pyridine (200 mg, 0.945 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^{1}$H-NMR (CDCl$_3$, 400 MHz) δ 8.31 (s, 2H), 7.40 (d, 1H), 6.60 (d, 1H), 6.55 (s, 1H), 4.41-4.40 (m, 1H), 3.95 (s, 3H), 3.29-3.27 (m, 2H), 2.38-2.33 (m, 1H), 2.26-2.19 (m, 1H), 1.94-1.83 (m, 2H), 1.78-1.66 (m, 1H), 1.49-1.48 (m, 1H), 1.47-1.43 (m, 1H); MS (ESI) m/z=307.1 (M+H)$^+$ Step 2. (1R,3S)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclopentan-1-ol The title compound as a pale yellow solid (23.9 mg) was prepared in the same fashion as Step 2 in Example 1, except that (1R,3S)-3-(((2-chloro-5-(1-methyl-1H-pyrazol-3-yl)pyridin-4-yl)amino)methyl)cyclopentan-1-ol (136 mg, 0.443 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^{1}$H-NMR (CDCl$_3$, 400 MHz) δ 8.67 (s, 1H), 8.50 (s, 1H), 8.39 (d, 1H), 8.33 (s, 1H), 8.25 (t, 1H), 7.41 (s, 1H), 7.40 (s, 1H), 7.19-7.15 (m, 2H), 6.60 (d, 1H), 4.41-4.40 (m, 1H), 3.96 (s, 3H), 3.42-3.39 (m, 2H), 2.85-2.81 (m, 1H), 2.46-2.43 (m, 1H), 2.27-2.24 (m, 1H), 2.23-1.73 (m, 4H), 1.60-1.49 (m, 3H), 1.23-1.21 (m, 2H); MS (ESI) m/z=536.2 (M+H)$^+$ Example 119. (1R,3S)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclopentan-1-ol Step 1. (1R,3S)-3-(((2-Chloro-5-(1-(difluoromethyl)-1H-pyrazol-3-yl)pyridin-4-yl)amino)methyl)cyclopentan-1-ol The title compound as a white solid (150 mg) was prepared in the same fashion as Reference Example 15, except that (1R,3S)-3-(aminomethyl)cyclopentan-1-ol (54 mg, 0.473 mmol) was used instead of (1s,4s)-4-amino-1-methylcyclohexan-1-ol. $^{1}$H-NMR (CDCl$_3$, 400 MHz) δ 8.35 (s, 1H), 8.03 (s, 1H), 7.88 (s, 1H), 7.42 (s, 1H), 7.27 (t, 1H), 6.84 (d, 1H), 6.59 (s, 1H), 4.42 (s, 1H), 3.32-3.29 (m, 2H), 2.39-2.35 (m, 1H), 2.24-2.20 (m, 1H), 1.91-1.63 (m, 5H), 1.49-1.45 (m, 1H); MS (ESI) m/z=343.1 (M+H)$^+$ Step 2. ((1R,3S)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclopentan-1-ol The title compound as a pale yellow solid (24 mg) was prepared in the same fashion as Step 2 in Example 1, except (1R,3S)-3-(((2-chloro-5-(1-(difluoromethyl)-1H-pyrazol-3-yl)pyridin-4-yl)amino)methyl)cyclopentan-1-ol (150 mg, 0.438 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^{1}$H-NMR (CDCl$_3$, 400 MHz) δ 8.67 (s, 1H), 8.50 (s, 1H), 8.42 (d, 1H), 8.37 (s, 1H), 8.00 (t, 1H), 7.87 (d, 1H), 7.44 (s, 1H), 7.24 (t, 1H), 7.17 (s, 1H), 7.14 (d, 1H), 6.84 (d, 1H), 4.34 (brs, 1H), 3.44 (t, 2H), 2.86-2.82 (m, 1H), 2.48-2.45 (m, 1H), 2.28-2.26 (m, 1H), 2.24-2.22 (m, 1H), 1.94-1.93 (m, 1H), 1.87-1.74 (m, 4H), 1.55-1.52 (m, 3H), 1.24-1.21 (m, 2H); MS (ESI) m/z=572.1 (M+H)$^+$ Example 120. (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-methylcyclohexan-1-ol Step 1. 4-(4-Bromothiazol-2-yl)morpholine The reaction mixture of 2,4-dibromothiazole (300 mg, 1.235 mmol), morpholine (0.16 mL, 1.852 mmol), and DIPEA (0.65 mL, 3.705 mmol) in DMA (3 mL) was stirred at 80° C. for 3 hours. The reaction mixture was cooled to room temperature, diluted in EA, washed by water, dried over MgSO$_4$, and then concentrated. The crude product was purified by column chromatography (EA/n-Hex=0-35%) to yield 4-(4-bromothiazol-2-yl)morpholine (562.5 mg) as an off-white solid. $^{1}$H-NMR (CDCl$_3$, 400 MHz) δ 6.47 (s, 1H), 3.82-8.80 (m, 4H), 3.48-3.46 (m, 4H); MS (ESI) m/z=249.0 (M+H)$^+$

Step 2. 4-(4-(6-Chloro-4-fluoropyridin-3-yl)thiazol-2-yl)morpholine

The reaction mixture of 4-(4-bromothiazol-2-yl)morpholine (244 mg, 0.980 mmol) prepared in Step 1, 2-chloro-4-fluoro-5-(4,4,5,5-tetramethyl-1,3,2-dioxaborolan-2-yl)pyridine (252 mg, 0.980 mmol), 3M $K_2CO_3$ soln. (0.98 mL, 2.94 mmol), and [1,1'-bis(diphenylphosphino)ferrocene]dichloropalladium(II) complex with dichloromethane (80 mg, 0.100 mmol) in 1,4-dioxane (3 mL) was stirred at 80° C. for 4 hours. The reaction mixture was cooled to room temperature, concentrated, and extracted with DCM/water. The organic layer was dried with $MgSO_4$, filtered, and concentrated. The crude residue was purified by silica gel column chromatography (EA/n-Hex=0-35%) to 4-(4-(6-chloro-4-fluoropyridin-3-yl)thiazol-2-yl)morpholine (190 mg) as a white solid. $^1$H-NMR (CDCl$_3$, 400 MHz) δ 9.13 (d, 1H), 7.15-7.12 (m, 2H), 3.86 (t, 4H), 3.55 (t, 4H); MS (ESI) m/z=299.9 (M+H)$^+$

Step 3. (1s,4s)-4-((2-Chloro-5-(2-morpholinothiazol-4-yl)pyridin-4-yl)amino)-1-methylcyclohexan-1-ol The title compound as a white solid (121 mg) was prepared in the same fashion as Reference Example 15, except that 4-(4-(6-chloro-4-fluoropyridin-3-yl)thiazol-2-yl)morpholine (100 mg, 0.334 mmol) prepared in Step 2 was used instead of 2-chloro-5-(1-(difluoromethyl)-1H-pyrazol-3-yl)-4-fluoropyridine. $^1$H-NMR (CDCl$_3$, 400 MHz) δ 8.18 (s, 1H), 7.84 (d, 1H), 6.73 (s, 1H), 6.48 (s, 1H), 3.85 (t, 4H), 3.49 (t, 1H), 3.32-3.28 (m, 1H), 1.94-1.90 (m, 2H), 1.76 (s, 3H), 1.66-1.52 (m, 5H), 1.30 (s, 1H); MS (ESI) m/z=409.1 (M+H)$^{+2}$

Step 4. (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-methylcyclohexan-1-ol The title compound as a pale yellow solid (19 mg) was prepared in the same fashion as Step 2 in Example 1, except (1s,4s)-4-((2-chloro-5-(2-morpholinothiazol-4-yl)pyridin-4-yl)amino)-1-methylcyclohexan-1-ol (110.22 mg, 0.27 mmol) prepared in Step 3 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.47 (s, 1H), 8.41 (d, 1H), 8.20 (s, 1H), 7.82 (d, 1H), 7.66 (brs, 1H), 7.53-4.48 (m, 1H), 7.00 (s, 1H), 6.69 (s, 1H), 3.86 (t, 4H), 8.52 (t, 1H), 3.47 (s, 1H), 2.86-2.80 (m, 1H), 2.06-1.98 (m, 2H), 1.76-1.62 (m, 4H), 1.53-1.51 (m, 3H), 1.31 (s, 3H), 1.29-1.19 (m, 3H); MS (ESI) m/z=638.2 (M+H)$^+$

Example 121. (1s,4s)-4-((2-((2-(1-(Cyclopropylsulfonyl)-1H-pyrazol-4-yl)pyrimidin-4-yl)amino)-5-(2-(4-methylpiperazin-1-yl)thiazol-4-yl)pyridin-4-yl)amino)-1-methylcyclohexan-1-ol

Step 1. 4-Bromo-2-(4-methylpiperazin-1-yl)thiazole

The title compound as pale yellow liquid (265 mg) was prepared in the same fashion as Step 1 in Example 120 except 1-methylpiperazine (185 mg, 1.852 mmol) was used instead of morpholine. $^1$H-NMR (CDCl$_3$, 400 MHz) δ 6.42 (s, 1H), 3.50 (t, 4H), 2.50 (t, 4H), 2.34 (s, 3H); MS (ESI) m/z=262.0 (M+H)$^+$

Step 2. 4-(6-Chloro-4-fluoropyridin-3-yl)-2-(4-methylpiperazin-1-yl)thiazole The title compound as a pale yellow solid (185 mg) was prepared in the same fashion as Step 2 in Example 120 except that 4-bromo-2-(4-methylpiperazin-1-yl)thiazole (257 mg, 0.979 mmol) prepared in Step 1 was used instead of 4-(4-bromothiazol-2-yl)morpholine. $^1$H-NMR (CDCl$_3$, 400 MHz) δ 9.13 (d, 1H), 7.20 (d, 1H), 7.10 (t, 1H), 3.59 (t, 4H), 2.56 (t, 4H), 2.38 (s, 3H); MS (ESI) m/z=313.0 (M+H)$^+$

Step 3. (1s,4s)-4-((2-Chloro-5-(2-(4-methylpiperazin-1-yl)thiazol-4-yl)pyridin-4-yl)amino)-1-methylcyclohexan-1-ol The title compound as a beige solid (75 mg) was prepared in the same fashion as Reference Example 15, except 4-(6-chloro-4-fluoropyridin-3-yl)-2-(4-methylpiperazin-1-yl)thiazole (104.35 mg, 0.334 mmol) prepared in Step 2 was used instead of 2-chloro-5-(1-(difluoromethyl)-1H-pyrazol-3-yl)-4-fluoropyridine. $^1$H-NMR (CDCl$_3$, 400 MHz) δ 9.19 (s, 1H), 7.94 (d, 1H), 6.70 (s, 1H), 6.48 (s, 1H), 3.54 (t, 4H), 3.31-3.28 (m, 1H), 2.55 (t, 4H), 2.37 (s, 3H), 1.96-1.92 (m, 2H), 1.77-1.66 (m, 2H), 1.63-1.60 (m, 2H), 1.56-1.53 (m, 2H), 1.30 (s, 3H), 1.27 (s, 1H); MS (ESI) m/z=422.1 (M+H)$^+$

Step 4. (1s,4s)-4-((2-((2-(1-(Cyclopropylsulfonyl)-1H-pyrazol-4-yl)pyrimidin-4-yl)amino)-5-(2-(4-methylpiperazin-1-yl)thiazol-4-yl)pyridin-4-yl)amino)-1-methylcyclohexan-1-ol The title compound as a colorless oil (1 mg) was prepared in the same fashion as Step 2 in Example 1, except (1s,4s)-4-((2-chloro-5-(2-(4-methylpiperazin-1-yl)thiazol-4-yl)pyridin-4-yl)amino)-1-methylcyclohexan-1-ol (75 mg, 0.178 mmol) prepared in Step 3 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.47 (s, 1H), 8.41 (d, 1H), 8.18 (s, 1H), 7.96 (s, 1H), 7.27 (s, 1H), 6.98 (s, 1H), 6.75 (s 1H), 3.56 (t, 4H), 3.53 (s, 1H), 2.86-2.80 (m, 1H), 2.56 (t, 3H), 2.18 (s, 3H), 2.13-1.98 (m, 3H), 1.75-1.63 (m, 5H), 1.54-1.51 (m, 3H), 1.31 (s, 3H), 1.29-1.19 (m, 2H); MS (ESI) m/z=651.3 (M+H)$^+$

Example 122. (1s,4s)-4-((2-((2-(1-(Cyclopropylsulfonyl)-1H-pyrazol-4-yl)pyrimidin-4-yl)amino)-5-(4-(difluoromethyl)thiazol-2-yl)pyridin-4-yl)amino)-1-methylcyclohexan-1-ol

Step 1. 2-(6-Chloro-4-fluoropyridin-3-yl)-4-(difluoromethyl)thiazole

The title compound as a white solid (79 mg) was prepared in the same fashion as Step 2 in Example 120 except that 2-bromo-4-(difluoromethyl)thiazole (125 mg, 0.583 mmol) was used instead of 4-(4-bromothiazol-2-yl)morpholine. $^1$H-NMR (CDCl$_3$, 400 MHz) δ 9.30 (d, 1H), 7.85 (s, 1H), 7.30 (s, 1H), 6.88 (t, 1H); MS (ESI) m/z=264.9 (M+H)$^+$

Step 2. (1s,4s)-4-((2-Chloro-5-(4-(difluoromethyl)thiazol-2-yl)pyridin-4-yl)amino)-1-methylcyclohexan-1-ol The title compound as a white solid (100 mg) was prepared in the same fashion as Reference Example 15, except 2-(6-chloro-4-fluoropyridin-3-yl)-4-(difluoromethyl) thiazole (75 mg, 0.283 mmol) prepared in Step 1 was used instead of 2-chloro-5-(1-(difluoromethyl)-1H-pyrazol-3-yl)-4-fluoropyridine. $^1$H-NMR (CDCl$_3$, 400 MHz) δ 9.02 (d, 1H), 8.49 (s, 1H), 7.55 (s, 1H), 6.77 (t, 1H), 6.62 (s, 1H), 3.42-3.40 (m, 1H), 1.97-1.92 (m, 2H), 1.81-1.62 (m, 4H), 1.59 (s, 1H), 1.32 (s, 3H), 1.18 (s, 1H); MS (ESI) m/z=374.0 (M+H)$^+$ Step 3. (1s,4s)-4-((2-((2-(1-(Cyclopropylsulfonyl)-1H-pyrazol-4-yl)pyrimidin-4-yl)amino)-5-(4-(difluoromethyl)thiazol-2-yl)pyridin-4-yl)amino)-1-methyl-cyclohexan-1-ol The title compound as a pale yellow solid (10 mg) was prepared in the same fashion as Step 2 in Example 1, except (1s,4s)-4-((2-chloro-5-(4-(difluoromethyl)thiazol-2-yl)pyridin-4-yl)amino)-1-methylcyclohexan-1-ol (85 mg, 0.227 mmol) prepared in Step 2 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.72 (brs, 1H), 9.34 (d, 1H), 8.66 (s, 1H), 8.50-8.44 (m, 2H), 8.38 (s, 1H) 7.59 (s, 1H), 7.52 (s, 1H), 7.12 (d, 1H), 6.78 (t, 1H), 3.67 (s, 1H), 2.87-2.81 (m, 1H), 2.06-1.88 (m, 2H) 1.86-1.74 (m, 4H), 1.67-1.60 (m, 2H), 1.56-1.54 (m, 2H), 1.33 (s, 3H), 1.24-1.23 (m, 2H); MS (ESI) m/z=603.2 (M+H)$^+$ Example 123. N$^2$-(2-(1-(Cyclopropylsulfonyl)-1H-pyrazol-4-yl)pyrimidin-4-yl)-5-(4-(difluoromethyl)thiazol-2-yl)-N$^4$-((1s,4s)-4-((2-fluoroethyl)amino)cyclohexyl)pyridine-2,4-diamine Step 1. (1s,4s)-N$^1$-(2-Chloro-5-(4-(difluoromethyl)thiazol-2-yl)pyridin-4-yl)-N$^4$-(2-fluoroethyl)cyclohexane-1,4-diamine The title compound as a white solid (110 mg) was prepared in the same fashion as Reference Example 15, except 2-(6-chloro-4-fluoropyridin-3-yl)-4-(difluoromethyl) thiazole (75 mg, 0.283 mmol) prepared in Step 1 of Example 122 and (1s,4s)-N$^1$-(2-fluoroethyl)cyclohexane-1,4-diamine (54 mg, 0.34 mmol) were used instead of 2-chloro-5-(1-(difluoromethyl)-1H-pyrazol-3-yl)-4-fluoropyridine and (1s,4s)-4-amino-1-methylcyclohexan-1-ol. $^1$H-NMR (CDCl$_3$, 400 MHz) δ 9.30 (d, 1H), 8.49 (s, 1H), 7.55 (s, 1H), 6.81 (t, 1H), 6.63 (s, 1H), 4.62 (d, 1H), 4.56 (d, 1H), 3.77-3.75 (m, 1H), 3.00 (t, 1H), 2.93 (t, 1H), 2.69-2.64 (m, 1H), 1.96-1.84 (m, 4H), 1.77-1.70 (m, 2H), 1.59-1.44 (m, 3H); MS (ESI) m/z=405.0 (M+H)$^+$ Step 2. N$^2$-(2-(1-(Cyclopropylsulfonyl)-1H-pyrazol-4-yl)pyrimidin-4-yl)-5-(4-(difluoromethyl)thiazol-2-yl)-N$^4$-((1s,4s)-4-((2-fluoroethyl)amino)cyclohexyl)pyridine-2,4-diamine The title compound as a pale yellow solid (13 mg) was prepared in the same fashion as Step 2 in Example 1, (1s,4s)-N$^1$-(2-chloro-5-(4-(difluoromethyl)thiazol-2-yl)pyridin-4-yl)-N$^4$-(2-fluoroethyl)cyclohexane-1,4-diamine (110 mg, 0.273 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.35 (d, 1H), 8.66 (s, 1H), 8.48 (d, 1H), 8.44 (d, 1H), 7.54 (d, 1H), 7.48 (s, 1H), 7.38 (s, 1H), 7.08 (d, 1H), 6.81 (t, 1H), 4.62 (d, 1H), 4.50 (d, 1H), 3.96 (s, 1H), 3.01 (t, 1H), 2.94 (t, 1H), 2.86-2.82 (m, 1H), 2.66-2.64 (m, 1H), 2.07-2.03 (m, 2H), 1.92-1.81 (m, 4H), 1.59-1.48 (m, 5H), 1.26-1.23 (m, 2H); MS (ESI) m/z=634.2 (M+H)$^+$ Example 124. N$^2$-(2-(1-(Cyclopropylsulfonyl)-1H-pyrazol-4-yl)pyrimidin-4-yl)-N$^4$-((1s,4s)-4-(dimethylamino)cyclohexyl)-5-(1-methyl-1H-pyrazol-3-yl) pyridine-2,4-diamine Step 1. (1s,4s)-N$^1$-(2-Chloro-5-(1-methyl-1H-pyrazol-3-yl)pyridin-4-yl)-N$^4$,N$^4$-dimethylcyclohexane-1,4-diamine The title compound as a white solid (150 mg) was prepared in the same fashion as Reference Example 15, except that (1s,4s)-N$^1$,N$^1$-dimethylcyclohexane-1,4-diamine (54 mg, 0.473 mmol) and 2-chloro-4-fluoro-5-(1-methyl-1H-pyrazol-3-yl)pyridine (117 mg, 0.473 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.53 (d, 1H), 8.29 (d, 1H), 7.83 (s, 1H), 6.58 (d, 1H), 6.52 (s, 1H), 3.92 (s, 3H), 3.71 (s, 1H), 3.43 (t, 1H), 2.29 (s, 6H), 1.98-1.96 (m, 2H), 1.73-1.68 (m, 2H), 1.65-1.60 (m, 4H); MS (ESI) m/z=334.0 (M+H)$^+$ Step 2. N$^2$-(2-(1-(Cyclopropylsulfonyl)-1H-pyrazol-4-yl)pyrimidin-4-yl)-N$^4$-((1s,4s)-4-(dimethylamino)cyclohexyl)-5-(1-methyl-1H-pyrazol-3-yl)pyridine-2,4-diamine The title compound as a white solid (3 mg) was prepared in the same fashion as Step 2 in Example 1, except (1s,4s)-N$^1$-(2-chloro-5-(1-methyl-1H-pyrazol-3-yl)pyridin-4-yl)-N$^4$,N$^4$-dimethylcyclohexane-1,4-diamine (138 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.59 (s, 1H), 8.54 (s, 2H), 8.45-8.41 (m, 2H), 8.13 (s, 1H), 8.09 (s, 1H) 7.48 (s, 1H), 7.05 (d, 1H), 6.59 (d, 1H) 4.14-4.10 (m, 1H), 4.01 (s, 3H), 3.01-2.88 (m, 1H), 2.87-2.83 (m, 1H), 2.70 (s, 6H), 2.30-2.27 (m, 2H), 2.15-2.05 (m, 2H), 1.98-1.87 (m, 2H), 1.84-1.81 (m, 2H), 1.59-1.53 (m, 2H), 1.31-1.21 (m, 3H); MS (ESI) m/z=563.3 (M+H)$^+$ Example 125. (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-(hydroxymethyl)cyclohexan-1-ol Step 1. (1s,4s)-4-((2-Chloro-5-(2-morpholinothiazol-4-yl)pyridin-4-yl)amino)-1-(hydroxymethyl)cyclohexan-1-ol The title compound as a white solid (78.4 mg) was prepared in the same fashion as Reference Example 15, except that 4-(4-(6-chloro-4-fluoropyridin-3-yl)thiazol-2-yl)morpholine (100 mg, 0.334 mmol) prepared in Step 2 of Example 120 and (1s,4s)-4-amino-1-(hydroxymethyl)cyclohexan-1-ol (52 mg, 0.36 mmol) were used instead of 2-chloro-5-(1-(difluoromethyl)-1H-pyrazol-3-yl)-4-fluoropyridine and (1s,4s)-4-amino-1-methylcyclohexan-1-ol. $^1$H-NMR (CDCl$_3$, 400 MHz) δ 8.20 (s, 1H), 7.89 (d, 1H), 6.75 (s, 1H), 6.49 (s, 1H), 3.86 (t, 4H), 3.52-3.49 (m, 6H), 3.34-3.31 (m, 1H) 2.01-1.97 (m, 2H), 1.84-1.81 (m, 3H), 1.71-1.61 (m, 2H); MS (ESI) m/z=425.0 (M+H)$^+$ Step 2. (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-(hydroxymethyl)cyclohexan-1-ol The title compound as a white solid (1.1 mg) was prepared in the same fashion as Step 2 in Example 1, except (1s,4s)-4-((2-chloro-5-(2-morpholinothiazol-4-yl)pyridin-4-yl)amino)-1-(hydroxymethyl)cyclohexan-1-ol (61 mg, 0.144 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.69 (d, 1H), 8.63 (d, 1H), 8.46-8.43 (m, 1H), 7.96 (s, 1H), 7.84 (s, 1H), 7.07 (d, 1H), 6.72 (s, 1H), 4.15-4.12 (m, 1H), 3.89-3.86 (m, 4H), 3.60-3.50 (m, 6H), 2.95-2.84 (m, 1H), 2.09-2.04 (m, 4H), 1.56-1.46 (m, 6H), 1.44-1.32 (m, 4H); MS (ESI)=654.3 m/z=(M+H)$^+$ Example 126. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-(2-morpholinothiazol-4-yl)pyridine-2,4-diamine Step 1. (1s,4s)-N$^1$-(2-Chloro-5-(2-morpholinothiazol-4-yl)pyridin-4-yl)-N$^4$-(2-fluoroethyl)cyclohexane-1,4-diamine The title compound as a white solid (97 mg) was prepared in the same fashion as Reference Example 15, except that 4-(4-(6-chloro-4-fluoropyridin-3-yl)thiazol-2-yl)morpholine (100 mg, 0.334 mmol) prepared in Step 2 of Example 120 and (1s,4s)-N$^1$-(2-fluoroethyl)cyclohexane-1,4-diamine (48 mg, 0.3 mmol) were used instead of 2-chloro-5-(1-(difluoromethyl)-1H-pyrazol-3-yl)-4-fluoropyridine and (1s,4s)-4-amino-1-methylcyclohexan-1-ol. $^1$H-NMR (CDCl$_3$, 400 MHz) δ 8.15 (s, 1H), 7.79 (d, 1H), 6.71 (s, 1H), 6.48 (s, 1H), 4.60 (t, 1H), 4.46 (t, 1H), 3.85-3.82 (m, 4H), 3.60 (s, 1H), 3.52-3.48 (m, 4H), 2.94-2.89 (m, 1H), 2.94 (t, 1H), 2.87 (t, 1H), 2.68-2.63 (m, 1H), 1.88-1.82 (m, 2H), 1.76-1.67 (m, 4H), 1.52-1.39 (m, 3H); MS (ESI) m/z=440.0 (M+H)$^+$ Step 2. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-(2-morpholinothiazol-4-yl)pyridine-2,4-diamine The title compound as a pale yellow solid (4.6 mg) was prepared in the same fashion as Step 2 in Example 1, except (1s,4s)-N$^1$-(2-chloro-5-(2-morpholinothiazol-4-yl)pyridin-4-yl)-N$^4$-(2-fluoroethyl)cyclohexane-1,4-diamine (63 mg, 0.144 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ $^1$H-NMR (CDCl$_3$, 400 MHz) δ 8.65 (s, 1H), 8.46 (s, 1H), 8.39 (d, 1H), 8.16 (s, 1H), 7.82 (d, 1H), 7.19 (s, 1H), 7.14-7.13 (m, 1H), 6.68 (s, 1H), 4.60 (t, 1H), 4.48 (t, 1H), 3.86-8.84 (m, 4H), 3.76-3.70 (m, 1H), 3.55-3.53 (m, 4H), 3.39 (t, 1H), 3.02 (s, 1H), 2.96-2.90 (m, 1H), 2.89-2.83 (m, 2H), 2.66-2.65 (m, 1H), 2.05-1.97 (m, 3H), 1.81-1.69 (m, 5H), 1.53-1.46 (m, 5H), 1.29-1.21 (m, 6H); MS (ESI) m/z=669.2 (M+H)$^+$ Example 127. 4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-4-methylcyclohexan-1-ol Step 1. 4-(((5-Chloro-2-(1-methyl-1H-pyrazol-3-yl)phenyl)amino)methyl)-4-methylcyclohexan-1-ol The title compound as a white solid (222 mg) was prepared in the same fashion as Reference Example 15, except that 4-(aminomethyl)-4-methyl-cyclohexanol (100 mg, 0.698 mmol) and 2-chloro-4-fluoro-5-(1-methyl-1H-pyrazol-3-yl)pyridine (147.75 mg, 0.698 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.44 (s, 1H), 8.32 (s, 1H), 7.40 (d, 1H), 6.62 (d, 1H), 6.57 (s, 1H), 3.94 (s, 3H), 3.82-8.78 (m, 1H), 3.14 (d, 2H), 1.83-1.80 (m, 4H), 1.66 (s, 3H), 1.61-1.52 (m, 3H), 1.37-1.30 (m, 2H), 1.26 (s, 3H); MS (ESI) m/z=335.0 (M+H)$^+$ Step 2. 4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-4-methylcyclohexan-1-ol The title compound as an off-white solid (26.5 mg) was prepared in the same fashion as Step 2 in Example 1, except 4-(((5-chloro-2-(1-methyl-1H-pyrazol-3-yl)phenyl)amino)methyl)-4-methylcyclohexan-1-ol (110 mg, 0.329 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.53 (s, 1H), 8.39 (d, 1H), 8.34 (s, 1H), 7.42 (s, 1H), 7.41 (s, 1H), 7.18-7.16 (m, 2H), 6.62 (d, 1H) 3.96 (s, 3H), 3.77-3.73 (m, 1H), 3.26 (d, 2H), 2.87-2.83 (m, 1H), 1.88-1.84 (m, 5H), 1.56-1.49 (m, 5H), 1.39-1.36 (m, 4H), 1.34-1.29 (m, 3H) 1.28 (s, 3H); MS (ESI) m/z=564.2 (M+H)$^+$ Example 128. 4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-4-methylcyclohexan-1-ol Step 1. 4-(((5-Chloro-2-(1-(difluoromethyl)-1H-pyrazol-3-yl)phenyl)amino)methyl)-4-methylcyclohexan-1-ol The title compound as a white solid (251 mg) was prepared in the same fashion as Reference Example 15, except that 4-(aminomethyl)-4-methyl-cyclohexanol (100 mg, 0.698 mmol) was used instead of (1s,4s)-4-amino-1-methylcyclohexan-1-ol. $^1$H-NMR (CDCl$_3$, 400 MHz) δ 8.37 (s, 1H), 8.19 (s, 1H), 7.87 (d, Is), 7.27 (t, 1H), 6.85 (d, 1H), 6.61 (s, 1H), 3.87 (s, 1H), 3.13 (d, 2H), 1.89-1.78 (m, 4H), 1.57-1.54 (m, 2H), 1.43 (s, 1H), 1.32-1.31 (m, 1H), 1.07 (s, 3H); MS (ESI) m/z=371.0 (M+H)$^+$ Step 2. 4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-4-methylcyclohexan-1-ol The title compound as an off-white solid (58 mg) was prepared in the same fashion as Step 2 in Example 1, except 4-(((5-chloro-2-(1-(difluoromethyl)-1H-pyrazol-3-yl)phenyl)amino)methyl)-4-methylcyclohexan-1-ol (121.82 mg, 0.329 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.59 (s, 1H), 8.41 (d, 1H), 8.39 (s, 1H), 8.14 (s, 1H), 7.86 (d, 1H), 7.73 (s, 1H), 7.42 (s, 1H), 7.18 (t, 1H), 7.17 (s, 1H), 6.85 (d, 1H), 3.83-3.81 (m, 1H), 3.25 (d, 2H), 2.88-2.81 (m, 2H), 1.93-1.82 (m, 5H), 1.61-1.51 (m, 5H), 1.37-1.15 (m, 6H), 1.13 (s, 3H); MS (ESI) m/z=600.2 (M+H)$^+$

Example 129. N²-(2-(1-(Cyclopropylsulfonyl)-1H-pyrazol-4-yl)pyrimidin-4-yl)-N⁴-(((1r,4r)-4-((2,2-difluoroethyl)amino)cyclohexyl)methyl)-5-(1-methyl-1H-pyrazol-3-yl)pyridine-2,4-diamine

Step 1. 2-Chloro-N-(((1r,4r)-4-((2,2-difluoroethyl)amino)cyclohexyl)methyl)-5-(1-methyl-1H-pyrazol-3-yl)pyridin-4-amine The title compound as a white solid (169 mg) was prepared in the same fashion as Reference Example 15, except that (1r,4r)-4-(aminomethyl)-N-(2,2-difluoroethyl)cyclohexan-1-amine (100 mg, 0.52 mmol) and 2-chloro-4-fluoro-5-(1-methyl-1H-pyrazol-3-yl)pyridine (110.08 mg, 0.52 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.33 (s, 1H), 8.31 (s, 1H), 7.41 (d, 1H), 6.61 (d, 1H), 6.52 (s, 1H), 5.85 (td, 2H), 3.94 (s, 3H), 3.11 (t, 2H), 3.01 (td, 2H), 2.52-2.47 (m, 1H), 2.06 (s, 2H), 2.02-2.00 (m, 2H), 1.69-1.68 (m, 1H), 1.26-1.20 (m, 4H); MS (ESI) m/z=384.0 (M+H)$^+$

Step 2. N²-(2-(1-(Cyclopropylsulfonyl)-1H-pyrazol-4-yl)pyrimidin-4-yl)-N⁴-(((1r,4r)-4-((2,2-difluoroethyl)amino)cyclohexyl)methyl)-5-(1-methyl-1H-pyrazol-3-yl)pyridine-2,4-diamine The title compound as an off-white solid (57.6 mg) was prepared in the same fashion as Step 2 in Example 1, except 2-chloro-N-(((1r,4r)-4-((2,2-difluoroethyl)amino)cyclohexyl)methyl)-5-(1-methyl-1H-pyrazol-3-yl)pyridin-4-amine (165 mg, 0.43 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.41 (d, 1H), 8.34 (s, 1H), 8.30 (s, 1H), 7.42 (s, 1H), 7.41 (s, 1H), 7.31 (d, 1H), 6.96 (s, 1H), 6.60 (d, 1H), 5.86 (tt, 1H), 3.95 (s, 3H), 3.23 (t, 1H), 3.02 (td, 2H), 2.85-2.81 (m, 1H), 2.52 (t, 1H), 2.05-1.67 (t, 4H), 1.76 (s, 1H), 1.55-1.51 (m, 3H), 1.28-1.13 (m, 6H); MS (ESI) m/z=613.3 (M+H)$^+$

Example 130. N²-(2-(1-(Cyclopropylsulfonyl)-1H-pyrazol-4-yl)pyrimidin-4-yl)-N⁴-(((1r,4r)-4-((2,2-difluoroethyl)amino)cyclohexyl)methyl)-5-(1-(difluoromethyl)-1H-pyrazol-3-yl)pyridine-2,4-diamine

Step 1. 2-Chloro-N-(((1r,4r)-4-((2,2-difluoroethyl)amino)cyclohexyl)methyl)-5-(1-(difluoromethyl)-1H-pyrazol-3-yl)pyridin-4-amine The title compound as a white solid (200 mg) was prepared in the same fashion as Reference Example 15, except that (1r,4r)-4-(aminomethyl)-N-(2,2-difluoroethyl)cyclohexan-1-amine (100 mg, 0.52 mmol) was used instead of (1s,4s)-4-amino-1-methylcyclohexan-1-ol. $^1$H-NMR (CDCl$_3$, 400 MHz) δ 8.36 (s, 1H), 8.03 (s, 1H), 7.87 (d, 1H), 7.17 (t, 1H), 6.84 (d, 1H), 6.57 (s, 1H), 5.84 (tt, 1H), 3.15-3.12 (m, 2H), 3.06-2.95 (m, 2H), 2.52-2.49 (m, 1H), 2.06-2.02 (m, 2H), 1.94-1.92 (m, 2H), 1.68-1.50 (m, 3H), 1.26-1.20 (m, 4H); MS (ESI) m/z=384.0 (M+H)$^+$

Step 2. N²-(2-(1-(Cyclopropylsulfonyl)-1H-pyrazol-4-yl)pyrimidin-4-yl)-N⁴-(((1r,4r)-4-((2,2-difluoroethyl)amino)cyclohexyl)methyl)-5-(1-(difluoromethyl)-1H-pyrazol-3-yl)pyridine-2,4-diamine The title compound as an off-white solid (100 mg) was prepared in the same fashion as Step 2 in Example 1, except 2-chloro-N-(((1r,4r)-4-((2,2-difluoroethyl)amino)cyclohexyl)methyl)-5-(1-(difluoromethyl)-1H-pyrazol-3-yl)pyridin-4-amine (180.47 mg, 0.43 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.43 (d, 1H), 8.38 (s, 1H), 7.98 (t, 1H), 7.86 (d, 1H), 7.47 (s, 1H), 7.33-7.31 (m, 1H), 7.18 (t, 1H), 7.02 (s, 1H), 6.84 (d, 1H), 5.83 (tt, 1H), 3.63-3.62 (m, 1H), 3.26-3.23 (m, 2H), 3.05 (td, 2H), 2.85-2.81 (m, 1H), 2.52-2.51 (m, 1H), 2.00-1.98 (m, 4H), 1.75 (s, 1H), 1.54-1.52 (m, 3H), 1.29-1.19 (m, 6H); MS (ESI) m/z=613.3 (M+H)$^+$

Example 131. N²-(2-(1-(Cyclopropylsulfonyl)-1H-pyrazol-4-yl)pyrimidin-4-yl)-N⁴-((4-((2-fluoroethyl)amino)cyclohexyl)methyl)-5-(1-methyl-1H-pyrazol-3-yl)pyridine-2,4-diamine

Step 1. 2-Chloro-N-((4-((2-fluoroethyl)amino)cyclohexyl)methyl)-5-(1-methyl-1H-pyrazol-3-yl)pyridin-4-amine The title compound as a white solid (115 mg) was prepared in the same fashion as Reference Example 15, except that 4-(aminomethyl)-N-(2-fluoroethyl)cyclohexan-1-amine (80 mg, 0.459 mmol) and 2-chloro-4-fluoro-5-(1-methyl-1H-pyrazol-3-yl)pyridine (97 mg, 0.459 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.33 (d, 1H), 8.31 (s, 1H), 7.41 (d, 1H), 6.61 (d, 1H), 6.52 (s, 1H), 4.62 (t, 1H), 4.50 (t, 1H), 3.94 (s, 3H), 3.11 (t, 2H), 2.99 (t, 1H), 2.93 (t, 1H), 2.50-2.49 (m, 1H), 2.04-2.02 (m, 2H), 1.96-1.94 (m, 2H), 1.19-1.14 (m, 4H); MS (ESI) m/z=366.1 (M+H)$^+$

Step 2. N²-(2-(1-(Cyclopropylsulfonyl)-1H-pyrazol-4-yl)pyrimidin-4-yl)-N⁴-((4-((2-fluoroethyl)amino)cyclohexyl)methyl)-5-(1-methyl-1H-pyrazol-3-yl)pyridine-2,4-diamine The title compound as a white solid (75 mg) was prepared in the same fashion as Step 2 in Example 1, except that 2-chloro-N-((4-((2-fluoroethyl)amino)cyclohexyl)methyl)-5-(1-methyl-1H-pyrazol-3-yl)pyridin-4-amine (110 mg, 0.301 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.37 (d, 1H), 8.31 (s, 1H), 8.29 (s, 1H), 7.41 (s, 1H), 7.33 (s, 1H), 7.32 (s, 1H), 6.95 (s, 1H), 6.61 (s, 1H), 4.62 (t, 1H), 4.50 (t, 1H), 3.95 (s, 3H), 3.22 (t, 2H), 3.00 (t, 1H), 2.93 (t, 1H), 2.84-2.82 (m, 1H), 2.01-1.98 (m, 2H), 1.62 (s, 1H), 1.54-1.51 (m, 2H), 1.29-1.16 (m, 8H); MS (ESI) m/z=595.3 (M+H)$^+$

Example 132. N²-(2-(1-(Cyclopropylsulfonyl)-1H-pyrazol-4-yl)pyrimidin-4-yl)-5-(1-(difluoromethyl)-1H-pyrazol-3-yl)-N⁴-((4-((2-fluoroethyl)amino)cyclohexyl)methyl)pyridine-2,4-diamine

Step 1. 2-Chloro-5-(1-(difluoromethyl)-1H-pyrazol-3-yl)-N-((4-((2-fluoroethyl)amino)cyclohexyl)methyl)pyridin-4-amine The title compound as a white solid (165 mg) was prepared in the same fashion as Reference Example 15, except that 4-(aminomethyl)-N-(2-fluoroethyl)cyclohexan- 1-amine (80 mg, 0.459 mmol) was used instead of (1s,4s)-4-amino-1-methylcyclohexan-1-ol. $^1$H-NMR (CDCl$_3$, 400 MHz) δ 8.35 (s, 1H), 8.03 (s, 1H), 7.87 (d, 1H), 7.17 (t, 1H), 6.84 (d, 1H), 6.57 (s, 1H), 4.62 (t, 1H), 4.50 (t, 1H), 3.13 (t, 2H), 3.00 (t, 1H), 2.92 (t, 1H), 2.51-2.49 (m, 1H), 2.50-2.49 (m, 2H), 2.10-1.92 (m, 2H), 1.19-1.14 (m, 4H); MS (ESI) m/z=402.0 (M+H)$^+$

Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((4-((2-fluoroethyl)amino)cyclohexyl)methyl)pyridine-2,4-diamine The title compound as a pale yellow solid (11 mg) was prepared in the same fashion as Step 2 in Example 1, except 2-chloro-5-(1-(difluoromethyl)-1H-pyrazol-3-yl)-N-((4-((2-fluoroethyl)amino)cyclohexyl)methyl)pyridin-4-amine (120.81 mg, 0.301 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.40 (d, 1H), 8.37 (s, 1H), 8.02 (s, 1H), 8.00 (s, 1H), 7.86 (d, 1H), 7.25 (s, 1H), 7.18 (t, 1H), 7.09 (s, 1H), 6.82 (d, 1H), 4.62 (t, 1H), 4.50 (t, 1H), 3.24 (t, 2H), 2.99 (t, 1H), 2.92 (t, 1H), 2.83-2.81 (m, 1H), 2.54-2.47 (m, 1H), 2.02-1.94 (m, 6H), 1.53-1.51 (m, 2H), 1.27-1.15 (m, 7H); MS (ESI) m/z=631.3 (M+H)$^+$

Example 133. 2-((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol

Step 1. 2-((1r,4r)-4-((2-Chloro-5-(1-difluoromethyl-1H-pyrazol-3-yl)pyridin-4-yl)amino)cyclohexyl)ethan-1-ol The title compound as a white solid (150 mg) was prepared in the same fashion as Reference Example 15, except that 2-((1r,4r)-4-aminocyclohexyl)ethan-1-ol hydrochloride (100 mg, 0.557 mmol) was used instead of (1s,4s)-4-amino-1-methylcyclohexan-1-ol. $^1$H-NMR (CDCl$_3$, 400 MHz) δ; MS (ESI) m/z=371.0 (M+H)$^+$

Step 2. 2-((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol The title compound as white solid (40 mg) was prepared in the same fashion as Step 2 in Example 1, except 2-((1r,4r)-4-((2-chloro-5-(1-difluoromethyl-1H-pyrazol-3-yl)pyridin-4-yl)amino)cyclohexyl)ethan-1-ol (97 mg, 0.263 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.48 (s, 1H), 8.42 (d, 1H), 8.36 (s, 1H), 7.86 (s, 2H), 7.57 (s, 1H), 7.35 (s, 1H), 7.20 (t, 1H), 6.95 (s, 1H), 6.82 (s, 1H), 3.73-3.71 (m, 2H), 3.46-3.45 (m, 1H), 2.86-2.83 (m, 1H), 2.26-2.23 (m, 2H), 1.90-1.87 (m, 2H), 1.54-1.44 (m, 4H), 1.40-1.34 (m, 3H), 1.30-1.24 (m, 5H); MS (ESI) m/z=600.2 (M+H)$^+$

Example 134. 2-((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol

Step 1. 2-((1r,4r)-4-((2-Chloro-5-(1-methyl-1H-pyrazol-3-yl)pyridin-4-yl)amino)cyclohexyl)ethan-1-ol The title compound as a white solid (136 mg) was prepared in the same fashion as Reference Example 15, except that 2-((1r,4r)-4-aminocyclohexyl)ethan-1-ol hydrochloride (100 mg, 0.557 mmol) and 2-chloro-4-fluoro-5-(1-methyl-1H-pyrazol-3-yl)pyridine (138 mg, 0.557 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.30 (s, 1H), 8.19 (d, 1H), 7.39 (s, 1H), 6.59 (s, 1H), 6.53 (s, 1H), 3.94 (s, 3H), 3.73 (d, 2H), 3.33-3.32 (m, 1H), 2.19 (d, 2H), 1.90 (d, 2H), 1.59-1.55 (m, 3H), 1.37-1.26 (m, 4H), 1.20-1.14 (m, 3H); MS (ESI) m/z=335.0 (M+H)$^+$

Step 2. 2-((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol The title compound as a white solid (17.6 mg) was prepared in the same fashion as Step 2 in Example 1, except that 2-((1r,4r)-4-((2-chloro-5-(1-methyl-1H-pyrazol-3-yl)pyridin-4-yl)amino)cyclohexyl)ethan-1-ol (88 mg, 0.263 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.49 (s, 1H), 8.40 (d, 1H), 8.32 (s, 1H), 8.18 (d, 1H), 7.40 (s, 1H), 7.38 (s, 1H), 7.37 (s, 1H), 6.89 (s, 1H), 6.58 (d, 1H), 3.95 (s, 3H), 3.75-3.71 (m, 2H), 3.45-3.43 (m, 1H), 2.86-2.82 (m, 2H), 2.26-2.23 (m, 2H), 1.90-1.87 (m, 2H), 1.57-1.38 (m, 5H), 1.34-1.29 (m, 3H), 1.26-1.18 (m, 4H); MS (ESI) m/z=564.2 (M+H)$^+$

Example 135. 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol

Step 1. 2-((1s,4s)-4-((2-Chloro-5-(1-(difluoromethyl)-1H-pyrazol-3-yl)pyridin-4-yl)amino)cyclohexyl)ethan-1-ol The title compound as a white solid (172 mg) was prepared in the same fashion as Reference Example 15, except that 2-((1s,4s)-4-aminocyclohexyl)ethan-1-ol (70 mg, 0.489 mmol) was used instead of (1s,4s)-4-amino-1-methylcyclohexan-1-ol. $^1$H-NMR (CDCl$_3$, 400 MHz) δ 8.36 (s, 1H), 8.30 (d, 1H), 7.87 (s, 1H), 7.19 (t, 1H), 6.84 (s, 1H), 6.59 (s, 1H), 3.82 (s, 1H), 3.73 (t, 2H), 1.90-1.87 (m, 2H), 1.72-1.62 (m, 5H), 1.58-1.39 (m, 2H), 1.39-1.26 (m, 2H); MS (ESI) m/z=371.0 (M+H)$^+$

Step 2. 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol The title compound as a white solid (65 mg) was prepared in the same fashion as Step 2 in Example 1, except 2-((1s, 4s)-4-((2-chloro-5-(1-(difluoromethyl)-1H-pyrazol-3-yl)pyridin-4-yl)amino)cyclohexyl)ethan-1-ol (138 mg, 0373 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.41 (d, 1H), 8.38 (s, 1H), 8.32 (d, 1H), 7.87 (s, 1H), 7.60 (s, 1H), 7.20 (t, 1H), 7.14 (d, 1H), 6.85 (s, 1H), 4.00 (s, 1H), 3.74 (t, 2H), 2.84-2.83 (m, 1H), 2.05-1.99 (m, 2H), 1.84-1.77 (m, 2H), 1.73-1.70 (m, 2H), 1.55-1.47 (m, 4H), 1.39-1.33 (m, 3H), 1.24-1.17 (m, 3H); MS (ESI) m/z=600.2 (M+H)$^+$ Example 136. 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol Step 1. 2-((1s,4s)-4-((2-Chloro-5-(1-methyl-1H-pyrazol-3-yl)pyridin-4-yl)amino)cyclohexyl)ethan-1-ol The title compound as a white solid (48 mg) was prepared in the same fashion as Reference Example 15, except that 2-((1s,4s)-4-aminocyclohexyl)ethan-1-ol (70 mg, 0.489 mmol) and 2-chloro-4-fluoro-5-(1-methyl-1H-pyrazol-3-yl)pyridine (103 mg, 0.489 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.61 (d, 1H), 8.32 (s, 1H), 7.41 (s, 1H), 6.61 (s, 1H), 6.54 (s, 1H), 3.95 (s, 3H), 3.79 (s, 1H), 3.73 (t, 2H), 1.90-1.87 (m, 2H), 1.71-1.64 (m, 4H), 1.58-1.55 (m, 3H), 1.40-1.35 (m, 2H); MS (ESI) m/z=335.0 (M+H)$^+$ Step 2. 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol The title compound as a pale yellow solid (47 mg) was prepared in the same fashion as Step 2 in Example 1, except that 2-((1s,4s)-4-((2-chloro-5-(1-methyl-1H-pyrazol-3-yl)pyridin-4-yl)amino)cyclohexyl)ethan-1-ol (125 mg, 0.373 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65-8.63 (m, 2H), 8.46 (s, 1H), 8.38 (d, 1H), 8.34 (s, 1H), 7.70 (s, 1H), 7.42 (s, 1H), 7.22 (s, 1H), 7.14 (s, 1H), 6.61 (s, 1H), 4.14-4.12 (m, 1H), 3.96 (s, 3H), 3.75 (t, 2H), 2.84 (s, 1H), 2.02-1.99 (m, 2H), 1.82-1.69 (m, 4H), 1.59-1.53 (m, 4H), 1.44-1.39 (m, 2H), 1.36-1.29 (m, 5H); MS (ESI) m/z=564.2 (M+H)$^+$ Example 137. (1s,4s)-4-((5-(1-(Difluoromethyl)-1H-pyrazol-3-yl)-2-((2-(1-(2,2,2-trifluoroethyl)-1H-pyrazol-4-yl)pyrimidin-4-yl)amino)pyridin-4-yl)amino)-1-methylcyclohexan-1-ol The title compound as a white solid (44.7 mg) was prepared in the same fashion as Step 2 in Example 1, except that 2-(1-(2,2,2-trifluoroethyl)-1H-pyrazol-4-yl)pyrimidin-4-amine (53 mg, 0.219 mmol) prepared in Reference Example 37 and (1s,4s)-4-((2-chloro-5-(1-(difluoromethyl)-1H-pyrazol-3-yl)pyridin-4-yl)amino)-1-methylcyclohexan-1-ol (65 mg, 0.182 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.77 (s, 1H), 8.39 (d, 2H), 8.31 (d, 1H), 8.21 (d, 1H), 8.15 (s, 1H), 7.96 (d, 1H), 7.73 (t, 1H), 7.31 (s, 2H), 7.03 (d, 1H), 5.16-5.09 (m, 2H), 1.94-1.79 (m, 3H), 1.59-1.56 (m, 4H), 1.41-1.38 (m, 3H), 1.09 (s, 3H); MS (ESI) m/z=564.2 (M+H)$^+$ Example 138. (1s,4s)-4-((5-(1-(Difluoromethyl)-1H-pyrazol-3-yl)-2-((2-(1-(2-methoxyethyl)-1H-pyrazol-4-yl)pyrimidin-4-yl)amino)pyridin-4-yl)amino)-1-methylcyclohexan-1-ol Step 1. 2-(1-(2-Methoxyethyl)-1H-pyrazol-4-yl)pyrimidin-4-amine The title compound as an off white solid (109 mg) was prepared in the same fashion as Reference Example 36, except that 1-(2-methoxyethyl)-4-(4,4,5,5-tetramethyl-1,3,2-dioxaborolan-2-yl)pyrazole (239.08 mg, 0.948 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.22 (d, 1H), 8.13 (d, 2H), 6.23 (d, 1H), 4.82 (s, 2H), 4.33 (t, 2H), 3.78 (t, 2H), 3.35 (s, 3H); MS (ESI) m/z=219.9 (M+H)$^+$ Step 2. (1s,4s)-4-((5-(1-(Difluoromethyl)-1H-pyrazol-3-yl)-2-((2-(1-(2-methoxyethyl)-1H-pyrazol-4-yl)pyrimidin-4-yl)amino)pyridin-4-yl)amino)-1-methylcyclohexan-1-ol The title compound as a white solid (5.4 mg) was prepared in the same fashion as Step 2 in Example 1, except that 2-(1-(2-methoxyethyl)-1H-pyrazol-4-yl)pyrimidin-4-amine (96 mg, 0.437 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (120 mg, 0.36 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.38-8.37 (m, 2H), 8.21 (s, 1H), 8.17 (s, 1H), 7.90 (d, 1H), 7.85 (d, 1H), 7.70 (s, 1H), 7.22 (t, 1H), 7.18 (d, 1H), 7.08 (s, 1H), 6.82 (d, 1H), 4.34 (t, 2H), 3.79 (t, 2H), 3.55 (s, 1H), 3.50 (s, 1H), 3.35 (s, 3H), 2.02-1.99 (m, 2H), 1.80-1.75 (m, 3H), 1.64-1.58 (m, 4H), 1.32 (s, 3H); MS (ESI) m/z=540.2 (M+H)$^+$ Example 139. (1s,4s)-4-((5-(1-(Difluoromethyl)-1H-pyrazol-3-yl)-2-((2-(1-methyl-1H-pyrazol-4-yl)pyrimidin-4-yl)amino)pyridin-4-yl)amino)-1-methylcyclohexan-1-ol Step 1. 2-(1-Methyl-1H-pyrazol-4-yl)pyrimidin-4-amine The title compound as an off solid (30 mg) was prepared in the same fashion as Reference Example 36, except 1-methyl-4-(4,4,5,5-tetramethyl-1,3,2-dioxaborolan-2-yl)-1H-pyrazole (197 mg, 0.948 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.22 (d, 1H), 8.10 (s, 1H), 8.01 (s, 1H), 6.24 (d, 1H), 7.80 (s, 2H), 3.95 (s, 3H); MS (ESI) m/z=175.9 (M+H)$^+$ Step 2. (1s,4s)-4-((5-(1-(Difluoromethyl)-1H-pyrazol-3-yl)-2-((2-(1-methyl-1H-pyrazol-4-yl)pyrimidin-4-yl)amino)pyridin-4-yl)amino)-1-methylcyclohexan-1-ol The title compound as a white solid (39 mg) was prepared in the same fashion as Step 2 in Example 1, except 2-(1-methyl-1H-pyrazol-4-yl)pyrimidin-4-amine (27 mg, 0.154 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (55 mg, 0.154 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.63 (s, 1H), 8.48 (s, 1H), 8.33-8.31 (m, 2H), 8.31 (s, 1H), 8.01 (s, 1H), 7.95 (d, 1H), 7.87 (s, 1H), 7.73 (t, 1H), 7.40 (s, 1H), 7.37 (s, 1H), 7.13 (d, 1H), 4.15 (s, 1H), 3.90 (s, 3H), 3.48-3.46 (m, 1H), 1.87-1.84 (m, 2H), 1.68-1.59 (m, 4H), 1.45-1.39 (m, 2H), 1.14 (s, 3H); MS (ESI) m/z=496.1 (M+H)$^+$ Example 140. (1s,4s)-4-((2-((2-(1-Cyclopropyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol Step 1.
2-(1-Cyclopropyl-1H-pyrazol-4-yl)pyrimidin-4-amine The title compound as a colorless oil (61.4 mg) was prepared in the same fashion as Reference Example 36, except 1-cyclopropyl-4-(4,4,5,5-tetramethyl-1,3,2-dioxaborolan-2-yl)-1H-pyrazole (242 mg, 1.034 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.22 (d, 1H), 8.09 (s, 2H), 6.24 (d, 1H), 4.82 (s, 2H), 3.66-3.64 (m, 1H), 1.17-1.15 (m, 2H), 1.06-1.04 (m, 2H); MS (ESI) m/z=201.9 (M+H)$^+$ Step 2. (1s,4s)-4-((2-((2-(1-Cyclopropyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol The title compound as a white solid (68.4 mg) was prepared in the same fashion as Step 2 in Example 1, except that 2-(1-cyclopropyl-1H-pyrazol-4-yl)pyrimidin-4-amine (46 mg, 0.23 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (82 mg, 0.23 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.83 (s, 1H), 8.48 (s, 1H), 8.33-8.31 (m, 3H), 8.01 (s, 1H), 7.95 (d, 1H), 7.87 (t, 1H), 7.41 (s, 1H), 7.36 (s, 1H), 7.13 (s, 1H), 4.15 (s, 1H), 3.85-3.80 (m, 1H), 3.47-3.46 (m, 1H), 1.90-1.84 (m, 2H), 1.68-1.59 (m, 4H), 1.45-1.40 (m, 2H), 1.23 (s, 2H), 1.17 (s, 3H), 1.14 (s, 2H), 1.11-1.01 (m, 2H); MS (ESI) m/z=522.1 (M+H)$^+$ Example 141. (1s,4s)-4-((2-((2-(1-Cyclopropylmethyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol Step 1. 2-(1-(Cyclopropylmethyl)-1H-pyrazol-4-yl)pyrimidin-4-amine The title compound as a colorless oil (54.6 mg) was prepared in the same fashion as Reference Example 36, except 1-cyclopropylmethyl-1H-pyrazole-4-boronic acid pinacol ester (257 mg, 1.034 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.23 (d, 1H), 8.17 (s, 1H), 8.13 (s, 1H), 6.24 (d, 1H), 4.83 (s, 2H), 4.02 (d, 2H), 1.37-1.31 (m, 1H), 0.70-0.68 (m, 2H), 0.42-0.41 (m, 2H); MS (ESI) m/z=215.9 (M+H)$^+$ Step 2. (1s,4s)-4-((2-((2-(1-(Cyclopropylmethyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol The title compound as a white solid (45.6 mg) was prepared in the same fashion as Step 2 in Example 1, except that 2-(1-(cyclopropylmethyl)-1H-pyrazol-4-yl)pyrimidin-4-amine (49 mg, 0.23 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (82 mg, 0.23 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.83 (s, 1H), 8.49 (s, 1H), 8.34-8.31 (m, 3H), 8.04 (s, 1H), 7.94 (d, 1H), 7.87 (t, 1H), 7.43 (s, 1H), 7.35 (s, 1H), 7.13 (s, 1H), 4.15 (s, 1H), 4.03 (d, 2H), 3.46 (s, 1H), 1.86-1.84 (m, 2H), 1.69-1.59 (m, 4H), 1.47-1.41 (m, 2H), 1.30-1.27 (m, 1H), 1.14 (s, 3H), 0.55-0.54 (m, 2H), 0.40-0.39 (m, 2H); MS (ESI) m/z=536.3 (M+H)$^+$ Example 142. (1s,4s)-4-((5-(1-(Difluoromethyl)-1H-pyrazol-3-yl)-2-((2-(1-(2-hydroxy-2-methylpropyl)-1H-pyrazol-4-yl)pyrimidin-4-yl)amino)pyridin-4-yl)amino)-1-methylcyclohexan-1-ol Step 1. 1-(4-(4-Aminopyrimidin-2-yl)-1H-pyrazol-1-yl)-2-methylpropan-2-ol The title compound as a colorless oil (37 mg) was prepared in the same fashion as Reference Example 36, except 2-methyl-1-(4-(4,4,5,5-tetramethyl-1,3,2-dioxaborolan-2-yl)-1H-pyrazol-1-yl)propan-2-ol (298 mg, 1.121 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.23 (d, 1H), 8.17 (s, 1H), 8.07 (s, 1H), 6.25 (d, 1H), 4.82 (s, 2H), 4.11 (s, 2H), 3.83 (s, 1H), 3.50 (s, 2H), 1.20 (s, 6H); MS (ESI) m/z=233.9 (M+H)$^+$ Step 2. (1s,4s)-4-((5-(1-(Difluoromethyl)-1H-pyrazol-3-yl)-2-((2-(1-(2-hydroxy-2-methylpropyl)-1H-pyrazol-4-yl)pyrimidin-4-yl)amino)pyridin-4-yl)amino)-1-methylcyclohexan-1-ol The title compound as a white solid (19.3 mg) was prepared in the same fashion as Step 2 in Example 1, except 1-(4-(4-aminopyrimidin-2-yl)-1H-pyrazol-1-yl)-2-methylpropan-2-ol (21 mg, 0.09 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (32 mg, 0.09 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.39-8.36 (m, 2H), 8.26 (s, 1H), 8.13 (s, 1H), 7.92 (d, 1H), 7.86 (s, 1H), 7.47 (s, 1H), 7.22 (t, 1H), 7.16 (d, 1H), 7.13 (s, 1H), 6.82 (s, 1H), 4.13 (s, 3H), 3.90 (s, 1H), 3.57 (s, 1H), 2.05-2.01 (m, 2H), 1.79-1.74 (m, 5H), 1.33 (s, 1H), 1.28-1.25 (m, 2H), 1.22 (s, 6H); MS (ESI) m/z=554.2 (M+H)+

Example 143. (1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl) amino)-1-methylcyclohexan-1-ol The title compound as a white solid (34.6 mg) was prepared in the same fashion as Step 2 in Example 1, except 2-(1-(2,2-difluoroethyl)-1H-pyrazol-4-yl)pyrimidin-4-amine (32 mg, 0.142 mmol) prepared in Reference Example 36 and (1s,4s)-4-((2-chloro-5-(1-(difluoromethyl)-1H-pyrazol-3-yl)pyridin-4-yl)amino)-1-methylcyclohexan-1-ol (56 mg, 0.156 mmol) prepared in Reference Example 15 were used instead of 2-(1-(cyclopropylsulfonyl)-1H-pyrazol-4-yl) pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.40-8.38 (m, 2H), 8.26 (s, 1H), 8.17 (s, 1H), 7.91 (d, 1H), 7.86 (s, 1H), 7.37 (s, 1H), 7.22 (t, 1H), 6.99 (s, 1H), 6.83 (s, 1H), 6.15 (tt, 1H), 4.52 (td, 2H), 3.55-3.54 (m, 1H), 2.02-2.00 (m, 2H), 1.79-1.74 (m, 4H), 1.64-1.61 (m, 2H), 1.32 (s, 3H), 1.17 (s, 1H); MS (ESI) m/z=546.2 (M+H)+

Example 144. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-isopropylpyridine-2,4-diamine Step 1. 2-Chloro-5-(1-(difluoromethyl)-1H-pyrazol-3-yl)-N-isopropylpyridin-4-amine The title compound as a white solid (52 mg) was prepared in the same fashion as Reference Example 2, except that 2-chloro-5-iodo-N-isopropylpyridin-4-amine (10 mg, 0.438 mmol) prepared in Step 1 of Example 92 was used instead of 2-chloro-4-fluoro-5-iodopyridine. $^1$H-NMR (CDCl$_3$, 400 MHz) δ 8.32 (s, 1H), 7.88 (s, 1H), 7.87-7.82 (m, 1H), 7.20 (t, 1H), 6.83 (d, 1H), 6.58 (s, 1H), 1.34 (s, 3H), 1.32 (s, 3H); MS (ESI) m/z=287.0 (M+H)+

Step 2. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-isopropylpyridine-2,4-diamine The title compound as a white solid (28 mg) was prepared in the same fashion as Step 2 in Example 1, except that 2-chloro-5-(1-(difluoromethyl)-1H-pyrazol-3-yl)-N-isopropylpyridin-4-amine (50 mg, 0.174 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.42 (d, 1H), 8.36 (s, 1H), 7.87 (d, 1H), 7.83 (d, 1H), 7.46 (s, 1H), 7.24 (s, 1H), 7.22 (t, 1H), 7.16 (d, 1H), 6.83 (d, 1H), 3.92-3.87 (m, 1H), 2.86-2.81 (m, 1H), 1.52-1.50-(m, 2H), 1.42 (s, 3H), 1.41 (s, 3H), 1.26-1.22 (m, 2H); MS (ESI) m/z=516.1 (M+H)+

Example 145. (1s,4s)-4-((5-(1-(Difluoromethyl)-1H-pyrazol-3-yl)-2-((2-(1-(2-fluoroethyl)-1H-pyrazol-4-yl)pyrimidin-4-yl)amino)pyridin-4-yl)amino)-1-methylcyclohexan-1-ol Step 1. 2-(1-(2-Fluoroethyl)-1H-pyrazol-4-yl)pyrimidin-4-amine The title compound as an off white solid (45.9 mg) was prepared in the same fashion as Reference Example 36, except 1-(2-fluoroethyl)-4-(4,4,5,5-tetramethyl-1,3,2-dioxaborolan-2-yl)pyrazole (150 mg, 0.625 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.23 (d, 1H), 8.15 (d, 2H), 7.25 (d, 1H), 4.86 (t, 1H), 4.83 (s, 2H), 4.75 (t, 1H), 4.49 (t, 1H), 4.43 (t, 1H); MS (ESI) m/z=207.9 (M+H)+

Step 2. (1s,4s)-4-((5-(1-(Difluoromethyl)-1H-pyrazol-3-yl)-2-((2-(1-(2-fluoroethyl)-1H-pyrazol-4-yl) pyrimidin-4-yl)amino)pyridin-4-yl)amino)-1-methylcyclohexan-1-ol The title compound as a white solid (34 mg) was prepared in the same fashion as Step 2 in Example 1, except 2-(1-(2-fluoroethyl)-1H-pyrazol-4-yl)pyrimidin-4-amine (22 mg, 0.106 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (42 mg, 0.117 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.39 (d, 1H), 8.33 (s, 1H), 8.25 (s, 1H), 8.19 (s, 1H), 7.98 (d, 1H), 7.93 (s, 1H), 7.86 (d, 1H), 7.22 (t, 1H), 7.18 (s, 1H), 6.82 (d, 1H), 4.88 (t, 1H), 4.76 (t, 1H), 4.51 (t, 1H), 4.45 (t, 1H), 3.58 (s, 1H), 2.06-2.01 (m, 3H), 1.83-1.76 (m, 5H), 1.67-1.59 (m, 3H), 1.32 (s, 3H); MS (ESI) m/z=528.2 (M+H)+

Example 146. 2-((1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl) amino)cyclohexyl)ethan-1-ol The title compound as a white solid (30 mg) was prepared in the same fashion as Step 2 in Example 1, except 2-(1-(2,2-difluoroethyl)-1H-pyrazol-4-yl)pyrimidin-4-amine (30 mg, 0.133 mmol) prepared in Reference Example 36 and 2-((1s,4s)-4-((2-chloro-5-(1-(difluoromethyl)-1H-pyrazol-3-yl)pyridin-4-yl)amino)cyclohexyl)ethan-1-ol (54 mg, 0.147 mmol) in Step 1 of Example 135 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.89 (s, 1H), 8.51 (s, 1H), 8.42 (d, 1H), 8.35 (s, 1H), 8.33 (d, 1H), 8.30 (d, 1H), 8.07 (s, 1H), 7.82 (t, 1H), 7.42-7.38 (m, 2H), 7.13 (s, 1H), 6.43 (tt, 1H), 4.73 (td, 2H), 4.32 (t, 1H), 3.94 (s, 1H), 3.45 (t, 2H), 1.87-1.84 (m, 2H), 1.69-1.59 (m, 4H), 1.52 (s, 1H), 1.39-1.36 (m, 2H), 1.34-1.25 (m, 3H); MS (ESI) m/z=560.2 (M+H)+

Example 147. 2-((1r,4r)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl) amino)cyclohexyl)ethan-1-ol The title compound as a white solid (20 mg) was prepared in the same fashion as Step 2 in Example 1, except 2-(1-(2,2-difluoroethyl)-1H-pyrazol-4-yl)pyrimidin-4-amine (30 mg, 0.133 mmol) prepared in Reference Example 36 and 2-((1r,4r)-4-((2-chloro-5-(1-difluoromethyl-1H-pyrazol-3-yl)pyridin-4-yl)amino)cyclohexyl)ethan-1-ol (54 mg, 0.146 mmol) in Step 1 of Example 133 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.86 (s, 1H), 8.49 (s, 1H), 8.36 (d, 2H), 8.31 (d, 1H), 8.10 (s, 1H), 7.93 (d, 1H), 7.87 (t, 1H), 7.53 (s, 1H), 7.24 (s, 1H), 7.13 (d, 1H), 6.40 (tt, 1H), 4.72 (td, 2H), 4.32 (t, 1H), 3.46-3.35 (m, 3H), 2.16-2.13 (m, 2H), 1.90-1.77 (m, 2H), 1.44-1.34 (m, 3H), 1.26-1.20 (m, 3H), 1.12-1.06 (m, 2H); MS (ESI) m/z=560.2 (M+H)$^+$ Example 148. 2-((1s,4s)-4-((2-((2-(1-(2,2-Difluoro-ethyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol The title compound as a white solid (12 mg) was prepared in the same fashion as Step 2 in Example 1, except 2-(1-(2,2-difluoroethyl)-1H-pyrazol-4-yl)pyrimidin-4-amine (30 mg, 0.133 mmol) prepared in Reference Example 36 and 2-((1s,4s)-4-((2-chloro-5-(1-(difluoromethyl)-1H-pyrazol-3-yl)pyridin-4-yl)amino)cyclohexyl)propan-2-ol (51 mg, 0.133 mmol) in Step 1 of Example 8 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.39-8.34 (m, 3H), 8.24 (s, 1H), 8.18 (s, 1H), 7.86 (d, 1H), 7.38 (s, 1H), 7.25 (t, 1H), 7.24 (s, 1H), 7.12 (d, 1H), 6.84 (d, 1H), 6.16 (tt, 1H), 4.54 (td, 2H), 4.04 (s, 1H), 2.14-2.11 (m, 2H), 1.83-1.80 (m, 2H), 1.72-1.68 (m, 2H), 1.49-1.45 (m, 3H), 1.23 (s, 6H); MS (ESI) m/z=574.2 (M+H)$^+$ Example 149. (1s,4s)-4-((5-(1-(Difluoromethyl)-1H-pyrazol-3-yl)-2-((2-(1-(difluoromethyl)-1H-pyrazol-4-yl)pyrimidin-4-yl)amino)pyridin-4-yl)amino)-1-methylcyclohexan-1-ol Step 1. 2-(1-(Difluoromethyl)-1H-pyrazol-4-yl)pyrimidin-4-amine The title compound as an off white solid (94.9 mg) was prepared in the same fashion as Reference Example 36, except 1-(difluoromethyl)pyrazole-4-boronic acid pinacol ester (210 mg, 0.862 mmol) was used instead of (1-(2,2,2-trifluoroethyl)-1H-pyrazol-4-yl)boronic acid. $^1$H-NMR (CDCl$_3$, 400 MHz) δ 8.47 (s, 1H), 8.27-8.25 (m, 2H), 7.22 (t, 1H), 6.31 (d, 1H), 4.87 (s, 2H); MS (ESI) m/z=211.9 (M+H)$^+$ Step 2. (1s,4s)-4-((5-(1-(Difluoromethyl)-1H-pyrazol-3-yl)-2-((2-(1-(difluoromethyl)-1H-pyrazol-4-yl)pyrimidin-4-yl)amino)pyridin-4-yl)amino)-1-methyl-cyclohexan-1-ol The title compound as a white solid (7 mg) was prepared in the same fashion as Step 2 in Example 1, except 2-(1-(difluoromethyl)-1H-pyrazol-4-yl)pyrimidin-4-amine (45 mg, 0.213 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (84 mg, 0.234 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.51 (s, 1H), 8.42 (d, 1H), 8.38 (s, 1H), 8.35 (s, 1H), 7.94 (d, 1H), 7.87 (d, 1H), 7.35 (s, 1H), 7.25 (t, 1H), 7.23 (t, 1H), 7.04 (s, 1H), 6.83 (d, 1H), 3.56-3.54 (m, 1H), 2.03-2.00 (m, 2H), 1.84-1.77 (m, 4H), 1.64-1.61 (m, 2H), 1.32 (s, 3H); MS (ESI) m/z=532.1 (M+H)$^+$ Example 150. (1s,4s)-4-((5-(1-(Difluoromethyl)-1H-pyrazol-3-yl)-2-((2-(1-((methylsulfonyl)methyl)-1H-pyrazol-4-yl)pyrimidin-4-yl)amino)pyridin-4-yl)amino)-1-methylcyclohexan-1-ol Step 1. 2-(1-((Methylsulfonyl)methyl)-1H-pyrazol-4-yl)pyrimidin-4-amine The title compound as an off white solid (26.5 mg) was prepared in the same fashion as Reference Example 36, except 1-(methylsulfonylmethyl)-4-(4,4,5,5-tetramethyl-1,3,2-dioxaborolan-2-yl)pyrazole (247 mg, 0.882 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.31 (s, 1H), 8.25-8.24 (m, 2H), 6.29 (d, 1H), 5.31 (s, 2H), 4.83 (s, 2H), 2.91 (s, 3H); MS (ESI) m/z=253.9 (M+H)$^+$ Step 2. (1s,4s)-4-((5-(1-(Difluoromethyl)-1H-pyrazol-3-yl)-2-((2-(1-((methylsulfonyl)methyl)-1H-pyrazol-4-yl)pyrimidin-4-yl)amino)pyridin-4-yl)amino)-1-methylcyclohexan-1-ol The title compound as a white solid (5 mg) was prepared in the same fashion as Step 2 in Example 1, except 2-(1-((methylsulfonyl)methyl)-1H-pyrazol-4-yl)pyrimidin-4-amine (26 mg, 0.103 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (40 mg, 0.113 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.41 (d, 1H), 8.38 (s, 1H), 8.35 (s, 1H), 8.32 (s 1H), 7.93 (d, 1H), 7.86 (d, 1H), 7.43 (d, 1H), 7.38 (s, 1H), 7.32 (t, 1H), 6.83-6.81 (m, 2H), 5.33 (s, 2H), 3.53 (s, 1H), 2.94 (s, 3H), 2.09-2.01 (m, 2H), 1.83-1.75 (m, 4H), 1.65-1.62 (m, 2H), 1.33 (s, 3H); MS (ESI) m/z=574.2 (M+H)$^+$ Example 151. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-fluorocyclohexyl)pyridine-2,4-diamine Step 1. 2-Chloro-5-(1-(difluoromethyl)-1H-pyrazol-3-yl)-N-((1s,4s)-4-fluorocyclohexyl)pyridin-4-amine The title compound as an off white solid (78.8 mg) was prepared in the same fashion as Reference Example 15, except that (1s,4s)-4-fluorocyclohexan-1-amine hydrochloride (65 mg, 0.424 mmol) was used instead of (1s,4s)-4-amino-1-methylcyclohexan-1-ol. $^1$H-NMR (CDCl$_3$, 400 MHz) δ 8.37 (s, 1H), 8.03 (d, 1H), 7.88 (d, 1H), 7.20 (t, 1H), 6.84 (d, 1H), 6.59 (s, 1H), 4.90-4.76 (m, 1H), 3.52-3.50 (m, 1H), 2.11-2.06 (m, 2H), 1.96-1.92 (m, 2H), 1.84-1.71 (m, 4H); MS (ESI) m/z=345.0 (M+H)$^+$ Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-fluorocyclohexyl)pyridine-2,4-diamine The title compound as a white solid (26 mg) was prepared in the same fashion as Step 2 in Example 1, except 2-chloro- 5-(1-(difluoromethyl)-1H-pyrazol-3-yl)-N-((1s,4s)-4-fluorocyclohexyl)pyridin-4-amine (67 mg, 0.194 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.43 (d, 1H), 8.39 (s, 1H), 8.07 (d, 1H), 7.88 (d, 1H), 7.40 (s, 1H), 7.21 (t, 1H), 7.08 (s, 1H), 6.84 (d, 1H), 4.80 (d, 1H), 3.69 (s, 1H), 2.85-2.81 (m, 1H), 2.06-1.96 (m, 4H), 1.88-1.77 (m, 4H), 1.55-1.52 (m, 2H), 1.26-1.22 (m, 2H); MS (ESI) m/z=574.1 (M+H)$^+$ Example 152. N$^2$-(2-(1-(Cyclopropylsulfonyl)-1H-pyrazol-4-yl)pyrimidin-4-yl)-N$^4$-((4-(difluoromethyl)cyclohexyl)methyl)-5-(1-methyl-1H-pyrazol-3-yl)pyridine-2,4-diamine Step 1. 2-Chloro-N-((4-(difluoromethyl)cyclohexyl)methyl)-5-(1-methyl-1H-pyrazol-3-yl)pyridin-4-amine The title compound as an off white solid (68 mg) was prepared in the same fashion as Reference Example 15, except that (4-(difluoromethyl)cyclohexyl)methanamine hydrochloride (73 mg, 0.368 mmol) and 2-chloro-4-fluoro-5-(1-methyl-1H-pyrazol-3-yl)pyridine (60 mg, 0.283 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.34-8.29 (m, 2H), 7.41 (d, 1H), 6.61 (d, 1H), 6.53 (d, 1H), 5.58 (td, 1H), 3.94 (s, 3H), 3.24-3.11 (m, 2H), 2.07-1.92 (m, 3H), 1.70-1.65 (m, 3H), 1.27-1.24 (m, 3H); MS (ESI) m/z=355.0 (M+H)$^+$ Step 2. N$^2$-(2-(1-(Cyclopropylsulfonyl)-1H-pyrazol-4-yl)pyrimidin-4-yl)-N$^4$-((4-(difluoromethyl)cyclohexyl)methyl)-5-(1-methyl-1H-pyrazol-3-yl)pyridine-2,4-diamine The title compound as a white solid (9 mg) was prepared in the same fashion as Step 2 in Example 1, except 2-chloro-N-((4-(difluoromethyl)cyclohexyl)methyl)-5-(1-methyl-1H-pyrazol-3-yl)pyridin-4-amine (88 mg, 0.192 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.40 (d, 1H), 8.35 (s, 1H), 8.29 (s, 1H), 7.43 (s, 1H), 7.41 (d, 1H), 7.32 (d, 1H), 6.95 (s, 1H), 6.61 (d, 1H), 5.58 (td, 1H), 3.95 (s, 3H), 3.24 (t, 2H), 2.85-2.81 (m, 1H), 2.06-2.03 (m, 2H), 1.96-1.93 (m, 2H), 1.78-1.69 (m, 3H), 1.56-1.51 (m, 2H), 1.28-1.19 (m, 5H); MS (ESI) m/z=584.1 (M+H)$^+$ Example 153. 1-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-4-ol Step 1. 1-((2-Chloro-5-(1-(difluoromethyl)-1H-pyrazol-3-yl)pyridin-4-yl)amino)piperidin-4-ol The reaction mixture of 2-chloro-5-(1-(difluoromethyl)-1H-pyrazol-3-yl)-4-fluoropyridine (70 mg, 0.283 mmol) prepared in Reference Example 2, 1-aminopiperidin-4-ol (43 mg, 0.368 mmol), and DIPEA (0.25 mL, 1.414 mmol) in DMF (3 mL) was stirred at 100° C. for 4 hours. The reaction mixture was cooled to room temperature, quenched with water and extracted with EA. The organic layer was dried over MgSO$_4$, filtered, and concentrated. The crude product was purified by column chromatography (EA/n-Hex=40%) to yield 1-((2-chloro-5-(1-(difluoromethyl)-1H-pyrazol-3-yl)pyridin-4-yl)amino)piperidin-4-ol (44.8 mg) as a white solid. $^1$H-NMR (CDCl$_3$, 400 MHz) δ 8.52 (s, 1H), 8.38 (s, 1H), 7.88 (d, 1H), 7.24 (s, 1H), 7.23 (t, 1H), 6.84 (d, 1H), 4.07-3.76 (m, 2H), 3.27-2.93 (m, 3H), 3.27 (s, 1H), 2.05-2.01 (m, 2H), 1.85-1.79 (m, 2H), 1.46 (s, 1H); MS (ESI) m/z=344.0 (M+H)$^+$ Step 2. 1-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-4-ol The title compound as a white solid (13.3 mg) was prepared in the same fashion as Step 2 in Example 1, except 1-((2-chloro-5-(1-(difluoromethyl)-1H-pyrazol-3-yl)pyridin-4-yl)amino)piperidin-4-ol (41 mg, 0.119 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 10.10 (s, 1H), 8.77 (brs, 1H), 8.65 (s, 1H), 8.59 (s, 1H), 8.53 (s, 1H), 8.41 (d, 1H), 8.34 (d, 1H), 7.90 (t, 1H), 7.38 (s, 1H), 7.15 (d, 1H), 4.67 (s, 1H), 3.27-3.22 (m, 2H), 2.88 (brs, 3H), 1.83 (brs, 2H), 1.63 (brs, 2H), 1.34-1.32 (m, 2H), 1.26-1.23 (brs, 2H); MS (ESI) m/z=573.2 (M+H)$^+$ Example 154. (1s,4s)-4-((5-(1-(Difluoromethyl)-1H-pyrazol-3-yl)-2-((2-(2,3-dihydro-1H-pyrido[2,3-b][1,4]oxazin-7-yl)pyrimidin-4-yl)amino)pyridin-4-yl)amino)-1-methylcyclohexan-1-ol Step 1. 2-(2,3-Dihydro-1H-pyrido[2,3-b][1,4]oxazin-7-yl)pyrimidin-4-amine The title compound as an off white solid (56.1 mg) was prepared in the same fashion as Reference Example 36, except 7-(4,4,5,5-tetramethyl-[1,3,2]dioxaborolan-2-yl)-2,3-dihydro-1H-pyrido[2,3-b][1,4]oxazine (226 mg, 0.862 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.62 (d, 1H), 8.29 (d, 1H), 7.82 (d, 1H), 6.32 (d, 1H), 4.87 (s, 2H), 4.48 (t, 2H), 3.90 (s, 2H), 3.46 (t, 2H); MS (ESI) m/z=230.1 (M+H)$^+$ Step 2. (1s,4s)-4-((5-(1-(Difluoromethyl)-1H-pyrazol-3-yl)-2-((2-(2,3-dihydro-1H-pyrido[2,3-b][1,4]oxazin-7-yl)pyrimidin-4-yl)amino)pyridin-4-yl)amino)-1-methylcyclohexan-1-ol The title compound as a white solid (34.5 mg) was prepared in the same fashion as Step 2 in Example 1, except 2-(2,3-dihydro-1H-pyrido[2,3-b][1,4]oxazin-7-yl)pyrimidin-4-amine (55 mg, 0.24 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (94 mg, 0.264 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.96 (s, 1H), 8.49 (s, 1H), 8.43-8.42 (m, 2H), 8.40 (s, 1H), 7.95 (d, 1H), 7.88 (t, 1H), 7.81 (d, 1H), 7.73 (s, 1H), 7.31 (s, 1H), 7.13 (d, 1H), 6.27 (s, 1H), 4.32-4.26 (m, 2H), 4.10-4.06 (m, 2H), 3.51-3.49 (m, 1H), 3.16 (d, 2H), 1.84-1.82 (m, 2H), 1.62-1.59 (m, 2H), 1.51-1.48 (m, 4H), 1.13 (s, 3H); MS (ESI) m/z=550.2 (M+H)+

Example 155. (1s,4s)-4-((2-((2-((1-(2,2-Difluoro-ethyl)-1H-pyrazol-5-yl)amino)pyrimidin-4-yl)amino)-5-(1-(difluoromethyl)-1H-pyrazol-3-yl)pyridin-4-yl)amino)-1-methylcyclohexan-1-ol Step 1. tert-Butyl (tert-butoxycarbonyl)(2-((1-(2,2-difluoroethyl)-1H-pyrazol-5-yl)amino)pyrimidin-4-yl)carbamate The reaction mixture of di-tert-butyl (2-bromopyrimidin-4-yl)iminodicarbonate (250 mg, 0.668 mmol) prepared in Reference Example 14, 2-(2,2-difluoroethyl)pyrazol-3-amine (98 mg, 0.668 mmol), tris(dibenzylideneacetone)dipalladium(0) (92 mg, 0.1 mmol), Xantphos (115.96 mg, 0.2 mmol), and cesium carbonate (554 mg, 1.67 mmol) in 1,4-dioxane (2.5 mL) was stirred at room temperature for 30 minutes, and then heated to 90° C. for 3 hours. The mixture was cooled at room temperature, filtered through Celite, and then concentrated. The crude product was purified by column chromatography (EA/n-Hex=20-100%) to yield tert-butyl (tert-butoxycarbonyl)(2-((1-(2,2-difluoroethyl)-1H-pyrazol-5-yl)amino)pyrimidin-4-yl)carbamate (140 mg) as a white solid. $^1$H-NMR (CDCl$_3$, 400 MHz) δ 8.48 (d, 1H), 7.71 (d, 1H), 7.58 (d, 1H), 7.19 (s, 1H), 6.25 (tt, 1H), 6.23 (s, 1H), 4.38 (td, 2H), 1.52 (s, 9H), 1.45 (s, 9H); MS (ESI) m/z=441.0 (M+H)+

Step 2. N$^2$-(1-(2,2-Difluoroethyl)-1H-pyrazol-5-yl)pyrimidine-2,4-diamine

TFA (243.24 uL, 3.179 mmol) was added to the solution of tert-butyl (tert-butoxycarbonyl)(2-((1-(2,2-difluoroethyl)-1H-pyrazol-5-yl)amino)pyrimidin-4-yl)carbamate (140 mg, 0.318 mmol) prepared in Step 1 in DCM (1 mL). The reaction mixture was stirred at 45° C. for 2 hours. The reaction mixture was cooled, dissolved in DCM and basified with sat NaHCO$_3$ soln. The organic layer was collected, dried over MgSO$_4$ and concentrated. The crude product was purified by column chromatography (MeOH/EA=0-15%) to yield N$^2$-(1-(2,2-difluoroethyl)-1H-pyrazol-5-yl)pyrimidine-2,4-diamine (20 mg) as a white solid. $^1$H-NMR (DMSO-d$_6$, 400 MHz) δ 8.91 (s, 1H), 7.78 (d, 1H), 7.40 (s, 1H), 6.81 (s, 2H), 6.29 (s, 1H), 6.28 (tt, 1H), 5.94 (d, 1H), 4.48 (td, 2H); MS (ESI) m/z=240.9 (M+H)+

Step 3. (1s,4s)-4-((2-((2-((1-(2,2-Difluoroethyl)-1H-pyrazol-5-yl)amino)pyrimidin-4-yl)amino)-5-(1-(difluoromethyl)-1H-pyrazol-3-yl)pyridin-4-yl)amino)-1-methylcyclohexan-1-ol The title compound as a white solid (1.1 mg) was prepared in the same fashion as Step 2 in Example 1, except N$^2$-(1-(2,2-difluoroethyl)-1H-pyrazol-5-yl)pyrimidine-2,4-diamine (18 mg, 0.075 mmol) prepared in Step 2 and (1s,4s)-4-((2-chloro-5-(1-(difluoromethyl)-1H-pyrazol-3-yl)pyridin-4-yl)amino)-1-methylcyclohexan-1-ol (29 mg, 0.082 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.52 (s, 1H), 8.13-8.10 (m, 2H), 7.83 (s, 1H), 7.52 (s, 1H), 7.20 (t, 1H), 6.71 (s, 2H), 6.37 (s, 1H), 6.21 (t, 2H), 4.59 (s, 2H), 3.35 (s, 1H), 1.94-1.91 (m, 2H), 1.79-1.74 (m, 4H), 1.53-1.47 (m, 2H), 1.30 (s, 3H), 1.26 (s, 1H); MS (ESI) m/z=561.2 (M+H)+

Example 156. (1s,4s)-4-((5-(1-(Difluoromethyl)-1H-pyrazol-3-yl)-2-((2-(1-(methylsulfonyl)-1,2,3,6-tetrahydropyridin-4-yl)pyrimidin-4-yl)amino)pyridin-4-yl)amino)-1-methylcyclohexan-1-ol Step 1. 2-(1-(Methylsulfonyl)-1,2,3,6-tetrahydropyridin-4-yl)pyrimidin-4-amine The title compound as a white solid (122 mg) was prepared in the same fashion as Reference Example 36, except 1-methylsulfonyl-4-(4,4,5,5-tetramethyl-1,3,2-dioxaborolan-2-yl)-3,6-dihydro-2H-pyridine (248 mg, 0.862 mmol) was used instead of 1-(2,2-difluoroethyl)-4-(4,4,5,5-tetramethyl-1,3,2-dioxaborolan-2-yl)pyrazole. $^1$H-NMR (DMSO-d$_6$, 400 MHz) δ 8.05 (d, 1H), 6.99 (s, 1H), 6.75 (s, 2H), 6.28 (d, 1H), 3.89 (d, 2H), 3.33 (s, 1H), 3.30 (s, 2H), 2.91 (s, 3H), 2.63 (s, 2H); MS (ESI) m/z=254.9 (M+H)+

Step 2. (1s,4s)-4-((5-(1-(Difluoromethyl)-1H-pyrazol-3-yl)-2-((2-(1-(methylsulfonyl)-1,2,3,6-tetrahydropyridin-4-yl)pyrimidin-4-yl)amino)pyridin-4-yl)amino)-1-methylcyclohexan-1-ol The title compound as a white solid (14.9 mg) was prepared in the same fashion as Step 2 in Example 1, except 2-(1-(methylsulfonyl)-1,2,3,6-tetrahydropyridin-4-yl)pyrimidin-4-amine (40 mg, 0.157 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (67 mg, 0.189 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.41 (d, 1H), 8.36 (s, 1H), 7.92 (d, 1H), 7.86 (d, 1H), 7.34 (s, 2H), 7.22 (t, 1H), 7.19 (s, 1H), 6.88 (s, 1H), 8.62 (d, 1H), 4.07 (d, 2H), 3.55 (t, 2H), 3.48-3.47 (m, 1H), 2.92-2.89 (m, 2H), 2.87 (s, 3H), 2.01-1.99 (m, 2H), 1.82-1.76 (m, 4H), 1.61 (s, 1H), 1.55-1.53 (m, 1H), 1.35 (s, 3H); MS (ESI) m/z=575.2 (M+H)+

Example 157. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-(difluoromethyl)cyclohexyl)pyridine-2,4-diamine Step 1. tert-Butyl ((1s,4s)-4-(difluoromethyl)cyclohexyl)carbamate Deoxo-Fluor (243.33 uL, 1.32 mmol) was added to the solution of tert-butyl ((1s,4s)-4-formylcyclohexyl)carbamate (150 mg, 0.66 mmol) in DCM (3 mL) at 0° C. The reaction mixture was stirred at room temperature for 3 hours. The reaction was diluted in DCM and quenched sat NaHCO$_3$ soln. at 0° C. The organic layer was dried over MgSO$_4$ and concentrated. The crude product was purified by column chromatography (EA/n-Hex=0-100%) to yield tert-butyl ((1s,4s)-4-(difluoromethyl)cyclohexyl)carbamate (126.8 mg) as a yellow solid. $^1$H-NMR (CDCl$_3$, 400 MHz) δ 5.63 (td, 1H), 4.63 (s, 1H), 3.80 (s, 1H), 1.83-1.52 (m, 8H), 1.46 (s, 10H)

Step 2. (1s,4s)-4-(Difluoromethyl)cyclohexan-1-amine

The title compound as a yellow solid (100 mg) was prepared in the same fashion as Step 2 in Example 155, tert-butyl ((1s,4s)-4-(difluoromethyl)cyclohexyl)carbamate (126 mg, 0.505 mmol) prepared in Step 1 was used instead of tert-butyl (tert-butoxycarbonyl)(2-((1-(2,2-difluoroethyl)-1H-pyrazol-5-yl)amino)pyrimidin-4-yl)carbamate. $^1$H-NMR (CDCl$_3$, 400 MHz) δ 7.93 (s, 2H), 5.64 (td, 1H), 3.42 (s, 1H), 1.92-1.86 (m, 3H), 1.81-1.67 (m, 6H)

Step 3. 2-Chloro-5-(1-(Difluoromethyl)-1H-pyrazol-3-yl)-N-((1s,4s)-4-(difluoromethyl)cyclohexyl)pyridin-4-amine The title compound as an off white solid (36.3 mg) was prepared in the same fashion as Reference Example 15, except that (1s,4s)-4-(difluoromethyl)cyclohexan-1-amine (36 mg, 0.242 mmol) prepared in Step 2 was used instead of (1s,4s)-4-amino-1-methylcyclohexan-1-ol. $^1$H-NMR (CDCl$_3$, 400 MHz) δ 8.39-8.37 (m, 2H), 7.89 (m, 1H), 7.17 (t, 1H), 6.86 (d, 1H), 6.61 (s, 1H), 5.66 (td, 1H), 3.93-3.91 (m, 1H), 2.06-2.02 (m, 2H), 1.98-1.89 (m, 1H), 1.81-1.77 (m, 2H), 1.73-1.66 (m, 2H), 1.60-1.56 (m, 1H), 1.29 (s, 1H); MS (ESI) m/z=377.0 (M+H)$^+$ Step 4. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-(difluoromethyl)cyclohexyl) pyridine-2,4-diamine The title compound as a white solid (6 mg) was prepared in the same fashion as Step 2 in Example 1, except 2-chloro-5-(1-(difluoromethyl)-1H-pyrazol-3-yl)-N-((1s,4s)-4-(difluoromethyl)cyclohexyl)pyridin-4-amine (30 mg, 0.08 mmol) prepared in Step 3 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H) 8.42-8.37 (m, 3H), 7.88 (d, 1H), 7.41 (s, 1H), 7.34 (d, 1H), 7.19 (t, 1H), 7.08 (d, 1H), 6.85 (d, 1H), 5.66 (td, 1H), 4.09 (s, 1H), 2.86-2.82 (m, 1H), 2.11-2.06 (m, 2H), 1.85-1.79 (m, 4H), 1.64-1.60 (m, 2H), 1.56-1.54 (m, 3H), 1.30-1.25 (m, 2H); MS (ESI) m/z=606.2 (M+H)

Example 158. (1s,4s)-4-((5-(1-(Difluoromethyl)-1H-pyrazol-3-yl)-2-((2-(1-(methylsulfonyl)piperidin-4-yl)pyrimidin-4-yl)amino)pyridin-4-yl)amino)-1-methylcyclohexan-1-ol Step 1. 2-(1-(Methylsulfonyl)piperidin-4-yl)pyrimidin-4-amine To a solution of 2-(1-(methylsulfonyl)-1,2,3,6-tetrahydropyridin-4-yl)pyrimidin-4-amine (37 mg, 0.145 mmol) prepared in Step 1 of Example 156 in MeOH (5 mL) was added palladium on carbon (15.48 mg, 0.145 mmol). The reaction mixture was stirred at room temperature for 3.5 hours under H$_2$. The reaction mixture was filtered through Celite to yield 2-(1-(methylsulfonyl)piperidin-4-yl)pyrimidin-4-amine (33.6 mg). $^1$H-NMR (CDCl$_3$, 400 MHz) δ 8.20 (d, 1H), 6.29 (d, 1H), 4.80 (s, 2H), 3.90-3.87 (m, 2H), 2.86-2.83 (m, 1H), 2.82 (s, 3H), 2.80-2.75 (m, 2H), 2.11-2.07 (m, 2H), 2.03-1.97 (m, 2H); MS (ESI) m/z=256.9 (M+H)

Step 2. (1s,4s)-4-((5-(1-(Difluoromethyl)-1H-pyrazol-3-yl)-2-((2-(1-(methylsulfonyl)piperidin-4-yl) pyrimidin-4-yl)amino)pyridin-4-yl)amino)-1-methylcyclohexan-1-ol The title compound as a white solid (16 mg) was prepared in the same fashion as Step 2 in Example 1, except 2-(1-(methylsulfonyl)piperidin-4-yl)pyrimidin-4-amine (30 mg, 0.117 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.36-8.34 (d, 2H), 7.97 (d, 1H), 7.86 (d, 1H), 7.36 (s, 1H), 7.22 (t, 1H), 7.20 (d, 1H), 7.06 (d, 1H), 6.82 (d, 1H), 3.93-3.90 (m, 2H), 3.56 (s, 1H), 2.88-2.85 (m, 3H), 2.82 (s, 3H), 2.19-2.01 (m, 7H), 1.81-1.78 (m, 4H), 1.64-1.58 (m, 2H), 1.36 (s, 3H); MS (ESI) m/z=577.3 (M+H)$^+$ Example 159. 1-(4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-3,6-dihydropyridin-1(2H)-yl)ethan-1-one Step 1. 1-(4-(4-Aminopyrimidin-2-yl)-3,6-dihydropyridin-1(2H)-yl)ethan-1-one The title compound as a white solid (100 mg) was prepared in the same fashion as Reference Example 36, except 1-(4-(4,4,5,5-tetramethyl-1,3,2-dioxaborolan-2-yl)-5,6-dihydropyridin-1-(2H)-yl)ethanone (216 mg, 0.862 mmol) was used instead of 1-(2,2-difluoroethyl)-4-(4,4,5,5-tetramethyl-1,3,2-dioxaborolan-2-yl)pyrazole. $^1$H-NMR (DMSO-d$_6$, 400 MHz) δ 7.98 (d, 1H), 6.69 (s, 2H), 6.22 (d 1H), 4.39-4.36 (m, 1H), 3.85-3.82 (m, 1H), 3.16-3.06 (m, 1H), 2.75-2.57 (m, 2H), 1.99 (s, 3H), 1.86-1.78 (m, 2H), 1.69-1.63 (m, 1H), 1.55-1.45 (m, 1H); MS (ESI) m/z=219.1 (M+H)$^+$ Step 2. 1-(4-(4-((5-(1-(Difluoromethyl)-1H-pyrazol-3-yl)-4-(((1s,4s)-4-hydroxy-4-methylcyclohexyl) amino)pyridin-2-yl)amino)pyrimidin-2-yl)-3,6-dihydropyridin-1(2H)-yl)ethan-1-one The title compound as a white solid (15 mg) was prepared in the same fashion as Step 2 in Example 1, except 1-(4-(4-aminopyrimidin-2-yl)-3,6-dihydropyridin-1(2H)-yl) ethan-1-one (34 mg, 0.154 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (66 mg, 0.185 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.85 (s, 1H), 8.48 (s, 1H), 8.36 (d, 1H), 8.31 (d, 1H), 7.97 (d, 1H), 7.87 (t, 1H), 7.41 (s, 1H), 7.33 (s, 1H), 7.12 (d, 2H), 4.24 (s, 1H), 4.18-4.17 (m, 2H), 3.67 (t, 1H), 3.61 (t, 1H), 3.39 (s, 2H), 2.71-2.63 (m, 2H), 2.12-2.04 (m, 3H), 1.86-1.84 (m, 2H), 1.68-1.62 (m, 4H), 1.42-1.41 (m, 2H), 1.17 (s, 3H); MS (ESI) m/z=539.2 (M+H)$^+$ Example 160. 1-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl) amino)piperidin-4-ol Step 1. 1-((2-Chloro-5-(1-methyl-5-(trifluoromethyl)-1H-pyrazol-3-yl)pyridin-4-yl)amino)piperidin-4-ol The title compound as a white solid (38 mg) was prepared in the same fashion as Step 1 in Example 153, except that 2-chloro-4-fluoro-5-(1-methyl-5-(trifluoromethyl)-1H-pyrazol-3-yl)pyridine (92 mg, 0.331 mmol) prepared in Step 1 of Reference Example 16 was used instead 2-chloro-5-(1-(difluoromethyl)-1H-pyrazol-3-yl)-4-fluoropyridine. $^1$H-NMR (CDCl$_3$, 400 MHz) δ 8.53 (s, 1H), 8.38 (s, 1H), 7.88 (s, 1H), 7.23 (t, 1H), 6.84 (d, 1H), 4.11 (brs, 1H), 3.73 (brs, 1H), 3.09 (brs, 1H) 2.94 (brs, 2H) 2.59 (brs, 1H), 2.04-2.01 (m, 2H), 1.85-1.73 (m, 2H), 1.27 (s, 1H); MS (ESI) m/z=376.0 (M+H)$^+$ Step 2. 1-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino) piperidin-4-ol The title compound as a white solid (14 mg) was prepared in the same fashion as Step 2 in Example 1, except 1-((2-chloro-5-(1-methyl-5-(trifluoromethyl)-1H-pyrazol-3-yl)pyridin-4-yl)amino)piperidin-4-ol (45 mg, 0.12 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.09 (s, 1H), 8.65 (s, 1H), 8.59 (s, 1H) 8.49 (s, 1H), 8.41 (d, 1H), 7.52 (s, 1H), 7.39 (b, 1H), 4.69 (d, 1H), 4.05 (s, 3H), 3.64 (brs, 1H), 3.32-3.25 (m, 1H), 3.00 (brs, 3H), 1.83 (brs, 2H), 1.63 (brs, 2H), 1.34-1.33 (brs, 2H), 1.25-1.23 (m, 2H); MS (ESI) m/z=605.2 (M+H)$^+$ Example 161. N$^2$-(2-(1-(2,2-Difluoroethyl)-1H-pyrazol-4-yl)pyrimidin-4-yl)-5-(1-(difluoromethyl)-1H-pyrazol-3-yl)-N$^4$-((1s,4s)-4-fluorocyclohexyl) pyridine-2,4-diamine The title compound as a white solid (11.2 mg) was prepared in the same fashion as Step 2 in Example 1, except 2-(1-(2,2-difluoroethyl)-1H-pyrazol-4-yl)pyrimidin-4-amine (30 mg, 0.133 mmol) prepared in Reference Example 36 and 2-chloro-5-(1-(difluoromethyl)-1H-pyrazol-3-yl)-N-((1s,4s)-4-fluorocyclohexyl)pyridin-4-amine (45.93 mg, 0.133 mmol) prepared in Step 1 of Example 151 were used instead 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.39-8.38 (m, 2H), 8.24 (s, 1H), 8.17 (s, 1H), 8.02 (d, 1H), 7.87 (d, 1H), 7.56 (s, 1H), 7.23 (t, 1H), 7.22 (s, 1H), 7.06 (d, 1H), 6.83 (d, 1H), 6.14 (tt, 1H), 4.87-4.75 (m, 1H), 4.52 (td, 2H), 4.68-4.67 (m, 1H), 2.07-1.96 (m, 4H), 1.89-1.64 (m, 4H); MS (ESI) m/z=605.2 (M+H)$^+$ Example 162. 1-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)piperidin-4-ol The title compound as a white solid (6 mg) was prepared in the same fashion as Step 2 in Example 1, except 2-(1-(2,2-difluoroethyl)-1H-pyrazol-4-yl)pyrimidin-4-amine (9 mg, 0.04 mmol) prepared in Reference Example 36 and 1-((2-chloro-5-(1-(difluoromethyl)-1H-pyrazol-3-yl)pyridin-4-yl)amino)piperidin-4-ol (14 mg, 0.04 mmol) prepared in Step 1 of Example 153 were used instead 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.30 (s, 1H), 8.42 (s, 1H), 8.38-8.37 (m, 2H), 8.25 (s, 1H), 8.20 (s, 1H), 7.87 (d, 1H), 7.39 (s, 1H), 7.24 (t, 1H) 6.84 (s, 1H), 6.14 (tt, 1H), 6.54 (td, 2H), 3.78 (brs, 1H), 3.27 (brs, 2H), 2.56 (brs, 3H), 2.11 (brs, 4H), 1.2-(s, 1H); MS (ESI) m/z=533.2 (M+H)$^+$ Example 163. 1-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl) amino)piperidin-4-ol The title compound as a white solid (6 mg) was prepared in the same fashion as Step 2 in Example 1, except 2-(1-(2,2-difluoroethyl)-1H-pyrazol-4-yl)pyrimidin-4-amine (9 mg, 0.04 mmol) prepared in Reference Example 36 and 1-((2-chloro-5-(1-methyl-5-(trifluoromethyl)-1H-pyrazol-3-yl)pyridin-4-yl)amino)piperidin-4-ol (15 mg, 0.04 mmol) prepared in Step 1 of Example 160 were used instead 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.27 (s, 1H), 8.45 (s, 1H), 8.37 (d, 1H), 8.30 (s, 1H), 8.20 (s, 1H), 7.41 (s, 1H), 6.95 (s, 1H), 6.80 (brs, 1H), 6.14 (tt, 1H), 4.54 (td, 2H), 4.06 (s, 3H), 3.76 (brs, 1H) 3.27 (brs, 1H), 2.99 (brs, 1H), 2.61 (brs, 2H), 2.01 (brs, 4H), 1.27 (s, 1H); MS (ESI) m/z=555.2 (M+H)$^+$ Example 164. N$^2$-(2-(1-(Cyclopropylsulfonyl)-1H-pyrazol-4-yl)pyrimidin-4-yl)-5-(4-(difluoromethyl) thiazol-2-yl)-N$^4$-((1s,4s)-4-fluorocyclohexyl)pyridine-2,4-diamine Step 1. 2-Chloro-5-(4-(difluoromethyl)thiazol-2-yl)-N-((1s,4s)-4-fluorocyclohexyl)pyridin-4-amine The title compound as an off white solid (88.3 mg) was prepared in the same fashion as Reference Example 15, except that (1s,4s)-4-fluorocyclohexan-1-amine hydrochloride (65 mg, 0.425 mmol) and 2-(6-chloro-4-fluoropyridin-3-yl)-4-(difluoromethyl)thiazole (75 mg, 0.283 mmol) prepared in Step 1 of Example 122 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 9.11 (d, 1H), 8.50 (s, 1H), 7.56 (s, 1H), 6.77 (t, 1H), 6.63 (s, 1H), 4.87-4.75 (m, 1H), 3.54 (s, 1H), 2.12-2.06 (m, 2H), 1.95-1.56 (m, 6H); MS (ESI) m/z=362.1 (M+H)$^+$ Step 2. N$^2$-(2-(1-(Cyclopropylsulfonyl)-1H-pyrazol-4-yl)pyrimidin-4-yl)-5-(4-(difluoromethyl)thiazol-2-yl)-N$^4$-((1s,4s)-4-fluorocyclohexyl)pyridine-2,4-diamine The title compound as a white solid (6 mg) was prepared in the same fashion as Step 2 in Example 1, except 2-chloro-5-(4-(difluoromethyl)thiazol-2-yl)-N-((1s,4s)-4-fluorocyclohexyl)pyridin-4-amine (39 mg, 0.109 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.16 (d, 1H), 8.65 (s, 1H), 8.52 (s, 1H), 8.46-8.44 (m, 2H), 7.49 (s, 1H), 7.38 (s, 1H), 7.22-7.18 (m, 2H), 6.77 (t, 1H), 4.84-4.72 (m, 1H), 3.72 (s, 1H), 2.86-2.82 (m, 1H), 2.06-1.82 (m, 9H), 1.26-1.23 (m, 2H); MS (ESI) m/z=591.2 (M+H)$^+$

Example 165. (1s,4s)-4-((5-(1-(Difluoromethyl)-1H-pyrazol-3-yl)-2-((2-(6-methoxypyridin-3-yl)pyrimidin-4-yl)amino)pyridin-4-yl)amino)-1-methylcyclohexan-1-ol Step 1.
2-(6-Methoxypyridin-3-yl)pyrimidin-4-amine The title compound as a white solid (74 mg) was prepared in the same fashion as Reference Example 36, except (6-methoxypyridin-3-yl)boronic acid (132 mg, 0.862 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 9.15 (s, 1H), 8.51 (dd, 1H), 8.31 (d, 1H), 6.80 (d, 1H), 6.34 (d, 1H), 4.89 (s, 2H), 4.01 (s, 3H); MS (ESI) m/z=203.2 (M+H)$^+$ Step 2. (1s,4s)-4-((5-(1-(Difluoromethyl)-1H-pyrazol-3-yl)-2-((2-(6-methoxypyridin-3-yl)pyrimidin-4-yl)amino)pyridin-4-yl)amino)-1-methylcyclohexan-1-ol The title compound as a white solid (40 mg) was prepared in the same fashion as Step 2 in Example 1, except 2-(6-methoxypyridin-3-yl)pyrimidin-4-amine (30 mg, 0.148 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (58 mg, 0.163 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.03 (s, 1H), 9.14 (s, 1H), 8.55 (d, 1H), 8.51 (s, 1H), 8.45 (d, 1H), 8.32 (d, 1H), 7.98 (d, 1H), 7.88 (t, 1H), 7.60 (s, 1H), 7.37 (s, 1H), 7.14 (d, 1H), 6.95 (d, 1H), 4.14 (s, 1H), 4.08 (d, 1H), 3.95 (s, 3H), 3.51-3.48 (m, 2H), 3.16 (d, 2H), 1.88-1.85 (m, 2H), 1.65-1.55 (m, 4H), 1.43-1.36 (m, 2H), 1.23 (s, 1H), 1.09 (s, 3H); MS (ESI) m/z=523.2 (M+H)$^+$

Example 166. (1s,4s)-4-((5-(1-(Difluoromethyl)-1H-pyrazol-3-yl)-2-((2-(2-fluoro-6-methoxypyridin-3-yl)pyrimidin-4-yl)amino)pyridin-4-yl)amino)-1-methylcyclohexan-1-ol Step 1. 2-(2-Fluoro-6-methoxypyridin-3-yl)pyrimidin-4-amine The title compound as a white solid (76 mg) was prepared in the same fashion as Reference Example 36, except 2-fluoro-6-methoxypyridine-3-boronic acid (147 mg, 0.862 mmol) was used instead of 1-(2,2-difluoroethyl)-4-(4,4,5,5-tetramethyl-1,3,2-dioxaborolan-2-yl)pyrazole. $^1$H-NMR (DMSO-d$_6$, 400 MHz) δ 8.38 (t, 1H), 8.15 (d, 1H), 6.94 (s, 2H), 6.84 (d, 1H), 6.38 (dd, 1H), 3.88 (s, 3H); MS (ESI) m/z=221.1 (M+H)$^+$ Step 2. (1s,4s)-4-((5-(1-(Difluoromethyl)-1H-pyrazol-3-yl)-2-((2-(2-fluoro-6-methoxypyridin-3-yl)pyrimidin-4-yl)amino)pyridin-4-yl)amino)-1-methylcyclohexan-1-ol The title compound as a white solid (11 mg) was prepared in the same fashion as Step 2 in Example 1, except 2-(2-fluoro-6-methoxypyridin-3-yl)pyrimidin-4-amine (33 mg, 0.148 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (58 mg, 0.163 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.52-8.46 (m, 2H), 8.35 (s, 1H), 7.98 (s, 1H), 7.89-7.85 (m, 2H), 7.53 (s, 1H), 7.22 (t, 1H), 6.80 (d, 1H), 6.97 (d, 1H), 6.77 (dd, 1H), 3.99 (s, 3H), 3.63-3.62 (m, 1H), 2.01-1.99 (m, 2H), 1.73-1.67 (m, 4H), 1.63-1.60 (m, 3H), 1.32 (s, 3H); MS (ESI) m/z=541.2 (M+H)$^+$

Example 167. (1s,4s)-4-((2-((2-(1-(Cyclopropylsulfonyl)-1H-pyrazol-4-yl)pyrimidin-4-yl)amino)-5-(3-(trifluoromethyl)-1H-pyrazol-1-yl)pyridin-4-yl)amino)-1-methylcyclohexan-1-ol Step 1. (1s,4s)-4-((2-Chloro-5-(3-(trifluoromethyl)-1H-pyrazol-1-yl)pyridin-4-yl)amino)-1-methylcyclohexan-1-ol The title compound as a solid (25 mg) was prepared in the same fashion as Step 1 in Example 102, except 3-trifluoromethyl pyrazole (50 mg, 0.367 mmol) was used instead of ethyl pyrazole-3-carboxylate. $^1$H-NMR (CDCl$_3$, 400 MHz) δ 8.05 (s, 1H), 7.79 (s, 1H), 6.77 (d, 1H), 6.65 (s, 1H), 6.47 (s, 1H), 3.33-3.29 (m, 1H), 1.93-1.89 (m, 2H), 1.76-1.55 (m, 6H), 1.31 (s, 3H); MS (ESI) m/z=375.1 (M+H)$^+$ Step 2. (1s,4s)-4-((2-((2-(1-(Cyclopropylsulfonyl)-1H-pyrazol-4-yl)pyrimidin-4-yl)amino)-5-(3-(trifluoromethyl)-1H-pyrazol-1-yl)pyridin-4-yl)amino)-1-methylcyclohexan-1-ol The title compound as a white solid (4 mg) was prepared in the same fashion as Step 2 in Example 1, except (1s,4s)-4-((2-chloro-5-(3-(trifluoromethyl)-1H-pyrazol-1-yl)pyridin-4-yl)amino)-1-methylcyclohexan-1-ol (23 mg, 0.061 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (d, 1H), 8.47-8.45 (m, 2H), 8.02 (s, 1H), 7.76 (s, 1H), 7.34 (s, 1H), 7.30-7.29 (m, 1H), 7.10 (s, 1H), 6.77 (s, 1H), 6.11 (d, 1H), 3.45 (s, 1H), 2.85-2.82 (m, 1H), 1.97-1.94 (m, 2H), 1.69-1.64 (m, 4H), 1.62-1.58 (m, 3H), 1.30 (s, 3H), 1.27-1.20 (m, 2H), 0.91 (s, 1H); MS (ESI) m/z=604.2 (M+H)$^+$

Example 168. (1s,4s)-4-((2-((2-(1-(Cyclopropylsulfonyl)-1H-pyrazol-4-yl)pyrimidin-4-yl)amino)-5-(3-methyl-1H-pyrazol-1-yl)pyridin-4-yl)amino)-1-methylcyclohexan-1-ol Step 1. (1s,4s)-4-((2-Chloro-5-(3-methyl-1H-pyrazol-1-yl)pyridin-4-yl)amino)-1-methylcyclohexan-1-ol The title compound as an off white solid (69.3 mg) was prepared in the same fashion as Step 1 in Example 102, except 3-methylpyrazole (30 mg, 0.347 mmol) was used instead of ethyl pyrazole-3-carboxylate. $^1$H-NMR (CDCl$_3$, 400 MHz) δ 7.96 (s, 1H), 7.61 (s, 1H), 6.93 (d, 1H), 6.59 (s, 1H), 6.25 (s, 1H), 3.30-3.28 (m, 1H), 2.06 (s, 3H), 1.93-1.89 (m, 2H), 1.76-1.53 (m, 7H), 1.30 (s, 3H); MS (ESI) m/z=321.0 (M+H)$^+$ Step 2. (1s,4s)-4-((2-((2-(1-(Cyclopropylsulfonyl)-1H-pyrazol-4-yl)pyrimidin-4-yl)amino)-5-(3-methyl-1H-pyrazol-1-yl)pyridin-4-yl)amino)-1-methylcyclohexan-1-ol The title compound as a white solid (4.5 mg) was prepared in the same fashion as Step 2 in Example 1, except (1s,4s)-4-((2-chloro-5-(3-methyl-1H-pyrazol-1-yl)pyridin-4-yl)amino)-1-methylcyclohexan-1-ol (64 mg, 0.199 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.47 (s 1H), 8.43 (d, 1H), 7.95 (s, 1H), 7.59 (s, 1H), 7.35-7.32 (m, 2H), 6.99 (s, 1H), 6.51 (d, 1H), 6.25 (s, 1H), 3.41 (s, 1H), 2.85-2.81 (m, 1H), 2.38 (s, 3H), 1.98-1.95 (m, 2H), 1.74-1.55 (m, 7H), 1.30 (s, 3H), 1.27-1.21 (m, 2H), 1.16-1.11 (m, 1H); MS (ESI) m/z=550.2 (M+H)$^+$ Example 169. (1s,4s)-4-((5-(1-(Difluoromethyl)-1H-pyrazol-3-yl)-2-((2-(2-methoxypyridin-4-yl)pyrimidin-4-yl)amino)pyridin-4-yl)amino)-1-methylcyclohexan-1-ol Step 1. 2-(2-Methoxypyridin-4-yl)pyrimidin-4-amine The title compound as a white solid (22.6 mg) was prepared in the same fashion as Reference Example 36, except (2-methoxypyridin-4-yl)boronic acid (132 mg, 0.862 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.37 (d, 1H), 8.27 (d, 1H), 8.04 (d, 1H), 7.67 (s, 1H), 6.41 (dd, 1H), 4.95 (s, 2H), 4.00 (s, 3H); MS (ESI) m/z=203.2 (M+H)$^+$ Step 2. (1s,4s)-4-((5-(1-(Difluoromethyl)-1H-pyrazol-3-yl)-2-((2-(2-methoxypyridin-4-yl)pyrimidin-4-yl)amino)pyridin-4-yl)amino)-1-methylcyclohexan-1-ol The title compound as a white solid (11 mg) was prepared in the same fashion as Step 2 in Example 1, except 2-(2-methoxypyridin-4-yl)pyrimidin-4-amine (20 mg, 0.099 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (39 mg, 0.109 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (MeOD, 400 MHz) δ 8.46 (d, 1H), 8.39 (s, 1H), 8.28 (d, 1H), 8.15 (d, 1H), 8.10 (s, 1H), 7.84 (d, 1H), 7.69 (d, 1H), 7.56 (t, 1H), 7.55 (s, 1H), 7.35 (d, 1H), 6.97 (s, 1H), 3.99 (s, 3H), 3.60 (s, 1H), 1.98-1.96 (m, 2H), 1.76-1.68 (m, 4H), 1.47-1.44 (m, 2H), 1.99 (s, 3H); MS (ESI) m/z=523.2 (M+H)$^+$ Example 170. (1s,4s)-4-((5-(1-(Difluoromethyl)-1H-pyrazol-3-yl)-2-((2-(2,6-difluoropyridin-3-yl)pyrimidin-4-yl)amino)pyridin-4-yl)amino)-1-methylcyclohexan-1-ol Step 1. 2-(2,6-Difluoropyridin-3-yl)pyrimidin-4-amine The title compound as a white solid (47.3 mg) was prepared in the same fashion as Reference Example 36, except 2,6-difluoro-3-pyridineboronic acid (110 mg, 0.69 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.63 (q, 1H), 8.38 (d, 1H), 6.93 (dd, 1H), 6.42 (d, 1H), 5.00 (s, 2H); MS (ESI) m/z=208.9 (M+H)$^+$ Step 2. (1s,4s)-4-((5-(1-(Difluoromethyl)-1H-pyrazol-3-yl)-2-((2-(2,6-difluoropyridin-3-yl)pyrimidin-4-yl)amino)pyridin-4-yl)amino)-1-methylcyclohexan-1-ol The title compound as a pale yellow solid (12 mg) was prepared in the same fashion as Step 2 in Example 1, except 2-(2,6-difluoropyridin-3-yl)pyrimidin-4-amine (27 mg, 0.13 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (51 mg, 0.143 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.70 (q, 1H), 8.50 (d, 1H), 8.35 (s, 1H), 7.90 (d, 1H), 7.86 (d, 1H), 7.55 (s, 1H), 7.40 (s, 1H), 7.23 (t, 1H), 7.13 (d, 1H), 6.97 (dd, 1H), 6.82 (d, 1H), 3.60 (s, 1H), 1.99-1.97 (m, 2H), 1.74-1.68 (m, 4H), 1.63-1.58 (m, 2H), 1.33 (s, 3H), 1.15-1.14 (m, 1H); MS (ESI) m/z=529.2 (M+H)$^+$ Example 171. (1s,4s)-4-((5-(1-(Difluoromethyl)-1H-pyrazol-3-yl)-2-((2-(2-fluoropyridin-3-yl)pyrimidin-4-yl)amino)pyridin-4-yl)amino)-1-methylcyclohexan-1-ol Step 1. 2-(2-Fluoropyridin-3-yl)pyrimidin-4-amine The title compound as a white solid (47.3 mg) was prepared in the same fashion as Reference Example 36, except 2-fluoro-3-(4,4,5,5-tetramethyl-1,3,2-dioxaborolan-2-yl)pyridine (154 mg, 0.69 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.46 (t, 1H), 8.40 (d, 1H), 8.30 (d, 1H), 7.30 (t, 1H), 6.43 (d, 1H), 5.00 (s, 2H); MS (ESI) m/z=190.9 (M+H)$^+$ Step 2. (1s,4s)-4-((5-(1-(Difluoromethyl)-1H-pyrazol-3-yl)-2-((2-(2-fluoropyridin-3-yl)pyrimidin-4-yl)amino)pyridin-4-yl)amino)-1-methylcyclohexan-1-ol The title compound as an off white solid (10 mg) was prepared in the same fashion as Step 2 in Example 1, except 2-(2-fluoropyridin-3-yl)pyrimidin-4-amine (25 mg, 0.13 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (51 mg, 0.143 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.54-8.52 (m, 2H), 8.33-8.32 (m, 2H), 7.90-7.86 (m, 2H), 7.53 (s, 1H), 7.45 (s, 1H), 7.35 (t, 1H), 7.22 (t, 1H), 7.13 (s, 1H), 6.82 (d, 1H), 3.60-3.59 (m, 1H), 1.99-1.97 (m, 2H), 1.75-1.69 (m, 6H), 1.31 (s, 3H); MS (ESI) m/z=511.1 (M+H)$^+$ Example 172. (1s,4s)-4-((2-((2-(1-(Cyclopropylsulfonyl)-1H-pyrazol-4-yl)pyrimidin-4-yl)amino)-5-(3-(difluoromethyl)-1H-pyrazol-1-yl)pyridin-4-yl)amino)-1-methylcyclohexan-1-ol Step 1. (1s,4s)-4-((2-Chloro-5-(3-(difluoromethyl)-1H-pyrazol-1-yl)pyridin-4-yl)amino)-1-methylcyclohexan-1-ol The title compound as an off white solid (75 mg) was prepared in the same fashion as Step 1 in Example 102, except 3-(difluoromethyl)-1H-pyrazole (43 mg, 0.367 mmol) was used instead of ethyl pyrazole-3-carboxylate. $^1$H-NMR (CDCl$_3$, 400 MHz) δ 8.02 (s, 1H), 7.76 (s, 1H), 6.76 (t, 1H), 6.73 (s, 1H), 6.64 (s, 1H), 6.41 (s, 1H), 3.32-3.30 (m, 1H), 1.91-1.89 (m, 2H), 1.76-1.58 (m, 5H), 1.31 (s, 3H), 1.09 (s, 1H); MS (ESI) m/z=357.1 (M+H)$^+$ Step 2. (1s,4s)-4-((2-((2-(1-(Cyclopropylsulfonyl)-1H-pyrazol-4-yl)pyrimidin-4-yl)amino)-5-(3-(difluoromethyl)-1H-pyrazol-1-yl)pyridin-4-yl)amino)-1-methylcyclohexan-1-ol The title compound as a white solid (21.4 mg) was prepared in the same fashion as Step 2 in Example 1, except (1s,4s)-4-((2-chloro-5-(3-(difluoromethyl)-1H-pyrazol-1-yl)pyridin-4-yl)amino)-1-methylcyclohexan-1-ol (74 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47-8.44 (m, 2H), 8.00 (s, 1H), 7.74 (s, 1H), 7.38 (s, 1H), 7.30 (d, 1H), 7.09 (s, 1H), 6.79 (t, 1H), 6.73 (s, 1H), 6.04 (d, 1H), 3.44 (s, 1H), 2.85-2.81 (m, 1H), 1.97-1.94 (m, 2H), 1.72-1.61 (m, 7H), 1.55-1.52 (m, 3H), 1.30 (s, 3H), 1.26-1.21 (m, 2H), 1.11 (s, 1H); MS (ESI) m/z=586.2 (M+H)$^+$ Example 173. (1s,4s)-4-((5-(1-(Difluoromethyl)-1H-pyrazol-3-yl)-2-((2-(1-(3-hydroxy-2,2-dimethylpropyl)-1H-pyrazol-4-yl)pyrimidin-4-yl)amino)pyridin-4-yl)amino)-1-methylcyclohexan-1-ol Step 1. 3-(4-(4-Aminopyrimidin-2-yl)-1H-pyrazol-1-yl)-2,2-dimethylpropan-1-ol The title compound as an off white solid (109 mg) was prepared in the same fashion as Reference Example 36, except that 2,2-dimethyl-3-[4-(4,4,5,5-tetramethyl-1,3,2-dioxaborolan-2-yl)pyrazol-1-yl]propan-1-ol (242 mg, 0.862 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.07 (s, 1H), 8.01 (d, 1H), 7.86 (s, 1H), 6.72 (s, 2H), 6.20 (d, 1H), 4.77 (t, 1H), 3.99 (s, 2H), 3.12 (d, 2H), 0.81 (s, 6H); MS (ESI) m/z=248.1 (M+H)$^+$ Step 2. (1s,4s)-4-((5-(1-(Difluoromethyl)-1H-pyrazol-3-yl)-2-((2-(1-(3-hydroxy-2,2-dimethylpropyl)-1H-pyrazol-4-yl)pyrimidin-4-yl)amino)pyridin-4-yl)amino)-1-methylcyclohexan-1-ol The title compound as a white solid (63 mg) was prepared in the same fashion as Step 2 in Example 1, except 3-(4-(4-aminopyrimidin-2-yl)-1H-pyrazol-1-yl)-2,2-dimethylpropan-1-ol (50 mg, 0.202 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (79 mg, 0.222 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.83 (s, 1H), 8.49 (s, 1H), 8.33-8.31 (m, 2H), 8.21 (s, 1H), 8.03 (d, 1H), 7.95 (d, 1H), 7.87 (t, 1H), 7.39 (s, 2H), 7.13 (d, 1H), 5.75 (s, 1H), 4.81 (t, 1H), 4.15 (s, 1H), 4.03 (s, 2H), 3.47-3.45 (m, 1H), 3.17-3.13 (m, 2H), 1.87-1.85 (m, 2H), 1.66-1.59 (m, 4H), 1.48-1.45 (m, 2H), 1.14 (s, 3H), 1.03 (d, 1H), 0.83 (s, 6H); MS (ESI) m/z=568.2 (M+H)$^+$ Example 174. N$^2$-(2-(1-(Cyclopropylsulfonyl)-1H-pyrazol-4-yl)pyrimidin-4-yl)-N$^4$-((1s,4s)-4-fluorocyclohexyl)-5-(1-methyl-1H-pyrazol-3-yl)pyridine-2,4-diamine Step 1. 2-Chloro-N-((1s,4s)-4-fluorocyclohexyl)-5-(1-methyl-1H-pyrazol-3-yl)pyridin-4-amine The title compound as a off white solid (60 mg) was prepared in the same fashion as Reference Example 15, except that (1s,4s)-4-fluorocyclohexan-1-amine hydrochloride (99 mg, 0.647 mmol) and 2-chloro-4-fluoro-5-(1-methyl-1H-pyrazol-3-yl)pyridine (114 mg, 0.539 mmol) prepared in Reference Example 3 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.42 (d, 1H), 8.33 (s, 1H), 7.41 (s, 1H), 6.61 (s, 1H), 6.54 (s, 1H), 4.87-4.75 (m, 1H), 3.95 (s, 3H), 3.52-3.51 (m, 1H), 2.09-2.05 (m, 2H), 1.94-1.89 (m, 2H), 1.85-1.73 (m, 4H); MS (ESI) m/z=309.1 (M+H)$^+$ Step 2. N$^2$-(2-(1-(Cyclopropylsulfonyl)-1H-pyrazol-4-yl)pyrimidin-4-yl)-N$^4$-((1s,4s)-4-fluorocyclohexyl)-5-(1-methyl-1H-pyrazol-3-yl)pyridine-2,4-diamine The title compound as a white solid (16 mg) was prepared in the same fashion as Step 2 in Example 1, except that 2-chloro-N-((1s,4s)-4-fluorocyclohexyl)-5-(1-methyl-1H-pyrazol-3-yl)pyridin-4-amine (44 mg, 0.142 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.93 (s, 1H), 8.63 (s, 1H), 8.43 (d, 1H), 8.39 (d, 1H), 7.79 (s, 1H), 7.55 (s, 1H), 7.25 (s, 1H), 6.79 (s, 1H), 4.83-4.71 (m, 1H), 3.90 (s, 3H), 3.65 (s, 1H), 1.91-1.84 (m, 4H), 1.77-1.71 (m, 3H), 1.34-1.33 (m, 2H), 1.26-1.24 (m, 2H); MS (ESI) m/z=538.2 (M+H)$^+$ Example 175. N$^2$-(2-(1-(Cyclopropylsulfonyl)-1H-pyrazol-4-yl)pyrimidin-4-yl)-N$^4$-((1s,4s)-4-fluorocyclohexyl)-5-(1-methyl-5-(trifluoromethyl)-1H-pyrazol-3-yl)pyridine-2,4-diamine Step 1. 2-Chloro-N-((1s,4s)-4-fluorocyclohexyl)-5-(1-methyl-5-(trifluoromethyl)-1H-pyrazol-3-yl)pyridin-4-amine The title compound as a off white solid (46 mg) was prepared in the same fashion as Reference Example 15, except that (1s,4s)-4-fluorocyclohexan-1-amine hydrochloride (37 mg, 0.24 mmol) and 2-chloro-4-fluoro-5-(1-methyl-5-(trifluoromethyl)-1H-pyrazol-3-yl)pyridine (56 mg, 0.2 mmol) prepared in Step 1 of Reference Example 16 were used instead of (1s,4s)-4-amino-1-methylcyclohexan-1-ol and 2-chloro-5-(1-(difluoromethyl)-1H-pyrazol-3-yl)-4-fluoropyridine. $^1$H-NMR (CDCl$_3$, 400 MHz) δ 8.31 (s, 1H), 8.06 (d, 1H), 6.97 (s, 1H), 6.57 (s, 1H), 4.89-4.76 (m, 1H), 4.05 (s, 3H), 3.52 (s, 1H), 2.11-2.06 (m, 2H), 1.94-1.61 (m, 2H), 1.85-1.70 (m, 4H); MS (ESI) m/z=377.1 (M+H)$^+$ Step 2. N$^2$-(2-(1-(Cyclopropylsulfonyl)-1H-pyrazol-4-yl)pyrimidin-4-yl)-N$^4$-((1s,4s)-4-fluorocyclohexyl)-5-(1-methyl-5-(trifluoromethyl)-1H-pyrazol-3-yl)pyridine-2,4-diamine The title compound as a white solid (14 mg) was prepared in the same fashion as Step 2 in Example 1, except that 2-chloro-N-((1s,4s)-4-fluorocyclohexyl)-5-(1-methyl-5-(trifluoromethyl)-1H-pyrazol-3-yl)pyridin-4-amine (54 mg, 0.142 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.01 (s, 1H), 8.64 (s, 1H), 8.50 (s, 1H), 8.45-8.42 (m, 2H), 7.97 (d, 1H), 7.54 (s, 2H), 7.30 (s, 1H), 4.84-4.72 (m, 1H), 4.02 (s, 3H), 3.65 (s, 1H), 1.92-1.89 (m, 5H), 1.76-1.70 (s, 4H), 1.34-1.33 (m, 2H), 1.26-1.24 (m, 3H); MS (ESI) m/z=606.2 (M+H)$^+$ Example 176. (1s,4s)-4-((5-(1-(Difluoromethyl)-1H-pyrazol-3-yl)-2-((2-(3,4-dihydro-2H-pyrano[2,3-b]pyridin-6-yl)pyrimidin-4-yl)amino)pyridin-4-yl)amino)-1-methylcyclohexan-1-ol Step 1. 2-(3,4-Dihydro-2H-pyrano[2,3-b]pyridin-6-yl)pyrimidin-4-amine The title compound as an off white solid (92.6 mg) was prepared in the same fashion as Reference Example 36, except 6-(4,4,5,5-tetramethyl-1,3,2-dioxaborolan-2-yl)-3,4-dihydro-2H-pyrano[2,3-b]pyridine (225 mg, 0.862 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 9.04 (s, 1H), 8.34 (s, 1H), 8.30 (d, 1H), 6.33 (d, 1H), 4.92 (s, 2H), 4.41 (t, 2H), 2.89 (t, 2H), 2.09-2.03 (m, 3H); MS (ESI) m/z=229.1 (M+H)$^+$ Step 2. (1s,4s)-4-((5-(1-(Difluoromethyl)-1H-pyrazol-3-yl)-2-((2-(3,4-dihydro-2H-pyrano[2,3-b]pyridin-6-yl)pyrimidin-4-yl)amino)pyridin-4-yl)amino)-1-methylcyclohexan-1-ol The title compound as a white solid (17 mg) was prepared in the same fashion as Step 2 in Example 1, except that 2-(3,4-dihydro-2H-pyrano[2,3-b]pyridin-6-yl)pyrimidin-4-amine (45 mg, 0.195 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (70 mg, 0.195 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.15 (s, 1H), 8.46 (d, 1H), 8.39-8.36 (m, 2H), 7.90 (d, 1H), 7.86 (s, 1H), 7.49 (s, 1H), 7.29 (s, 1H), 7.27 (t, 1H), 7.18 (d, 1H), 6.83 (s, 1H), 4.42 (t, 2H), 3.61 (s, 1H), 3.50 (s, 2H), 2.92 (t, 2H), 2.09-2.01 (m, 4H), 1.76-1.67 (m, 6H), 1.33 (s, 3H); MS (ESI) m/z=549.2 (M+H)$^+$ Example 177. (1s,4s)-4-((2-((2-(1-(2,2-Difluoroethyl)-1H-pyrazol-4-yl)pyrimidin-4-yl)amino)-5-(3-(difluoromethyl)-1H-pyrazol-1-yl)pyridin-4-yl)amino)-1-methylcyclohexan-1-ol The title compound as a white solid (4.4 mg) was prepared in the same fashion as Step 2 in Example 1, except (1s,4s)-4-((2-chloro-5-(3-(difluoromethyl)-1H-pyrazol-1-yl)pyridin-4-yl)amino)-1-methylcyclohexan-1-ol (52 mg, 0.146 mmol) prepared in Step 1 of Example 172 and 2-(1-(2,2-difluoroethyl)-1H-pyrazol-4-yl)pyrimidin-4-amine (36 mg, 0.16 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.41 (d, 1H), 8.24 (s, 1H), 8.17 (s, 1H), 7.99 (s, 1H), 7.73 (s, 1H), 7.51 (s, 1H), 7.21 (d, 1H), 7.13 (s, 1H), 6.78 (t, 1H), 6.72 (s, 1H), 6.14 (td, 1H), 5.98 (d, 1H), 4.52 (td, 2H), 3.45-3.43 (m, 1H), 1.95-1.92 (m, 2H), 1.74-1.54 (m, 5H), 1.29 (s, 3H), 1.16 (s, 1H); MS (ESI) m/z=546.3 (M+H)$^+$ Example 178. (1s,4s)-4-((5-(1-(Difluoromethyl)-1H-pyrazol-3-yl)-2-((2-(5-fluoro-6-methoxypyridin-3-yl)pyrimidin-4-yl)amino)pyridin-4-yl)amino)-1-methylcyclohexan-1-ol Step 1. 2-(5-Fluoro-6-methoxypyridin-3-yl)pyrimidin-4-amine The title compound as an off solid (180 mg) was prepared in the same fashion as Reference Example 36, except 3-fluoro-2-methoxy-5-(4,4,5,5-tetramethyl-1,3,2-dioxaborolan-2-yl)pyridine (218 mg, 0.862 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.37 (d, 1H), 8.08 (d, 1H), 7.84 (d, 1H), 6.40 (d, 1H), 5.06 (s, 2H), 4.00 (s, 3H); MS (ESI) m/z=221.1 (M+H)$^+$ Step 2. (1s,4s)-4-((5-(1-(Difluoromethyl)-1H-pyrazol-3-yl)-2-((2-(5-fluoro-6-methoxypyridin-3-yl)pyrimidin-4-yl)amino)pyridin-4-yl)amino)-1-methylcyclohexan-1-ol The title compound as a white solid (11.2 mg) was prepared in the same fashion as Step 2 in Example 1, except that 2-(5-fluoro-6-methoxypyridin-3-yl)pyrimidin-4-amine (43 mg, 0.195 mmol) prepared in Step 1 and (1s,4s)-4-((2-chloro-5-(1-(difluoromethyl)-1H-pyrazol-3-yl)pyridin-4-yl)amino)-1-methylcyclohexan-1-ol (70 mg, 0.195 mmol) prepared in Reference Example 15 were used instead of 2-(1-(cyclopropylsulfonyl)-1H-pyrazol-4-yl)pyrimidin-4-amine and 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.51 (d, 1H), 8.37 (s, 1H), 8.11 (d, 1H), 7.94 (s, 1H), 7.93 (d, 1H), 7.85 (s, 2H), 7.36 (s, 1H), 7.21 (t, 1H), 7.16 (d, 1H), 6.81 (s, 1H), 4.01 (s, 3H), 3.38-3.36 (m, 1H), 2.05 (s, 3H), 1.92-1.91 (m, 2H), 1.69-1.63 (m, 4H), 1.31-1.25 (m, 3H); MS (ESI) m/z=541.4 (M+H)$^+$ Example 179. N$^2$-(2-(1-(Cyclopropylsulfonyl)-1H-pyrazol-4-yl)pyrimidin-4-yl)-N$^4$-(3,3-difluorocyclopentyl)-5-(1-(difluoromethyl)-1H-pyrazol-3-yl)pyridine-2,4-diamine Step 1. 2-Chloro-N-(3,3-difluorocyclopentyl)-5-(1-(difluoromethyl)-1H-pyrazol-3-yl)pyridin-4-amine The title compound as an off white solid (100 mg) was prepared in the same fashion as Reference Example 15, except that 3,3-difluorocyclopentanamine hydrochloride (66 mg, 0.42 mmol) was used instead of (1s,4s)-4-amino-1-methylcyclohexan-1-ol. $^1$H-NMR (CDCl$_3$, 400 MHz) δ 8.40 (s, 1H), 8.27 (d, 1H), 7.89 (d, 1H), 7.19 (t, 1H), 6.85 (d, 1H), 6.56 (s, 1H), 4.15-4.10 (m, 1H), 2.73-2.60 (m, 1H), 2.38-2.12 (m, 4H), 2.05-1.96 (m, 1H); MS (ESI) m/z=349.1 (M+H)$^+$ Step 2. N$^2$-(2-(1-(Cyclopropylsulfonyl)-1H-pyrazol-4-yl)pyrimidin-4-yl)-N$^4$-(3,3-difluorocyclopentyl)-5-(1-(difluoromethyl)-1H-pyrazol-3-yl)pyridine-2,4-diamine The title compound as a white solid (9 mg) was prepared in the same fashion as Step 2 in Example 1, except that 2-chloro-N-(3,3-difluorocyclopentyl)-5-(1-(difluoromethyl)-1H-pyrazol-3-yl)pyridin-4-amine (48 mg, 0.136 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46-8.43 (m, 2H), 8.40 (s, 1H), 8.28 (d, 1H), 7.88 (s, 1H), 7.35 (s, 1H), 7.24 (d, 1H), 7.20 (t, 1H), 7.10 (s, 1H), 6.84 (s, 1H), 4.28-4.26 (m, 1H), 2.85-2.80 (m, 1H), 2.74-2.64 (m, 1H), 2.43-2.18 (m, 5H), 2.06-2.00 (m, 1H), 1.27-1.23 (m, 2H); MS (ESI) m/z=578.2 (M+H)$^+$ Example 180. $N^2$-(2-(1-(2,2-Difluoroethyl)-1H-pyrazol-4-yl)pyrimidin-4-yl)-5-(1-(difluoromethyl)-1H-pyrazol-3-yl)-$N^4$-(3-fluorocyclohexyl)pyridine-2,4-diamine Step 1. 2-Chloro-5-(1-(difluoromethyl)-1H-pyrazol-3-yl)-N-(3-fluorocyclohexyl)pyridin-4-amine The title compound as an off white solid (95 mg) was prepared in the same fashion as Reference Example 15, except that 3-fluorocyclohexanamine hydrochloride (65 mg, 0.42 mmol) was used instead of (1s,4s)-4-amino-1-methylcyclohexan-1-ol. $^1$H-NMR (CDCl$_3$, 400 MHz) δ 8.48-8.37 (m, 1H), 7.91-7.87 (m, 2H), 7.34-7.03 (m, 1H), 6.84 (d, 1H), 6.64-6.56 (m, 1H), 5.06-4.78 (m, 1H), 3.85-3.69 (m, 1H), 2.42-2.40 (m, 1H), 2.13-2.10 (m, 1H), 2.06-1.59 (m, 5H), 1.52-1.39 (m, 1H), 1.29-1.25 (m, 1H); MS (ESI) m/z=345.1 (M+H)$^+$ Step 2. $N^2$-(2-(1-(2,2-Difluoroethyl)-1H-pyrazol-4-yl)pyrimidin-4-yl)-5-(1-(difluoromethyl)-1H-pyrazol-3-yl)-$N^4$-(3-fluorocyclohexyl)pyridine-2,4-diamine The title compound as a white solid (3.5 mg) was prepared in the same fashion as Step 2 in Example 1, except that 2-chloro-5-(1-(difluoromethyl)-1H-pyrazol-3-yl)-N-(3-fluorocyclohexyl)pyridin-4-amine (47 mg, 0.136 mmol) prepared in Step 1 and 2-(1-(2,2-difluoroethyl)-1H-pyrazol-4-yl)pyrimidin-4-amine (31 mg, 0.136 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.41-8.38 (m, 2H), 8.26-8.23 (m, 1H), 8.19-8.17 (m, 1H), 7.89-7.86 (m, 2H), 7.34 (s, 1H), 7.22-7.19 (m, 1H), 7.06-7.01 (m, 1H), 6.83 (d, 1H), 6.16 (tt, 1H), 5.11-4.99 (m, 1H), 4.55 (td, 2H), 4.00-3.97 (m, 1H), 2.46 (s, 1H), 2.20-2.18 (m, 1H), 2.05-2.02 (m, 1H), 1.87-1.63 (m, 4H), 1.46-1.27 (m, 1H); MS (ESI) m/z=534.2 (M+H)$^+$ Example 181. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(3-fluorocyclohexyl)pyridine-2,4-diamine The title compound as a white solid (3.5 mg) was prepared in the same fashion as Step 2 in Example 1, except that 2-chloro-5-(1-(difluoromethyl)-1H-pyrazol-3-yl)-N-(3-fluorocyclohexyl)pyridin-4-amine (47 mg, 0.136 mmol) prepared in Step 1 of Example 180 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66-8.65 (m, 1H), 8.54 (s, 1H), 8.46-8.45 (m, 1H), 8.45-8.43 (m, 2H), 8.40-8.37 (m, 1H), 7.90-7.86 (m, 2H), 7.53-7.52 (m, 1H), 7.38-7.35 (m, 1H), 7.14 (t, 1H), 6.83- 6.80 (m, 2H), 5.04-4.86 (m, 1H), 4.13-3.88 (m, 1H), 2.85-2.81 (m, 1H), 2.14-2.02 (m, 2H), 1.94-1.89 (m, 4H), 1.96-1.67 (m, 2H), 1.55 (s, 2H), 1.27-1.20 (m, 2H); MS (ESI) m/z=574.2 (M+H)$^+$ Example 182. (1s,4s)-4-((2-((2-(1-(Cyclopropylsulfonyl)-1H-pyrazol-4-yl)pyrimidin-4-yl)amino)-5-(3-methyl-4-(trifluoromethyl)-1H-pyrazol-1-yl)pyridin-4-yl)amino)-1-methylcyclohexan-1-ol Step 1. (1s,4s)-4-((2-Chloro-5-(3-methyl-4-(trifluoromethyl)-1H-pyrazol-1-yl)pyridin-4-yl)amino)-1-methylcyclohexan-1-ol The title compound as an off white solid (73 mg) was prepared in the same fashion as Step 1 in Example 102, except 3-methyl-4-(trifluoromethyl)-1H-pyrazole (55 mg, 0.367 mmol) was used instead of ethyl pyrazole-3-carboxylate. $^1$H-NMR (CDCl$_3$, 400 MHz) δ 7.97 (s, 1H), 7.90 (s, 1H), 7.74 (s, 1H), 6.63 (s, 1H), 6.52 (d, 1H), 3.31-3.29 (m, 1H), 2.43 (d, 3H), 2.06-1.93 (m, 2H), 1.77-1.74 (m, 3H), 1.68-1.55 (m, 6H), 1.31 (s, 3H); MS (ESI) m/z=389.0 (M+H)$^+$ Step 2. (1s,4s)-4-((2-((2-(1-(Cyclopropylsulfonyl)-1H-pyrazol-4-yl)pyrimidin-4-yl)amino)-5-(3-methyl-4-(trifluoromethyl)-1H-pyrazol-1-yl)pyridin-4-yl)amino)-1-methylcyclohexan-1-ol The title compound as a white solid (13.7 mg) was prepared in the same fashion as Step 2 in Example 1, except (1s,4s)-4-((2-chloro-5-(3-methyl-4-(trifluoromethyl)-1H-pyrazol-1-yl)pyridin-4-yl)amino)-1-methylcyclohexan-1-ol (70 mg, 0.18 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47-8.44 (m, 2H), 7.94 (s, 1H), 7.87 (s, 1H), 7.34-7.29 (m, 2H), 7.08 (s, 1H), 6.15 (d, 1H), 3.43 (s, 1H), 2.86-2.80 (m, 1H), 2.46 (s, 3H), 1.98-1.95 (m, 2H), 1.74-1.55 (m, 6H), 1.54-1.52 (m, 1H), 1.31 (s, 3H), 1.26-1.21 (m, 2H), 1.10 (s, 1H); MS (ESI) m/z=618.3 (M+H)$^+$ Example 183. (1s,4s)-4-((2-((2-(1-(Cyclopropylsulfonyl)-1H-pyrazol-4-yl)pyrimidin-4-yl)amino)-5-(3-(methylsulfonyl)-1H-pyrazol-1-yl)pyridin-4-yl)amino)-1-methylcyclohexan-1-ol Step 1. (1s,4s)-4-((2-Chloro-5-(3-(methylsulfonyl)-1H-pyrazol-1-yl)pyridin-4-yl)amino)-1-methylcyclohexan-1-ol The title compound as an off white solid (50 mg) was prepared in the same fashion as Step 1 in Example 102, except 3-methylsulfonyl-1H-pyrazole (54 mg, 0.367 mmol) was used instead of ethyl pyrazole-3-carboxylate. $^1$H-NMR (CDCl$_3$, 400 MHz) δ 8.07 (s, 1H), 7.83 (s, 1H), 7.05 (s, 1H), 6.68 (s, 1H), 6.41 (d, 1H), 3.41 (s, 1H), 3.24 (s, 3H), 1.94-1.91 (m, 2H), 1.88-1.62 (m, 8H), 1.31 (s, 3H); MS (ESI) m/z=385.0 (M+H)$^+$ Step 2. (1s,4s)-4-((2-((2-(1-(Cyclopropylsulfonyl)-1H-pyrazol-4-yl)pyrimidin-4-yl)amino)-5-(3-(methylsulfonyl)-1H-pyrazol-1-yl)pyridin-4-yl)amino)-1-methylcyclohexan-1-ol The title compound as a white solid (10 mg) was prepared in the same fashion as Step 2 in Example 1, except (1s,4s)-

4-((2-chloro-5-(3-(methylsulfonyl)-1H-pyrazol-1-yl)pyridin-4-yl)amino)-1-methylcyclohexan-1-ol (38 mg, 0.099 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.47-8.45 (m, 2H), 8.40 (s, 1H), 7.82 (s, 1H), 7.38 (s, 1H), 7.25-7.21 (m, 2H), 7.04 (s, 1H), 6.16 (d, 1H), 3.59 (s, 1H), 3.27 (s, 3H), 2.87-2.81 (m, 1H), 2.02 (s, 2H), 1.92-1.72 (m, 5H), 4.65-1.56 (m, 2H), 1.30 (s, 3H), 1.26-1.21 (m, 2H); MS (ESI) m/z=614.1 (M+H)$^+$ Example 184. (1s,4s)-4-((2-((2-(1-(Cyclopropylsulfonyl)-1H-pyrazol-4-yl)pyrimidin-4-yl)amino)-5-(4-methyl-1H-pyrazol-1-yl)pyridin-4-yl)amino)-1-methylcyclohexan-1-ol Step 1. (1s,4s)-4-((2-Chloro-5-(4-methyl-1H-pyrazol-1-yl)pyridin-4-yl)amino)-1-methylcyclohexan-1-ol The title compound as an off white solid (95 mg) was prepared in the same fashion as Step 1 in Example 102, except 4-methylpyrazole (31 mg, 0.378 mmol) was used instead of ethyl pyrazole-3-carboxylate. $^1$H-NMR (CDCl$_3$, 400 MHz) δ 7.97 (s, 1H), 7.57 (s, 1H), 7.50 (s, 1H), 6.95 (d 1H), 6.59 (s, 1H), 3.29-3.28 (m, 1H), 2.17 (s, 3H), 1.91-1.88 (m, 2H), 1.75-1.54 (m, 6H), 1.29 (s, 3H); MS (ESI) m/z=320.9 (M+H)$^+$ Step 2. (1s,4s)-4-((2-((2-(1-(Cyclopropylsulfonyl)-1H-pyrazol-4-yl)pyrimidin-4-yl)amino)-5-(4-methyl-1H-pyrazol-1-yl)pyridin-4-yl)amino)-1-methylcyclohexan-1-ol The title compound as a white solid (2.5 mg) was prepared in the same fashion as Step 2 in Example 1, except (1s,4s)-4-((2-chloro-5-(4-methyl-1H-pyrazol-1-yl)pyridin-4-yl)amino)-1-methylcyclohexan-1-ol (43 mg, 0.134 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (MeOD, 400 MHz) δ 8.96 (s, 1H), 8.61 (d, 1H), 8.58 (s, 1H), 8.31 (s, 1H), 7.92 (s, 1H), 7.73 (s, 1H), 6.98 (d, 1H), 6.66 (s, 1H), 3.57-3.56 (m, 1H), 3.07-3.05 (m, 1H), 2.21 (s, 3H), 1.94-1.90 (m, 2H), 1.82-1.74 (m, 4H), 1.61-1.54 (m, 2H), 1.47 (s, 2H), 1.33-1.26 (m, 7H); MS (ESI) m/z=550.2 (M+H)$^+$ Example 185. N$^2$-(2-(1-(Cyclopropylsulfonyl)-1H-pyrazol-4-yl)pyrimidin-4-yl)-N$^4$-((1s,4s)-4-(2,2-difluoroethyl)cyclohexyl)-5-(1-(difluoromethyl)-1H-pyrazol-3-yl)pyridine-2,4-diamine Step 1. tert-Butyl ((1s,4s)-4-(2,2-difluoroethyl)cyclohexyl)carbamate The title compound as a yellow solid (350 mg) was prepared in the same fashion as Step 1 in Example 157, except that tert-butyl ((1s,4s)-4-(2-oxoethyl)cyclohexyl)carbamate (300 mg, 1.243 mmol) was used instead of tert-butyl ((1s,4s)-4-formylcyclohexyl)carbamate. $^1$H-NMR (CDCl$_3$, 400 MHz) δ 5.87 (tt, 1H), 4.60 (s, 1H), 3.40-3.26 (m, 2H), 1.81-1.74 (m, 2H), 1.64 (s, 7H), 1.46 (s, 9H), 1.30-1.27 (m, 3H)

Step 2. (1s,4s)-4-(2,2-Difluoroethyl)cyclohexan-1-amine

The title compound as a yellow solid (250 mg) was prepared in the same fashion as Step 2 in Example 155, except that tert-butyl ((1s,4s)-4-(2,2-difluoroethyl)cyclohexyl)carbamate (350 mg, 1.329 mmol) prepared in Step1 was used instead of tert-butyl (tert-butoxycarbonyl)(2-((1-(2,2-difluoroethyl)-1H-pyrazol-5-yl)amino)pyrimidin-4-yl)carbamate. $^1$H-NMR (CDCl$_3$, 400 MHz) δ 7.88 (s, 2H), 5.87 (t, 1H), 3.35 (tt, 2H), 1.88-1.77 (m, 6H), 1.68 (s, 1H), 1.58-1.51 (m, 3H)

Step 3. 2-Chloro-N-((1s,4s)-4-(2,2-difluoroethyl)cyclohexyl)-5-(1-(difluoromethyl)-1H-pyrazol-3-yl)pyridin-4-amine The title compound as a pale yellow solid (35 mg) was prepared in the same fashion as Reference Example 15, except that (1s,4s)-4-(2,2-difluoroethyl)cyclohexan-1-amine (50 mg, 0.202 mmol) prepared in Step 2 was used instead of (1s,4s)-4-amino-1-methylcyclohexan-1-ol. $^1$H-NMR (CDCl$_3$, 400 MHz) δ 8.38 (s, 1H), 8.31 (d, 1H), 7.88 (s, 1H), 7.17 (t, 1H), 6.86 (s, 1H), 6.59 (s, 1H), 5.91 (tt, 1H), 3.84 (s, 1H), 1.92-1.81 (m, 3H), 1.75-1.67 (m, 5H), 1.41-1.38 (m, 2H), 1.27 (s, 1H); MS (ESI) m/z=391.0 (M+H)$^+$ Step 4. N$^2$-(2-(1-(Cyclopropylsulfonyl)-1H-pyrazol-4-yl)pyrimidin-4-yl)-N$^4$-((1s,4s)-4-(2,2-difluoroethyl)cyclohexyl)-5-(1-(difluoromethyl)-1H-pyrazol-3-yl)pyridine-2,4-diamine The title compound as a white solid (7 mg) was prepared in the same fashion as Step 2 in Example 1, except 2-chloro-N-((1s,4s)-4-(2,2-difluoroethyl)cyclohexyl)-5-(1-(difluoromethyl)-1H-pyrazol-3-yl)pyridin-4-amine (31 mg, 0.08 mmol) prepared in Step 3 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.41 (d, 1H), 8.39 (s, 1H), 8.32 (d, 1H), 7.87 (s, 1H), 7.33 (s, 1H), 7.18 (t, 1H), 7.13 (d, 1H), 6.85 (s, 1H), 5.92 (tt, 1H), 4.01-3.98 (m, 1H), 2.88-2.81 (m, 1H), 2.05-2.01 (m, 2H), 1.86-1.66 (m, 7H), 1.47-1.38 (m, 2H), 1.30-1.27 (m, 2H); MS (ESI) m/z=620.2 (M+H)$^+$ Example 186. (1s,4s)-4-((2-((2-(1-(Cyclopropylsulfonyl)-1H-pyrazol-4-yl)pyrimidin-4-yl)amino)-5-(4-methyl-3-(trifluoromethyl)-1H-pyrazol-1-yl)pyridin-4-yl)amino)-1-methylcyclohexan-1-ol Step 1. (1s,4s)-4-((2-Chloro-5-(4-methyl-3-(trifluoromethyl)-1H-pyrazol-1-yl)pyridin-4-yl)amino)-1-methylcyclohexan-1-ol The title compound as an off white solid (97 mg) was prepared in the same fashion as Step 1 in Example 102, except 4-methyl-3-(trifluoromethyl)-1H-pyrazole (57 mg, 0.378 mmol) was used instead of ethyl pyrazole-3-carboxylate. $^1$H-NMR (CDCl$_3$, 400 MHz) δ 8.02 (s, 1H), 7.58 (s, 1H), 6.63 (s, 2H), 3.30 (s, 1H), 2.26 (s, 3H), 1.91-1.89 (m, 3H), 1.76-1.53 (m, 5H), 1.31 (s, 3H), 1.09 (s, 1H); MS (ESI) m/z=388.9 (M+H)$^+$ Step 2. (1s,4s)-4-((2-((2-(1-(Cyclopropylsulfonyl)-1H-pyrazol-4-yl)pyrimidin-4-yl)amino)-5-(4-methyl-3-(trifluoromethyl)-1H-pyrazol-1-yl)pyridin-4-yl)amino)-1-methylcyclohexan-1-ol The title compound as a white solid (12.7 mg) was prepared in the same fashion as Step 2 in Example 1, except (1s,4s)-4-((2-chloro-5-(4-methyl-3-(trifluoromethyl)-1H-pyrazol-1-yl)pyridin-4-yl)amino)-1-methylcyclohexan-1-ol (48 mg, 0.123 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46-8.44 (m, 2H), 7.99 (s, 1H), 7.54 (d, 1H), 7.39 (s, 1H), 7.29 (s, 1H), 7.09 (s, 1H), 6.24 (d, 1H), 3.44 (s, 1H), 2.86-2.80 (m, 1H), 2.28 (s, 3H), 1.94 (s, 2H), 1.73-1.56 (m, 6H), 1.47-1.23 (m, 6H), 1.10 (s, 1H); MS (ESI) m/z=618.2 (M+H)$^+$ Example 187. (1s,4s)-4-((2-((2-(1-(Cyclopropylsulfonyl)-1H-pyrazol-4-yl)pyrimidin-4-yl)amino)-5-(3-(difluoromethoxy)-1H-pyrazol-1-yl)pyridin-4-yl)amino)-1-methylcyclohexan-1-ol Step 1. (1s,4s)-4-((2-Chloro-5-(3-(difluoromethoxy)-1H-pyrazol-1-yl)pyridin-4-yl)amino)-1-methylcyclohexan-1-ol The title compound as an off white solid (86 mg) was prepared in the same fashion as Step 1 in Example 102, except 3-(difluoromethoxy)-1H-pyrazole (51 mg, 0.378 mmol) was used instead of ethyl pyrazole-3-carboxylate. $^1$H-NMR (CDCl$_3$, 400 MHz) δ 7.95 (s, 1H), 7.59 (s, 1H), 6.85 (t, 1H), 6.61 (s, 1H), 6.35 (d, 1H), 6.12 (s, 1H), 3.29 (d, 1H), 1.91-1.89 (m, 2H), 1.76-1.59 (m, 5H), 1.31 (s, 3H), 1.01 (s, 1H); MS (ESI) m/z=373.0 (M+H)$^+$ Step 2. (1s,4s)-4-((2-((2-(1-(Cyclopropylsulfonyl)-1H-pyrazol-4-yl)pyrimidin-4-yl)amino)-5-(3-(difluoromethoxy)-1H-pyrazol-1-yl)pyridin-4-yl)amino)-1-methylcyclohexan-1-ol The title compound as a white solid (9 mg) was prepared in the same fashion as Step 2 in Example 1, except (1s,4s)-4-((2-chloro-5-(3-(difluoromethoxy)-1H-pyrazol-1-yl)pyridin-4-yl)amino)-1-methylcyclohexan-1-ol (42 mg, 0.113 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.58 (s, 1H), 8.65 (s, 1H), 8.46-8.43 (m, 2H), 7.84 (s, 1H), 7.57 (s, 2H), 7.11 (d, 1H), 6.89 (t, 1H), 6.96 (d, 1H), 6.14 (s, 1H), 4.14-4.12 (m, 1H), 3.51 (s, 1H), 2.84-2.82 (m, 1H), 2.05 (s, 1H), 1.98-1.96 (m, 2H), 1.75-1.69 (m, 4H), 1.61-1.54 (m, 4H), 1.26-1.22 (m, 6H); MS (ESI) m/z=602.2 (M+H)$^+$ Example 188. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(hydroxymethyl)cyclohexan-1-ol Step 1. (1s,4s)-4-((2-Chloro-5-(1-(difluoromethyl)-1H-pyrazol-3-yl)pyridin-4-yl)amino)-1-(hydroxymethyl)cyclohexan-1-ol The title compound as a white solid (287.3 mg) was prepared in the same fashion as Reference Example 15, except that (1s,4s)-4-amino-1-(hydroxymethyl)cyclohexan-1-ol (220 mg, 1.515 mmol) was used instead of (1s,4s)-4-amino-1-methylcyclohexan-1-ol. MS (ESI) m/z=373.1 (M+H)$^+$ Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(hydroxymethyl)cyclohexan-1-ol The title compound as pale yellow solid (50.2 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-(hydroxymethyl)cyclohexan-1-ol (77 mg, 0.21 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.99 (s, 1H), 8.64 (s, 1H), 8.51 (s, 1H), 8.44 (s, 1H), 8.43 (d, 1H), 8.33 (s, 1H), 7.96 (d, 1H), 7.88 (t, 1H), 7.73 (s, 1H), 7.14 (s, 2H), 4.54 (brs, 1H), 4.03 (s, 1H), 3.25-3.20 (m, 3H), 1.91-1.89 (m, 2H), 1.64-1.48 (m, 6H), 1.34 (s, 2H), 1.26-1.23 (m, 2H); MS (ESI) m/z=602.2 (M+H)$^+$ Example 189. ((1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutyl)methanol Step 1. ((1r,3r)-3-(((2-Chloro-5-(1-(difluoromethyl)-1H-pyrazol-3-yl)pyridin-4-yl)amino)methyl)cyclobutyl)methanol The title compound as a white solid (200.6 mg) was prepared in the same fashion as Reference Example 15, except that ((1r,3r)-3-(aminomethyl)cyclobutyl)methanol hydrochloride (184 mg, 1.212 mmol) was used instead of (1s,4s)-4-amino-1-methylcyclohexan-1-ol. MS (ESI) m/z=343.1 (M+H)$^+$ Step 2. ((1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutyl)methanol The title compound as pale yellow solid (121.9 mg) was prepared in the same fashion as Step 2 in Example 1, except that ((1r,3r)-3-(((2-chloro-5-(1-(difluoromethyl)-1H-pyrazol-3-yl)pyridin-4-yl)amino)methyl)cyclobutyl)methanol (213 mg, 0.622 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.18 (s, 1H), 8.66 (s, 1H), 8.51 (s, 1H), 8.45 (s, 1H), 8.42 (d, 1H), 8.32 (d, 1H), 8.06 (t, 1H), 7.84 (t, 1H), 7.44 (s, 2H), 7.15 (d, 1H), 4.52 (t, 1H), 3.44 (t, 2H), 3.38 (t, 2H), 3.28-3.23 (m, 1H), 2.70-2.62 (m, 1H), 2.45-2.38 (m, 1H), 1.91-1.87 (m, 4H), 1.36-1.32 (m, 2H), 1.27-1.22 (m, 2H); MS (ESI) m/z=572.2 (M+H)$^+$ Example 190. (4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-fluorocyclohexyl)methanol Step 1. (4-((2-Chloro-5-(1-(difluoromethyl)-1H-pyrazol-3-yl)pyridin-4-yl)amino)-1-fluorocyclohexyl)methanol The title compound as a white solid (302.1 mg) was prepared in the same fashion as Reference Example 15, except that (4-amino-1-fluoro-cyclohexyl)methanol (223 mg, 1.515 mmol) was used instead of (1s,4s)-4-amino-1-methylcyclohexan-1-ol. MS (ESI) m/z=375.1 (M+H)$^+$ Step 2. (4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-fluorocyclohexyl)methanol The title compound as pale yellow solid (7.6 mg) was prepared in the same fashion as Step 2 in Example 1, except that (4-((2-chloro-5-(1-(difluoromethyl)-1H-pyrazol-3-yl)pyridin-4-yl)amino)-1-fluorocyclohexyl)methanol (78 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.01 (s, 1H), 8.65 (s, 1H), 8.53 (s, 1H), 8.51 (s, 1H), 8.43 (d, 1H), 8.33 (d, 1H), 8.05 (d, 1H), 7.90 (t, 1H), 7.63 (s, 1H), 7.24 (s, 1H), 7.15 (d, 1H), 4.96 (t, 1H), 3.53 (s, 1H), 3.46 (d, 1H), 3.40 (d, 1H), 3.28-3.22 (m, 1H), 2.04-2.00 (m, 2H), 1.92-1.88 (m, 2H), 1.66-1.49 (m, 4H), 1.37-1.33 (m, 2H), 1.27-1.23 (m, 2H); MS (ESI) m/z=604.1 (M+H)$^+$ Example 191. N$^2$-(2-(1-(Cyclopropylsulfonyl)-1H-pyrazol-4-yl)pyrimidin-4-yl)-N$^4$-(3-((2,2-difluoroethyl)amino)cyclohexyl)-5-(1-(difluoromethyl)-1H-pyrazol-3-yl)pyridine-2,4-diamine Step 1. N$^1$-(2-Chloro-5-(1-(difluoromethyl)-1H-pyrazol-3-yl)pyridin-4-yl)-N$^3$-(2,2-difluoroethyl)cyclohexane-1,3-diamine The title compound as a white solid (425.6 mg) was prepared in the same fashion as Reference Example 15, except that N$^1$-(2,2-difluoroethyl)cyclohexane-1,3-diamine (324 mg, 1.817 mmol) was used instead of (1s,4s)-4-amino-1-methylcyclohexan-1-ol. MS (ESI) m/z=406.1 (M+H)$^+$ Step 2. N$^2$-(2-(1-(Cyclopropylsulfonyl)-1H-pyrazol-4-yl)pyrimidin-4-yl)-N$^4$-(3-((2,2-difluoroethyl)amino)cyclohexyl)-5-(1-(difluoromethyl)-1H-pyrazol-3-yl)pyridine-2,4-diamine The title compound as pale yellow solid (190.8 mg) was prepared in the same fashion as Step 2 in Example 1, except that N$^1$-(2-chloro-5-(1-(difluoromethyl)-1H-pyrazol-3-yl)pyridin-4-yl)-N$^3$-(2,2-difluoroethyl)cyclohexane-1,3-diamine (337 mg, 0.829 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.42 (d, 1H), 8.41 (s, 1H), 8.17 (d, 1H), 7.87 (s, 1H), 7.63 (s, 1H), 7.22 (s, 1H), 7.19 (t, 1H), 7.17 (d, 1H), 6.84 (s, 1H), 5.82 (tt, 1H), 4.12 (s, 1H), 3.08-2.88 (m, 3H), 2.88-2.81 (m, 1H), 2.14-2.11 (m, 1H), 1.98-1.95 (m, 1H), 1.84-1.78 (m, 3H), 1.69-1.61 (m, 2H), 1.56-1.52 (m, 2H), 1.32-1.27 (m, 1H), 1.25-1.20 (m, 2H); MS (ESI) m/z=635.1 (M+H)$^+$ Example 192. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(((1r,4r)-4-((methylamino)methyl)cyclohexyl)methyl)pyridine-2,4-diamine Step 1. tert-Butyl (((1r,4r)-4-(((2-chloro-5-(1-(difluoromethyl)-1H-pyrazol-3-yl)pyridin-4-yl)amino)methyl)cyclohexyl)methyl)(methyl)carbamate The title compound as a white solid (270 mg) was prepared in the same fashion as Reference Example 15, except that tert-butyl (((1r,4r)-4-(aminomethyl)cyclohexyl)methyl)(methyl)carbamate (233 mg, 0.909 mmol) was used instead of (1s,4s)-4-amino-1-methylcyclohexan-1-ol. MS (ESI) m/z=484.2 (M+H)$^+$ Step 2. tert-Butyl (((1r,4r)-4-(((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methyl)(methyl)carbamate The title compound as an off-white solid (60 mg) was prepared in the same fashion as Step 2 in Example 1, except that tert-butyl (((1r,4r)-4-(((2-chloro-5-(1-(difluoromethyl)-1H-pyrazol-3-yl)pyridin-4-yl)amino)methyl)cyclohexyl)methyl)(methyl)carbamate (261 mg, 0.539 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=713.2 (M+H)$^+$ Step 3. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(((1r,4r)-4-((methylamino)methyl)cyclohexyl)methyl)pyridine-2,4-diamine The suspension of tert-butyl (((1r,4r)-4-(((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methyl)(methyl)carbamate (60 mg, 0.084 mmol) prepared in Step 2 and TFA (0.5 mL) in DCM (5 mL) was stirred at room temperature for overnight, and then concentrated. The residue was diluted in DCM, added 1 N NaOH soln. (>pH8), washed by water, dried over MgSO$_4$, and then concentrated. The crude product was purified by column chromatography (MeOH/DCM=0-20%) to yield N$^2$-(2-(1-(cyclopropylsulfonyl)-1H-pyrazol-4-yl)pyrimidin-4-yl)-5-(1-(difluoromethyl)-1H-pyrazol-3-yl)-N$^4$-(((1r,4r)-4-((methylamino)methyl)cyclohexyl)methyl)pyridine-2,4-diamine (31 mg) as a white solid. $^1$H-NMR (MeOD, 400 MHz) δ 8.76 (s, 1H), 8.47 (s, 1H), 8.41 (s, 1H), 8.37 (d, 1H), 8.12 (d, 1H), 7.56 (t, 1H), 7.30 (s, 1H), 7.25 (d, 1H), 6.98 (d, 1H), 4.63 (s, 2H), 3.29 (d, 2H), 3.07-3.01 (m, 1H), 2.89 (d, 2H), 2.71 (s, 3H), 2.03 (d, 2H), 1.90 (d, 2H), 1.81-1.68 (m, 2H), 1.47-1.43 (m, 2H), 1.33-1.24 (m, 4H), 1.19-1.10 (m, 2H); MS (ESI) m/z=613.3 (M+H)$^+$ Example 193. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(((1r,4r)-4-(methylamino)cyclohexyl)methyl)pyridine-2,4-diamine Step 1. tert-Butyl ((1r,4r)-4-(((2-chloro-5-(1-(difluoromethyl)-1H-pyrazol-3-yl)pyridin-4-yl)amino)methyl)cyclohexyl)(methyl)carbamate The title compound as a white solid (268.1 mg) was prepared in the same fashion as Reference Example 15, except that tert-butyl ((1r,4r)-4-(aminomethyl)cyclohexyl)(methyl)carbamate (220 mg, 0.909 mmol) was used instead of (1s,4s)-4-amino-1-methylcyclohexan-1-ol. MS (ESI) m/z=470.2 (M+H)$^+$ Step 2. tert-Butyl ((1r,4r)-4-(((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)(methyl)carbamate The title compound as an off white solid (82 mg) was prepared in the same fashion as Step 2 in Example 1, except that tert-butyl ((1r,4r)-4-(((2-chloro-5-(1-(difluoromethyl)-1H-pyrazol-3-yl)pyridin-4-yl)amino)methyl)cyclohexyl)(methyl)carbamate (253 mg, 0.539 mmol) prepared in Step 1 was used instead of 2-chloro-5-(1-cyclopropyl-1H-pyrazol-4-yl)-4-((1-methyl-1H-pyrazol-4-yl)ethynyl)pyridine. MS (ESI) m/z=699.2 (M+H)$^+$ Step 3. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(((1r,4r)-4-(methylamino)cyclohexyl)methyl)pyridine-2,4-diamine The title compound as an off-white solid (41.3 mg) was prepared in the same fashion as Step 3 in Example 192, except that tert-butyl ((1r,4r)-4-(((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)(methyl)carbamate (82 mg, 0.117 mmol) prepared in Step 2 was used instead of tert-butyl (((1r,4r)-4-(((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methyl)(methyl)carbamate. $^1$H-NMR (MeOD, 400 MHz) δ 8.70 (s, 1H), 8.42 (s, 1H), 8.34 (s, 1H), 8.30 (d, 1H), 8.07 (d, 1H), 7.53 (t, 1H), 7.28 (d, 1H), 7.25 (s, 1H), 6.93 (d, 1H), 3.20 (d, 2H), 3.05-3.00 (m, 1H), 2.38 (s, 4H), 2.04 (d, 2H), 1.96 (d, 2H), 1.74 (s, 1H), 1.47-1.42 (m, 2H), 1.29-1.24 (m, 4H), 1.20-1.10 (m, 2H); MS (ESI) m/z=599.2 (M+H)$^+$ Example 194. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(3-((2-fluoroethyl)amino)cyclohexyl)pyridine-2,4-diamine Step 1. $N^1$-(2-Chloro-5-(1-(difluoromethyl)-1H-pyrazol-3-yl)pyridin-4-yl)-$N^3$-(2-fluoroethyl)cyclohexane-1,3-diamine The title compound as a white solid (406 mg) was prepared in the same fashion as Reference Example 15, except that $N^1$-(2-fluoroethyl)cyclohexane-1,3-diamine (291 mg, 1.817 mmol) was used instead of (1s,4s)-4-amino-1-methylcyclohexan-1-ol. MS (ESI) m/z=388.1 (M+H)$^+$ Step 2. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(3-((2-fluoroethyl)amino)cyclohexyl)pyridine-2,4-diamine The title compound as pale yellow solid (262 mg) was prepared in the same fashion as Step 2 in Example 1, except that $N^1$-(2-chloro-5-(1-(difluoromethyl)-1H-pyrazol-3-yl)pyridin-4-yl)-$N^3$-(2-fluoroethyl)cyclohexane-1,3-diamine (354 mg, 0.912 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.40 (d, 1H), 8.39 (s, 1H), 8.18 (d, 1H), 7.86 (d, 2H), 7.20 (s, 2H), 7.20 (t, 1H), 6.83 (d, 1H), 4.59 (t, 1H), 4.47 (t, 1H), 4.12 (brs, 1H), 2.99-2.81 (m, 4H), 2.13-2.10 (m, 1H), 1.98-1.96 (m, 1H), 1.86-1.77 (m, 3H), 1.71-1.61 (m, 2H), 1.56-1.52 (m, 2H), 1.34-1.19 (m, 4H); MS (ESI) m/z=617.2 (M+H)$^+$ Example 195. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((dimethylamino)methyl)cyclohexyl)pyridine-2,4-diamine Step 1. 2-Chloro-5-(1-(difluoromethyl)-1H-pyrazol-3-yl)-N-((1s,4s)-4-((dimethylamino)methyl)cyclohexyl)pyridin-4-amine The title compound as a white solid (297.3 mg) was prepared in the same fashion as Reference Example 15, except that (1s,4s)-4-((dimethylamino)methyl)cyclohexan-1-amine dihydrochloride (278 mg, 1.212 mmol) was used instead of (1s,4s)-4-amino-1-methylcyclohexan-1-ol. MS (ESI) m/z=384.1 (M+H)$^+$ Step 2. $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((dimethylamino)methyl)cyclohexyl)pyridine-2,4-diamine The title compound as pale yellow solid (102.7 mg) was prepared in the same fashion as Step 2 in Example 1, except that 2-chloro-5-(1-(difluoromethyl)-1H-pyrazol-3-yl)-N-((1s,4s)-4-((dimethylamino)methyl)cyclohexyl)pyridin-4-amine (145 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.40 (d, 1H), 8.39 (s, 1H), 8.32 (d, 1H), 7.87 (d, 1H), 7.73 (s, 1H), 7.27 (s, 1H), 7.20 (t, 1H), 7.12 (d, 1H), 6.84 (d, 1H), 4.02-4.00 (m, 1H), 2.87-2.81 (m, 1H), 2.23 (s, 6H), 2.14-2.12 (m, 2H), 2.03-2.00 (m, 2H), 1.83-1.7 (m, 4H), 1.67-1.60 (m, 1H), 1.56-1.52 (m, 2H), 1.32-1.20 (m, 4H); MS (ESI) m/z=613.2 (M+H)$^+$ Example 196. ((2R,5S)-5-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)tetrahydro-2H-pyran-2-yl)methanol Step 1. ((2R,5S)-5-((2-Chloro-5-(1-(difluoromethyl)-1H-pyrazol-3-yl)pyridin-4-yl)amino)tetrahydro-2H-pyran-2-yl)methanol The title compound as a white solid (188.3 mg) was prepared in the same fashion as Reference Example 15, except that ((2R,5S)-5-aminotetrahydro-2H-pyran-2-yl)methanol hydrochloride (152 mg, 0.909 mmol) was used instead of (1s,4s)-4-amino-1-methylcyclohexan-1-ol. MS (ESI) m/z=359.0 (M+H)$^+$ Step 2. ((2R,5S)-5-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)tetrahydro-2H-pyran-2-yl)methanol The title compound as pale yellow solid (53.2 mg) was prepared in the same fashion as Step 2 in Example 1, except that ((2R,5S)-5-((2-Chloro-5-(1-(difluoromethyl)-1H-pyrazol-3-yl)pyridin-4-yl)amino)tetrahydro-2H-pyran-2-yl)methanol (179 mg, 0.498 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 8.65 (s, 1H), 8.53 (s, 1H), 8.48 (s, 1H), 8.44 (d, 1H), 8.34 (d, 1H), 7.89 (t, 1H), 7.88 (d, 1H), 7.60 (brs, 1H), 7.39 (brs, 1H), 7.16 (d, 1H), 4.64 (t, 1H), 4.19-4.15 (m, 1H), 3.62-3.59 (m, 2H), 3.49-3.39 (m, 2H), 3.29-3.22 (m, 1H), 3.10 (t, 1H), 2.24 (d, 1H), 1.80 (d, 1H), 1.61-1.42 (m, 2H), 1.38-1.34 (m, 2H), 1.28-1.22 (m, 2H); MS (ESI) m/z=588.1 (M+H)$^+$ Example 197. (3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)oxetan-3-yl)methanol Step 1. (3-(((2-Chloro-5-(1-(difluoromethyl)-1H-pyrazol-3-yl)pyridin-4-yl)amino)methyl)oxetan-3-yl)methanol The title compound as a white solid (149.6 mg) was prepared in the same fashion as Reference Example 15, except that (3-(aminomethyl)oxetan-3-yl)methanol (106 mg, 0.909 mmol) was used instead of (1s,4s)-4-amino-1-methylcyclohexan-1-ol. MS (ESI) m/z=345.0 (M+H)$^+$ Step 2. (3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)oxetan-3-yl)methanol The title compound as pale yellow solid (17.2 mg) was prepared in the same fashion as Step 2 in Example 1, except that (3-(((2-chloro-5-(1-(difluoromethyl)-1H-pyrazol-3-yl)pyridin-4-yl)amino)methyl)oxetan-3-yl)methanol (114 mg, 0.332 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 8.68 (s, 1H), 8.53 (s, 1H), 8.48 (s, 1H), 8.43 (d, 1H), 8.33 (d, 1H), 8.20 (t, 1H), 7.79 (t, 1H), 7.50-7.45 (m, 2H), 7.16 (d, 1H), 5.11 (t, 1H), 4.42 (q, 4H), 3.75 (d, 2H), 3.63 (d, 2H), 3.30-3.25 (m, 1H), 1.34-1.28 (m, 2H), 1.28-1.24 (m, 2H); MS (ESI) m/z=574.2 (M+H)$^+$ Example 198. ((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol Step 1. ((1r,4r)-4-((2-Chloro-5-(1-(difluoromethyl)-1H-pyrazol-3-yl)pyridin-4-yl)amino)cyclohexyl)methanol The title compound as a white solid (176.4 mg) was prepared in the same fashion as Reference Example 15, except that ((1r,4r)-4-aminocyclohexyl)methanol (117 mg, 0.909 mmol) was used instead of (1s,4s)-4-amino-1-methylcyclohexan-1-ol. MS (ESI) m/z=357.1 (M+H)$^+$ Step 2. ((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol The title compound as pale yellow solid (84 mg) was prepared in the same fashion as Step 2 in Example 1, except that ((1r,4r)-4-((2-chloro-5-(1-(difluoromethyl)-1H-pyrazol-3-yl)pyridin-4-yl)amino)cyclohexyl)methanol (170 mg, 0.477 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.01 (s, 1H), 8.65 (s, 1H), 8.51 (s, 1H), 8.46 (s, 1H), 8.43 (d, 1H), 8.33 (d, 1H), 7.96 (d, 1H), 7.88 (t, 1H), 7.66 (brs, 1H), 7.19 (brs, 1H), 7.14 (d, 1H), 4.44 (t, 1H), 3.27-3.22 (m, 3H), 2.17-2.15 (m, 2H), 1.82-1.79 (m, 2H), 1.44-1.39 (m, 1H), 1.36-1.32 (m, 2H), 1.30-1.20 (m, 4H), 1.10-1.02 (m, 2H); MS (ESI) m/z=586.2 (M+H)$^+$ Example 199. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-((dimethylamino)methyl)cyclohexan-1-ol Step 1. (1s,4s)-4-((2-Chloro-5-(1-(difluoromethyl)-1H-pyrazol-3-yl)pyridin-4-yl)amino)-1-((dimethylamino)methyl)cyclohexan-1-ol The title compound as a white solid (173 mg) was prepared in the same fashion as Reference Example 15, except that (1s,4s)-4-amino-1-((dimethylamino)methyl)cyclohexan-1-ol dihydrochloride (223 mg, 0.909 mmol) was used instead of (1s,4s)-4-amino-1-methylcyclohexan-1-ol. MS (ESI) m/z=400.1 (M+H)$^+$ Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-((dimethylamino)methyl)cyclohexan-1-ol The title compound as pale yellow solid (63.1 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-((dimethylamino)methyl)cyclohexan-1-ol (173 mg, 0.433 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.00 (s, 1H), 8.65 (s, 1H), 8.51 (s, 1H), 8.46 (s, 1H), 8.43 (d, 1H), 8.32 (d, 1H), 7.99 (d, 1H), 7.87 (t, 1H), 7.60 (brs, 1H), 7.27 (brs, 1H), 7.14 (d, 1H), 4.00 (s, 1H), 3.40 (brs, 1H), 3.28-3.21 (m, 1H), 2.24 (s, 6H), 2.21 (s, 2H), 1.88-1.86 (m, 2H), 1.67-1.59 (m, 4H), 1.49-1.43 (m, 2H), 1.36-1.32 (m, 2H), 1.27-1.22 (m, 2H); MS (ESI) m/z=630.1 (M+H)$^+$ Example 200. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(difluoromethyl)cyclohexan-1-ol Step 1. (1s,4s)-4-((2-Chloro-5-(1-(difluoromethyl)-1H-pyrazol-3-yl)pyridin-4-yl)amino)-1-(difluoromethyl)cyclohexan-1-ol The title compound as a white solid (122 mg) was prepared in the same fashion as Reference Example 15, except that (1s,4s)-4-amino-1-(difluoromethyl)cyclohexan-1-ol (100 mg, 0.606 mmol) was used instead of (1s,4s)-4-amino-1-methylcyclohexan-1-ol. MS (ESI) m/z=393.1 (M+H)$^+$ Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(difluoromethyl)cyclohexan-1-ol The title compound as pale yellow solid (42 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-(difluoromethyl)cyclohexan-1-ol (122 mg, 0.311 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.97 (s, 1H), 8.65 (s, 1H), 8.52 (s, 1H), 8.45 (s, 1H), 8.44 (d, 1H), 8.33 (s, 1H), 7.95 (d, 1H), 7.89 (t, 1H), 7.34 (s, 1H), 7.15 (s, 1H), 7.12 (s, 1H), 5.70 (t, 1H), 5.16 (s, 1H), 2.02-1.97 (m, 2H), 1.69-1.52 (m, 6H), 1.34-1.24 (m, 4H); MS (ESI) m/z=622.1 (M+H)$^+$ Example 201. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N,N-dimethylcyclohexane-1-carboxamide Step 1. (1s,4s)-4-((2-Chloro-5-(1-(difluoromethyl)-1H-pyrazol-3-yl)pyridin-4-yl)amino)-N,N-dimethylcyclohexane-1-carboxamide The title compound as a white solid (155 mg) was prepared in the same fashion as Reference Example 15, except that (1s,4s)-4-amino-N,N-dimethylcyclohexane-1-carboxamide hydrochloride (125 mg, 0.606 mmol) was used instead of (1s,4s)-4-amino-1-methylcyclohexan-1-ol. MS (ESI) m/z=398.1 (M+H)$^+$ Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N,N-dimethylcyclohexane-1-carboxamide The title compound as pale yellow solid (67.2 mg) was prepared in the same fashion as Step 2 in Example 1, except that (1s,4s)-4-((2-chloro-5-(1-(difluoromethyl)-1H-pyrazol-3-yl)pyridin-4-yl)amino)-N,N-dimethylcyclohexane-1-carboxamide (148 mg, 0.373 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (d, 1H), 8.67 (s, 1H), 8.46 (s, 1H), 8.39 (d, 1H), 8.37 (s, 1H), 7.89 (d, 1H), 7.84 (brs, 1H), 7.82 (t, 1H), 7.44 (s, 1H), 7.00 (d, 1H), 6.83 (d, 1H), 4.10-4.08 (m, 1H), 3.10 (s, 3H), 2.97 (s, 3H), 2.87-2.81 (m, 1H), 2.75-2.69 (m, 1H), 2.06-1.93 (m, 4H), 1.86-1.71 (m, 4H), 1.56-1.52 (m, 2H), 1.26-1.20 (m, 2H); MS (ESI) m/z=627.2 (M+H)$^+$ Example 202. ((1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol Step 1. ((1S,3S)-3-((2-Chloro-5-(1-(difluoromethyl)-1H-pyrazol-3-yl)pyridin-4-yl)amino)cyclohexyl)methanol The title compound as a white solid (123.6 mg) was prepared in the same fashion as Reference Example 15, except that ((1S,3S)-3-aminocyclohexyl)methanol hydrochloride (100 mg, 0.606 mmol) was used instead of (1s,4s)-4-amino-1-methylcyclohexan-1-ol. MS (ESI) m/z=357.1 (M+H)$^+$ Step 2. ((1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol The title compound as pale yellow solid (39.1 mg) was prepared in the same fashion as Step 2 in Example 1, except that ((1S,3S)-3-((2-chloro-5-(1-(difluoromethyl)-1H-pyrazol-3-yl)pyridin-4-yl)amino)cyclohexyl)methanol (118 mg, 0.332 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.64 (s, 1H), 8.45 (s, 1H), 8.36-8.32 (m, 3H), 7.85 (d, 2H), 7.32 (brs, 1H), 7.21 (t, 1H), 7.02 (d, 1H), 6.80 (d, 1H), 4.07 (brs, 1H), 3.57-3.48 (m, 2H), 2.88-2.81 (m, 2H), 2.14-2.11 (m, 1H), 1.99-1.96 (m, 1H), 1.87-1.63 (m, 6H), 1.56-1.47 (m, 2H), 1.26-1.31 (m, 3H); MS (ESI) m/z=586.2 (M+H)$^+$ Example 203. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(((1s,3s)-3-((dimethylamino)methyl)cyclobutyl)methyl)pyridine-2,4-diamine Step 1. 2-Chloro-5-(1-(difluoromethyl)-1H-pyrazol-3-yl)-N-(((1s,3s)-3-((dimethylamino)methyl)cyclobutyl)methyl)pyridin-4-amine The title compound as a white solid (134 mg) was prepared in the same fashion as Reference Example 15, except that 1-((1s,3s)-3-(aminomethyl)cyclobutyl)-N,N-dimethylmethanamine dihydrochloride (130 mg, 1.212 mmol) was used instead of (1s,4s)-4-amino-1-methylcyclohexan-1-ol. MS (ESI) m/z=370.1 (M+H)$^+$ Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(((1s,3s)-3-((dimethylamino)methyl)cyclobutyl)methyl)pyridine-2,4-diamine The title compound as pale yellow solid (48.8 mg) was prepared in the same fashion as Step 2 in Example 1, except that 2-chloro-5-(1-(difluoromethyl)-1H-pyrazol-3-yl)-N-(((1s,3s)-3-((dimethylamino)methyl)cyclobutyl)methyl)pyridin-4-amine (119 mg, 0.32 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.41 (d, 1H), 8.37 (s, 1H), 7.86 (d, 1H), 7.84 (t, 1H), 7.78 (brs, 1H), 7.24 (s, 1H), 7.22 (t, 1H), 7.09 (s, 1H), 6.83 (d, 1H), 3.34-3.32 (m, 2H), 2.86-2.82 (m, 1H), 2.70-2.60 (m, 1H), 2.49-2.41 (m, 1H), 2.36-2.30 (m, 4H), 2.22 (s, 6H), 1.61-1.51 (m, 4H), 1.24-1.20 (m, 2H); MS (ESI) m/z=599.2 (M+H)$^+$ Example 204. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-(2,2-difluoroethyl)-N-methylcyclohexane-1-carboxamide Step 1. (1s,4s)-4-((2-Chloro-5-(1-(difluoromethyl)-1H-pyrazol-3-yl)pyridin-4-yl)amino)-N-(2,2-difluoroethyl)-N-methylcyclohexane-1-carboxamide The title compound as a white solid (251 mg) was prepared in the same fashion as Reference Example 15, except that (1s,4s)-4-amino-N-(2,2-difluoroethyl)-N-methylcyclohexane-1-carboxamide (156 mg, 0.709 mmol) was used instead of (1s,4s)-4-amino-1-methylcyclohexan-1-ol. MS (ESI) m/z=448.1 (M+H)$^+$ Step 2. (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-(2,2-difluoroethyl)-N-methylcyclohexane-1-carboxamide The title compound as pale yellow solid (44.8 mg) was prepared in the same fashion as Step 2 in Example 1, except that (1s,4s)-4-((2-chloro-5-(1-(difluoromethyl)-1H-pyrazol-3-yl)pyridin-4-yl)amino)-N-(2,2-difluoroethyl)-N-methylcyclohexane-1-carboxamide (186 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.04 (s, 1H), 8.64 (s, 1H), 8.53 (s, 1H), 8.47-8.37 (m, 3H), 8.36 (d, 1H), 7.86 (t, 1H), 7.46 (brs, 1H), 7.43 (brs, 1H), 7.18 (d, 1H), 6.05 (tt, 1H), 3.98 (brs, 1H), 3.70 (td, 2H), 3.30-3.24 (m, 1H), 3.12 (s, 3H), 2.80-2.75 (m, 1H), 1.95-1.92 (m, 2H), 1.83-1.67 (m, 4H), 1.63-1.55 (m, 2H), 1.37-1.34 (m, 2H), 1.30-1.21 (m, 2H); MS (ESI) m/z=677.2 (M+H)$^+$

Example 205. 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)-N,N-dimethylacetamide

Step 1. 2-((1s,4s)-4-((2-Chloro-5-(1-(difluoromethyl)-1H-pyrazol-3-yl)pyridin-4-yl)amino)cyclohexyl)-N,N-dimethylacetamide The title compound as a white solid (150.6 mg) was prepared in the same fashion as Reference Example 15, except that 2-((1s,4s)-4-aminocyclohexyl)-N,N-dimethylacetamide hydrochloride (156 mg, 0.709 mmol) was used instead of (1s,4s)-4-amino-1-methylcyclohexan-1-ol. MS (ESI) m/z=412.1 (M+H)$^+$

Step 2. 2-((1s,4s)-4-((2-((2-(1-Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)-N,N-dimethylacetamide The title compound as pale yellow solid (42.5 mg) was prepared in the same fashion as Step 2 in Example 1, except that 2-((1s,4s)-4-((2-chloro-5-(1-(difluoromethyl)-1H-pyrazol-3-yl)pyridin-4-yl)amino)cyclohexyl)-N,N-dimethylacetamide (116 mg, 0.283 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.45 (s, 1H), 8.38-8.34 (m, 3H), 8.03 (brs, 1H), 7.86 (d, 1H), 7.31 (t, 1H), 7.28 (s, 1H), 7.11 (d, 1H), 6.83 (d, 1H), 4.00-3.99 (m, 1H), 3.02 (s, 3H), 2.95 (s, 3H), 2.87-2.81 (m, 1H), 2.28 (d, 2H), 2.02-1.99 (m, 3H), 1.86-1.72 (m, 4H), 1.55-1.51 (m, 2H), 1.45-1.35 (m, 2H), 1.26-1.20 (m, 2H); MS (ESI) m/z=641.2 (M+H)$^+$

Example 206. N$^2$-(2-(1-(Cyclopropylsulfonyl)-1H-pyrazol-4-yl)pyrimidin-4-yl)-N$^4$-((1s,4s)-4-(((2,2-difluoroethyl)(methyl)amino)methyl)cyclohexyl)-5-(1-(difluoromethyl)-1H-pyrazol-3-yl)pyridine-2,4-diamine

Step 1. 2-Chloro-N-((1s,4s)-4-(((2,2-difluoroethyl)(methyl)amino)methyl)cyclohexyl)-5-(1-(difluoromethyl)-1H-pyrazol-3-yl)pyridin-4-amine The title compound as a white solid (202 mg) was prepared in the same fashion as Reference Example 15, except that (1s,4s)-4-(((2,2-difluoroethyl)(methyl)amino)methyl)cyclohexan-1-amine (146 mg, 0.709 mmol) was used instead of (1s,4s)-4-amino-1-methylcyclohexan-1-ol. MS (ESI) m/z=434.1 (M+H)$^+$

Step 2. N$^2$-(2-(1-(Cyclopropylsulfonyl)-1H-pyrazol-4-yl)pyrimidin-4-yl)-N$^4$-((1s,4s)-4-(((2,2-difluoroethyl)(methyl)amino)methyl)cyclohexyl)-5-(1-(difluoromethyl)-1H-pyrazol-3-yl)pyridine-2,4-diamine The title compound as pale yellow solid (60.3 mg) was prepared in the same fashion as Step 2 in Example 1, except that 2-chloro-N-((1s,4s)-4-(((2,2-difluoroethyl)(methyl)amino)methyl)cyclohexyl)-5-(1-(difluoromethyl)-1H-pyrazol-3-yl)pyridin-4-amine (157 mg, 0.362 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.39 (d, 1H), 8.38 (s, 1H), 8.33 (d, 1H), 7.86 (s, 2H), 7.33 (d, 1H), 7.18 (t, 1H), 7.09 (d, 1H), 6.84 (d, 1H), 5.82 (tt, 1H), 2.87-2.81 (m, 1H), 2.74 (td, 2H), 2.32 (d, 2H), 2.03-2.00 (m, 2H), 1.81-1.75 (m, 6H), 1.64-1.58 (m, 1H), 1.56-1.52 (m, 2H), 1.30-1.20 (m, 2H); MS (ESI) m/z=663.2 (M+H)$^+$

Example 207. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(4-((dimethylamino)methyl)-4-methylcyclohexyl)pyridine-2,4-diamine

Step 1. 2-Chloro-5-(1-(difluoromethyl)-1H-pyrazol-3-yl)-N-(4-((dimethylamino)methyl)-4-methylcyclohexyl)pyridin-4-amine The title compound as a white solid (162 mg) was prepared in the same fashion as Reference Example 15, except that 4-((dimethylamino)methyl)-4-methylcyclohexan-1-amine dihydrochloride (155 mg, 0.638 mmol) was used instead of (1s,4s)-4-amino-1-methylcyclohexan-1-ol. MS (ESI) m/z=398.2 (M+H)$^+$

Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(4-((dimethylamino)methyl)-4-methylcyclohexyl)pyridine-2,4-diamine The title compound as pale yellow solid (68.8 mg) was prepared in the same fashion as Step 2 in Example 1, except that 2-chloro-5-(1-(difluoromethyl)-1H-pyrazol-3-yl)-N-(4-((dimethylamino)methyl)-4-methylcyclohexyl)pyridin-4-amine (127 mg, 0.32 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.43 (d, 1H), 8.41 (d, 1H), 8.07 (dt, 1H), 7.86 (d, 1H), 7.71 (d, 1H), 7.37 (dd, 1H), 7.18 (t, 1H), 7.01 (d, 1H), 6.84 (d, 1H), 3.21 (dd, 2H), 2.85-2.81 (m, 1H), 2.33 (s, 3H), 2.28 (s, 3H), 2.15 (t, 1H), 1.84-1.78 (m, 7H), 1.67-1.65 (m, 1H), 1.55-1.41 (m, 4H), 1.36-1.18 (m, 4H), 1.11 (s, 3H); MS (ESI) m/z=627.3 (M+H)$^+$

Example 208. N$^4$-((1s,4s)-4-(Azetidin-1-ylmethyl)cyclohexyl)-N$^2$-(2-(1-cyclopropylsulfonyl)-1H-pyrazol-4-yl)pyrimidin-4-yl)-5-(1-(difluoromethyl)-1H-pyrazol-3-yl)pyridine-2,4-diamine

Step 1. N-((1s,4s)-4-(Azetidin-1-ylmethyl)cyclohexyl)-2-chloro-5-(1-(difluoromethyl)-1H-pyrazol-3-yl)pyridin-4-amine The title compound as colorless oil (101 mg) was prepared in the same fashion as Reference Example 15, except that (1s,4s)-4-(azetidin-1-ylmethyl)cyclohexan-1-amine (102 mg, 0.606 mmol) was used instead of (1s,4s)-4-amino-1-methylcyclohexan-1-ol. MS (ESI) m/z=396.1 (M+H)$^+$

Step 2. N$^4$-((1s,4s)-4-(Azetidin-1-ylmethyl)cyclohexyl)-N$^2$-(2-(1-cyclopropylsulfonyl)-1H-pyrazol-4-yl)pyrimidin-4-yl)-5-(1-(difluoromethyl)-1H-pyrazol-3-yl)pyridine-2,4-diamine The title compound as pale yellow solid (35.1 mg) was prepared in the same fashion as Step 2 in Example 1, except that N-((1s,4s)-4-(azetidin-1-ylmethyl)cyclohexyl)-2-chloro-5-(1-(difluoromethyl)-1H-pyrazol-3-yl)pyridin-4-amine (82 mg, 0.207 mmol) prepared in Step 1 was used instead of 2-chloro-5-(1-cyclopropyl-1H-pyrazol-4-yl)-4-

((1-methyl-1H-pyrazol-4-yl)ethynyl)pyridine. $^1$H-NMR (CDCl$_3$, 400 MHz) δ 8.65 (s, 1H), 8.46 (s, 1H), 8.41 (d, 1H), 8.38 (s, 1H), 8.32 (d, 1H), 7.87 (d, 1H), 7.85 (brs, 1H), 7.27 (s, 1H), 7.27 (t, 1H), 7.13 (s, 1H), 6.84 (d, 1H), 3.98 (brs, 1H), 3.27 (t, 4H), 2.87-2.81 (m, 1H), 2.36 (d, 2H), 2.15-2.08 (m, 2H), 2.01-1.97 (m, 2H), 1.80-1.69 (m, 4H), 1.53-1.50 (m, 3H), 1.35-1.20 (m, 4H); MS (ESI) m/z=625.2 (M+H)$^+$ Example 209. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(((1r,3r)-3-((dimethylamino)methyl)cyclobutyl)methyl)pyridine-2,4-diamine Step 1. 2-Chloro-5-(1-(difluoromethyl)-1H-pyrazol-3-yl)-N-(((1r,3r)-3-((dimethylamino)methyl)cyclobutyl)methyl)pyridin-4-amine The title compound as pale yellow solid (117.3 mg) was prepared in the same fashion as Reference Example 15, except that 1-((1r,3r)-3-(aminomethyl)cyclobutyl)-N,N-dimethylmethanamine dihydrochloride (153 mg, 0.709 mmol) was used instead of (1s,4s)-4-amino-1-methylcyclohexan-1-ol. MS (ESI) m/z=370.0 (M+H)$^+$ Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(((1r,3r)-3-((dimethylamino)methyl)cyclobutyl)methyl)pyridine-2,4-diamine The title compound as pale yellow solid (48.8 mg) was prepared in the same fashion as Step 2 in Example 1, except that 2-chloro-5-(1-(difluoromethyl)-1H-pyrazol-3-yl)-N-(((1r,3r)-3-((dimethylamino)methyl)cyclobutyl)methyl)pyridin-4-amine (98 mg, 0.264 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.46 (s, 1H), 8.41 (d, 1H), 8.38 (s, 1H), 7.92-7.86 (m, 3H), 7.26 (s, 1H), 7.21 (t, 1H), 7.13 (s, 1H), 6.83 (d, 1H), 3.45 (dd, 1H), 2.87-2.80 (m, 1H), 2.73-2.65 (m, 1H), 2.62-2.60 (m, 1H), 2.43 (d, 2H), 2.09-2.03 (m, 2H), 2.00-1.93 (m, 2H), 1.55-1.51 (m, 2H), 1.28-1.18 (m, 2H); MS (ESI) m/z=599.3 (M+H)$^+$ Example 210. N$^4$-(sec-Butyl)-N$^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine Step 1. N-(sec-Butyl)-2-chloro-5-(1-(difluoromethyl)-1H-pyrazol-3-yl)pyridin-4-amine The title compound as a white solid (99.9 mg) was prepared in the same fashion as Reference Example 15, except that butan-2-amine (44 mg, 0.606 mmol) was used instead of (1s,4s)-4-amino-1-methylcyclohexan-1-ol. MS (ESI) m/z=301.8 (M+H)$^+$ Step 2. N$^4$-(sec-Butyl)-N$^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine The title compound as pale yellow solid (32 mg) was prepared in the same fashion as Step 2 in Example 1, except that N-(sec-butyl)-2-chloro-5-(1-(difluoromethyl)-1H-pyrazol-3-yl)pyridin-4-amine (87 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.42 (d, 1H), 8.37 (s, 1H), 7.88 (d, 1H), 7.87 (s, 1H), 7.53 (s, 1H), 7.24 (d, 1H), 7.20 (t, 1H), 7.12 (s, 1H), 6.83 (d, 1H), 3.74-3.66 (m, 1H), 2.87-2.81 (m, 1H), 1.79-1.70 (m, 2H), 1.56-1.51 (m, 2H), 1.36 (d, 3H), 1.28-1.21 (m, 2H), 1.04 (t, 3H); MS (ESI) m/z=530.0 (M+H)$^+$ Example 211. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-(2-(dimethylamino)ethyl)cyclohexyl)pyridine-2,4-diamine Step 1. 2-Chloro-5-(1-(difluoromethyl)-1H-pyrazol-3-yl)-N-((1s,4s)-4-(2-(dimethylamino)ethyl)cyclohexyl)pyridin-4-amine The title compound as a white solid (72.5 mg) was prepared in the same fashion as Reference Example 15, except that (1s,4s)-4-(2-(dimethylamino)ethyl)cyclohexan-1-amine dihydrochloride (147 mg, 0.602 mmol) was used instead of (1s,4s)-4-amino-1-methylcyclohexan-1-ol. $^1$H-NMR (CDCl$_3$, 400 MHz) δ 8.36 (s, 1H), 8.27 (d, 1H), 7.87 (d, 1H), 7.18 (t, 1H), 6.80 (d, 1H), 6.58 (s, 1H), 3.81-3.78 (m 1H), 2.30 (dd, 2H), 2.24 (s, 6H), 1.89-1.85 (m, 2H), 1.72-1.65 (m, 4H), 1.46-1.41 (m, 3H), 1.33-1.27 (m, 2H)

Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-(2-(dimethylamino)ethyl)cyclohexyl)pyridine-2,4-diamine The title compound as pale yellow solid (23.8 mg) was prepared in the same fashion as Step 2 in Example 1, except that 2-chloro-5-(1-(difluoromethyl)-1H-pyrazol-3-yl)-N-((1s,4s)-4-(2-(dimethylamino)ethyl)cyclohexyl)pyridin-4-amine (67 mg, 0.17 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.48 (s, 1H), 8.40 (d, 1H), 8.37 (s, 1H), 8.36 (s, 1H), 7.87 (d, 1H), 7.85 (s, 1H), 7.30 (s, 1H), 7.25 (t, 1H), 7.13 (d, 1H), 6.84 (d, 1H), 3.99 (brs, 1H), 2.87-2.81 (m, 1H), 2.54-2.50 (m, 2H), 2.41 (s, 6H), 2.02-1.98 (m, 2H), 1.83-1.76 (m, 2H), 1.71-1.69 (m, 2H), 1.58-1.52 (m, 3H), 1.38-1.26 (m, 4H); MS (ESI) m/z=627.3 (M+H)$^+$ Example 212. (R)—N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(4-fluorobutan-2-yl)pyridine-2,4-diamine Step 1. (R)-2-Chloro-5-(1-(difluoromethyl)-1H-pyrazol-3-yl)-N-(4-fluorobutan-2-yl)pyridin-4-amine The title compound as a white solid (112 mg) was prepared in the same fashion as Reference Example 15, except that (R)-4-fluorobutan-2-amine hydrochloride (77 mg, 0.606 mmol) was used instead of (1s,4s)-4-amino-1-methylcyclohexan-1-ol. $^1$H-NMR (CDCl$_3$, 400 MHz) δ 8.37 (s, 1H), 7.99 (d, 1H), 7.87 (d, 1H), 7.19 (t, 1H), 6.84 (d, 1H), 6.63 (s, 1H), 4.72-4.63 (m, 1H), 4.60-4.52 (m, 1H), 3.92-3.82 (m, 1H), 2.08-2.04 (m, 1H), 2.02-1.96 (m, 1H), 1.37 (d, 3H), Step 2. (R)—N²-(2-(1-(Cyclopropylsulfonyl)-1H-pyrazol-4-yl)pyrimidin-4-yl)-5-(1-(difluoromethyl)-1H-pyrazol-3-yl)-N⁴-(4-fluorobutan-2-yl)pyridine-2,4-diamine The title compound as pale yellow solid (7.8 mg) was prepared in the same fashion as Step 2 in Example 1, except that (R)-2-chloro-5-(1-(difluoromethyl)-1H-pyrazol-3-yl)-N-(4-fluorobutan-2-yl)pyridin-4-amine (47 mg, 0.147 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.67 (s, 1H), 8.47 (s, 1H), 8.43 (d, 1H), 8.35 (s, 1H), 8.15 (s, 1H), 7.88 (d, 1H), 7.33 (brs, 1H), 7.21 (s, 1H), 7.20 (t, 1H), 6.83 (s, 1H), 4.74-4.69 (m, 1H), 4.62-4.59 (m, 1H), 4.09-4.06 (m, 1H), 2.87-2.81 (m, 1H), 1.57-1.52 (m, 2H), 1.46 (d, 3H), 1.28-1.22 (m, 4H); MS (ESI) m/z=548.2 (M+H)⁺

Example 213. N²-(2-(1-(Cyclopropylsulfonyl)-1H-pyrazol-4-yl)pyrimidin-4-yl)-5-(1-(difluoromethyl)-1H-pyrazol-3-yl)-N⁴-(1,1-difluoropropan-2-yl)pyridine-2,4-diamine Step 1. 2-Chloro-5-(1-(difluoromethyl)-1H-pyrazol-3-yl)-N-(1,1-difluoropropan-2-yl)pyridin-4-amine The title compound as a white solid (59 mg) was prepared in the same fashion as Reference Example 15, except that 1,1-difluoropropan-2-amine hydrochloride (80 mg, 0.606 mmol) was used instead of (1s,4s)-4-amino-1-methylcyclohexan-1-ol. ¹H-NMR (CDCl₃, 400 MHz) δ 8.42 (s, 1H), 8.17 (d, 1H), 7.80 (d, 1H), 7.20 (t, 1H), 6.86 (d, 1H), 6.67 (s, 1H), 5.85 (td, 1H), 4.02-3.93 (m, 1H), 1.41 (d, 3H)

Step 2. N²-(2-(1-(Cyclopropylsulfonyl)-1H-pyrazol-4-yl)pyrimidin-4-yl)-5-(1-(difluoromethyl)-1H-pyrazol-3-yl)-N⁴-(1,1-difluoropropan-2-yl)pyridine-2,4-diamine The title compound as pale yellow solid (8.2 mg) was prepared in the same fashion as Step 2 in Example 1, except that 2-chloro-5-(1-(difluoromethyl)-1H-pyrazol-3-yl)-N-(1,1-difluoropropan-2-yl)pyridin-4-amine (47 mg, 0.147 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.67 (s, 1H), 8.46 (s, 1H), 8.44 (d, 1H), 8.42 (s, 1H), 8.17 (d, 1H), 7.89 (d, 1H), 7.48 (s, 1H), 7.21 (t, 1H), 7.20 (d, 1H), 6.85 (d, 1H), 5.98 (t, 1H), 4.15-4.09 (m, 1H), 2.87-2.81 (m, 1H), 1.57-1.53 (m, 2H), 1.48 (d, 3H), 1.27-1.22 (m, 2H); MS (ESI) m/z=552.1 (M+H)⁺

Example 214. N²-(2-(1-(Cyclopropylsulfonyl)-1H-pyrazol-4-yl)pyrimidin-4-yl)-5-(1-(difluoromethyl)-1H-pyrazol-3-yl)-N⁴-(4-fluorocyclohexyl)pyridine-2,4-diamine Step 1. 2-Chloro-5-(1-(difluoromethyl)-1H-pyrazol-3-yl)-N-(4-fluorocyclohexyl)pyridin-4-amine The title compound as a white solid (163.9 mg) was prepared in the same fashion as Reference Example 15, except that 4-fluorocyclohexan-1-amine hydrochloride (140 mg, 0.909 mmol) was used instead of (1s,4s)-4-amino-1-methylcyclohexan-1-ol. ¹H-NMR (MeOD, 400 MHz) δ 8.46 (s, 1H), 8.38 (d, 1H), 8.14 (s, 1H), 7.59 (t, 1H), 7.03 (d, 1H), 6.80 (s, 1H), 4.83-4.61 (m, 1H), 3.73-3.69 (m, 1H), 2.15-1.99 (m, 3H), 1.93-1.88 (m, 1H), 1.83-1.74 (m, 3H), 1.59-1.55 (m, 1H)

Step 2. N²-(2-(1-(Cyclopropylsulfonyl)-1H-pyrazol-4-yl)pyrimidin-4-yl)-5-(1-(difluoromethyl)-1H-pyrazol-3-yl)-N⁴-(4-fluorocyclohexyl)pyridine-2,4-diamine The title compound as pale yellow solid (23.6 mg) was prepared in the same fashion as Step 2 in Example 1, except that 2-chloro-5-(1-(difluoromethyl)-1H-pyrazol-3-yl)-N-(4-fluorocyclohexyl)pyridin-4-amine (62 mg, 0.181 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (DMSO-d₆, 400 MHz) δ 10.03 (s, 1H), 8.65 (s, 1H), 8.53 (s, 1H), 8.46 (d, 1H), 8.43 (d, 1H), 8.32 (s, 1H), 8.15 (dd, 1H), 7.86 (td, 1H), 7.57 (brs, 1H), 7.30 (brs, 1H), 7.15 (s, 1H), 4.82-4.68 (m, 1H), 3.67 (brs, 1H), 3.29-3.24 (m, 1H), 2.13-2.09 (m, 1H), 1.98-1.82 (m, 4H), 1.79-1.67 (m, 2H), 1.53-1.51 (m, 1H), 1.34-1.27 (m, 2H), 1.25-1.20 (m, 2H); MS (ESI) m/z=574.1 (M+H)⁺

Example 215. N²-(2-(1-(Cyclopropylsulfonyl)-1H-pyrazol-4-yl)pyrimidin-4-yl)-N⁴-(4,4-difluorocyclohexyl)-5-(1-(difluoromethyl)-1H-pyrazol-3-yl)pyridine-2,4-diamine Step 1. 2-Chloro-N-(4,4-difluorocyclohexyl)-5-(1-(difluoromethyl)-1H-pyrazol-3-yl)pyridin-4-amine The title compound as a white solid (191 mg) was prepared in the same fashion as Reference Example 15, except that 4,4-difluorocyclohexan-1-amine hydrochloride (156 mg, 0.909 mmol) was used instead of (1s,4s)-4-amino-1-methylcyclohexan-1-ol. ¹H-NMR (MeOD, 400 MHz) δ 8.49 (d, 1H), 8.41 (s, 1H), 8.15 (d, 1H), 7.60 (t, 1H), 7.04 (d, 1H), 6.86 (s, 1H), 3.83-3.81 (m, 1H), 2.12-1.97 (m, 6H), 1.79-1.71 (m, 2H)

Step 2. N²-(2-(1-(Cyclopropylsulfonyl)-1H-pyrazol-4-yl)pyrimidin-4-yl)-N⁴-(4,4-difluorocyclohexyl)-5-(1-(difluoromethyl)-1H-pyrazol-3-yl)pyridine-2,4-diamine The title compound as pale yellow solid (21.7 mg) was prepared in the same fashion as Step 2 in Example 1, except that 2-chloro-N-(4,4-difluorocyclohexyl)-5-(1-(difluoromethyl)-1H-pyrazol-3-yl)pyridin-4-amine (66 mg, 0.181 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (DMSO-d₆, 400 MHz) δ 10.05 (s, 1H), 8.65 (s, 1H), 8.55 (s, 1H), 8.46 (s, 1H), 8.43 (d, 1H), 8.33 (s, 1H), 8.21 (d, 1H), 7.87 (t, 1H), 7.53 (s, 1H), 7.37 (s, 1H), 7.16 (s, 1H), 3.83 (brs, 1H), 3.28-3.22 (m, 1H), 2.09-1.98 (m, 6H), 1.76-1.74 (m, 2H), 1.34-1.27 (m, 2H), 1.26-1.22 (m, 2H); MS (ESI) m/z=592.1 (M+H)⁺

Example 216. N²-(2-(1-(Cyclopropylsulfonyl)-1H-pyrazol-4-yl)pyrimidin-4-yl)-5-(1-(difluoromethyl)-1H-pyrazol-3-yl)-N⁴-(4-(2-fluoroethyl)cyclohexyl)pyridine-2,4-diamine Step 1. 2-Chloro-5-(1-(difluoromethyl)-1H-pyrazol-3-yl)-N-(4-(2-fluoroethyl)cyclohexyl)pyridin-4-amine The title compound as a white solid (202 mg) was prepared in the same fashion as Reference Example 15, except that 4-(2-fluoroethyl)cyclohexan-1-amine (132 mg, 0.909 mmol) was used instead of (1s,4s)-4-amino-1-methylcyclohexan-1-ol. $^1$H-NMR (CDCl$_3$, 400 MHz) δ 8.35 (d 1H), 7.87 (s, 1H), 7.86 (s, 1H), 7.19 (td, 1H), 6.83 (td, 1H), 6.58 (d, 1H), 4.59 (t, 1H), 4.47 (t, 1H), 3.83-3.30 (m, 1H), 2.20-2.17 (m, 1H), 1.93-1.83 (m, 2H), 1.72-1.53 (m, 5H), 1.44-1.30 (m, 2H), 1.24-1.17 (m, 1H)

Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(4-(2-fluoroethyl)cyclohexyl)pyridine-2,4-diamine The title compound as pale yellow solid (15.7 mg) was prepared in the same fashion as Step 2 in Example 1, except that 2-chloro-5-(1-(difluoromethyl)-1H-pyrazol-3-yl)-N-(4-(2-fluoroethyl)cyclohexyl)pyridin-4-amine (67 mg, 0.181 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.03 (d, 1H), 8.63 (d, 1H), 8.53-8.40 (m, 3H), 8.31 (s, 1H), 7.97 (d, 1H), 7.87 (t, 1H), 7.60 (s, 1H), 7.24 (s, 1H), 7.14 (s, 1H), 4.50 (dt, 2H), 3.42 (brs, 1H), 3.29-3.23 (m, 1H), 2.01 (dd, 2H), 1.79 (dd, 2H), 1.66-1.47 (m, 3H), 1.34-1.12 (m, 6H); MS (ESI) m/z=602.2 (M+H)$^+$ Example 217. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(1-(2-fluoroethyl)piperidin-4-yl)pyridine-2,4-diamine Step 1. 2-Chloro-5-(1-(difluoromethyl)-1H-pyrazol-3-yl)-N-(1-(2-fluoroethyl)piperidin-4-yl)pyridin-4-amine The title compound as a white solid (166 mg) was prepared in the same fashion as Reference Example 15, except that 1-(2-fluoroethyl)piperidin-4-amine hydrochloride (96 mg, 0.525 mmol) was used instead of (1s,4s)-4-amino-1-methylcyclohexan-1-ol. MS (ESI) m/z=374.2 (M+H)$^+$ Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(1-(2-fluoroethyl)piperidin-4-yl)pyridine-2,4-diamine The title compound as pale yellow solid (5.7 mg) was prepared in the same fashion as Step 2 in Example 1, except that 2-chloro-5-(1-(difluoromethyl)-1H-pyrazol-3-yl)-N-(1-(2-fluoroethyl)piperidin-4-yl)pyridin-4-amine (47 mg, 0.124 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.02 (s, 1H), 8.64 (s, 1H), 8.53 (s, 1H), 8.46 (s, 1H), 8.43 (d, 1H), 8.32 (d, 1H), 8.18 (d, 1H), 7.87 (t, 1H), 7.55 (s, 1H), 7.32 (s, 1H), 7.15 (d, 1H), 4.59 (t, 1H), 4.47 (t, 1H), 3.64 (brs, 1H), 3.25-3.21 (m, 1H), 2.71 (brs, 1H), 2.66 (t, 1H), 2.59 (t, 1H), 2.38-2.32 (m, 2H), 2.03-1.97 (m, 2H), 1.97-1.91 (m, 1H), 1.61-1.58 (m, 2H), 1.44-1.29 (m, 4H); MS (ESI) m/z=603.2 (M+H)$^+$ Example 218. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(1-(2-fluoroethyl)piperidin-3-yl)pyridine-2,4-diamine Step 1. 2-Chloro-5-(1-(difluoromethyl)-1H-pyrazol-3-yl)-N-(1-(2-fluoroethyl)piperidin-3-yl)pyridin-4-amine The title compound as a white solid (132 mg) was prepared in the same fashion as Reference Example 15, except that 1-(2-fluoroethyl)piperidin-3-amine dihydrochloride (115 mg, 0.525 mmol) was used instead of (1s,4s)-4-amino-1-methylcyclohexan-1-ol. MS (ESI) m/z=374.1 (M+H)$^+$ Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-(1-(2-fluoroethyl)piperidin-3-yl)pyridine-2,4-diamine The title compound as pale yellow solid (6.8 mg) was prepared in the same fashion as Step 2 in Example 1, except that 2-chloro-5-(1-(difluoromethyl)-1H-pyrazol-3-yl)-N-(1-(2-fluoroethyl)piperidin-3-yl)pyridin-4-amine (47 mg, 0.124 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.03 (s, 1H), 8.63 (s, 1H), 8.50 (s, 1H), 8.45 (s, 1H), 8.42 (d, 1H), 8.33 (d, 1H), 8.30 (d, 1H), 7.76 (t, 1H), 7.53 (s, 1H), 7.35 (s, 1H), 7.14 (d, 1H), 4.54 (dt, 2H), 3.79 (brs, 1H), 3.28-3.23 (m, 1H), 2.80-2.78 (m, 1H), 2.67 (dt, 2H), 2.55 (brs, 1H), 2.41 (brs, 1H), 1.97-1.93 (m, 1H), 1.76-1.56 (m, 4H), 1.44-1.29 (m, 4H); MS (ESI) m/z=603.2 (M+H)$^+$ Example 219. N$^2$-(2-(1-(Cyclopropylsulfonyl)-1H-pyrazol-4-yl)pyrimidin-4-yl)-N$^4$-(1-(2,2-difluoroethyl)piperidin-4-yl)-5-(1-(difluoromethyl)-1H-pyrazol-3-yl)pyridine-2,4-diamine Step 1. 2-Chloro-N-(1-(2,2-difluoroethyl)piperidin-4-yl)-5-(1-(difluoromethyl)-1H-pyrazol-3-yl)pyridin-4-amine The title compound as a white solid (118 mg) was prepared in the same fashion as Reference Example 15, except that 1-(2,2-difluoroethyl)piperidin-4-amine (86 mg, 0.525 mmol) was used instead of (1s,4s)-4-amino-1-methylcyclohexan-1-ol. MS (ESI) m/z=392.1 (M+H)$^+$ Step 2. N$^2$-(2-(1-(Cyclopropylsulfonyl)-1H-pyrazol-4-yl)pyrimidin-4-yl)-N$^4$-(1-(2,2-difluoroethyl)piperidin-4-yl)-5-(1-(difluoromethyl)-1H-pyrazol-3-yl)pyridine-2,4-diamine The title compound as pale yellow solid (20.8 mg) was prepared in the same fashion as Step 2 in Example 1, except that 2-chloro-N-(1-(2,2-difluoroethyl)piperidin-4-yl)-5-(1-(difluoromethyl)-1H-pyrazol-3-yl)pyridin-4-amine (49 mg, 0.124 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.02 (s, 1H), 8.65 (s, 1H), 8.53 (s, 1H), 8.46 (s, 1H), 8.43 (d, 1H), 8.33 (d, 1H), 8.17 (d, 1H), 7.88 (t, 1H), 7.56 (s, 1H), 7.32 (s, 1H), 7.15 (d, 1H), 6.13 (tt, 1H), 3.64 (brs, 1H), 3.28-3.23 (m, 1H), 2.77-2.67 (m, 4H), 2.45 (brs, 2H), 2.05-2.02 (m, 2H), 1.62-1.58 (m, 2H), 1.35-1.23 (m, 4H); MS (ESI) m/z=621.2 (M+H)$^+$

Example 220. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-fluoro-4-methylcyclohexyl)pyridine-2,4-diamine

Step 1. 2-Chloro-5-(1-(difluoromethyl)-1H-pyrazol-3-yl)-N-((1s,4s)-4-fluoro-4-methylcyclohexyl)pyridin-4-amine The title compound as a white solid (100.5 mg) was prepared in the same fashion as Reference Example 15, except that (1s,4s)-4-fluoro-4-methylcyclohexan-1-amine (79 mg, 0.473 mmol) was used instead of (1s,4s)-4-amino-1-methylcyclohexan-1-ol. MS (ESI) m/z=359.1 (M+H)$^+$

Step 2. N$^2$-(2-(1-(Cyclopropylsulfonyl)-1H-pyrazol-4-yl)pyrimidin-4-yl)-5-(1-(difluoromethyl)-1H-pyrazol-3-yl)-N$^4$-((1s,4s)-4-fluoro-4-methylcyclohexyl)pyridine-2,4-diamine The title compound as pale yellow solid (7 mg) was prepared in the same fashion as Step 2 in Example 1, except that 2-chloro-5-(1-(difluoromethyl)-1H-pyrazol-3-yl)-N-((1s,4s)-4-fluoro-4-methylcyclohexyl)pyridin-4-amine (45 mg, 0.124 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.48 (s, 1H), 8.42 (d, 1H), 8.37 (s, 1H), 7.97 (d, 1H), 7.88 (d, 1H), 7.87 (s, 1H), 7.25 (s, 1H), 7.22 (t, 1H), 7.10 (s, 1H), 6.83 (s, 1H), 3.56-3.54 (m, 1H), 2.86-2.79 (m, 1H), 2.05-1.99 (m, 4H), 1.79-1.62 (m, 4H), 1.59-1.45 (m, 2H), 1.29-1.25 (m, 2H); MS (ESI) m/z=588.2 (M+H)$^+$

Example 221. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(hydroxymethyl)cyclohexan-1-ol

Step 1. (1s,4s)-4-((2-Chloro-5-(1-methyl-1H-pyrazol-3-yl)pyridin-4-yl)amino)-1-(hydroxymethyl)cyclohexan-1-ol The title compound as a white solid (69.1 mg) was prepared in the same fashion as Reference Example 15, except that 2-chloro-4-fluoro-5-(1-methyl-1H-pyrazol-3-yl)pyridine (250 mg, 1.181 mmol) prepared in Reference Example 3 and (1s,4s)-4-amino-1-(hydroxymethyl)cyclohexan-1-ol (257 mg, 1.772 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=337.1 (M+H)$^+$

Step 2. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(hydroxymethyl)cyclohexan-1-ol The title compound as pale yellow solid (6.2 mg) was prepared in the same fashion as Step 2 in Example 1, except that (1s,4s)-4-((2-chloro-5-(1-methyl-1H-pyrazol-3-yl)pyridin-4-yl)amino)-1-(hydroxymethyl)cyclohexan-1-ol (63 mg, 0.19 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.64 (s, 1H), 8.48 (s, 1H), 8.38 (d, 2H), 8.31 (s, 1H), 7.40 (d, 1H), 7.23 (brs, 1H), 7.15 (brs, 1H), 6.58 (d, 1H), 3.95 (s, 3H), 2.54 (s, 3H), 2.88-2.82 (m, 1H), 2.08-2.06 (m, 2H), 1.85-1.79 (m, 4H), 1.57-1.51 (m, 4H), 1.31-1.22 (m, 4H); MS (ESI) m/z=566.2 (M+H)$^+$

Example 222. (4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-fluorocyclohexyl)methanol

Step 1. (4-((2-Chloro-5-(1-methyl-1H-pyrazol-3-yl)pyridin-4-yl)amino)-1-fluorocyclohexyl)methanol The title compound as a white solid (220.6 mg) was prepared in the same fashion as Reference Example 15, except that 2-chloro-4-fluoro-5-(1-methyl-1H-pyrazol-3-yl)pyridine (250 mg, 1.181 mmol) prepared in Reference Example 3 and (4-amino-1-fluoro-cyclohexyl)methanol (261 mg, 1.772 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=339.1 (M+H)$^+$

Step 2. (4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-fluorocyclohexyl)methanol The title compound as pale yellow solid (41.2 mg) was prepared in the same fashion as Step 2 in Example 1, except that (4-((2-chloro-5-(1-methyl-1H-pyrazol-3-yl)pyridin-4-yl)amino)-1-fluorocyclohexyl)methanol (64 mg, 0.19 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.92 (s, 1H), 8.64 (s, 1H), 8.45 (s, 1H), 8.41 (d, 1H), 8.39 (s, 1H), 8.27 (d, 1H), 7.78 (d, 1H), 7.62 (s, 1H), 7.18 (s, 1H), 6.78 (d, 1H), 4.96 (t, 1H), 3.90 (s, 3H), 3.50 (brs, 1H), 3.43 (dd, 2H), 3.29-3.22 (m, 1H), 2.03-2.00 (m, 2H), 1.91-1.88 (m, 2H), 1.64-1.53 (m, 4H), 1.34-1.25 (m, 4H); MS (ESI) m/z=568.2 (M+H)$^+$

Example 223. ((1r,3r)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclobutyl)methanol

Step 1. ((1r,3r)-3-(((2-Chloro-5-(1-methyl-1H-pyrazol-3-yl)pyridin-4-yl)amino)methyl)cyclobutyl)methanol The title compound as a white solid (223.8 mg) was prepared in the same fashion as Reference Example 15, except that 2-chloro-4-fluoro-5-(1-methyl-1H-pyrazol-3-yl)pyridine (200 mg, 0.95 mmol) prepared in Reference Example 3 and ((1r,3r)-3-(aminomethyl)cyclobutyl)methanol hydrochloride (215 mg, 1.418 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=307.0 (M+H)$^+$

Step 2. ((1r,3r)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclobutyl)methanol The title compound as pale yellow solid (143.3 mg) was prepared in the same fashion as Step 2 in Example 1, except that ((1r,3r)-3-(((2-chloro-5-(1-methyl-1H-pyrazol-3-yl)pyridin-4-yl)amino)methyl)cyclobutyl)methanol (191 mg, 0.622 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.98 (s, 1H), 8.65 (s, 1H), 8.45 (s, 1H), 8.40 (d, 1H), 8.38 (s, 1H), 8.28 (t, 1H), 7.78 (s, 1H), 7.43 (s, 1H), 7.36 (s, 1H), 6.78 (s, 1H), 4.52 (t, 1H), 3.89 (s, 3H), 3.45 (t, 2H), 3.35 (t, 2H), 3.28-3.25 (m, 1H), 2.71-2.64 (m, 1H), 2.45-2.40 (m, 1H), 1.90 (t, 4H), 1.34-1.33 (m, 2H), 1.25-1.23 (m, 2H); MS (ESI) m/z=536.2 (M+H)$^+$ Example 224. N$^2$-(2-(1-(Cyclopropylsulfonyl)-1H-pyrazol-4-yl)pyrimidin-4-yl)-N$^4$-(3-((2,2-difluoroethyl)amino)cyclohexyl)-5-(1-methyl-1H-pyrazol-3-yl)pyridine-2,4-diamine Step 1. N$^1$-(2-Chloro-5-(1-methyl-1H-pyrazol-3-yl)pyridin-4-yl)-N$^3$-(2,2-difluoroethyl)cyclohexane-1,3-diamine The title compound as a white solid (347.1 mg) was prepared in the same fashion as Reference Example 15, except that 2-chloro-4-fluoro-5-(1-methyl-1H-pyrazol-3-yl)pyridine (250 mg, 1.181 mmol) prepared in Reference Example 3 and N$^1$-(2,2-difluoroethyl)cyclohexane-1,3-diamine (284 mg, 1.772 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=370.1 (M+H)$^+$ Step 2. N$^2$-(2-(1-(Cyclopropylsulfonyl)-1H-pyrazol-4-yl)pyrimidin-4-yl)-N$^4$-(3-((2,2-difluoroethyl)amino)cyclohexyl)-5-(1-methyl-1H-pyrazol-3-yl)pyridine-2,4-diamine The title compound as pale yellow solid (205 mg) was prepared in the same fashion as Step 2 in Example 1, except that N$^1$-(2-chloro-5-(1-methyl-1H-pyrazol-3-yl)pyridin-4-yl)-N$^3$-(2,2-difluoroethyl)cyclohexane-1,3-diamine (307 mg, 0.829 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.48 (d, 1H), 8.47 (s, 1H), 8.39 (d, 1H), 8.36 (s, 1H), 7.71 (s, 1H), 7.41 (s, 1H), 7.16 (s, 2H), 6.61 (d, 1H), 5.82 (tt, 1H), 4.10 (s, 1H), 3.96 (s, 3H), 3.03-2.91 (m, 3H), 2.87-2.81 (m, 1H), 2.16-2.13 (m, 1H), 1.98-1.95 (m, 1H), 1.87-1.77 (m, 3H), 1.72-1.61 (m, 2H), 1.56-1.52 (m, 2H), 1.32-1.25 (m, 1H), 1.25-1.21 (m, 2H); MS (ESI) m/z=599.1 (M+H)$^+$ Example 225. N$^2$-(2-(1-(Cyclopropylsulfonyl)-1H-pyrazol-4-yl)pyrimidin-4-yl)-N$^4$-(3-((2-fluoroethyl)amino)cyclohexyl)-5-(1-methyl-1H-pyrazol-3-yl)pyridine-2,4-diamine Step 1. N$^1$-(2-Chloro-5-(1-methyl-1H-pyrazol-3-yl)pyridin-4-yl)-N$^3$-(2-fluoroethyl)cyclohexane-1,3-diamine The title compound as a white solid (364 mg) was prepared in the same fashion as Reference Example 15, except that 2-chloro-4-fluoro-5-(1-methyl-1H-pyrazol-3-yl)pyridine (250 mg, 1.181 mmol) prepared in Reference Example 3 and N$^1$-(2-fluoroethyl)cyclohexane-1,3-diamine (284 mg, 1.772 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=352.1 (M+H)$^+$ Step 2. N$^2$-(2-(1-(Cyclopropylsulfonyl)-1H-pyrazol-4-yl)pyrimidin-4-yl)-N$^4$-(3-((2-fluoroethyl)amino)cyclohexyl)-5-(1-methyl-1H-pyrazol-3-yl)pyridine-2,4-diamine The title compound as pale yellow solid (171.2 mg) was prepared in the same fashion as Step 2 in Example 1, except that N$^1$-(2-chloro-5-(1-methyl-1H-pyrazol-3-yl)pyridin-4-yl)-N$^3$-(2-fluoroethyl)cyclohexane-1,3-diamine (321 mg, 0.912 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.49 (d, 1H), 8.47 (s, 1H), 8.39 (d, 1H), 8.36 (s, 1H), 7.66 (brs, 1H), 7.41 (d, 1H), 7.23 (d, 1H), 7.10 (s, 1H), 6.61 (d, 1H), 4.59 (t, 1H), 4.47 (t, 1H), 4.10 (brs, 1H), 3.96 (s, 3H), 2.99-2.89 (m, 3H), 2.87-2.81 (m, 1H), 2.16-2.13 (m, 1H), 1.98-1.95 (m, 1H), 1.88-1.82 (m, 1H), 1.76-1.63 (m, 4H), 1.56-1.52 (m, 2H), 1.34-1.25 (m, 2H), 1.25-1.19 (m, 2H); MS (ESI) m/z=581.2 (M+H)$^+$ Example 226. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(1-methyl-1H-pyrazol-3-yl)pyridine-2,4-diamine Step 1. 2-Chloro-N-((1s,4s)-4-((dimethylamino)methyl)cyclohexyl)-5-(1-methyl-1H-pyrazol-3-yl)pyridin-4-amine The title compound as a white solid (225 mg) was prepared in the same fashion as Reference Example 15, except that 2-chloro-4-fluoro-5-(1-methyl-1H-pyrazol-3-yl)pyridine (200 mg, 0.95 mmol) prepared in Reference Example 3 and (1s,4s)-4-((dimethylamino)methyl)cyclohexan-1-amine dihydrochloride (284 mg, 1.772 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=348.1 (M+H)$^+$ Step 2. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(1-methyl-1H-pyrazol-3-yl)pyridine-2,4-diamine The title compound as pale yellow solid (73 mg) was prepared in the same fashion as Step 2 in Example 1, except that 2-chloro-N-((1s,4s)-4-((dimethylamino)methyl)cyclohexyl)-5-(1-methyl-1H-pyrazol-3-yl)pyridin-4-amine (131 mg, 0.377 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.61 (d, 1H), 8.47 (s, 1H), 8.38 (d, 1H), 8.35 (s, 1H), 7.75 (brs, 1H), 7.41 (d, 1H), 7.20 (s, 1H), 7.14 (d, 1H), 6.61 (d, 1H), 3.99-3.96 (m, 1H), 3.96 (s, 3H), 2.87-2.81 (m, 1H), 2.23 (s, 6H), 2.15 (d, 2H), 2.03-2.00 (m, 2H), 1.82-1.74 (m, 4H), 1.67-1.62 (m, 1H), 1.56-1.51 (m, 2H), 1.39-1.29 (m, 2H), 1.24-1.19 (m, 2H); MS (ESI) m/z=577.2 (M+H)$^+$

Example 227. ((2R,5S)-5-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)tetrahydro-2H-pyran-2-yl)methanol

Step 1. ((2R,5S)-5-((2-Chloro-5-(1-methyl-1H-pyrazol-3-yl)pyridin-4-yl)amino)tetrahydro-2H-pyran-2-yl)methanol The title compound as a white solid (161.4 mg) was prepared in the same fashion as Reference Example 15, except that 2-chloro-4-fluoro-5-(1-methyl-1H-pyrazol-3-yl)pyridine (150 mg, 0.71 mmol) prepared in Reference Example 3 and ((2R,5S)-5-aminotetrahydro-2H-pyran-2-yl)methanol hydrochloride (178 mg, 1.063 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=323.1 (M+H)$^+$

Step 2. ((2R,5S)-5-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)tetrahydro-2H-pyran-2-yl)methanol The title compound as pale yellow solid (87.1 mg) was prepared in the same fashion as Step 2 in Example 1, except that ((2R,5S)-5-((2-chloro-5-(1-methyl-1H-pyrazol-3-yl)pyridin-4-yl)amino)tetrahydro-2H-pyran-2-yl)methanol (161 mg, 0.498 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.70 (d, 2H), 8.35 (d, 1H), 8.33 (s, 1H), 8.19 (d, 1H), 7.95 (s, 1H), 7.83 (brs, 1H), 7.41 (d, 1H), 6.70 (d, 1H), 6.60 (d, 1H), 4.56 (dd, 1H), 4.21 (brs, 1H), 3.96 (s, 3H), 3.81-3.75 (m, 1H), 3.62-3.52 (m, 2H), 3.26 (t, 2H), 2.93-2.86 (m, 1H), 2.38-2.35 (m, 1H), 2.13-2.04 (m, 1H), 1.78-1.75 (m, 1H), 1.60-1.52 (m, 2H), 1.24-1.20 (m, 2H); MS (ESI) m/z=552.1 (M+H)$^+$

Example 228. (3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)oxetan-3-yl)methanol

Step 1. (3-(((2-Chloro-5-(1-methyl-1H-pyrazol-3-yl)pyridin-4-yl)amino)methyl)oxetan-3-yl)methanol The title compound as a white solid (151.9 mg) was prepared in the same fashion as Reference Example 15, except that 2-chloro-4-fluoro-5-(1-methyl-1H-pyrazol-3-yl)pyridine (150 mg, 0.71 mmol) prepared in Reference Example 3 and (3-(aminomethyl)oxetan-3-yl)methanol (125 mg, 1.063 mmol) were used instead of 2-chloro-5-(1-(difluoromethyl)-1H-pyrazol-3-yl)-4-fluoropyridine and (1s,4s)-4-amino-1-methylcyclohexan-1-ol. $^1$H-NMR (CDCl$_3$, 400 MHz) δ 8.56 (s, 1H), 8.29 (s, 1H), 7.40 (s, 1H), 6.59 (d, 2H), 4.62-4.55 (m, 4H), 4.04 (s, 2H), 3.97 (s, 3H), 3.59 (s, 2H)

Step 2. (3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)oxetan-3-yl)methanol The title compound as pale yellow solid (58.6 mg) was prepared in the same fashion as Step 2 in Example 1, except that (3-(((2-chloro-5-(1-methyl-1H-pyrazol-3-yl)pyridin-4-yl)amino)methyl)oxetan-3-yl)methanol (147 mg, 0.48 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.99 (s, 1H), 8.67 (s, 1H), 8.49 (t, 1H), 8.47 (s, 1H), 8.41 (d, 1H), 8.40 (s, 1H), 7.78 (d, 1H), 7.50 (brs, 1H), 7.36 (brs, 1H), 6.79 (d, 1H), 5.12 (t, 1H), 4.44 (s, 4H), 3.87 (s, 3H), 3.75 (d, 2H), 3.58 (d, 2H), 3.29-3.23 (m, 1H), 1.34 (d, 2H), 1.25 (d, 2H); MS (ESI) m/z=538.1 (M+H)$^+$

Example 229. ((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol

Step 1. ((1r,4r)-4-((2-Chloro-5-(1-methyl-1H-pyrazol-3-yl)pyridin-4-yl)amino)cyclohexyl)methanol The title compound as a white solid (193.5 mg) was prepared in the same fashion as Reference Example 15, except that 2-chloro-4-fluoro-5-(1-methyl-1H-pyrazol-3-yl)pyridine (150 mg, 0.71 mmol) prepared in Reference Example 3 and ((1r,4r)-4-aminocyclohexyl)methanol (137 mg, 1.063 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=321.1 (M+H)$^+$

Step 2. ((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol The title compound as pale yellow solid (84 mg) was prepared in the same fashion as Step 2 in Example 1, except that ((1r,4r)-4-((2-chloro-5-(1-methyl-1H-pyrazol-3-yl)pyridin-4-yl)amino)cyclohexyl)methanol (153 mg, 0.477 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.50 (s, 1H), 8.40 (d, 1H), 8.33 (s, 1H), 8.19 (d, 1H), 7.62 (brs, 1H), 7.40 (d, 1H), 7.31 (d, 1H), 6.97 (s, 1H), 6.59 (d, 1H), 3.95 (s, 3H), 3.56 (d, 2H), 3.49-3.42 (m, 1H), 2.89-2.82 (m, 1H), 2.30-2.28 (m, 2H), 1.92-1.89 (m, 2H), 1.55-1.51 (m, 2H), 1.41-1.33 (m, 3H), 1.29-1.19 (m, 4H); MS (ESI) m/z=550.2 (M+H)$^+$

Example 230. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-((dimethylamino)methyl)cyclohexan-1-ol

Step 1. (1s,4s)-4-((2-Chloro-5-(1-methyl-1H-pyrazol-3-yl)pyridin-4-yl)amino)-1-((dimethylamino)methyl)cyclohexan-1-ol The title compound as a white solid (166 mg) was prepared in the same fashion as Reference Example 15, except that 2-chloro-4-fluoro-5-(1-methyl-1H-pyrazol-3-yl)pyridine (150 mg, 0.71 mmol) prepared in Reference Example 3 and (1s,4s)-4-amino-1-((dimethylamino)methyl)cyclohexan-1-ol dihydrochloride (261 mg, 1.063 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=364.1 (M+H)$^+$ Step 2. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-((dimethylamino)methyl)cyclohexan-1-ol The title compound as pale yellow solid (85 mg) was prepared in the same fashion as Step 2 in Example 1, except that (1s,4s)-4-((2-chloro-5-(1-methyl-1H-pyrazol-3-yl)pyridin-4-yl)amino)-1-((dimethylamino)methyl)cyclohexan-1-ol (158 mg, 0.433 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.91 (s, 1H), 8.64 (s, 1H), 8.45 (s, 1H), 8.40 (d, 1H), 8.37 (s, 1H), 8.25 (d, 1H), 7.77 (d, 1H), 7.57 (brs, 1H), 7.22 (brs, 1H), 6.77 (d, 1H), 4.02 (s, 1H), 3.90 (s, 3H), 3.28-3.21 (m, 1H), 2.24 (s, 6H), 2.22 (s, 2H), 1.88-1.85 (m, 2H), 1.67-1.59 (m, 4H) 1.50-1.44 (m, 2H), 1.36-1.32 (m, 2H), 1.27-1.24 (m, 2H); MS (ESI) m/z=593.2 (M+H)$^+$ Example 231. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(difluoromethyl)cyclohexan-1-ol Step 1. (1s,4s)-4-((2-Chloro-5-(1-methyl-1H-pyrazol-3-yl)pyridin-4-yl)amino)-1-(difluoromethyl)cyclohexan-1-ol The title compound as a white solid (132 mg) was prepared in the same fashion as Reference Example 15, except that 2-chloro-4-fluoro-5-(1-methyl-1H-pyrazol-3-yl)pyridine (100 mg, 0.47 mmol) prepared in Reference Example 3 and (1s,4s)-4-amino-1-(difluoromethyl)cyclohexan-1-ol (117 mg, 0.709 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=357.1 (M+H)$^+$ Step 2. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(difluoromethyl)cyclohexan-1-ol The title compound as pale yellow solid (56 mg) was prepared in the same fashion as Step 2 in Example 1, except that (1s,4s)-4-((2-chloro-5-(1-methyl-1H-pyrazol-3-yl)pyridin-4-yl)amino)-1-(difluoromethyl)cyclohexan-1-ol (111 mg, 0.311 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.88 (s, 1H), 8.64 (s, 1H), 8.45 (s, 1H), 8.41 (d, 1H), 8.39 (s, 1H), 8.18 (d, 1H), 7.78 (d, 1H), 7.72 (brs, 1H), 6.78 (d, 1H), 5.70 (t, 1H), 5.16 (s, 1H), 3.90 (s, 3H), 3.27-3.20 (m, 1H), 2.00-1.97 (m, 2H), 1.69-1.49 (m, 6H), 1.36-1.33 (m, 2H), 1.32-1.27 (m, 2H); MS (ESI) m/z=586.1 (M+H)$^+$ Example 232. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N,N-dimethylcyclohexane-1-carboxamide Step 1. (1s,4s)-4-((2-Chloro-5-(1-methyl-1H-pyrazol-3-yl)pyridin-4-yl)amino)-N,N-dimethylcyclohexane-1-carboxamide The title compound as a white solid (143 mg) was prepared in the same fashion as Reference Example 15, except that 2-chloro-4-fluoro-5-(1-methyl-1H-pyrazol-3-yl)pyridine (100 mg, 0.47 mmol) prepared in Reference Example 3 and (1s,4s)-4-amino-N,N-dimethylcyclohexane-1-carboxamide hydrochloride (147 mg, 0.709 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=362.1 (M+H)$^+$ Step 2. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N,N-dimethyl-cyclohexane-1-carboxamide The title compound as pale yellow solid (10.7 mg) was prepared in the same fashion as Step 2 in Example 1, except that (1s,4s)-4-((2-chloro-5-(1-methyl-1H-pyrazol-3-yl)pyridin-4-yl)amino)-N,N-dimethylcyclohexane-1-carboxamide (123 mg, 0.340 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 9.88 (s, 1H), 8.64 (s, 1H), 8.45 (s, 1H), 8.41 (d, 1H), 8.39 (s, 1H), 8.18 (d, 1H), 7.78 (d, 1H), 7.72 (brs, 1H), 6.78 (d, 1H), 5.70 (t, 1H), 5.16 (s, 1H), 3.90 (s, 3H), 3.27-3.20 (m, 1H), 2.00-1.97 (m, 2H), 1.69-1.49 (m, 6H), 1.36-1.33 (m, 2H), 1.32-1.27 (m, 2H); MS (ESI) m/z=591.2 (M+H)$^+$ Example 233. ((1S,3S)-3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol Step 1. ((1S,3S)-3-((2-Chloro-5-(1-methyl-1H-pyrazol-3-yl)pyridin-4-yl)amino)cyclohexyl)methanol The title compound as a white solid (134.4 mg) was prepared in the same fashion as Reference Example 15, except that 2-chloro-4-fluoro-5-(1-methyl-1H-pyrazol-3-yl)pyridine (100 mg, 0.47 mmol) prepared in Reference Example 3 and ((1S,3S)-3-aminocyclohexyl)methanol hydrochloride (117 mg, 0.709 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=321.1 (M+H)$^+$ Step 2. ((1S,3S)-3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol The title compound as pale yellow solid (69.1 mg) was prepared in the same fashion as Step 2 in Example 1, except that ((1S,3S)-3-((2-chloro-5-(1-methyl-1H-pyrazol-3-yl)pyridin-4-yl)amino)cyclohexyl)methanol (106 mg, 0.332 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.64 (s, 1H), 8.63 (d, 1H), 8.45 (s, 1H), 8.33 (d, 1H), 8.32 (s, 1H), 7.39 (d, 1H), 7.25 (s, 1H), 7.04 (d, 1H), 6.58 (d, 1H), 4.05 (brs, 1H), 3.95 (s, 3H), 3.55-3.48 (m, 2H), 2.87-2.80 (m, 1H), 2.11-2.08 (m, 2H), 1.96-1.72 (m, 6H), 1.54-1.43 (m, 3H), 1.24-1.18 (m, 2H); MS (ESI) m/z=550.2 (M+H)$^+$ Example 234. N²-(2-(1-(Cyclopropylsulfonyl)-1H-pyrazol-4-yl)pyrimidin-4-yl)-N⁴-(((1s,3s)-3-((dimethylamino)methyl)cyclobutyl)methyl)-5-(1-methyl-1H-pyrazol-3-yl)pyridine-2,4-diamine Step 1. 2-Chloro-N-(((1s,3s)-3-((dimethylamino)methyl)cyclobutyl)methyl)-5-(1-methyl-1H-pyrazol-3-yl)pyridin-4-amine The title compound as a white solid (113.8 mg) was prepared in the same fashion as Reference Example 15, except that 2-chloro-4-fluoro-5-(1-methyl-1H-pyrazol-3-yl)pyridine (100 mg, 0.47 mmol) prepared in Reference Example 3 and 1-((1s,3s)-3-(aminomethyl)cyclobutyl)-N,N-dimethylmethanamine dihydrochloride (153 mg, 1.709 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=334.1 (M+H)⁺

Step 2. N²-(2-(1-(Cyclopropylsulfonyl)-1H-pyrazol-4-yl)pyrimidin-4-yl)-N⁴-(((1s,3s)-3-((dimethylamino)methyl)cyclobutyl)methyl)-5-(1-methyl-1H-pyrazol-3-yl)pyridine-2,4-diamine The title compound as pale yellow solid (40.8 mg) was prepared in the same fashion as Step 2 in Example 1, except that 2-chloro-N-(((1s,3s)-3-((dimethylamino)methyl)cyclobutyl)methyl)-5-(1-methyl-1H-pyrazol-3-yl)pyridin-4-amine (107 mg, 0.32 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.67 (s, 1H), 8.46 (s, 1H), 8.38 (d, 1H), 8.33 (s, 1H), 8.14 (t, 1H), 7.40 (d, 1H), 7.21 (d, 1H), 7.06 (s, 1H), 6.59 (d, 1H), 3.95 (s, 3H), 3.92 (dd, 2H), 3.85-3.81 (m, 1H), 2.70-2.63 (m, 1H), 2.50-2.42 (m, 1H), 2.37-2.31 (m, 4H), 2.22 (s, 6H), 1.60-1.53 (m, 4H), 1.25-1.20 (m, 2H); MS (ESI) m/z=563.3 (M+H)⁺

Example 235. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-(2,2-difluoroethyl)-N-methylcyclohexane-1-carboxamide Step 1. (1s,4s)-4-((2-Chloro-5-(1-methyl-1H-pyrazol-3-yl)pyridin-4-yl)amino)-N-(2,2-difluoroethyl)-N-methylcyclohexane-1-carboxamide The title compound as a white solid (200 mg) was prepared in the same fashion as Reference Example 15, except that 2-chloro-4-fluoro-5-(1-methyl-1H-pyrazol-3-yl)pyridine (100 mg, 0.47 mmol) prepared in Reference Example 3 and (1s,4s)-4-amino-N-(2,2-difluoroethyl)-N-methylcyclohexane-1-carboxamide (156 mg, 0.709 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=412.1 (M+H)⁺

Step 2. (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-(2,2-difluoroethyl)-N-methylcyclohexane-1-carboxamide The title compound as pale yellow solid (45.6 mg) was prepared in the same fashion as Step 2 in Example 1, except that (1s,4s)-4-((2-chloro-5-(1-methyl-1H-pyrazol-3-yl)pyridin-4-yl)amino)-N-(2,2-difluoroethyl)-N-methylcyclohexane-1-carboxamide (155 mg, 0.38 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (DMSO-d₆, 400 MHz) δ 8.67 (s, 1H), 8.46 (s, 1H), 8.38 (d, 1H), 8.33 (s, 1H), 8.14 (t, 1H), 7.40 (d, 1H), 7.21 (d, 1H), 7.06 (s, 1H), 6.59 (d, 1H), 3.95 (s, 3H), 3.32 (dd, 2H), 3.85-3.81 (m, 1H), 2.70-2.63 (m, 1H), 2.50-2.42 (m, 1H), 2.37-2.31 (m, 4H), 2.22 (s, 6H), 1.60-1.53 (m, 4H), 1.25-1.20 (m, 2H); MS (ESI) m/z=641.2 (M+H)⁺

Example 236. 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)-N,N-dimethylacetamide Step 1. 2-((1s,4s)-4-((2-Chloro-5-(1-methyl-1H-pyrazol-3-yl)pyridin-4-yl)amino)cyclohexyl)-N,N-dimethylacetamide The title compound as a white solid (154 mg) was prepared in the same fashion as Reference Example 15, except that 2-chloro-4-fluoro-5-(1-methyl-1H-pyrazol-3-yl)pyridine (100 mg, 0.47 mmol) prepared in Reference Example 3 and 2-((1s,4s)-4-aminocyclohexyl)-N,N-dimethylacetamide hydrochloride (156 mg, 0.709 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=376.1 (M+H)⁺

Step 2. 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)-N,N-dimethylacetamide The title compound as pale yellow solid (43.2 mg) was prepared in the same fashion as Step 2 in Example 1, except that 2-((1s,4s)-4-((2-chloro-5-(1-methyl-1H-pyrazol-3-yl)pyridin-4-yl)amino)cyclohexyl)-N,N-dimethylacetamide (106 mg, 0.283 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.64 (s, 1H), 8.61 (d, 1H), 8.45 (s, 1H), 8.35 (d, 1H), 8.34 (s, 1H), 7.41 (d, 1H), 7.22 (s, 1H), 7.11 (d, 1H), 6.60 (d, 1H), 3.97 (s, 3H), 3.95 (brs, 1H), 3.03 (s, 3H), 2.96 (s, 3H), 2.87-2.80 (m, 1H), 2.29 (d, 2H), 2.03-1.98 (m, 3H), 1.84-1.72 (m, 4H), 1.55-1.50 (m, 2H), 1.47-1.38 (m, 2H), 1.26-1.19 (m, 2H); MS (ESI) m/z=605.3 (M+H)⁺

Example 237. N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-methyl-1H-pyrazol-3-yl)pyridine-2,4-diamine Step 1. 2-Chloro-N-((1s,4s)-4-(((2,2-difluoroethyl)(methyl)amino)methyl)cyclohexyl)-5-(1-methyl-1H-pyrazol-3-yl)pyridin-4-amine The title compound as a white solid (195 mg) was prepared in the same fashion as Reference Example 15, except that 2-chloro-4-fluoro-5-(1-methyl-1H-pyrazol-3-yl)pyridine (100 mg, 0.47 mmol) prepared in Reference Example 3 and (1s,4s)-4-(((2,2-difluoroethyl)(methyl)amino)methyl)cyclohexan-1-amine (146 mg, 0.709 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=398.1 (M+H)⁺

Step 2. N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-methyl-1H-pyrazol-3-yl)pyridine-2,4-diamine The title compound as pale yellow solid (45.2 mg) was prepared in the same fashion as Step 2 in Example 1, except that 2-chloro-N-((1s,4s)-4-(((2,2-difluoroethyl)(methyl)amino)methyl)cyclohexyl)-5-(1-methyl-1H-pyrazol-3-yl)pyridin-4-amine (144 mg, 0.362 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.66 (s, 1H), 8.61 (d, 1H), 8.46 (s, 1H), 8.38 (d, 1H), 7.41 (d, 1H), 7.24 (s, 1H), 7.10 (d, 1H), 6.61 (d, 1H), 5.83 (tt, 1H), 3.99-3.95 (m, 1H), 3.94 (s, 3H), 2.87-2.81 (m, 1H), 2.75 (td, 2H), 2.35 (s, 3H), 2.33 (d, 2H), 2.03-2.00 (m, 2H), 1.80-1.75 (m, 4H), 1.65-1.59 (m, 1H), 1.55-1.51 (m, 2H), 1.36-1.26 (m, 2H) 1.24-1.18 (m, 2H); MS (ESI) m/z=627.2 (M+H)⁺

Example 238. N²-(2-(1-(Cyclopropylsulfonyl)-1H-pyrazol-4-yl)pyrimidin-4-yl)-N⁴-(4-((dimethylamino)methyl)-4-methylcyclohexyl)-5-(1-methyl-1H-pyrazol-3-yl)pyridine-2,4-diamine Step 1. 2-Chloro-N-(4-((dimethylamino)methyl)-4-methylcyclohexyl)-5-(1-methyl-1H-pyrazol-3-yl)pyridin-4-amine The title compound as a white solid (127 mg) was prepared in the same fashion as Reference Example 15, except that 2-chloro-4-fluoro-5-(1-methyl-1H-pyrazol-3-yl)pyridine (90 mg, 0.43 mmol) prepared in Reference Example 3 and 4-((dimethylamino)methyl)-4-methylcyclohexan-1-amine dihydrochloride (155 mg, 0.638 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=362.1 (M+H)⁺

Step 2. N²-(2-(1-(Cyclopropylsulfonyl)-1H-pyrazol-4-yl)pyrimidin-4-yl)-N⁴-(4-((dimethylamino)methyl)-4-methylcyclohexyl)-5-(1-methyl-1H-pyrazol-3-yl)pyridine-2,4-diamine The title compound as pale yellow solid (60.6 mg) was prepared in the same fashion as Step 2 in Example 1, except that 2-chloro-N-(4-((dimethylamino)methyl)-4-methylcyclohexyl)-5-(1-methyl-1H-pyrazol-3-yl)pyridin-4-amine (116 mg, 0.32 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.66 (s, 1H), 8.47 (s, 1H), 8.43-8.38 (m, 2H), 8.35 (s, 1H), 7.40 (s, 1H), 7.37 (dd, 1H), 6.95 (d, 1H), 6.61 (d, 1H), 3.94 (d, 3H), 3.20 (dd, 2H), 2.85-2.79 (m, 1H), 2.29 (d, 6H), 2.15-1.67 (m, 5H), 1.53-1.42 (m, 4H), 1.35-1.21 (m, 3H), 1.14 (s, 3H); MS (ESI) m/z=591.3 (M+H)⁺

Example 239. N²-(2-(1-(Cyclopropylsulfonyl)-1H-pyrazol-4-yl)pyrimidin-4-yl)-N⁴-(((1r,3r)-3-((dimethylamino)methyl)cyclobutyl)methyl)-5-(1-methyl-1H-pyrazol-3-yl)pyridine-2,4-diamine Step 1. 2-Chloro-N-(((1r,3r)-3-((dimethylamino)methyl)cyclobutyl)methyl)-5-(1-methyl-1H-pyrazol-3-yl)pyridin-4-amine The title compound as a white solid (116 mg) was prepared in the same fashion as Reference Example 15, except that 2-chloro-4-fluoro-5-(1-methyl-1H-pyrazol-3-yl)pyridine (100 mg, 0.47 mmol) prepared in Reference Example 3 and 1-((1r,3r)-3-(aminomethyl)cyclobutyl)-N,N-dimethylmethanamine dihydrochloride (153 mg, 0.709 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=334.0 (M+H)⁺

Step 2. N²-(2-(1-(Cyclopropylsulfonyl)-1H-pyrazol-4-yl)pyrimidin-4-yl)-N⁴-(((1r,3r)-3-((dimethylamino)methyl)cyclobutyl)methyl)-5-(1-methyl-1H-pyrazol-3-yl)pyridine-2,4-diamine The title compound as pale yellow solid (47.3 mg) was prepared in the same fashion as Step 2 in Example 1, except that 2-chloro-N-(((1r,3r)-3-((dimethylamino)methyl)cyclobutyl)methyl)-5-(1-methyl-1H-pyrazol-3-yl)pyridin-4-amine (88 mg, 0.26 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.67 (s, 1H), 8.46 (s, 1H), 8.38 (d, 1H), 8.35 (s, 1H), 8.21 (t, 1H), 7.92 (brs, 1H), 7.39 (d, 1H), 7.27 (s, 1H), 7.04 (s, 1H), 6.59 (d, 1H), 3.93 (s, 3H), 3.43 (d, 2H), 2.86-2.79 (m, 1H), 2.77-2.70 (m, 1H), 2.65-2.57 (m, 1H), 2.41 (d, 2H), 2.22 (s, 6H), 2.10-1.91 (m, 4H), 1.54-1.50 (m, 2H), 1.23-1.17 (m, 2H); MS (ESI) m/z=563.2 (M+H)⁺

Example 240. N²-(2-(1-(Cyclopropylsulfonyl)-1H-pyrazol-4-yl)pyrimidin-4-yl)-N⁴-((1s,4s)-4-(2-(dimethylamino)ethyl)cyclohexyl)-5-(1-methyl-1H-pyrazol-3-yl)pyridine-2,4-diamine Step 1. 2-Chloro-N-((1s,4s)-4-(2-(dimethylamino)ethyl)cyclohexyl)-5-(1-methyl-1H-pyrazol-3-yl)pyridin-4-amine The title compound as a white solid (100.4 mg) was prepared in the same fashion as Reference Example 15, except that 2-chloro-4-fluoro-5-(1-methyl-1H-pyrazol-3-yl)pyridine (85 mg, 0.40 mmol) prepared in Reference Example 3 and (1s,4s)-4-(2-(dimethylamino)ethyl)cyclohexan-1-amine dihydrochloride (147 mg, 0.602 mmol) were used instead of 2-chloro-5-(1-(difluoromethyl)-1H-pyrazol-3-yl)-4-fluoropyridine and (1s,4s)-4-amino-1-methylcyclohexan-1-ol. ¹H-NMR (CDCl₃, 400 MHz) δ 8.60 (d, 1H), 8.32 (s, 1H), 7.41 (d, 1H), 6.61 (d, 1H), 6.54 (s, 1H), 3.95 (s, 3H), 3.79-3.77 (m, 1H), 2.31 (dd, 2H), 2.24 (s, 6H), 1.89-1.86 (m, 2H), 1.70-1.64 (m, 4H), 1.48-1.42 (m, 3H), 1.39-1.30 (m, 2H)

Step 2. N²-(2-(1-(Cyclopropylsulfonyl)-1H-pyrazol-4-yl)pyrimidin-4-yl)-N⁴-((1s,4s)-4-(2-(dimethylamino)ethyl)cyclohexyl)-5-(1-methyl-1H-pyrazol-3-yl)pyridine-2,4-diamine The title compound as pale yellow solid (14.8 mg) was prepared in the same fashion as Step 2 in Example 1, except that 2-chloro-N-((1s,4s)-4-(2-(dimethylamino)ethyl)cyclohexyl)-5-(1-methyl-1H-pyrazol-3-yl)pyridin-4-amine (61 mg, 0.17 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.65 (s, 1H), 8.62 (d, 1H), 8.46 (s, 1H), 8.37 (d, 1H), 8.35 (s, 1H), 7.96 (brs, 1H), 7.41 (d, 1H), 7.20 (s, 1H), 7.14 (d, 1H), 6.61 (d, 1H), 3.96 (s, 3H), 3.95 (s, 1H), 2.86-2.80 (m, 1H), 2.32 (t, 2H), 2.24 (s, 6H), 2.00-1.97 (m, 2H), 1.80-1.68 (m, 4H), 1.54-1.51 (m, 2H), 1.48-1.37 (m, 5H), 1.26-1.24 (m, 2H); MS (ESI) m/z=591.3 (M+H)+

Example 241. (1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)-1-methylcyclohexan-1-ol The title compound as pale yellow solid (17.3 mg) was prepared in the same fashion as Step 2 in Example 1, except (1s,4s)-4-((2-chloro-5-(1-(2,2-difluoroethyl)-1H-pyrazol-3-yl)pyridin-4-yl)amino)-1-methylcyclohexan-1-ol (62 mg, 0.17 mmol) prepared in Reference Example 17 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.47 (s, 1H), 8.38 (d, 1H), 8.36 (s, 1H), 8.14 (d, 2H), 7.51 (d, 1H), 7.25 (1H), 7.06 (s, 1H), 6.66 (d, 1H), 6.13 (tt, 1H), 4.51 (td, 2H), 3.55-3.53 (m, 1H), 2.85-2.79 (m, 1H), 2.02-1.98 (m, 2H), 1.83-1.74 (m, 4H), 1.63-1.56 (m, 2H), 1.54-1.50 (m, 2H), 1.32 (s, 3H), 1.23-1.18 (m, 2H); MS (ESI) m/z=600.2 (M+H)+

Example 242. N$^2$-(2-(1-(Cyclopropylsulfonyl)-1H-pyrazol-4-yl)pyrimidin-4-yl)-5-(1-(2,2-difluoroethyl)-1H-pyrazol-3-yl)-N$^4$-((1s,4s)-4-((2-fluoroethyl)amino)cyclohexyl)pyridine-2,4-diamine Step 1. (1s,4s)-N$^1$-(2-Chloro-5-(1-(2,2-difluoroethyl)-1H-pyrazol-3-yl)pyridin-4-yl)-N$^4$-(2-fluoroethyl)cyclohexane-1,4-diamine The title compound as a white solid (77 mg) was prepared in the same fashion as Step 2 in Reference Example 17, except that (1s,4s)-N$^1$-(2-fluoroethyl)cyclohexane-1,4-diamine (64 mg, 0.40 mmol) was used instead of (1s,4s)-4-amino-1-methylcyclohexan-1-ol. MS (ESI) m/z=402.0 (M+H)+

Step 2. N$^2$-(2-(1-(Cyclopropylsulfonyl)-1H-pyrazol-4-yl)pyrimidin-4-yl)-5-(1-(2,2-difluoroethyl)-1H-pyrazol-3-yl)-N$^4$-((1s,4s)-4-((2-fluoroethyl)amino)cyclohexyl)pyridine-2,4-diamine The title compound as pale yellow solid (24.8 mg) was prepared in the same fashion as Step 2 in Example 1, except that (1s,4s)-N$^1$-(2-chloro-5-(1-(2,2-difluoroethyl)-1H-pyrazol-3-yl)pyridin-4-yl)-N$^4$-(2-fluoroethyl)cyclohexane-1,4-diamine (76 mg, 0.19 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.42 (d, 1H), 8.39 (d, 1H), 8.35 (s, 1H), 7.68 (brs, 1H), 7.53 (d, 1H), 7.25 (s, 1H), 7.12 (d, 1H), 6.69 (d, 1H), 6.26 (tt, 1H), 4.62 (t, 1H), 4.57-4.49 (m, 3H), 3.94 (brs, 1H), 2.95 (dt, 2H), 2.87-2.80 (m, 1H), 2.70-2.65 (m, 1H), 2.03-2.00 (m, 2H), 1.85-1.79 (m, 4H), 1.56-1.48 (m, 4H), 1.26-1.20 (m, 2H); MS (ESI) m/z=631.2 (M+H)+

Example 243. 2-((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)propan-2-ol Step 1. 2-((1s,4s)-4-((2-Chloro-5-(1-(2,2-difluoroethyl)-1H-pyrazol-3-yl)pyridin-4-yl)amino)cyclohexyl)propan-2-ol The title compound as a white solid (188.6 mg) was prepared in the same fashion as Step 2 in Reference Example 17, except that 2-((1s,4s)-4-aminocyclohexyl)propan-2-ol (135 mg, 0.86 mmol) was used instead of (1s,4s)-4-amino-1-methylcyclohexan-1-ol. MS (ESI) m/z=399.0 (M+H)+

Step 2. 2-((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)propan-2-ol The title compound as pale yellow solid (88.2 mg) was prepared in the same fashion as Step 2 in Example 1, except that 2-((1s,4s)-4-((2-chloro-5-(1-(2,2-difluoroethyl)-1H-pyrazol-3-yl)pyridin-4-yl)amino)cyclohexyl)propan-2-ol (180 mg, 0.45 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.98 (s, 1H), 8.62 (s, 1H), 8.44-8.38 (m, 4H), 7.89 (d, 1H), 7.49 (brs, 1H), 7.37 (brs, 1H), 6.91 (d, 1H), 6.39 (tt, 1H), 4.65 (td, 2H), 4.08 (s, 1H), 3.93 (brs, 1H), 3.30-3.24 (m, 1H), 1.99-1.96 (m, 2H), 1.70-1.64 (m, 4H), 1.37-1.32 (m, 2H), 1.30-1.22 (m, 5H), 1.06 (S, 6H); MS (ESI) m/z=628.2.2 (M+H)+

Example 244. ((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)methanol Step 1. ((1s,4s)-4-((2-Chloro-5-(1-(2,2-difluoroethyl)-1H-pyrazol-3-yl)pyridin-4-yl)amino)cyclohexyl)methanol The title compound as a white solid (126 mg) was prepared in the same fashion as Step 2 in Reference Example 17, except that ((1s,4s)-4-aminocyclohexyl)methanol hydrochloride (95 mg, 0.573 mmol) was used instead of (1s,4s)-4-amino-1-methylcyclohexan-1-ol. $^1$H-NMR (DMSO-d$_6$, 400 MHz) δ 8.63 (d, 1H), 8.42 (s, 1H), 7.93 (d, 1H), 6.97 (d, 1H), 6.68 (s, 1H), 6.38 (tt, 1H), 4.68 (td, 2H), 4.45 (t, 1H), 3.90-3.88 (m, 1H), 3.27 (t, 2H), 1.74-1.70 (m, 2H), 1.63-1.57 (m, 4H), 1.47-1.44 (m, 1H), 1.31-1.22 (m, 2H)

Step 2. ((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)methanol The title compound as pale yellow solid (40.9 mg) was prepared in the same fashion as Step 2 in Example 1, except that ((1s,4s)-4-((2-chloro-5-(1-(2,2-difluoroethyl)-1H-pyrazol-3-yl)pyridin-4-yl)amino)cyclohexyl)methanol (108 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.45 (s, 1H), 8.44 (d, 1H), 8.35 (s, 2H), 7.52 (s, 1H), 7.34 (s, 1H), 7.04 (s, 1H), 6.67 (s, 1H), 6.13 (tt, 1H), 4.52 (td, 2H), 4.00 (brs, 1H), 3.55 (d, 2H), 2.83 (brs, 1H), 2.04-2.01 (m, 2H), 1.82-1.76 (m, 2H), 1.71-1.68 (m, 3H), 1.51-1.41 (m, 4H), 1.22-1.20 (m, 2H); MS (ESI) m/z=600.2 (M+H)+

Example 245. N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-(2,2-difluoroethyl)-1H-pyrazol-3-yl)pyridine-2,4-diamine Step 1. 2-Chloro-N-((1s,4s)-4-(((2,2-difluoroethyl)(methyl)amino)methyl)cyclohexyl)-5-(1-(2,2-difluoroethyl)-1H-pyrazol-3-yl)pyridin-4-amine The title compound as a white solid (194 mg) was prepared in the same fashion as Step 2 in Reference Example 17, except that (1s,4s)-4-(((2,2-difluoroethyl)(methyl)amino)methyl)cyclohexan-1-amine (146 mg, 0.709 mmol) was used instead of (1s,4s)-4-amino-1-methylcyclohexan-1-ol. MS (ESI) m/z=448.1 (M+H)⁺

Step 2. N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-(2,2-difluoroethyl)-1H-pyrazol-3-yl)pyridine-2,4-diamine The title compound as pale yellow solid (66.6 mg) was prepared in the same fashion as Step 2 in Example 1, except 2-chloro-N-((1s,4s)-4-(((2,2-difluoroethyl)(methyl)amino)methyl)cyclohexyl)-5-(1-(2,2-difluoroethyl)-1H-pyrazol-3-yl)pyridin-4-amine (162 mg, 0.36 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.65 (s, 1H), 8.46 (s, 1H), 8.40-8.34 (m, 3H), 7.79 (brs, 1H), 7.53 (d, 1H), 7.27 (s, 1H), 7.09 (d, 1H), 6.70 (d, 1H), 6.25-5.68 (m, 2H), 4.51 (td, 2H), 3.99 (brs, 1H), 2.87-2.81 (m, 1H), 2.74 (td, 2H), 2.35 (s, 3H), 2.32 (d, 2H), 2.05-1.99 (m, 2H), 1.78-1.74 (m, 3H), 1.63-1.59 (m, 1H), 1.55-1.51 (m, 2H), 1.30-1.19 (m, 5H); MS (ESI) m/z=677.2 (M+H)⁺

Example 246. N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-(4-((dimethylamino)methyl)-4-methylcyclohexyl)pyridine-2,4-diamine Step 1. 2-Chloro-5-(1-(2,2-difluoroethyl)-1H-pyrazol-3-yl)-N-(4-((dimethylamino)methyl)-4-methylcyclohexyl)pyridin-4-amine The title compound as a white solid (151 mg) was prepared in the same fashion as Step 2 in Reference Example 17, except that 4-((dimethylamino)methyl)-4-methylcyclohexan-1-amine dihydrochloride (155 mg, 0.638 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=412.1 (M+H)⁺

Step 2. N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-(4-((dimethylamino)methyl)-4-methylcyclohexyl)pyridine-2,4-diamine The title compound as pale yellow solid (55.9 mg) was prepared in the same fashion as Step 2 in Example 1, except that 2-chloro-5-(1-(2,2-difluoroethyl)-1H-pyrazol-3-yl)-N-(4-((dimethylamino)methyl)-4-methylcyclohexyl)pyridin-4-amine (132 mg, 0.32 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.67 (s, 1H), 8.47 (s, 1H), 8.40 (t, 1H), 8.36 (s, 1H), 8.15 (dt, 1H), 7.70 (brs, 1H), 7.53 (s, 1H), 7.36 (dd, 1H), 6.97 (d, 1H), 6.70 (d, 1H), 6.10 (tt, 1H), 4.54-4.46 (m, 2H), 3.20 (dd, 2H), 2.84-2.80 (m, 1H), 2.29 (d, 6H), 2.13-2.03 (m, 1H), 1.87-1.65 (m, 4H), 1.55-1.51 (m, 2H), 1.47-1.26 (m, 3H), 1.23-1.18 (m, 2H), 1.10 (s, 3H); MS (ESI) m/z=641.3 (M+H)⁺

Example 247. N⁴-((1s,4s)-4-(Azetidin-1-ylmethyl)cyclohexyl)-N²-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine Step 1. N-((1s,4s)-4-(Azetidin-1-ylmethyl)cyclohexyl)-2-chloro-5-(1-(2,2-difluoroethyl)-1H-pyrazol-3-yl)pyridin-4-amine The title compound as a white solid (87.2 mg) was prepared in the same fashion as Step 2 in Reference Example 17, except that (1s,4s)-4-(azetidin-1-ylmethyl)cyclohexan-1-amine (102 mg, 0.606 mmol) was used instead of (1s,4s)-4-amino-1-methylcyclohexan-1-ol. MS (ESI) m/z=410.2 (M+H)⁺

Step 2. N⁴-((1s,4s)-4-(Azetidin-1-ylmethyl)cyclohexyl)-N²-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine The title compound as pale yellow solid (20 mg) was prepared in the same fashion as Step 2 in Example 1, except that N-((1s,4s)-4-(azetidin-1-ylmethyl)cyclohexyl)-2-chloro-5-(1-(2,2-difluoroethyl)-1H-pyrazol-3-yl)pyridin-4-amine (85 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.65 (s, 1H), 8.45 (s, 1H), 8.42-8.35 (m, 3H), 8.00 (brs, 1H), 7.52 (s, 1H), 7.24 (s, 1H), 7.12 (d, 1H), 6.69 (s, 1H), 6.13 (tt, 1H), 4.53 (td, 2H), 3.95 (brs, 1H), 3.22 (t, 4H), 2.86-2.80 (m, 1H), 2.32 (d, 2H), 2.12-2.06 (m, 2H), 2.00-1.97 (m, 2H), 1.80-1.69 (m, 4H), 1.52-1.48 (m, 3H), 1.34-1.19 (m, 4H); MS (ESI) m/z=639.2 (M+H)⁺

Example 248. N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-isopropylpyridine-2,4-diamine Step 1. 2-Chloro-5-(1-(2,2-difluoroethyl)-1H-pyrazol-3-yl)-N-isopropylpyridin-4-amine The title compound as a white solid (103 mg) was prepared in the same fashion as Step 2 in Reference Example 17, except that isopropylamine (45 mg, 0.764 mmol) was used instead of (1s,4s)-4-amino-1-methylcyclohexan-1-ol. MS (ESI) m/z=301.1 (M+H)⁺

Step 2. N²-(2-(1-(Cyclopropylsulfonyl)-1H-pyrazol-4-yl)pyrimidin-4-yl)-5-(1-(2,2-difluoroethyl)-1H-pyrazol-3-yl)-N⁴-isopropylpyridine-2,4-diamine The title compound as pale yellow solid (23.6 mg) was prepared in the same fashion as Step 2 in Example 1, except that 2-chloro-5-(1-(2,2-difluoroethyl)-1H-pyrazol-3-yl)-N-isopropylpyridin-4-amine (87 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (MeOD, 400 MHz) δ 8.73 (s, 1H), 8.46 (s, 1H), 8.34 (d, 1H), 8.30 (s, 1H), 7.74 (d, 1H), 7.36 (s, 1H), 7.27 (d, 1H), 6.74 (d, 1H), 6.22 (tt, 1H), 4.64 (td, 2H), 3.94-3.88 (m, 1H), 3.08-3.01 (m, 1H), 1.47-1.43 (m, 2H), 1.38 (d, 6H), 1.34-1.26 (m, 2H); MS (ESI) m/z=530.2 (M+H)$^+$ Example 249. N$^2$-(2-(1-(Cyclopropylsulfonyl)-1H-pyrazol-4-yl)pyrimidin-4-yl)-5-(1-(2,2-difluoroethyl)-1H-pyrazol-3-yl)-N$^4$-(((1r,3r)-3-((dimethylamino)methyl)cyclobutyl)methyl)pyridine-2,4-diamine Step 1. 2-Chloro-5-(1-(2,2-difluoroethyl)-1H-pyrazol-3-yl)-N-(((1r,3r)-3-((dimethylamino)methyl)cyclobutyl)methyl)pyridin-4-amine The title compound as a white solid (120 mg) was prepared in the same fashion as Step 2 in Reference Example 17, except that 1-((1r,3r)-3-(aminomethyl)cyclobutyl)-N,N-dimethylmethanamine dihydrochloride (153 mg, 0.709 mmol) was used instead of (1s,4s)-4-amino-1-methylcyclohexan-1-ol. MS (ESI) m/z=384.0 (M+H)$^+$ Step 2. N$^2$-(2-(1-(Cyclopropylsulfonyl)-1H-pyrazol-4-yl)pyrimidin-4-yl)-5-(1-(2,2-difluoroethyl)-1H-pyrazol-3-yl)-N$^4$-(((1r,3r)-3-((dimethylamino)methyl)cyclobutyl)methyl)pyridine-2,4-diamine The title compound as pale yellow solid (61.1 mg) was prepared in the same fashion as Step 2 in Example 1, except that 2-chloro-5-(1-(2,2-difluoroethyl)-1H-pyrazol-3-yl)-N-(((1r,3r)-3-((dimethylamino)methyl)cyclobutyl)methyl)pyridin-4-amine (101 mg, 0.26 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.73 (s, 1H), 8.46 (s, 1H), 8.34 (d, 1H), 8.30 (s, 1H), 7.74 (d, 1H), 7.36 (s, 1H), 7.27 (d, 1H), 6.74 (d, 1H), 6.22 (tt, 1H), 4.64 (td, 2H), 3.94-3.88 (m, 1H), 3.08-3.01 (m, 1H), 1.47-1.43 (m, 2H), 1.38 (d, 6H), 1.34-1.26 (m, 2H); MS (ESI) m/z=613.2 (M+H)$^+$ Example 250. N$^4$-(sec-Butyl)-N$^2$-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine Step 1. N-(sec-Butyl)-2-chloro-5-(1-(2,2-difluoroethyl)-1H-pyrazol-3-yl)pyridin-4-amine The title compound as a white solid (103 mg) was prepared in the same fashion as Step 2 in Reference Example 17, except that butan-2-amine (44 mg, 0.606 mmol) was used instead of (1s,4s)-4-amino-1-methylcyclohexan-1-ol. MS (ESI) m/z=316.0 (M+H)$^+$ Step 2. N$^4$-(sec-Butyl)-N$^2$-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine The title compound as pale yellow solid (38.8 mg) was prepared in the same fashion as Step 2 in Example 1, except that N-(sec-butyl)-2-chloro-5-(1-(2,2-difluoroethyl)-1H-pyrazol-3-yl)pyridin-4-amine (91 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.39 (d, 1H), 8.35 (s, 1H), 8.01 (d, 1H), 7.96 (brs, 1H), 7.52 (d, 1H), 7.21 (d, 1H), 7.12 (s, 1H), 6.67 (d, 1H), 6.10 (tt, 1H), 4.50 (td, 2H), 3.72-3.65 (m, 1H), 2.86-2.80 (m, 1H), 1.78-1.69 (m, 2H), 1.55-1.51 (m, 2H), 1.35 (d, 3H), 1.24-1.18 (m, 2H), 1.03 (t, 3H); MS (ESI) m/z=544.2 (M+H)$^+$ Example 251. N$^2$-(2-(1-(Cyclopropylsulfonyl)-1H-pyrazol-4-yl)pyrimidin-4-yl)-5-(1-(2,2-difluoroethyl)-1H-pyrazol-3-yl)-N$^4$-((1s,4s)-4-(2-(dimethylamino)ethyl)cyclohexyl)pyridine-2,4-diamine Step 1. 2-Chloro-5-(1-(2,2-difluoroethyl)-1H-pyrazol-3-yl)-N-((1s,4s)-4-(2-(dimethylamino)ethyl)cyclohexyl)pyridin-4-amine The title compound as a white solid (103 mg) was prepared in the same fashion as Step 2 in Reference Example 17, except that (1s,4s)-4-(2-(dimethylamino)ethyl)cyclohexan-1-amine dihydrochloride (147 mg, 0.602 mmol) was used instead of (1s,4s)-4-amino-1-methylcyclohexan-1-ol. $^1$H-NMR (CDCl$_3$, 400 MHz) δ 8.35 (d, 1H), 8.31 (s, 1H), 7.53 (d, 1H), 6.71 (d, 1H), 6.55 (s, 1H), 6.08 (tt, 1H), 4.50 (td, 2H), 3.78-3.76 (m, 1H), 2.32 (dd, 2H), 2.24 (s, 6H), 1.88-1.85 (m, 2H), 1.72-1.66 (m, 4H), 1.47-1.41 (m, 3H), 1.34-1.28 (m, 2H)

Step 2. N$^2$-(2-(1-(Cyclopropylsulfonyl)-1H-pyrazol-4-yl)pyrimidin-4-yl)-5-(1-(2,2-difluoroethyl)-1H-pyrazol-3-yl)-N$^4$-((1s,4s)-4-(2-(dimethylamino)ethyl)cyclohexyl)pyridine-2,4-diamine The title compound as pale yellow solid (34.2 mg) was prepared in the same fashion as Step 2 in Example 1, except that 2-chloro-5-(1-(2,2-difluoroethyl)-1H-pyrazol-3-yl)-N-((1s,4s)-4-(2-(dimethylamino)ethyl)cyclohexyl)pyridin-4-amine (70 mg, 0.17 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.47 (d, 1H), 8.46 (s, 1H), 8.39 (d, 1H), 8.33 (s, 1H), 7.54 (d, 1H), 7.26 (s, 1H), 7.14 (d, 1H), 6.70 (d, 1H), 6.14 (tt, 1H), 4.54 (td, 2H), 3.96 (brs, 1H), 2.88-2.81 (m, 1H), 2.47-2.44 (m, 2H), 2.35 (s, 6H), 2.01-1.98 (m, 2H), 1.83-1.69 (m, 4H), 1.55-1.51 (m, 5H), 1.35-1.29 (m, 2H), 1.26-1.20 (m, 2H); MS (ESI) m/z=641.3 (M+H)$^+$ Example 252. (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol The title compound as pale yellow solid (20.1 mg) was prepared in the same fashion as Step 2 in Example 1, except that (1s,4s)-4-((2-chloro-5-(1-methyl-5-(trifluoromethyl)-1H-pyrazol-3-yl)pyridin-4-yl)amino)-1-methylcyclohexan-1-ol (64 mg, 0.17 mmol) prepared in Reference Example 16 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.48 (s, 1H), 8.41 (d, 1H), 8.30 (s, 1H), 7.97 (d, 1H), 7.47 (brs, 1H), 7.02 (brs, 1H), 6.94 (s, 1H), 4.04 (s, 3H), 3.54 (brs, 1H), 2.80 (brs, 1H), 2.03-2.01 (m, 2H), 1.80-1.76 (m, 4H), 1.61-1.55 (m, 4H), 1.33 (s, 3H), 1.26-1.21 (m, 2H); MS (ESI) m/z=618.2 (M+H)$^+$ Example 253. ((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol Step 1. ((1s,4s)-4-((2-Chloro-5-(1-methyl-5-(trifluoromethyl)-1H-pyrazol-3-yl)pyridin-4-yl)amino)cyclohexyl)methanol The title compound as a white solid (70.6 mg) was prepared in the same fashion as Step 2 in Reference Example 16, except that ((1s,4s)-4-aminocyclohexyl)methanol hydrochloride (62 mg, 0.4376 mmol) was used instead of (1s,4s)-4-amino-1-methylcyclohexan-1-ol. MS (ESI) m/z=389.1 (M+H)$^+$ Step 2. ((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol The title compound as pale yellow solid (22.4 mg) was prepared in the same fashion as Step 2 in Example 1, except that ((1s,4s)-4-((2-chloro-5-(1-methyl-5-(trifluoromethyl)-1H-pyrazol-3-yl)pyridin-4-yl)amino)cyclohexyl)methanol (64 mg, 0.17 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.02 (s, 1H), 8.62 (s 1H), 8.50 (s, 1H), 8.44 (s, 1H), 8.40 (d, 1H), 8.24 (d, 1H), 7.55 (s, 1H), 7.50 (brs, 1H), 7.37 (brs, 1H), 4.48 (t, 1H), 4.02 (s, 3H), 3.96 (brs, 1H), 3.31-3.24 (m, 3H), 1.90-1.87 (m, 2H), 1.75-1.63 (m, 4H), 1.49 (brs, 1H), 1.36-1.24 (m, 4H); MS (ESI) m/z=618.2 (M+H)$^+$ Example 254. 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)propan-2-ol Step 1. 2-((1s,4s)-4-((2-Chloro-5-(1-methyl-5-(trifluoromethyl)-1H-pyrazol-3-yl)pyridin-4-yl)amino)cyclohexyl)propan-2-ol The title compound as a white solid (81.1 mg) was prepared in the same fashion as Step 2 in Reference Example 16, except that 2-((1s,4s)-4-aminocyclohexyl)propan-2-ol (59 mg, 0.376 mmol) was used instead of (1s,4s)-4-amino-1-methylcyclohexan-1-ol. MS (ESI) m/z=417.1 (M+H)$^+$ Step 2. 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)propan-2-ol The title compound as pale yellow solid (22.5 mg) was prepared in the same fashion as Step 2 in Example 1, except that 2-((1s,4s)-4-((2-chloro-5-(1-methyl-5-(trifluoromethyl)-1H-pyrazol-3-yl)pyridin-4-yl)amino)cyclohexyl)propan-2-ol (69 mg, 0.17 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.39 (d, 1H), 8.32 (s, 1H), 8.31 (d, 1H), 7.60 (brs, 1H), 7.33 (brs, 1H), 7.06 (d, 1H), 6.98 (s, 1H), 4.04 (s, 4H), 2.88-2.81 (m, 1H), 2.13-2.10 (m, 2H), 1.82-1.76 (m, 4H), 1.57-1.45 (m, 4H), 1.24 (d, 6H), 1.24-1.21 (m, 2H); MS (ESI) m/z=646.2 (M+H)$^+$ Example 255. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-(1-methyl-5-(trifluoromethyl)-1H-pyrazol-3-yl)pyridine-2,4-diamine Step 1. (1s,4s)-N$^1$-(2-Chloro-5-(1-methyl-5-(trifluoromethyl)-1H-pyrazol-3-yl)pyridin-4-yl)-N$^4$-(2-fluoroethyl)cyclohexane-1,4-diamine The title compound as a white solid (82 mg) was prepared in the same fashion as Step 2 in Reference Example 16, except that (1s,4s)-N$^1$-(2-fluoroethyl)cyclohexane-1,4-diamine (60 mg, 0.376 mmol) was used instead of (1s,4s)-4-amino-1-methylcyclohexan-1-ol. MS (ESI) m/z=420.1 (M+H)$^+$ Step 2. N$^2$-(2-(1-(Cyclopropylsulfonyl)-1H-pyrazol-4-yl)pyrimidin-4-yl)-N$^4$-((1s,4s)-4-((2-fluoroethyl)amino)cyclohexyl)-5-(1-methyl-5-(trifluoromethyl)-1H-pyrazol-3-yl)pyridine-2,4-diamine The title compound as pale yellow solid (4.4 mg) was prepared in the same fashion as Step 2 in Example 1, except that (1s,4s)-N$^1$-(2-chloro-5-(1-methyl-5-(trifluoromethyl)-1H-pyrazol-3-yl)pyridin-4-yl)-N$^4$-(2-fluoroethyl)cyclohexane-1,4-diamine (63 mg, 0.15 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.40 (d, 1H), 8.29 (s, 1H), 8.24 (d, 1H), 7.11 (brs, 1H), 6.96 (s, 1H), 4.63 (t, 1H), 4.51 (t, 1H), 4.05 (s, 3H), 3.90 (brs, 1H), 3.00 (t, 1H), 2.93 (t, 1H), 2.87-2.81 (m, 1H), 2.69-2.66 (m, 1H), 2.05-2.03 (m, 4H), 1.87-1.81 (m, 4H), 1.55-1.50 (m, 3H), 1.27-1.24 (m, 2H); MS (ESI) m/z=649.2 (M+H)$^+$ Example 256. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(1-methyl-5-(trifluoromethyl)-1H-pyrazol-3-yl)pyridine-2,4-diamine Step 1. 2-Chloro-N-((1s,4s)-4-((dimethylamino)methyl)cyclohexyl)-5-(1-methyl-5-(trifluoromethyl)-1H-pyrazol-3-yl)pyridin-4-amine The title compound as a white solid (87.9 mg) was prepared in the same fashion as Step 2 in Reference Example 16, except that (1s,4s)-4-((dimethylamino)methyl)cyclohexan-1-amine dihydrochloride (123 mg, 0.536 mmol) was used instead of (1s,4s)-4-amino-1-methylcyclohexan-1-ol. MS (ESI) m/z=416.2 (M+H)$^+$ Step 2. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(1-methyl-5-(trifluoromethyl)-1H-pyrazol-3-yl)pyridine-2,4-diamine The title compound as pale yellow solid (28.1 mg) was prepared in the same fashion as Step 2 in Example 1, except that. 2-chloro-N-((1s,4s)-4-((dimethylamino)methyl)cyclohexyl)-5-(1-methyl-5-(trifluoromethyl)-1H-pyrazol-3-yl)pyridin-4-amine (78 mg, 0.118 mmol) prepared in Step 1 was used instead of 2-chloro-5-(1-cyclopropyl-1H-pyrazol-4-yl)-4-((1-methyl-1H-pyrazol-4-yl)ethynyl)pyridine.

¹H-NMR (CDCl₃, 400 MHz) δ 8.66 (s, 1H), 8.46 (s, 1H), 8.38 (d, 1H), 8.31 (s, 2H), 8.07 (brs, 1H), 7.33 (s, 1H), 7.07 (s, 1H), 6.97 (d, 1H), 4.05 (s, 3H), 4.00 (brs, 1H), 2.87-2.82 (m, 1H), 2.25 (s, 6H), 2.17 (d, 2H), 2.05-2.01 (m, 4H), 1.79-1.67 (m, 5H), 1.54-1.51 (m, 2H), 1.30-1.23 (m, 2H); MS (ESI) m/z=645.2 (M+H)⁺

Example 257. (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-N,N-dimethylcyclohexane-1-carboxamide Step 1. (1s,4s)-4-((2-Chloro-5-(1-methyl-5-(trifluoromethyl)-1H-pyrazol-3-yl)pyridin-4-yl)amino)-N,N-dimethylcyclohexane-1-carboxamide The title compound as a white solid (103 mg) was prepared in the same fashion as Step 2 in Reference Example 16, except that (1s,4s)-4-amino-N,N-dimethylcyclohexane-1-carboxamide (111 mg, 0.536 mmol) was used instead of (1s,4s)-4-amino-1-methylcyclohexan-1-ol. MS (ESI) m/z=430.1 (M+H)⁺

Step 2. (1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-N,N-dimethylcyclohexane-1-carboxamide The title compound as pale yellow solid (37.2 mg) was prepared in the same fashion as Step 2 in Example 1, except that (1s,4s)-4-((2-chloro-5-(1-methyl-5-(trifluoromethyl)-1H-pyrazol-3-yl)pyridin-4-yl)amino)-N,N-dimethylcyclohexane-1-carboxamide (81 mg, 0.118 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.66 (s, 1H), 8.43 (s, 1H), 8.38 (d, 1H), 8.35 (s, 2H), 7.98 (brs, 1H), 7.43 (s, 1H), 6.97 (d, 2H), 4.17 (s, 3H), 4.12 (brs, 1H), 3.11 (s, 3H), 2.97 (s, 3H), 2.87-2.82 (m, 1H), 2.74-2.70 (m, 1H), 2.09-1.77 (m, 8H), 1.55-1.51 (m, 2H), 1.25-1.23 (m, 2H); MS (ESI) m/z=659.2 (M+H)⁺

Example 258. 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)-N,N-dimethylacetamide Step 1. 2-((1s,4s)-4-((2-Chloro-5-(1-methyl-5-(trifluoromethyl)-1H-pyrazol-3-yl)pyridin-4-yl)amino)cyclohexyl)-N,N-dimethylacetamide The title compound as a white solid (128.8 mg) was prepared in the same fashion as Step 2 in Reference Example 16, except that 2-((1s,4s)-4-aminocyclohexyl)-N,N-dimethylacetamide (156 mg, 0.709 mmol) was used instead of (1s,4s)-4-amino-1-methylcyclohexan-1-ol. MS (ESI) m/z=444.1 (M+H)⁺

Step 2. 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)-N,N-dimethylacetamide The title compound as pale yellow solid (42.5 mg) was prepared in the same fashion as Step 2 in Example 1, except that 2-((1s,4s)-4-((2-chloro-5-(1-methyl-5-(trifluoromethyl)-1H-pyrazol-3-yl)pyridin-4-yl)amino)cyclohexyl)-N,N-dimethylacetamide (125 mg, 0.283 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.65 (s, 1H), 8.45 (s, 1H), 8.38 (d, 1H), 8.31 (s, 1H), 8.26 (d, 1H), 7.87 (s, 1H), 7.26 (d, 1H), 7.10 (d, 1H), 6.97 (s, 1H), 4.07 (s, 3H), 3.98-3.96 (m, 1H), 3.03 (s, 3H), 2.96 (s, 3H), 2.87-2.83 (m, 1H), 2.30 (d, 2H), 2.03-2.00 (m, 2H), 1.86-1.75 (m, 5H), 1.56-1.51 (m, 2H), 1.44-1.35 (m, 2H), 1.26-1.20 (m, 2H); MS (ESI) m/z=673.2 (M+H)⁺

Example 259. N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-methyl-5-(trifluoromethyl)-1H-pyrazol-3-yl)pyridine-2,4-diamine Step 1. 2-Chloro-N-((1s,4s)-4-(((2,2-difluoroethyl)(methyl)amino)methyl)cyclohexyl)-5-(1-methyl-5-(trifluoromethyl)-1H-pyrazol-3-yl)pyridin-4-amine The title compound as a white solid (171 mg) was prepared in the same fashion as Step 2 in Reference Example 16, except that (1s,4s)-4-(((2,2-difluoroethyl)(methyl)amino)methyl)cyclohexan-1-amine (146 mg, 0.709 mmol) was used instead of (1s,4s)-4-amino-1-methylcyclohexan-1-ol. MS (ESI) m/z=466.1 (M+H)⁺

Step 2. N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-methyl-5-(trifluoromethyl)-1H-pyrazol-3-yl)pyridine-2,4-diamine The title compound as pale yellow solid (37.7 mg) was prepared in the same fashion as Step 2 in Example 1, except that 2-chloro-N-((1s,4s)-4-(((2,2-difluoroethyl)(methyl)amino)methyl)cyclohexyl)-5-(1-methyl-5-(trifluoromethyl)-1H-pyrazol-3-yl)pyridin-4-amine (169 mg, 0.362 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 8.66 (s, 1H), 8.46 (s, 1H), 8.40 (d, 1H), 8.31 (s, 1H), 8.29 (d, 1H), 7.90 (brs, 1H), 7.31 (s, 1H), 7.07 (d, 1H), 6.97 (s, 1H), 5.83 (tt, 1H), 4.04 (s, 3H), 4.01-3.99 (m, 1H), 2.87-2.81 (m, 1H), 2.75 (td, 2H), 2.36 (s, 3H), 2.34 (d, 2H), 2.03-2.00 (m, 2H), 1.82-1.77 (m, 4H), 1.63 (brs, 1H), 1.56-1.51 (m, 2H), 1.32-1.20 (m, 4H); MS (ESI) m/z=695.2 (M+H)⁺

Example 260. ((1S,3S)-3-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol Step 1. ((1S,3S)-3-((2-Chloro-5-(1-methyl-5-(trifluoromethyl)-1H-pyrazol-3-yl)pyridin-4-yl)amino)cyclohexyl)methanol The title compound as a white solid (116.5 mg) was prepared in the same fashion as Step 2 in Reference Example 16, except that ((1S,3S)-3-aminocyclohexyl)methanol hydrochloride (89 mg, 0.536 mmol) was used instead of (1s,4s)-4-amino-1-methylcyclohexan-1-ol. MS (ESI) m/z=389.1 (M+H)⁺

Step 2. ((1S,3S)-3-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol The title compound as pale yellow solid (41.3 mg) was prepared in the same fashion as Step 2 in Example 1, except that ((1S,3S)-3-((2-chloro-5-(1-methyl-5-(trifluoromethyl)-1H-pyrazol-3-yl)pyridin-4-yl)amino)cyclohexyl)methanol (113 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.63 (s, 1H), 8.44 (s, 1H), 8.32 (d, 1H), 8.30 (d, 1H), 8.24 (s, 1H), 8.12 (brs, 1H), 7.33 (s, 1H), 6.96 (d, 1H), 6.91 (s, 1H), 4.07-4.06 (m, 1H), 4.04 (s, 3H), 3.57-3.47 (m, 2H), 2.86-2.82 (m, 1H), 2.16-2.13 (m, 1H), 1.98-1.74 (m, 6H), 1.54-1.49 (m, 3H), 1.26-1.18 (m, 3H); MS (ESI) m/z=618.2 (M+H)$^+$ Example 261. (1R,3S)-3-(((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)methyl)cyclopentan-1-ol Step 1. (1R,3S)-3-(((2-Chloro-5-(1-methyl-5-(trifluoromethyl)-1H-pyrazol-3-yl)pyridin-4-yl)amino)methyl)cyclopentan-1-ol The title compound as a white solid (119.2 mg) was prepared in the same fashion as Step 2 in Reference Example 16, except that (1R,3S)-3-(aminomethyl)cyclopentan-1-ol hydrochloride (81 mg, 0.536 mmol) was used instead of (1s,4s)-4-amino-1-methylcyclohexan-1-ol. MS (ESI) m/z=375.1 (M+H)$^+$ Step 2. (1R,3S)-3-(((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)methyl)cyclopentan-1-ol The title compound as pale yellow solid (38.8 mg) was prepared in the same fashion as Step 2 in Example 1, except that (1R,3S)-3-(((2-chloro-5-(1-methyl-5-(trifluoromethyl)-1H-pyrazol-3-yl)pyridin-4-yl)amino)methyl)cyclopentan-1-ol (109 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (MeOD, 400 MHz) δ 8.72 (s, 1H), 8.44 (s, 1H), 8.32 (d, 1H), 8.31 (s, 1H), 7.34 (d, 1H), 7.20 (s, 1H), 7.19 (s, 1H), 4.32-4.30 (m, 1H), 4.06 (s, 3H), 3.37 (d, 2H), 3.06-3.02 (m, 1H), 2.41-2.39 (m, 1H), 2.23-2.20 (m, 1H), 1.93-1.83 (m, 2H), 1.75-1.65 (m, 2H), 1.48-1.43 (m, 3H), 1.29-1.24 (m, 2H); MS (ESI) m/z=604.2 (M+H)$^+$ Example 262. 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol Step 1. 2-((1s,4s)-4-((2-Chloro-5-(1-methyl-5-(trifluoromethyl)-1H-pyrazol-3-yl)pyridin-4-yl)amino)cyclohexyl)ethan-1-ol The title compound as a white solid (124.3 mg) was prepared in the same fashion as Step 2 in Reference Example 16, except that 2-((1s,4s)-4-aminocyclohexyl)ethan-1-ol (77 mg, 0.536 mmol) was used instead of (1s,4s)-4-amino-1-methylcyclohexan-1-ol. MS (ESI) m/z=403.1 (M+H)$^+$ Step 2. 2-((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol The title compound as pale yellow solid (40.2 mg) was prepared in the same fashion as Step 2 in Example 1, except that 2-((1s,4s)-4-((2-chloro-5-(1-methyl-5-(trifluoromethyl)-1H-pyrazol-3-yl)pyridin-4-yl)amino)cyclohexyl)ethan-1-ol (117 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (MeOD, 400 MHz) δ 8.68 (s, 1H), 8.42 (s, 1H), 8.32 (t, 2H), 7.40 (s, 1H), 7.22 (d, 1H), 7.21 (s, 1H), 4.06 (s, 3H), 3.99 (s, 1H), 3.64 (t, 2H), 3.06-3.01 (m, 1H), 2.02-1.97 (m, 2H), 1.86-1.79 (m, 2H), 1.75-1.71 (m, 2H), 1.63-1.60 (m, 1H), 1.56-1.51 (m, 2H), 1.47-1.43 (m, 2H), 1.41-1.34 (m, 2H), 1.31-1.25 (m, 2H); MS (ESI) m/z=632.2 (M+H)$^+$ Example 263. 2-((1r,4r)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol Step 1. 2-((1r,4r)-4-((2-Chloro-5-(1-methyl-5-(trifluoromethyl)-1H-pyrazol-3-yl)pyridin-4-yl)amino)cyclohexyl)ethan-1-ol The title compound as a white solid (121 mg) was prepared in the same fashion as Step 2 in Reference Example 16, except that 2-((1r,4r)-4-aminocyclohexyl)ethan-1-ol hydrochloride (96 mg, 0.536 mmol) was used instead of (1s,4s)-4-amino-1-methylcyclohexan-1-ol. MS (ESI) m/z=403.1 (M+H)$^+$ Step 2. 2-((1r,4r)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol The title compound as pale yellow solid (39.9 mg) was prepared in the same fashion as Step 2 in Example 1, except that 2-((1r,4r)-4-((2-chloro-5-(1-methyl-5-(trifluoromethyl)-1H-pyrazol-3-yl)pyridin-4-yl)amino)cyclohexyl)ethan-1-ol (117 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.97 (s, 1H), 8.65 (s, 1H), 8.46 (s, 1H), 8.45 (d, 1H), 8.42 (d, 1H), 7.79 (d, 1H), 7.58 (brs, 1H), 7.50 (s, 1H), 7.19 (brs, 1H), 4.35 (t, 1H), 4.01 (s, 3H), 3.45 (t, 2H), 3.28-3.20 (m, 1H), 2.14-2.12 (m, 2H), 1.79-1.76 (m, 2H), 1.43-1.39 (m, 1H), 1.37-1.32 (m, 4H), 1.30-1.25 (m, 4H), 1.13-1.07 (m, 2H); MS (ESI) m/z=632.2 (M+H)$^+$ Example 264. N$^4$-((1s,4s)-4-(Azetidin-1-ylmethyl)cyclohexyl)-N$^2$-(2-(1-(cyclopropylsulfonyl)-1H-pyrazol-4-yl)pyrimidin-4-yl)-5-(1-methyl-5-(trifluoromethyl)-1H-pyrazol-3-yl)pyridine-2,4-diamine Step 1. N-((1s,4s)-4-(Azetidin-1-ylmethyl)cyclohexyl)-2-chloro-5-(1-methyl-5-(trifluoromethyl)-1H-pyrazol-3-yl)pyridin-4-amine The title compound as a white solid (117.9 mg) was prepared in the same fashion as Step 2 in Reference Example 16, except that (1s,4s)-4-(azetidin-1-ylmethyl)cyclohexan-1-amine (102 mg, 0.606 mmol) was used instead of (1s,4s)-4-amino-1-methylcyclohexan-1-ol. MS (ESI) m/z=428.2 (M+H)$^+$ Step 2. N$^4$-((1s,4s)-4-(Azetidin-1-ylmethyl)cyclohexyl)-N$^2$-(2-(1-(cyclopropylsulfonyl)-1H-pyrazol-4-yl)pyrimidin-4-yl)-5-(1-methyl-5-(trifluoromethyl)-1H-pyrazol-3-yl)pyridine-2,4-diamine The title compound as pale yellow solid (41.1 mg) was prepared in the same fashion as Step 2 in Example 1, except that N-((1s,4s)-4-(azetidin-1-ylmethyl)cyclohexyl)-2-chloro-5-(1-methyl-5-(trifluoromethyl)-1H-pyrazol-3-yl)pyridin-4-amine (89 mg, 0.207 mmol) prepared in Step 1 were used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.46 (s, 1H), 8.39 (d, 1H), 8.31 (s, 1H), 8.27 (d, 1H), 7.81 (brs, 1H), 7.27 (s, 1H), 7.09 (s, 1H), 6.96 (s, 1H), 4.05 (s, 3H), 3.96 (brs, 1H), 3.21 (t, 4H), 2.87-2.81 (m, 1H), 2.34 (d, 2H), 2.13-2.06 (m, 2H), 2.00-1.97 (m, 2H), 1.81-1.71 (m, 4H), 1.54-1.50 (m, 3H), 1.35-1.19 (m, 4H); MS (ESI) m/z=657.2 (M+H)$^+$ Example 265. 2-((1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)propan-2-ol Step 1. 2-((1s,4s)-4-((2-Chloro-5-(1-(2,2,2-trifluoroethyl)-1H-pyrazol-3-yl)pyridin-4-yl)amino)cyclohexyl)propan-2-ol The title compound as a white solid (138 mg) was prepared in the same fashion as Reference Example 15, except that 2-chloro-4-fluoro-5-(1-(2,2,2-trifluoroethyl)-1H-pyrazol-3-yl)pyridine (100 mg, 0.358 mmol) prepared in Reference Example 21 and 2-((1s,4s)-4-aminocyclohexyl)propan-2-ol (84 mg, 0.536 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=417.1 (M+H)$^+$ Step 2. 2-((1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)propan-2-ol The title compound as pale yellow solid (35 mg) was prepared in the same fashion as Step 2 in Example 1, except that 2-((1s,4s)-4-((2-chloro-5-(1-(2,2,2-trifluoroethyl)-1H-pyrazol-3-yl)pyridin-4-yl)amino)cyclohexyl)propan-2-ol (69 mg, 0.166 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.01 (s, 1H), 8.62 (s, 1H), 8.44 (d, 2H), 8.39 (d, 1H), 8.36 (d, 1H), 7.97 (d, 1H), 7.50 (brs, 1H), 7.36 (brs, 1H), 6.97 (d, 1H), 5.12 (q, 2H), 4.12 (s, 1H), 3.93 (brs, 1H), 3.30-3.24 (m, 1H), 1.98-1.95 (m, 2H), 1.68 (brs, 4H), 1.34-1.25 (m, 6H), 1.04 (s, 6H); MS (ESI) m/z=646.2 (M+H)$^+$ Example 266. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(1-(2,2,2-trifluoroethyl)-1H-pyrazol-3-yl)pyridine-2,4-diamine Step 1. 2-Chloro-N-((1s,4s)-4-((dimethylamino)methyl)cyclohexyl)-5-(1-(2,2,2-trifluoroethyl)-1H-pyrazol-3-yl)pyridin-4-amine The title compound as a white solid (137.2 mg) was prepared in the same fashion as Reference Example 15, except that 2-chloro-4-fluoro-5-(1-(2,2,2-trifluoroethyl)-1H-pyrazol-3-yl)pyridine (100 mg, 0.358 mmol) prepared in Reference Example 21 and (1s,4s)-4-((dimethylamino)methyl)cyclohexan-1-amine dihydrochloride (123 mg, 0.536 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=416.1 (M+H)$^+$ Step 2. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(1-(2,2,2-trifluoroethyl)-1H-pyrazol-3-yl)pyridine-2,4-diamine The title compound as pale yellow solid (38.6 mg) was prepared in the same fashion as Step 2 in Example 1, except that 2-chloro-N-((1s,4s)-4-((dimethylamino)methyl)cyclohexyl)-5-(1-(2,2,2-trifluoroethyl)-1H-pyrazol-3-yl)pyridin-4-amine (133 mg, 0.32 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.46 (s, 1H), 8.39-8.36 (m, 3H), 7.71 (brs, 1H), 7.56 (d, 1H), 7.22 (s, 1H), 7.13 (d, 1H), 6.75 (d, 1H), 4.74 (q, 2H), 3.99-3.97 (m, 1H), 2.86-2.81 (m, 1H), 2.22 (s, 6H), 2.12 (d, 2H), 2.03-1.99 (m, 2H), 1.82-1.73 (m, 4H), 1.63 (brs, 1H), 1.54-1.51 (m, 2H), 1.31-1.24 (m, 4H); MS (ESI) m/z=645.2 (M+H)$^+$ Example 267. N$^2$-(2-(1-(Cyclopropylsulfonyl)-1H-pyrazol-4-yl)pyrimidin-4-yl)-N$^4$-(4-((dimethylamino)methyl)-4-methylcyclohexyl)-5-(1-(2,2,2-trifluoroethyl)-1H-pyrazol-3-yl)pyridine-2,4-diamine Step 1. 2-Chloro-N-(4-((dimethylamino)methyl)-4-methylcyclohexyl)-5-(1-(2,2,2-trifluoroethyl)-1H-pyrazol-3-yl)pyridin-4-amine The title compound as a white solid (133 mg) was prepared in the same fashion as Reference Example 15, except that 2-chloro-4-fluoro-5-(1-(2,2,2-trifluoroethyl)-1H-pyrazol-3-yl)pyridine (119 mg, 0.425 mmol) prepared in Reference Example 21 and 4-((dimethylamino)methyl)-4-methylcyclohexan-1-amine dihydrochloride (155 mg, 0.638 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=402.0 (M+H)$^+$ Step 2. N$^2$-(2-(1-(Cyclopropylsulfonyl)-1H-pyrazol-4-yl)pyrimidin-4-yl)-N$^4$-(4-((dimethylamino)methyl)-4-methylcyclohexyl)-5-(1-(2,2,2-trifluoroethyl)-1H-pyrazol-3-yl)pyridine-2,4-diamine The title compound as pale yellow solid (47.7 mg) was prepared in the same fashion as Step 2 in Example 1, except that 2-chloro-N-(4-((dimethylamino)methyl)-4-methylcyclohexyl)-5-(1-(2,2,2-trifluoroethyl)-1H-pyrazol-3-yl)pyridin-4-amine (138 mg, 0.32 mmol) prepared in Step 1 was used instead of 2-chloro-5-(1-cyclopropyl-1H-pyrazol-4-yl)-4-((1-methyl-1H-pyrazol-4-yl)ethynyl)pyridine.
¹H-NMR (CDCl₃, 400 MHz) δ 8.66 (s, 1H), 8.47 (s, 1H), 8.40 (t, 1H), 8.36 (s, 1H), 8.11 (dt, 1H), 7.71 (brs, 1H), 7.56 (s, 1H), 7.36 (dd, 1H), 6.97 (d, 1H), 6.74 (d, 1H), 4.71 (q, 2H), 3.19 (dd, 2H), 2.84-2.80 (m, 1H), 2.29 (d, 6H), 2.13-2.03 (m, 1H), 1.87-1.65 (m, 4H), 1.55-1.50 (m, 2H), 1.49-1.26 (m, 3H), 1.23-1.18 (m, 2H), 1.09 (s, 3H); MS (ESI) m/z=659.2 (M+H)⁺

Example 268. (1R,3S)-3-(((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)methyl)cyclopentan-1-ol Step 1. (1R,3S)-3-(((2-Chloro-5-(1-(2,2,2-trifluoroethyl)-1H-pyrazol-3-yl)pyridin-4-yl)amino)methyl)cyclopentan-1-ol The title compound as a white solid (114.5 mg) was prepared in the same fashion as Reference Example 15, except that 2-chloro-4-fluoro-5-(1-(2,2,2-trifluoroethyl)-1H-pyrazol-3-yl)pyridine (100 mg, 0.358 mmol) prepared in Reference Example 21 and (1R,3S)-3-(aminomethyl)cyclopentan-1-ol hydrochloride (81 mg, 0.536 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=375.1 (M+H)⁺

Step 2. (1R,3S)-3-(((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)methyl)cyclopentan-1-ol The title compound as pale yellow solid (37.6 mg) was prepared in the same fashion as Step 2 in Example 1, except that (1R,3S)-3-(((2-chloro-5-(1-(2,2,2-trifluoroethyl)-1H-pyrazol-3-yl)pyridin-4-yl)amino)methyl)cyclopentan-1-ol (109 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (MeOD, 400 MHz) δ 8.72 (s, 1H), 8.45 (s, 1H), 8.33 (d, 1H), 8.32 (s, 1H), 7.79 (d, 1H), 7.32 (d, 1H), 7.17 (s, 1H), 6.80 (d, 1H), 5.01 (q, 2H), 4.32-4.28 (m, 1H), 3.36 (d, 2H), 3.05-3.01 (m, 1H), 2.40-2.32 (m, 1H), 2.26-2.20 (m, 1H), 1.92-1.82 (m, 2H), 1.73-1.62 (m, 2H), 1.47-1.43 (m, 3H), 1.29-1.25 (m, 2H); MS (ESI) m/z=604.2 (M+H)⁺

Example 269. 2-((1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol Step 1. 2-((1s,4s)-4-((2-Chloro-5-(1-(2,2,2-trifluoroethyl)-1H-pyrazol-3-yl)pyridin-4-yl)amino)cyclohexyl)ethan-1-ol The title compound as a white solid (131 mg) was prepared in the same fashion as Reference Example 15, except that 2-chloro-4-fluoro-5-(1-(2,2,2-trifluoroethyl)-1H-pyrazol-3-yl)pyridine (100 mg, 0.358 mmol) prepared in Reference Example 21 and 2-((1s,4s)-4-aminocyclohexyl)ethan-1-ol (77 mg, 0.536 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=403.1 (M+H)⁺

Step 2. 2-((1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol The title compound as pale yellow solid (41.1 mg) was prepared in the same fashion as Step 2 in Example 1, except that 2-((1s,4s)-4-((2-chloro-5-(1-(2,2,2-trifluoroethyl)-1H-pyrazol-3-yl)pyridin-4-yl)amino)cyclohexyl)ethan-1-ol (117 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (MeOD, 400 MHz) δ 8.71 (s, 1H), 8.44 (s, 1H), 8.34 (s, 1H), 8.33 (d, 1H), 7.82 (d, 1H), 7.37 (s, 1H), 7.23 (d, 1H), 6.84 (d, 1H), 4.99 (q, 2H), 3.98 (brs, 1H), 3.64 (t, 2H), 3.07-3.01 (m, 1H), 2.00-1.97 (m, 2H), 1.85-1.79 (m, 2H), 1.72-1.68 (m, 2H), 1.61-1.59 (m, 1H), 1.54-1.51 (m, 2H), 1.49-1.43 (m, 2H), 1.41-1.35 (m, 2H), 1.30-1.25 (m, 2H); MS (ESI) m/z=632.2 (M+H)⁺

Example 270. 2-((1r,4r)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol Step 1. 2-((1r,4r)-4-((2-Chloro-5-(1-(2,2,2-trifluoroethyl)-1H-pyrazol-3-yl)pyridin-4-yl)amino)cyclohexyl)ethan-1-ol The title compound as a white solid (124.6 mg) was prepared in the same fashion as Reference Example 15, except that 2-chloro-4-fluoro-5-(1-(2,2,2-trifluoroethyl)-1H-pyrazol-3-yl)pyridine (100 mg, 0.358 mmol) prepared in Reference Example 21 and 2-((1r,4r)-4-aminocyclohexyl)ethan-1-ol hydrochloride (96 mg, 0.536 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=403.1 (M+H)⁺

Step 2. 2-((1r,4r)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol The title compound as pale yellow solid (36 mg) was prepared in the same fashion as Step 2 in Example 1, except that 2-((1r,4r)-4-((2-chloro-5-(1-(2,2,2-trifluoroethyl)-1H-pyrazol-3-yl)pyridin-4-yl)amino)cyclohexyl)ethan-1-ol (117 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (MeOD, 400 MHz) δ 8.74 (s, 1H), 8.48 (s, 1H), 8.35 (d, 1H), 8.32 (s, 1H), 7.80 (d, 1H), 7.36 (d, 1H), 7.11 (s, 1H), 6.79 (d, 1H), 5.00 (q, 2H), 3.62 (t, 2H), 3.51-3.46 (m, 1H), 3.06-3.01 (m, 1H), 2.24-2.21 (m, 2H), 1.88-1.86 (m, 2H), 1.51-1.43 (m, 4H), 1.35-1.22 (m, 7H); MS (ESI) m/z=632.2 (M+H)⁺

Example 271. ((1S,3S)-3-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)methanol Step 1. ((1S,3S)-3-((2-Chloro-5-(1-(2,2,2-trifluoroethyl)-1H-pyrazol-3-yl)pyridin-4-yl)amino)cyclohexyl)methanol The title compound as a white solid (122.9 mg) was prepared in the same fashion as Reference Example 15, except that 2-chloro-4-fluoro-5-(1-(2,2,2-trifluoroethyl)-1H-pyrazol-3-yl)pyridine (100 mg, 0.358 mmol) prepared in Reference Example 21 and ((1S,3S)-3-aminocyclohexyl) methanol hydrochloride (89 mg, 0.536 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=389.1 (M+H)$^+$ Step 2. ((1S,3S)-3-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino) cyclohexyl)methanol The title compound as pale yellow solid (37.5 mg) was prepared in the same fashion as Step 2 in Example 1, except that ((1S,3S)-3-((2-chloro-5-(1-(2,2,2-trifluoroethyl)-1H-pyrazol-3-yl)pyridin-4-yl)amino)cyclohexyl)methanol (113 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.99 (s, 1H), 8.62 (s, 1H), 8.46-8.44 (m, 3H), 8.39 (d, 1H), 7.96 (d, 1H), 7.43 (brs, 2H), 6.97 (d, 1H), 5.17 (q, 2H), 4.41 (t, 1H), 4.00 (brs, 1H), 3.25-3.00 (m, 1H), 3.16 (d, 2H), 1.96-1.92 (m, 1H), 1.84-1.81 (m, 1H), 1.71-1.55 (m, 5H), 1.40-1.32 (m, 3H), 1.29-1.23 (m, 2H), 1.04-0.98 (m, 1H); MS (ESI) m/z=618.2 (M+H)$^+$ Example 272. N$^4$-((1s,4s)-4-(Azetidin-1-ylmethyl) cyclohexyl)-N$^2$-(2-(1-(cyclopropylsulfonyl)-1H-pyrazol-4-yl)pyrimidin-4-yl)-5-(1-(2,2,2-trifluoroethyl)-1H-pyrazol-3-yl)pyridine-2,4-diamine Step 1. N-((1s,4s)-4-(Azetidin-1-ylmethyl)cyclohexyl)-2-chloro-5-(1-(2,2,2-trifluoroethyl)-1H-pyrazol-3-yl)pyridin-4-amine The title compound as a white solid (124.4 mg) was prepared in the same fashion as Reference Example 15, except that 2-chloro-4-fluoro-5-(1-(2,2,2-trifluoroethyl)-1H-pyrazol-3-yl)pyridine (113 mg, 0.404 mmol) prepared in Reference Example 21 and (1s,4s)-4-(azetidin-1-ylmethyl) cyclohexan-1-amine (102 mg, 0.606 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=428.1 (M+H)$^+$ Step 2. N$^4$-((1s,4s)-4-(Azetidin-1-ylmethyl)cyclohexyl)-N$^2$-(2-(1-(cyclopropylsulfonyl)-1H-pyrazol-4-yl)pyrimidin-4-yl)-5-(1-(2,2,2-trifluoroethyl)-1H-pyrazol-3-yl)pyridine-2,4-diamine The title compound as pale yellow solid (37.9 mg) was prepared in the same fashion as Step 2 in Example 1, except that N-((1s,4s)-4-(azetidin-1-ylmethyl)cyclohexyl)-2-chloro-5-(1-(2,2,2-trifluoroethyl)-1H-pyrazol-3-yl)pyridin-4-amine (89 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.45 (s, 1H), 8.39 (s, 1H), 8.38 (s, 1H), 8.35 (s, 1H), 7.86 (brs, 1H), 7.56 (s, 1H), 7.22 (s, 1H), 7.14 (d, 1H), 6.74 (s, 1H), 4.79 (q, 2H), 3.95 (brs, 1H), 3.25 (t, 4H), 2.87-2.81 (m, 1H), 2.33 (d, 2H), 2.15-2.08 (m, 2H), 2.00-1.97 (m, 2H), 1.80-1.69 (m, 4H), 1.54-1.51 (m, 3H), 1.35-1.19 (m, 4H); MS (ESI) m/z=657.2 (M+H)$^+$ Example 273. (1s,4s)-4-((2-((2-(1-(Cyclopropylsulfonyl)-1H-pyrazol-4-yl)pyrimidin-4-yl)amino)-5-(1-(difluoromethyl)-1H-imidazol-4-yl)pyridin-4-yl) amino)-1-methylcyclohexan-1-ol The title compound as pale yellow solid (7.7 mg) was prepared in the same fashion as Step 2 in Example 1, except that (1s,4s)-4-((2-chloro-5-(1-(difluoromethyl)-1H-imidazol-4-yl)pyridin-4-yl)amino)-1-methylcyclohexan-1-ol (22 mg, 0.062 mmol) prepared in Reference Example 19 was used instead of 2-chloro-5-(1-cyclopropyl-1H-pyrazol-4-yl)-4-((1-methyl-1H-pyrazol-4-yl)ethynyl)pyridine.
$^1$H-NMR (CDCl$_3$, 400 MHz) δ 8.66 (s, 1H), 8.48 (s, 1H), 8.41 (d, 1H), 8.19 (s, 1H), 8.15 (d, 1H), 7.89 (s, 1H), 7.63 (brs, 1H), 7.44 (s, 1H), 7.30 (s, 1H), 7.15 (t, 1H), 6.95 (s, 1H), 3.50-3.46 (m, 1H), 2.86-2.80 (m, 1H), 2.06-1.98 (m, 2H), 1.81-1.74 (m, 4H), 1.64-1.56 (m, 2H), 1.56-1.51 (m, 2H), 1.31 (s, 3H), 1.24-1.19 (m, 2H); MS (ESI) m/z=586.2 (M+H)$^+$ Example 274. (1s,4s)-4-((2-((2-(1-(Cyclopropylsulfonyl)-1H-pyrazol-4-yl)pyrimidin-4-yl)amino)-5-(6,7-dihydro-5H-pyrrolo[1,2-a]imidazol-2-yl)pyridin-4-yl)amino)-1-methylcyclohexan-1-ol The title compound as pale yellow solid (1.1 mg) was prepared in the same fashion as Step 2 in Example 1, except that (1s,4s)-4-((2-chloro-5-(6,7-dihydro-5H-pyrrolo[1,2-a] imidazol-2-yl)pyridin-4-yl)amino)-1-methylcyclohexan-1-ol (22 mg, 0.062 mmol) prepared in Reference Example 20 was used instead of 2-chloro-5-(1-cyclopropyl-1H-pyrazol-4-yl)-4-((1-methyl-1H-pyrazol-4-yl)ethynyl)pyridine.
$^1$H-NMR (CDCl$_3$, 400 MHz) δ 8.86 (s, 1H), 8.65 (s, 1H), 8.46 (s, 1H), 8.40 (d, 1H), 8.04 (s, 1H), 7.30 (s, 1H), 7.27 (s, 1H), 7.14 (s, 1H), 7.05 (s, 1H), 4.89 (s, 1H), 4.06 (t, 2H), 3.50 (s, 1H), 2.93 (t, 2H), 2.86-2.82 (m, 1H), 2.69-2.64 (m, 2H), 2.05-1.99 (m, 2H), 1.84-1.74 (m, 4H), 1.64-1.61 (m, 2H), 1.57-1.53 (m, 2H), 1.31 (s, 3H), 1.23-1.21 (m, 2H); MS (ESI) m/z=576.2 (M+H)$^+$, Example 275. (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-(hydroxymethyl)cyclohexan-1-ol Step 1. (1s,4s)-4-((2-Chloro-5-(4,5,6,7-tetrahydropyrazolo[1,5-a]pyridin-2-yl)pyridin-4-yl)amino)-1-(hydroxymethyl)cyclohexan-1-ol The title compound as a white solid (225 mg) was prepared in the same fashion as Reference Example 15, except that 2-(6-chloro-4-fluoropyridin-3-yl)-4,5,6,7-tetrahydropyrazolo[1,5-a]pyridine (250 mg, 0.993 mmol) prepared in Reference Example 7 and (1s,4s)-4-amino-1-(hydroxymethyl)cyclohexan-1-ol (216 mg, 1.49 mmol) were used instead of 2-chloro-5-(1-(difluoromethyl)-1H-pyrazol-3-yl)-4-fluoropyridine and (1s,4s)-4-amino-1-methylcyclohexan-1-ol. $^1$H-NMR (MeOD, 400 MHz) δ 8.20 (d, 1H), 6.67 (s, 1H), 6.42 (s, 1H), 4.62 (s, 1H), 4.15 (t, 2H), 3.46 (s, 1H), 3.40 (s, 2H), 2.86 (t, 2H), 2.11-2.09 (m, 2H), 1.94-1.90 (m, 4H), 1.76-1.59 (m, 6H); MS (ESI) m/z=377.1 (M+H)$^+$ Step 2. (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl) amino)-1-(hydroxymethyl)cyclohexan-1-ol The title compound as pale yellow solid (6.7 mg) was prepared in the same fashion as Step 2 in Example 1, except that (1s,4s)-4-((2-chloro-5-(4,5,6,7-tetrahydropyrazolo[1,5-a]pyridin-2-yl)pyridin-4-yl)amino)-1-(hydroxymethyl)cyclohexan-1-ol (156 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine.
$^1$H-NMR (DMSO-d$_6$, 400 MHz) δ 9.87 (s, 1H), 8.62 (s, 1H), 8.44 (s, 1H), 8.40 (d, 1H), 8.32 (s, 1H), 8.26 (d, 1H), 7.71 (brs, 1H), 7.04 (brs, 1H), 6.51 (s, 1H), 4.53 (t, 1H), 4.10 (t, 2H), 4.04 (s, 1H), 3.28-3.25 (m, 1H), 3.23 (quin, 2H), 2.79 (t, 2H), 1.99-1.80 (m, 6H), 1.61-1.45 (m, 4H), 1.34-1.24 (m, 4H); MS (ESI) m/z=606.3 (M+H)$^+$ Example 276. (4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-fluorocyclohexyl)methanol Step 1. (4-((2-Chloro-5-(4,5,6,7-tetrahydropyrazolo[1,5-a]pyridin-2-yl)pyridin-4-yl)amino)-1-fluorocyclohexyl)methanol The title compound as a white solid (324.7 mg) was prepared in the same fashion as Reference Example 15, except that 2-(6-chloro-4-fluoropyridin-3-yl)-4,5,6,7-tetrahydropyrazolo[1,5-a]pyridine (250 mg, 0.993 mmol) prepared in Reference Example 7 and (4-amino-1-fluorocyclohexyl)methanol (219 mg, 1.49 mmol) were used instead of 2-chloro-5-(1-(difluoromethyl)-1H-pyrazol-3-yl)-4-fluoropyridine and (1s,4s)-4-amino-1-methylcyclohexan-1-ol.
$^1$H-NMR (CDCl$_3$, 400 MHz) δ 8.44 (d, 1H), 8.29 (s, 1H), 6.52 (s, 1H), 6.32 (s, 1H), 4.15 (t, 2H), 3.65 (d, 2H), 3.45-3.38 (m, 1H), 2.84 (t, 2H), 2.17-2.03 (m, 6H), 1.92-1.86 (m, 2H), 1.75-1.49 (m, 4H); MS (ESI) m/z=379.1 (M+H)$^+$, Step 2. (4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-fluorocyclohexyl)methanol The title compound as pale yellow solid (86.2 mg) was prepared in the same fashion as Step 2 in Example 1, except that (4-((2-chloro-5-(4,5,6,7-tetrahydropyrazolo[1,5-a]pyridin-2-yl)pyridin-4-yl)amino)-1-fluorocyclohexyl)methanol (157 mg, 0.415 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.90 (s, 1H), 8.63 (s, 1H), 8.45 (s, 1H), 8.40 (d, 1H), 8.35 (d, 1H), 8.33 (s, 1H), 7.63 (brs, 1H), 7.15 (brs, 1H), 6.52 (s, 1H), 4.96 (t, 1H), 4.10 (t, 2H), 3.49 (s, 1H), 3.43 (dd, 2H), 3.29-3.22 (m, 1H), 2.79 (t, 2H), 2.01-1.98 (m, 2H), 1.91-1.79 (m, 4H), 1.67-1.1.47 (m, 4H), 1.36-1.32 (m, 2H), 1.27-1.22 (m, 2H); MS (ESI) m/z=608.2 (M+H)$^+$ Example 277. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(4,5,6,7-tetrahydropyrazolo[1,5-a]pyridin-2-yl)pyridine-2,4-diamine Step 1. 2-Chloro-N-((1s,4s)-4-((dimethylamino)methyl)cyclohexyl)-5-(4,5,6,7-tetrahydropyrazolo[1,5-a]pyridin-2-yl)pyridin-4-amine The title compound as a white solid (202 mg) was prepared in the same fashion as Reference Example 15, except that 2-(6-chloro-4-fluoropyridin-3-yl)-4,5,6,7-tetrahydropyrazolo[1,5-a]pyridine (150 mg, 0.596 mmol) prepared in Reference Example 7 and (1s,4s)-4-((dimethylamino)methyl)cyclohexan-1-amine dihydrochloride (205 mg, 0.894 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=388.2 (M+H)$^+$ Step 2. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(4,5,6,7-tetrahydropyrazolo[1,5-a]pyridin-2-yl)pyridine-2,4-diamine The title compound as pale yellow solid (109 mg) was prepared in the same fashion as Step 2 in Example 1, except that 2-chloro-N-((1s,4s)-4-((dimethylamino)methyl)cyclohexyl)-5-(4,5,6,7-tetrahydropyrazolo[1,5-a]pyridin-2-yl)pyridin-4-amine (190 mg, 0.49 mmol) prepared in Step 1 was used instead of 2-chloro-5-(1-cyclopropyl-1H-pyrazol-4-yl)-4-((1-methyl-1H-pyrazol-4-yl)ethynyl)pyridine.
$^1$H-NMR (CDCl$_3$, 400 MHz) δ 8.76 (d, 1H), 8.66 (s, 1H), 8.47 (s, 1H), 8.37 (d, 1H), 8.32 (s, 1H), 7.77 (brs, 1H), 7.19 (s, 1H), 7.13 (s, 1H), 6.34 (s, 1H), 4.16 (t, 2H), 3.97 (brs, 1H), 2.88-2.80 (m, 3H), 2.23 (s, 6H), 2.15 (d, 2H), 2.13-2.07 (m, 2H), 2.03-2.00 (m, 2H), 1.94-1.88 (m, 2H), 1.80-1.61 (m, 5H), 1.55-1.51 (m, 2H), 1.40-1.30 (m, 2H), 1.24-1.19 (m, 2H); MS (ESI) m/z=617.3 (M+H)$^+$ Example 278. 2-((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)propan-2-ol Step 1. 2-((1s,4s)-4-((2-Chloro-5-(1-(3-(dimethylamino)propyl)-1H-pyrazol-3-yl)pyridin-4-yl)amino)cyclohexyl)propan-2-ol The title compound as a white solid (52.1 mg) was prepared in the same fashion as Reference Example 15, except that 3-(3-(6-chloro-4-fluoropyridin-3-yl)-1H-pyrazol-1-yl)-N,N-dimethylpropan-1-amine (100 mg, 0.354 mmol) prepared in Reference Example 22 and 2-((1s,4s)-4-aminocyclohexyl)propan-2-ol (83 mg, 0.531 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=420.2 (M+H)$^+$ Step 2. 2-((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)propan-2-ol The title compound as pale yellow solid (13.2 mg) was prepared in the same fashion as Step 2 in Example 1, except that 2-((1s,4s)-4-((2-chloro-5-(1-(3-(dimethylamino)propyl)-1H-pyrazol-3-yl)pyridin-4-yl)amino)cyclohexyl)propan-2-ol (48 mg, 0.113 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 2H), 8.47 (s, 1H), 8.37 (d, 1H), 8.34 (s, 1H), 7.44 (d, 1H), 7.11 (d, 1H), 6.59 (d, 1H), 4.22 (t, 2H), 4.00 (brs, 1H), 2.87-2.82 (m, 1H), 2.26 (t, 2H), 2.22 (s, 6H), 2.13-2.03 (m, 4H), 1.80-1.74 (m, 5H), 1.56-1.51 (m, 4H), 1.25-1.23 (m, 8H); MS (ESI) m/z=649.3 (M+H)$^+$ Example 279. (3-(((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)methyl)oxetan-3-yl)methanol Step 1. (3-(((2-Chloro-5-(1-(3-(dimethylamino)propyl)-1H-pyrazol-3-yl)pyridin-4-yl)amino)methyl)oxetan-3-yl)methanol The title compound as a white solid (78.8 mg) was prepared in the same fashion as Reference Example 15, except that 3-(3-(6-chloro-4-fluoropyridin-3-yl)-1H-pyrazol-1-yl)-N,N-dimethylpropan-1-amine (100 mg, 0.354 mmol) prepared in Reference Example 22 and (3-(aminomethyl)oxetan-3-yl)methanol (62 mg, 0.531 mmol) were used instead of 2-chloro-5-(1-(difluoromethyl)-1H-pyrazol-3-yl)-4-fluoropyridine and (1s,4s)-4-amino-1-methylcyclohexan-1-ol. $^1$H-NMR (CDCl$_3$), 400 MHz) δ 8.52 (s, 1H), 8.28 (s, 1H), 7.40 (d, 1H), 6.68 (s, 1H), 6.55 (d, 1H), 4.56 (dd, 4H), 4.15 (t, 2H), 3.92 (s, 2H), 3.67 (d, 2H), 2.26 (s, 6H), 2.24-2.15 (m, 4H); MS (ESI) m/z=380.1 (M+H)$^+$, Step 2. (3-(((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)methyl)oxetan-3-yl)methanol The title compound as pale yellow solid (36.9 mg) was prepared in the same fashion as Step 2 in Example 1, except that (3-(((2-chloro-5-(1-(3-(dimethylamino)propyl)-1H-pyrazol-3-yl)pyridin-4-yl)amino)methyl)oxetan-3-yl) methanol (72 mg, 0.118 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.51 (s, 1H), 8.49 (s, 1H), 8.37 (d, 1H), 8.32 (s, 1H), 7.41 (d, 1H), 7.32 (s, 1H), 7.15 (d, 1H), 6.55 (d, 1H), 4.62 (s, 4H), 4.16 (t, 2H), 3.96 (s, 2H), 3.77 (d, 2H), 2.86-2.79 (m, 1H), 2.26 (s, 6H), 2.23-2.15 (m, 4H), 1.55-1.50 (m, 2H), 1.23-1.18 (m, 2H); MS (ESI) m/z=610.3 (M+H)$^+$ Example 280. ((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)methanol Step 1. ((1s,4s)-4-((2-Chloro-5-(1,5-dimethyl-1H-pyrazol-3-yl)pyridin-4-yl)amino)cyclohexyl)methanol The title compound as a white solid (93.3 mg) was prepared in the same fashion as Reference Example 15, except that 2-chloro-5-(1,5-dimethyl-1H-pyrazol-3-yl)-4-fluoropyridine (100 mg, 0.443 mmol) prepared in Reference Example 23 and ((1s,4s)-4-aminocyclohexyl)methanol hydrochloride (110 mg, 0.665 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=335.1 (M+H)$^+$ Step 2. ((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)methanol The title compound as pale yellow solid (62.6 mg) was prepared in the same fashion as Step 2 in Example 1, except that ((1s,4s)-4-((2-chloro-5-(1,5-dimethyl-1H-pyrazol-3-yl)pyridin-4-yl)amino)cyclohexyl)methanol (82 mg, 0.245 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (d, 1H), 8.65 (s, 1H), 8.46 (s, 1H), 8.34 (d, 1H), 8.29 (s, 1H), 7.28 (s, 1H), 7.05 (d, 1H), 6.36 (s, 1H), 3.99 (brs, 1H), 3.81 (s, 3H), 3.55 (d, 2H), 2.84-2.82 (m, 1H), 2.32 (s, 3H), 2.05-2.02 (m, 2H), 1.81-1.66 (m, 5H), 1.53-1.39 (m, 4H), 1.26-1.18 (m, 2H); MS (ESI) m/z=564.2 (M+H)$^+$ Example 281. 2-((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)propan-2-ol Step 1. 2-((1s,4s)-4-((2-Chloro-5-(1,5-dimethyl-1H-pyrazol-3-yl)pyridin-4-yl)amino)cyclohexyl)propan-2-ol The title compound as a white solid (97.5 mg) was prepared in the same fashion as Reference Example 15, except that 2-chloro-5-(1,5-dimethyl-1H-pyrazol-3-yl)-4-fluoropyridine (100 mg, 0.443 mmol) prepared in Reference Example 23 and 2-((1s,4s)-4-aminocyclohexyl)propan-2-ol (105 mg, 0.665 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=363.2 (M+H)$^+$ Step 2. 2-((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)propan-2-ol The title compound as pale yellow solid (51.4 mg) was prepared in the same fashion as Step 2 in Example 1, except that 2-((1s,4s)-4-((2-chloro-5-(1,5-dimethyl-1H-pyrazol-3-yl)pyridin-4-yl)amino)cyclohexyl)propan-2-ol (89 mg, 0.245 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (d, 1H), 8.65 (s, 1H), 8.46 (s, 1H), 8.34 (d, 1H), 8.30 (s, 1H), 8.27 (s, 1H), 7.07 (d, 1H), 6.38 (s, 1H), 3.99 (brs, 1H), 3.82 (s, 3H), 2.87-2.81 (m, 1H), 2.33 (s, 3H), 2.13-2.10 (m, 2H), 1.78-1.71 (m, 4H), 1.54-1.46 (m, 5H), 1.26-1.21 (m, 8H); MS (ESI) m/z=592.2 (M+H)$^+$ Example 282. ((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)methanol Step 1. ((1s,4s)-4-((2-Chloro-5-(1-(oxetan-3-yl)-1H-pyrazol-3-yl)pyridin-4-yl)amino)cyclohexyl)methanol The title compound as a white solid (119 mg) was prepared in the same fashion as Reference Example 15, except that 2-chloro-4-fluoro-5-(1-(oxetan-3-yl)-1H-pyrazol-3-yl)pyridine (100 mg, 0.394 mmol) prepared in Reference Example 24 and ((1s,4s)-4-aminocyclohexyl)methanol hydrochloride (98 mg, 0.591 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=363.1 (M+H)$^+$

Step 2. ((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)methanol The title compound as pale yellow solid (35.6 mg) was prepared in the same fashion as Step 2 in Example 1, except that ((1s,4s)-4-((2-chloro-5-(1-(oxetan-3-yl)-1H-pyrazol-3-yl)pyridin-4-yl)amino)cyclohexyl)methanol (83 mg, 0.228 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.65 (d, 1H), 8.47 (s, 1H), 8.39 (s, 1H), 8.37 (d, 1H), 8.04 (brs, 1H), 7.50 (s, 1H), 7.31 (s, 1H), 7.09 (d, 1H), 6.67 (s, 1H), 5.46 (q, 1H), 5.22 (t, 2H), 5.11 (t, 2H), 4.04 (brs, 1H), 3.53 (s, 2H), 2.85-2.83 (m, 1H), 2.11-2.03 (m, 2H), 1.87-1.73 (m, 4H), 1.70-1.59 (m, 3H), 1.54-1.51 (m, 2H), 1.26-1.19 (m, 2H); MS (ESI) m/z=592.2 (M+H)$^+$

Example 283. 2-((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)propan-2-ol

Step 1. 2-((1s,4s)-4-((2-Chloro-5-(1-(oxetan-3-yl)-1H-pyrazol-3-yl)pyridin-4-yl)amino)cyclohexyl)propan-2-ol The title compound as a white solid (94 mg) was prepared in the same fashion as Reference Example 15, except that 2-chloro-4-fluoro-5-(1-(oxetan-3-yl)-1H-pyrazol-3-yl)pyridine (100 mg, 0.394 mmol) prepared in Reference Example 24 and 2-((1s,4s)-4-aminocyclohexyl)propan-2-ol (93 mg, 0.591 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=391.1 (M+H)$^+$

Step 2. 2-((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)propan-2-ol The title compound as pale yellow solid (31.9 mg) was prepared in the same fashion as Step 2 in Example 1, except that 2-((1s,4s)-4-((2-chloro-5-(1-(oxetan-3-yl)-1H-pyrazol-3-yl)pyridin-4-yl)amino)cyclohexyl)propan-2-ol (89 mg, 0.228 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.65 (d, 1H), 8.47 (s, 1H), 8.39 (s, 1H), 8.38 (d, 1H), 7.80 (brs, 1H), 7.51 (s, 1H), 7.27 (s, 1H), 7.11 (d, 1H), 6.68 (s, 1H), 5.48-5.42 (m, 1H), 5.21 (t, 2H), 5.11 (t, 2H), 4.01 (brs, 1H), 2.87-2.81 (m, 1H), 2.18-2.15 (m, 2H), 1.84-1.78 (m, 2H), 1.65-1.59 (m, 2H), 1.55-1.53 (m, 2H), 1.42-1.38 (m, 1H), 1.26-1.22 (m, 2H), 1.22 (s, 6H); MS (ESI) m/z=620.2 (M+H)$^+$

Example 284. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(1-(oxetan-3-yl)-1H-pyrazol-3-yl)pyridine-2,4-diamine

Step 1. 2-Chloro-N-((1s,4s)-4-((dimethylamino)methyl)cyclohexyl)-5-(1-(oxetan-3-yl)-1H-pyrazol-3-yl)pyridin-4-amine The title compound as a white solid (125 mg) was prepared in the same fashion as Reference Example 15, except that 2-chloro-4-fluoro-5-(1-(oxetan-3-yl)-1H-pyrazol-3-yl)pyridine (100 mg, 0.394 mmol) prepared in Reference Example 24 and (1s,4s)-4-((dimethylamino)methyl)cyclohexan-1-amine dihydrochloride (136 mg, 0.591 mmol) were used instead of 2-chloro-5-(1-(difluoromethyl)-1H-pyrazol-3-yl)-4-fluoropyridine and (1s,4s)-4-amino-1-methylcyclohexan-1-ol. MS (ESI) m/z=390.2 (M+H)$^+$

Step 2. N$^2$-(2-(1-(Cyclopropylsulfonyl)-1H-pyrazol-4-yl)pyrimidin-4-yl)-N$^4$-((1s,4s)-4-((dimethylamino)methyl)cyclohexyl)-5-(1-(oxetan-3-yl)-1H-pyrazol-3-yl)pyridine-2,4-diamine The title compound as pale yellow solid (39.3 mg) was prepared in the same fashion as Step 2 in Example 1, except that 2-chloro-N-((1s,4s)-4-((dimethylamino)methyl)cyclohexyl)-5-(1-(oxetan-3-yl)-1H-pyrazol-3-yl)pyridin-4-amine (81 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.65 (d, 1H), 8.47 (s, 1H), 8.39 (s, 1H), 8.38 (d, 1H), 7.80 (brs, 1H), 7.51 (s, 1H), 7.27 (s, 1H), 7.11 (d, 1H), 6.68 (s, 1H), 5.48-5.42 (m, 1H), 5.21 (t, 2H), 5.11 (t, 2H), 4.01 (brs, 1H), 2.87-2.81 (m, 1H), 2.18-2.15 (m, 2H), 1.84-1.78 (m, 2H), 1.65-1.59 (m, 2H), 1.55-1.53 (m, 2H), 1.42-1.38 (m, 1H), 1.26-1.22 (m, 2H), 1.22 (s, 6H); MS (ESI) m/z=619.2 (M+H)$^+$

Example 285. (1s,4s)-4-((2-((2-(1-(Cyclopropylsulfonyl)-1H-pyrazol-4-yl)pyrimidin-4-yl)amino)-5-(1-(trifluoromethyl)-1H-pyrazol-3-yl)pyridin-4-yl)amino)-1-methylcyclohexan-1-ol

Step 1. (1s,4s)-4-((2-Chloro-5-(1-(trifluoromethyl)-1H-pyrazol-3-yl)pyridin-4-yl)amino)-1-methylcyclohexan-1-ol The title compound as a white solid (65 mg) was prepared in the same fashion as Reference Example 15, except that 2-chloro-4-fluoro-5-(1-(trifluoromethyl)-1H-pyrazol-3-yl)pyridine (57.84 mg, 0.218 mmol) prepared in Reference Example 25 was used instead of 2-chloro-5-(1-(difluoromethyl)-1H-pyrazol-3-yl)-4-fluoropyridine. $^1$H-NMR (MeOH, 400 MHz) δ 8.42 (s, 1H), 8.30 (d, 1H), 8.22 (d, 1H), 7.13 (d, 1H), 6.80 (s, 1H), 3.57-3.53 (m, 1H), 1.94-1.90 (m, 2H), 1.77-1.68 (m, 4H), 1.64-1.57 (m, 2H), 1.26 (s, 3H)

Step 2. (1s,4s)-4-((2-((2-(1-(Cyclopropylsulfonyl)-1H-pyrazol-4-yl)pyrimidin-4-yl)amino)-5-(1-(trifluoromethyl)-1H-pyrazol-3-yl)pyridin-4-yl)amino)-1-methylcyclohexan-1-ol The title compound as pale yellow solid (39.3 mg) was prepared in the same fashion as Step 2 in Example 1, except that (1s,4s)-4-((2-chloro-5-(1-(trifluoromethyl)-1H-pyrazol-3-yl)pyridin-4-yl)amino)-1-methylcyclohexan-1-ol (81 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 8.67 (s, 1H), 8.65 (d, 1H), 8.47 (s, 1H), 8.39 (s, 1H), 8.38 (d, 1H), 7.80 (brs, 1H), 7.51 (s, 1H), 7.27 (s, 1H), 7.11 (d, 1H), 6.68 (s, 1H), 5.48-5.42 (m, 1H), 5.21 (t, 2H), 5.11 (t, 2H), 4.01 (brs, 1H), 2.87-2.81 (m, 1H), 2.18-2.15 (m, 2H), 1.84-1.78 (m, 2H), 1.65-1.59 (m, 2H), 1.55-1.53 (m, 2H), 1.42-1.38 (m, 1H), 1.26-1.22 (m, 2H), 1.22 (s, 6H); MS (ESI) m/z=604.1 (M+H)$^+$

Example 286. N²-(2-(1-(Cyclopropylsulfonyl)-1H-pyrazol-4-yl)pyrimidin-4-yl)-N⁴-((1s,4s)-4-fluorocyclohexyl)-5-(1-(trifluoromethyl)-1H-pyrazol-3-yl)pyridine-2,4-diamine Step 1. 2-Chloro-N-((1s,4s)-4-fluorocyclohexyl)-5-(1-(trifluoromethyl)-1H-pyrazol-3-yl)pyridin-4-amine The title compound as a white solid (48.3 mg) was prepared in the same fashion as Reference Example 15, except that 2-chloro-4-fluoro-5-(1-(trifluoromethyl)-1H-pyrazol-3-yl)pyridine (40 mg, 0.151 mmol) prepared in Reference Example 25 and (1s,4s)-4-fluorocyclohexan-1-amine hydrochloride (30 mg, 0.196 mmol) were used instead of 2-chloro-5-(1-(difluoromethyl)-1H-pyrazol-3-yl)-4-fluoropyridine and (1s,4s)-4-amino-1-methylcyclohexan-1-ol. $^1$H-NMR (DMSO-$d_6$, 400 MHz) δ 8.66 (d, 1H), 8.60 (s, 1H), 8.11 (d, 1H), 7.38 (d, 1H), 6.89 (s, 1H), 4.77 (d, 1H), 3.80-3.78 (m, 1H), 1.86-1.80 (m, 6H), 1.61-1.56 (m, 2H)

Step 2. N²-(2-(1-(Cyclopropylsulfonyl)-1H-pyrazol-4-yl)pyrimidin-4-yl)-N⁴-((1s,4s)-4-fluorocyclohexyl)-5-(1-(trifluoromethyl)-1H-pyrazol-3-yl)pyridine-2,4-diamine The title compound as pale yellow solid (25.7 mg) was prepared in the same fashion as Step 2 in Example 1, except 2-chloro-N-((1s,4s)-4-fluorocyclohexyl)-5-(1-(trifluoromethyl)-1H-pyrazol-3-yl)pyridin-4-amine (47 mg, 0.13 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-$d_6$, 400 MHz) δ 10.08 (s, 1H), 8.64 (s, 1H), 8.60 (s, 2H), 8.45 (s, 1H), 8.44 (d, 1H), 8.03 (d, 1H), 7.53 (brs, 1H), 8.38 (brs, 1H), 8.34 (d, 1H), 4.74 (dt, 1H), 3.74 (brs, 1H), 3.28-3.23 (m, 1H), 1.89-1.79 (m, 6H), 1.75-1.72 (m, 2H), 1.35-1.32 (m, 2H), 1.26-1.23 (m, 2H); MS (ESI) m/z=592.2 (M+H)⁺

Example 287. (1s,4s)-4-((2-((2-(1-(Cyclopropylsulfonyl)-1H-pyrazol-4-yl)pyrimidin-4-yl)amino)-5-(1-(1-methylpiperidin-4-yl)-1H-pyrazol-3-yl)pyridin-4-yl)amino)-1-methylcyclohexan-1-ol Step 1. (1s,4s)-4-((2-Chloro-5-(1-(1-methylpiperidin-4-yl)-1H-pyrazol-3-yl)pyridin-4-yl)amino)-1-methylcyclohexan-1-ol The title compound as a white solid (61 mg) was prepared in the same fashion as Reference Example 15, except that 2-chloro-4-fluoro-5-(1-(1-methylpiperidin-4-yl)-1H-pyrazol-3-yl)pyridine (120 mg, 0.407 mmol) prepared in Reference Example 26 was used instead of 2-chloro-5-(1-(difluoromethyl)-1H-pyrazol-3-yl)-4-fluoropyridine. MS (ESI) m/z=404.2 (M+H)⁺

Step 2. (1s,4s)-4-((2-((2-(1-(Cyclopropylsulfonyl)-1H-pyrazol-4-yl)pyrimidin-4-yl)amino)-5-(1-(1-methylpiperidin-4-yl)-1H-pyrazol-3-yl)pyridin-4-yl)amino)-1-methylcyclohexan-1-ol The title compound as pale yellow solid (15.3 mg) was prepared in the same fashion as Step 2 in Example 1, except that (1s,4s)-4-((2-chloro-5-(1-(1-methylpiperidin-4-yl)-1H-pyrazol-3-yl)pyridin-4-yl)amino)-1-methylcyclohexan-1-ol (30 mg, 0.074 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (MeOD, 400 MHz) δ 8.74 (s, 1H), 8.48 (s, 1H), 8.34 (d, 1H), 8.30 (s, 1H), 7.72 (d, 1H), 7.32 (d, 1H), 7.21 (s, 1H), 6.68 (d, 1H), 4.28-4.22 (m, 1H), 3.57 (brs, 1H), 3.06-3.01 (m, 3H), 2.37 (s, 3H), 2.35-2.28 (m, 2H), 2.20-2.15 (m, 4H), 2.04-1.99 (m, 2H), 1.83-1.76 (m, 4H), 1.63-1.57 (m, 2H), 1.47-1.44 (m, 2H), 1.35-1.28 (m, 2H), 1.27 (s, 3H); MS (ESI) m/z=633.3 (M+H)⁺

Example 288. (1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)-1-methylcyclohexan-1-ol Step 1. (1s,4s)-4-((2-Chloro-5-(1-(3-(dimethylamino)propyl)-1H-pyrazol-3-yl)pyridin-4-yl)amino)-1-methylcyclohexan-1-ol The title compound as a white solid (124 mg) was prepared in the same fashion as Reference Example 2, except that (1s,4s)-4-((2-chloro-5-iodopyridin-4-yl)amino)-1-methylcyclohexan-1-ol (150 mg, 0.409 mmol) prepared in Reference Example 10 and N,N-dimethyl-3-(3-(4,4,5,5-tetramethyl-1,3,2-dioxaborolan-2-yl)pyrazol-1-yl)propan-1-amine (148 mg, 0.532 mmol) was used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=392.2 (M+H)⁺

Step 2. (1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)-1-methylcyclohexan-1-ol The title compound as pale yellow solid (104.1 mg) was prepared in the same fashion as Step 2 in Example 1, except that (1s,4s)-4-((2-chloro-5-(1-(3-(dimethylamino)propyl)-1H-pyrazol-3-yl)pyridin-4-yl)amino)-1-methylcyclohexan-1-ol (118 mg, 0.302 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.47 (s, 1H), 8.45 (d, 1H), 8.39 (d, 1H), 8.36 (s, 1H), 7.94 (brs, 1H), 7.43 (d, 1H), 7.24 (d, 1H), 7.07 (s, 1H), 6.58 (d, 1H), 4.22 (t, 2H), 3.63 (brs, 1H), 2.86-2.79 (m, 1H), 2.26-2.22 (m, 8H), 2.15-2.09 (m, 2H), 2.05-1.97 (m, 2H), 1.87-1.75 (m, 4H), 1.66-1.59 (m, 2H), 1.55-1.51 (m, 2H), 1.31 (s, 3H), 1.24-1.18 (m, 2H); MS (ESI) m/z=621.2 (M+H)⁺

Example 289. (1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)-1-methylcyclohexan-1-ol Step 1. (1s,4s)-4-((2-Chloro-5-(1-(2,2,2-trifluoroethyl)-1H-pyrazol-3-yl)pyridin-4-yl)amino)-1-methylcyclohexan-1-ol The title compound as a white solid (143 mg) was prepared in the same fashion as Reference Example 2, except that (1s,4s)-4-((2-chloro-5-iodopyridin-4-yl)amino)-1-methylcyclohexan-1-ol (150 mg, 0.409 mmol) prepared in Reference Example 10 and 3-(4,4,5,5-tetramethyl-1,3,2-dioxaborolan-2-yl)-1-(2,2,2-trifluoroethyl)pyrazole (147 mg, 0.532 mmol) were used instead of 2-chloro-4-fluoro-5- iodopyridine and 1-(difluoromethyl)-3-(4,4,5,5-tetramethyl-1,3,2-dioxaborolan-2-yl)pyrazole. MS (ESI) m/z=389.1 (M+H)$^+$ Step 2. (1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)-1-methylcyclohexan-1-ol The title compound as pale yellow solid (32.9 mg) was prepared in the same fashion as Step 2 in Example 1, except that (1s,4s)-4-((2-chloro-5-(1-(2,2,2-trifluoroethyl)-1H-pyrazol-3-yl)pyridin-4-yl)amino)-1-methylcyclohexan-1-ol (137 mg, 0.352 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.96 (s, 1H), 8.65 (s, 1H), 8.46 (s, 1H), 8.42 (s, 1H), 8.40 (d, 1H), 8.12 (d, 1H), 7.94 (d, 1H), 7.55 (brs, 1H), 7.25 (brs, 1H), 6.92 (d, 1H), 5.21 (q, 2H), 4.14 (s, 1H), 3.27-3.21 (m, 1H), 1.85-1.82 (m, 2H), 1.65-1.58 (m, 4H), 1.44-1.39 (m, 2H), 1.33-1.31 (m, 2H), 1.24-1.20 (m, 2H), 1.13 (s, 3H); MS (ESI) m/z=618.2 (M+H)$^+$ Example 290. (1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)-1-methylcyclohexan-1-ol Step 1. (1s,4s)-4-((2-Chloro-5-(1-cyclopropyl-1H-pyrazol-3-yl)pyridin-4-yl)amino)-1-methylcyclohexan-1-ol The title compound as a white solid (132.8 mg) was prepared in the same fashion as Reference Example 2, except that (1s,4s)-4-((2-chloro-5-iodopyridin-4-yl)amino)-1-methylcyclohexan-1-ol (150 mg, 0.409 mmol) prepared in Reference Example 10 and 1-cyclopropyl-3-(4,4,5,5-tetramethyl-1,3,2-dioxaborolan-2-yl)pyrazole (115 mg, 0.491 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=347.1 (M+H)$^+$ Step 2. (1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)-1-methylcyclohexan-1-ol The title compound as pale yellow solid (40 mg) was prepared in the same fashion as Step 2 in Example 1, except that (1s,4s)-4-((2-chloro-5-(1-cyclopropyl-1H-pyrazol-3-yl)pyridin-4-yl)amino)-1-methylcyclohexan-1-ol (122 mg, 0.352 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.91 (s, 1H), 8.64 (s, 1H), 8.46 (s, 1H), 8.39 (d, 1H), 8.37 (s, 1H), 8.26 (d, 1H), 7.87 (d, 1H), 7.56-7.48 (m, 2H), 7.24 (brs, 1H), 6.77 (d, 1H), 4.20 (s, 1H), 3.82-3.77 (m, 1H), 3.27-3.20 (m, 1H), 1.87-1.85 (m, 2H), 1.68-1.59 (m, 4H), 1.47-1.41 (m, 2H), 1.36-1.32 (m, 2H), 1.27-1.21 (m, 2H), 1.14 (s, 3H), 1.11-1.07 (m, 4H); MS (ESI) m/z=576.2 (M+H)$^+$ Example 291. (1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)-1-methylcyclohexan-1-ol Step 1. (1s,4s)-4-((2-Chloro-5-(1,5-dimethyl-1H-pyrazol-3-yl)pyridin-4-yl)amino)-1-methylcyclohexan-1-ol The title compound as a white solid (91 mg) was prepared in the same fashion as Reference Example 2, except that (1s,4s)-4-((2-chloro-5-iodopyridin-4-yl)amino)-1-methylcyclohexan-1-ol (100 mg, 0.273 mmol) prepared in Reference Example 10 and 1,5-dimethyl-3-(4,4,5,5-tetramethyl-1,3,2-dioxaborolan-2-yl)pyrazole (73 mg, 0.327 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=335.1 (M+H)$^+$ Step 2. (1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)-1-methylcyclohexan-1-ol The title compound as pale yellow solid (32 mg) was prepared in the same fashion as Step 2 in Example 1, except that (1s,4s)-4-((2-chloro-5-(1,5-dimethyl-1H-pyrazol-3-yl)pyridin-4-yl)amino)-1-methylcyclohexan-1-ol (90 mg, 0.27 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.88 (s, 1H), 8.63 (s, 1H), 8.45 (s, 1H), 8.39 (d, 1H), 8.28 (s, 1H), 8.27 (d, 1H), 7.51 (brs, 1H), 7.22 (brs, 1H), 6.54 (s, 1H), 4.20 (s, 1H), 3.77 (s, 3H), 3.26-3.20 (m, 1H), 2.29 (s, 3H), 1.85-1.83 (m, 2H), 1.68-1.58 (m, 4H), 1.46-1.40 (m, 2H), 1.34-1.32 (m, 2H), 1.27-1.22 (m, 2H), 1.15 (s, 3H); MS (ESI) m/z=564.2 (M+H)$^+$ Example 292. (1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)-1-methylcyclohexan-1-ol Step 1. (1s,4s)-4-((2-Chloro-5-(1-(oxetan-3-yl)-1H-pyrazol-3-yl)pyridin-4-yl)amino)-1-methylcyclohexan-1-ol The title compound as a white solid (98.8 mg) was prepared in the same fashion as Reference Example 2, except that (1s,4s)-4-((2-chloro-5-iodopyridin-4-yl)amino)-1-methylcyclohexan-1-ol (100 mg, 0.273 mmol) prepared in Reference Example 10 and (1-(oxetan-3-yl)-1H-pyrazol-3-yl)boronic acid (55 mg, 0.327 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.50 (d, 1H), 8.35 (s, 1H), 7.55 (s, 1H), 6.68 (s, 1H), 6.59 (s, 1H), 5.46-5.41 (m, 1H), 5.16-5.07 (m, 4H), 3.53 (brs, 1H), 1.94-1.87 (m, 2H), 1.82-1.77 (m, 4H), 1.64 (s, 6H), 1.64-1.60 (m, 2H), 1.30 (s, 3H)

Step 2. (1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)-1-methylcyclohexan-1-ol The title compound as pale yellow solid (55.3 mg) was prepared in the same fashion as Step 2 in Example 1, except that (1s,4s)-4-((2-chloro-5-(1-(oxetan-3-yl)-1H-pyrazol-3-yl)pyridin-4-yl)amino)-1-methylcyclohexan-1-ol (96 mg, 0.264 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.65 (s, 1H), 8.53 (d, 1H), 8.47 (s, 1H), 8.38 (s, 2H), 8.10 (brs, 1H), 7.53 (s, 1H), 7.19 (s, 2H), 6.66 (s, 1H), 5.47-5.41 (m, 1H), 5.19-5.11 (m, 4H), 3.74 (brs, 1H), 2.86-2.80 (m, 1H), 2.03-2.00 (m, 2H), 1.85-1.79 (m, 4H), 1.70-1.64 (m, 2H), 1.55-1.52 (m, 2H), 1.30 (s, 3H), 1.26-1.20 (m, 2H); MS (ESI) m/z=592.2 (M+H)$^+$ Example 293. (1s,4s)-4-((2-((2-(1-(Cyclopropylsulfonyl)-1H-pyrazol-4-yl)pyrimidin-4-yl)amino)-5-(5-(2-hydroxypropan-2-yl)-1-methyl-1H-pyrazol-3-yl)pyridin-4-yl)amino)-1-methylcyclohexan-1-ol Step 1. (1s,4s)-4-((2-Chloro-5-(5-(2-hydroxypropan-2-yl)-1-methyl-1H-pyrazol-3-yl)pyridin-4-yl)amino)-1-methylcyclohexan-1-ol The title compound as a white solid (84 mg) was prepared in the same fashion as Reference Example 2, except that (1s,4s)-4-((2-chloro-5-iodopyridin-4-yl)amino)-1-methylcyclohexan-1-ol (142.42 mg, 0.388 mmol) prepared in Reference Example 10 and 2-(1-methyl-3-(4,4,5,5-tetramethyl-1,3,2-dioxaborolan-2-yl)-1H-pyrazol-5-yl)propan-2-ol (168 mg, 0.466 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (MeOD, 400 MHz) δ 8.22 (s, 1H), 6.67 (s, 1H), 6.59 (s, 1H), 4.09 (s, 3H), 3.51-3.46 (m, 1H), 1.91-1.87 (m, 2H), 1.77-1.66 (m, 4H), 1.65 (s, 6H), 1.63-1.56 (m, 2H), 1.26 (s, 3H)

Step 2. (1s,4s)-4-((2-((2-(1-(Cyclopropylsulfonyl)-1H-pyrazol-4-yl)pyrimidin-4-yl)amino)-5-(5-(2-hydroxypropan-2-yl)-1-methyl-1H-pyrazol-3-yl)pyridin-4-yl)amino)-1-methylcyclohexan-1-ol The title compound as pale yellow solid (22.2 mg) was prepared in the same fashion as Step 2 in Example 1, except that (1s,4s)-4-((2-chloro-5-(5-(2-hydroxypropan-2-yl)-1-methyl-1H-pyrazol-3-yl)pyridin-4-yl)amino)-1-methylcyclohexan-1-ol (79 mg, 0.207 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (MeOD, 400 MHz) δ 8.72 (s, 1H), 8.46 (s, 1H), 8.32 (d, 1H), 8.25 (s, 1H), 7.27 (d, 1H), 7.18 (s, 1H), 6.54 (s, 1H), 4.09 (s, 3H), 3.57 (brs, 1H), 3.06-3.01 (m, 1H), 1.98-1.95 (m, 2H), 1.81-1.73 (m, 4H), 1.66 (s, 6H), 1.62-1.55 (m, 2H), 1.47-1.44 (m, 2H), 1.31-1.27 (m, 5H); MS (ESI) m/z=608.3 (M+H)$^+$ Example 294. (1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)-1-methylcyclohexan-1-ol Step 1. (1s,4s)-4-((2-Chloro-5-(1-(methoxymethyl)-1H-pyrazol-3-yl)pyridin-4-yl)amino)-1-methylcyclohexan-1-ol The title compound as a white solid (100 mg) was prepared in the same fashion as Reference Example 2, except that (1s,4s)-4-((2-chloro-5-iodopyridin-4-yl)amino)-1-methylcyclohexan-1-ol (123.64 mg, 0.337 mmol) prepared in Reference Example 10 and (1-(methoxymethyl)-1H-pyrazol-3-yl)boronic acid (63 mg, 0.405 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.36 (d, 1H), 8.34 (s, 1H), 7.61 (d, 1H), 6.71 (d, 1H), 6.56 (s, 1H), 5.42 (s, 2H), 3.42-3.37 (m, 1H), 3.36 (s, 3H), 1.95-1.93 (m, 2H), 1.79-1.69 (m, 4H), 1.63-1.56 (m, 2H), 1.31 (s, 3H)

Step 2. (1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)-1-methylcyclohexan-1-ol The title compound as pale yellow solid (31 mg) was prepared in the same fashion as Step 2 in Example 1, except that (1s,4s)-4-((2-chloro-5-(1-(methoxymethyl)-1H-pyrazol-3-yl)pyridin-4-yl)amino)-1-methylcyclohexan-1-ol (93 mg, 0.264 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.41-8.37 (m, 3H), 7.90 (s, 1H), 7.61 (d, 1H), 7.26 (s, 1H), 7.06 (s, 1H), 6.70 (d, 1H), 5.43 (s, 2H), 3.59-3.57 (m, 1H), 3.39 (s, 3H), 2.86-2.79 (m, 1H), 2.02-1.97 (m, 2H), 1.83-1.75 (m, 4H), 1.65-1.59 (m, 2H), 1.58-1.51 (m, 2H), 1.32 (s, 3H), 1.24-1.18 (m, 2H); MS (ESI) m/z=580.2 (M+H)$^+$ Example 295. (1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)-1-methylcyclohexan-1-ol Step 1. (1s,4s)-4-((2-Chloro-5-(1-(3,3,3-trifluoropropyl)-1H-pyrazol-3-yl)pyridin-4-yl)amino)-1-methylcyclohexan-1-ol The title compound as a white solid (115 mg) was prepared in the same fashion as Reference Example 2, except that (1s,4s)-4-((2-chloro-5-iodopyridin-4-yl)amino)-1-methylcyclohexan-1-ol (124 mg, 0.337 mmol) prepared in Reference Example 10 and (1-(3,3,3-trifluoropropyl)-1H-pyrazol-3-yl)boronic acid (84 mg, 0.405 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.31 (s, 1H), 8.12 (d, 1H), 7.46 (d, 1H), 6.61 (d, 1H), 6.55 (s, 1H), 4.41 (t, 2H), 3.41-3.34 (m, 1H), 2.81-2.70 (m, 2H), 1.98-1.94 (m, 2H), 1.80-1.69 (m, 4H), 1.65-1.57 (m, 2H), 1.32 (s, 3H)

Step 2. (1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)-1-methylcyclohexan-1-ol The title compound as pale yellow solid (49.1 mg) was prepared in the same fashion as Step 2 in Example 1, except that (1s,4s)-4-((2-chloro-5-(1-(3,3,3-trifluoropropyl)-1H-pyrazol-3-yl)pyridin-4-yl)amino)-1-methylcyclohexan-1-ol (100 mg, 0.249 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (MeOD, 400 MHz) δ 8.73 (s, 1H), 8.47 (s, 1H), 8.33 (d, 1H), 8.30 (s, 1H), 7.71 (d, 1H), 7.30 (d, 1H), 7.20 (s, 1H), 6.68 (d, 1H), 4.49 (t, 2H), 3.58-3.56 (m, 1H), 3.06-3.00 (m, 1H), 2.92-2.80 (m, 2H), 2.00-1.96 (m, 2H), 1.82-1.74 (m, 4H), 1.64-1.56 (m, 2H), 1.47-1.43 (m, 2H), 1.29-1.24 (m, 5H); MS (ESI) m/z=632.2 (M+H)$^+$ Example 296. ((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)methanol Step 1. ((1s,4s)-4-((2-Chloro-5-(1-(3-(dimethylamino)propyl)-1H-pyrazol-3-yl)pyridin-4-yl)amino)cyclohexyl)methanol The title compound as a white solid (137 mg) was prepared in the same fashion as Reference Example 2, except that ((1s,4s)-4-((2-chloro-5-iodopyridin-4-yl)amino)cyclohexyl)methanol (150 mg, 0.409 mmol) prepared in Reference Example 28 and N,N-dimethyl-3-(3-(4,4,5,5-tetramethyl-1,3,2-dioxaborolan-2-yl)pyrazol-1-yl)propan-1-amine (148 mg, 0.532 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=392.2 (M+H)$^+$ Step 2. ((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)methanol The title compound as pale yellow solid (60.9 mg) was prepared in the same fashion as Step 2 in Example 1, except that ((1s,4s)-4-((2-chloro-5-(1-(3-(dimethylamino)propyl)-1H-pyrazol-3-yl)pyridin-4-yl)amino)cyclohexyl)methanol (126 mg, 0.32 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (d, 1H), 8.65 (s, 1H), 8.46 (s, 1H), 8.36 (s, 1H), 8.33 (d, 1H), 7.42 (s, 1H), 7.31 (brs, 1H), 7.04 (brs, 1H), 6.58 (s, 1H), 4.19 (t, 2H), 4.01 (brs, 1H), 3.50 (d, 2H), 2.86-2.79 (m, 1H), 2.30 (t, 2H), 2.24 (s, 6H), 2.19-2.13 (m, 2H), 2.06-2.03 (m, 2H), 1.79-1.73 (m, 2H), 1.68-1.65 (m, 3H), 1.55-1.49 (m, 4H), 1.21-1.19 (m, 2H); MS (ESI) m/z=621.2 (M+H)$^+$ Example 297. ((1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)cyclohexyl)methanol Step 1. ((1s,4s)-4-((2-Chloro-5-(1-cyclopropyl-1H-pyrazol-3-yl)pyridin-4-yl)amino)cyclohexyl)methanol The title compound as a white solid (126.8 mg) was prepared in the same fashion as Reference Example 2, except that ((1s,4s)-4-((2-chloro-5-iodopyridin-4-yl)amino)cyclohexyl)methanol (150 mg, 0.409 mmol) prepared in Reference Example 28 and 1-cyclopropyl-3-(4,4,5,5-tetramethyl-1,3,2-dioxaborolan-2-yl)pyrazole (115 mg, 0.491 mmol) was used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=347.1 (M+H)$^+$ Step 2. ((1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)cyclohexyl)methanol The title compound as pale yellow solid (34.4 mg) was prepared in the same fashion as Step 2 in Example 1, except that ((1s,4s)-4-((2-chloro-5-(1-cyclopropyl-1H-pyrazol-3-yl)pyridin-4-yl)amino)cyclohexyl)methanol (122 mg, 0.352 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.95 (s, 1H), 8.62 (s, 1H), 8.56 (d, 1H) 8.44 (s, 1H), 8.39 (s, 1H), 8.38 (d, 1H), 7.87 (d, 1H), 7.44 (s, 1H), 7.39 (s, 1H), 6.80 (d, 1H), 4.46 (t, 1H), 3.94 (brs, 1H), 3.78-3.73 (m, 1H), 3.30-3.24 (m, 3H), 1.91-1.88 (m, 2H), 1.75-1.65 (m, 4H), 1.49 (brs, 1H), 1.34-1.21 (m, 6H), 1.11-0.98 (m, 4H); MS (ESI) m/z=576.2 (M+H)$^+$ Example 298. 2-(3-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-1-methyl-1H-pyrazol-5-yl)propan-2-ol Step 1. 2-((1s,4s)-4-((2-Chloro-5-iodopyridin-4-yl)amino)cyclohexyl)propan-2-ol The title compound as a pale yellow liquid (1.26 mg) was prepared in the same fashion as Reference Example 9, except that 2-((1s,4s)-4-aminocyclohexyl)propan-2-ol (916 mg, 5.827 mmol) was used instead of cis-4-aminocyclohexanol hydrochloride. MS (ESI) m/z=367.0 (M+H)$^+$ Step 2. 2-(3-(6-Chloro-4-(((1s,4s)-4-(2-hydroxypropan-2-yl)cyclohexyl)amino)pyridin-3-yl)-1-methyl-1H-pyrazol-5-yl)propan-2-ol The title compound as a white solid (141 mg) was prepared in the same fashion as Reference Example 2, except that 2-((1s,4s)-4-((2-chloro-5-iodopyridin-4-yl)amino)cyclohexyl)propan-2-ol (150 mg, 0.38 mmol) prepared in Step1 and 2-(1-methyl-3-(4,4,5,5-tetramethyl-1,3,2-dioxaborolan-2-yl)-1H-pyrazol-5-yl)propan-2-ol (164 mg, 0.456 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (MeOD, 400 MHz) δ 8.25 (s, 1H), 6.65 (s, 1H), 6.62 (s, 1H), 4.11 (s, 3H), 3.89 (s, 1H), 2.01-1.97 (m, 2H), 1.81-1.78 (m, 2H), 1.68-1.65 (m, 2H), 1.65 (s, 6H), 1.42 (brs, 2H), 1.18 (s, 3H)

Step 3. 2-(3-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-1-methyl-1H-pyrazol-5-yl)propan-2-ol The title compound as pale yellow solid (28.8 mg) was prepared in the same fashion as Step 2 in Example 1, except that 2-(3-(6-chloro-4-(((1s,4s)-4-(2-hydroxypropan-2-yl)cyclohexyl)amino)pyridin-3-yl)-1-methyl-1H-pyrazol-5-yl)propan-2-ol (84 mg, 0.207 mmol) prepared in Step 2 was used instead of 2-chloro-5-(1-cyclopropyl-1H-pyrazol-4-yl)-4-((1-methyl-1H-pyrazol-4-yl)ethynyl)pyridine.
$^1$H-NMR (MeOD, 400 MHz) δ 8.72 (d, 1H), 8.67 (s, 1H), 8.41 (s, 1H), 8.29 (d, 1H), 8.24 (s, 1H), 7.36 (s, 1H), 7.14 (d, 1H), 6.54 (s, 1H), 4.10 (s, 3H), 3.97 (brs, 1H), 3.07-3.01 (m, 1H), 2.10-2.06 (m, 2H), 1.79-1.73 (m, 4H), 1.66 (s, 6H), 1.46-1.42 (m, 5H), 1.29-1.24 (m, 2H), 1.18 (s, 6H); MS (ESI) m/z=636.3 (M+H)$^+$

Example 299. 2-((1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)cyclohexyl)propan-2-ol

Step 1. 2-((1s,4s)-4-((2-Chloro-5-(1-(methoxymethyl)-1H-pyrazol-3-yl)pyridin-4-yl)amino)cyclohexyl)propan-2-ol The title compound as a white solid (121 mg) was prepared in the same fashion as Reference Example 2, except that 2-((1s,4s)-4-((2-chloro-5-iodopyridin-4-yl)amino)cyclohexyl)propan-2-ol (133.1 mg, 0.337 mmol) prepared Step1 in Example 298 and (1-(methoxymethyl)-1H-pyrazol-3-yl)boronic acid (63 mg, 0.405 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.66 (d, 1H), 8.35 (s, 1H), 7.62 (d, 1H), 6.73 (d, 1H), 6.57 (s, 1H), 5.41 (s, 2H), 3.86-3.83 (m, 1H), 3.33 (s, 3H), 2.05-2.01 (m, 2H), 1.79-1.76 (m, 2H), 1.67-1.61 (m, 2H), 1.49-1.39 (m 3H), 1.22 (s, 6H)

Step 2. 2-((1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)cyclohexyl)propan-2-ol The title compound as pale yellow solid (37.7 mg) was prepared in the same fashion as Step 2 in Example 1, except that 2-((1s,4s)-4-((2-chloro-5-(1-(methoxymethyl)-1H-pyrazol-3-yl)pyridin-4-yl)amino)cyclohexyl)propan-2-ol (100 mg, 0.264 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.65 (s, 1H), 8.47 (s, 1H), 8.39 (d, 1H), 8.38 (s, 1H), 7.70 (brs, 1H), 7.62 (d, 1H), 7.27 (s, 1H), 7.10 (d, 1H), 6.72 (d, 1H), 5.43 (s, 2H), 4.01 (brs, 1H), 3.35 (s, 3H), 2.87-2.81 (m, 1H), 2.14-2.10 (m, 2H), 1.81-1.74 (m, 4H), 1.56-1.43 (m, 5H), 1.25-1.20 (m, 8H); MS (ESI) m/z=608.2 (M+H)$^+$

Example 300. 2-((1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)cyclohexyl)propan-2-ol

Step 1. 2-((1s,4s)-4-((2-Chloro-5-(1-(3,3,3-trifluoropropyl)-1H-pyrazol-3-yl)pyridin-4-yl)amino)cyclohexyl)propan-2-ol The title compound as a white solid (133 mg) was prepared in the same fashion as Reference Example 2, except that 2-((1s,4s)-4-((2-chloro-5-iodopyridin-4-yl)amino)cyclohexyl)propan-2-ol (133 mg, 0.337 mmol) prepared Step1 in Example 298 and (1-(3,3,3-trifluoropropyl)-1H-pyrazol-3-yl)boronic acid (84 mg, 0.405 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.43 (d, 1H), 8.34 (s, 1H), 7.47 (d, 1H), 6.65 (d, 1H), 6.56 (s, 1H), 4.42 (t, 2H), 3.84-3.82 (m, 1H), 2.82-2.71 (m, 2H), 2.06-2.03 (m, 2H), 1.81-1.79 (m, 2H), 1.68-163 (m, 2H), 1.45-1.37 (m, 3H), 1.22 (s, 6H)

Step 2. 2-((1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)cyclohexyl)propan-2-ol The title compound as pale yellow solid (52 mg) was prepared in the same fashion as Step 2 in Example 1, except that 2-((1s,4s)-4-((2-chloro-5-(1-(3,3,3-trifluoropropyl)-1H-pyrazol-3-yl)pyridin-4-yl)amino)cyclohexyl)propan-2-ol (107 mg, 0.249 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 9.98 (s, 1H), 8.62 (s, 1H), 8.44-8.38 (m, 4H), 7.91 (d, 1H), 7.46 (brs, 1H), 7.36 (brs, 1H), 6.84 (d, 1H), 4.44 (t, 2H), 3.92 (brs, 1H), 3.29-3.24 (m, 1H), 2.97-2.85 (m, 2H), 2.01-1.98 (m, 2H), 1.71-1.66 (m, 4H), 1.34-1.24 (m, 6H), 1.05 (s, 6H); MS (ESI) m/z=660.2 (M+H)$^+$

Example 301. N$^2$-(2-(1-(Cyclopropylsulfonyl)-1H-pyrazol-4-yl)pyrimidin-4-yl)-5-(1-(3-(dimethylamino)propyl)-1H-pyrazol-3-yl)-N$^4$-((1s,4s)-4-((2-fluoroethyl)amino)cyclohexyl)pyridine-2,4-diamine

Step 1. (1s,4s)-N$^1$-(2-Chloro-5-(1-(3-(dimethylamino)propyl)-1H-pyrazol-3-yl)pyridin-4-yl)-N$^4$-(2-fluoroethyl)cyclohexane-1,4-diamine The title compound as a white solid (129 mg) was prepared in the same fashion as Reference Example 2, except that (1s,4s)-N$^1$-(2-chloro-5-iodopyridin-4-yl)-N$^4$-(2-fluoroethyl)cyclohexane-1,4-diamine (150 mg, 0.377 mmol) prepared in Reference Example 29 and N,N-dimethyl-3-(3-(4,4,5,5-tetramethyl-1,3,2-dioxaborolan-2-yl)-1H-pyrazol-1-yl)propan-1-amine (137 mg, 0.49 mmol) were used instead of 2-chloro-4-fluoro-5-iodopyridine and 1-(difluoromethyl)-3-(4,4,5,5-tetramethyl-1,3,2-dioxaborolan-2-yl)pyrazole. MS (ESI) m/z=423.2 (M+H)$^+$

Step 2. N$^2$-(2-(1-(Cyclopropylsulfonyl)-1H-pyrazol-4-yl)pyrimidin-4-yl)-5-(1-(3-(dimethylamino)propyl)-1H-pyrazol-3-yl)-N$^4$-((1s,4s)-4-((2-fluoroethyl)amino)cyclohexyl)pyridine-2,4-diamine The title compound as pale yellow solid (57.2 mg) was prepared in the same fashion as Step 2 in Example 1, except that (1s,4s)-N$^1$-(2-chloro-5-(1-(3-(dimethylamino)propyl)-1H-pyrazol-3-yl)pyridin-4-yl)-N$^4$-(2-fluoroethyl)cyclohexane-1,4-diamine (128 mg, 0.302 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.77 (brs, 1H), 8.64 (s, 1H), 8.59 (d, 1H), 8.45 (s, 1H), 8.36 (s, 1H), 8.33 (d, 1H), 7.43 (s, 1H), 7.30 (brs, 1H), 7.05 (brs, 1H), 6.57 (d, 1H), 4.54 (dt, 2H), 4.22 (t, 2H), 3.88 (brs, 1H), 2.94 (dt, 2H), 2.85-2.78 (m, 1H), 2.67-2.62 (m, 1H), 2.27-2.20 (m, 8H), 2.09-2.01 (m, 4H), 1.84-1.77 (m, 4H), 1.56-1.50 (m, 4H), 1.22-1.17 (m, 2H); MS (ESI) m/z=652.3 (M+H)$^+$

Example 302. 2-(3-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)-1-methyl-1H-pyrazol-5-yl)propan-2-ol

Step 1. 2-(3-(6-Chloro-4-(((1s,4s)-4-((dimethylamino)methyl)cyclohexyl)amino)pyridin-3-yl)-1-methyl-1H-pyrazol-5-yl)propan-2-ol The title compound as a white solid (141 mg) was prepared in the same fashion as Reference Example 2, except that 2-chloro-N-((1s,4s)-4-((dimethylamino)methyl)cyclohexyl)-5-iodopyridin-4-amine (150 mg, 0.38 mmol) prepared in Reference Example 27 and 2-(1-methyl-3-(4,4,5,5-tetramethyl-1,3,2-dioxaborolan-2-yl)-1H-pyrazol-5-yl)propan-2-ol (164 mg, 0.456 mmol) were used instead of 2-chloro-4-fluoro-5-iodopyridine and 1-(difluoromethyl)-3-(4,4,5,5-tetramethyl-1,3,2-dioxaborolan-2-yl)pyrazole.
$^1$H-NMR (MeOD, 400 MHz) δ 8.93 (d, 1H), 8.25 (s, 1H), 6.65 (s, 1H), 6.63 (s, 1H), 4.11 (s, 3H), 3.91-3.88 (m, 1H), 2.25 (s, 6H), 2.24-2.22 (m, 2H), 1.90-1.87 (m, 2H), 1.76-1.66 (m, 4H), 1.63 (s, 6H), 1.37-1.27 (m, 2H)

Step 2. 2-(3-(6-(((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)-1-methyl-1H-pyrazol-5-yl)propan-2-ol The title compound as pale yellow solid (35.6 mg) was prepared in the same fashion as Step 2 in Example 1, except that 2-(3-(6-chloro-4-(((1s,4s)-4-((dimethylamino)methyl)cyclohexyl)amino)pyridin-3-yl)-1-methyl-1H-pyrazol-5-yl)propan-2-ol (77 mg, 0.188 mmol) prepared in Step 1 was used instead of 2-chloro-5-(1-cyclopropyl-1H-pyrazol-4-yl)-4-((1-methyl-1H-pyrazol-4-yl)ethynyl)pyridine.
$^1$H-NMR (MeOD, 400 MHz) δ 8.68 (s, 1H), 8.42 (s, 1H), 8.30 (d, 1H), 8.25 (s, 1H), 7.34 (s, 1H), 7.18 (d, 1H), 6.55 (s, 1H), 4.11 (s, 3H), 3.98 (brs, 1H), 3.07-3.01 (m, 1H), 2.31 (s, 6H), 2.30 (d, 2H), 2.02-1.99 (m, 2H), 1.84-1.67 (m, 5H), 1.67 (s, 6H), 1.44-1.26 (m, 6H); MS (ESI) m/z=635.3 (M+H)$^+$ Example 303. N$^2$-(2-(1-(Cyclopropylsulfonyl)-1H-pyrazol-4-yl)pyrimidin-4-yl)-N$^4$-isopropyl-5-(1-(methoxymethyl)-1H-pyrazol-3-yl)pyridine-2,4-diamine Step 1. 2-Chloro-N-isopropyl-5-(1-(methoxymethyl)-1H-pyrazol-3-yl)pyridin-4-amine The title compound as a white solid (83.6 mg) was prepared in the same fashion as Reference Example 2, except that 2-chloro-5-iodo-N-isopropylpyridin-4-amine (100 mg, 0.337 mmol) prepared in Step1 of Example 92 and (1-(methoxymethyl)-1H-pyrazol-3-yl)boronic acid (63 mg, 0.405 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.33 (s, 1H), 8.18 (d, 1H), 7.61 (d, 1H), 6.71 (d, 1H), 6.56 (s, 1H), 5.42 (s, 2H), 3.77-3.69 (m, 1H), 3.39 (s, 3H), 1.32 (d, 6H)

Step 2. N$^2$-(2-(1-(Cyclopropylsulfonyl)-1H-pyrazol-4-yl)pyrimidin-4-yl)-N$^4$-isopropyl-5-(1-(methoxymethyl)-1H-pyrazol-3-yl)pyridine-2,4-diamine The title compound as pale yellow solid (31.1 mg) was prepared in the same fashion as Step 2 in Example 1, except that 2-chloro-N-isopropyl-5-(1-(methoxymethyl)-1H-pyrazol-3-yl)pyridin-4-amine (81 mg, 0.29 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.47 (s, 1H), 8.39 (d, 1H), 8.36 (s, 1H), 8.19 (d, 1H), 7.88 (s, 1H), 7.61 (d, 1H), 7.23 (s, 1H), 7.14 (d, 1H), 6.70 (d, 1H), 5.43 (s, 2H), 3.92-3.84 (m, 1H), 3.42 (s, 3H), 2.87-2.80 (m, 1H), 1.55-1.51 (m, 2H), 1.40 (d, 6H), 1.29-1.19 (m, 2H); MS (ESI) m/z=510.2 (M+H)$^+$ Example 304. N$^2$-(2-(1-(Cyclopropylsulfonyl)-1H-pyrazol-4-yl)pyrimidin-4-yl)-N$^4$-isopropyl-5-(1-(3,3,3-trifluoropropyl)-1H-pyrazol-3-yl)pyridine-2,4-diamine Step 1. 2-Chloro-N-isopropyl-5-(1-(3,3,3-trifluoropropyl)-1H-pyrazol-3-yl)pyridin-4-amine The title compound as a white solid (90.6 mg) was prepared in the same fashion as Reference Example 2, except that 2-chloro-5-iodo-N-isopropylpyridin-4-amine (100 mg, 0.337 mmol) prepared in Step1 of Example 92 and (1-(3,3,3-trifluoropropyl)-1H-pyrazol-3-yl)boronic acid (84 mg, 0.405 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.31 (s, 1H), 8.00 (d, 1H), 7.46 (d, 1H), 6.62 (d, 1H), 6.55 (s, 1H), 4.41 (t, 2H), 3.77-3.69 (m, 1H), 2.82-2.70 (m, 2H), 1.32 (d, 6H)

Step 2. N$^2$-(2-(1-(Cyclopropylsulfonyl)-1H-pyrazol-4-yl)pyrimidin-4-yl)-N$^4$-isopropyl-5-(1-(3,3,3-trifluoropropyl)-1H-pyrazol-3-yl)pyridine-2,4-diamine The title compound as pale yellow solid (32.2 mg) was prepared in the same fashion as Step 2 in Example 1, except that 2-chloro-N-isopropyl-5-(1-(3,3,3-trifluoropropyl)-1H-pyrazol-3-yl)pyridin-4-amine (83 mg, 0.249 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-d$_6$, 400 MHz) δ 10.00 (s, 1H), 8.63 (s, 1H), 8.45 (s, 1H), 8.40 (d, 1H), 8.38 (s, 1H), 8.14 (d, 1H), 7.89 (d, 1H), 7.41 (brs, 2H), 6.79 (d, 1H), 4.45 (t, 2H), 3.86-3.78 (m, 1H), 3.29-3.24 (m, 1H), 2.97-2.85 (m, 2H), 1.32-1.28 (m, 8H), 1.23 (m, 2H); MS (ESI) m/z=562.2 (M+H)$^+$ Example 305. N$^2$-(2-(1-(Cyclopropylsulfonyl)-1H-pyrazol-4-yl)pyrimidin-4-yl)-N$^4$-((1s,4s)-4-fluorocyclohexyl)-5-(1-(2,2,2-trifluoroethyl)-1H-pyrazol-3-yl)pyridine-2,4-diamine Step 1. 2-Chloro-N-((1s,4s)-4-fluorocyclohexyl)-5-(1-(2,2,2-trifluoroethyl)-1H-pyrazol-3-yl)pyridin-4-amine The title compound as a white solid (142.3 mg) was prepared in the same fashion as Reference Example 2, except that 2-chloro-N-((1s,4s)-4-fluorocyclohexyl)-5-iodopyridin-4-amine (145 mg, 0.409 mmol) prepared in Reference Example 30 and 3-(4,4,5,5-tetramethyl-1,3,2-dioxaborolan-2-yl)-1-(2,2,2-trifluoroethyl)pyrazole (103 mg, 0.532 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.34 (s, 1H), 8.19 (d, 1H), 7.56 (d, 1H), 6.73 (d, 1H), 6.56 (s, 1H), 4.82 (d, 1H), 4.76-4.70 (m, 2H), 3.49 (brs, 1H), 2.10-2.05 (m, 2H), 1.93-1.87 (m, 2H), 1.84-1.68 (m, 4H)

Step 2. N$^2$-(2-(1-(Cyclopropylsulfonyl)-1H-pyrazol-4-yl)pyrimidin-4-yl)-N$^4$-((1s,4s)-4-fluorocyclohexyl)-5-(1-(2,2,2-trifluoroethyl)-1H-pyrazol-3-yl)pyridine-2,4-diamine The title compound as pale yellow solid (21.4 mg) was prepared in the same fashion as Step 2 in Example 1, except that 2-chloro-N-((1s,4s)-4-fluorocyclohexyl)-5-(1-(2,2,2- trifluoroethyl)-1H-pyrazol-3-yl)pyridin-4-amine (68 mg, 0.181 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (DMSO-d₆, 400 MHz) δ 10.00 (s, 1H), 8.63 (s, 1H), 8.45 (s, 1H), 8.40 (d, 1H), 8.38 (s, 1H), 8.14 (d, 1H), 7.89 (d, 1H), 7.41 (brs, 2H), 6.79 (d, 1H), 4.45 (t, 2H), 3.86-3.78 (m, 1H), 3.29-3.24 (m, 1H), 2.97-2.85 (m, 2H), 1.32-1.28 (m, 8H), 1.23 (m, 2H); MS (ESI) m/z=606.2 (M+H)⁺

Example 306. N²-(2-(1-(Cyclopropylsulfonyl)-1H-pyrazol-4-yl)pyrimidin-4-yl)-N⁴-((1s,4s)-4-fluorocyclohexyl)-5-(1-(3,3,3-trifluoropropyl)-1H-pyrazol-3-yl)pyridine-2,4-diamine Step 1. 2-Chloro-N-((1s,4s)-4-fluorocyclohexyl)-5-(1-(3,3,3-trifluoropropyl)-1H-pyrazol-3-yl)pyridin-4-amine The title compound as a white solid (153.4 mg) was prepared in the same fashion as Reference Example 2, except that 2-chloro-N-((1s,4s)-4-fluorocyclohexyl)-5-iodopyridin-4-amine (145 mg, 0.409 mmol) prepared in Reference Example 30 and (1-(3,3,3-trifluoropropyl)-1H-pyrazol-3-yl)boronic acid (154 mg, 0.432 mmol) were used instead of 2-chloro-4-fluoro-5-iodopyridine and 1-(difluoromethyl)-3-(4,4,5,5-tetramethyl-1,3,2-dioxaborolan-2-yl)pyrazole. ¹H-NMR (CDCl₃, 400 MHz) δ 8.34 (s, 1H), 8.23 (d, 1H), 7.47 (d, 1H), 6.63 (d, 1H), 6.56 (s, 1H), 4.81 (d, 1H), 4.42 (t, 2H), 3.52 (brs, 1H), 2.83-2.70 (m, 2H), 2.21-2.04 (m, 2H), 1.94-1.86 (m, 2H), 1.83-1.71 (m, 4H)

Step 2. N²-(2-(1-(Cyclopropylsulfonyl)-1H-pyrazol-4-yl)pyrimidin-4-yl)-N⁴-((1s,4s)-4-fluorocyclohexyl)-5-(1-(3,3,3-trifluoropropyl)-1H-pyrazol-3-yl)pyridine-2,4-diamine The title compound as pale yellow solid (16.8 mg) was prepared in the same fashion as Step 2 in Example 1, except that 2-chloro-N-((1s,4s)-4-fluorocyclohexyl)-5-(1-(3,3,3-trifluoropropyl)-1H-pyrazol-3-yl)pyridin-4-amine (71 mg, 0.181 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (DMSO-d₆, 400 MHz) δ 10.00 (s, 1H), 8.63 (s, 1H), 8.45 (s, 1H), 8.40 (d, 1H), 8.38 (s, 1H), 8.14 (d, 1H), 7.89 (d, 1H), 7.41 (brs, 2H), 6.79 (d, 1H), 4.45 (t, 2H), 3.86-3.78 (m, 1H), 3.29-3.24 (m, 1H), 2.97-2.85 (m, 2H), 1.32-1.28 (m, 8H), 1.23 (m, 2H); MS (ESI) m/z=620.2 (M+H)⁺

Example 307. (1s,4s)-4-((2-((2-(1-(Cyclopropylsulfonyl)-1H-pyrazol-4-yl)pyrimidin-4-yl)amino)-5-(5-(4,4-difluoropiperidin-1-yl)-1-methyl-1H-pyrazol-3-yl)pyridin-4-yl)amino)-1-methylcyclohexan-1-ol Step 1. (1s,4s)-4-((2-Chloro-5-(5-(4,4-difluoropiperidin-1-yl)-1-methyl-1H-pyrazol-3-yl)pyridin-4-yl)amino)-1-methylcyclohexan-1-ol The title compound as a pale yellow solid (126.8 mg) was prepared in the same fashion as Step 1 in Reference Example 19, except that (1s,4s)-4-((2-chloro-5-(4,4,5,5-tetramethyl-1,3,2-dioxaborolan-2-yl)pyridin-4-yl)amino)-1-methylcyclohexan-1-ol (189 mg, 0.51 mmol) prepared in Reference Example 31 and 1-(3-bromo-1-methyl-1H-pyrazol-5-yl)-4,4-difluoropiperidine (120 mg, 0.43 mmol) were used instead of 2-chloro-4-fluoro-5-(4,4,5,5-tetramethyl-1,3,2-dioxaborolan-2-yl)pyridine and 4-bromo-1-(difluoromethyl)imidazole. MS (ESI) m/z=440.2 (M+H)⁺

Step 2. (1s,4s)-4-((2-((2-(1-(Cyclopropylsulfonyl)-1H-pyrazol-4-yl)pyrimidin-4-yl)amino)-5-(5-(4,4-difluoropiperidin-1-yl)-1-methyl-1H-pyrazol-3-yl)pyridin-4-yl)amino)-1-methylcyclohexan-1-ol The title compound as pale yellow solid (8.4 mg) was prepared in the same fashion as Step 2 in Example 1, except that (1s,4s)-4-((2-chloro-5-(5-(4,4-difluoropiperidin-1-yl)-1-methyl-1H-pyrazol-3-yl)pyridin-4-yl)amino)-1-methylcyclohexan-1-ol (36 mg, 0.081 mmol) prepared in Step 1 was used instead of 2-chloro-5-(1-cyclopropyl-1H-pyrazol-4-yl)-4-((1-methyl-1H-pyrazol-4-yl)ethynyl)pyridine. ¹H-NMR (CDCl₃, 400 MHz) δ 9.01 (s, 1H), 8.68 (s, 1H), 8.45 (s, 1H), 8.39 (d, 1H), 8.12 (s, 1H), 7.35 (s, 1H), 7.21 (s, 1H), 6.18 (s, 1H), 4.89 (brs, 1H), 3.77 (s, 3H), 3.55 (brs, 1H), 3.13-3.10 (m, 4H), 2.90-2.84 (m, 1H), 2.23-2.14 (m, 4H), 2.04-1.99 (m, 2H), 1.84-1.73 (m, 4H), 1.64-1.61 (m, 2H), 1.57-1.54 (m, 2H), 1.31 (s, 3H), 1.31-1.25 (m, 2H); MS (ESI) m/z=669.2 (M+H)⁺

Example 308. (1s,4s)-4-((5-(1-(Difluoromethyl)-1H-pyrazol-3-yl)-2-((2-(1-(ethylsulfonyl)-1H-pyrazol-4-yl)pyrimidin-4-yl)amino)pyridin-4-yl)amino)-1-methylcyclohexan-1-ol The title compound as pale yellow solid (8.6 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (84.52 mg, 0.24 mmol) prepared in Reference Example 15 and 2-(1-(ethylsulfonyl)-1H-pyrazol-4-yl)pyrimidin-4-amine (60 mg, 0.24 mmol) prepared in Reference Example 40 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. ¹H-NMR (CDCl₃, 400 MHz) δ 8.70 (s, 1H), 8.49 (s, 1H), 8.41 (d, 1H), 8.38 (s, 1H), 7.99 (d, 1H), 7.92 (brs, 1H), 7.86 (d, 1H), 7.38 (d, 1H), 7.23 (t, 1H), 7.07 (s, 1H), 6.82 (d, 1H), 3.60-3.54 (m, 3H), 2.04-2.00 (m, 2H), 1.84-1.71 (m, 4H), 1.64-1.57 (m, 2H), 1.32 (s, 3H), 1.29 (t, 3H); MS (ESI) m/z=574.1 (M+H)⁺

Example 309. (1s,4s)-4-((5-(1-(Difluoromethyl)-1H-pyrazol-3-yl)-2-((2-(1-(ethylsulfonyl)-1H-pyrazol-3-yl)pyrimidin-4-yl)amino)pyridin-4-yl)amino)-1-methylcyclohexan-1-ol The title compound as pale yellow solid (5.2 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (85 mg, 0.24 mmol) prepared in Reference Example 15 and 2-(1-(ethylsulfonyl)-1H-pyrazol-3-yl)pyrimidin-4-amine (60 mg, 0.24 mmol) prepared in Reference Example 41 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. ¹H-NMR (CDCl₃, 400 MHz) δ 8.55 (d, 1H), 8.38 (s, 1H), 8.14 (d, 1H), 7.97 (d, 1H), 7.87 (d, 1H), 7.71 (brs, 1H), 7.22 (t, 1H), 7.20 (d, 1H), 6.81 (d, 1H), 6.78 (brs, 1H), 3.65 (q, 2H), 3.51 (brs, 1H), 2.02-1.97 (m, 2H), 1.78-1.53 (m, 6H), 1.32 (s, 3H), 1.28 (t, 3H); MS (ESI) m/z=574.2 (M+H)⁺

Example 310. (1s,4s)-4-((5-(1-(Difluoromethyl)-1H-pyrazol-3-yl)-2-((2-(1-(methoxymethyl)-1H-pyrazol-4-yl)pyrimidin-4-yl)amino)pyridin-4-yl)amino)-1-methylcyclohexan-1-ol The title compound as pale yellow solid (41.9 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (100 mg, 0.28 mmol) prepared in Reference Example 15 and 2-(1-(methoxymethyl)-1H-pyrazol-4-yl)pyrimidin-4-amine (58 mg, 0.28 mmol) prepared in Reference Example 42 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-$d_6$, 400 MHz) δ 9.87 (s, 1H), 8.49 (s, 1H), 8.44 (s, 1H), 8.35 (d, 1H), 8.31 (s, 1H), 8.13 (s, 1H), 7.95 (d, 1H), 7.86 (t, 1H), 7.41 (s, 1H), 7.38 (s, 1H), 7.13 (s, 1H), 5.45 (s, 2H), 4.17 (s, 1H), 3.46 (brs, 1H), 3.27 (s, 3H), 1.87-1.84 (m, 2H), 1.68-1.58 (m, 4H), 1.46-1.40 (m, 2H), 1.13 (s, 3H); MS (ESI) m/z=526.2 (M+H)$^+$ Example 311. 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrazole-1-carboxamide The title compound as pale yellow solid (28.3 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (100 mg, 0.28 mmol) prepared in Reference Example 15 and 4-(4-aminopyrimidin-2-yl)-N,N-dimethyl-1H-pyrazole-1-carboxamide (65 mg, 0.28 mmol) prepared in Reference Example 43 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-$d_6$, 400 MHz) δ 9.95 (s, 1H), 8.62 (s, 1H), 8.49 (s, 1H), 8.38 (d, 1H), 8.31 (s, 1H), 8.28 (s, 1H), 7.99 (s, 1H), 7.86 (t, 1H), 7.41 (brs, 2H), 7.13 (s, 1H), 4.18 (s, 1H), 3.45 (brs, 1H), 3.15 (s, 6H), 1.88-1.86 (m, 2H), 1.69-1.57 (m, 4H), 1.47-1.41 (m, 2H), 1.12 (s, 3H); MS (ESI) m/z=553.2 (M+H)$^+$ Example 312. (1s,4s)-4-((5-(1-(Difluoromethyl)-1H-pyrazol-3-yl)-2-((2'-methoxy-[2,5'-bipyrimidin]-4-yl)amino)pyridin-4-yl)amino)-1-methylcyclohexan-1-ol The title compound as pale yellow solid (61.1 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (100 mg, 0.28 mmol) prepared in Reference Example 15 and 2'-methoxy-[2,5'-bipyrimidin]-4-amine (64 mg, 0.28 mmol) prepared in Reference Example 44 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-$d_6$, 400 MHz) δ 10.11 (s, 1H), 9.39 (s, 1H), 8.50 (s, 1H), 8.47 (d, 1H), 8.31 (d, 1H), 7.99 (d, 1H), 7.87 (t, 1H), 7.53 (brs, 1H), 7.43 (brs, 1H), 7.14 (d, 1H), 4.16 (s, 1H), 4.01 (s, 3H), 3.45-3.40 (m, 1H), 1.86-1.84 (m, 2H), 1.68-1.56 (m, 4H), 1.47-1.41 (m, 2H), 1.13 (s, 3H); MS (ESI) m/z=524.2 (M+H)$^+$ Example 313. (1s,4s)-4-((5-(1-(Difluoromethyl)-1H-pyrazol-3-yl)-2-((2-((2-(methylsulfonyl)phenyl)amino)pyrimidin-4-yl)amino)pyridin-4-yl)amino)-1-methylcyclohexan-1-ol The title compound as pale yellow solid (97.1 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (148.5 mg, 0.416 mmol) prepared in Reference Example 15 and $N^2$-(2-(methylsulfonyl)phenyl)pyrimidine-2,4-diamine (100 mg, 0.378 mmol) were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 9.06 (s, 1H), 8.62 (d, 1H), 8.34 (s, 1H), 8.17 (d, 1H), 7.94 (d, 1H), 7.90 (d, 1H), 7.85 (s, 1H), 7.62 (t, 1H), 7.39 (s, 1H), 7.22 (t, 1H), 7.15 (t, 1H), 6.80 (s, 1H), 6.67 (d, 1H), 3.58 (brs, 1H), 3.11 (s, 3H), 2.00-1.80 (m, 2H), 1.76-1.69 (m, 6H), 1.28 (s, 3H); MS (ESI) m/z=585.2 (M+H)$^+$ Example 314. (1s,4s)-4-((5-(1-(Difluoromethyl)-1H-pyrazol-3-yl)-2-((2-(1-(tetrahydro-2H-pyran-2-yl)-1H-pyrazol-4-yl)pyrimidin-4-yl)amino)pyridin-4-yl)amino)-1-methylcyclohexan-1-ol The title compound as pale yellow solid (50.8 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (96 mg, 0.269 mmol) prepared in Reference Example 15 and 2-(1-(tetrahydro-2H-pyran-2-yl)-1H-pyrazol-4-yl)pyrimidin-4-amine (60 mg, 0.245 mmol) prepared in Reference Example 45 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-$d_6$, 400 MHz) δ 9.85 (s, 1H), 8.48 (s, 1H), 8.37 (s, 1H), 8.34 (d, 1H), 8.30 (d, 1H), 8.09 (s, 1H), 7.95 (d, 1H), 7.86 (t, 1H), 7.41 (s, 1H), 7.35 (s, 1H), 7.12 (d, 1H), 5.48 (dd, 1H), 4.18 (s, 1H), 3.93 (d, 1H), 3.69-3.61 (m, 1H), 2.15-2.08 (m, 1H), 1.96-1.84 (m, 4H), 1.68-1.55 (m, 7H), 1.46-1.40 (m, 2H), 1.14 (s, 3H); MS (ESI) m/z=566.2 (M+H)$^+$ Example 315. 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N,3-trimethyl-1H-pyrazole-1-sulfonamide The title compound as pale yellow solid (91.8 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (100 mg, 0.28 mmol) prepared in Reference Example 15 and 4-(4-aminopyrimidin-2-yl)-N,N,3-trimethyl-1H-pyrazole-1-sulfonamide (79 mg, 0.28 mmol) prepared in Reference Example 46 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.58 (s, 1H), 8.42 (d, 1H), 8.38 (s, 1H), 7.96 (d, 1H), 7.86 (d, 1H), 7.80 (brs, 1H), 7.32 (d, 1H), 7.22 (t, 1H), 6.90 (s, 1H), 6.81 (d, 1H), 3.52-3.49 (m, 1H), 2.97 (s, 6H), 2.69 (s, 3H), 2.02-1.97 (m, 2H), 1.81-1.72 (m, 4H), 1.60-1.53 (m, 2H), 1.31 (s, 3H); MS (ESI) m/z=603.2 (M+H)$^+$

Example 316. (1s,4s)-4-((2-((2-(1-(Cyclopropylsulfonyl)-1H-pyrazol-4-yl)-5-fluoropyrimidin-4-yl)amino)-5-(1-(difluoromethyl)-1H-pyrazol-3-yl)pyridin-4-yl)amino)-1-methylcyclohexan-1-ol The title compound as pale yellow solid (31.3 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 and 2-(1-(cyclopropylsulfonyl)-1H-pyrazol-4-yl)-5-fluoropyrimidin-4-amine (40 mg, 0.14 mmol) prepared in Reference Example 35 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-$d_6$, 400 MHz) δ 9.63 (brs, 1H), 8.62 (s, 1H), 8.53 (s, 1H), 8.50 (d, 1H), 8.44 (s, 1H), 8.34 (d, 1H), 8.10 (d, 1H), 7.89 (t, 1H), 7.65 (s, 1H), 7.18 (d, 1H), 4.13 (s, 1H), 3.51 (brs, 1H), 3.25-3.19 (m, 1H), 1.86-1.83 (m, 2H), 1.70-1.61 (m, 2H), 1.56-1.53 (m, 2H), 1.40-1.18 (m, 6H), 1.17 (s, 3H); MS (ESI) m/z=604.2 (M+H)$^+$

Example 317. 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrazole-1-sulfonamide The title compound as pale yellow solid (26.7 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (73 mg, 0.205 mmol) prepared in Reference Example 15 and 4-(4-aminopyrimidin-2-yl)-N,N-dimethyl-1H-pyrazole-1-sulfonamide (50 mg, 0.186 mmol) prepared in Reference Example 39 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-$d_6$, 400 MHz) δ 9.99 (s, 1H), 8.58 (s, 1H), 8.50 (s, 1H), 8.42 (d, 1H), 8.41 (s, 1H), 8.32 (d, 1H), 7.99 (d, 1H), 7.87 (t, 1H), 7.52 (s, 1H), 7.31 (s, 1H), 7.14 (d, 1H), 4.16 (s, 1H), 3.45 (brs, 1H), 2.91 (d, 6H), 1.88-1.85 (m, 2H), 1.70-1.59 (m, 4H), 1.46-1.41 (m, 2H), 1.14 (s, 3H); MS (ESI) m/z=589.2 (M+H)$^+$

Example 318. (1s,4s)-4-((5-(1-(Difluoromethyl)-1H-pyrazol-3-yl)-2-((2-(1-(tetrahydrofuran-2-yl)-1H-pyrazol-4-yl)pyrimidin-4-yl)amino)pyridin-4-yl)amino)-1-methylcyclohexan-1-ol The title compound as pale yellow solid (38.6 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 and 2-(1-(tetrahydrofuran-2-yl)-1H-pyrazol-4-yl)pyrimidin-4-amine (32 mg, 0.14 mmol) prepared in Reference Example 47 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.38 (s, 1H), 8.36 (s, 1H), 8.29 (d, 1H), 8.21 (s, 1H), 8.09 (s, 1H), 7.56 (t, 1H), 7.36 (s, 1H), 7.23 (d, 1H), 6.96 (s, 1H), 6.08 (d, 1H), 4.19 (q, 1H), 4.02 (q, 1H), 3.60 (brs, 1H), 2.54-2.51 (m, 1H), 2.46-2.37 (m, 1H), 2.26-2.18 (m, 1H), 2.12-2.05 (m, 1H), 2.04-1.97 (m, 2H), 1.82-1.73 (m, 4H), 1.62-1.56 (m, 2H), 1.25 (s, 3H); MS (ESI) m/z=552.2 (M+H)$^+$

Example 319. (1s,4s)-4-((5-(1-(Difluoromethyl)-1H-pyrazol-3-yl)-2-((2-(5-fluoro-1,3-dimethyl-1H-pyrazol-4-yl)pyrimidin-4-yl)amino)pyridin-4-yl)amino)-1-methylcyclohexan-1-ol The title compound as pale yellow solid (17.6 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (57 mg, 0.159 mmol) prepared in Reference Example 15 and 2-(5-fluoro-1,3-dimethyl-1H-pyrazol-4-yl)pyrimidin-4-amine (30 mg, 0.145 mmol) prepared in Reference Example 48 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.46 (d, 1H), 8.35 (s, 1H), 7.93 (s, 1H), 7.86 (d, 1H), 7.45 (brs, 1H), 7.37 (s, 1H), 7.22 (t, 1H), 6.82 (d, 2H), 3.76 (s, 3H), 3.50 (brs, 1H), 2.58 (s, 3H), 2.00-1.96 (m, 2H), 1.79-1.70 (m, 4H), 1.58-1.55 (m, 2H), 1.31 (s, 3H); MS (ESI) m/z=528.2 (M+H)$^+$

Example 320. (1s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)-1-methylcyclohexan-1-ol The title compound as pale yellow solid (33.1 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (61 mg, 0.171 mmol) prepared in Reference Example 15 and 2-(3-methyl-1-(2,2,2-trifluoroethyl)-1H-pyrazol-4-yl)pyrimidin-4-amine (40 mg, 0.156 mmol) prepared in Reference Example 38 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.44 (d, 1H), 8.40 (s, 1H), 8.15 (s, 1H), 7.88 (d, 1H), 7.86 (d, 1H), 7.60 (d, 1H), 7.33 (s, 1H), 7.22 (t, 1H), 6.82 (d, 1H), 6.50 (s, 1H), 4.67 (q, 2H), 3.45-3.41 (m, 1H), 2.67 (s, 3H), 2.00-1.95 (m, 2H), 1.78-1.69 (m, 4H), 1.62-1.51 (m, 2H), 1.31 (s, 3H); MS (ESI) m/z=578.2 (M+H)$^+$

Example 321. (1s,4s)-4-((2-((2-(1-(2,2-Difluoroethyl)-3,5-dimethyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol The title compound as pale yellow solid (48 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (77 mg, 0.217 mmol) prepared in Reference Example 15 and 2-(1-(2,2-difluoroethyl)-3,5-dimethyl-1H-pyrazol-4-yl)pyrimidin-4-amine (50 mg, 0.197 mmol) prepared in Reference Example 49 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.46 (d, 1H), 8.39 (s, 1H), 7.87 (d, 1H), 7.86 (s, 1H), 7.75 (s, 1H), 7.40 (d, 1H), 7.21 (t, 1H), 6.81 (d, 1H), 6.72 (s, 1H), 6.13 (tt, 1H), 4.39 (td, 2H), 3.41-3.38 (m, 1H), 2.62 (s, 3H), 2.54 (s, 3H), 1.96-1.93 (m, 2H), 1.77-1.67 (m, 4H), 1.50-1.43 (m, 2H), 1.28 (s, 3H); MS (ESI) m/z=574.2M+H)⁺

Example 322. (1s,4s)-4-((5-(1-(Difluoromethyl)-1H-pyrazol-3-yl)-2-((2-(1-(2,2,3,3-tetrafluoropropyl)-1H-pyrazol-4-yl)pyrimidin-4-yl)amino)pyridin-4-yl)amino)-1-methylcyclohexan-1-ol The title compound as pale yellow solid (46 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (77 mg, 0.217 mmol) prepared in Reference Example 15 and 2-(1-(2,2,3,3-tetrafluoropropyl)-1H-pyrazol-4-yl)pyrimidin-4-amine (54 mg, 0.197 mmol) prepared in Reference Example 50 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. ¹H-NMR (CDCl₃, 400 MHz) δ 8.39 (d, 1H), 8.38 (s, 1H), 8.28 (s, 1H), 8.20 (s, 1H), 7.93 (d, 1H), 7.86 (d, 1H), 7.74 (s, 1H), 7.26 (s, 1H), 7.22 (t, 1H), 7.03 (s, 1H), 6.82 (d, 1H), 5.89 (tt, 1H), 4.71 (td, 2H), 3.54-3.50 (m, 1H), 2.03-1.99 (m, 2H), 1.82-1.76 (m, 4H), 1.64-1.57 (m, 2H), 1.31 (s, 3H); MS (ESI) m/z=596.2 (M+H)⁺

Example 323. (1s,4s)-4-((5-(1-(Difluoromethyl)-1H-pyrazol-3-yl)-2-((2-(1-(pyrrolidin-1-ylsulfonyl)-1H-pyrazol-4-yl)pyrimidin-4-yl)amino)pyridin-4-yl)amino)-1-methylcyclohexan-1-ol The title compound as pale yellow solid (15.5 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (44 mg, 0.122 mmol) prepared in Reference Example 15 and 2-(1-(pyrrolidin-1-ylsulfonyl)-1H-pyrazol-4-yl)pyrimidin-4-amine (30 mg, 0.102 mmol) prepared in Reference Example 51 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. ¹H-NMR (DMSO-d₆, 400 MHz) δ 9.99 (s, 1H), 8.59 (s, 1H), 8.51 (s, 1H), 8.41 (d, 1H), 8.39 (s, 1H), 8.32 (d, 1H), 8.00 (d, 1H), 7.87 (t, 1H), 7.50 (brs, 1H), 7.33 (brs, 1H), 7.14 (d, 1H), 4.17 (s, 1H), 3.42 (brs, 4H), 1.88-1.85 (m, 2H), 1.77 (brs, 4H), 1.70-1.59 (m, 4H), 1.47-1.41 (m, 2H), 1.14 (s, 3H); MS (ESI) m/z=615.3 (M+H)⁺

Example 324. (1s,4s)-4-((5-(1-(Difluoromethyl)-1H-pyrazol-3-yl)-2-((2-(1-((3-fluoroazetidin-1-yl)sulfonyl)-1H-pyrazol-4-yl)pyrimidin-4-yl)amino)pyridin-4-yl)amino)-1-methylcyclohexan-1-ol The title compound as pale yellow solid (5.5 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (43 mg, 0.121 mmol) prepared in Reference Example 15 and 2-(1-((3-fluoroazetidin-1-yl)sulfonyl)-1H-pyrazol-4-yl)pyrimidin-4-amine (30 mg, 0.101 mmol) prepared in Reference Example 52 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. ¹H-NMR (CDCl₃, 400 MHz) δ 8.69 (s, 1H), 8.49 (s, 1H), 8.42 (d, 1H), 8.38 (s, 1H), 7.99 (d, 1H), 7.87 (d, 1H), 7.63 (s, 1H), 7.31 (s, 1H), 7.23 (t, 1H), 7.03 (s, 1H), 6.83 (d, 1H), 5.20 (d, 1H), 4.46-4.26 (m, 4H), 3.55 (brs, 1H), 2.04-2.01 (m, 2H), 1.83-1.76 (m, 4H), 1.66-1.51 (m, 2H), 1.13 (s, 3H); MS (ESI) m/z=619.2 (M+H)⁺

Example 325. N²-(2-(1-(Cyclopropylsulfonyl)-1H-pyrazol-4-yl)-5-fluoropyrimidin-4-yl)-5-(1-(difluoromethyl)-1H-pyrazol-3-yl)-N⁴-((1s,4s)-4-(2-(dimethylamino)ethyl)cyclohexyl)pyridine-2,4-diamine The title compound as pale yellow solid (18.1 mg) was prepared in the same fashion as Step 2 in Example 1, except that 2-chloro-5-(1-(difluoromethyl)-1H-pyrazol-3-yl)-N-((1s,4s)-4-(2-(dimethylamino)ethyl)cyclohexyl)pyridin-4-amine (40 mg, 0.101 mmol) prepared in Step 1 of Example 211 and 2-(1-(cyclopropylsulfonyl)-1H-pyrazol-4-yl)-5-fluoropyrimidin-4-amine (34 mg, 0.121 mmol) prepared in Reference Example 35 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. ¹H-NMR (CDCl₃, 400 MHz) δ 8.59 (s, 1H), 8.42 (s, 1H), 8.39 (d, 1H), 8.37 (s, 1H), 8.27 (d, 1H), 7.96 (s, 1H), 7.87 (d, 1H), 7.65 (brs, 1H), 7.21 (t, 1H), 6.86 (d, 1H), 4.10-4.07 (m, 1H), 2.88-2.82 (m, 1H) 2.39-2.37 (m, 2H), 2.29 (s, 6H), 2.06-2.02 (m, 2H), 1.89-1.83 (m, 2H), 1.73-1.69 (m, 2H), 1.51-1.47 (m, 5H), 1.37-1.25 (m, 4H); MS (ESI) m/z=645.2 (M+H)⁺

Example 326. 2-((1s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)cyclohexyl)ethan-1-ol The title compound as pale yellow solid (26.2 mg) was prepared in the same fashion as Step 2 in Example 1, except that 2-((1s,4s)-4-((2-chloro-5-(1-(difluoromethyl)-1H-pyrazol-3-yl)pyridin-4-yl)amino)cyclohexyl)ethan-1-ol (43 mg, 0.115 mmol) prepared in Step 1 of Example 135 and 2-(3-methyl-1-(2,2,2-trifluoroethyl)-1H-pyrazol-4-yl)pyrimidin-4-amine (27 mg, 0.105 mmol) prepared in Reference Example 38 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. ¹H-NMR (DMSO-d₆, 400 MHz) δ 9.75 (s, 1H), 8.52 (s, 1H), 8.38 (t, 2H), 8.30 (s, 2H), 7.82 (t, 1H), 7.65 (d, 1H), 7.13 (d, 1H), 7.01 (s, 1H), 5.13 (q, 2H), 4.32 (t, 1H), 3.86 (brs, 1H), 3.43 (q, 2H), 2.55 (s, 3H), 1.83-1.80 (m, 2H), 1.64-1.56 (m, 4H), 1.49 (brs, 1H), 1.38-1.33 (m, 2H), 1.28-1.19 (m, 2H); MS (ESI) m/z=592.2 (M+H)⁺

Example 327. N⁴-((1s,4s)-4-(Azetidin-1-ylmethyl)cyclohexyl)-N²-(2-(1-(cyclopropylsulfonyl)-1H-pyrazol-4-yl)-5-fluoropyrimidin-4-yl)-5-(1-(difluoromethyl)-1H-pyrazol-3-yl)pyridine-2,4-diamine The title compound as pale yellow solid (36.1 mg) was prepared in the same fashion as Step 2 in Example 1, except that N-((1s,4s)-4-(azetidin-1-ylmethyl)cyclohexyl)-2-chloro-5-(1-(difluoromethyl)-1H-pyrazol-3-yl)pyridin-4-amine (50 mg, 0.126 mmol) prepared in Step 1 of Example 208 and 2-(1-(cyclopropylsulfonyl)-1H-pyrazol-4-yl)-5-fluoropyrimidin-4-amine (43 mg, 0.152 mmol) prepared in Reference Example 35 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. ¹H-NMR (DMSO-d₆, 400 MHz) δ 9.75 (s, 1H), 8.52 (s, 1H), 8.38 (t, 2H), 8.30 (s, 2H), 7.82 (t, 1H), 7.65 (d, 1H), 7.13 (d, 1H), 7.01 (s, 1H), 5.13 (q, 2H), 4.32 (t, 1H), 3.86 (brs, 1H), 3.43 (q, 2H), 2.55 (s, 3H), 1.83-1.80 (m, 2H), 1.64-1.56 (m, 4H), 1.49 (brs, 1H), 1.38-1.33 (m, 2H), 1.28-1.19 (m, 2H); MS (ESI) m/z=643.2 (M+H)$^+$ Example 328. (1s,4s)-4-((2-((2-(1-(Cyclopropylsulfonyl)-1H-pyrazol-4-yl)-5-fluoropyrimidin-4-yl)amino)-5-(1-methyl-5-(trifluoromethyl)-1H-pyrazol-3-yl)pyridin-4-yl)amino)-1-methylcyclohexan-1-ol The title compound as pale yellow solid (22.5 mg) was prepared in the same fashion as Step 2 in Example 1, except that (1s,4s)-4-((2-chloro-5-(1-methyl-5-(trifluoromethyl)-1H-pyrazol-3-yl)pyridin-4-yl)amino)-1-methylcyclohexan-1-ol (50 mg, 0.129 mmol) prepared in Reference Example 16 and 2-(1-(cyclopropylsulfonyl)-1H-pyrazol-4-yl)-5-fluoropyrimidin-4-amine (36.43 mg, 0.129 mmol) prepared in Reference Example 35 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.61 (s, 1H), 8.61 (s, 1H), 8.51 (s, 1H), 8.49 (d, 1H), 8.44 (s, 1H), 7.98 (d, 1H), 7.66 (s, 1H), 7.57 (s, 1H), 4.17 (s, 1H), 4.04 (s, 3H), 3.54 (s, 1H), 3.25-3.19 (m, 1H), 1.86-1.83 (m, 2H), 1.71-1.64 (m, 2H), 1.57-1.54 (m, 2H), 1.41-1.39 (m, 2H), 1.36-1.32 (m, 2H), 1.26-1.21 (m, 2H), 1.10 (s, 3H); MS (ESI) m/z=636.2 (M+H)$^+$ Example 329. (1s,4s)-1-Methyl-4-((5-(1-methyl-5-(trifluoromethyl)-1H-pyrazol-3-yl)-2-((2-(1-(2,2,2-trifluoroethyl)-1H-pyrazol-4-yl)pyrimidin-4-yl)amino)pyridin-4-yl)amino)cyclohexan-1-ol The title compound as pale yellow solid (24.1 mg) was prepared in the same fashion as Step 2 in Example 1, except that (1s,4s)-4-((2-chloro-5-(1-methyl-5-(trifluoromethyl)-1H-pyrazol-3-yl)pyridin-4-yl)amino)-1-methylcyclohexan-1-ol (50 mg, 0.129 mmol) prepared in Reference Example 16 and 2-(1-(2,2,2-trifluoroethyl)-1H-pyrazol-4-yl)pyrimidin-4-amine (31 mg, 0.129 mmol) prepared in Reference Example 37 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.87 (s, 1H), 8.46 (s, 1H), 8.41 (s, 1H), 8.36 (d, 1H), 8.15 (s, 1H), 7.81 (d, 1H), 7.51 (s, 1H), 7.46 (brs, 1H), 7.29 (brs, 1H), 5.23 (q, 2H), 4.17 (s, 1H), 4.02 (s, 3H), 3.45 (brs, 1H), 1.86-1.83 (m, 2H), 1.70-1.59 (m, 4H), 1.46-1.40 (m, 2H), 1.13 (s, 3H); MS (ESI) m/z=596.2 (M+H)$^+$ Example 330. 4-(4-(((1s,4s)-4-Hydroxy-4-methylcyclohexyl)amino)-5-(1-methyl-5-(trifluoromethyl)-1H-pyrazol-3-yl)pyridin-2-yl)amino)pyrimidin-2-yl)-N,N-dimethyl-1H-pyrazole-1-sulfonamide The title compound as pale yellow solid (43.2 mg) was prepared in the same fashion as Step 2 in Example 1, except that (1s,4s)-4-((2-chloro-5-(1-methyl-5-(trifluoromethyl)-1H-pyrazol-3-yl)pyridin-4-yl)amino)-1-methylcyclohexan-1-ol (60 mg, 0.154 mmol) prepared in Reference Example 16 and 4-(4-aminopyrimidin-2-yl)-N,N-dimethyl-1H-pyrazole-1-sulfonamide (41 mg, 0.154 mmol) prepared in Reference Example 39 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.75 (s, 1H), 8.52 (s, 1H), 8.38 (t, 2H), 8.30 (s, 2H), 7.82 (t, 1H), 7.65 (d, 1H), 7.13 (d, 1H), 7.01 (s, 1H), 5.13 (q, 2H), 4.32 (t, 1H), 3.86 (brs, 1H), 3.43 (q, 2H), 2.55 (s, 3H), 1.83-1.80 (m, 2H), 1.64-1.56 (m, 4H), 1.49 (brs, 1H), 1.38-1.33 (m, 2H), 1.28-1.19 (m, 2H); MS (ESI) m/z=621.2 (M+H)$^+$ Example 331. (1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol The title compound as pale yellow solid (15.5 mg) was prepared in the same fashion as Step 2 in Example 1, except that (1s,4s)-4-((2-chloro-5-(1-methyl-5-(trifluoromethyl)-1H-pyrazol-3-yl)pyridin-4-yl)amino)-1-methylcyclohexan-1-ol (50 mg, 0.129 mmol) prepared in Reference Example 16 and 2-(1-(2,2-difluoroethyl)-1H-pyrazol-4-yl)pyrimidin-4-amine (29 mg, 0.129 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.84 (s, 1H), 8.46 (s, 1H), 8.35 (s, 1H), 8.34 (d, 1H), 8.10 (s, 1H), 7.82 (d, 1H), 7.51 (s, 1H), 7.45 (s, 1H), 7.29 (s, 1H), 6.41 (tt, 1H), 4.71 (td, 2H), 4.18 (s, 1H), 4.02 (s, 3H), 3.50-3.42 (m, 1H), 1.86-1.83 (m, 2H), 1.70-1.59 (m, 4H), 1.47-1.41 (m, 2H), 1.14 (s, 3H); MS (ESI) m/z=578.2 (M+H)$^+$ Example 332. (1s,4s)-1-Methyl-4-((2-((2-(3-methyl-1-(2,2,2-trifluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexan-1-ol The title compound as pale yellow solid (17.7 mg) was prepared in the same fashion as Step 2 in Example 1, except that (1s,4s)-4-((2-chloro-5-(1-methyl-5-(trifluoromethyl)-1H-pyrazol-3-yl)pyridin-4-yl)amino)-1-methylcyclohexan-1-ol (58 mg, 0.15 mmol) prepared in Reference Example 16 and 2-(3-methyl-1-(2,2,2-trifluoroethyl)-1H-pyrazol-4-yl)pyrimidin-4-amine (35 mg, 0.136 mmol) prepared in Reference Example 38 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.43 (d, 1H), 8.32 (s, 1H), 8.15 (s, 1H), 7.87 (d, 1H), 7.57 (d, 1H), 7.31 (s, 1H), 6.94 (s, 1H), 6.49 (s, 1H), 4.97 (q, 2H), 4.03 (s, 3H), 3.42 (brs, 1H), 2.67 (s, 3H), 1.99-1.96 (m, 2H), 1.79-1.75 (m, 4H), 1.61-1.51 (m, 2H), 1.31 (s, 3H); MS (ESI) m/z=610.2 (M+H)$^+$ Example 333. 2-((1s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol The title compound as pale yellow solid (19.9 mg) was prepared in the same fashion as Step 2 in Example 1, except that 2-((1s,4s)-4-((2-chloro-5-(1-methyl-5-(trifluoromethyl)-1H-pyrazol-3-yl)pyridin-4-yl)amino)cyclohexyl)ethan-1-ol (49 mg, 0.122 mmol) prepared in Step 1 of Example 262 and 2-(1-(2,2-difluoroethyl)-1H-pyrazol-4-yl)pyrimidin-4-amine (29 mg, 0.129 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400

MHz) δ 8.36 (s, 1H), 8.31 (s, 1H), 8.29 (d, 1H), 8.19 (s, 1H), 7.32 (s, 1H), 7.25 (d, 2H), 6.26 (tt, 1H), 4.66 (td, 2H), 4.07 (s, 3H), 4.00 (brs, 1H), 3.65 (t, 2H), 2.00-1.98 (m, 2H), 1.82-1.73 (m, 4H), 1.63-1.53 (m, 3H), 1.44-1.37 (m, 2H); MS (ESI) m/z=592.2 (M+H)$^+$ Example 334. 2-((1s,4s)-4-((2-((2-(3-Methyl-1-(2,2,2-trifluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol The title compound as pale yellow solid (15.5 mg) was prepared in the same fashion as Step 2 in Example 1, except that 2-((1s,4s)-4-((2-chloro-5-(1-methyl-5-(trifluoromethyl)-1H-pyrazol-3-yl)pyridin-4-yl)amino)cyclohexyl)ethan-1-ol (47 mg, 0.115 mmol) prepared in Step 1 of Example 262 and 2-(3-methyl-1-(2,2,2-trifluoroethyl)-1H-pyrazol-4-yl)pyrimidin-4-amine (27 mg, 0.105 mmol) prepared in Reference Example 38 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.73 (s, 1H), 8.49 (s, 1H), 8.38 (d, 1H), 8.29 (s, 1H), 8.12 (d, 1H), 7.62 (d, 1H), 7.54 (s, 1H), 7.00 (s, 1H), 5.13 (q, 2H), 4.34 (t, 1H), 4.02 (s, 3H), 3.83 (brs, 1H), 3.46 (q, 2H), 2.55 (s, 3H), 1.83-1.81 (m, 2H), 1.66-1.60 (m, 4H), 1.52 (brs, 1H), 1.43-1.38 (m, 2H), 1.25-1.22 (m, 2H); MS (ESI) m/z=624.2 (M+H)$^+$ Example 335. (1s,4s)-4-((5-(1-(2,2-Difluoroethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)-1-methylcyclohexan-1-ol The title compound as pale yellow solid (18.5 mg) was prepared in the same fashion as Step 2 in Example 1, except that (1s,4s)-4-((2-chloro-5-(1-(2,2-difluoroethyl)-1H-pyrazol-3-yl)pyridin-4-yl)amino)-1-methylcyclohexan-1-ol (56 mg, 0.15 mmol) prepared in Reference Example 17 and 2-(3-methyl-1-(2,2,2-trifluoroethyl)-1H-pyrazol-4-yl)pyrimidin-4-amine (35 mg, 0.136 mmol) prepared in Reference Example 38 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.42 (d, 1H), 8.37 (s, 1H), 8.15 (s, 1H), 8.03 (d, 1H), 7.58 (d, 1H), 7.51 (d, 1H), 7.32 (s, 1H), 6.67 (d, 1H), 6.48 (s, 1H), 6.12 (tt, 1H), 4.67 (q, 2H), 4.51 (td, 2H), 3.43 (brs, 1H), 2.67 (s, 3H), 1.99-1.94 (m, 2H), 1.79-1.70 (m, 4H), 1.62-1.51 (m, 2H), 1.31 (s, 3H); MS (ESI) m/z=592.2 (M+H)$^+$ Example 336. 2-((1s,4s)-4-((2-((2-(1-(Cyclopropylsulfonyl)-1H-pyrazol-4-yl)-5-fluoropyrimidin-4-yl)amino)-5-(1-(2,2-difluoroethyl)-1H-pyrazol-3-yl)pyridin-4-yl)amino)cyclohexyl)ethan-1-ol Step 1. 2-((1s,4s)-4-((2-Chloro-5-(1-(2,2-difluoroethyl)-1H-pyrazol-3-yl)pyridin-4-yl)amino)cyclohexyl)ethan-1-ol The title compound as a white solid (143 mg) was prepared in the same fashion as Step 2 in Reference Example 17, except that 2-((1s,4s)-4-aminocyclohexyl)ethan-1-ol (87 mg, 0.606 mmol) was used instead of (1s,4s)-4-amino-1-methylcyclohexan-1-ol. $^1$H-NMR (CDCl$_3$, 400 MHz) δ 8.77 (d, 1H), 8.31 (s, 1H), 7.79 (s, 1H), 6.84 (d, 1H), 6.89 (s, 1H), 6.21 (tt, 1H), 4.64 (td, 2H), 3.89-3.87 (m, 1H), 3.63 (t, 2H), 1.90-1.86 (m, 2H), 1.76-1.69 (m, 4H), 1.63-1.50 (m, 3H), 1.40-1.31 (m, 2H)

Step 2. 2-((1s,4s)-4-((2-((2-(1-(Cyclopropylsulfonyl)-1H-pyrazol-4-yl)-5-fluoropyrimidin-4-yl)amino)-5-(1-(2,2-difluoroethyl)-1H-pyrazol-3-yl)pyridin-4-yl)amino)cyclohexyl)ethan-1-ol The title compound as pale yellow solid (8.5 mg) was prepared in the same fashion as Step 2 in Example 1, except that 2-((1s,4s)-4-((2-chloro-5-(1-(2,2-difluoroethyl)-1H-pyrazol-3-yl)pyridin-4-yl)amino)cyclohexyl)ethan-1-ol (45 mg, 0.116 mmol) prepared in Step 1 and 2-(1-(cyclopropylsulfonyl)-1H-pyrazol-4-yl)-5-fluoropyrimidin-4-amine (30 mg, 0.106 mmol) prepared in Reference Example 35 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.49 (s, 1H), 8.77 (s, 1H), 8.56 (s, 1H), 8.48 (d, 1H), 8.45 (s, 1H), 8.40 (s, 1H), 7.91 (d, 1H), 7.72 (s, 1H), 6.95 (d, 1H), 6.39 (tt, 1H), 4.67 (td, 2H), 4.35 (t, 1H), 3.97 (brs, 1H), 3.17-3.10 (m, 1H), 1.89-1.86 (m, 2H), 1.75-1.68 (m, 2H), 1.61-1.59 (m, 2H), 1.49 (brs, 1H), 1.40-1.31 (m, 4H), 1.28-1.20 (m, 6H); MS (ESI) m/z=632.2 (M+H)$^+$ Example 337. 2-((1s,4s)-4-((5-(1-(2,2-Difluoroethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)cyclohexyl)ethan-1-ol The title compound as pale yellow solid (22.1 mg) was prepared in the same fashion as Step 2 in Example 1, except that 2-((1s,4s)-4-((2-chloro-5-(1-(2,2-difluoroethyl)-1H-pyrazol-3-yl)pyridin-4-yl)amino)cyclohexyl)ethan-1-ol (44 mg, 0.115 mmol) prepared in Step 1 of Example 336 and 2-(3-methyl-1-(2,2,2-trifluoroethyl)-1H-pyrazol-4-yl)pyrimidin-4-amine (27 mg, 0.105 mmol) prepared in Reference Example 38 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.67 (s, 1H), 8.41 (s, 1H), 8.37 (d, 2H), 8.29 (s, 1H), 7.89 (d, 1H), 7.66 (brs, 1H), 6.93 (s, 1H), 6.90 (d, 1H), 6.38 (tt, 1H), 5.13 (q, 2H), 4.66 (td, 2H), 4.33 (t, 1H), 3.79 (brs, 1H), 3.44 (q, 2H), 2.55 (s, 3H), 1.83-1.80 (m, 2H), 1.65-1.49 (m, 5H), 1.40-1.35 (m, 2H), 1.29-1.21 (m, 2H); MS (ESI) m/z=606.3 (M+H)$^+$ Example 338. 2-((1s,4s)-4-((2-((2-(1-(2,2-Difluoroethyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol The title compound as pale yellow solid (8.4 mg) was prepared in the same fashion as Step 2 in Example 1, except that 2-((1s,4s)-4-((2-chloro-5-(1-(2,2,2-trifluoroethyl)-1H-pyrazol-3-yl)pyridin-4-yl)amino)cyclohexyl)ethan-1-ol (49 mg, 0.122 mmol) prepared in Step 1 of Example 269 and 2-(1-(2,2-difluoroethyl)-1H-pyrazol-4-yl)pyrimidin-4-amine (25 mg, 0.111 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.52 (d, 1H), 8.35 (s, 1H), 8.31 (s, 1H), 8.29 (d, 1H), 8.20 (s, 1H), 7.82 (d, 1H), 7.29 (s, 1H), 7.23 (d, 1H), 6.84 (d, 1H), 6.27 (tt, 1H), 4.99 (q, 2H), 4.66 (td, 2H), 3.98 (brs, 1H), 3.64 (t, 2H), 2.00-1.97 (m, 2H), 1.81-1.69 (m, 4H), 1.62-1.60 (m, 1H), 1.55-1.50 (m, 2H), 1.44-1.35 (m, 2H); MS (ESI) m/z=592.2 (M+H)$^+$ Example 339. $N^2$-(2-(1-(2,2-Difluoroethyl)-1H-pyrazol-4-yl)pyrimidin-4-yl)-$N^4$-((1s,4s)-4-fluorocyclohexyl)-5-(1-(2,2,2-trifluoroethyl)-1H-pyrazol-3-yl)pyridine-2,4-diamine The title compound as pale yellow solid (19.6 mg) was prepared in the same fashion as Step 2 in Example 1, except that 2-chloro-N-((1s,4s)-4-fluorocyclohexyl)-5-(1-(2,2,2-trifluoroethyl)-1H-pyrazol-3-yl)pyridin-4-amine (50 mg, 0.133 mmol) prepared in Step 1 of Example 305 and 2-(1-(2,2-difluoroethyl)-1H-pyrazol-4-yl)pyrimidin-4-amine (25 mg, 0.111 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.38 (d, 1H), 8.37 (s, 1H), 8.23 (s, 1H), 8.18 (d, 1H), 8.16 (s, 1H), 7.60 (d, 1H), 7.41 (s, 1H), 7.24 (d, 1H), 7.02 (s, 1H), 6.72 (d, 1H), 6.15 (tt, 1H), 4.86 (d, 1H), 4.73 (q, 2H), 4.52 (td, 2H), 3.67-3.63 (m, 1H), 2.05-1.94 (m, 4H), 1.89-1.74 (m, 4H); MS (ESI) m/z=566.2 (M+H)$^+$ Example 340. (1s,4s)-4-((2-((2-(1-(2,2-Difluoroethyl)-1H-pyrazol-4-yl)pyrimidin-4-yl)amino)-5-(1-(trifluoromethyl)-1H-pyrazol-3-yl)pyridin-4-yl)amino)-1-methylcyclohexan-1-ol The title compound as pale yellow solid (19 mg) was prepared in the same fashion as Step 2 in Example 1, except that (1s,4s)-4-((2-chloro-5-(1-(trifluoromethyl)-1H-pyrazol-3-yl)pyridin-4-yl)amino)-1-methylcyclohexan-1-ol (37 mg, 0.098 mmol) prepared in Step 1 of Example 285 and 2-(1-(2,2-difluoroethyl)-1H-pyrazol-4-yl)pyrimidin-4-amine (20 mg, 0.089 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.91 (s, 1H), 8.58 (d, 1H), 8.55 (s, 1H), 8.37 (d, 1H), 8.36 (s, 1H), 8.10 (s, 1H), 7.81 (d, 1H), 7.47 (s, 1H), 7.32 (d, 1H), 7.30 (s, 1H), 6.41 (tt, 1H), 4.74 (td, 2H), 4.18 (s, 1H), 3.47 (brs, 1H), 1.87-1.84 (m, 2H), 1.65-1.58 (m, 4H), 1.47-1.40 (m, 2H), 1.14 (s, 3H); MS (ESI) m/z=564.1 (M+H)$^+$ Example 341. (1s,4s)-1-Methyl-4-((2-((2-(3-methyl-1-(2,2,2-trifluoroethyl)-1H-pyrazol-4-yl)pyrimidin-4-yl)amino)-5-(1-(trifluoromethyl)-1H-pyrazol-3-yl)pyridin-4-yl)amino)cyclohexan-1-ol The title compound as pale yellow solid (13.1 mg) was prepared in the same fashion as Step 2 in Example 1, except that (1s,4s)-4-((2-chloro-5-(1-(trifluoromethyl)-1H-pyrazol-3-yl)pyridin-4-yl)amino)-1-methylcyclohexan-1-ol (43 mg, 0.115 mmol) prepared in Step 1 of Example 285 and 2-(3-methyl-1-(2,2,2-trifluoroethyl)-1H-pyrazol-4-yl)pyrimidin-4-amine (27 mg, 0.105 mmol) prepared in Reference Example 38 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.75 (s, 1H), 8.58 (d, 1H), 8.56 (s, 1H), 8.41 (d, 1H), 8.31 (s, 1H), 7.78 (dd, 2H), 7.30 (d, 1H), 6.89 (s, 1H), 5.13 (q, 2H), 4.18 (s, 1H), 2.55 (s, 3H), 1.84-1.81 (m, 2H), 1.64-1.58 (m, 4H), 1.40-1.34 (m, 2H), 1.13 (s, 3H); MS (ESI) m/z=596.2 (M+H)$^+$ Example 342. (1s,4s)-4-((2-((2-(1-(2,2-Difluoroethyl)-1H-pyrazol-4-yl)pyrimidin-4-yl)amino)-5-(1-(1-methylpiperidin-4-yl)-1H-pyrazol-3-yl)pyridin-4-yl)amino)-1-methylcyclohexan-1-ol The title compound as pale yellow solid (9.1 mg) was prepared in the same fashion as Step 2 in Example 1, except that (1s,4s)-4-((2-chloro-5-(1-(1-methylpiperidin-4-yl)-1H-pyrazol-3-yl)pyridin-4-yl)amino)-1-methylcyclohexan-1-ol (30 mg, 0.074 mmol) prepared in Step 1 of Example 287 and 2-(1-(2,2-difluoroethyl)-1H-pyrazol-4-yl)pyrimidin-4-amine (20 mg, 0.089 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.31-3.28 (m, 3H), 8.23 (s, 1H), 7.72 (s, 1H), 7.27 (d, 1H), 7.18 (s, 1H), 6.67 (s, 1H), 6.25 (tt, 1H), 4.62 (td, 2H), 4.26-4.16 (m, 1H), 3.55 (brs, 1H), 3.03-3.00 (m, 2H), 2.36 (s, 3H), 2.33-2.26 (m, 2H), 2.20-2.14 (m, 4H), 2.04-1.98 (m, 4H), 1.81-1.75 (m, 2H), 1.61-1.55 (m, 2H), 1.30 (s, 3H); MS (ESI) m/z=593.3 (M+H)$^+$ Example 343. (1s,4s)-4-((5-(1-(2,2-Difluoroethyl)-1H-pyrazol-3-yl)-2-((2-(1-(2,2-difluoroethyl)-1H-pyrazol-4-yl)pyrimidin-4-yl)amino)pyridin-4-yl)amino)-1-methylcyclohexan-1-ol The title compound as pale yellow solid (19.7 mg) was prepared in the same fashion as Step 2 in Example 1, except that (1s,4s)-4-((2-chloro-5-(1-(2,2-difluoroethyl)-1H-pyrazol-3-yl)pyridin-4-yl)amino)-1-methylcyclohexan-1-ol (50 mg, 0.13 mmol) prepared in Reference Example 17 and 2-(1-(2,2-difluoroethyl)-1H-pyrazol-4-yl)pyrimidin-4-amine (30.37 mg, 0.13 mmol) prepared in Reference Example 36 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.31 (s, 2H), 8.29 (d, 1H), 8.22 (s, 1H), 7.73 (d, 1H), 7.27 (d, 1H), 7.20 (s, 1H), 6.74 (d, 1H), 6.24 (tq, 2H), 4.64 (qd, 4H), 3.59-3.55 (m, 1H), 1.98-1.94 (m, 2H), 1.81-1.73 (m, 4H), 1.61-1.54 (m, 2H), 1.25 (s, 3H); MS (ESI) m/z=560.2 (M+H)$^+$ Example 344. (1s,4s)-4-((5-(1-(2,2-Difluoroethyl)-1H-pyrazol-3-yl)-2-((2-(1-(2,2,2-trifluoroethyl)-1H-pyrazol-4-yl)pyrimidin-4-yl)amino)pyridin-4-yl)amino)-1-methylcyclohexan-1-ol The title compound as pale yellow solid (22.5 mg) was prepared in the same fashion as Step 2 in Example 1, except that (1s,4s)-4-((2-chloro-5-(1-(2,2-difluoroethyl)-1H-pyrazol-3-yl)pyridin-4-yl)amino)-1-methylcyclohexan-1-ol (50 mg, 0.13 mmol) prepared in Reference Example 17 and 2-(1-(2,2,2-trifluoroethyl)-1H-pyrazol-4-yl)pyrimidin-4-amine (33 mg, 0.13 mmol) prepared in Reference Example 37 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.37 (s, 1H), 8.31 (s, 1H), 8.30 (d, 1H), 8.25 (s, 1H), 7.74 (d, 1H), 7.30 (d, 1H), 7.20 (s, 1H), 6.75 (d, 1H), 6.24 (tt, 1H), 5.05 (q, 2H), 4.62

(td, 2H), 3.60-3.55 (m, 1H), 1.98-1.94 (m, 2H), 1.81-1.73 (m, 4H), 1.62-1.55 (m, 2H), 1.25 (s, 3H); MS (ESI) m/z=578.2 (M+H)+

Example 345. (1s,4s)-4-((2-((2-(1-(Cyclopropylsulfonyl)-1H-pyrazol-4-yl)-5-fluoropyrimidin-4-yl)amino)-5-(1-(2,2-difluoroethyl)-1H-pyrazol-3-yl)pyridin-4-yl)amino)-1-methylcyclohexan-1-ol The title compound as pale yellow solid (19.5 mg) was prepared in the same fashion as Step 2 in Example 1, except that (1s,4s)-4-((2-chloro-5-(1-(2,2-difluoroethyl)-1H-pyrazol-3-yl)pyridin-4-yl)amino)-1-methylcyclohexan-1-ol (50 mg, 0.13 mmol) prepared in Reference Example 17 and 2-(1-(cyclopropylsulfonyl)-1H-pyrazol-4-yl)-5-fluoropyrimidin-4-amine (38 mg, 0.36 mmol) prepared in Reference Example 35 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.67 (s, 1H), 8.44 (s, 1H), 8.35 (d, 1H), 8.32 (s, 1H), 7.77 (s, 1H), 7.75 (d, 1H), 6.77 (d, 1H), 6.25 (tt, 1H), 4.64 (td, 2H), 3.68 (brs, 1H), 3.06-3.00 (m, 1H), 2.02-1.97 (m, 2H), 1.85-1.72 (m, 4H), 1.63-1.56 (m, 2H), 1.47-1.43 (m, 2H), 1.31-1.26 (m, 5H); MS (ESI) m/z=618.2 (M+H)+

Example 346. (1s,4s)-4-((2-((2-(3,3-Difluoro-4-(hydroxymethyl)pyrrolidin-1-yl)pyrimidin-4-yl)amino)-5-(1-(difluoromethyl)-1H-pyrazol-3-yl)pyridin-4-yl)amino)-1-methylcyclohexan-1-ol The title compound as pale yellow solid (9.3 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 and (1-(4-aminopyrimidin-2-yl)-4,4-difluoropyrrolidin-3-yl)methanol (32 mg, 0.14 mmol) prepared in Reference Example 53 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.34 (s, 1H), 8.09 (s, 1H), 7.98 (d, 1H), 7.55 (t, 1H), 7.47 (s, 1H), 6.95 (d, 1H), 6.49 (d, 1H), 4.07-3.99 (m, 2H), 3.93-3.89 (m, 1H), 3.77-3.72 (m, 1H), 3.69-3.65 (m, 1H), 3.59 (brs, 1H), 2.92-2.81 (m, 1H), 1.95-1.91 (m, 2H), 1.78-1.75 (m, 4H), 1.63-1.58 (m, 2H), 1.26 (s, 3H); MS (ESI) m/z=551.2 (M+H)+

Example 347. (1s,4s)-4-((5-(1-(Difluoromethyl)-1H-pyrazol-3-yl)-2-((2-(4-(hydroxymethyl)-3,3-dimethylpyrrolidin-1-yl)pyrimidin-4-yl)amino)pyridin-4-yl)amino)-1-methylcyclohexan-1-ol The title compound as pale yellow solid (16.8 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 and (1-(4-aminopyrimidin-2-yl)-4,4-dimethylpyrrolidin-3-yl)methanol (31 mg, 0.14 mmol) prepared in Reference Example 54 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.33 (s, 1H), 8.09 (d, 1H), 7.92 (d, 1H), 7.55 (t, 1H), 7.51 (brs, 1H), 6.94 (d, 1H), 6.38 (d, 1H), 4.02-3.78 (m, 2H), 3.71-3.49 (m, 4H), 2.19-2.16 (m, 1H), 1.94-1.91 (m, 2H), 1.80-1.77 (m, 4H), 1.63-1.57 (m, 2H), 1.27 (s, 3H), 1.23 (s, 3H), 1.05 (s, 3H); MS (ESI) m/z=543.3 (M+H)+

Example 348. 1-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-3,3-difluoropiperidin-4-ol The title compound as pale yellow solid (50.3 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 and 1-(4-aminopyrimidin-2-yl)-3,3-difluoropiperidin-4-ol (32 mg, 0.14 mmol) prepared in Reference Example 56 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-$d_6$, 400 MHz) δ 8.33 (s, 1H), 8.08 (s, 1H), 7.98 (d, 1H), 7.55 (t, 1H), 7.17 (s, 1H), 6.94 (s, 1H), 6.56 (d, 1H), 4.30-4.21 (m, 1H), 4.09-3.98 (m, 3H), 3.83-3.79 (m, 1H), 3.60-3.58 (m, 1H), 2.01-1.93 (m, 3H), 1.84-1.75 (m, 5H), 1.63-1.56 (m, 2H); MS (ESI) m/z=551.2 (M+H)+

Example 349. 1-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-4,4-difluoropyrrolidin-3-ol The title compound as pale yellow solid (50.3 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 and 1-(4-aminopyrimidin-2-yl)-4,4-difluoropyrrolidin-3-ol (30 mg, 0.14 mmol) prepared in Reference Example 55 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.33 (s, 1H), 8.08 (s, 1H), 7.98 (d, 1H), 7.55 (t, 1H), 7.49 (s, 1H), 6.94 (s, 1H), 6.46 (d, 1H), 4.37 (brs, 1H), 4.03-3.93 (m, 3H), 3.72-3.70 (m, 1H), 3.57 (brs, 1H), 2.02-1.94 (m, 2H), 1.78-1.76 (m, 4H), 1.64-1.58 (m, 2H), 1.27 (s, 3H); MS (ESI) m/z=537.2 (M+H)+

Example 350. 1-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-4,4-difluoropiperidin-3-ol The title compound as pale yellow solid (22.1 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (35 mg, 0.1 mmol) prepared in Reference Example 15 and 1-(4-aminopyrimidin-2-yl)-4,4-difluoropiperidin-3-ol (23 mg, 0.1 mmol) prepared in Reference Example 57 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.31 (s, 1H), 8.05 (d, 1H), 7.94 (d, 1H), 7.84 (s, 1H), 7.51 (brs, 1H), 7.20 (t, 1H), 6.95 (s, 1H), 6.79 (s, 1H), 6.55 (d, 1H), 4.32-4.22 (m, 2H), 3.96-3.86 (m, 2H), 3.75-3.70 (m, 1H), 3.50 (brs, 1H), 2.34-2.26 (m, 1H), 1.98-1.95 (m, 3H), 1.80-1.72 (m, 4H), 1.60-1.54 (m, 2H), 1.32 (s, 3H); MS (ESI) m/z=551.2 (M+H)$^+$ Example 351. (S)-1-(4-((5-(1-(Difluoromethyl)-1H-pyrazol-3-yl)-4-(((1s,4R)-4-hydroxy-4-methylcyclohexyl)amino)pyridin-2-yl)amino)pyrimidin-2-yl)piperidin-3-ol The title compound as pale yellow solid (46.6 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 and (S)-1-(4-aminopyrimidin-2-yl)piperidin-3-ol (27 mg, 0.14 mmol) prepared in Reference Example 58 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 8.35 (s, 1H), 8.11 (d, 1H), 7.98 (d, 1H), 7.58 (t, 1H), 7.29 (s, 1H), 6.97 (d, 1H), 6.49 (d, 1H), 4.52 (dd, 1H), 4.33 (d, 1H), 3.72-3.60 (m, 2H), 3.23-3.17 (m, 1H), 3.12-3.06 (m, 1H), 2.10-2.04 (m, 1H), 1.99-1.93 (m, 2H), 1.88-1.78 (m, 5H), 1.67-1.55 (m, 4H), 1.29 (s, 3H); MS (ESI) m/z=515.3 (M+H)$^+$ Example 352. (R)-1-(4-((5-(1-(Difluoromethyl)-1H-pyrazol-3-yl)-4-(((1s,4S)-4-hydroxy-4-methylcyclohexyl)amino)pyridin-2-yl)amino)pyrimidin-2-yl)piperidin-3-ol The title compound as pale yellow solid (46.6 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (50 mg, 0.14 mmol) prepared in Reference Example 15 and (R)-1-(4-aminopyrimidin-2-yl)piperidin-3-ol (27 mg, 0.14 mmol) prepared in Reference Example 59 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.35 (s, 1H), 8.11 (d, 1H), 7.98 (d, 1H), 7.58 (t, 1H), 7.28 (s, 1H), 6.97 (d, 1H), 6.49 (d, 1H), 4.52 (dd, 1H), 4.33 (d, 1H), 3.70-3.63 (m, 2H), 3.21-3.19 (m, 1H), 3.12-3.06 (m, 1H), 2.07-1.97 (m, 3H), 1.86-1.78 (m, 5H), 1.67-1.55 (m, 4H), 1.29 (s, 3H); MS (ESI) m/z=515.2 (M+H)$^+$ Example 353. 3,3-Difluoro-1-(4-((4-(((1s,4s)-4-hydroxy-4-methylcyclohexyl)amino)-5-(1-methyl-5-(trifluoromethyl)-1H-pyrazol-3-yl)pyridin-2-yl)amino)pyrimidin-2-yl)piperidin-4-ol The title compound as pale yellow solid (10.2 mg) was prepared in the same fashion as Step 2 in Example 1, except that (1s,4s)-4-((2-chloro-5-(1-methyl-5-(trifluoromethyl)-1H-pyrazol-3-yl)pyridin-4-yl)amino)-1-methylcyclohexan-1-ol (60 mg, 0.15 mmol) prepared in Reference Example 16 and 1-(4-aminopyrimidin-2-yl)-3,3-difluoropiperidin-4-ol (36 mg, 0.15 mmol) prepared in Reference Example 56 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (MeOD, 400 MHz) δ 8.29 (s, 1H), 7.99 (d, 1H), 7.19 (s, 1H), 7.12 (s, 1H), 6.52 (s, 1H), 4.24-4.19 (m, 1H), 4.09-3.98 (m, 1H), 4.05 (s, 3H), 3.83 (brs, 1H), 3.58 (brs, 1H), 1.95-1.92 (m, 3H), 1.84-1.75 (m, 5H), 1.63-1.57 (m, 2H), 1.26 (s, 3H); MS (ESI) m/z=583.2 (M+H)$^+$ Example 354. (1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyridin-4-yl)amino)-1-methylcyclohexan-1-ol The title compound as pale yellow solid (45.6 mg) was prepared in the same fashion as Step 2 in Example 1, except that (1s,4s)-4-((2-chloro-5-(1-(difluoromethyl)-1H-pyrazol-3-yl)pyridin-4-yl)amino)-1-methylcyclohexan-1-ol (100 mg, 0.28 mmol) prepared in Reference Example 15 and 2-(1-(cyclopropylsulfonyl)-1H-pyrazol-4-yl)pyridin-4-amine (74 mg, 0.28 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.40 (s, 1H), 8.59 (s, 1H), 8.52 (s, 1H), 8.38 (s, 1H), 8.30 (d, 1H), 8.29 (d, 1H), 8.05 (s, 1H), 7.86 (t, 1H), 7.85 (s, 1H), 7.52 (d, 1H), 7.12 (d, 1H), 6.23 (s, 1H), 4.17 (s, 1H), 3.23-3.19 (m, 1H), 1.85-1.83 (m, 2H), 1.68-1.62 (m, 4H), 1.46-1.40 (m, 2H), 1.33-1.31 (m, 2H), 1.25-1.20 (m, 2H), 1.15 (s, 3H); MS (ESI) m/z=585.2 (M+H)$^+$ Example 355. (1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)-1-methylcyclohexan-1-ol Step 1. (1s,4s)-4-((2-Chloro-5-(1-(difluoromethyl)-1H-pyrazol-3-yl)pyrimidin-4-yl)amino)-1-methylcyclohexan-1-ol The title compound as a white solid (75.1 mg) was prepared in the same fashion as Reference Example 2, except that (1s,4s)-4-((5-bromo-2-chloropyrimidin-4-yl)amino)-1-methylcyclohexan-1-ol (100 mg, 1.817 mmol) prepared in Reference Example 32 was used instead of 2-chloro-4-fluoro-5-iodopyridine. MS (ESI) m/z=358.1 (M+H)$^+$ Step 2. (1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)-1-methylcyclohexan-1-ol The title compound as an off white solid (7.5 mg) was prepared in the same fashion as Step 2 in Example 1, except that (1s,4s)-4-((2-chloro-5-(1-(difluoromethyl)-1H-pyrazol-3-yl)pyrimidin-4-yl)amino)-1-methylcyclohexan-1-ol (37 mg, 0.104 mmol) prepared in Step 1 and 2-(1-(cyclopropylsulfonyl)-1H-pyrazol-4-yl)pyridin-4-amine (25 mg, 0.095 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine.
$^1$H-NMR (CDCl$_3$, 400 MHz) δ 9.80 (s, 1H), 8.64 (s, 1H), 8.62 (s, 1H), 8.41 (s, 1H), 8.36-8.32 (m, 3H), 8.25 (s, 1H), 7.89 (t, 1H), 7.59 (dd, 1H), 7.15 (d, 1H), 4.13 (s, 1H), 4.03 (brs, 1H), 3.21-3.15 (m, 1H), 1.87-1.83 (m, 2H), 1.67-1.62 (m, 2H), 1.57-1.53 (m, 2H), 1.38-1.30 (m, 4H), 1.29-1.21 (m, 2H), 1.18 (s, 3H); MS (ESI) m/z=586.2 (M+H)$^+$ Example 356. (1s,4s)-4-((2-((2-(1-(Cyclopropylsulfonyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol Step 1. (1s,4s)-4-((2-Chloro-5-(1-methyl-5-(trifluoromethyl)-1H-pyrazol-3-yl)pyrimidin-4-yl)amino)-1-methylcyclohexan-1-ol The title compound as a white solid (92 mg) was prepared in the same fashion as Step 1 in Reference Example 16, except that (1s,4s)-4-((5-bromo-2-chloropyrimidin-4-yl)amino)-1-methylcyclohexan-1-ol (100 mg, 0.312 mmol) prepared in Reference Example 32 was used instead of 2-chloro-4-fluoro-5-iodopyridine. MS (ESI) m/z=390.1 (M+H)$^+$ Step 2. (1s,4s)-4-((2-((2-(1-(Cyclopropylsulfonyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol The title compound as an off white solid (7.5 mg) was prepared in the same fashion as Step 2 in Example 1, except that (1s,4s)-4-((2-chloro-5-(1-methyl-5-(trifluoromethyl)-1H-pyrazol-3-yl)pyrimidin-4-yl)amino)-1-methylcyclohexan-1-ol (53 mg, 0.136 mmol) prepared in Step 1 and 2-(1-(cyclopropylsulfonyl)-1H-pyrazol-4-yl)pyridin-4-amine (30 mg, 0.114 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.50 (s, 1H), 8.43 (d, 1H), 8.34-8.30 (m, 3H), 7.99 (s, 1H), 7.46 (d, 1H), 7.19 (s, 1H), 6.92 (s, 1H), 4.12-4.10 (m, 1H), 4.04 (s, 3H), 2.85-2.79 (m, 1H), 2.07-2.05 (m, 2H), 1.82-1.76 (m, 4H), 1.62-1.53 (m, 4H), 1.31 (s, 3H), 1.23-1.17 (m, 2H); MS (ESI) m/z=618.2 (M+H)$^+$ Example 357. (1s,4s)-4-((2-((2-(1-(Cyclopropylsulfonyl)-1H-pyrazol-4-yl)pyridin-4-yl)amino)-5-(1-(2,2-difluoroethyl)-1H-pyrazol-3-yl)pyrimidin-4-yl)amino)-1-methylcyclohexan-1-ol Step 1. (1s,4s)-4-((2-Chloro-5-(1-(2,2-difluoroethyl)-1H-pyrazol-3-yl)pyrimidin-4-yl)amino)-1-methylcyclohexan-1-ol The title compound as a white solid (88 mg) was prepared in the same fashion as Step 1 in Reference Example 17, except that (1s,4s)-4-((5-bromo-2-chloropyrimidin-4-yl)amino)-1-methylcyclohexan-1-ol (100 mg, 1.817 mmol) prepared in Reference Example 32 was used instead of 2-chloro-4-fluoro-5-iodopyridine. $^1$H-NMR (CDCl$_3$, 400 MHz) δ 8.53 (d, 1H), 8.32 (s, 1H), 7.54 (d, 1H), 6.68 (d, 1H), 6.10 (tt, 1H), 4.54 (td, 2H), 4.16-4.10 (m, 1H), 1.98-1.95 (m, 2H), 1.76-1.1.59 (m, 6H), 1.31 (s, 3H)

Step 2. (1s,4s)-4-((2-((2-(1-(Cyclopropylsulfonyl)-1H-pyrazol-4-yl)pyridin-4-yl)amino)-5-(1-(2,2-difluoroethyl)-1H-pyrazol-3-yl)pyrimidin-4-yl)amino)-1-methylcyclohexan-1-ol The title compound as an off white solid (14 mg) was prepared in the same fashion as Step 2 in Example 1, except that (1s,4s)-4-((2-chloro-5-(1-(2,2-difluoroethyl)-1H-pyrazol-3-yl)pyrimidin-4-yl)amino)-1-methylcyclohexan-1-ol (46 mg, 0.125 mmol) prepared in Step 1 and 2-(1-(cyclopropylsulfonyl)-1H-pyrazol-4-yl)pyridin-4-amine (30 mg, 0.114 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.50 (s, 1H), 8.49 (d, 1H), 8.42 (d, 1H), 8.37 (s, 1H), 8.32 (s, 1H), 7.99 (d, 1H), 7.52 (d, 1H), 7.48 (dd, 1H), 7.43 (s, 1H), 6.64 (d, 1H), 6.12 (tt, 1H), 4.51 (td, 2H), 4.14-4.10 (m, 1H), 2.85-2.78 (m, 1H), 2.05-2.02 (m, 2H), 1.82-1.76 (m, 4H), 1.62-1.50 (m, 4H), 1.31 (s, 3H), 1.22-1.17 (m, 2H); MS (ESI) m/z=600.2 (M+H)$^+$ Example 358. (1s,4s)-4-((2-((2-(1-(Cyclopropylsulfonyl)-1H-pyrazol-4-yl)pyridin-4-yl)amino)-5-(1-(methoxymethyl)-1H-pyrazol-3-yl)pyrimidin-4-yl)amino)-1-methylcyclohexan-1-ol Step 1. (1s,4s)-4-((2-Chloro-5-(1-(methoxymethyl)-1H-pyrazol-3-yl)pyrimidin-4-yl)amino)-1-methylcyclohexan-1-ol The title compound as a white solid (95.6 mg) was prepared in the same fashion as Reference Example 2, except that (1s,4s)-4-((5-bromo-2-chloropyrimidin-4-yl)amino)-1-methylcyclohexan-1-ol (100 mg, 1.817 mmol) prepared in Reference Example 32 and (1-(methoxymethyl)-1H-pyrazol-3-yl)boronic acid (58 mg, 0.374 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.77 (d, 1H), 8.34 (s, 1H), 7.63 (d, 1H), 6.71 (d, 1H), 5.43 (s, 2H), 4.17-4.14 (m, 1H), 3.39 (s, 3H), 1.98-1.94 (m, 2H), 1.77-1.58 (m, 6H), 1.30 (s, 3H)

Step 2. (1s,4s)-4-((2-((2-(1-(Cyclopropylsulfonyl)-1H-pyrazol-4-yl)pyridin-4-yl)amino)-5-(1-(methoxymethyl)-1H-pyrazol-3-yl)pyrimidin-4-yl)amino)-1-methylcyclohexan-1-ol The title compound as an off white solid (25.2 mg) was prepared in the same fashion as Step 2 in Example 1, except that (1s,4s)-4-((2-chloro-5-(1-(methoxymethyl)-1H-pyrazol-3-yl)pyrimidin-4-yl)amino)-1-methylcyclohexan-1-ol (44 mg, 0.125 mmol) prepared in Step 1 and 2-(1-(cyclopropylsulfonyl)-1H-pyrazol-4-yl)pyridin-4-amine (25 mg, 0.095 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.75 (d, 1H), 8.50 (s, 1H), 8.42 (d, 1H), 8.38 (s, 1H), 8.32 (s, 1H), 8.02 (s, 1H), 7.61 (s, 1H), 7.46 (d, 1H), 7.42 (s, 1H), 6.67 (d, 1H), 5.43 (s, 2H), 4.15 (brs, 1H), 3.40 (s, 3H), 2.85-2.79 (m, 1H), 2.05-2.01 (m, 2H), 1.82-1.75 (m, 4H), 1.63-1.51 (m, 4H), 1.23 (s, 3H), 1.11-1.05 (m, 2H); MS (ESI) m/z=580.2 (M+H)$^+$ Example 359. (1s,4s)-4-((2-((2-(1-(Cyclopropylsulfonyl)-1H-pyrazol-4-yl)pyridin-4-yl)amino)-5-(1-(3,3,3-trifluoropropyl)-1H-pyrazol-3-yl)pyrimidin-4-yl)amino)-1-methylcyclohexan-1-ol Step 1. (1s,4s)-4-((2-Chloro-5-(1-(3,3,3-trifluoropropyl)-1H-pyrazol-3-yl)pyrimidin-4-yl)amino)-1-methylcyclohexan-1-ol The title compound as a white solid (91.8 mg) was prepared in the same fashion as Reference Example 2, except that (1s,4s)-4-((5-bromo-2-chloropyrimidin-4-yl)amino)-1-methylcyclohexan-1-ol (100 mg, 1.817 mmol) prepared in Reference Example 32 and (1-(3,3,3-trifluoropropyl)-1H-pyrazol-3-yl)boronic acid (78 mg, 0.374 mmol) were used instead of 2-chloro-4-fluoro-5-iodopyridine and 1-(difluoromethyl)-3-(4,4,5,5-tetramethyl-1,3,2-dioxaborolan-2-yl)pyrazole. $^1$H-NMR (CDCl$_3$, 400 MHz) δ 8.56 (d, 1H), 8.32 (s, 1H), 7.48 (d, 1H), 6.62 (d, 1H), 4.43 (t, 2H), 4.14-4.12 (m, 1H), 2.81-2.70 (m, 2H), 1.99-1.95 (m, 2H), 1.77-1.57 (m, 6H), 1.31 (s, 3H)

Step 2. (1s,4s)-4-((2-((2-(1-(Cyclopropylsulfonyl)-1H-pyrazol-4-yl)pyridin-4-yl)amino)-5-(1-(3,3,3-trifluoropropyl)-1H-pyrazol-3-yl)pyrimidin-4-yl)amino)-1-methylcyclohexan-1-ol The title compound as an off white solid (12.3 mg) was prepared in the same fashion as Step 2 in Example 1, except that (1s,4s)-4-((2-chloro-5-(1-(3,3,3-trifluoropropyl)-1H-pyrazol-3-yl)pyrimidin-4-yl)amino)-1-methylcyclohexan-1-ol (50 mg, 0.125 mmol) prepared in Step 1 and 2-(1-(cyclopropylsulfonyl)-1H-pyrazol-4-yl)pyridin-4-amine (25 mg, 0.095 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.52 (d, 1H), 8.50 (s, 1H), 8.42 (d, 1H), 8.36 (s, 1H), 8.32 (s, 1H), 8.00 (s, 1H), 7.47 (d, 1H), 7.46 (s, 1H), 7.32 (s, 1H), 6.58 (d, 1H), 4.42 (t, 2H), 4.14-4.11 (m, 1H), 2.85-2.72 (m, 3H), 2.06-2.03 (m, 2H), 1.82-1.77 (m, 4H), 1.62-1.59 (m, 2H), 1.55-1.51 (m, 2H), 1.31 (s 3H), 1.23-1.18 (m, 2H); MS (ESI) m/z=632.2 (M+H)$^+$ Example 360. (1s,4s)-4-((2-((2-(1-(Cyclopropylsulfonyl)-1H-pyrazol-4-yl)pyridin-4-yl)amino)-5-(1-(2,2,2-trifluoroethyl)-1H-pyrazol-3-yl)pyrimidin-4-yl)amino)-1-methylcyclohexan-1-ol Step 1. (1s,4s)-4-((2-Chloro-5-(1-(2,2,2-trifluoroethyl)-1H-pyrazol-3-yl)pyrimidin-4-yl)amino)-1-methylcyclohexan-1-ol The title compound as a white solid (95.6 mg) was prepared in the same fashion as Reference Example 21, except that (1s,4s)-4-((5-bromo-2-chloropyrimidin-4-yl)amino)-1-methylcyclohexan-1-ol (100 mg, 1.817 mmol) prepared in Reference Example 32 was used instead of 2-chloro-4-fluoro-5-iodopyridine. $^1$H-NMR (CDCl$_3$, 400 MHz) δ 8.53 (d, 1H), 8.32 (s, 1H), 7.58 (d, 1H), 6.72 (d, 1H), 4.75 (q, 2H), 4.13-4.10 (m, 1H), 1.98-1.95 (m, 2H), 1.76-1.57 (m, 6H), 1.30 (s, 3H)

Step 2. (1s,4s)-4-((2-((2-(1-(Cyclopropylsulfonyl)-1H-pyrazol-4-yl)pyridin-4-yl)amino)-5-(1-(2,2,2-trifluoroethyl)-1H-pyrazol-3-yl)pyrimidin-4-yl)amino)-1-methylcyclohexan-1-ol The title compound as an off white solid (21.1 mg) was prepared in the same fashion as Step 2 in Example 1, except that (1s,4s)-4-((2-chloro-5-(1-(2,2,2-trifluoroethyl)-1H-pyrazol-3-yl)pyrimidin-4-yl)amino)-1-methylcyclohexan-1-ol (49 mg, 0.125 mmol) prepared in Step 1 and 2-(1-(cyclopropylsulfonyl)-1H-pyrazol-4-yl)pyridin-4-amine (25 mg, 0.095 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.50 (s, 1H), 8.49 (d, 1H), 8.43 (d, 1H), 8.37 (s, 1H), 8.32 (s, 1H), 7.99 (s, 1H), 7.55 (d, 1H), 7.48 (d, 1H), 7.32 (s, 1H), 6.68 (d, 1H), 4.74 (q, 2H), 4.10-4.08 (m, 1H), 2.85-2.79 (m, 1H), 2.05-2.02 (m, 2H), 1.82-1.75 (m, 4H), 1.61-1.51 (m, 4H), 1.30 (s, 3H), 1.23-1.18 (m, 2H); MS (ESI) m/z=618.2 (M+H)$^+$ Example 361. (1s,4s)-4-((2-((2-(1-(2,2-Difluoroethyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol The title compound as an off white solid (20.2 mg) was prepared in the same fashion as Step 2 in Example 1, except that (1s,4s)-4-((2-chloro-5-(1-methyl-5-(trifluoromethyl)-1H-pyrazol-3-yl)pyrimidin-4-yl)amino)-1-methylcyclohexan-1-ol (42 mg, 0.107 mmol) prepared in Step 1 of Example 356 and 2-(1-(2,2-difluoroethyl)-1H-pyrazol-4-yl)pyridin-4-amine (20 mg, 0.089 mmol) prepared in Reference Example 61 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.40 (d, 1H), 8.32 (s, 1H), 8.27 (d, 1H), 8.04 (d, 1H), 7.83 (s, 1H), 7.48 (d, 1H), 7.16 (s, 1H), 6.91 (s, 1H), 6.14 (tt, 1H), 4.52 (td, 2H), 4.13 (brs, 1H), 4.04 (s, 3H), 2.05-2.03 (m, 2H), 1.81-1.73 (m, 4H), 1.62-1.59 (m, 2H), 1.30 (s, 3H); MS (ESI) m/z=578.2 (M+H)$^+$ Example 362. (1s,4s)-4-((2-((2-(1-(2,2-Difluoroethyl)-1H-pyrazol-4-yl)pyridin-4-yl)amino)-5-(1-(difluoromethyl)-1H-pyrazol-3-yl)pyrimidin-4-yl)amino)-1-methylcyclohexan-1-ol The title compound as an off white solid (30.7 mg) was prepared in the same fashion as Step 2 in Example 1, except that (1s,4s)-4-((2-chloro-5-(1-(difluoromethyl)-1H-pyrazol-3-yl)pyrimidin-4-yl)amino)-1-methylcyclohexan-1-ol (57 mg, 0.161 mmol) prepared in Step 1 of Example 355 and 2-(1-(2,2-difluoroethyl)-1H-pyrazol-4-yl)pyridin-4-amine (30 mg, 0.134 mmol) prepared in Reference Example 61 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-d$_6$, 400 MHz) δ 9.94 (brs, 1H), 8.66 (s, 1H), 8.38-8.30 (m, 4H), 8.14 (s, 1H), 8.02 (s, 1H), 7.90 (t, 1H), 7.66 (d, 1H), 7.16 (s, 1H), 6.40 (tt, 1H), 4.71 (td, 1H), 4.13 (s, 1H), 4.02 (brs, 1H), 1.87-1.84 (m, 2H), 1.71-1.56 (m, 4H), 1.40-1.34 (m, 2H), 1.10 (s, 3H); MS (ESI) m/z=546.2 (M+H)$^+$ Example 363. N$^2$-(2-(1-(Cyclopropylsulfonyl)-1H-pyrazol-4-yl)pyridin-4-yl)-5-(1-(difluoromethyl)-1H-pyrazol-3-yl)-N$^4$-isopropylpyrimidine-2,4-diamine Step 1. 5-Bromo-2-chloro-N-isopropylpyrimidin-4-amine The title compound as a white solid (203.3 mg) was prepared in the same fashion as Reference Example 9, except that 5-bromo-2,4-dichloropyrimidine (300 mg, 1.32 mmol) and isopropylamine (117 mg, 1.975 mmol) were used instead of 2-chloro-4-fluoro-5-iodopyridine and cis-4-aminocyclohexanol hydrochloride. $^1$H-NMR (CDCl$_3$, 400 MHz) δ 8.10 (s, 1H), 5.31 (s, 1H), 4.38-1.30 (m, 1H), 1.28 (d, 6H)

Step 2. 2-Chloro-5-(1-(difluoromethyl)-1H-pyrazol-3-yl)-N-isopropylpyrimidin-4-amine The title compound as a white solid (79.1 mg) was prepared in the same fashion as Reference Example 2, except that 5-bromo-2-chloro-N-isopropylpyrimidin-4-amine (100 mg, 0.399 mmol) prepared in Step 1 was used instead of 2-chloro-4-fluoro-5-iodopyridine. $^1$H-NMR (CDCl$_3$, 400 MHz) δ 8.36 (s, 1H), 8.22 (brs, 1H), 7.90 (d, 1H), 7.22 (t, 1H), 6.83 (d, 1H), 4.50-4.42 (m, 1H), 1.33 (d, 6H)

Step 3. N$^2$-(2-(1-(Cyclopropylsulfonyl)-1H-pyrazol-4-yl)pyridin-4-yl)-5-(1-(difluoromethyl)-1H-pyrazol-3-yl)-N$^4$-isopropylpyrimidine-2,4-diamine The title compound as an off white solid (16.3 mg) was prepared in the same fashion as Step 2 in Example 1, except that 2-chloro-5-(1-(difluoromethyl)-1H-pyrazol-3-yl)-N-isopropylpyrimidin-4-amine (36 mg, 0.125 mmol) prepared in Step 2 and 2-(1-(cyclopropylsulfonyl)-1H-pyrazol-4-yl)pyridin-4-amine (30 mg, 0.114 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.50 (s, 1H), 7.43 (d, 1H), 8.40 (s, 1H), 8.34 (s, 1H), 8.23 (s, 1H), 8.19 (d, 1H), 7.87 (d, 1H), 7.28 (d, 1H), 7.23 (t, 1H), 6.80 (d, 1H), 4.54-4.45 (m, 1H), 2.86-2.80 (m, 1H), 1.56-1.52 (m, 2H), 1.42 (d, 6H), 1.24-1.19 (m, 2H); MS (ESI) m/z=516.1 (M+H)$^+$

Example 364. ((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)methanol

Step 1. ((1s,4s)-4-((5-Bromo-2-chloropyrimidin-4-yl)amino)cyclohexyl)methanol The title compound as a white solid (321 mg) was prepared in the same fashion as Reference Example 9, except that 5-bromo-2,4-dichloropyrimidine (300 mg, 1.32 mmol) and ((1s,4s)-4-aminocyclohexyl)methanol hydrochloride (327 mg, 1.975 mmol) were used instead of 2-chloro-4-fluoro-5-iodopyridine and cis-4-aminocyclohexanol hydrochloride. $^1$H-NMR (MeOD, 400 MHz) δ 8.14 (s, 1H), 4.22-4.16 (m, 1H), 3.53 (d, 2H), 1.84-1.66 (m, 7H), 1.58-1.54 (m, 2H)

Step 2. ((1s,4s)-4-((2-Chloro-5-(1-(difluoromethyl)-1H-pyrazol-3-yl)pyrimidin-4-yl)amino)cyclohexyl)methanol The title compound as a white solid (50.3 mg) was prepared in the same fashion as Reference Example 2, except that ((1s,4s)-4-((5-bromo-2-chloropyrimidin-4-yl)amino)cyclohexyl)methanol (128 mg, 0.399 mmol) prepared in Step 1 were used instead of 2-chloro-4-fluoro-5-iodopyridine. MS (ESI) m/z=358.1 (M+H)$^+$

Step 3. ((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)methanol The title compound as an off white solid (15.5 mg) was prepared in the same fashion as Step 2 in Example 1, except that ((1s,4s)-4-((2-chloro-5-(1-(difluoromethyl)-1H-pyrazol-3-yl)pyrimidin-4-yl)amino)cyclohexyl)methanol (45 mg, 0.125 mmol) prepared in Step 2 and 2-(1-(cyclopropylsulfonyl)-1H-pyrazol-4-yl)pyridin-4-amine (30 mg, 0.114 mmol) prepared in Reference Example 60 was used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine.
$^1$H-NMR (CDCl$_3$, 400 MHz) δ 8.85 (d, 1H), 8.50 (s, 1H), 8.44-8.41 (m, 2H), 8.33 (s, 1H), 8.25 (s, 1H), 7.87 (d, 1H), 7.42 (s, 1H), 7.25 (t, 1H), 6.81 (d, 1H), 4.66-4.64 (m, 1H), 3.60 (d, 2H), 2.86-2.80 (m, 1H), 2.05-2.02 (m, 2H), 1.85-1.69 (m, 5H), 1.56-1.43 (m, 4H), 1.27-1.19 (m, 2H); MS (ESI) m/z=586.2 (M+H)$^+$

Example 365. 2-((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)propan-2-ol

Step 1. 2-((1s,4s)-4-((5-Bromo-2-chloropyrimidin-4-yl)amino)cyclohexyl)propan-2-ol The title compound as a white solid (282 mg) was prepared in the same fashion as Reference Example 9, except that 5-bromo-2,4-dichloropyrimidine (300 mg, 1.32 mmol) and 2-((1s,4s)-4-aminocyclohexyl)propan-2-ol hydrochloride (383 mg, 1.975 mmol) were used instead of 2-chloro-4-fluoro-5-iodopyridine and cis-4-aminocyclohexanol hydrochloride. $^1$H-NMR (CDCl$_3$, 400 MHz) δ 8.12 (s, 1H), 5.75 (d, 1H), 4.40-4.37 (m, 1H), 2.04-2.00 (m, 2H), 1.83-1.80 (m, 2H), 1.69-1.62 (m, 2H), 1.44-1.36 (m, 1H), 1.26-1.21 (m, 8H)

Step 2. 2-((1s,4s)-4-((2-Chloro-5-(1-(difluoromethyl)-1H-pyrazol-3-yl)pyrimidin-4-yl)amino)cyclohexyl)propan-2-ol The title compound as a white solid (72.6 mg) was prepared in the same fashion as Reference Example 2, except that 2-((1s,4s)-4-((5-bromo-2-chloropyrimidin-4-yl)amino)cyclohexyl)propan-2-ol (139 mg, 0.399 mmol) prepared in Step 1 was used instead of 2-chloro-4-fluoro-5-iodopyridine. $^1$H-NMR (CDCl$_3$, 400 MHz) δ 8.91 (d, 1H), 8.38 (s, 1H), 7.90 (d, 1H), 7.30 (t, 1H), 6.85 (d, 1H), 4.67-4.63 (m, 1H), 2.00-1.97 (m, 2H), 1.83-1.81 (m, 1H), 1.69-1.63 (m, 2H), 1.41-1.33 (m, 3H), 1.25 (s, 6H)

Step 3. 2-((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)propan-2-ol The title compound as an off white solid (18.9 mg) was prepared in the same fashion as Step 2 in Example 1, except that 2-((1s,4s)-4-((2-chloro-5-(1-(difluoromethyl)-1H-pyrazol-3-yl)pyrimidin-4-yl)amino)cyclohexyl)propan-2-ol (48 mg, 0.125 mmol) prepared in Step 2 and 2-(1-(cyclopropylsulfonyl)-1H-pyrazol-4-yl)pyridin-4-amine (30 mg, 0.114 mmol) prepared in Reference Example 60 was used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine.
$^1$H-NMR (CDCl$_3$, 400 MHz) δ 8.84 (d, 1H), 8.50 (s, 1H), 8.44-8.41 (m, 2H), 8.33 (s, 1H), 8.28 (s, 1H), 7.87 (d, 1H), 7.31 (s, 1H), 7.28 (t, 1H), 7.23 (d, 1H), 6.82 (d, 1H), 4.67-4.66 (m, 1H), 2.86-2.80 (m, 1H), 2.12-2.09 (m, 2H), 1.85-1.74 (m, 4H), 1.61 (brs, 1H), 1.56-1.43 (m, 4H), 1.26 (s, 6H), 1.25-1.21 (m, 2H); MS (ESI) m/z=614.2 (M+H)$^+$ Example 366. N$^2$-(2-(1-(Cyclopropylsulfonyl)-1H-pyrazol-4-yl)pyridin-4-yl)-N$^4$-((1s,4s)-4-fluorocyclohexyl)-5-(1-(2,2,2-trifluoroethyl)-1H-pyrazol-3-yl)pyrimidine-2,4-diamine Step 1. 2-Chloro-N-((1s,4s)-4-fluorocyclohexyl)-5-(1-(2,2,2-trifluoroethyl)-1H-pyrazol-3-yl)pyrimidin-4-amine The title compound as a white solid (97.4 mg) was prepared in the same fashion as Reference Example 21, except that 2-chloro-N-((1s,4s)-4-fluorocyclohexyl)-5-iodopyrimidin-4-amine (100 mg, 0.281 mmol) prepared in Reference Example 33 was used instead of 2-chloro-4-fluoro-5-iodopyridine. $^1$H-NMR (MeOD, 400 MHz) δ 9.01 (d, 1H), 8.44 (s, 1H), 7.88 (s, 1H), 6.93 (d, 1H), 5.06 (q, 2H), 4.71 (brs, 1H), 4.23-4.19 (m, 1H), 2.01-1.87 (m, 4H), 1.83-1.71 (m, 4H)

Step 2. N$^2$-(2-(1-(Cyclopropylsulfonyl)-1H-pyrazol-4-yl)pyridin-4-yl)-N$^4$-((1s,4s)-4-fluorocyclohexyl)-5-(1-(2,2,2-trifluoroethyl)-1H-pyrazol-3-yl)pyrimidine-2,4-diamine The title compound as an off white solid (15.1 mg) was prepared in the same fashion as Step 2 in Example 1, except that 2-chloro-N-((1s,4s)-4-fluorocyclohexyl)-5-(1-(2,2,2-trifluoroethyl)-1H-pyrazol-3-yl)pyrimidin-4-amine (47 mg, 0.125 mmol) prepared in Step 1 and 2-(1-(cyclopropylsulfonyl)-1H-pyrazol-4-yl)pyridin-4-amine (30 mg, 0.114 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.77 (d, 1H), 8.52 (s, 1H), 8.43 (d, 1H), 8.34 (d, 2H), 7.97 (s, 1H), 7.58 (s, 1H), 7.51 (d, 1H), 6.70 (s, 1H), 4.82 (d, 1H), 4.74 (q, 2H), 4.23 (brs, 1H), 2.85-2.80 (m, 1H), 2.06-1.98 (m, 5H), 1.87-1.82 (m, 2H), 1.77-1.71 (m, 1H), 1.54-1.51 (m, 2H), 1.28 (s, 3H), 1.25-1.20 (m, 2H); MS (ESI) m/z=606.2 (M+H)$^+$ Example 367. N$^2$-(2-(1-(Cyclopropylsulfonyl)-1H-pyrazol-4-yl)pyridin-4-yl)-N$^4$-((1s,4s)-4-fluorocyclohexyl)-5-(1-(3,3,3-trifluoropropyl)-1H-pyrazol-3-yl)pyrimidine-2,4-diamine Step 1. 2-Chloro-N-((1s,4s)-4-fluorocyclohexyl)-5-(1-(3,3,3-trifluoropropyl)-1H-pyrazol-3-yl)pyrimidin-4-amine The title compound as a white solid (97.4 mg) was prepared in the same fashion as Reference Example 21, except that 2-chloro-N-((1s,4s)-4-fluorocyclohexyl)-5-iodopyrimidin-4-amine (100 mg, 0.281 mmol) prepared in Reference Example 33 and 3-(4,4,5,5-tetramethyl-1,3,2-dioxaborolan-2-yl)-1-(3,3,3-trifluoropropyl)pyrazole (98 mg, 0.337 mmol) were used instead of 2-chloro-4-fluoro-5-iodopyridine and (1-(2,2,2-trifluoroethyl)-1H-pyrazol-3-yl) boronic acid. $^1$H-NMR (MeOD, 400 MHz) δ 9.07 (d, 1H), 8.41 (s, 1H), 7.89 (s, 1H), 6.83 (d, 1H), 4.78 (d, 1H), 4.53 (t, 2H), 4.24-4.20 (m, 1H), 2.90-2.78 (m, 2H), 2.03-1.92 (m, 5H), 1.86-1.73 (m, 3H)

Step 2. N$^2$-(2-(1-(Cyclopropylsulfonyl)-1H-pyrazol-4-yl)pyridin-4-yl)-N$^4$-((1s,4s)-4-fluorocyclohexyl)-5-(1-(3,3,3-trifluoropropyl)-1H-pyrazol-3-yl)pyrimidine-2,4-diamine The title compound as an off white solid (15.1 mg) was prepared in the same fashion as Step 2 in Example 1, except that 2-chloro-N-((1s,4s)-4-fluorocyclohexyl)-5-(1-(3,3,3-trifluoropropyl)-1H-pyrazol-3-yl)pyrimidin-4-amine (49 mg, 0.125 mmol) prepared in Step 1 and 2-(1-(cyclopropylsulfonyl)-1H-pyrazol-4-yl)pyridin-4-amine (30 mg, 0.114 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine $^1$H-NMR (CDCl$_3$, 400 MHz) δ 8.73 (d, 1H), 8.49 (s, 1H), 8.42 (d, 1H), 8.38 (s, 1H), 8.31 (s, 1H), 7.97 (s, 1H), 7.48 (s, 2H), 6.60 (s, 1H), 4.80 (d, 1H), 4.43 (t, 2H), 4.27 (brs, 1H), 2.85-2.71 (m, 3H), 2.04-1.77 (m, 6H), 1.54-1.51 (m, 2H), 1.31-1.26 (m, 2H), 1.25-1.22 (m, 2H); MS (ESI) m/z=620.2 (M+H)$^+$ Example 368. (1s,4s)-4-((5-(1-(Difluoromethyl)-1H-pyrazol-3-yl)-2-((2-(3-methyl-1-(2,2,2-trifluoroethyl)-1H-pyrazol-4-yl)pyridin-4-yl)amino)pyrimidin-4-yl)amino)-1-methylcyclohexan-1-ol The title compound as an off white solid (13.9 mg) was prepared in the same fashion as Step 2 in Example 1, except that (1s,4s)-4-((2-chloro-5-(1-(difluoromethyl)-1H-pyrazol-3-yl)pyrimidin-4-yl)amino)-1-methylcyclohexan-1-ol (42 mg, 0.117 mmol) prepared in Step 1 of Example 355 and 2-(3-methyl-1-(2,2,2-trifluoroethyl)-1H-pyrazol-4-yl)pyridin-4-amine (25 mg, 0.098 mmol) prepared in Reference Example 62 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine $^1$H-NMR (CDCl$_3$, 400 MHz) δ 9.76 (s, 1H), 8.63 (s, 1H), 8.33-8.31 (m, 3H), 8.14 (s, 1H), 7.89 (t, 1H), 7.85 (s, 1H), 7.83 (d, 1H), 7.14 (d, 1H), 5.09 (q, 2H), 4.14 (s, 1H), 4.00-3.94 (m, 1H), 2.44 (s, 3H), 1.86-1.84 (m, 2H), 1.70-1.57 (m, 4H), 1.39-1.33 (m, 2H), 1.12 (s, 3H); MS (ESI) m/z=578.2 (M+H)$^+$ Example 369. (1s,4s)-1-Methyl-4-((2-((2-(3-methyl-1-(2,2,2-trifluoroethyl)-1H-pyrazol-4-yl)pyridin-4-yl)amino)-5-(1-methyl-5-(trifluoromethyl)-1H-pyrazol-3-yl)pyrimidin-4-yl)amino)cyclohexan-1-ol The title compound as an off white solid (13.1 mg) was prepared in the same fashion as Step 2 in Example 1, except that (1s,4s)-4-((2-chloro-5-(1-methyl-5-(trifluoromethyl)-1H-pyrazol-3-yl)pyrimidin-4-yl)amino)-1-methylcyclohexan-1-ol (46 mg, 0.117 mmol) prepared in Step 1 of Example 356 and 2-(3-methyl-1-(2,2,2-trifluoroethyl)-1H-pyrazol-4-yl)pyridin-4-amine (25 mg, 0.098 mmol) prepared in Reference Example 62 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine $^1$H-NMR (DMSO-d$_6$, 400 MHz) δ 9.73 (s, 1H), 8.59 (s, 1H), 8.32 (d, 1H), 8.19 (d, 1H), 8.14 (s, 1H), 7.84 (s, 1H), 7.84 (s, 1H), 7.81 (d, 1H), 7.53 (s, 1H), 5.09 (q, 2H), 4.16 (s, 1H), 4.03 (s, 3H), 4.00-3.98 (m, 1H), 2.44 (s, 3H), 1.85-1.82 (m, 2H), 1.72-1.58 (m, 4H), 1.39-1.34 (m, 2H), 1.12 (s, 3H); MS (ESI) m/z=610.2 (M+H)$^+$ Example 370. (1s,4s)-1-Methyl-4-((2-((2-(3-methyl-1-(2,2,2-trifluoroethyl)-1H-pyrazol-4-yl)pyridin-4-yl)amino)-5-(1-(2,2,2-trifluoroethyl)-1H-pyrazol-3-yl)pyrimidin-4-yl)amino)cyclohexan-1-ol The title compound as an off white solid (9.9 mg) was prepared in the same fashion as Step 2 in Example 1, except that (1s,4s)-4-((2-chloro-5-(1-(2,2,2-trifluoroethyl)-1H-pyrazol-3-yl)pyrimidin-4-yl)amino)-1-methylcyclohexan-1-ol (46 mg, 0.117 mmol) prepared in Step 1 of Example 360 and 2-(3-methyl-1-(2,2,2-trifluoroethyl)-1H-pyrazol-4-yl)pyridin-4-amine (25 mg, 0.098 mmol) prepared in Reference Example 62 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (CDCl$_3$, 400 MHz) δ 8.65 (d, 1H), 8.39 (s, 1H), 8.29 (d, 1H), 8.04 (s, 1H), 7.99 (s, 1H), 7.79 (d, 1H), 7.74 (d, 1H), 6.79 (d, 1H), 5.00 (q, 2H), 4.92 (q, 2H), 4.06-4.03 (m, 1H), 2.48 (s, 3H), 1.97-1.94 (m, 2H), 1.79-1.70 (m, 4H), 1.47-1.40 (m, 2H), 1.28 (s, 3H); MS (ESI) m/z=610.3 (M+H)$^+$ Example 371. N$^2$-(2-(1-(Cyclopropylsulfonyl)-1H-pyrazol-4-yl)pyridin-4-yl)-N$^4$-((1s,4s)-4-fluorocyclohexyl)-5-(1-methyl-5-(trifluoromethyl)-1H-pyrazol-3-yl)pyrimidine-2,4-diamine Step 1. 2,4-Dichloro-5-(1-methyl-5-(trifluoromethyl)-1H-pyrazol-3-yl)pyrimidine The title compound as a white solid (174.5 mg) was prepared in the same fashion as Reference Example 2, except that 2,4-dichloro-5-iodo-pyrimidine (250 mg, 0.91 mmol) and 1-methyl-3-(4,4,5,5-tetramethyl-1,3,2-dioxaborolan-2-yl)-5-(trifluoromethyl)-1H-pyrazole (326 mg, 1.182 mmol) were used instead of 2-chloro-4-fluoro-5-iodopyridine and 1-(difluoromethyl)-3-(4,4,5,5-tetramethyl-1,3,2-dioxaborolan-2-yl)-1H-pyrazole. $^1$H-NMR (CDCl$_3$, 400 MHz) δ 9.08 (s, 1H), 7.24 (s, 1H), 4.10 (s, 3H)

Step 2. 2-Chloro-N-((1s,4s)-4-fluorocyclohexyl)-5-(1-methyl-5-(trifluoromethyl)-1H-pyrazol-3-yl)pyrimidin-4-amine The title compound as a white solid (90.3 mg) was prepared in the same fashion as Step 2 in Reference Example 16, except that 2,4-dichloro-5-(1-methyl-5-(trifluoromethyl)-1H-pyrazol-3-yl)pyrimidine (97 mg, 0.327 mmol) prepared in Step 1 and (1s,4s)-4-fluorocyclohexan-1-amine hydrochloride (65 mg, 0.426 mmol) were used instead of 2-chloro-4-fluoro-5-(1-methyl-5-(trifluoromethyl)-1H-pyrazol-3-yl)pyridine and (1s,4s)-4-amino-1-methylcyclohexan-1-ol. MS (ESI) m/z=378.1 (M+H)$^+$ Step 3. N$^2$-(2-(1-(Cyclopropylsulfonyl)-1H-pyrazol-4-yl)pyridin-4-yl)-N$^4$-((1s,4s)-4-fluorocyclohexyl)-5-(1-methyl-5-(trifluoromethyl)-1H-pyrazol-3-yl)pyrimidine-2,4-diamine The title compound as an off white solid (11.6 mg) was prepared in the same fashion as Step 2 in Example 1, except that 2-chloro-N-((1s,4s)-4-fluorocyclohexyl)-5-(1-methyl-5-(trifluoromethyl)-1H-pyrazol-3-yl)pyrimidin-4-amine (51 mg, 0.136 mmol) prepared in Step 2 and 2-(1-(cyclopropylsulfonyl)-1H-pyrazol-4-yl)pyridin-4-amine (30 mg, 0.113 mmol) prepared in Reference Example 60 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine
$^1$H-NMR (CDCl$_3$, 400 MHz) δ 9.80 (s, 1H), 8.63 (s, 1H), 8.60 (s, 1H), 8.39 (s, 1H), 8.37-8.35 (m, 2H), 8.20 (s, 1H), 7.63 (d, 1H), 7.55 (s, 1H), 4.76 (d, 1H), 4.22 (brs, 1H), 4.03 (s, 3H), 3.24-3.17 (m, 1H), 1.90-1.87 (m, 4H), 1.77-1.68 (m, 4H), 1.33-1.22 (m, 4H); MS (ESI) m/z=606.2 (M+H)$^+$ Example 372. (1s,4s)-4-((6-((2-(1-(Cyclopropylsulfonyl)-1H-pyrazol-4-yl)pyrimidin-4-yl)amino)-3-(1-(difluoromethyl)-1H-pyrazol-3-yl)pyridazin-4-yl)amino)-1-methylcyclohexan-1-ol Step 1. (1s,4s)-4-((6-Chloro-3-(1-(difluoromethyl)-1H-pyrazol-3-yl)pyridazin-4-yl)amino)-1-methylcyclohexan-1-ol The title compound as a white solid (61.6 mg) was prepared in the same fashion as Reference Example 2, except that (1s,4s)-4-((3-bromo-6-chloropyridazin-4-yl)amino)-1-methylcyclohexan-1-ol (100 mg, 0.312 mmol) prepared in Reference Example 34 was used instead of 2-chloro-4-fluoro-5-iodopyridine. $^1$H-NMR (CDCl$_3$, 400 MHz) δ 8.12 (d, 1H), 7.90 (d, 1H), 7.43 (d, 1H), 7.24 (t, 1H), 6.64 (s, 1H), 3.37-3.34 (m, 1H), 1.97-1.93 (m, 2H), 1.81-1.75 (m, 4H), 1.63-1.56 (m, 2H), 1.33 (s, 3H)

Step 2. (1s,4s)-4-((6-((2-(1-(Cyclopropylsulfonyl)-1H-pyrazol-4-yl)pyrimidin-4-yl)amino)-3-(1-(difluoromethyl)-1H-pyrazol-3-yl)pyridazin-4-yl)amino)-1-methylcyclohexan-1-ol The title compound as an off white solid (8.8 mg) was prepared in the same fashion as Step 2 in Example 1, except that (1s,4s)-4-((6-chloro-3-(1-(difluoromethyl)-1H-pyrazol-3-yl)pyridazin-4-yl)amino)-1-methylcyclohexan-1-ol (59 mg, 0.166 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.68 (s, 1H), 8.49 (d, 1H), 8.48 (s, 1H), 8.39 (d, 1H), 8.04 (d, 1H), 7.96 (t, 1H), 7.62 (s, 1H), 7.46 (s, 1H), 7.23 (d, 1H), 4.21 (s, 1H), 3.28-3.20 (m, 1H), 1.87-1.85 (m, 2H), 1.73-1.58 (m, 4H), 1.47-1.42 (m, 2H), 1.34-1.22 (m, 4H), 1.16 (s, 3H); MS (ESI) m/z=587.2 (M+H)$^+$ Example 373. (1s,4s)-4-((6-((2-(1-(Cyclopropylsulfonyl)-1H-pyrazol-4-yl)pyrimidin-4-yl)amino)-3-(1-methyl-5-(trifluoromethyl)-1H-pyrazol-3-yl)pyridazin-4-yl)amino)-1-methylcyclohexan-1-ol Step 1. (1s,4s)-4-((6-Chloro-3-(1-methyl-5-(trifluoromethyl)-1H-pyrazol-3-yl)pyridazin-4-yl)amino)-1-methylcyclohexan-1-ol The title compound as a white solid (93 mg) was prepared in the same fashion as Step 1 in Reference Example 16, except that (1s,4s)-4-((3-bromo-6-chloropyridazin-4-yl)amino)-1-methylcyclohexan-1-ol (100 mg, 0.312 mmol) prepared in Reference Example 34 was used instead of 2-chloro-4-fluoro-5-iodopyridine. $^1$H-NMR (CDCl$_3$, 400 MHz) δ 8.17 (d, 1H), 7.57 (s, 1H), 6.61 (s, 1H), 4.08 (s, 3H), 3.39-3.33 (m, 1H), 1.98-1.94 (m, 2H), 1.81-1.74 (m, 4H), 1.63-1.56 (m, 2H), 1.33 (s, 3H)

Step 2. (1s,4s)-4-((6-((2-(1-(Cyclopropylsulfonyl)-1H-pyrazol-4-yl)pyrimidin-4-yl)amino)-3-(1-methyl-5-(trifluoromethyl)-1H-pyrazol-3-yl)pyridazin-4-yl)amino)-1-methylcyclohexan-1-ol The title compound as an off white solid (4.2 mg) was prepared in the same fashion as Step 2 in Example 1, except that (1s,4s)-4-((6-chloro-3-(1-methyl-5-(trifluoromethyl)-1H-pyrazol-3-yl)pyridazin-4-yl)amino)-1-methylcyclohexan-1-ol (65 mg, 0.166 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (DMSO-$d_6$, 400 MHz) δ 10.40 (s, 1H), 8.67 (s, 1H), 8.48 (d, 1H), 8.47 (s, 1H), 7.93 (d, 1H), 7.62 (s, 1H), 7.51 (s, 1H), 7.42 (s, 1H), 4.24 (s, 1H), 4.09 (s, 3H), 3.25-3.21 (m, 1H), 1.88-1.84 (m, 2H), 1.71-1.69 (m, 2H), 1.61-1.58 (m, 2H), 1.48-1.43 (m, 2H), 1.34-1.25 (m, 2H), 1.24-1.14 (m, 2H), 1.03 (s, 3H); MS (ESI) m/z=619.2 (M+H)$^+$ Example 374. (1s,4s)-4-((6-((2-(1-(Cyclopropylsulfonyl)-1H-pyrazol-4-yl)pyrimidin-4-yl)amino)-3-(1-(2,2,2-trifluoroethyl)-1H-pyrazol-3-yl)pyridazin-4-yl)amino)-1-methylcyclohexan-1-ol Step 1. (1s,4s)-4-((6-Chloro-3-(1-(2,2,2-trifluoroethyl)-1H-pyrazol-3-yl)pyridazin-4-yl)amino)-1-methylcyclohexan-1-ol The title compound as a white solid (95.3 mg) was prepared in the same fashion as Reference Example 21, except that (1s,4s)-4-((3-bromo-6-chloropyridazin-4-yl)amino)-1-methylcyclohexan-1-ol (100 mg, 0.312 mmol) prepared in Reference Example 34 was used instead of 2-chloro-4-fluoro-5-iodopyridine. $^1$H-NMR (CDCl$_3$, 400 MHz) δ 8.35 (d, 1H), 7.58 (d, 1H), 7.31 (d, 1H), 6.60 (s, 1H), 4.76 (q, 2H), 3.36-3.29 (m, 1H), 1.97-1.92 (m, 2H), 1.82-1.73 (m, 4H), 1.62-1.55 (m, 2H), 1.32 (s, 3H)

Step 2. (1s,4s)-4-((6-((2-(1-(Cyclopropylsulfonyl)-1H-pyrazol-4-yl)pyrimidin-4-yl)amino)-3-(1-(2,2,2-trifluoroethyl)-1H-pyrazol-3-yl)pyridazin-4-yl)amino)-1-methylcyclohexan-1-ol The title compound as an off white solid (10.1 mg) was prepared in the same fashion as Step 2 in Example 1, except that (1s,4s)-4-((6-chloro-3-(1-(2,2,2-trifluoroethyl)-1H-pyrazol-3-yl)pyridazin-4-yl)amino)-1-methylcyclohexan-1-ol (65 mg, 0.166 mmol) prepared in Step 1 was used instead of 2-chloro-5-(1-cyclopropyl-1H-pyrazol-4-yl)-4-((1-methyl-1H-pyrazol-4-yl)ethynyl)pyridine $^1$H-NMR (DMSO-$d_6$, 400 MHz) δ 8.67 (s, 1H), 8.48 (d, 1H), 8.47 (s, 1H), 8.23 (d, 1H), 8.02 (d, 1H), 7.55 (s, 1H), 7.46 (s, 1H), 7.07 (d, 1H), 5.29 (q, 2H), 4.17 (s, 1H), 3.26-3.21 (m, 1H), 1.86-1.83 (m, 2H), 1.71-1.58 (m, 4H), 1.47-1.41 (m, 2H), 1.34-1.32 (m, 2H), 1.27-1.24 (m, 2H), 1.17 (s, 3H); MS (ESI) m/z=619.2 (M+H)$^+$ Example 375. (1s,4s)-4-((3-(1-(Difluoromethyl)-1H-pyrazol-3-yl)-6-((2-(3-methyl-1-(2,2,2-trifluoroethyl)-1H-pyrazol-4-yl)pyrimidin-4-yl)amino)pyridazin-4-yl)amino)-1-methylcyclohexan-1-ol The title compound as an off white solid (9.2 mg) was prepared in the same fashion as Step 2 in Example 1, except that (1s,4s)-4-((6-chloro-3-(1-(difluoromethyl)-1H-pyrazol-3-yl)pyridazin-4-yl)amino)-1-methylcyclohexan-1-ol (46 mg, 0.128 mmol) prepared in Step 1 of Example 372 and 2-(3-methyl-1-(2,2,2-trifluoroethyl)-1H-pyrazol-4-yl)pyrimidin-4-amine (30 mg, 0.117 mmol) prepared in Reference Example 38 were used instead of 2-chloro-5-(1-cyclopropyl-1H-pyrazol-4-yl)-4-((1-methyl-1H-pyrazol-4-yl)ethynyl)pyridine and 2-(1-(cyclopropylsulfonyl)-1H-pyrazol-4-yl)pyrimidin-4-amine. $^1$H-NMR (DMSO-$d_6$, 400 MHz) δ 10.01 (s, 1H), 8.46 (d, 1H), 8.40 (s, 1H), 8.33 (s, 1H), 7.96 (s, 1H), 7.94 (t, 1H), 7.70 (d, 1H), 7.23 (s, 1H), 7.12 (s, 1H), 5.13 (q, 2H), 4.19 (s, 1H), 2.55 (s, 3H), 1.84-1.81 (m, 2H), 1.70-1.58 (m, 4H), 1.38-1.33 (m, 2H), 1.12 (s, 3H); MS (ESI) m/z=579.3 (M+H)$^+$ Example 376. (1s,4s)-4-((2-((2-(1-(Cyclopropylsulfonyl)-1H-pyrazol-4-yl)pyrimidin-4-yl)amino)-5-(1H-pyrazol-1-yl)pyridin-4-yl)amino)-1-methylcyclohexan-1-ol Step 1. (1s,4s)-4-((2-Chloro-5-(1H-pyrazol-1-yl)pyridin-4-yl)amino)-1-methylcyclohexan-1-ol The title compound as a solid (50 mg) was prepared in the same fashion as Step 1 in Example 102, except pyrazole (19 mg, 0.273 mmol) was used instead of ethyl pyrazole-3-carboxylate. $^1$H-NMR (CDCl$_3$, 400 MHz) δ 7.99 (s, 1H), 7.76 (d, 1H), 7.72 (d, 1H), 7.62 (s, 1H), 6.82 (d, 1H), 6.61 (s, 1H), 6.48 (t, 1H), 3.32-3.25 (m, 1H), 1.91-1.87 (m, 2H), 1.75-1.50 (m, 6H), 1.31 (s, 3H)

Step 2. (1s,4s)-4-((2-((2-(1-(Cyclopropylsulfonyl)-1H-pyrazol-4-yl)pyrimidin-4-yl)amino)-5-(1H-pyrazol-1-yl)pyridin-4-yl)amino)-1-methylcyclohexan-1-ol The title compound as an off white solid (3.6 mg) was prepared in the same fashion as Step 2 in Example 1, except that (1s,4s)-4-((2-chloro-5-(1H-pyrazol-1-yl)pyridin-4-yl)amino)-1-methylcyclohexan-1-ol (23 mg, 0.075 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.66 (s, 1H), 8.47 (s, 1H), 8.43 (d, 1H), 7.96 (s, 1H), 7.82-7.80 (m, 2H), 7.71 (d, 1H), 7.19 (s, 1H), 6.56 (d, 1H), 6.52-6.49 (m, 2H), 3.45 (m, 1H), 2.85-2.81 (m, 1H), 1.97-1.94 (m, 2H), 1.73-1.52 (m, 8H), 1.30 (s, 3H), 1.20-1.23 (m, 2H); MS (ESI) m/z=536.2 (M+H)$^+$ Example 377. ((1s,3s)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclobutyl)methanol Step 1. ((1s,3s)-3-((2-Chloro-5-(1-(difluoromethyl)-1H-pyrazol-3-yl)pyridin-4-yl)amino)cyclobutyl)methanol The title compound as a white solid (127 mg) was prepared in the same fashion as Step 1 in Example 7, except that ((1s,3s)-3-aminocyclobutyl)methanol (53 mg, 0.525 mmol) was used instead of 3-amino-3-methylbutan-2-ol. $^1$H-NMR (MeOD, 400 MHz) δ 8.42-8.38 (m, 2H), 8.15 (d, 1H), 7.62 (t, 1H), 7.03 (d, 1H), 6.63 (s, 1H), 4.06-3.96 (m, 1H), 3.56 (d, 2H), 2.67-2.60 (m, 2H), 2.41-2.33 (m, 1H), 2.17-1.74 (m, 2H)

Step 2. ((1s,3s)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclobutyl)methanol The title compound as an off white solid (24 mg) was prepared in the same fashion as Step 2 in Example 1, except that ((1s,3s)-3-((2-chloro-5-(1-(difluoromethyl)-1H-pyrazol-3-yl)pyridin-4-yl)amino)cyclobutyl)methanol (81 mg, 0.245 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.69 (s, 1H), 8.48 (s, 1H), 8.40 (d, 1H), 8.37 (s, 1H), 7.99 (d, 1H), 7.87 (d, 1H), 7.24 (t, 1H), 7.18 (d, 1H), 7.03 (brs, 1H), 6.81 (d, 1H), 4.04 (m, 1H), 3.66 (d, 2H), 2.86-2.83 (m, 1H), 2.69-2.64 (m, 2H), 2.47 (m, 1H), 1.56-1.52 (m, 2H), 1.25-1.20 (m, 2H); MS (ESI) m/z=558.1 (M+H)$^+$ Example 378. ((1s,3s)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclobutyl)methanol Step 1. ((1s,3s)-3-((2-Chloro-5-(1-(difluoromethyl)-1H-pyrazol-3-yl)pyridin-4-yl)amino)-1-methylcyclobutyl)methanol The title compound as a white solid (100 mg) was prepared in the same fashion as Step 1 in Example 7, except that ((1s,3s)-3-amino-1-methylcyclobutyl)methanol (61 mg, 0.525 mmol) was used instead of 3-amino-3-methylbutan-2-ol. $^1$H-NMR (CDCl$_3$, 400 MHz) δ 8.31 (s, 1H), 8.01 (d, 1H), 7.85 (d, 1H), 7.23 (t, 1H), 6.78 (d, 1H), 6.41 (s, 1H), 4.04-3.99 (m, 1H), 3.46 (d, 2H), 2.28-2.23 (m, 2H), 2.01-1.96 (m, 2H), 1.25 (s, 3H)

Step 2. ((1s,3s)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclobutyl)methanol The title compound as an off white solid (22 mg) was prepared in the same fashion as Step 2 in Example 1, except that ((1s,3s)-3-((2-chloro-5-(1-(difluoromethyl)-1H-pyrazol-3-yl)pyridin-4-yl)amino)-1-methylcyclobutyl)methanol (84 mg, 0.245 mmol) prepared in Step 1 was used instead of 2-chloro-5-(1-cyclopropyl-1H-pyrazol-4-yl)-4-((1-methyl-1H-pyrazol-4-yl)ethynyl)pyridine. $^1$H-NMR (CDCl$_3$, 400 MHz) δ 8.67 (s, 1H), 8.48 (s, 1H), 8.40 (d, 1H), 8.37 (s, 1H), 7.99 (d, 1H), 7.86 (d, 1H), 7.33 (d, 1H), 7.24 (t, 1H), 6.81 (d, 1H), 6.75 (s, 1H), 4.15-4.10 (m, 1H), 3.48 (d, 2H), 2.84-2.80 (m, 1H), 2.31-2.26 (m, 2H), 2.05-1.98 (m, 2H), 1.52-1.51 (m, 2H), 1.26 (s, 3H), 1.24-1.20 (m, 2H); MS (ESI) m/z=572.1 (M+H)$^+$

BIOLOGICAL ASSAYS

1. Biochemical EGFR Inhibition Assays

Biochemical EGFR kinase assays were conducted using Lance Ultra time-resolved fluorescence resonance energy transfer (TR-FRET) technology from Perkin-Elmer. Compounds of the invention were initially diluted to 20 mM in 100% DMSO for storage and made into kinase buffer solution to create a compound concentration ranging from 0.003 μM and 10 μM.

Briefly, each EGFR enzyme wildtype, double mutant [del19/C797S and L858R/C797S], triple mutant [del19/T790M/C797S and L858R/T790M/C797S], serial diluted EGFR inhibitors, substrate of ULight-poly-GT peptide (PerkinElmer; TRF0100-M) and different concentrations of ATP (Km and 100 μM final assay concentration) were mixed in kinase assay buffer (50 mM HEPES pH 7.4, 10 mM MgCl$_2$, 1 mM EGTA, 2 mM DTT and 0.01% Tween-20) and were added to a 384-well plate (Optiplate™ 384, white, PerkinElmer; 6007290).

Each kinase reactions were incubated at room temperature for 1 hour and then stopped by the addition of 4 μL of stop solution (10 mM EDTA). The specific Europium-labeled-anti-phosphopeptide antibody (PerkinElmer, AD0069) diluted in LANCE detection buffer was then added to a final concentration of 2 nM. After 60 minutes incubation at room temperature the LANCE signal was measured on an EnVision Multilabel Reader (Perkin-Elmer). Excitation wavelength was set at 320 nm and emission monitored at 615 nm (donor) and 665 nm (acceptor). The IC$_{50}$ values were determined using GraphPad prism software (GraphPad Software, Inc., San Diego, CA, USA).

The IC$_{50}$ values of compounds of formula (I) on the activity of each EGFR kinase evaluated as above are shown in Tables 3 to 15 below.

TABLE 3

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 1 | 99.0 | | 5.9 | | 63.0 | | | | 88.5 | |
| 2 | 31.3 | | | | 371.2 | | | | | |
| 3 | 6.4 | | | | 39.7 | | | | 228.6 | |
| 4 | 3.2 | | 0.8 | | | | 75.9 | | 214.3 | |
| 5 | 10.6 | | 13.2 | | 316.6 | | | | | |
| 6 | 16.1 | | 19.5 | | 347.1 | | | | | |
| 7 | | 2.6 | | 6.0 | | 281.3 | | 246.2 | | >10000 |
| 8 | | 5.5 | | 5.7 | | 18.8 | | 21.9 | | >10000 |
| 9 | | 0.5 | | 0.5 | | 4.3 | | 7.6 | | 7095.0 |
| 10 | | 1.1 | | 1.3 | | 3.2 | | 2.7 | | 1063.0 |
| 11 | | 8.6 | | 21.8 | | 552.8 | | 267.1 | | >10000 |
| 12 | | 1.2 | | 2.8 | | 30.0 | | 46.9 | | >10000 |
| 13 | | 0.7 | | 1.0 | | 3.8 | | 12.4 | | 5615.0 |
| 14 | | 0.6 | | 0.9 | | 4.9 | | 14.2 | | 7508.0 |
| 15 | | 0.6 | | 0.9 | | 3.2 | | 9.7 | | >10000 |

TABLE 3-continued

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 16 | | 0.3 | | 0.3 | | 2.0 | | 2.1 | | 3395.0 |
| 17 | | 1.0 | | 2.6 | | 19.1 | | 691.3 | | >10000 |
| 18 | 0.3 | 0.4 | 0.2 | 0.6 | 0.9 | 1.4 | 1.9 | 13.0 | 3.0 | >10000 |
| 19 | 0.3 | 0.3 | 0.1 | 0.5 | 0.5 | 0.7 | 0.7 | 3.5 | 10.0 | >10000 |
| 20 | 0.3 | 0.9 | 0.2 | 1.5 | 1.0 | 3.4 | 3.1 | 51.9 | 21.1 | >10000 |
| 21 | 0.3 | 1.3 | 0.2 | 0.9 | 0.3 | 0.7 | 0.9 | 8.9 | 5.4 | 5011.0 |
| 22 | 0.9 | 1.1 | 0.4 | 1.2 | 1.5 | 2.1 | 4.4 | 21.5 | 22.4 | >10000 |
| 23 | 0.7 | 1.3 | 0.4 | 1.0 | 0.8 | 0.9 | 1.8 | 7.4 | 6.9 | >10000 |
| 24 | 0.3 | 0.5 | 0.2 | 0.3 | 0.7 | 0.8 | 2.0 | 14.3 | 6.9 | >10000 |
| 25 | 0.1 | 0.1 | 0.02 | 0.1 | 0.2 | 0.3 | 0.3 | 1.5 | 2.7 | 2048.0 |
| 26 | 0.1 | 0.2 | 0.1 | 0.3 | 1.3 | 1.8 | 2.3 | 26.5 | 6.7 | 3737.0 |
| 27 | 0.7 | 0.6 | 0.2 | 0.4 | 0.2 | 0.3 | 0.5 | 2.2 | 0.7 | 162.5 |
| 28 | 0.9 | 1.1 | 0.8 | 5.5 | 95.7 | 62.7 | 21.8 | 598.1 | 241.0 | >10000 |
| 29 | 1.1 | 2.4 | 1.0 | 7.7 | 89.9 | 77.1 | 26.2 | 590.2 | 217.9 | >10000 |
| 30 | 0.6 | 2.4 | 0.3 | 2.8 | 0.5 | 2.2 | 1.5 | 41.3 | 15.4 | >10000 |

TABLE 4

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 31 | 0.4 | 1.3 | 0.2 | 1.5 | 0.5 | 1.3 | 1.3 | 18.7 | 10.5 | >10000 |
| 32 | 0.5 | 1.6 | 0.2 | 2.5 | 1.0 | 2.5 | 1.9 | 45.2 | 18.5 | >10000 |
| 33 | 0.5 | 1.0 | 0.5 | 1.4 | 0.5 | 1.5 | 0.7 | 13.5 | 7.0 | >10000 |
| 34 | 0.4 | 0.9 | 0.2 | 1.6 | 1.9 | 4.2 | 2.0 | 53.3 | 19.4 | >10000 |
| 35 | 0.4 | 0.3 | 0.2 | 0.9 | 5.2 | 5.4 | 6.5 | 57.6 | 32.9 | >10000 |
| 36 | 0.8 | 1.0 | 0.3 | 1.2 | 5.4 | 6.8 | 3.9 | 33.8 | 25.1 | >10000 |
| 37 | 1.2 | 1.4 | 0.7 | 6.6 | 12.1 | 16.6 | 5.0 | 263.5 | 107.8 | >10000 |
| 38 | 0.5 | 0.5 | 0.3 | 2.5 | 23.7 | 24.8 | 9.1 | 182.4 | 60.7 | >10000 |
| 39 | 1.6 | 3.6 | 1.2 | 7.9 | 7.2 | 17.6 | 27.8 | 261.6 | 142.6 | >10000 |
| 40 | 0.5 | 0.5 | 0.3 | 2.0 | 2.3 | 7.6 | 4.5 | 174.3 | 36.3 | >10000 |
| 41 | | 2.0 | | 6.8 | | 34.8 | | >10000 | | >10000 |
| 42 | 0.9 | 1.4 | 0.6 | 1.9 | 1.6 | 2.1 | 1.0 | 11.3 | 6.8 | 7827.0 |
| 43 | 0.2 | 0.3 | 0.1 | 0.3 | 0.7 | 1.5 | 0.4 | 14.7 | 4.9 | 5238.0 |
| 44 | 0.2 | 0.2 | 0.1 | 0.2 | 0.2 | 0.2 | 0.2 | 0.8 | 1.0 | >10000 |
| 45 | 0.6 | 0.2 | 0.2 | 0.2 | 0.6 | 0.4 | 0.7 | 2.8 | 2.2 | 918.0 |
| 46 | 0.1 | 0.2 | 0.1 | 0.1 | 0.3 | 0.3 | 0.4 | 1.9 | 2.0 | 742.5 |
| 47 | 0.6 | 0.6 | 0.1 | 0.5 | 0.5 | 0.8 | 0.8 | 6.5 | 4.5 | >10000 |
| 48 | 0.4 | 0.4 | 0.2 | 0.5 | 0.9 | 0.9 | 1.9 | 6.1 | 5.8 | 9602.0 |
| 49 | | 18.8 | | 28.7 | | 200.0 | | 278.4 | | >10000 |
| 50 | | 1.1 | | 1.6 | | 25.6 | | 42.2 | | >10000 |
| 51 | | 2.4 | | 2.9 | | 3.7 | | 7.0 | | >10000 |
| 52 | 0.6 | 0.6 | 0.4 | 0.6 | 1.3 | 0.8 | 1.6 | 10.0 | 18.0 | >10000 |
| 53 | 8.5 | 9.4 | 2.9 | 11.3 | 7.7 | 14.2 | 15.0 | 264.2 | 105.5 | >10000 |
| 54 | | 1.4 | | 2.9 | | 21.5 | | 18.9 | | >10000 |
| 55 | | 0.5 | | 0.8 | | 11.7 | | 39.1 | | >10000 |
| 56 | | 0.6 | | 0.8 | | 13.2 | | 7.1 | | >10000 |
| 57 | 1.0 | 1.1 | 0.6 | 1.1 | 0.8 | 0.7 | 0.6 | 2.7 | 3.5 | 1551.0 |
| 58 | 0.9 | 1.1 | 0.7 | 1.3 | 1.0 | 0.8 | 0.5 | 2.6 | 4.5 | >10000 |
| 59 | 0.7 | 0.8 | 0.3 | 0.6 | 1.0 | 1.9 | 0.6 | 1.6 | 1.5 | 367.6 |
| 60 | 1.1 | 4.3 | 0.5 | 1.5 | 1.1 | 2.5 | 1.1 | 2.4 | 2.2 | 325.6 |

TABLE 5

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 61 | 2.0 | 4.3 | 0.8 | 2.4 | 1.9 | 6.2 | 2.9 | 8.8 | 7.9 | 2898.0 |
| 62 | 0.2 | 0.3 | 0.1 | 0.2 | 0.2 | 0.5 | 0.2 | 1.9 | 1.1 | 617.0 |
| 63 | 3.2 | 2.9 | 0.7 | 3.3 | 1.8 | 2.2 | 2.2 | 7.7 | 4.4 | >10000 |
| 64 | 1.0 | 1.0 | 0.5 | 1.1 | 2.7 | 3.3 | 1.5 | 21.0 | 42.9 | >10000 |
| 65 | 0.8 | 1.2 | 0.6 | 4.2 | 33.5 | 54.5 | 33.5 | 622.2 | 149.0 | >10000 |
| 66 | 0.3 | 0.4 | 0.3 | 2.7 | 7.7 | 4.5 | 5.0 | 80.1 | 38.9 | >10000 |
| 67 | 3.4 | 3.6 | 3.8 | 15.7 | 111.3 | 110.6 | 23.5 | 596.4 | 336.4 | >10000 |
| 68 | 0.5 | 0.6 | 0.2 | 1.7 | 7.3 | 6.1 | 6.3 | 55.9 | 95.8 | >10000 |
| 69 | 0.3 | 0.5 | 0.2 | 1.9 | 11.2 | 18.7 | 14.7 | 257.1 | 114.2 | >10000 |
| 70 | 10.2 | 9.7 | 3.8 | 13.5 | 202.1 | 189.8 | 57.0 | 1488.0 | 1744.0 | >10000 |
| 71 | 0.2 | 0.2 | 0.1 | 0.8 | 3.4 | 1.7 | 2.6 | 42.3 | 26.0 | >10000 |
| 72 | 0.9 | 0.8 | 0.8 | 5.8 | 31.4 | 21.8 | 9.4 | 188.9 | 198.5 | >10000 |
| 73 | 0.5 | 0.4 | 0.2 | 1.1 | 3.6 | 1.8 | 2.9 | 41.3 | 65.3 | >10000 |
| 74 | | 8.3 | | 25.2 | | 103.1 | | 1378.0 | | >10000 |
| 75 | | 1.1 | | 16.8 | | 37.1 | | 172.8 | | >10000 |
| 76 | | 0.7 | | 2.3 | | 0.4 | | 36 | | 1522.0 |
| 77 | | 8.8 | | 11.4 | | 80.8 | | 478.9 | | >10000 |
| 78 | | 4.8 | | 5.4 | | 38.5 | | 161.2 | | >10000 |
| 79 | | 0.5 | | 0.5 | | 0.7 | | 0.8 | | 58.1 |
| 80 | | 0.7 | | 0.8 | | 1.2 | | 1.4 | | 213.9 |
| 81 | | 1.1 | | 1.2 | | 3.4 | | 4.8 | | 1235.0 |
| 82 | | 1.7 | | 1.8 | | 2.1 | | 3.9 | | 2406.0 |
| 83 | 0.3 | 0.6 | 0.3 | 0.7 | 0.8 | 1.9 | 0.7 | 18.0 | 8.6 | >10000 |
| 84 | | 0.6 | | 1.0 | | 2.9 | | 6.7 | | >10000 |
| 85 | 0.7 | 0.8 | 0.3 | 0.8 | 0.7 | 1.3 | 0.5 | 1.2 | 3.3 | 1122.0 |
| 86 | | 0.2 | | 0.3 | | 3.2 | | 14.8 | | 8509.0 |
| 87 | | 0.2 | | 0.7 | | 6.9 | | 31.4 | | >10000 |
| 88 | 0.2 | 0.3 | 0.1 | 0.3 | 0.5 | 1.0 | 0.3 | 3.1 | 3.2 | 1982.0 |
| 89 | | 1.3 | | 3.8 | | 82.5 | | 232.0 | | >10000 |
| 90 | | 2.6 | | 7.1 | | 366.7 | | 1493.0 | | >10000 |

TABLE 6

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 91 | | 1.0 | | 2.3 | | 0.8 | | 8.7 | | >10000 |
| 92 | | 2.6 | | 7.7 | | 10.0 | | 103.4 | | >10000 |
| 93 | | 4.0 | | 1.4 | | 5.3 | | 15.7 | | >10000 |
| 94 | | 3.4 | | 4.0 | | 54.1 | | 58.1 | | >10000 |
| 95 | | 1.3 | | 1.9 | | 57.7 | | 45.2 | | >10000 |
| 96 | 2.7 | 3.5 | 2.0 | 6.2 | 89.1 | 159.0 | 22.7 | 689.5 | 417.7 | >10000 |
| 97 | | 0.7 | | 3.2 | | 18.0 | | 160.1 | | >10000 |
| 98 | | 0.7 | | 2.7 | | 1.9 | | 7.7 | | 1408.0 |
| 99 | | 0.5 | | 0.8 | | 1.7 | | 4.8 | | 612.5 |
| 100 | 0.5 | 0.6 | 0.3 | 0.5 | 0.5 | 0.4 | 0.3 | 1.4 | 1.0 | 582.0 |
| 101 | 0.3 | 0.3 | 0.1 | 0.3 | 0.4 | 0.4 | 0.8 | 3.8 | 1.5 | 828.0 |
| 102 | 0.5 | 0.4 | 0.3 | 0.6 | 6.3 | 10.6 | 4.4 | 122.5 | 183.4 | >10000 |
| 103 | | 0.8 | | 0.4 | | 31.0 | | 24.0 | | 58.2 |
| 104 | | 4.3 | | 5.9 | | 948.5 | | 15.6 | | 984.0 |
| 105 | 7.7 | 6.2 | 2.5 | 4.8 | 48.2 | 73.0 | 50.7 | 1100.0 | 73.2 | >10000 |
| 106 | 3.9 | 3.9 | 1.5 | 2.6 | 19.6 | 22.7 | 19.0 | 452.9 | 46.9 | 9958.0 |
| 107 | | 2.7 | | 4.6 | | 112.7 | | 346.1 | | >10000 |
| 108 | | 1.2 | | 0.5 | | 23.7 | | 2.0 | | 57.2 |
| 109 | | 9.5 | | 2.2 | | 178.3 | | 14.5 | | 538.3 |
| 110 | | 2.5 | | 1.9 | | 24.7 | | 23.7 | | 34.5 |
| 111 | 1.4 | 1.6 | 0.1 | 0.2 | 86.8 | 253.4 | 19.7 | 67.2 | 53.7 | >10000 |
| 112 | 1.2 | 2.1 | 0.5 | 4.9 | 34.5 | 75.4 | 34.9 | 60.7 | 220.4 | >10000 |
| 113 | | 17.5 | | 186.1 | | 605.6 | | 483.3 | >10000 | >10000 |
| 114 | | 0.6 | | 0.2 | | 1.5 | | 1.0 | | 4.2 |
| 115 | | 1.9 | | 1.3 | | 3.7 | | 2.1 | | 20.2 |
| 116 | | 0.6 | | 0.7 | | 27.6 | | 5.0 | | 77.2 |
| 117 | | 0.5 | | 0.5 | | 0.8 | | 0.2 | | 1.6 |
| 118 | 0.2 | 0.2 | 0.1 | 0.3 | 0.3 | 0.2 | 0.2 | 3.6 | 4.9 | 1321.0 |

TABLE 6-continued

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 119 | 0.4 | 0.4 | 0.1 | 0.6 | 0.5 | 0.5 | 0.4 | 15.1 | 6.1 | >10000 |
| 120 | 0.6 | 0.9 | 0.3 | 0.9 | 1.4 | 2.3 | 3.0 | 41.7 | 29.7 | >10000 |

TABLE 7

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 121 | 1.2 | 1.7 | 0.4 | 1.4 | 1.5 | 1.6 | 2.4 | 19.8 | 12.8 | 8922.0 |
| 122 | 1.8 | 0.6 | 0.3 | 0.4 | 2.2 | 2.6 | 2.2 | 8.5 | 9.0 | 1419.0 |
| 123 | 0.3 | 0.2 | 0.1 | 0.2 | 1.4 | 1.3 | 1.9 | 22.5 | 21.6 | >10000 |
| 124 | 0.1 | 0.2 | 0.1 | 0.1 | 0.4 | 0.6 | 0.5 | 9.6 | 1.1 | 801.3 |
| 125 | 0.7 | 1.1 | 0.4 | 1.5 | 20.4 | 18.5 | 10.8 | 218.3 | 143.8 | >10000 |
| 126 | 0.7 | 0.8 | 0.4 | 1.3 | 21.0 | 30.3 | | 379.3 | 112.4 | >10000 |
| 127 | 0.7 | 1.0 | 0.7 | 1.8 | 16.9 | 25.8 | 19.6 | 354.9 | 53.0 | >10000 |
| 128 | | 3.1 | | 6.4 | | 40.8 | | 1120.0 | | >10000 |
| 129 | | 0.7 | | 0.7 | | 2.0 | | 14.3 | | >10000 |
| 130 | | 2.1 | | 2.0 | | 6.3 | | 96.5 | | >10000 |
| 131 | 0.2 | 0.3 | 0.1 | 0.3 | 0.2 | 0.5 | 0.4 | 1.1 | 2.8 | 1543.0 |
| 132 | 0.3 | 0.4 | 0.1 | 0.5 | 0.5 | 1.1 | 0.8 | 2.3 | 5.2 | 4689.0 |
| 133 | 0.3 | 0.5 | 0.1 | 3.2 | 0.3 | 1.4 | 1.0 | 99.3 | 92.1 | >10000 |
| 134 | 0.2 | 0.5 | 0.1 | 0.5 | 0.6 | 0.8 | 0.4 | 9.2 | 4.4 | >10000 |
| 135 | 1.5 | 2.9 | 0.5 | 2.1 | 0.7 | 1.1 | 4.5 | 58.0 | 5.7 | >10000 |
| 136 | 0.8 | 0.9 | 0.4 | 1.0 | 0.3 | 1.2 | 0.2 | 0.8 | 1.3 | 320.8 |
| 137 | 0.5 | 1.2 | 0.2 | 0.9 | 24.3 | 65.7 | 35.9 | 269.3 | 1780.0 | >10000 |
| 138 | 0.2 | 0.4 | 0.1 | 0.8 | 45.1 | 47.6 | 26.9 | 295.3 | 77.7 | >10000 |
| 139 | 1.7 | 1.1 | 0.8 | 5.2 | 50.2 | 99.1 | 57.1 | 165.2 | 61.0 | >10000 |
| 140 | 1.0 | 3.7 | 1.1 | 3.4 | 27.3 | 37.2 | 7.1 | 91.5 | 137.2 | 8955.0 |
| 141 | | 15.8 | | 3.2 | | 110.9 | | 197.7 | | >10000 |
| 142 | | 17.6 | | 33.8 | | 113.7 | | 37.5 | 486.3 | >10000 |
| 143 | 0.1 | 0.1 | 0.1 | 0.2 | 2.9 | 2.7 | 0.9 | 11.6 | 62.7 | >10000 |
| 144 | 1.2 | | 0.7 | | 24.0 | | 12.5 | | 687.2 | |
| 145 | 0.6 | | 0.5 | | 23.0 | | 7.2 | | 198.6 | |
| 146 | 1.1 | | 0.4 | | 10.8 | | 4.7 | | 19.9 | |
| 147 | 1.5 | | 0.8 | | 93.9 | | 32.6 | | 51.5 | |
| 148 | 1.4 | | 1.7 | | 75.5 | | 27.0 | | 127.6 | |
| 149 | 2.7 | | 2.7 | | 143.5 | | 47.2 | | 1731.0 | |
| 150 | 1.6 | | 1.2 | | 21.2 | | 14.7 | | 104.0 | |

TABLE 8

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 151 | 1.6 | | 0.9 | | 43.5 | | 4.7 | | 72.0 | |
| 152 | 8.5 | | 3.5 | | 117.9 | | 16.1 | | 85.1 | |
| 153 | 0.1 | | 0.1 | | 1.3 | | 0.1 | | 3.9 | |
| 154 | 0.3 | | 0.2 | | 127.7 | | 16.2 | | 377.2 | |
| 155 | 4.2 | | 2.8 | | 161.7 | | 139.3 | | 1105.0 | |
| 156 | 35.2 | | 3.2 | | >10000 | | 339.5 | | 986.1 | |
| 157 | 30.9 | | 9.7 | | 124.6 | | 55.7 | | 408.3 | |
| 158 | 109.5 | | 9.4 | | 6333.0 | | 449.9 | | 635.5 | |
| 159 | 19.2 | | 11.7 | | 2052.0 | | 291.0 | | 326.8 | |
| 160 | 1.0 | | 0.5 | | 2.0 | | 1.0 | | 8.3 | |
| 161 | 3.2 | | 2.4 | | 275.8 | | 60.6 | | 639.5 | |
| 162 | 0.9 | | 0.2 | | 33.4 | | 275.5 | | 270.7 | |

TABLE 8-continued

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 163 | 1.8 | | 0.9 | | 55.3 | | 743.6 | | 736.8 | |
| 164 | 8.8 | | 4.8 | | 369.5 | | 134.9 | | 1210.0 | |
| 165 | 3.0 | | 2.3 | | 1264.0 | | 883.6 | | 6827.0 | |
| 166 | 7.2 | | 3.6 | | 737.1 | | 197.8 | | 503.5 | |
| 167 | 0.6 | | 0.4 | | 58.9 | | 47.7 | | 129.2 | |
| 168 | 0.2 | | 0.1 | | 6.5 | | 3.0 | | 26.9 | |
| 169 | 20.1 | | 15.5 | | 110.3 | | 43.4 | | 324.7 | |
| 170 | 49.7 | | 16.9 | | 1335.0 | | 813.7 | | 1980.0 | |
| 171 | 2.6 | | 2.2 | | 96.6 | | 86.4 | | 523.3 | |
| 172 | 0.3 | | 0.1 | | 13.7 | | 9.3 | | 3.4 | |
| 173 | 3.9 | | 0.9 | | 332.9 | | 106.8 | | 16.7 | |
| 174 | 1.4 | | 0.8 | | 2.4 | | 0.5 | | 13.2 | |
| 175 | 25.3 | | 14.5 | | 41.8 | | 8.0 | | 91.9 | |
| 176 | 0.3 | | 0.04 | | 263.5 | | 10.4 | | 752.4 | |
| 177 | 0.8 | | 0.8 | | 1318.0 | | 36.6 | | 4620.0 | |
| 178 | 46.2 | | 16.8 | | 102.1 | | 3.0 | | 2114.0 | |
| 179 | 3.1 | | 2.1 | | 168.5 | | 7.4 | | 263.8 | |
| 180 | 1.3 | | 1.1 | | 409.9 | | 23.2 | | 417.6 | |

TABLE 9

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 181 | 2.1 | | 2.1 | | 6.7 | | 13.2 | | 44.6 | |
| 182 | 0.8 | | 0.8 | | 26.8 | | 116.5 | | 781.2 | |
| 183 | 0.8 | | 0.6 | | 42.8 | | 37.1 | | 624.3 | |
| 184 | 0.1 | | 0.05 | | 4.8 | | 2.0 | | 32.0 | |
| 185 | 11.0 | | 3.8 | | 51.5 | | 59.5 | | 87.1 | |
| 186 | 1.3 | | 0.4 | | 32.9 | | 30.4 | | 166.5 | |
| 187 | 0.7 | | 0.5 | | 15.4 | | 15.3 | | 281.6 | |
| 188 | 0.3 | 0.2 | 0.1 | 0.2 | 0.3 | 0.3 | 1.1 | 7.8 | 6.1 | >10000 |
| 189 | 0.5 | 0.4 | 0.3 | 0.2 | 1.2 | 1.8 | 3.1 | 27.1 | 20.1 | >10000 |
| 190 | 0.9 | 1.2 | 0.6 | 1.8 | 9.1 | 11.9 | 6.7 | 119.1 | 109.1 | >10000 |
| 191 | | 1.7 | | 2.4 | | 35.5 | | 1396.0 | | >10000 |
| 192 | 0.2 | 0.4 | 0.1 | 0.2 | 0.3 | 0.7 | 0.4 | 3.7 | 1.1 | 383.6 |
| 193 | 0.2 | 0.2 | 0.1 | 0.1 | 0.3 | 0.7 | 1.0 | 7.2 | 4.0 | 2054.0 |
| 194 | 0.3 | 0.2 | 0.1 | 0.6 | 4.4 | 7.5 | 5.8 | 32.1 | 19.9 | >10000 |
| 195 | 0.1 | 0.1 | 0.04 | 0.1 | 0.2 | 0.3 | 0.1 | 0.8 | 0.3 | 145.0 |
| 196 | | 3.7 | | 13.3 | | 131.1 | | 9102.0 | | >10000 |
| 197 | 0.1 | 0.2 | 0.1 | 0.3 | 1.1 | 2.2 | 2.1 | 70.0 | 7.9 | >10000 |
| 198 | | 0.3 | 0.1 | 3.3 | 0.7 | 2.2 | 4.2 | 3043.0 | 84.7 | >10000 |
| 199 | 0.5 | 0.6 | 0.2 | 0.8 | 8.0 | 9.1 | 5.4 | 92.5 | 23.2 | >10000 |
| 200 | 0.6 | 1.0 | 0.4 | 2.1 | 13.5 | 13.7 | 15.4 | 292.6 | 2845.0 | >10000 |
| 201 | 0.8 | 0.5 | 0.3 | 0.5 | 1.1 | 2.1 | 0.7 | 2.9 | | >10000 |
| 202 | 1.1 | 1.3 | 0.5 | 1.4 | 1.4 | 6.6 | 2.7 | 17.8 | 10.6 | >10000 |
| 203 | | 0.1 | | 0.2 | | 1.1 | | 8.3 | | 2966.0 |
| 204 | 0.9 | 0.9 | 0.4 | 0.8 | 1.5 | 4.0 | 1.5 | 36.1 | 9.5 | >10000 |
| 205 | 0.3 | 0.6 | 0.2 | 0.4 | 0.6 | 1.0 | 0.4 | 10.1 | 4.4 | 3963.0 |
| 206 | | 22.1 | | 13.8 | | 26.9 | | 206.4 | | >10000 |
| 207 | 0.8 | 0.7 | 0.3 | 1.0 | 2.6 | 4.3 | 10.5 | 199.9 | 15.3 | 5122.0 |
| 208 | 0.3 | 0.3 | 0.1 | 0.1 | 0.2 | 0.2 | 0.2 | 0.6 | | 128.1 |
| 209 | 0.3 | | 0.1 | | 6.4 | | 4.8 | | 13.1 | |
| 210 | 1.7 | | 1.3 | | 70.5 | | 6.5 | | 90.5 | |

TABLE 10

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 211 | 0.6 | | 0.3 | | 0.4 | | 0.1 | | 0.3 | |
| 212 | 2.1 | | 2.3 | | 72.0 | | 38.5 | | 294.4 | |
| 213 | 3.4 | | 2.7 | | 370.3 | | 123.2 | | 488.1 | |
| 214 | 5.2 | | 3.1 | | 9.9 | | 3.4 | | 45.2 | |
| 215 | 11.9 | | 8.6 | | 70.2 | | 32.5 | | 433.8 | |
| 216 | 25.9 | | 9.1 | | 119.0 | | 26.5 | | 276.2 | |
| 217 | 0.2 | | 0.4 | | 28.7 | | 23.7 | | 454.4 | |
| 218 | 0.5 | | 0.8 | | 43.9 | | 30.7 | | 233.4 | |
| 219 | 0.8 | | 0.5 | | 133.9 | | 21.4 | | 8627.0 | |
| 220 | 16.6 | | 11.4 | | 538.8 | | 462.6 | | 719.9 | |
| 221 | 0.3 | 0.3 | 0.2 | 0.2 | 0.4 | 0.5 | 1.0 | 4.9 | 4.9 | 1513.0 |
| 222 | 0.3 | 0.2 | 0.1 | 0.2 | 1.1 | 0.9 | 3.3 | 18.8 | 14.9 | >10000 |
| 223 | 0.2 | 0.2 | 0.1 | 0.2 | 0.3 | 0.6 | 0.7 | 5.9 | 3.2 | 3020.0 |
| 224 | 0.5 | 0.7 | 0.3 | 0.7 | 3.3 | 4.7 | 6.6 | 131.9 | 37.8 | >10000 |
| 225 | 0.3 | 0.2 | 0.2 | 0.6 | 2.9 | 6.7 | 5.0 | 15.3 | 27.4 | >10000 |
| 226 | 0.1 | 0.1 | 0.1 | 0.1 | 0.1 | 0.2 | 0.1 | 1.5 | 0.2 | 96.9 |
| 227 | | 2.1 | | 6.7 | | 44.4 | | 962.1 | | >10000 |
| 228 | 0.1 | 0.2 | 0.1 | 0.2 | 0.6 | 0.8 | 0.9 | 24.5 | 3.3 | 2361.0 |
| 229 | | 0.1 | 0.1 | 1.4 | 0.4 | 0.8 | 1.4 | 43.9 | 10.0 | >10000 |
| 230 | 0.2 | 0.5 | 0.2 | 0.5 | 4.8 | 6.0 | 3.3 | 33.8 | 9.4 | 4666.0 |
| 231 | 0.3 | 0.5 | 0.3 | 0.7 | 2.4 | 2.0 | 3.1 | 11.5 | 37.3 | >10000 |
| 232 | 0.6 | 0.4 | 0.3 | 0.4 | 0.5 | 1.1 | 0.4 | 1.6 | | 247.2 |
| 233 | 0.4 | 0.5 | 0.2 | 0.4 | 0.5 | 1.3 | 0.9 | 4.2 | 3.6 | 3139.0 |
| 234 | | 0.1 | | 0.2 | | 1.7 | | 8.7 | | 1793.0 |
| 235 | 0.2 | 0.2 | 0.1 | 0.2 | 2.5 | 1.1 | 0.3 | 7.0 | 1.6 | 616.3 |
| 236 | 0.3 | 0.3 | 0.2 | 0.3 | 0.2 | 0.5 | 0.1 | 2.0 | 0.5 | 564.7 |
| 237 | 12.1 | 7.4 | 3.0 | 5.4 | 17.5 | 6.7 | 6.5 | 61.4 | 15.5 | 2798.0 |
| 238 | 0.8 | 0.6 | 0.4 | 0.6 | 2.0 | 4.9 | 7.1 | 178.2 | 7.5 | 3598.0 |
| 239 | 0.3 | | 0.1 | | 4.6 | | 3.6 | | 10.1 | |
| 240 | 0.4 | | 0.1 | | 0.2 | | 0.04 | | 0.2 | |

TABLE 11

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 241 | 0.5 | 0.6 | 0.3 | 0.7 | 0.5 | 0.5 | 0.5 | 2.9 | 5.0 | 2978.0 |
| 242 | 0.1 | 0.2 | 0.1 | 0.2 | 0.4 | 0.8 | 1.2 | 20.9 | 6.0 | 6324.0 |
| 243 | 1.5 | 2.7 | 0.2 | 1.0 | 1.7 | 2.0 | 4.5 | 10.0 | 8.4 | 4008.0 |
| 244 | 0.3 | 0.2 | 0.1 | 0.4 | 0.6 | 0.5 | 0.5 | 1.9 | 2.3 | 974.7 |
| 245 | | 13.1 | | 12.8 | | 27.8 | | 259.0 | | >10000 |
| 246 | 1.0 | 0.9 | 0.3 | 1.1 | 7.1 | 10.2 | 19.9 | 399.5 | 15.4 | 4507.0 |
| 247 | 0.3 | 0.2 | 0.1 | 0.1 | 0.2 | 0.3 | 0.2 | 0.7 | 0.7 | 149.7 |
| 248 | 0.5 | | 0.3 | | 14.7 | | 4.8 | | 286.1 | |
| 249 | 0.4 | | 0.1 | | 11.5 | | 6.1 | | 7.5 | |
| 250 | 0.9 | | 0.9 | | 63.8 | | 4.4 | | 56.1 | |
| 251 | 0.7 | | 0.2 | | 0.4 | | 0.1 | | 0.3 | |
| 252 | 1.7 | 0.7 | 0.8 | 1.7 | 1.2 | 2.5 | 4.3 | 9.8 | 3.0 | >10000 |
| 253 | 1.5 | 1.1 | 0.9 | 2.1 | 2.3 | 3.2 | 7.0 | 10.6 | 3.4 | 618.1 |
| 254 | 3.7 | 3.9 | 1.7 | 6.5 | 5.5 | 6.5 | 18.5 | 33.5 | 12.9 | >10000 |
| 255 | 0.6 | 0.8 | 0.2 | 1.2 | 1.1 | 2.4 | 5.3 | 25.4 | 8.2 | >10000 |
| 256 | 1.4 | 1.3 | 0.4 | 0.5 | 0.8 | 2.0 | 1.9 | 7.5 | 0.5 | 123.0 |
| 257 | 4.3 | 3.7 | 1.1 | 1.6 | 2.1 | 6.0 | 5.2 | 29.1 | 7.5 | 294.0 |
| 258 | 2.5 | 5.1 | 1.4 | 2.8 | 1.8 | 3.6 | 1.5 | 26.7 | 9.0 | 2074.0 |
| 259 | | 171.6 | | 63.9 | | 151.1 | | 819.3 | | >10000 |
| 260 | 8.6 | 9.8 | 3.8 | 4.3 | 5.0 | 8.7 | 2.7 | 59.9 | 27.1 | 5226.0 |
| 261 | 0.1 | 1.2 | 0.8 | 1.4 | 5.8 | 77.9 | 5.6 | 22.7 | 6.4 | >10000 |
| 262 | 0.1 | 6.6 | 2.1 | 7.3 | 4.5 | 33.4 | 5.7 | 5.3 | 8.4 | 1882.0 |
| 263 | 0.3 | 9.9 | 2.6 | 11.5 | 15.5 | 236.8 | 6.3 | 32.5 | 54.5 | >10000 |
| 264 | 1.7 | 1.4 | 0.4 | 0.6 | 0.8 | 0.9 | 0.4 | 2.2 | 1.5 | 244.1 |
| 265 | | 5.4 | | 7.4 | 11.8 | 12.2 | 6.6 | 186.5 | 86.8 | >10000 |
| 266 | | 0.1 | | 0.1 | | 0.3 | | 0.9 | | 206.2 |

TABLE 11-continued

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 µM ATP | Km ATP | 100 µM ATP | Km ATP | 100 µM ATP | Km ATP | 100 µM ATP | Km ATP | 100 µM ATP |
| 267 | 0.2 | 0.1 | 0.5 | 0.1 | 6.7 | 8.8 | 25.4 | 576.5 | 28.7 | 8272.0 |
| 268 | 2.5 | 0.6 | 0.3 | 0.6 | 7.6 | 200.0 | 3.2 | 10.7 | 74.4 | >10000 |
| 269 | 2.8 | 1.3 | 0.5 | 1.4 | 1.3 | 29.9 | 1.4 | 4.0 | 7.1 | 5753.0 |
| 270 | 7.2 | 2.1 | 0.7 | 1.2 | 23.6 | 2702.0 | 11.2 | 35.4 | 619.9 | >10000 |

TABLE 12

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 µM ATP | Km ATP | 100 µM ATP | Km ATP | 100 µM ATP | Km ATP | 100 µM ATP | Km ATP | 100 µM ATP |
| 271 | 0.6 | 1.4 | 0.5 | 1.4 | 10.3 | 121.7 | 4.6 | 8.7 | 50.1 | >10000 |
| 272 | 0.3 | 0.5 | 0.1 | 0.2 | 23.9 | 0.5 | 0.4 | 1.1 | 1.4 | 324.6 |
| 273 | 3.1 | 1.4 | 1.1 | 1.3 | 1.5 | 0.9 | 1.4 | 5.5 | 5.9 | 7309.0 |
| 274 | 0.3 | 0.5 | 0.2 | 0.3 | 0.6 | 0.5 | 0.3 | 3.8 | 3.4 | 4884.0 |
| 275 | 0.4 | 0.6 | 0.2 | 0.5 | 0.4 | 0.6 | 0.4 | 4.7 | 1.8 | 2940.0 |
| 276 | 0.8 | 1.1 | 0.4 | 0.9 | 1.2 | 1.4 | 1.9 | 120.6 | 14.9 | >10000 |
| 277 | 0.2 | 0.3 | 0.1 | 0.3 | 0.2 | 0.5 | 0.2 | 1.6 | 0.4 | 47.5 |
| 278 | 0.6 | 0.4 | 0.1 | 0.3 | 0.6 | 1.0 | 0.3 | 3.4 | 1.2 | 668.7 |
| 279 | 0.5 | 0.3 | 0.3 | 0.4 | 0.6 | 1.0 | 0.6 | 14.2 | 4.9 | 4686.0 |
| 280 | 0.8 | 1.0 | 1.0 | 0.7 | 0.2 | 0.7 | 0.3 | 3.8 | 0.4 | 51.9 |
| 281 | 1.8 | 2.8 | 0.6 | 2.3 | 0.9 | 1.1 | 2.8 | 40.4 | 2.9 | 806.5 |
| 282 | 0.3 | 0.3 | 0.1 | 0.3 | 0.1 | 0.5 | 0.1 | 0.7 | 0.6 | 369.5 |
| 283 | 0.6 | 0.6 | 0.3 | 0.5 | 0.3 | 1.6 | 0.6 | 2.9 | 4.8 | 1997.0 |
| 284 | 0.1 | 0.1 | 0.1 | 0.1 | 0.1 | 0.4 | 0.1 | 0.9 | 0.8 | 387.3 |
| 285 | 1.1 | | 0.7 | | 2.3 | | 0.6 | | 3.2 | |
| 286 | 20.2 | | 4.8 | | 90.9 | | 188.0 | | 1005.0 | |
| 287 | 0.2 | | 0.1 | | 0.3 | | 0.1 | | 0.3 | |
| 288 | | 0.2 | | 0.2 | | 0.2 | | 0.4 | | 132.6 |
| 289 | | 1.5 | | 1.7 | 2.5 | 2.7 | 1.4 | 27.4 | 17.4 | >10000 |
| 290 | 0.1 | 0.1 | 0.1 | 0.2 | 0.2 | 0.5 | 0.3 | 3.4 | 2.0 | 2497.0 |
| 291 | 0.3 | 0.4 | 0.2 | 0.3 | 0.2 | 0.6 | 0.3 | 2.6 | 0.3 | 940.6 |
| 292 | 0.5 | 0.2 | 0.1 | 0.2 | 0.4 | 0.8 | 0.1 | 6.6 | 1.4 | 6970.0 |
| 293 | 0.4 | 0.6 | 0.2 | 0.4 | 0.8 | 0.9 | 0.3 | 2.1 | 0.6 | 182.7 |
| 294 | 0.4 | | 0.2 | | 1.0 | | 0.1 | | 0.9 | |
| 295 | 0.7 | | 0.6 | | 2.9 | | 0.3 | | 3.8 | |
| 296 | 0.1 | 0.2 | 0.1 | 0.1 | 0.1 | 0.3 | 0.1 | 0.5 | 0.3 | 48.8 |
| 297 | 0.1 | 0.2 | 0.1 | 0.5 | 0.5 | 0.7 | 0.3 | 3.9 | 1.6 | 581.5 |
| 298 | 1.5 | 1.8 | 0.3 | 1.0 | 1.0 | 0.8 | 1.1 | 1.7 | 1.6 | 504.0 |
| 299 | 1.1 | | 0.3 | | 4.1 | | 0.5 | | 5.0 | |
| 300 | 1.3 | | 0.8 | | 32.6 | | 0.5 | | 44.8 | |

TABLE 13

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 µM ATP | Km ATP | 100 µM ATP | Km ATP | 100 µM ATP | Km ATP | 100 µM ATP | Km ATP | 100 µM ATP |
| 301 | | 0.1 | | 0.1 | | 0.4 | | 3.5 | | 1369.0 |
| 302 | 0.3 | 0.4 | 0.1 | 0.2 | 0.2 | 0.3 | 0.1 | 0.2 | 0.2 | 38.9 |
| 303 | 0.6 | | 0.3 | | 2.2 | | 0.2 | | 1.7 | |
| 304 | 1.1 | | 1.8 | | 340.5 | | 0.8 | | 355.5 | |
| 305 | 8.0 | | 5.3 | | 67.7 | | 12.0 | | 853.1 | |
| 306 | 9.1 | | 5.9 | | 171.3 | | 47.9 | | 1286.0 | |
| 307 | | 1.5 | | | 7.5 | | 2.1 | | 20.9 | |
| 308 | 0.4 | 0.4 | 0.2 | 0.4 | 0.5 | 0.4 | 0.4 | 4.1 | 44.2 | 3640.0 |
| 309 | 4.4 | 3.8 | 4.9 | 29.9 | 460.2 | 342.8 | 42.9 | >10000 | 5.5 | >10000 |
| 310 | | 4.0 | | 19.0 | 0.1 | 36.8 | | 236.8 | | >10000 |

TABLE 13-continued

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 311 | | 3.5 | | 25.6 | | 30.1 | | 1022.0 | | >10000 |
| 312 | 1.3 | 2.4 | 1.3 | 6.6 | | 353.1 | | >10000 | | >10000 |
| 313 | | 2.1 | | 12.6 | 39.9 | 74.5 | 145.9 | 626.5 | 1605.0 | >10000 |
| 314 | 1.9 | 5.2 | 0.5 | 1.9 | 132.7 | 300.1 | 75.2 | 1477.0 | 594.8 | >10000 |
| 315 | 0.6 | 1.9 | 0.5 | 1.1 | 6.3 | 11.0 | 5.4 | 37.4 | 14.2 | >10000 |
| 316 | 0.4 | 0.7 | 0.2 | 1.0 | 6.0 | 10.5 | 11.2 | 406.4 | 46.0 | >10000 |
| 317 | 0.5 | 0.3 | 0.1 | 0.2 | 5.5 | 16.8 | 2.2 | 53.6 | 12.1 | >10000 |
| 318 | 3.6 | 3.0 | 0.5 | 4.8 | 57.1 | 289.7 | 42.7 | 277.4 | 255.1 | >10000 |
| 319 | 0.4 | | 0.3 | | 47.3 | | 16.9 | | 184.4 | |
| 320 | 0.4 | | 0.2 | | 3.9 | | 1.8 | | 33.5 | |
| 321 | 2.8 | | 2.3 | | 20.2 | | 10.4 | | 74.8 | |
| 322 | 1.9 | | 0.6 | | 175.5 | | 15.5 | | 1521.0 | |
| 323 | 10.4 | | 4.6 | | 1065.0 | | 143.4 | | 466.3 | |
| 324 | 4.6 | | 1.7 | | 66.9 | | 13.2 | | 55.5 | |
| 325 | 0.2 | | 0.1 | | 0.6 | | 0.3 | | 1.2 | |
| 326 | 1.4 | | 0.7 | | 13.3 | | 7.9 | | 18.8 | |
| 327 | 0.4 | | 0.2 | | 1.7 | | 2.8 | | 6.5 | |
| 328 | 4.8 | 8.0 | 2.0 | 6.5 | 9.3 | 11.5 | 19.5 | 377.9 | 110.1 | >10000 |
| 329 | 2.5 | 6.5 | 1.2 | 4.1 | 24.6 | 37.1 | 75.0 | 1141.0 | 288.1 | >10000 |
| 330 | 2.6 | 2.2 | 1.1 | 3.9 | 15.7 | 35.1 | 1.6 | 63.3 | 65.3 | >10000 |

TABLE 14

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 331 | 2.3 | | 2.6 | | 11.9 | | 6.8 | | 141.9 | |
| 332 | 5.9 | | 3.2 | | 10.1 | | 6.0 | | 98.0 | |
| 333 | 4.4 | | 2.9 | | 16.5 | | | | 61.5 | |
| 334 | 4.2 | | 2.8 | | 41.2 | | 17.1 | | 24.6 | |
| 335 | 1.6 | | 0.7 | | 7.9 | | 4.6 | | 98.8 | |
| 336 | 1.0 | | 1.1 | | 37.3 | | 20.5 | | 2547.0 | |
| 337 | 0.8 | | 0.5 | | 6.1 | | 3.7 | | 9.0 | |
| 338 | 0.7 | | 0.4 | | 13.2 | | 3.9 | | 45.1 | |
| 339 | 2.9 | | 0.4 | | 1072.0 | | 113.0 | | 424.4 | |
| 340 | 0.5 | | 0.3 | | 21.4 | | 6.7 | | 173.2 | |
| 341 | 1.5 | | 0.9 | | 22.0 | | 14.8 | | 48.4 | |
| 342 | 0.2 | | 0.1 | | 1.8 | | 1.3 | | 2.7 | |
| 343 | 0.1 | | 0.2 | | 4.7 | | 0.3 | | 35.3 | |
| 344 | 0.4 | | 0.4 | | 29.5 | | 0.2 | | 58.6 | |
| 345 | 0.4 | | 0.9 | | 4.6 | | 0.3 | | 22.2 | |
| 346 | | 6.3 | | 3.7 | | 124.2 | | 408.8 | 334.6 | >10000 |
| 347 | 1.9 | 3.1 | 0.7 | 1.9 | 99.0 | 329.4 | 48.2 | 449.3 | 399.7 | >10000 |
| 348 | 0.5 | 3.5 | 0.2 | 0.6 | 134.1 | 134.2 | 14.6 | 148.8 | 145.4 | >10000 |
| 349 | 2.4 | 1.0 | 0.3 | 2.8 | 53.7 | 276.3 | 77.2 | 303.9 | 189.4 | >10000 |
| 350 | 4.2 | | 2.6 | | 95.1 | | 117.3 | | 261.4 | |
| 351 | 2.7 | | 2.8 | | 197.9 | | 44.3 | | 235.5 | |
| 352 | 7.3 | | 4.8 | | 653.3 | | 105.0 | | 456.6 | |
| 353 | 0.7 | 0.9 | 0.3 | 0.8 | 133.1 | 251.8 | 15.7 | 275.2 | 175.0 | >10000 |
| 354 | | 2.0 | | 13.1 | | 135.3 | | 2542.0 | | >10000 |
| 355 | 0.7 | | 0.3 | | 11.0 | | 13.3 | | 64.4 | |
| 356 | 1.1 | | 1.8 | | 9.8 | | 12.1 | | 96.6 | |
| 357 | 0.2 | | 0.4 | | 5.2 | | 8.4 | | 46.2 | |
| 358 | 0.2 | | 0.3 | | 2.3 | | 3.7 | | 39.6 | |
| 359 | 0.6 | | 1.6 | | 15.4 | | 18.3 | | 208.0 | |
| 360 | 0.5 | | 0.9 | | 9.5 | | 16.7 | | 140.5 | |

TABLE 15

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 µM ATP | Km ATP | 100 µM ATP | Km ATP | 100 µM ATP | Km ATP | 100 µM ATP | Km ATP | 100 µM ATP |
| 361 | 0.5 | | 1.1 | | 14.2 | | 20.0 | | 684.9 | |
| 362 | 0.2 | | 0.1 | | 12.8 | | 5.0 | | 159.2 | |
| 363 | 3.4 | | 4.3 | | 404.0 | | 665.2 | | 4269.0 | |
| 364 | 0.4 | | 0.8 | | 7.9 | | 9.0 | | 55.6 | |
| 365 | 1.5 | | 2.3 | | 45.4 | | 48.4 | | 305.7 | |
| 366 | 8.5 | | 3.1 | | 249.3 | | 127.0 | | 3315.0 | |
| 367 | 17.1 | | 7.2 | | 391.1 | | 251.0 | | 4997.0 | |
| 368 | 1.9 | | 0.9 | | 12.6 | | 10.7 | | 33.6 | |
| 369 | 3.1 | | 1.0 | | 8.1 | | 10.1 | | 72.7 | |
| 370 | 3.4 | | 1.2 | | 17.4 | | 8.3 | | 146.5 | |
| 371 | 0.9 | | 1.8 | | 38.9 | | 91.0 | | 1984.0 | |
| 372 | 0.6 | | 0.2 | | 6.9 | | 3.7 | | 107.5 | |
| 373 | 0.5 | | 3.0 | | 663.3 | | 225.7 | | 714.3 | |
| 374 | 0.3 | | 0.6 | | 240.6 | | 25.9 | | 1051.0 | |
| 375 | 16.4 | | 11.1 | | 1150.0 | | 51.4 | | 2292.0 | |
| 376 | 0.2 | 0.4 | 0.1 | 0.9 | 6.0 | 8.0 | 11.0 | 125.6 | 143.6 | >10000 |
| 377 | 0.2 | 0.4 | 0.1 | 0.7 | 4.2 | 5.8 | 5.7 | 171.9 | 98.8 | >10000 |
| 378 | 1.2 | 1.7 | 0.3 | 3.1 | 16.7 | 23.9 | 14.4 | 518.1 | 254.3 | >10000 |

What is claimed is:

1. A compound of formula (I) or a pharmaceutically acceptable salt thereof,

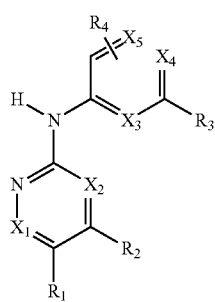

(I)

wherein $X_1$ and $X_2$ are, independently each other, —CH= or —N=, with the proviso that $X_1$ and $X_2$ cannot be —N= at the same time, $X_3$, $X_4$, and $X_5$ are, independently each other, —CH= or —N=, with the proviso that $X_3$, $X_4$, and $X_5$ cannot be —CH= at the same time, $R_1$ is -A or -A-$(R_{1A})_m$, A is 5-membered heteroaryl, 4,5,6,7-tetrahydropyrazolo[1,5-a]pyridinyl, or 6,7-dihydropyrrolo[1,2-a]imidazolyl, $R_{1A}$ is independently selected from the group consisting of:

OH;

halogen;

cyano;

$C_{1-6}$alkyl optionally substituted by one or more substituents selected from the group consisting of OH, halogen, $C_{1-3}$ alkoxy, $C_{3-6}$ cycloalkyl, —NH$C_{1-6}$ alkyl, —N($C_{1-6}$ alkyl)$_2$, and 4-7 membered heterocyclyl optionally or independently substituted by one or more substituents selected from the group consisting of OH, halogen, and $C_{1-6}$ alkyl;

$C_{3-6}$ cycloalkyl;

$C_{1-3}$ alkoxy optionally substituted by one or more substituents selected from the group consisting of OH, halogen, —N($C_{1-6}$ alkyl)$_2$, and 3-7 membered heterocyclyl optionally or independently substituted by one or more substituents selected from the group consisting of halogen and $C_{1-6}$ alkyl;

—NH$C_{1-6}$ alkyl optionally substituted by one or more substituents selected from the group consisting of OH, halogen, —N($C_{1-6}$alkyl)$_2$ and 3-7 membered heterocyclyl optionally substituted by one or more substituents selected from the group consisting of OH, halogen, and $C_{1-6}$alkyl;

—NH$C_{3-6}$cycloalkyl optionally substituted by one or more substituents selected from the group consisting of OH, halogen and $C_{1-6}$alkyl optionally substituted by OH;

—NH 3-7 membered heterocyclyl optionally substituted by one or more substituents selected from the group consisting of OH, halogen, and $C_{1-6}$alkyl;

—N($C_{1-6}$alkyl)$_2$ optionally substituted by one or more substituents selected from the group consisting of OH and halogen;

—NHC(O)$C_{1-6}$alkyl optionally substituted by one or more substituents selected from the group consisting of OH and halogen;

—NHC(O)$C_{3-6}$cycloalkyl optionally substituted by one or more substituents selected from the group consisting of OH and halogen;

—O-4-7 membered heterocyclyl optionally or independently substituted by one or more substituents selected from the group consisting of $C_{1-6}$alkyl and $C_{1-6}$haloalkyl;

4-7 membered heterocyclyl optionally or independently substituted by one or more substituents selected from the group consisting of OH, halogen, $C_{1-6}$alkyl, $C_{1-3}$alkoxy, $C_{1-6}$hydroxyalkyl, and $C_{1-6}$haloalkyl;

—S(O)$_2C_{1-6}$alkyl optionally substituted by one or more halogens;

—S(O)$_2C_{3-6}$cycloalkyl optionally substituted by one or more halogens;

—S(O)$_2$N($C_{1-6}$alkyl)$_2$ optionally substituted by one or more halogens;

—S(O)$_2$-3-7 membered heterocyclyl optionally substituted by one or more substituents selected from the group consisting of OH, halogen, and C$_{1-6}$alkyl;

—C(O)OC$_{1-6}$alkyl;

—C(O)C$_{1-6}$alkyl; and

—C(O)-3-7 membered heterocyclyl optionally substituted by one or more substituents selected from the group consisting of OH, halogen, and C$_{1-6}$alkyl, m is 1 or 2, R$_2$ is —XC$_{1-6}$alkyl optionally substituted by one or more substituents selected from the group consisting of OH, halogen, and —N(C$_{1-6}$alkyl)$_2$; —X(CH$_2$)$_n$-B; or -X(CH$_2$)$_n$-B-(R$_{2A}$)$_o$, X is —NH—, —O—, bond or —C≡C—, n is an integer of 0 to 3, o is an integer of 1 to 3, B is selected from the group consisting of C$_{3-8}$ cycloalkyl; C$_{6-10}$ aryl; 4-11 membered heterocyclyl; and 5-6 membered heteroaryl, R$_{2A}$ is independently selected from the group consisting of:

OH;

halogen;

NH$_2$;

C$_{1-6}$alkyl optionally substituted by one or more substituents selected from the group consisting of OH, NH$_2$, halogen, C$_{3-6}$cycloalkyl, C$_{1-3}$alkoxy, —NHC$_{1-6}$alkyl, —NHC$_{1-6}$hydroxyalkyl, —NHC$_{1-6}$haloalkyl, —NHC$_{3-6}$cycloalkyl, —N(C$_{1-6}$alkyl)$_2$, —N(C$_{1-6}$haloalkyl)$_2$, —N(C$_{1-6}$alkyl)(C$_{1-6}$haloalkyl), —NHC(O)C$_{1-6}$alkyl, —C(O)NHC$_{1-6}$alkyl, —C(O)N(C$_{1-6}$alkyl)$_2$, 3-7 membered heterocyclyl optionally substituted by one or more halogens, and 5-6 membered heteroaryl;

C$_{3-6}$cycloalkyl;

C$_{1-3}$alkoxy optionally substituted by one or more halogens;

—C(O)NHC$_{1-6}$alkyl optionally substituted by one or more substituents selected from the group consisting of OH and halogen;

—C(O)N(C$_{1-6}$alkyl)$_2$ optionally substituted by one or more substituents selected from the group consisting of OH and halogen;

—NHC$_{1-6}$alkyl optionally substituted by one or more substituents selected from the group consisting of OH, halogen, —NHC$_{1-6}$alkyl, —N(C$_{1-6}$alkyl)$_2$, 3-7 membered heterocyclyl optionally substituted by halogen or —N(C$_{1-6}$alkyl)$_2$;

—N(C$_{1-6}$alkyl)$_2$ where C$_{1-6}$alkyl is optionally substituted by one or more halogens;

—NH-4-7 membered heterocyclyl optionally substituted by C$_{1-6}$alkyl;

4-7 membered heterocyclyl; and

=O,

R$_3$ is Y-Q or Y-Q-(R$_{3A}$)$_p$,

Y is —NH— or bond,

Q is selected from the group consisting of ethynyl; 4-7 membered heterocyclyl; 2,3-dihydropyrido[2,3-b][1,4]oxazinyl; 3,4-dihydropyrano[2,3-b]pyridinyl; C$_{6-10}$ aryl; and 5 membered heteroaryl, p is an integer of 1 to 3, R$_{3A}$ is independently selected from the group consisting of

OH;

halogen;

C$_{1-3}$alkoxy;

C$_{1-6}$alkyl optionally or independently substituted by one or more substituents selected from the group consisting of OH, halogen, C$_{1-3}$alkoxy, C$_{3-6}$cycloalkyl, and S(O)$_2$C$_{1-6}$alkyl;

C$_{2-6}$alkenyl;

C$_{3-6}$cycloalkyl;

4-7 membered heterocyclyl;

—C(O)C$_{1-6}$alkyl;

—C(O)N(C$_{1-6}$alkyl)$_2$;

—S(O)$_2$C$_{1-6}$alkyl optionally substituted by one or more halogens;

—S(O)$_2$C$_{2-6}$alkenyl;

—S(O)$_2$C$_{3-6}$cycloalkyl optionally substituted by one or more halogens;

—S(O)$_2$N(C$_{1-6}$alkyl)$_2$; and

—S(O)$_2$-4-7 membered heterocyclyl optionally substituted by one or more substituents selected from the group consisting of OH, halogen, and C$_{1-6}$alkyl, and R$_4$ is selected from the group consisting of H, halogen and C$_{1-6}$alkyl.

2. The compound of claim 1, or a pharmaceutically acceptable salt thereof, wherein X$_1$ and X$_2$ are —CH=.

3. The compound of claim 1, or a pharmaceutically acceptable salt thereof, wherein X$_1$ is —N= and X$_2$ is —CH=.

4. The compound of claim 1, or a pharmaceutically acceptable salt thereof, wherein X$_1$ is —CH= and X$_2$ is —N=.

5. The compound of claim 1, or a pharmaceutically acceptable salt thereof, wherein X$_3$ and X$_4$ are —N=; and X$_5$ is —CH=.

6. The compound of claim 1, or a pharmaceutically acceptable salt thereof, wherein X$_4$ is —N=; and X$_3$ and X$_5$ are —CH=.

7. The compound of claim 1, or a pharmaceutically acceptable salt thereof, wherein X$_3$ and X$_5$ are —N=; and X$_4$ is —CH=.

8. The compound of claim 1, or a pharmaceutically acceptable salt thereof, wherein A is 5-membered heteroaryl.

9. The compound of claim 1, or a pharmaceutically acceptable salt thereof, wherein A is pyrazolyl, 4,5,6,7-tetrahydropyrazolo[1,5-a]pyridinyl, isoxazolyl, thiazolyl, furanyl, imidazolyl, or 6,7-dihydropyrrolo[1,2-a]imidazolyl.

10. The compound of claim 1, or a pharmaceutically acceptable salt thereof, wherein R$_{1A}$ is F; Cl; C$_{1-4}$alkyl optionally substituted by one to three substituents selected from the group consisting of OH, F, Cl, C$_{1-3}$alkoxy, C$_{3-6}$cycloalkyl, —NHC$_{1-4}$alkyl, —N(C$_{1-4}$alkyl)$_2$, 4-6 membered heterocyclyl optionally substituted by C$_{1-3}$alkyl; C$_{3-6}$cycloalkyl; C$_{1-2}$alkoxy optionally substituted by one to three F or Cl; —NHC$_{1-4}$alkyl optionally substituted by one to three substituents selected from the group consisting of OH, F and Cl; —NHC$_{3-6}$cycloalkyl optionally substituted by one to three substituents selected from the group consisting of OH, F and Cl; —N(C$_{1-6}$alkyl)$_2$ optionally substituted by one to three substituents selected from the group consisting of OH, F and Cl; —NHC(O)C$_{1-6}$alkyl optionally substituted by one to three substituents selected from the group consisting of OH, F and Cl; —NHC(O)C$_{3-6}$cycloalkyl optionally substituted by one to three substituents selected from the group consisting of OH, F and Cl; 4-6 membered heterocyclyl optionally or independently substituted by one to three substituents selected from the group consisting of F, Cl, C$_{1-6}$alkyl, C$_{1-6}$hydroxyalkyl, and C$_{1-6}$haloalkyl; —S(O)$_2$C$_{1-6}$alkyl optionally substituted by one or more halogens; or —C(O)OC$_{1-6}$alkyl.

11. The compound of claim 1, or a pharmaceutically acceptable salt thereof, wherein $R_{1A}$ is $C_{1-6}$alkyl optionally substituted by one or more substituents selected from the group consisting of OH, halogen, $C_{3-6}$cycloalkyl, —NHC$_{1-6}$alkyl, —N(C$_{1-6}$alkyl)$_2$, and 4-7 membered heterocyclyl optionally substituted by $C_{1-6}$alkyl.

12. The compound of claim 1, or a pharmaceutically acceptable salt thereof, wherein $R_{1A}$ is independently selected from the group consisting of
    Halogen;
    $C_{1-6}$alkyl optionally substituted by one or more substituents selected from the group consisting of OH, halogen, $C_{1-3}$alkoxy, $C_{3-6}$cycloalkyl, and —N(C$_{1-6}$alkyl)$_2$;
    $C_{3-6}$cycloalkyl;
    $C_{1-3}$alkoxy optionally substituted by one or more halogens;
    4-7 membered heterocyclyl optionally or independently substituted by one or more substituents selected from the group consisting of halogen and $C_{1-6}$alkyl;
    —S(O)$_2$C$_{1-6}$alkyl; and
    —C(O)OC$_{1-6}$alkyl.

13. The compound of claim 12, or a pharmaceutically acceptable salt thereof, wherein the 4-7 membered heterocyclyl is tetrahydropyranyl, morpholinyl, piperazinyl, oxetanyl, or piperidinyl.

14. The compound of claim 1, or a pharmaceutically acceptable salt thereof, wherein $R_2$ is —XC$_{1-6}$alkyl optionally substituted by one or more substituents selected from the group consisting of OH and halogen.

15. The compound of claim 1, or a pharmaceutically acceptable salt thereof, wherein $R_2$ is —X(CH$_2$)$_n$-B-(R$_{2A}$)$_o$.

16. The compound of claim 1, or a pharmaceutically acceptable salt thereof, wherein B is $C_{3-6}$cycloalkyl; phenyl; 4-10 membered heterocycloalkyl having one to three heteroatoms selected from a group consisting of N, O and S; or 5-6 membered heteroaryl having one to three heteroatoms selected from a group consisting of N, O and S.

17. The compound of claim 1, or a pharmaceutically acceptable salt thereof, wherein B is $C_{3-6}$cycloalkyl.

18. The compound of claim 1, or a pharmaceutically acceptable salt thereof, wherein B is 4-10 membered heterocycloalkyl or 5-6 membered heteroaryl having one to three heteroatoms selected from a group consisting of N and O.

19. The compound of claim 1, or a pharmaceutically acceptable salt thereof, wherein B is $C_{3-8}$cycloalkyl, pyrazolyl, azepanyl, azaspiro[4.5]decanonly, azaspiro[3.3]heptanyl, azaspiro[3.5]nonanyl, piperidinonyl, bicyclo[2.2.1]heptanyl, spiro[3.3]hepatanyl, tetrahydropyranyl, imidazolyl, piperidinyl, or oxetanyl.

20. The compound of claim 1, or a pharmaceutically acceptable salt thereof, wherein $R_{2A}$ is independently selected from the group consisting of
    OH;
    halogen;
    NH$_2$;
    $C_{1-6}$alkyl optionally substituted by one or more substituents selected from the group consisting of OH, halogen, —NHC$_{1-6}$alkyl, —N(C$_{1-6}$alkyl)$_2$, —N(C$_{1-6}$alkyl)(C$_{1-6}$haloalkyl), —C(O)N(C$_{1-6}$alkyl)$_2$, and azetidinyl;
    $C_{3-6}$cycloalkyl;
    $C_{1-3}$alkoxy optionally substituted by one or more halogens;
    —C(O)NHC$_{1-6}$alkyl;
    —C(O)N(C$_{1-6}$alkyl)$_2$ optionally substituted by one or more halogens;
    —NHC$_{1-6}$alkyl optionally substituted by one or more substituents selected from the group consisting of OH, halogen, and —N(C$_{1-6}$alkyl)$_2$;
    —N(C$_{1-6}$alkyl)$_2$; and
    =O.

21. The compound of claim 1, or a pharmaceutically acceptable salt thereof, wherein Q is ethynyl, pyrazolyl, pyrrolyl, piperidinyl, 2,3-dihydropyrido[2,3-b][1,4]oxazinyl, tetrahydropyridinyl, 3,4-dihydropyrano[2,3-b]pyridinyl, phenyl, or pyrrolidinyl.

22. The compound of claim 1, or a pharmaceutically acceptable salt thereof, wherein $R_{3A}$ is independently selected from the group consisting of
    OH;
    halogen;
    $C_{1-3}$alkoxy;
    $C_{1-6}$alkyl optionally or independently substituted by one or more substituents selected from the group consisting of OH, halogen, $C_{1-3}$alkoxy, $C_{3-6}$cycloalkyl, and S(O)$_2$C$_{1-6}$alkyl;
    $C_{2-6}$alkenyl;
    $C_{3-6}$cycloalkyl;
    4-7 membered heterocyclyl;
    —C(O)C$_{1-6}$alkyl;
    —C(O)N(C$_{1-6}$alkyl)$_2$;
    —S(O)$_2$C$_{1-6}$alkyl;
    —S(O)$_2$C$_{2-6}$alkenyl;
    —S(O)$_2$C$_{3-6}$cycloalkyl;
    —S(O)$_2$N(C$_{1-6}$alkyl)$_2$; and
    —S(O)$_2$ 4-7 membered heterocyclyl optionally substituted by one or more halogens.

23. The compound of claim 22, or a pharmaceutically acceptable salt thereof, wherein the 4-7 membered heterocyclyl is tetrahydrofuranyl, tetrahydropyranyl, pyrrolidinyl, or azetidinyl.

24. The compound of claim 1, or a pharmaceutically acceptable salt thereof, wherein $R_4$ is H or halogen.

25. The compound of claim 1, which is selected from any one of the compounds as described below, or a pharmaceutically acceptable salt thereof:
    (1) N-(5-(1-Cyclopropyl-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine;
    (2) 2-(1-(Cyclopropylsulfonyl)-1H-pyrazol-4-yl)-N-(5-(1-(difluoromethyl)-1H-pyrazol-4-yl)-4-((1-methyl-1H-pyrazol-4-yl)ethynyl)pyridin-2-yl)pyrimidin-4-amine;
    (3) N-(5-(1-(Cyclopropylmethyl)-1H-pyrazol-4-yl)-4-((1-methyl-1H-pyrazol-4-yl)ethynyl)pyridin-2-yl)-2-(1-(cyclopropylsulfonyl)-1H-pyrazol-4-yl)pyrimidin-4-amine;
    (4) 4-(2-((2-(1-(Cyclopropylsulfonyl)-1H-pyrazol-4-yl)pyrimidin-4-yl)amino)-5-(1-methyl-1H-pyrazol-4-yl)pyridin-4-yl)-2-methylbut-3-yn-2-ol;
    (5) N-(5-(1-Cyclopropyl-1H-pyrazol-4-yl)-4-((1-cyclopropyl-1H-pyrazol-4-yl)ethynyl)pyridin-2-yl)-2-(1-(cyclopropylsulfonyl)-1H-pyrazol-4-yl)pyrimidin-4-amine;
    (6) N-(5-(1-Cyclopropyl-1H-pyrazol-4-yl)-4-((1-isopropyl-1H-pyrazol-4-yl)ethynyl)pyridin-2-yl)-2-(1-(cyclopropylsulfonyl)-1H-pyrazol-4-yl)pyrimidin-4-amine;
    (7) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-3-methylbutan-2-ol;

(8) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol;

(9) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((2-fluoroethyl)amino)cyclohexyl)pyridine-2,4-diamine;

(10) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(11) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(trifluoromethyl)cyclohexan-1-ol;

(12) (1R,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(13) (1S,3R)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(14) (1R,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(15) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(16) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(methylamino)cyclohexyl)pyridine-2,4-diamine;

(17) (S)-$N^4$-(Azepan-4-yl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(18) ((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(19) (5s,8s)-8-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-azaspiro[4.5]decan-2-one;

(20) (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(21) (1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(22) ((1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexyl)methanol;

(23) $N^2$-(2-(1-(Cyclopropylsulfonyl)-1H-pyrazol-4-yl)pyrimidin-4-yl)-$N^4$-((1s,4s)-4-((2,2-difluoroethyl)amino)cyclohexyl)-5-(1-(difluoromethyl)-1H-pyrazol-3-yl)pyridine-2,4-diamine;

(24) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-methylcyclohexane-1-carboxamide;

(25) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1r,4r)-4-(dimethylamino)cyclohexyl)methyl)pyridine-2,4-diamine;

(26) $N^4$-((2-Azaspiro[3.3]heptan-6-yl)methyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(27) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(2-azaspiro[3.5]nonan-7-yl)pyridine-2,4-diamine;

(28) 2-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(29) 2-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclopentan-1-ol;

(30) (1s,4s)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(31) (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(32) 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclohexan-1-ol;

(33) 3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclopentan-1-ol;

(34) (1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutan-1-ol;

(35) (1s,3s)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutan-1-ol;

(36) (1r,4r)-4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-1-methylcyclohexan-1-ol;

(37) 5-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylpiperidin-2-one;

(38) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-2-one;

(39) 6-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)bicycle[2.2.1]heptan-2-ol;

(40) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclobutan-1-ol;

(41) $N^4$-(3-(1H-Imidazol-1-yl)propyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(42) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)propan-2-ol;

(43) N²-(2-(1-(Cyclopropylsulfonyl)-1H-pyrazol-4-yl)pyrimidin-4-yl)-N⁴-((1s,4s)-4-((2-fluoroethyl)amino)cyclohexyl)-5-(1-methyl-1H-pyrazol-3-yl)pyridine-2,4-diamine;

(44) (5s,8s)-8-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-azaspiro[4.5]decan-2-one;

(45) N²-(2-(1-(Cyclopropylsulfonyl)-1H-pyrazol-4-yl)pyrimidin-4-yl)-N⁴-((1 s,4s)-4-((2,2-difluoroethyl)amino)cyclohexyl)-5-(1-methyl-1H-pyrazol-3-yl)pyridine-2,4-diamine;

(46) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-methylcyclohexane-1-carboxamide;

(47) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclohexan-1-ol;

(48) (1r,4r)-4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-1-methylcyclohexan-1-ol;

(49) 2-((1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexyl)propan-2-ol;

(50) N²-(2-(1-(Cyclopropylsulfonyl)-1H-pyrazol-4-yl)pyrimidin-4-yl)-N⁴-((1s,4s)-4-((2-fluoroethyl)amino)cyclohexyl)-5-(2-(trifluoromethyl)thiazol-4-yl)pyridine-2,4-diamine;

(51) (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-methylcyclohexan-1-ol;

(52) (5s,8s)-8-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)-1-azaspiro[4.5]decan-2-one;

(53) N²-(2-(1-(Cyclopropylsulfonyl)-1H-pyrazol-4-yl)pyrimidin-4-yl)-N⁴-((1 s,4s)-4-((2,2-difluoroethyl)amino)cyclohexyl)-5-(2-(trifluoromethyl)thiazol-4-yl)pyridine-2,4-diamine;

(54) 2-(4-(6-((2-(1-(Cyclopropylsulfonyl)-1H-pyrazol-4-yl)pyrimidin-4-yl)amino)-4-(((1 s,4s)-4-(2-hydroxypropan-2-yl)cyclohexyl)amino)pyridin-3-yl)thiazol-2-yl)propan-2-ol;

(55) 2-(4-(6-((2-(1-(Cyclopropylsulfonyl)-1H-pyrazol-4-yl)pyrimidin-4-yl)amino)-4-(((1 s,4s)-4-((2-fluoroethyl)amino)cyclohexyl)amino)pyridin-3-yl)thiazol-2-yl)propan-2-ol;

(56) 2-(4-(6-((2-(1-(Cyclopropylsulfonyl)-1H-pyrazol-4-yl)pyrimidin-4-yl)amino)-4-(((1 s,4s)-4-(methylamino)cyclohexyl)amino)pyridin-3-yl)thiazol-2-yl)propan-2-ol;

(57) (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)cyclohexan-1-ol;

(58) (1s,4s)-4-((2-((2-(1-(Cyclopropylsulfonyl)-1H-pyrazol-4-yl)pyrimidin-4-yl)amino)-5-(1-(tetrahydro-2H-pyran-4-yl)-1H-pyrazol-3-yl)pyridin-4-yl)amino)-1-methylcyclohexan-1-ol;

(59) (1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-methylcyclohexan-1-ol;

(60) ((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)methanol;

(61) 2-((1s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)cyclohexyl)propan-2-ol;

(62) N²-(2-(1-(Cyclopropylsulfonyl)-1H-pyrazol-4-yl)pyrimidin-4-yl)-N⁴-((1 s,4s)-4-((2-fluoroethyl)amino)cyclohexyl)-5-(4,5,6,7-tetrahydropyrazolo[1,5-a]pyridin-2-yl)pyridine-2,4-diamine;

(63) N²-(2-(1-(Cyclopropylsulfonyl)-1H-pyrazol-4-yl)pyrimidin-4-yl)-N⁴-((1 s,4s)-4-((2,2-difluoroethyl)amino)cyclohexyl)-5-(4,5,6,7-tetrahydropyrazolo[1,5-a]pyridin-2-yl)pyridine-2,4-diamine;

(64) (1s,4s)-4-((2-((2-(1-(Cyclopropylsulfonyl)-1H-pyrazol-4-yl)pyrimidin-4-yl)amino)-5-(3-isopropylisoxazol-5-yl)pyridin-4-yl)amino)-1-methylcyclohexan-1-ol;

(65) 2-(1-(Cyclopropylsulfonyl)-1H-pyrazol-4-yl)-N-(5-(1-(difluoromethyl)-1H-pyrazol-3-yl)-4-(((1 s,4s)-4-(methylamino)cyclohexyl)oxy)pyridin-2-yl)pyrimidin-4-amine;

(66) 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)cyclohexan-1-ol;

(67) 3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)oxy)cyclopentan-1-ol;

(68) 4-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)oxy)-1-methylcyclohexan-1-ol;

(69) 2-(1-(Cyclopropylsulfonyl)-1H-pyrazol-4-yl)-N-(5-(1-(difluoromethyl)-1H-pyrazol-4-yl)-4-(((1 s,4s)-4-(methylamino)cyclohexyl)oxy)pyridin-2-yl)pyrimidin-4-amine;

(70) 2-(1-(Cyclopropylsulfonyl)-1H-pyrazol-4-yl)-N-(4-((4-(difluoromethoxy)cyclohexyl)oxy)-5-(1-(difluoromethyl)-1H-pyrazol-4-yl)pyridin-2-yl)pyrimidin-4-amine;

(71) 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclohexan-1-ol;

(72) 3-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)cyclopentan-1-ol;

(73) 4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)oxy)-1-methylcyclohexan-1-ol;

(74) N-(4-((4-Amino-4-methylcyclohexyl)oxy)-5-(1-(difluoromethyl)-1H-pyrazol-4-yl)pyridin-2-yl)-2-(1-(cyclopropylsulfonyl)-1H-pyrazol-4-yl)pyrimidin-4-amine;

(75) (1s,4s)-4-((2-((2-(1-(Cyclopropylsulfonyl)-1H-pyrazol-4-yl)pyrimidin-4-yl)amino)-5-(2-methylthiazol-5-yl)pyridin-4-yl)amino)cyclohexan-1-ol;

(76) (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)cyclohexan-1-ol;

(77) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-4-yl)pyridin-4-yl)amino)cyclohexan-1-ol;

(78) (1s,4s)-4-((5-(1-Cyclopropyl-1H-pyrazol-4-yl)-2-((2-(1-(cyclopropylsulfonyl)-1H-pyrazol-4-yl)pyrimidin-4-yl)amino)pyridin-4-yl)amino)cyclohexan-1-ol;

(79) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexan-1-ol;

(80) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(81) (1s,4s)-4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol;

(82) (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)cyclohexan-1-ol;

(83) (1s,4s)-4-((2-((2-(1-(Cyclopropylsulfonyl)-1H-pyrazol-4-yl)pyrimidin-4-yl)amino)-5-(furan-2-yl)pyridin-4-yl)amino)cyclohexan-1-ol;

(84) (1s,4s)-4-((2-((2-(1-(Cyclopropylsulfonyl)-1H-pyrazol-4-yl)pyrimidin-4-yl)amino)-5-(1-isopropyl-1H-pyrazol-3-yl)pyridin-4-yl)amino)-1-methylcyclohexan-1-ol;

(85) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-methylcyclohexan-1-ol;

(86) $N^2$-(2-(1-(Cyclopropylsulfonyl)-1H-pyrazol-4-yl)pyrimidin-4-yl)-5-(1-isopropyl-1H-pyrazol-3-yl)-$N^4$-((1s,4s)-4-(methylamino)cyclohexyl)pyridine-2,4-diamine;

(87) $N^2$-(2-(1-(Cyclopropylsulfonyl)-1H-pyrazol-4-yl)pyrimidin-4-yl)-5-(furan-2-yl)-$N^4$-((1s,4s)-4-(methylamino)cyclohexyl)pyridine-2,4-diamine;

(88) $N^2$-(2-(1-(Cyclopropylsulfonyl)-1H-pyrazol-4-yl)pyrimidin-4-yl)-5-(1-methyl-1H-pyrazol-3-yl)-$N^4$-((1s,4s)-4-(methylamino)cyclohexyl)pyridine-2,4-diamine;

(89) 1-(2-((2-(1-Cyclopropylsulfonylpyrazol-4-yl)pyrimidin-4-yl)amino)-5-(2-methylthiazol-5-yl)-4-pyridyl)piperidin-4-ol;

(90) 3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-2,2-dimethylpropan-1-ol;

(91) (1S,3S)-3-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino) cyclohexan-1-ol;

(92) 2-(4-(6-((2-(1-(Cyclopropylsulfonyl)-1H-pyrazol-4-yl)pyrimidin-4-yl)amino)-4-(isopropylamino)pyridin-3-yl)thiazol-2-yl)propan-2-ol;

(93) (1s,4s)-4-((2-((2-(1-(Cyclopropylsulfonyl)-1H-pyrazol-4-yl)pyrimidin-4-yl)amino)-5-(2-(2-hydroxypropan-2-yl)thiazol-4-yl)pyridin-4-yl)amino)-1-methylcyclohexan-1-ol;

(94) (1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(trifluoromethyl)cyclohexan-1-ol;

(95) 3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-3-methylbutan-2-ol;

(96) (1 S,3R)-3-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexan-1-ol;

(97) 2-((4-((2-((2-(1-(Cyclopropylsulfonyl)-1H-pyrazol-4-yl)pyrimidin-4-yl)amino)-5-(2-(trifluoromethyl)thiazol-4-yl)pyridin-4-yl)amino)cyclohexyl)amino)ethan-1-ol;

(98) $N^2$-(2-(1-(Cyclopropylsulfonyl)-1H-pyrazol-4-yl)pyrimidin-4-yl)-$N^4$-(4-((2-(dimethylamino)ethyl)amino)cyclohexyl)-5-(2-(trifluoromethyl)thiazol-4-yl)pyridine-2,4-diamine;

(99) $N^2$-(2-(1-(cyclopropylsulfonyl)-1H-pyrazol-4-yl)pyrimidin-4-yl)-5-(1-(difluoromethyl)-1H-pyrazol-3-yl)-N4-(4-((2-(dimethylamino)ethyl)amino)cyclohexyl)pyridine-2,4-diamine;

(100) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1 r,4r)-4-((dimethylamino)methyl)cyclohexyl)methyl)pyridine-2,4-diamine;

(101) $N^2$-(2-(1-(Cyclopropylsulfonyl)-1H-pyrazol-4-yl)pyrimidin-4-yl)-$N^4$-(((1r,4r)-4-((dimethylamino)methyl)cyclohexyl)methyl)-5-(2-(trifluoromethyl)thiazol-4-yl)pyridine-2,4-diamine;

(102) Ethyl 1-(6-((2-(1-(cyclopropylsulfonyl)-1H-pyrazol-4-yl)pyrimidin-4-yl)amino)-4-(((1 s,4s)-4-hydroxy-4-methylcyclohexyl)amino)pyridin-3-yl)-1H-pyrazole-3-carboxylate;

(103) 6-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)spiro[3.3]heptan-2-ol;

(104) (1 s,4s)-4-((5-(1-(Difluoromethyl)-1H-pyrazol-3-yl)-2-((2-(3-methoxyprop-1-yn-1-yl)pyrimidin-4-yl)amino)pyridin-4-yl)amino)-1-methylcyclohexan-1-ol;

(105) 4-((2-((2-(1-(Cyclopropylsulfonyl)-1H-pyrazol-4-yl)pyrimidin-4-yl)amino)-5-(1-(difluoromethy)-1H-pyrazol-3-yl)pyridin-4-yl)amino)-2-methylcyclohexan-1-ol;

(106) 4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-2,2-dimethylcyclohexan-1-ol;

(107) (S)-1-(2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)-3-methylpiperidin-3-ol;

(108) (1 s,4s)-4-((5-(1-(Difluoromethyl)-1H-pyrazol-3-yl)-2-((2-(1-(methylsulfonyl)-1H-pyrrol-3-yl)pyrimidin-4-yl)amino)pyridin-4-yl)amino)-1-methylcyclohexan-1-ol;

(109) 3-(4-((5-(1-(Difluoromethyl)-1H-pyrazol-3-yl)-4-(((1 s,4s)-4-hydroxy-4-methylcyclohexyl)amino)pyridin-2-yl)amino)pyrimidin-2-yl)-N,N-dimethyl-1H-pyrrole-1-sulfonamide;

(110) 1-Cyclopropyl-4-((2-((2-(1-(cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexan-1-ol;

(111) (1 s,4s)-4-((5-(1-(Difluoromethyl)-1H-pyrazol-3-yl)-2-((2-((3R,4S)-3-fluoro-4-methoxypiperidin-1-yl)pyrimidin-4-yl)amino)pyridin-4-yl)amino)-1-methylcyclohexan-1-ol;

(112) (1s,4s)-4-((5-(1-(Difluoromethyl)-1H-pyrazol-3-yl)-2-((2-(1-(methylsulfonyl)-1H-pyrazol-4-yl)pyrimidin-4-yl)amino)pyridin-4-yl)amino)-1-methylcyclohexan-1-ol;

(114) (1s,4s)-4-((5-(1-(Difluoromethyl)-1H-pyrazol-3-yl)-2-((2-(1-((tetrahydrofuran-3-yl)sulfonyl)-1H-pyrazol-4-yl)pyrimidin-4-yl)amino)pyridin-4-yl)amino)-1-methylcyclohexan-1-ol;

(115) (1s,4s)-4-((2-((2-(1-(Cyclopentylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(116) (1s,4s)-4-((2-((2-(1-Allyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(117) (1s,4s)-4-((2-((2-(1-(But-3-en-1-ylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(118) (1R,3S)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclopentan-1-ol;

(119) (1R,3S)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclopentan-1-ol;

(120) (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-methylcyclohexan-1-ol;

(121) (1s,4s)-4-((2-((2-(1-(Cyclopropylsulfonyl)-1H-pyrazol-4-yl)pyrimidin-4-yl)amino)-5-(2-(4-methylpiperazin-1-yl)thiazol-4-yl)pyridin-4-yl)amino)-1-methylcyclohexan-1-ol;

(122) (1s,4s)-4-((2-((2-(1-(Cyclopropylsulfonyl)-1H-pyrazol-4-yl)pyrimidin-4-yl)amino)-5-(4-(difluoromethyl)thiazol-2-yl)pyridin-4-yl)amino)-1-methylcyclohexan-1-ol;

(123) $N^2$-(2-(1-(Cyclopropylsulfonyl)-1H-pyrazol-4-yl)pyrimidin-4-yl)-5-(4-(difluoromethyl)thiazol-2-yl)-$N^4$-((1s,4s)-4-((2-fluoroethyl)amino)cyclohexyl)pyridine-2,4-diamine;

(124) $N^2$-(2-(1-(Cyclopropylsulfonyl)-1H-pyrazol-4-yl)pyrimidin-4-yl)-$N^4$-((1s,4s)-4-(dimethylamino)cyclohexyl)-5-(1-methyl-1H-pyrazol-3-yl)pyridine-2,4-diamine;

(125) (1s,4s)-4-((2-((2-(1-(Cyclopropylsulfonyl)-1H-pyrazol-4-yl)pyrimidin-4-yl)amino)-5-(2-morpholinothiazol-4-yl)pyridin-4-yl)amino)-1-(hydroxymethyl)cyclohexan-1-ol;

(126) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(2-morpholinothiazol-4-yl)pyridine-2,4-diamine;

(127) 4-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)-4-methylcyclohexan-1-ol;

(128) 4-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)-4-methylcyclohexan-1-ol;

(129) $N^2$-(2-(1-(Cyclopropylsulfonyl)-1H-pyrazol-4-yl)pyrimidin-4-yl)-$N^4$-(((1r,4r)-4-((2,2-difluoroethyl)amino)cyclohexyl)methyl)-5-(1-methyl-1H-pyrazol-3-yl)pyridine-2,4-diamine;

(130) $N^2$-(2-(1-(Cyclopropylsulfonyl)-1H-pyrazol-4-yl)pyrimidin-4-yl)-$N^4$-(((1r,4r)-4-((2,2-difluoroethyl)amino)cyclohexyl)methyl)-5-(1-(difluoromethyl)-1H-pyrazol-3-yl)pyridine-2,4-diamine;

(131) $N^2$-(2-(1-(Cyclopropylsulfonyl)-1H-pyrazol-4-yl)pyrimidin-4-yl)-$N^4$-((4-((2-fluoroethyl)amino)cyclohexyl)methyl)-5-(1-methyl-1H-pyrazol-3-yl)pyridine-2,4-diamine;

(132) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((4-((2-fluoroethyl)amino)cyclohexyl)methyl)pyridine-2,4-diamine;

(133) 2-((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(134) 2-((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol;

(135) 2-((1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(136) 2-((1s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)ethan-1-ol;

(137) (1s,4s)-4-((5-(1-(Difluoromethyl)-1H-pyrazol-3-yl)-2-((2-(1-(2,2,2-trifluoroethyl)-1H-pyrazol-4-yl)pyrimidin-4-yl)amino)pyridin-4-yl)amino)-1-methylcyclohexan-1-ol;

(138) (1s,4s)-4-((5-(1-(Difluoromethyl)-1H-pyrazol-3-yl)-2-((2-(1-(2-methoxyethyl)-1H-pyrazol-4-yl)pyrimidin-4-yl)amino)pyridin-4-yl)amino)-1-methylcyclohexan-1-ol;

(139) (1s,4s)-4-((5-(1-(Difluoromethyl)-1H-pyrazol-3-yl)-2-((2-(1-methyl-1H-pyrazol-4-yl)pyrimidin-4-yl)amino)pyridin-4-yl)amino)-1-methylcyclohexan-1-ol;

(140) (1s,4s)-4-((2-((2-(1-Cyclopropyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(141) (1s,4s)-4-((2-((2-(1-(Cyclopropylmethyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(142) (1s,4s)-4-((5-(1-(Difluoromethyl)-1H-pyrazol-3-yl)-2-((2-(1-(2-hydroxy-2-methylpropyl)-1H-pyrazol-4-yl)pyrimidin-4-yl)amino)pyridin-4-yl)amino)-1-methylcyclohexan-1-ol;

(143) (1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(144) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-isopropylpyridine-2,4-diamine;

(145) (1s,4s)-4-((5-(1-(Difluoromethyl)-1H-pyrazol-3-yl)-2-((2-(1-(2-fluoroethyl)-1H-pyrazol-4-yl)pyrimidin-4-yl)amino)pyridin-4-yl)amino)-1-methylcyclohexan-1-ol;

(146) 2-((1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(147) 2-((1r,4r)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)cyclohexyl)ethan-1-ol;

(148) 2-((1s,4s)-4-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)cyclohexyl)propan-2-ol;

(149) (1 s,4s)-4-((5-(1-(Difluoromethyl)-1H-pyrazol-3-yl)-2-((2-(1-(difluoromethyl)-1H-pyrazol-4-yl)pyrimidin-4-yl)amino)pyridin-4-yl)amino)-1-methylcyclohexan-1-ol;

(150) (1 s,4s)-4-((5-(1-(Difluoromethyl)-1H-pyrazol-3-yl)-2-((2-(1-((methylsulfonyl)methyl)-1H-pyrazol-4-yl)pyrimidin-4-yl)amino)pyridin-4-yl)amino)-1-methylcyclohexan-1-ol;

(151) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-fluorocyclohexyl)pyridine-2,4-diamine;

(152) $N^2$-(2-(1-(Cyclopropylsulfonyl)-1H-pyrazol-4-yl)pyrimidin-4-yl)-$N^4$-((4-(difluoromethyl)cyclohexyl)methyl)-5-(1-methyl-1H-pyrazol-3-yl)pyridine-2,4-diamine;

(153) 1-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)piperidin-4-ol;

(154) (1 s,4s)-4-((5-(1-(Difluoromethyl)-1H-pyrazol-3-yl)-2-((2-(2,3-dihydro-1H-pyrido[2,3-b][1, 4]oxazin-7-yl)pyrimidin-4-yl)amino)pyridin-4-yl)amino)-1-methylcyclohexan-1-ol;

(155) (1s,4s)-4-((2-((2-((1-(2,2-Difluoroethyl)-1H-pyrazol-5-yl)amino)pyrimidin-4-yl)amino)-5-(1-(difluoromethyl)-1H-pyrazol-3-yl)pyridin-4-yl)amino)-1-methylcyclohexan-1-ol;

(156) (1 s,4s)-4-((5-(1-(Difluoromethyl)-1H-pyrazol-3-yl)-2-((2-(1-(methylsulfonyl)-1,2,3,6-tetrahydropyridin-4-yl)pyrimidin-4-yl)amino)pyridin-4-yl)amino)-1-methylcyclohexan-1-ol;

(157) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(difluoromethyl)cyclohexyl)pyridine-2,4-diamine;

(158) (1 s,4s)-4-((5-(1-(Difluoromethyl)-1H-pyrazol-3-yl)-2-((2-(1-(methylsulfonyl)piperidin-4-yl)pyrimidin-4-yl)amino)pyridin-4-yl)amino)-1-methylcyclohexan-1-ol;

(159) 1-(4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-3,6-dihydropyridin-1(2H)-yl)ethan-1-one;

(160) 1-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)piperidin-4-ol;

(161) $N^2$-(2-(1-(2,2-Difluoroethyl)-1H-pyrazol-4-yl)pyrimidin-4-yl)-5-(1-(difluoromethyl)-1H-pyrazol-3-yl)-$N^4$-((1s,4s)-4-fluorocyclohexyl)pyridine-2,4-diamine;

(162) 1-((2-((2-(1-(2,2-Difluoroethyl)-1H-pyrazol-4-yl)pyrimidin-4-yl)amino)-5-(1-(difluoromethyl)-1H-pyrazol-3-yl)pyridin-4-yl)amino)piperidin-4-ol;

(163) 1-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)piperidin-4-ol;

(164) $N^2$-(2-(1-(Cyclopropylsulfonyl)-1H-pyrazol-4-yl)pyrimidin-4-yl)-5-(4-(difluoromethyl)thiazol-2-yl)-$N^4$-((1s,4s)-4-fluorocyclohexyl)pyridine-2,4-diamine;

(167) (1s,4s)-4-((2-((2-(1-(Cyclopropylsulfonyl)-1H-pyrazol-4-yl)pyrimidin-4-yl)amino)-5-(3-(trifluoromethyl)-1H-pyrazol-1-yl)pyridin-4-yl)amino)-1-methylcyclohexan-1-ol;

(168) (1s,4s)-4-((2-((2-(1-(Cyclopropylsulfonyl)-1H-pyrazol-4-yl)pyrimidin-4-yl)amino)-5-(3-methyl-1H-pyrazol-1-yl)pyridin-4-yl)amino)-1-methylcyclohexan-1-ol;

(172) (1s,4s)-4-((2-((2-(1-(Cyclopropylsulfonyl)-1H-pyrazol-4-yl)pyrimidin-4-yl)amino)-5-(3-(difluoromethyl)-1H-pyrazol-1-yl)pyridin-4-yl)amino)-1-methylcyclohexan-1-ol;

(173) (1 s,4s)-4-((5-(1-(Difluoromethyl)-1H-pyrazol-3-yl)-2-((2-(1-(3-hydroxy-2,2-dimethylpropyl)-1H-pyrazol-4-yl)pyrimidin-4-yl)amino)pyridin-4-yl)amino)-1-methylcyclohexan-1-ol;

(174) $N^2$-(2-(1-(Cyclopropylsulfonyl)-1H-pyrazol-4-yl)pyrimidin-4-yl)-$N^4$-((1s,4s)-4-fluorocyclohexyl)-5-(1-methyl-1H-pyrazol-3-yl)pyridine-2,4-diamine;

(175) $N^2$-(2-(1-(Cyclopropylsulfonyl)-1H-pyrazol-4-yl)pyrimidin-4-yl)-$N^4$-((1s,4s)-4-fluorocyclohexyl)-5-(1-methyl-5-(trifluoromethyl)-1H-pyrazol-3-yl)pyridine-2,4-diamine;

(176) (1 s,4s)-4-((5-(1-(Difluoromethyl)-1H-pyrazol-3-yl)-2-((2-(3,4-dihydro-2H-pyrano[2,3-b]pyridin-6-yl)pyrimidin-4-yl)amino)pyridin-4-yl)amino)-1-methylcyclohexan-1-ol;

(177) (1s,4s)-4-((2-((2-(1-(2,2-Difluoroethyl)-1H-pyrazol-4-yl)pyrimidin-4-yl)amino)-5-(3-(difluoromethyl)-1H-pyrazol-1-yl)pyridin-4-yl)amino)-1-methylcyclohexan-1-ol;

(179) $N^2$-(2-(1-(Cyclopropylsulfonyl)-1H-pyrazol-4-yl)pyrimidin-4-yl)-$N^4$-(3,3-difluorocyclopentyl)-5-(1-(difluoromethyl)-1H-pyrazol-3-yl)pyridine-2,4-diamine;

(180) $N^2$-(2-(1-(2,2-Difluoroethyl)-1H-pyrazol-4-yl)pyrimidin-4-yl)-5-(1-(difluoromethyl)-1H-pyrazol-3-yl)-$N^4$-(3-fluorocyclohexyl)pyridine-2,4-diamine;

(181) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(3-fluorocyclohexyl)pyridine-2,4-diamine;

(182) (1s,4s)-4-((2-((2-(1-(Cyclopropylsulfonyl)-1H-pyrazol-4-yl)pyrimidin-4-yl)amino)-5-(3-methyl-4-(trifluoromethyl)-1H-pyrazol-1-yl)pyridin-4-yl)amino)-1-methylcyclohexan-1-ol;

(183) (1s,4s)-4-((2-((2-(1-(Cyclopropylsulfonyl)-1H-pyrazol-4-yl)pyrimidin-4-yl)amino)-5-(3-(methylsulfonyl)-1H-pyrazol-1-yl)pyridin-4-yl)amino)-1-methylcyclohexan-1-ol;

(184) (1s,4s)-4-((2-((2-(1-(Cyclopropylsulfonyl)-1H-pyrazol-4-yl)pyrimidin-4-yl)amino)-5-(4-methyl-1H-pyrazol-1-yl)pyridin-4-yl)amino)-1-methylcyclohexan-1-ol;

(185) $N^2$-(2-(1-(Cyclopropylsulfonyl)-1H-pyrazol-4-yl)pyrimidin-4-yl)-$N^4$-((1s,4s)-4-(2,2-difluoroethyl)cyclohexyl)-5-(1-(difluoromethyl)-1H-pyrazol-3-yl)pyridine-2,4-diamine;

(186) (1s,4s)-4-((2-((2-(1-(Cyclopropylsulfonyl)-1H-pyrazol-4-yl)pyrimidin-4-yl)amino)-5-(4-methyl-3-(trifluoromethyl)-1H-pyrazol-1-yl)pyridin-4-yl)amino)-1-methylcyclohexan-1-ol;

(187) (1s,4s)-4-((2-((2-(1-(Cyclopropylsulfonyl)-1H-pyrazol-4-yl)pyrimidin-4-yl)amino)-5-(3-(difluoromethoxy)-1H-pyrazol-1-yl)pyridin-4-yl)amino)-1-methylcyclohexan-1-ol;

(188) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(hydroxymethyl)cyclohexan-1-ol;

(189) ((1r,3r)-3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)cyclobutyl)methanol;

(190) (4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-fluorocyclohexyl)methanol;

(191) $N^2$-(2-(1-(Cyclopropylsulfonyl)-1H-pyrazol-4-yl)pyrimidin-4-yl)-$N^4$-(3-((2,2-difluoroethyl)amino)cyclohexyl)-5-(1-(difluoromethyl)-1H-pyrazol-3-yl)pyridine-2,4-diamine;

(192) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1 r,4r)-4-((methylamino)methyl)cyclohexyl)methyl)pyridine-2,4-diamine;

(193) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1 r,4r)-4-(methylamino)cyclohexyl)methyl)pyridine-2,4-diamine;

(194) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(3-((2-fluoroethyl)amino)cyclohexyl)pyridine-2,4-diamine;

(195) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-((dimethylamino)methyl)cyclohexyl)pyridine-2,4-diamine;

(196) ((2R,5S)-5-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)tetrahydro-2H-pyran-2-yl)methanol;

(197) (3-(((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)methyl)oxetan-3-yl)methanol;

(198) ((1r,4r)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(199) (1s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-((dimethylamino)methyl)cyclohexan-1-ol;

(200) (1 s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-(difluoromethyl)cyclohexan-1-ol;

(201) (1 s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N,N-dimethylcyclohexane-1-carboxamide;

(202) ((1S,3S)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)methanol;

(203) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1 s,3s)-3-((dimethylamino)methyl)cyclobutyl)methyl)pyridine-2,4-diamine;

(204) (1 s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-N-(2,2-difluoroethyl)-N-methylcyclohexane-1-carboxamide;

(205) 2-((1 s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclohexyl)-N,N-dimethylacetamide;

(206) $N^2$-(2-(1-(Cyclopropylsulfonyl)-1H-pyrazol-4-yl)pyrimidin-4-yl)-$N^4$-((1s,4s)-4-(((2,2-difluoroethyl)(methyl)amino)methyl)cyclohexyl)-5-(1-(difluoromethyl)-1H-pyrazol-3-yl)pyridine-2,4-diamine;

(207) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-((dimethylamino)methyl)-4-methylcyclohexyl)pyridine-2,4-diamine;

(208) $N^4$-((1 s,4s)-4-(Azetidin-1-ylmethyl)cyclohexyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(209) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(((1 r,3r)-3-((dimethylamino)methyl)cyclobutyl)methyl)pyridine-2,4-diamine;

(210) $N^4$-(sec-Butyl)-$N^2$-(2-(1-(cyclopropylsulfonyl)-1H-pyrazol-4-yl)pyrimidin-4-yl)-5-(1-(difluoromethyl)-1H-pyrazol-3-yl)pyridine-2,4-diamine;

(211) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-(dimethylamino)ethyl)cyclohexyl)pyridine-2,4-diamine;

(212) (R)-$N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-fluorobutan-2-yl)pyridine-2,4-diamine;

(213) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(1,1-difluoropropan-2-yl)pyridine-2,4-diamine;

(214) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-fluorocyclohexyl)pyridine-2,4-diamine;

(215) $N^2$-(2-(1-(Cyclopropylsulfonyl)-1H-pyrazol-4-yl)pyrimidin-4-yl)-$N^4$-(4,4-difluorocyclohexyl)-5-(1-(difluoromethyl)-1H-pyrazol-3-yl)pyridine-2,4-diamine;

(216) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-(2-fluoroethyl)cyclohexyl)pyridine-2,4-diamine;

(217) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(1-(2-fluoroethyl)piperidin-4-yl)pyridine-2,4-diamine;

(218) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(1-(2-fluoroethyl)piperidin-3-yl)pyridine-2,4-diamine;

(219) $N^2$-(2-(1-(Cyclopropylsulfonyl)-1H-pyrazol-4-yl)pyrimidin-4-yl)-$N^4$-(1-(2,2-difluoroethyl)piperidin-4-yl)-5-(1-(difluoromethyl)-1H-pyrazol-3-yl)pyridine-2,4-diamine;

(220) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1s,4s)-4-fluoro-4-methylcyclohexyl)pyridine-2,4-diamine;

(221) (1 s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(hydroxymethyl)cyclohexan-1-ol;

(222) (4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-fluorocyclohexyl)methanol;

(223) ((1r,3r)-3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)cyclobutyl)methanol;

(224) $N^2$-(2-(1-(Cyclopropylsulfonyl)-1H-pyrazol-4-yl)pyrimidin-4-yl)-$N^4$-(3-((2,2-difluoroethyl)amino)cyclohexyl)-5-(1-methyl-1H-pyrazol-3-yl)pyridine-2,4-diamine;

(225) $N^2$-(2-(1-(Cyclopropylsulfonyl)-1H-pyrazol-4-yl)pyrimidin-4-yl)-$N^4$-(3-((2-fluoroethyl)amino)cyclohexyl)-5-(1-methyl-1H-pyrazol-3-yl)pyridine-2,4-diamine;

(226) $N^2$-(2-(1-(Cyclopropylsulfonyl)-1H-pyrazol-4-yl)pyrimidin-4-yl)-$N^4$-((1s,4s)-4-((dimethylamino)methyl)cyclohexyl)-5-(1-methyl-1H-pyrazol-3-yl)pyridine-2,4-diamine;

(227) ((2R,5S)-5-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)tetrahydro-2H-pyran-2-yl)methanol;

(228) (3-(((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)methyl)oxetan-3-yl)methanol;

(229) ((1r,4r)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol;

(230) (1 s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-((dimethylamino)methyl)cyclohexan-1-ol;

(231) (1 s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-1-(difluoromethyl)cyclohexan-1-ol;

(232) (1 s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N,N-dimethylcyclohexane-1-carboxamide;

(233) ((1S,3S)-3-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)methanol;

(234) $N^2$-(2-(1-(Cyclopropylsulfonyl)-1H-pyrazol-4-yl)pyrimidin-4-yl)-$N^4$-(((1s,3s)-3-((dimethylamino)methyl)cyclobutyl)methyl)-5-(1-methyl-1H-pyrazol-3-yl)pyridine-2,4-diamine;

(235) (1 s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)-N-(2,2-difluoroethyl)-N-methylcyclohexane-1-carboxamide;

(236) 2-((1 s,4s)-4-((2-((2-(1-(Cyclopropylsulfonyl)-1H-pyrazol-4-yl)pyrimidin-4-yl)amino)-5-(1-methyl-1H-pyrazol-3-yl)pyridin-4-yl)amino)cyclohexyl)-N,N-dimethylacetamide;

(237) $N^2$-(2-(1-(Cyclopropylsulfonyl)-1H-pyrazol-4-yl)pyrimidin-4-yl)-$N^4$-((1s,4s)-4-(((2,2-difluoroethyl)(methyl)amino)methyl)cyclohexyl)-5-(1-methyl-1H-pyrazol-3-yl)pyridine-2,4-diamine;

(238) $N^2$-(2-(1-(Cyclopropylsulfonyl)-1H-pyrazol-4-yl)pyrimidin-4-yl)-$N^4$-(4-((dimethylamino)methyl)-4-methylcyclohexyl)-5-(1-methyl-1H-pyrazol-3-yl)pyridine-2,4-diamine;

(239) $N^2$-(2-(1-(Cyclopropylsulfonyl)-1H-pyrazol-4-yl)pyrimidin-4-yl)-$N^4$-(((1r,3r)-3-((dimethylamino)methyl)cyclobutyl)methyl)-5-(1-methyl-1H-pyrazol-3-yl)pyridine-2,4-diamine;

(240) $N^2$-(2-(1-(Cyclopropylsulfonyl)-1H-pyrazol-4-yl)pyrimidin-4-yl)-$N^4$-((1s,4s)-4-(2-(dimethylamino)ethyl)cyclohexyl)-5-(1-methyl-1H-pyrazol-3-yl)pyridine-2,4-diamine;

(241) (1 s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)-1-methylcyclohexan-1-ol;

(242) $N^2$-(2-(1-(Cyclopropylsulfonyl)-1H-pyrazol-4-yl)pyrimidin-4-yl)-5-(1-(2,2-difluoroethyl)-1H-pyrazol-3-yl)-$N^4$-((1 s,4s)-4-((2-fluoroethyl)amino)cyclohexyl)pyridine-2,4-diamine;

(243) 2-((1 s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)propan-2-ol;

(244) ((1s,4s)-4-((2-((2-(1-(Cyclopropylsulfonyl)-1H-pyrazol-4-yl)pyrimidin-4-yl)amino)-5-(1-(2,2-difluoroethyl)-1H-pyrazol-3-yl)pyridin-4-yl)amino)cyclohexyl)methanol;

(245) $N^2$-(2-(1-(Cyclopropylsulfonyl)-1H-pyrazol-4-yl)pyrimidin-4-yl)-$N^4$-((1s,4s)-4-(((2,2-difluoroethyl)(methyl)amino)methyl)cyclohexyl)-5-(1-(2,2-difluoroethyl)-1H-pyrazol-3-yl)pyridine-2,4-diamine;

(246) $N^2$-(2-(1-(Cyclopropylsulfonyl)-1H-pyrazol-4-yl)pyrimidin-4-yl)-5-(1-(2,2-difluoroethyl)-1H-pyrazol-3-yl)-$N^4$-(4-((dimethylamino)methyl)-4-methylcyclohexyl)pyridine-2,4-diamine;

(247) $N^4$-((1 s,4s)-4-(Azetidin-1-ylmethyl)cyclohexyl)-$N^2$-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine;

(248) $N^2$-(2-(1-(Cyclopropylsulfonyl)-1H-pyrazol-4-yl)pyrimidin-4-yl)-5-(1-(2,2-difluoroethyl)-1H-pyrazol-3-yl)-$N^4$-isopropylpyridine-2,4-diamine;

(249) $N^2$-(2-(1-(Cyclopropylsulfonyl)-1H-pyrazol-4-yl)pyrimidin-4-yl)-5-(1-(2,2-difluoroethyl)-1H-pyrazol-3-yl)-$N^4$-(((1r,3r)-3-((dimethylamino)methyl)cyclobutyl)methyl)pyridine-2,4-diamine;

(250) $N^4$-(sec-Butyl)-$N^2$-(2-(1-(cyclopropylsulfonyl)-1H-pyrazol-4-yl)pyrimidin-4-yl)-5-(1-(2,2-difluoroethyl)-1H-pyrazol-3-yl)pyridine-2,4-diamine;

(251) $N^2$-(2-(1-(Cyclopropylsulfonyl)-1H-pyrazol-4-yl)pyrimidin-4-yl)-5-(1-(2,2-difluoroethyl)-1H-pyrazol-3-yl)-$N^4$-((1 s,4s)-4-(2-(dimethylamino)ethyl)cyclohexyl)pyridine-2,4-diamine;

(252) (1 s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(253) ((1s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol;

(254) 2-((1 s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)propan-2-ol;

(255) $N^2$-(2-(1-(Cyclopropylsulfonyl)-1H-pyrazol-4-yl)pyrimidin-4-yl)-$N^4$-((1s,4s)-4-((2-fluoroethyl)amino)cyclohexyl)-5-(1-methyl-5-(trifluoromethyl)-1H-pyrazol-3-yl)pyridine-2,4-diamine;

(256) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(1-methyl-5-(trifluoromethyl)-1H-pyrazol-3-yl)pyridine-2,4-diamine;

(257) (1 s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)-N,N-dimethylcyclohexane-1-carboxamide;

(258) 2-((1 s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)-N,N-dimethylacetamide;

(259) N²-(2-(1-(Cyclopropylsulfonyl)-1H-pyrazol-4-yl)pyrimidin-4-yl)-N⁴-((1s,4s)-4-(((2,2-difluoroethyl)(methyl)amino)methyl)cyclohexyl)-5-(1-methyl-5-(trifluoromethyl)-1H-pyrazol-3-yl)pyridine-2,4-diamine;

(260) ((1S,3S)-3-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)methanol (261) (1R,3S)-3-(((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)methyl)cyclopentan-1-ol;

(262) 2-((1 s,4s)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(263) 2-((1r,4r)-4-((2-((2-(1-(Cyclopropylsulfonyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(264) N⁴-((1s,4s)-4-(Azetidin-1-ylmethyl)cyclohexyl)-N²-(2-(1-(cyclopropylsulfonyl)-1H-pyrazol-4-yl)pyrimidin-4-yl)-5-(1-methyl-5-(trifluoromethyl)-1H-pyrazol-3-yl)pyridine-2,4-diamine;

(265) 2-((1 s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)propan-2-ol;

(266) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(1-(2,2,2-trifluoroethyl)-1H-pyrazol-3-yl)pyridine-2,4-diamine;

(267) N²-(2-(1-(Cyclopropylsulfonyl)-1H-pyrazol-4-yl)pyrimidin-4-yl)-N⁴-(4-((dimethylamino)methyl)-4-methylcyclohexyl)-5-(1-(2,2,2-trifluoroethyl)-1H-pyrazol-3-yl)pyridine-2,4-diamine;

(268) (1R,3S)-3-(((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)methyl)cyclopentan-1-ol;

(269) 2-((1 s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol;

(270) 2-((1r,4r)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol;

(271) ((1S,3S)-3-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)methanol;

(272) N⁴-((1 s,4s)-4-(Azetidin-1-ylmethyl)cyclohexyl)-N²-(2-(1-(cyclopropylsulfonyl)-1H-pyrazol-4-yl)pyrimidin-4-yl)-5-(1-(2,2,2-trifluoroethyl)-1H-pyrazol-3-yl)pyridine-2,4-diamine;

(273) (1 s,4s)-4-((2-((2-(1-(Cyclopropylsulfonyl)-1H-pyrazol-4-yl)pyrimidin-4-yl)amino)-5-(1-(difluoromethyl)-1H-imidazol-4-yl)pyridin-4-yl)amino)-1-methylcyclohexan-1-ol;

(274) (1 s,4s)-4-((2-((2-(1-(Cyclopropylsulfonyl)-1H-pyrazol-4-yl)pyrimidin-4-yl)amino)-5-(6,7-dihydro-5H-pyrrolo[1,2-a]imidazol-2-yl)pyridin-4-yl)amino)-1-methylcyclohexan-1-ol;

(275) (1 s,4s)-4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-(hydroxymethyl)cyclohexan-1-ol;

(276) (4-((2-((2-(1-(Cyclopropylsulfonyl)-1H-pyrazol-4-yl)pyrimidin-4-yl)amino)-5-(4,5,6,7-tetrahydropyrazolo[1,5-a]pyridin-2-yl)pyridin-4-yl)amino)-1-fluorocyclohexyl)methanol;

(277) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(4,5,6,7-tetrahydropyrazolo[1,5-a]pyridin-2-yl)pyridine-2,4-diamine;

(278) 2-((1 s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)propan-2-ol;

(279) (3-(((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)methyl)oxetan-3-yl)methanol;

(280) ((1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)methanol;

(281) 2-((1 s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)cyclohexyl)propan-2-ol;

(282) ((1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)methanol;

(283) 2-((1 s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)cyclohexyl)propan-2-ol;

(284) N²-(2-(1-(Cyclopropylsulfonyl)-1H-pyrazol-4-yl)pyrimidin-4-yl)-N⁴-((1s,4s)-4-((dimethylamino)methyl)cyclohexyl)-5-(1-(oxetan-3-yl)-1H-pyrazol-3-yl)pyridine-2,4-diamine;

(285) (1 s,4s)-4-((2-((2-(1-(Cyclopropylsulfonyl)-1H-pyrazol-4-yl)pyrimidin-4-yl)amino)-5-(1-(trifluoromethyl)-1H-pyrazol-3-yl)pyridin-4-yl)amino)-1-methylcyclohexan-1-ol;

(286) N²-(2-(1-(Cyclopropylsulfonyl)-1H-pyrazol-4-yl)pyrimidin-4-yl)-N⁴-((1s,4s)-4-fluorocyclohexyl)-5-(1-(trifluoromethyl)-1H-pyrazol-3-yl)pyridine-2,4-diamine;

(287) (1 s,4s)-4-((2-((2-(1-(Cyclopropylsulfonyl)-1H-pyrazol-4-yl)pyrimidin-4-yl)amino)-5-(1-(1-methylpiperidin-4-yl)-1H-pyrazol-3-yl)pyridin-4-yl)amino)-1-methylcyclohexan-1-ol;

(288) (1 s,4s)-4-((2-((2-(1-(Cyclopropylsulfonyl)-1H-pyrazol-4-yl)pyrimidin-4-yl)amino)-5-(1-(3-(dimeth- (288) ...ylamino)propyl)-1H-pyrazol-3-yl)pyridin-4-yl)amino)-1-methylcyclohexan-1-ol;

(289) (1s,4s)-4-((2-((2-(1-(Cyclopropylsulfonyl)-1H-pyrazol-4-yl)pyrimidin-4-yl)amino)-5-(1-(2,2,2-trifluoroethyl)-1H-pyrazol-3-yl)pyridin-4-yl)amino)-1-methylcyclohexan-1-ol;

(290) (1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)-1-methylcyclohexan-1-ol;

(291) (1s,4s)-4-((2-((2-(1-(Cyclopropylsulfonyl)-1H-pyrazol-4-yl)pyrimidin-4-yl)amino)-5-(1,5-dimethyl-1H-pyrazol-3-yl)pyridin-4-yl)amino)-1-methylcyclohexan-1-ol;

(292) (1s,4s)-4-((2-((2-(1-(Cyclopropylsulfonyl)-1H-pyrazol-4-yl)pyrimidin-4-yl)amino)-5-(1-(oxetan-3-yl)-1H-pyrazol-3-yl)pyridin-4-yl)amino)-1-methylcyclohexan-1-ol;

(293) (1s,4s)-4-((2-((2-(1-(Cyclopropylsulfonyl)-1H-pyrazol-4-yl)pyrimidin-4-yl)amino)-5-(5-(2-hydroxypropan-2-yl)-1-methyl-1H-pyrazol-3-yl)pyridin-4-yl)amino)-1-methylcyclohexan-1-ol;

(294) (1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)-1-methylcyclohexan-1-ol;

(295) (1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)-1-methylcyclohexan-1-ol;

(296) ((1s,4s)-4-((2-((2-(1-(Cyclopropylsulfonyl)-1H-pyrazol-4-yl)pyrimidin-4-yl)amino)-5-(1-(3-(dimethylamino)propyl)-1H-pyrazol-3-yl)pyridin-4-yl)amino)cyclohexyl)methanol;

(297) ((1s,4s)-4-((5-(1-Cyclopropyl-1H-pyrazol-3-yl)-2-((2-(1-(cyclopropylsulfonyl)-1H-pyrazol-4-yl)pyrimidin-4-yl)amino)pyridin-4-yl)amino)cyclohexyl)methanol;

(298) 2-(3-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)-1-methyl-1H-pyrazol-5-yl)propan-2-ol;

(299) 2-((1s,4s)-4-((2-((2-(1-(Cyclopropylsulfonyl)-1H-pyrazol-4-yl)pyrimidin-4-yl)amino)-5-(1-(methoxymethyl)-1H-pyrazol-3-yl)pyridin-4-yl)amino)cyclohexyl)propan-2-ol;

(300) 2-((1s,4s)-4-((2-((2-(1-(Cyclopropylsulfonyl)-1H-pyrazol-4-yl)pyrimidin-4-yl)amino)-5-(1-(3,3,3-trifluoropropyl)-1H-pyrazol-3-yl)pyridin-4-yl)amino)cyclohexyl)propan-2-ol;

(301) $N^2$-(2-(1-(Cyclopropylsulfonyl)-1H-pyrazol-4-yl)pyrimidin-4-yl)-5-(1-(3-(dimethylamino)propyl)-1H-pyrazol-3-yl)-$N^4$-((1s,4s)-4-((2-fluoroethyl)amino)cyclohexyl)pyridine-2,4-diamine;

(302) 2-(3-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)-1-methyl-1H-pyrazol-5-yl)propan-2-ol;

(303) $N^2$-(2-(1-(Cyclopropylsulfonyl)-1H-pyrazol-4-yl)pyrimidin-4-yl)-$N^4$-isopropyl-5-(1-(methoxymethyl)-1H-pyrazol-3-yl)pyridine-2,4-diamine;

(304) $N^2$-(2-(1-(Cyclopropylsulfonyl)-1H-pyrazol-4-yl)pyrimidin-4-yl)-$N^4$-isopropyl-5-(1-(3,3,3-trifluoropropyl)-1H-pyrazol-3-yl)pyridine-2,4-diamine;

(305) $N^2$-(2-(1-(Cyclopropylsulfonyl)-1H-pyrazol-4-yl)pyrimidin-4-yl)-$N^4$-((1s,4s)-4-fluorocyclohexyl)-5-(1-(2,2,2-trifluoroethyl)-1H-pyrazol-3-yl)pyridine-2,4-diamine;

(306) $N^2$-(2-(1-(Cyclopropylsulfonyl)-1H-pyrazol-4-yl)pyrimidin-4-yl)-$N^4$-((1s,4s)-4-fluorocyclohexyl)-5-(1-(3,3,3-trifluoropropyl)-1H-pyrazol-3-yl)pyridine-2,4-diamine;

(307) (1s,4s)-4-((2-((2-(1-(Cyclopropylsulfonyl)-1H-pyrazol-4-yl)pyrimidin-4-yl)amino)-5-(4,4-difluoropiperidin-1-yl)-1-methyl-1H-pyrazol-3-yl)pyridin-4-yl)amino)-1-methylcyclohexan-1-ol;

(308) (1s,4s)-4-((5-(1-(Difluoromethyl)-1H-pyrazol-3-yl)-2-((2-(1-(ethylsulfonyl)-1H-pyrazol-4-yl)pyrimidin-4-yl)amino)pyridin-4-yl)amino)-1-methylcyclohexan-1-ol;

(309) (1s,4s)-4-((5-(1-(Difluoromethyl)-1H-pyrazol-3-yl)-2-((2-(1-(ethylsulfonyl)-1H-pyrazol-3-yl)pyrimidin-4-yl)amino)pyridin-4-yl)amino)-1-methylcyclohexan-1-ol;

(310) (1s,4s)-4-((5-(1-(Difluoromethyl)-1H-pyrazol-3-yl)-2-((2-(1-(methoxymethyl)-1H-pyrazol-4-yl)pyrimidin-4-yl)amino)pyridin-4-yl)amino)-1-methylcyclohexan-1-ol;

(311) 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrazole-1-carboxamide;

(313) (1s,4s)-4-((5-(1-(Difluoromethyl)-1H-pyrazol-3-yl)-2-((2-((2-(methylsulfonyl)phenyl)amino)pyrimidin-4-yl)amino)pyridin-4-yl)amino)-1-methylcyclohexan-1-ol;

(314) (1s,4s)-4-((5-(1-(Difluoromethyl)-1H-pyrazol-3-yl)-2-((2-(1-(tetrahydro-2H-pyran-2-yl)-1H-pyrazol-4-yl)pyrimidin-4-yl)amino)pyridin-4-yl)amino)-1-methylcyclohexan-1-ol;

(315) 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N,3-trimethyl-1H-pyrazole-1-sulfonamide;

(316) (1s,4s)-4-((2-((2-(1-(Cyclopropylsulfonyl)-1H-pyrazol-4-yl)-5-fluoropyrimidin-4-yl)amino)-5-(1-(difluoromethyl)-1H-pyrazol-3-yl)pyridin-4-yl)amino)-1-methylcyclohexan-1-ol;

(317) 4-(4-((5-(1-(Difluoromethyl)-1H-pyrazol-3-yl)-4-(((1s,4s)-4-hydroxy-4-methylcyclohexyl)amino)pyridin-2-yl)amino)pyrimidin-2-yl)-N,N-dimethyl-1H-pyrazole-1-sulfonamide;

(318) (1s,4s)-4-((5-(1-(Difluoromethyl)-1H-pyrazol-3-yl)-2-((2-(1-(tetrahydrofuran-2-yl)-1H-pyrazol-4-yl)pyrimidin-4-yl)amino)pyridin-4-yl)amino)-1-methylcyclohexan-1-ol;

(319) (1s,4s)-4-((5-(1-(Difluoromethyl)-1H-pyrazol-3-yl)-2-((2-(5-fluoro-1,3-dimethyl-1H-pyrazol-4-yl)pyrimidin-4-yl)amino)pyridin-4-yl)amino)-1-methylcyclohexan-1-ol;

(320) (1s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)-1-methylcyclohexan-1-ol;

(321) (1s,4s)-4-((2-((2-(1-(2,2-Difluoroethyl)-3,5-dimethyl-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(322) (1 s,4s)-4-((5-(1-(Difluoromethyl)-1H-pyrazol-3-yl)-2-((2-(1-(2,2,3,3-tetrafluoropropyl)-1H-pyrazol-4-yl)pyrimidin-4-yl)amino)pyridin-4-yl)amino)-1-methylcyclohexan-1-ol;

(323) (1 s,4s)-4-((5-(1-(Difluoromethyl)-1H-pyrazol-3-yl)-2-((2-(1-(pyrrolidin-1-ylsulfonyl)-1H-pyrazol-4-yl)pyrimidin-4-yl)amino)pyridin-4-yl)amino)-1-methylcyclohexan-1-ol;

(324) (1 s,4s)-4-((5-(1-(Difluoromethyl)-1H-pyrazol-3-yl)-2-((2-(1-((3-fluoroazetidin-1-yl)sulfonyl)-1H-pyrazol-4-yl)pyrimidin-4-yl)amino)pyridin-4-yl)amino)-1-methylcyclohexan-1-ol;

(325) $N^2$-(2-(1-(Cyclopropylsulfonyl)-1H-pyrazol-4-yl)-5-fluoropyrimidin-4-yl)-5-(1-(difluoromethyl)-1H-pyrazol-3-yl)-$N^4$-((1s,4s)-4-(2-(dimethylamino)ethyl)cyclohexyl)pyridine-2,4-diamine;

(326) 2-((1 s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)cyclohexyl)ethan-1-ol;

(327) $N^4$-((1 s,4s)-4-(Azetidin-1-ylmethyl)cyclohexyl)-$N^2$-(2-(1-(cyclopropylsulfonyl)-1H-pyrazol-4-yl)-5-fluoropyrimidin-4-yl)-5-(1-(difluoromethyl)-1H-pyrazol-3-yl)pyridine-2,4-diamine;

(328) (1 s,4s)-4-((2-((2-(1-(Cyclopropylsulfonyl)-1H-pyrazol-4-yl)-5-fluoropyrimidin-4-yl)amino)-5-(1-methyl-5-(trifluoromethyl)-1H-pyrazol-3-yl)pyridin-4-yl)amino)-1-methylcyclohexan-1-ol;

(329) (1 s,4s)-1-Methyl-4-((5-(1-methyl-5-(trifluoromethyl)-1H-pyrazol-3-yl)-2-((2-(1-(2,2,2-trifluoroethyl)-1H-pyrazol-4-yl)pyrimidin-4-yl)amino)pyridin-4-yl)amino)cyclohexan-1-ol;

(330) 4-(4-((4-(((1s,4s)-4-Hydroxy-4-methylcyclohexyl)amino)-5-(1-methyl-5-(trifluoromethyl)-1H-pyrazol-3-yl)pyridin-2-yl)amino)pyrimidin-2-yl)-N,N-dimethyl-1H-pyrazole-1-sulfonamide;

(331) (1 s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)-1-methylcyclohexan-1-ol;

(332) (1 s,4s)-1-Methyl-4-((2-((2-(3-methyl-1-(2,2,2-trifluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexan-1-ol;

(333) 2-((1 s,4s)-4-((2-((2-(1-(2,2-Difluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(334) 2-((1 s,4s)-4-((2-((2-(3-Methyl-1-(2,2,2-trifluoroethyl)-1H-pyrazol-4-yl)pyrimidin-4-yl)amino)-5-(1-methyl-5-(trifluoromethyl)-1H-pyrazol-3-yl)pyridin-4-yl)amino)cyclohexyl)ethan-1-ol;

(335) (1 s,4s)-4-((5-(1-(2,2-Difluoroethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)-1-methylcyclohexan-1-ol;

(336) 2-((1 s,4s)-4-((2-((2-(1-(Cyclopropylsulfonyl)-1H-pyrazol-4-yl)-5-fluoropyrimidin-4-yl)amino)-5-(1-(2,2-difluoroethyl)-1H-pyrazol-3-yl)pyridin-4-yl)amino)cyclohexyl)ethan-1-ol;

(337) 2-((1 s,4s)-4-((5-(1-(2,2-Difluoroethyl)-1H-pyrazol-3-yl)-2-((2-(3-methyl-1-(2,2,2-trifluoroethyl)-1H-pyrazol-4-yl)pyrimidin-4-yl)amino)pyridin-4-yl)amino)cyclohexyl)ethan-1-ol;

(338) 2-((1 s,4s)-4-((2-((2-(1-(2,2-Difluoroethyl)-1H-pyrazol-4-yl)pyrimidin-4-yl)amino)-5-(1-(2,2,2-trifluoroethyl)-1H-pyrazol-3-yl)pyridin-4-yl)amino)cyclohexyl)ethan-1-ol;

(339) $N^2$-(2-(1-(2,2-Difluoroethyl)-1H-pyrazol-4-yl)pyrimidin-4-yl)-$N^4$-((1s,4s)-4-fluorocyclohexyl)-5-(1-(2,2,2-trifluoroethyl)-1H-pyrazol-3-yl)pyridine-2,4-diamine;

(340) (1 s,4s)-4-((2-((2-(1-(2,2-Difluoroethyl)-1H-pyrazol-4-yl)pyrimidin-4-yl)amino)-5-(1-(trifluoromethyl)-1H-pyrazol-3-yl)pyridin-4-yl)amino)-1-methylcyclohexan-1-ol;

(341) (1 s,4s)-1-Methyl-4-((2-((2-(3-methyl-1-(2,2,2-trifluoroethyl)-1H-pyrazol-4-yl)pyrimidin-4-yl)amino)-5-(1-(trifluoromethyl)-1H-pyrazol-3-yl)pyridin-4-yl)amino)cyclohexan-1-ol;

(342) (1 s,4s)-4-((2-((2-(1-(2,2-Difluoroethyl)-1H-pyrazol-4-yl)pyrimidin-4-yl)amino)-5-(1-(1-methylpiperidin-4-yl)-1H-pyrazol-3-yl)pyridin-4-yl)amino)-1-methylcyclohexan-1-ol;

(343) (1 s,4s)-4-((5-(1-(2,2-Difluoroethyl)-1H-pyrazol-3-yl)-2-((2-(1-(2,2-difluoroethyl)-1H-pyrazol-4-yl)pyrimidin-4-yl)amino)pyridin-4-yl)amino)-1-methylcyclohexan-1-ol;

(344) (1 s,4s)-4-((5-(1-(2,2-Difluoroethyl)-1H-pyrazol-3-yl)-2-((2-(1-(2,2,2-trifluoroethyl)-1H-pyrazol-4-yl)pyrimidin-4-yl)amino)pyridin-4-yl)amino)-1-methylcyclohexan-1-ol;

(345) (1 s,4s)-4-((2-((2-(1-(Cyclopropylsulfonyl)-1H-pyrazol-4-yl)-5-fluoropyrimidin-4-yl)amino)-5-(1-(2,2-difluoroethyl)-1H-pyrazol-3-yl)pyridin-4-yl)amino)-1-methylcyclohexan-1-ol;

(346) (1s,4s)-4-((2-((2-(3,3-Difluoro-4-(hydroxymethyl)pyrrolidin-1-yl)pyrimidin-4-yl)amino)-5-(1-(difluoromethyl)-1H-pyrazol-3-yl)pyridin-4-yl)amino)-1-methylcyclohexan-1-ol;

(347) (1 s,4s)-4-((5-(1-(Difluoromethyl)-1H-pyrazol-3-yl)-2-((2-(4-(hydroxymethyl)-3,3-dimethylpyrrolidin-1-yl)pyrimidin-4-yl)amino)pyridin-4-yl)amino)-1-methylcyclohexan-1-ol;

(348) 1-(4-((5-(1-(Difluoromethyl)-1H-pyrazol-3-yl)-4-(((1 s,4s)-4-hydroxy-4-methylcyclohexyl)amino)pyridin-2-yl)amino)pyrimidin-2-yl)-3,3-difluoropiperidin-4-ol;

(349) 1-(4-((5-(1-(Difluoromethyl)-1H-pyrazol-3-yl)-4-(((1 s,4s)-4-hydroxy-4-methylcyclohexyl)amino)pyridin-2-yl)amino)pyrimidin-2-yl)-4,4-difluoropyrrolidin-3-ol;

(350) 1-(4-((5-(1-(Difluoromethyl)-1H-pyrazol-3-yl)-4-(((1 s,4s)-4-hydroxy-4-methylcyclohexyl)amino)pyridin-2-yl)amino)pyrimidin-2-yl)-4,4-difluoropiperidin-3-ol;

(351) (S)-1-(4-((5-(1-(Difluoromethyl)-1H-pyrazol-3-yl)-4-(((1s,4R)-4-hydroxy-4-methylcyclohexyl)amino)pyridin-2-yl)amino)pyrimidin-2-yl)piperidin-3-ol;

(352) (R)-1-(4-((5-(1-(Difluoromethyl)-1H-pyrazol-3-yl)-4-(((1s,4S)-4-hydroxy-4-methylcyclohexyl)amino)pyridin-2-yl)amino)pyrimidin-2-yl)piperidin-3-ol;

(353) 3,3-Difluoro-1-(4-((4-(((1 s,4s)-4-hydroxy-4-methylcyclohexyl)amino)-5-(1-methyl-5-(trifluoromethyl)-1H-pyrazol-3-yl)pyridin-2-yl)amino)pyrimidin-2-yl)piperidin-4-ol;

(354) (1 s,4s)-4-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(355) (1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)-1-methylcyclohexan-1-ol;

(356) (1s,4s)-4-((2-((2-(1-(Cyclopropylsulfonyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol;

(357) (1s,4s)-4-((2-((2-(1-(Cyclopropylsulfonyl)-1H-pyrazol-4-yl)pyridin-4-yl)amino)-5-(1-(2,2-difluoroethyl)-1H-pyrazol-3-yl)pyrimidin-4-yl)amino)-1-methylcyclohexan-1-ol;

(358) (1s,4s)-4-((2-((2-(1-(Cyclopropylsulfonyl)-1H-pyrazol-4-yl)pyridin-4-yl)amino)-5-(1-(methoxymethyl)-1H-pyrazol-3-yl)pyrimidin-4-yl)amino)-1-methylcyclohexan-1-ol;

(359) (1s,4s)-4-((2-((2-(1-(Cyclopropylsulfonyl)-1H-pyrazol-4-yl)pyridin-4-yl)amino)-5-(1-(3,3,3-trifluoropropyl)-1H-pyrazol-3-yl)pyrimidin-4-yl)amino)-1-methylcyclohexan-1-ol;

(360) (1s,4s)-4-((2-((2-(1-(Cyclopropylsulfonyl)-1H-pyrazol-4-yl)pyridin-4-yl)amino)-5-(1-(2,2,2-trifluoroethyl)-1H-pyrazol-3-yl)pyrimidin-4-yl)amino)-1-methylcyclohexan-1-ol;

(361) (1s,4s)-4-((2-((2-(1-(2,2-Difluoroethyl)-1H-pyrazol-4-yl)pyridin-4-yl)amino)-5-(1-methyl-5-(trifluoromethyl)-1H-pyrazol-3-yl)pyrimidin-4-yl)amino)-1-methylcyclohexan-1-ol;

(362) (1s,4s)-4-((2-((2-(1-(2,2-Difluoroethyl)-1H-pyrazol-4-yl)pyridin-4-yl)amino)-5-(1-(difluoromethyl)-1H-pyrazol-3-yl)pyrimidin-4-yl)amino)-1-methylcyclohexan-1-ol;

(363) $N^2$-(2-(1-(Cyclopropylsulfonyl)-1H-pyrazol-4-yl)pyridin-4-yl)-5-(1-(difluoromethyl)-1H-pyrazol-3-yl)-$N^4$-isopropylpyrimidine-2,4-diamine;

(364) ((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)methanol;

(365) 2-((1s,4s)-4-((2-((2-(1-(Cyclopropylsulfonyl)-1H-pyrazol-4-yl)pyridin-4-yl)amino)-5-(1-(difluoromethyl)-1H-pyrazol-3-yl)pyrimidin-4-yl)amino)cyclohexyl)propan-2-ol;

(366) $N^2$-(2-(1-(Cyclopropylsulfonyl)-1H-pyrazol-4-yl)pyridin-4-yl)-$N^4$-((1s,4s)-4-fluorocyclohexyl)-5-(1-(2,2,2-trifluoroethyl)-1H-pyrazol-3-yl)pyrimidine-2,4-diamine;

(367) $N^2$-(2-(1-(Cyclopropylsulfonyl)-1H-pyrazol-4-yl)pyridin-4-yl)-$N^4$-((1s,4s)-4-fluorocyclohexyl)-5-(1-(3,3,3-trifluoropropyl)-1H-pyrazol-3-yl)pyrimidine-2,4-diamine;

(368) (1s,4s)-4-((5-(1-(Difluoromethyl)-1H-pyrazol-3-yl)-2-((2-(3-methyl-1-(2,2,2-trifluoroethyl)-1H-pyrazol-4-yl)pyrimidin-4-yl)amino)pyrimidin-4-yl)amino)-1-methylcyclohexan-1-ol;

(369) (1s,4s)-1-Methyl-4-((2-((2-(3-methyl-1-(2,2,2-trifluoroethyl)-1H-pyrazol-4-yl)pyridin-4-yl)amino)-5-(1-methyl-5-(trifluoromethyl)-1H-pyrazol-3-yl)pyrimidin-4-yl)amino)cyclohexan-1-ol;

(370) (1s,4s)-1-Methyl-4-((2-((2-(3-methyl-1-(2,2,2-trifluoroethyl)-1H-pyrazol-4-yl)pyridin-4-yl)amino)-5-(1-(2,2,2-trifluoroethyl)-1H-pyrazol-3-yl)pyrimidin-4-yl)amino)cyclohexan-1-ol;

(371) $N^2$-(2-(1-(Cyclopropylsulfonyl)-1H-pyrazol-4-yl)pyridin-4-yl)-$N^4$-((1s,4s)-4-fluorocyclohexyl)-5-(1-methyl-5-(trifluoromethyl)-1H-pyrazol-3-yl)pyrimidine-2,4-diamine;

(372) (1s,4s)-4-((6-((2-(1-(Cyclopropylsulfonyl)-1H-pyrazol-4-yl)pyrimidin-4-yl)amino)-3-(1-(difluoromethyl)-1H-pyrazol-3-yl)pyridazin-4-yl)amino)-1-methylcyclohexan-1-ol;

(373) (1s,4s)-4-((6-((2-(1-(Cyclopropylsulfonyl)-1H-pyrazol-4-yl)pyrimidin-4-yl)amino)-3-(1-methyl-5-(trifluoromethyl)-1H-pyrazol-3-yl)pyridazin-4-yl)amino)-1-methylcyclohexan-1-ol;

(374) (1s,4s)-4-((6-((2-(1-(Cyclopropylsulfonyl)-1H-pyrazol-4-yl)pyrimidin-4-yl)amino)-3-(1-(2,2,2-trifluoroethyl)-1H-pyrazol-3-yl)pyridazin-4-yl)amino)-1-methylcyclohexan-1-ol;

(375) (1s,4s)-4-((3-(1-(Difluoromethyl)-1H-pyrazol-3-yl)-6-((2-(3-methyl-1-(2,2,2-trifluoroethyl)-1H-pyrazol-4-yl)pyrimidin-4-yl)amino)pyridazin-4-yl)amino)-1-methylcyclohexan-1-ol;

(376) (1s,4s)-4-((2-((2-(1-(Cyclopropylsulfonyl)-1H-pyrazol-4-yl)pyrimidin-4-yl)amino)-5-(1H-pyrazol-1-yl)pyridin-4-yl)amino)-1-methylcyclohexan-1-ol;

(377) ((1s,3s)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)cyclobutyl)methanol;

(378) ((1s,3s)-3-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-1-methylcyclobutyl)methanol;

(379) (1s,4s)-4-((2-((2-(1-(Butylsulfonyl)-1H-pyrazol-4-yl)pyrimidin-4-yl)amino)-5-(1-(difluoromethyl)-1H-pyrazol-3-yl)pyridin-4-yl)amino)-1-methylcyclohexan-1-ol;

(380) 1-((2-((2-(1-(Cyclopropylsulfonyl)-1H-pyrazol-4-yl)pyrimidin-4-yl)amino)-5-(1-(difluoromethyl)-1H-pyrazol-3-yl)pyridin-4-yl)amino)-4-methylpiperidin-4-ol;

(381) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-(4-(fluoromethyl)piperidin-1-yl)pyridine-2,4-diamine;

(382) (1s,4s)-4-((2-((2-(1-(Cyclopropylsulfonyl)-1H-pyrazol-4-yl)pyrimidin-4-yl)amino)-5-(5-fluoro-1-methyl-1H-pyrazol-3-yl)pyridin-4-yl)amino)-1-methylcyclohexan-1-ol;

(383) (1s,4s)-4-((2-((2-(1-(Cyclopropylsulfonyl)-1H-pyrazol-4-yl)pyrimidin-4-yl)amino)-5-(2-(difluoromethyl)-1-methyl-1H-imidazol-4-yl)pyridin-4-yl)amino)-1-methylcyclohexan-1-ol;

(384) $N^2$-(2-(1-(Cyclopropylsulfonyl)-1H-pyrazol-4-yl)pyrimidin-4-yl)-$N^4$-((1r,4r)-4-(fluoromethyl)cyclohexyl)-5-(1-methyl-5-(trifluoromethyl)-1H-pyrazol-3-yl)pyridine-2,4-diamine;

(385) $N^2$-(2-(1-(Cyclopropylsulfonyl)-1H-pyrazol-4-yl)pyrimidin-4-yl)-5-(1-(difluoromethyl)-1H-pyrazol-3-yl)-$N^4$-((1r,4r)-4-fluorocyclohexyl)pyridine-2,4-diamine;

(386) $N^2$-(2-(1-(Cyclopropylsulfonyl)-1H-pyrazol-4-yl)pyrimidin-4-yl)-$N^4$-((1r,4r)-4-fluorocyclohexyl)-5-(1-methyl-5-(trifluoromethyl)-1H-pyrazol-3-yl)pyridine-2,4-diamine;

(387) (1s,4s)-4-((2-((2-(1-(Cyclopropylsulfonyl)-1H-pyrazol-4-yl)pyrimidin-4-yl)amino)-5-(4-fluoro-1-methyl-1H-pyrazol-3-yl)pyridin-4-yl)amino)-1-methylcyclohexan-1-ol; and (388) (1s,4s)-4-((2-((6-(1-(Cyclopropylsulfonyl)-1H-pyrazol-4-yl)pyrazin-2-yl)amino)-5-(1-(difluoromethyl)-1H-pyrazol-3-yl)pyridin-4-yl)amino)-1-methylcyclohexan-1-ol.

\* \* \* \* \*